(12) United States Patent
Lee et al.

(10) Patent No.: US 11,518,769 B2
(45) Date of Patent: *Dec. 6, 2022

(54) HETEROCYCLIC COMPOUNDS AND ORGANIC LIGHT EMITTING DEVICE USING THE SAME

(71) Applicant: LG CHEM, LTD., Seoul (KR)

(72) Inventors: Jung Ha Lee, Daejeon (KR); Dong Hoon Lee, Daejeon (KR); Tae Yoon Park, Daejeon (KR); Seong Mi Cho, Daejeon (KR); Dong Uk Heo, Daejeon (KR); Min Woo Jung, Daejeon (KR)

(73) Assignee: LG Chem, Ltd., Seoul (KR)

(*) Notice: Subject to any disclaimer, the term of this patent is extended or adjusted under 35 U.S.C. 154(b) by 319 days.

This patent is subject to a terminal disclaimer.

(21) Appl. No.: 16/619,912

(22) PCT Filed: Jul. 20, 2018

(86) PCT No.: PCT/KR2018/008236
§ 371 (c)(1),
(2) Date: Dec. 5, 2019

(87) PCT Pub. No.: WO2019/017734
PCT Pub. Date: Jan. 24, 2019

(65) Prior Publication Data
US 2020/0207754 A1 Jul. 2, 2020

(30) Foreign Application Priority Data

Jul. 20, 2017 (KR) .................. 10-2017-0092174
Jul. 19, 2018 (KR) .................. 10-2018-0084349

(51) Int. Cl.
*C07D 307/91* (2006.01)
*C07D 491/048* (2006.01)
(Continued)

(52) U.S. Cl.
CPC ....... *C07D 491/048* (2013.01); *C07D 209/82* (2013.01); *C07D 307/91* (2013.01);
(Continued)

(58) Field of Classification Search
None
See application file for complete search history.

(56) References Cited

U.S. PATENT DOCUMENTS 8,946,984 B2   2/2015   Tanabe et al.
8,951,647 B2   2/2015   Parham et al.
(Continued)

FOREIGN PATENT DOCUMENTS

CN   102077384   5/2011
CN   104370904   2/2015
(Continued)

OTHER PUBLICATIONS

International Search Report from PCT/KR2018/008233, dated Oct. 31, 2018.
(Continued)

*Primary Examiner* — Robert S Loewe
(74) *Attorney, Agent, or Firm* — Dentons US LLP

(57) ABSTRACT

Provided is a heterocyclic compound of Formula 1:

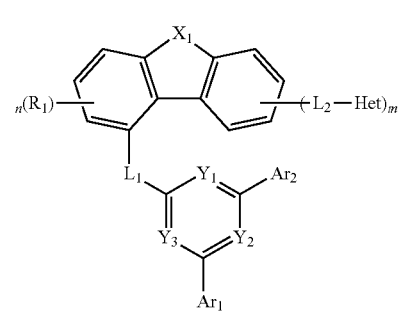

[Formula 1]

and an organic light emitting device comprising the same.

15 Claims, 1 Drawing Sheet

(51) Int. Cl.
*C07D 209/82* (2006.01)
*C07D 333/52* (2006.01)
*C07D 495/04* (2006.01)
*H01L 51/00* (2006.01)
*C07D 407/14* (2006.01)
*C07D 409/14* (2006.01)
*C07D 471/04* (2006.01)
*C07D 487/04* (2006.01)
*C07D 413/14* (2006.01)
*C07D 417/14* (2006.01)
*H01L 51/50* (2006.01)

(52) U.S. Cl.
CPC ......... *C07D 333/52* (2013.01); *C07D 407/14* (2013.01); *C07D 409/14* (2013.01); *C07D 413/14* (2013.01); *C07D 417/14* (2013.01); *C07D 471/04* (2013.01); *C07D 487/04* (2013.01); *C07D 495/04* (2013.01); *H01L 51/0052* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/508* (2013.01); *H01L 51/5016* (2013.01); *H01L 51/5024* (2013.01); *H01L 51/5072* (2013.01); *H01L 51/5092* (2013.01)

(56) References Cited

U.S. PATENT DOCUMENTS

| | | | |
|---|---|---|---|
| 9,614,161 | B2 | 4/2017 | Park et al. |
| 9,865,822 | B2 | 1/2018 | Song et al. |
| 2004/0251816 | A1 | 12/2004 | Leo et al. |
| 2011/0095282 | A1 | 4/2011 | Pflumm et al. |
| 2011/0309343 | A1 | 12/2011 | Langer et al. |
| 2014/0077191 | A1 | 3/2014 | Mizutani et al. |
| 2014/0291645 | A1 | 10/2014 | Inoue et al. |
| 2014/0346483 | A1 | 11/2014 | Yu et al. |
| 2015/0207082 | A1 | 7/2015 | Dyatkin et al. |
| 2016/0093808 | A1 | 3/2016 | Adamovich et al. |
| 2016/0111657 | A1 | 4/2016 | Lee et al. |
| 2016/0181548 | A1 | 6/2016 | Parham et al. |
| 2016/0226001 | A1 | 8/2016 | Parham et al. |
| 2016/0276603 | A1* | 9/2016 | Beers .................. C07F 15/0033 |
| 2016/0308142 | A1 | 10/2016 | Kim et al. |
| 2016/0329502 | A1 | 11/2016 | Dyatkin et al. |
| 2016/0351826 | A1 | 12/2016 | Kim et al. |
| 2017/0012216 | A1 | 1/2017 | Kim et al. |
| 2017/0025618 | A1 | 1/2017 | Zheng et al. |
| 2017/0054087 | A1 | 2/2017 | Zeng et al. |
| 2017/0179403 | A1 | 6/2017 | Kim et al. |
| 2017/0186965 | A1 | 6/2017 | Parham et al. |
| 2017/0186971 | A1 | 6/2017 | Kanamoto et al. |
| 2017/0200903 | A1 | 7/2017 | Park et al. |
| 2017/0207399 | A1 | 7/2017 | Parham et al. |
| 2017/0222157 | A1 | 8/2017 | Jatsch et al. |
| 2017/0237017 | A1 | 8/2017 | Parham et al. |
| 2018/0037546 | A1 | 2/2018 | Sugino et al. |
| 2018/0162843 | A1 | 6/2018 | Parham et al. |
| 2018/0166641 | A1 | 6/2018 | Inoue et al. |
| 2019/0165282 | A1 | 5/2019 | Parham et al. |
| 2020/0058877 | A1 | 2/2020 | Cha et al. |
| 2020/0144511 | A1* | 5/2020 | Bae .................... H01L 51/0071 |
| 2020/0259098 | A1 | 8/2020 | Lee et al. |

FOREIGN PATENT DOCUMENTS

| | | |
|---|---|---|
| CN | 105189455 A | 12/2015 |
| CN | 105934436 A | 9/2016 |
| CN | 106459018 | 2/2017 |
| CN | 106565433 | 4/2017 |
| CN | 106661006 A | 5/2017 |
| CN | 108250189 A | 7/2018 |
| CN | 108884086 A | 11/2018 |
| CN | 108884087 A | 11/2018 |
| CN | 110268036 A | 9/2019 |
| CN | 110313078 A | 10/2019 |
| CN | 110869372 A | 3/2020 |
| CN | 111183204 A | 5/2020 |
| JP | 2013131518 | 7/2013 |
| JP | 5831654 | 12/2015 |
| JP | 6128119 | 5/2017 |
| JP | 2017098561 | 6/2017 |
| JP | 2017107992 | 6/2017 |
| KR | 10-20100007143 | 1/2010 |
| KR | 10-20100077675 | 7/2010 |
| KR | 10-20100118690 | 11/2010 |
| KR | 10-20120033017 | 4/2012 |
| KR | 10-20130036048 | 4/2013 |
| KR | 10-20130069431 | 6/2013 |
| KR | 10-20130073537 | 7/2013 |
| KR | 10-20140065863 | 5/2014 |
| KR | 10-20150054797 | 5/2015 |
| KR | 10-20150074603 | 7/2015 |
| KR | 10-20150084657 | 7/2015 |
| KR | 10-20150121394 | 10/2015 |
| KR | 10-20150129282 | 11/2015 |
| KR | 10-20150136942 | 12/2015 |
| KR | 10-20160026661 | 3/2016 |
| KR | 10-20160028524 | 3/2016 |
| KR | 1020160045507 A | 4/2016 |
| KR | 10-20170003502 | 1/2017 |
| KR | 10-20170039209 | 4/2017 |
| KR | 10-1857703 | 5/2018 |
| KR | 10-20180055698 | 5/2018 |
| KR | 10-2018-0068869 A | 6/2018 |
| KR | 10-20180133376 | 12/2018 |
| WO | 2003012890 | 2/2003 |
| WO | 2006128800 | 12/2006 |
| WO | 2009069442 | 6/2009 |
| WO | 2010015306 | 2/2010 |
| WO | 2010126270 | 11/2010 |
| WO | 2011126224 | 10/2011 |
| WO | 2011157790 | 12/2011 |
| WO | 2011158204 | 12/2011 |
| WO | 2013168534 | 11/2013 |
| WO | 2014042420 | 3/2014 |
| WO | 2014123369 | 8/2014 |
| WO | 2014178532 | 11/2014 |
| WO | 2015014434 | 2/2015 |
| WO | 2015036080 | 3/2015 |
| WO | 2015083974 | 6/2015 |
| WO | 2015169412 | 11/2015 |
| WO | 2016012075 | 1/2016 |
| WO | 2016013735 | 1/2016 |
| WO | 2016015810 | 2/2016 |
| WO | 2016023608 | 2/2016 |
| WO | 2016027938 | 2/2016 |
| WO | 2016129672 | 8/2016 |
| WO | 2016198144 | 12/2016 |
| WO | 2017016630 | 2/2017 |
| WO | 2017178311 | 10/2017 |

OTHER PUBLICATIONS

International Search Report from PCT/KR2018/008232, dated Oct. 31, 2018.
International Search Report from PCT/KR2018/008236, dated Oct. 31, 2018.
Written Opinion of the ISA from PCT/KR2018/008233, dated Oct. 31, 2018.
Written Opinion of the ISA from PCT/KR2018/008232, dated Oct. 31, 2018.
Written Opinion of the ISA from PCT/KR2018/008236, dated Oct. 31, 2018.
Office Action of Taiwanese Patent Office in Appl'n No. 107125258, dated Jul. 23, 2019.

* cited by examiner

【FIG. 1】
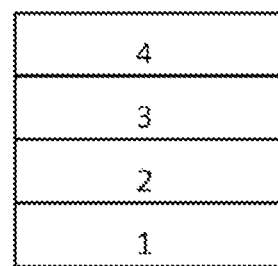
【FIG. 2】
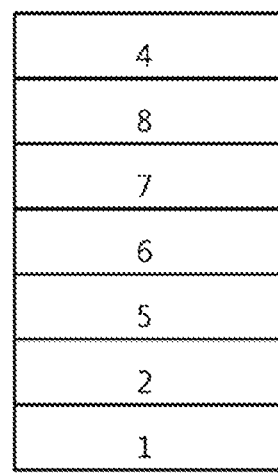

HETEROCYCLIC COMPOUNDS AND ORGANIC LIGHT EMITTING DEVICE USING THE SAME

CROSS-REFERENCE TO RELATED APPLICATIONS

This application is a National Stage Application of International Application No. PCT/KR2018/008236 filed on Jul. 20, 2018, which claims priority to and the benefit of Korean Patent Application No. 10-2017-0092174 filed on Jul. 20, 2017 and Korean Patent Application No. 110-2018-0084349 filed on Jul. 19, 2018 with the Korean Intellectual Property Office, the disclosures of which are incorporated herein by reference in their entirety.

TECHNICAL FIELD

The present invention relates to a novel heterocyclic compound and an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies about it have proceeded.

The organic light emitting device generally has a structure which includes an anode, a cathode, and an organic material layer interposed between the anode and the cathode. The organic material layer can have a multilayered structure that includes different materials in order to enhance efficiency and stability of the organic light emitting device, and for example, the organic material layer can be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state.

There is a continuing need for the development of new materials for the organic materials used in such organic light emitting devices.

PRIOR ART LITERATURE

Patent Literature (Patent Literature 0001) Korean Patent Laid-open Publication No. 10-2013-073537

DETAILED DESCRIPTION OF THE INVENTION

Technical Problem

It is an object of the present invention to provide a novel heterocyclic compound and an organic light emitting device including the same.

Technical Solution

In order to achieve the above object, the present invention provides a compound of the following Formula 1:

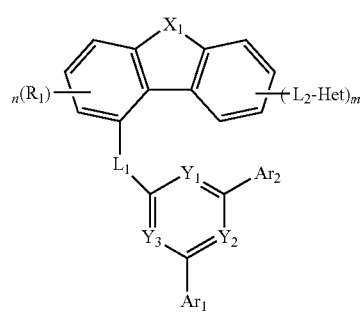

[Formula 1]

wherein in Formula 1 above;

$X_1$ is O or S;

$R_1$ is hydrogen or a substituted or unsubstituted $C_{1-60}$ alkyl;

$L_1$ and $L_2$ are each independently a direct bond or a substituted or unsubstituted $C_{6-60}$ arylene;

$Y_1$, $Y_2$, and $Y_3$ are each independently N or $CR_2$, provided that at least one of $Y_1$, $Y_2$, and $Y_3$ is N;

$R_2$ is hydrogen or a substituted or unsubstituted $C_{1-60}$ alkyl;

Ar1 and Ar2 are each independently a substituted 5 or unsubstituted C6-60 aryl or a substituted or unsubstituted $C_{5-60}$ heteroaryl containing at least one of N, O, and S, which can be combined with adjacent Y1, Y2, and Y3 to form a ring, n and m are each independently 1 or 2.

each Het is independently a substituent of the following Formula 1-1:

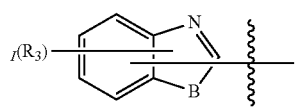

[Formula 1-1]

wherein in Formula 1-1 above:

B is O, S, or $NR_4$;

each $R_3$ is independently hydrogen, a substituted or unsubstituted $C_{1-60}$ alkyl, or a substituted or unsubstituted $C_{6-60}$ aryl;

$R_4$ is a substituted or unsubstituted $C_{1-60}$ alkyl, or a substituted or unsubstituted $C_{6-60}$ aryl; and 1 is 1 or 2.

The present invention also provides an organic light emitting device including: a first electrode; a second electrode provided at a side opposite to the first electrode; and at least one organic material layer provided between the first electrode and the second electrode, wherein the at least one organic material layer includes the compound of the present invention described above.

Advantageous Effects

The compound of Formula 1 described above can be used as a material of an organic material layer of an organic light emitting device, and can allow improvement of the efficiency, the low driving voltage, and/or the lifetime characteristic when applied to the organic light emitting device. In particular, the compound of Formula 1 can be used as a material for hole injection, hole transport, hole injection and transport, light emission, electron transport, or electron injection.

BRIEF DESCRIPTION OF DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present invention will be described in more detail to help understanding of the present invention.

The present invention provides a compound of Formula 1 as follows.

A compound of the following Formula 1:

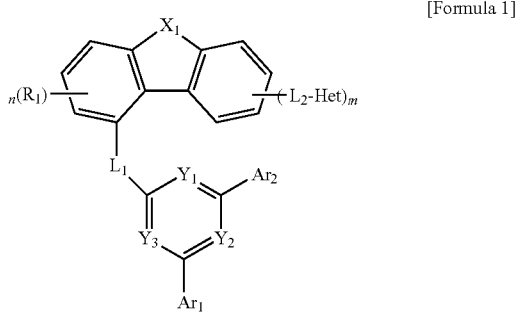

[Formula 1]

wherein in Formula 1 above:

$X_1$ is O or S;

$R_1$ is hydrogen or a substituted or unsubstituted $C_{1-60}$ alkyl;

$L_1$ and $L_2$ are each independently a direct bond or a substituted or unsubstituted $C_{6-60}$ arylene;

$Y_1$, $Y_2$, and $Y_3$ are each independently N or $CR_2$, provided that at least one of them is N;

$R_2$ is hydrogen or a substituted or unsubstituted $C_{1-60}$ alkyl;

$Ar_1$ and $Ar_2$ are each independently a substituted or unsubstituted $C_{6-60}$ aryl or a substituted or unsubstituted $C_{5-60}$ heteroaryl containing at least one of N, O, and S, which can be combined with an adjacent $Y_1$, Y2, or Y3 to form a ring;

each Het is independently a compound of the following Formula 1-1:

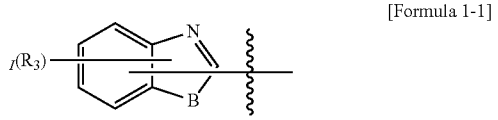

[Formula 1-1]

wherein in Formula 1-1 above:

B is O, S, or $NR_4$;

each $R_3$ is independently hydrogen, a substituted or unsubstituted $C_{1-60}$ alkyl, or a substituted or unsubstituted $C_{6-60}$ aryl;

$R_4$ is a substituted or unsubstituted $C_{1-60}$ alkyl, or a substituted or unsubstituted $C_{6-60}$ aryl; and l is 1 or 2.

In the present specification,

means a bond connected to another substituent group.

As used herein, the term "substituted or unsubstituted" means that substitution is performed with one or more substituent groups selected from the group consisting of deuterium, a halogen group, a nitrile group, a nitro group, a hydroxyl group, a carbonyl group, an ester group, an imide group, an amino group a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, or a heterocyclic group containing at least one of N, O, and S atoms, or there is no substituent group, or substitution is performed with a substituent group where two or more substituent groups of the exemplified substituent groups are linked or there is no substituent group. For example, the term "substituent group where two or more substituent groups are connected" can be a biphenyl group. That is, the biphenyl group can be an aryl group, or can be interpreted as a substituent group in which two phenyl groups are connected.

In the present specification, the number of carbon atoms in a carbonyl group is not particularly limited, but is preferably 1 to 40. Specifically, the carbonyl group can be a compound having one of the following structures, but is not limited thereto:

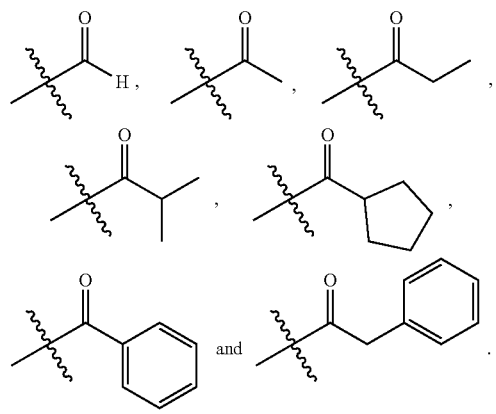

In the present specification, the ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having one of the following structures, but is not limited thereto:

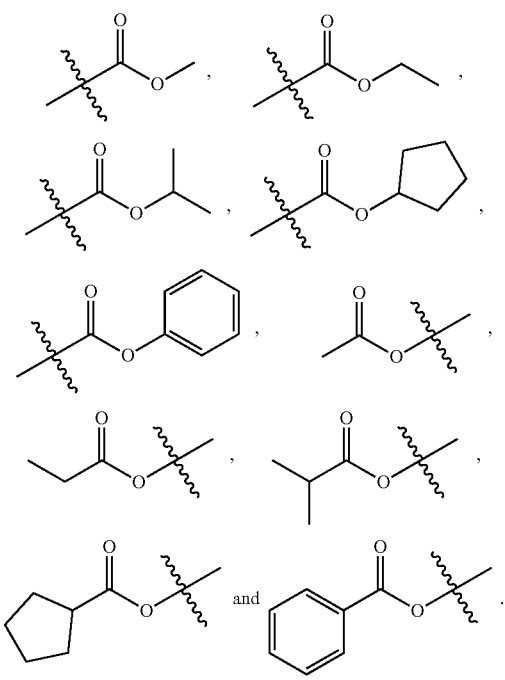

In the present specification, the number of carbon atoms in an imide group is not particularly limited, but is preferably 1 to 25. Specifically, the imide group can be a compound having one of the following structures, but is not limited thereto:

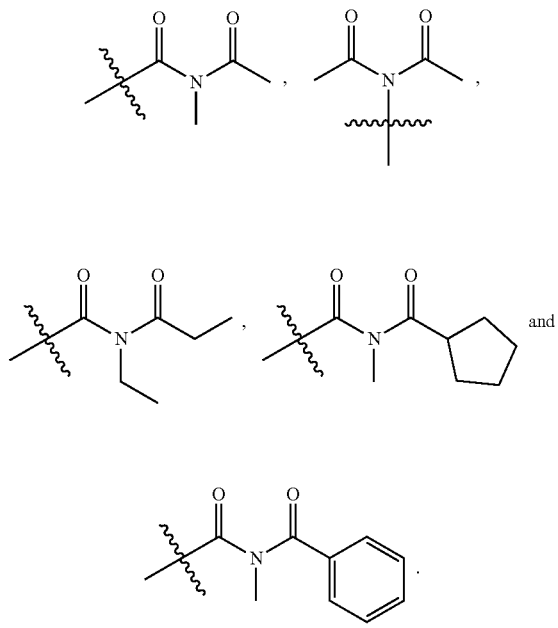

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of the halogen group include fluorine, chlorine, bromine, and iodine.

In the present specification, the alkyl group can be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, the alkenyl group can be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to still another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and can be a monocyclic aryl group or a polycyclic aryl group. According to one embodiment, the aryl group has 6 to 30 carbon atoms. According to one embodiment, the aryl group has 6 to 20 carbon atoms. The aryl group can be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrycenyl group, a fluorenyl group, and the like, but are not limited thereto.

In the present specification, a fluorenyl group can be substituted, and two substituent groups can be combined with each other to form a Spiro structure. In the case where the fluorenyl group is substituted,

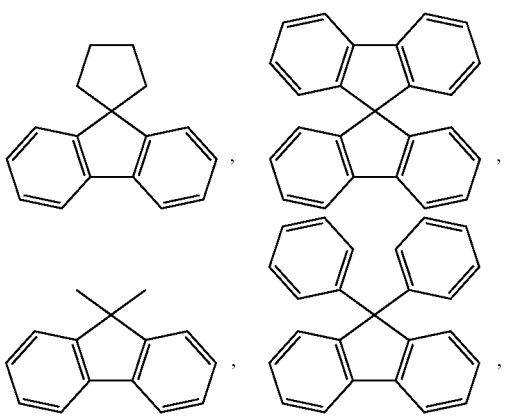

and the like can be formed. However, the structure is not limited thereto.

In the present specification, the heterocyclic group is a heterocyclic group containing at least one of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heterocyclic group can be applied, except that the heterocycle is not a monovalent group but is formed by combining two substituent groups.

Preferably, the compound of Formula 1 can be any one selected from compounds of the following Formulas 2 to 6:

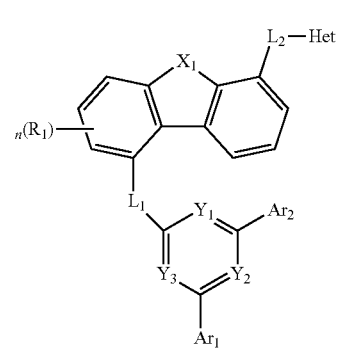

[Formula 2]

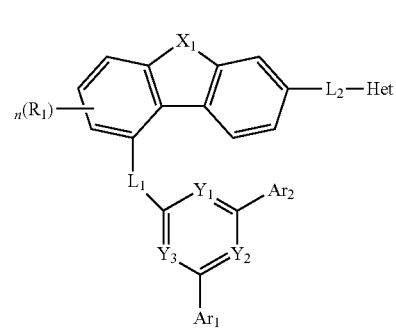

[Formula 3]

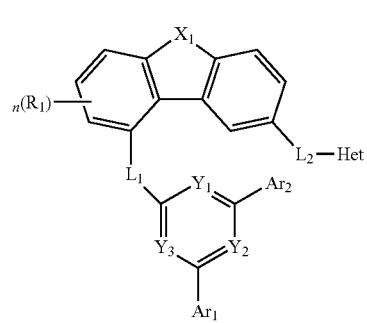

[Formula 4]

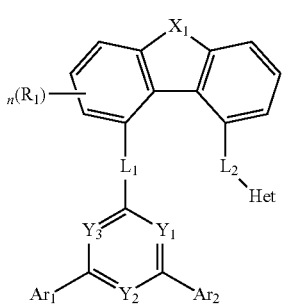

[Formula 5]

[Formula 6]

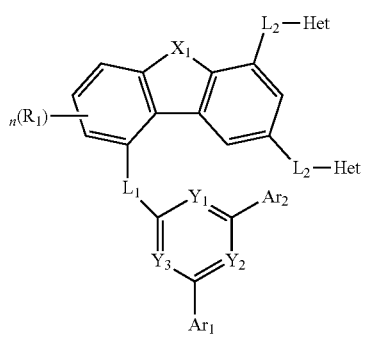

wherein in Formulas 2 to 6 above:

$X_1$, $L_1$, $L_2$, Het, $Y_1$, $Y_2$, $Y_3$, $R_1$, $Ar_1$, $Ar_2$, and n are as defined above.

Further, more preferably, the compound of Formula 1 can be a compound of Formula 2, 4, or 6.

Further, preferably, the compound of Formula 1 can be any one selected from compounds of the following Formulas 7 to 9:

[Formula 7]

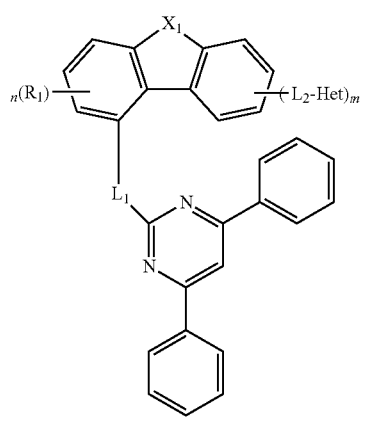

[Formula 8]

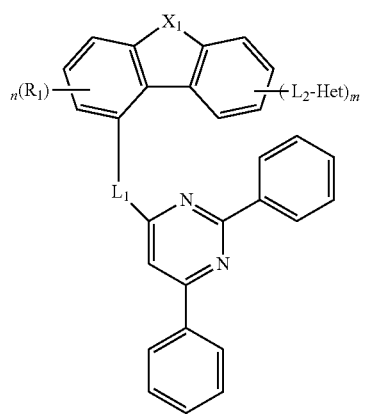

[Formula 9]

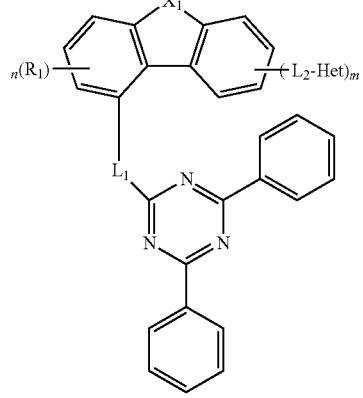

wherein in Formulas 7 to 9 above:

$X_1$, $L_1$, $L_2$, Het, $R_1$, n, and m are as defined above.

Preferably, in Formula 1, $R_1$ can be hydrogen or a substituted or unsubstituted $C_{1-10}$ alkyl, and more preferably hydrogen.

Preferably, in Formula 1, L and $L_2$ are each independently a direct bond or

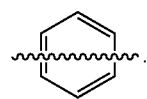.

Preferably, in Formula 1, $Ar_1$ and $Ar_2$ are each independently selected from the group consisting of the following formulas:

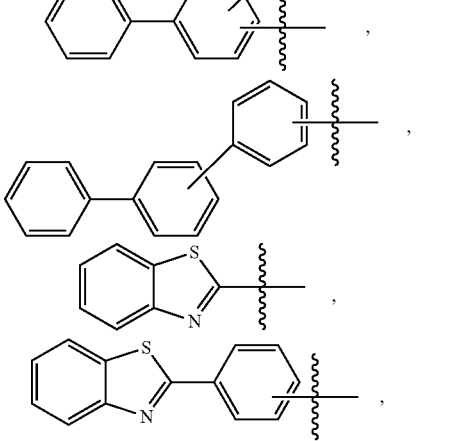

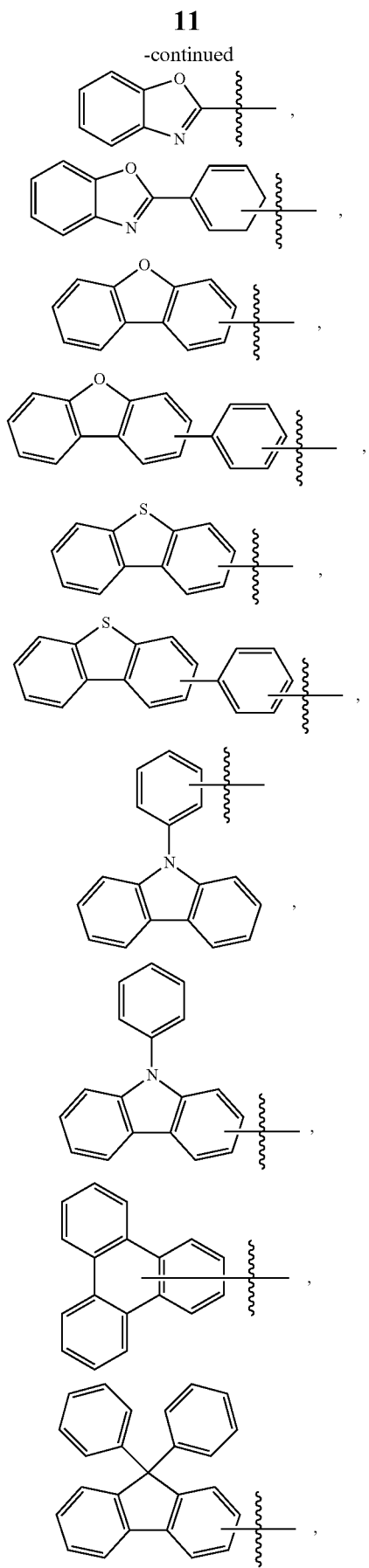
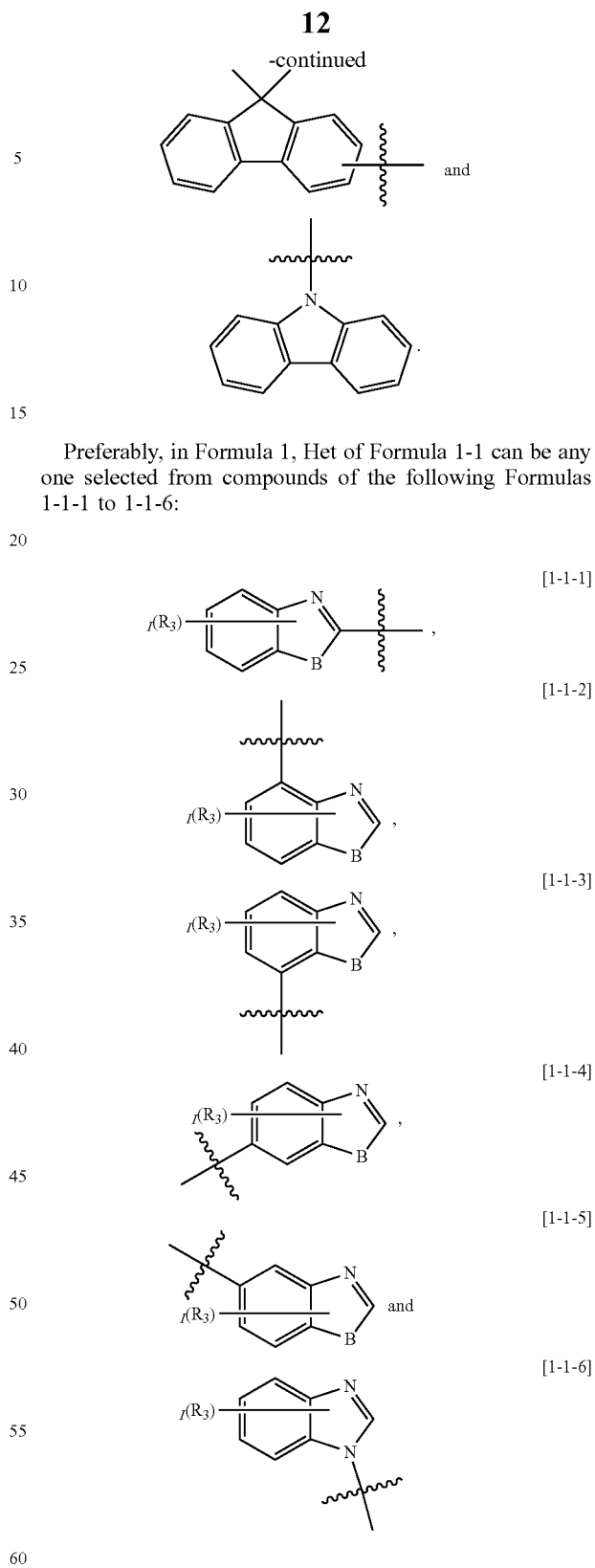
Preferably, in Formula 1, Het of Formula 1-1 can be any one selected from compounds of the following Formulas 1-1-1 to 1-1-6:
wherein in Formulas 1-1-1 to 1-1-6 above:
$R_3$, B, and 1 are as defined above.
Preferably, in Formula 1, $R_3$ can be hydrogen or phenyl.
Preferably, in Formula 1, Het can be any one selected from the group consisting of substituents of the following formulas:

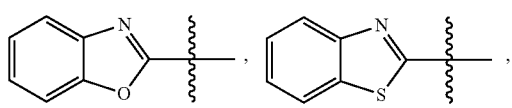
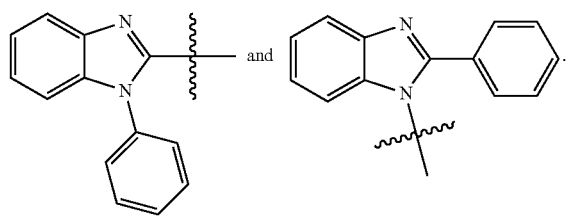
Preferably, the compound of Formula 1 can be any one selected from the group consisting of compounds of the following formulas:
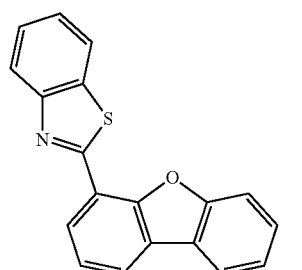
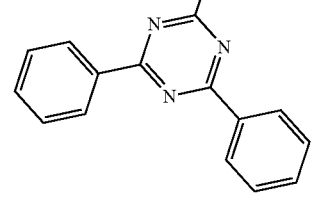
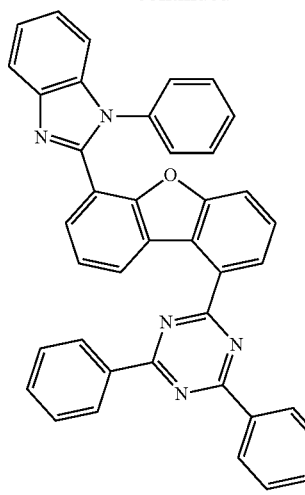
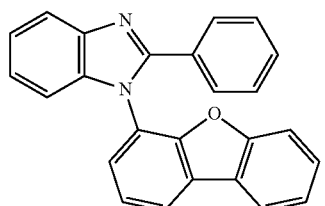
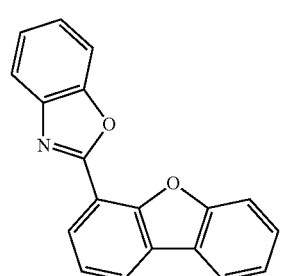
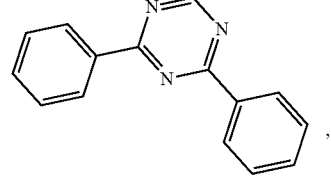
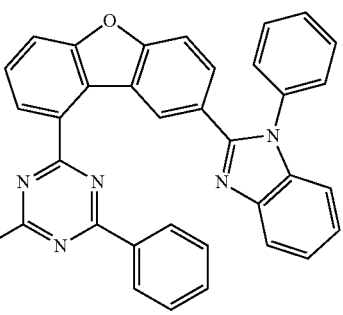
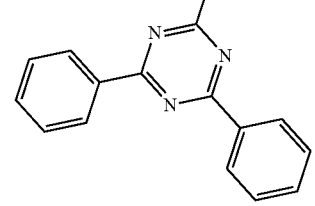
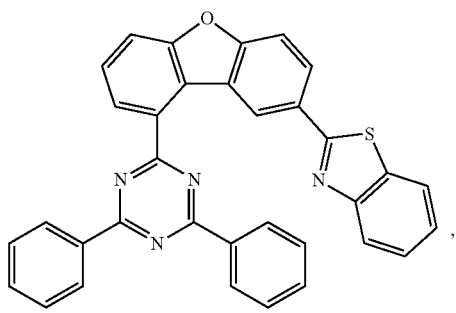

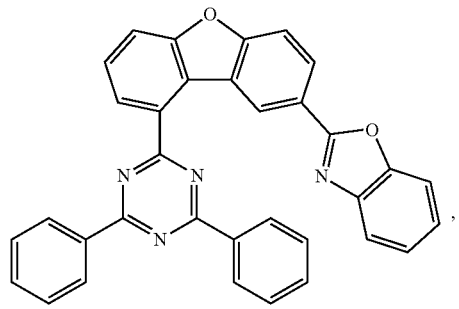
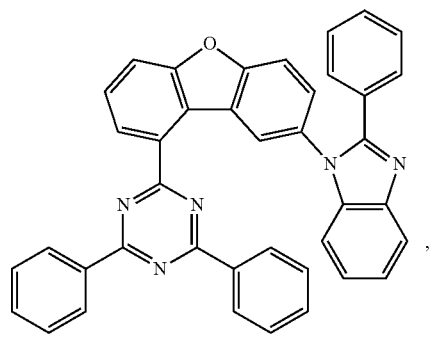
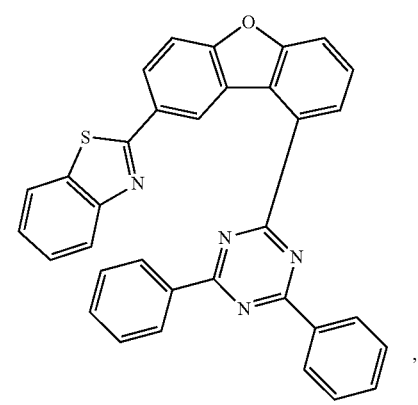
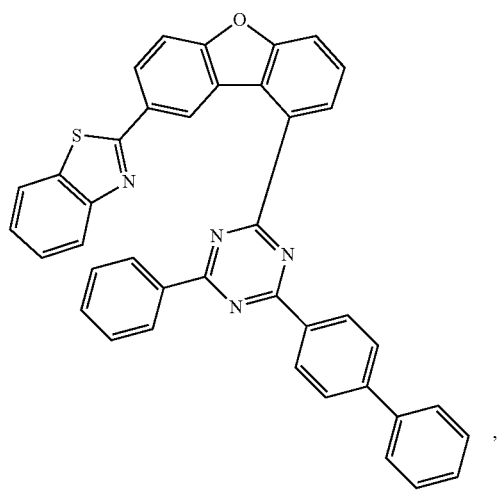
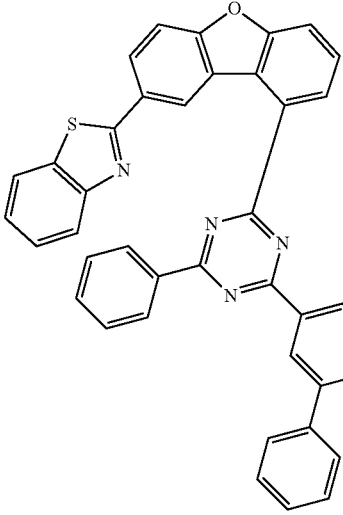
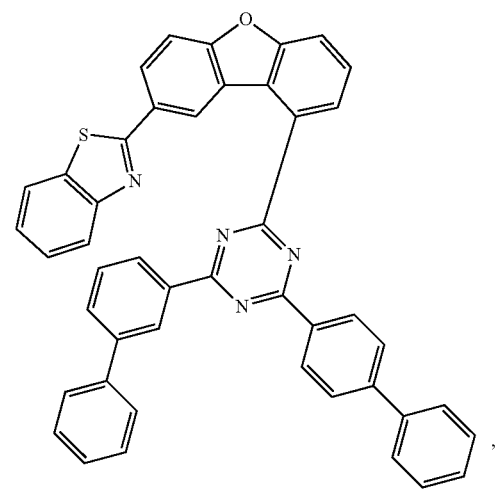
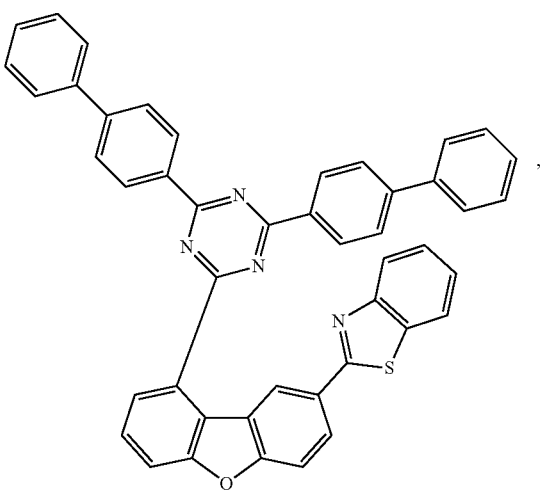

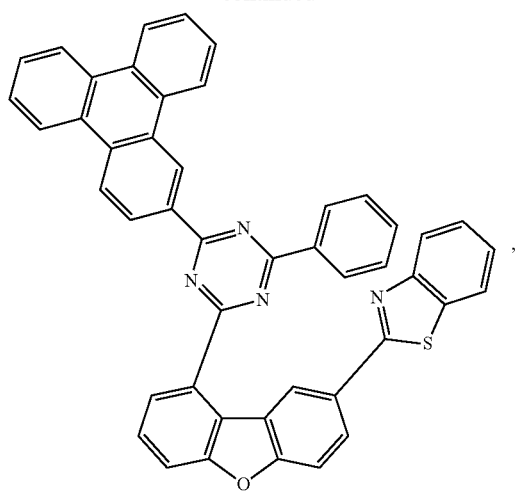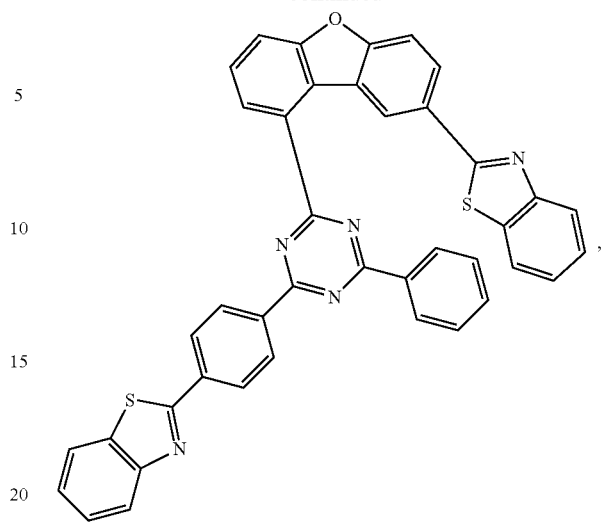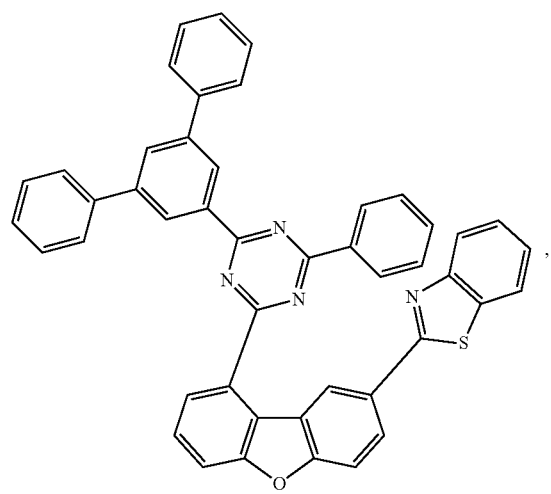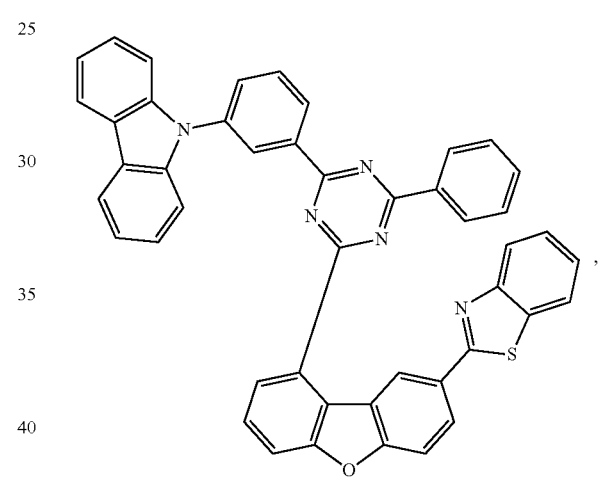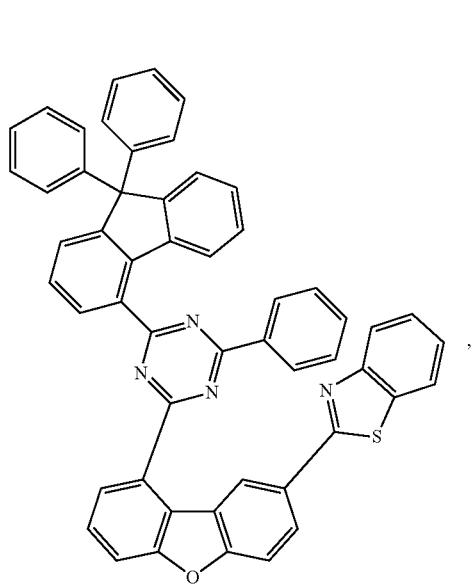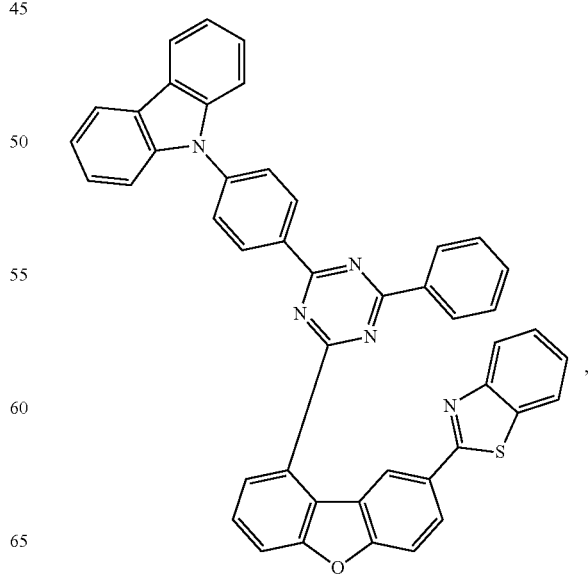

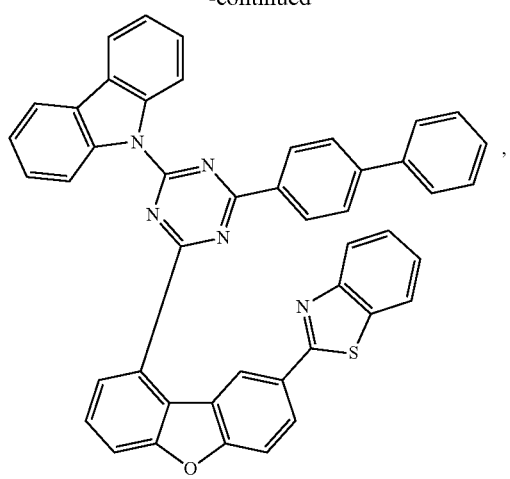
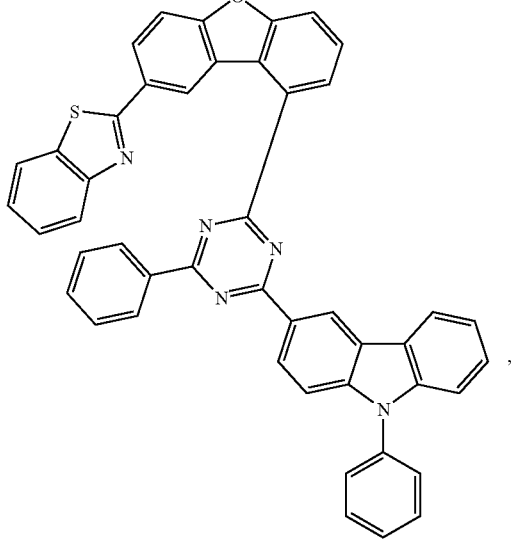
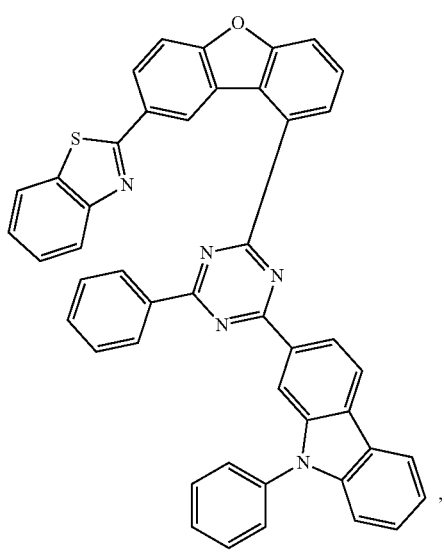
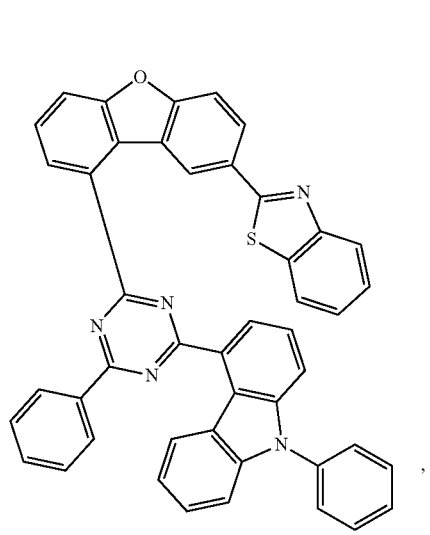
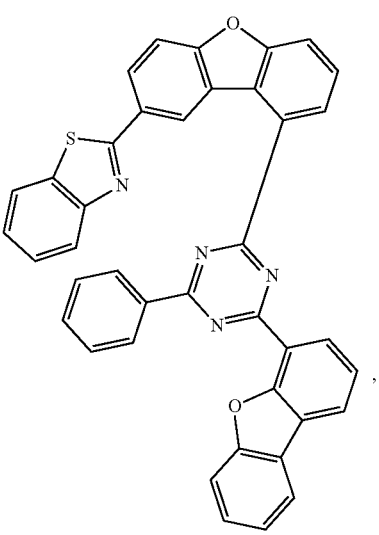

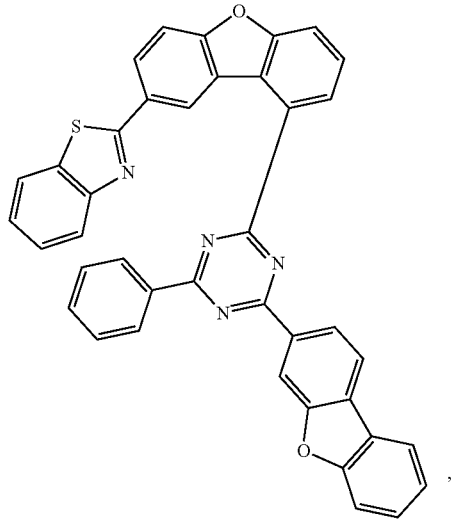
,
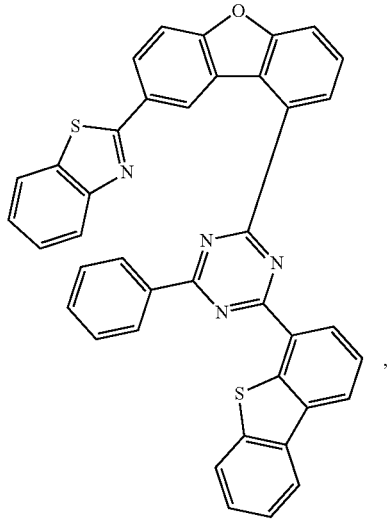
,
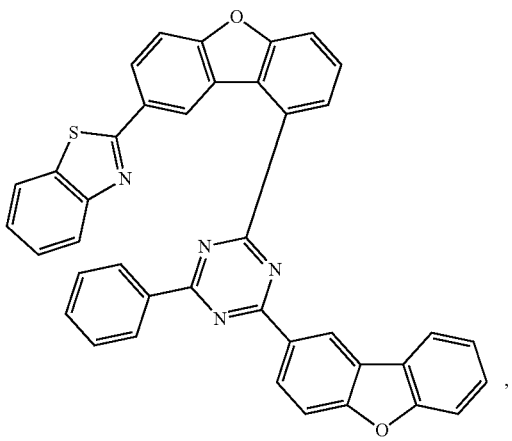
,
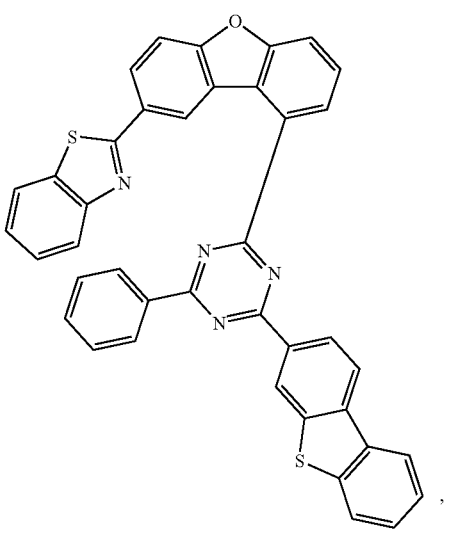
,
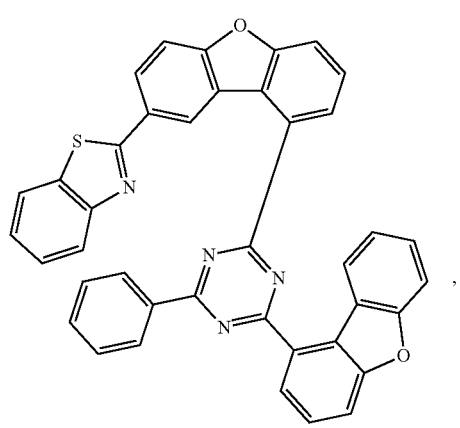
,
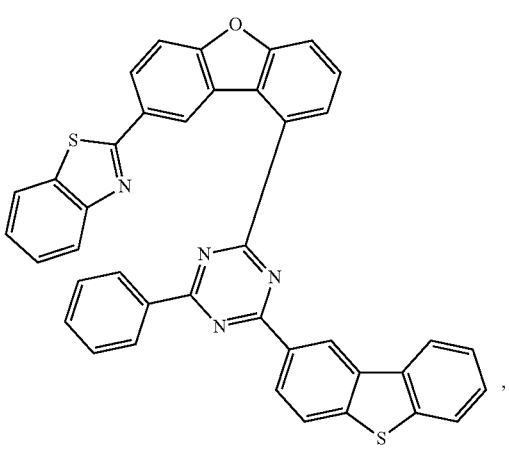
,

-continued
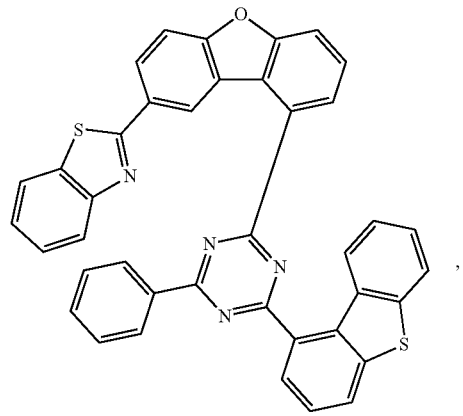
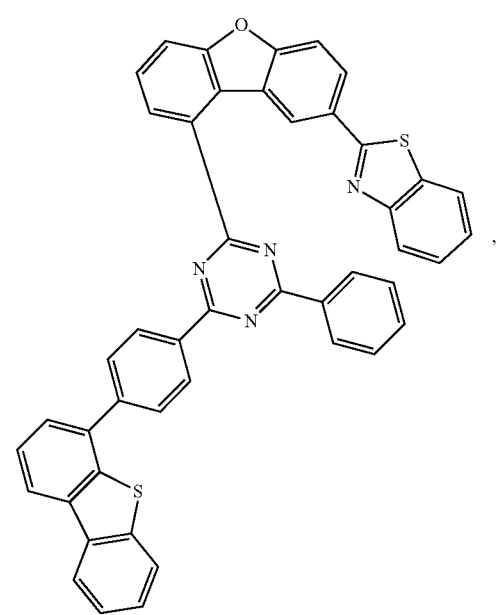
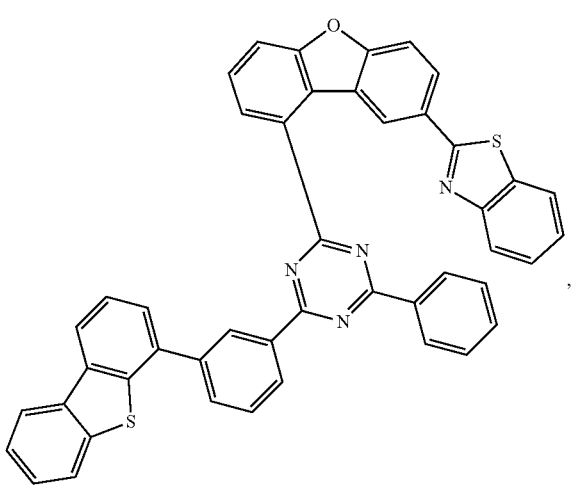
-continued
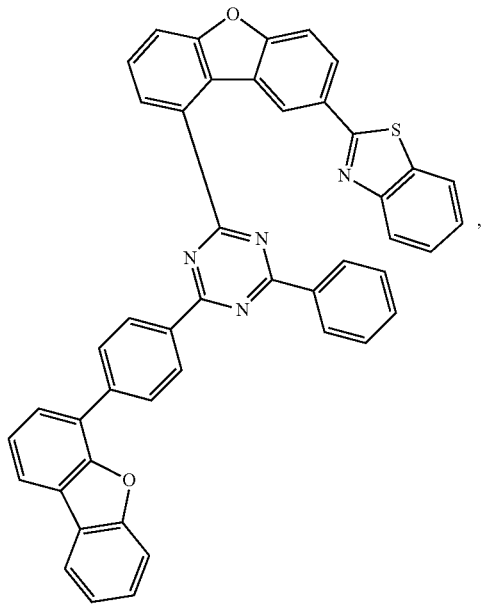
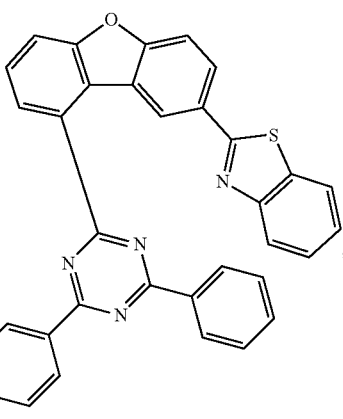
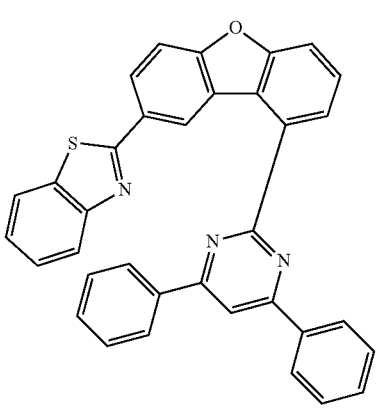

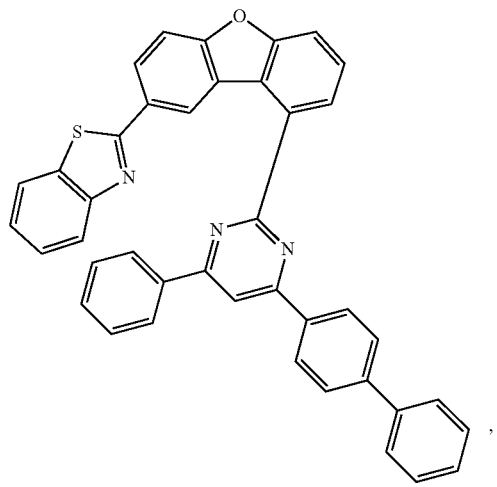
,
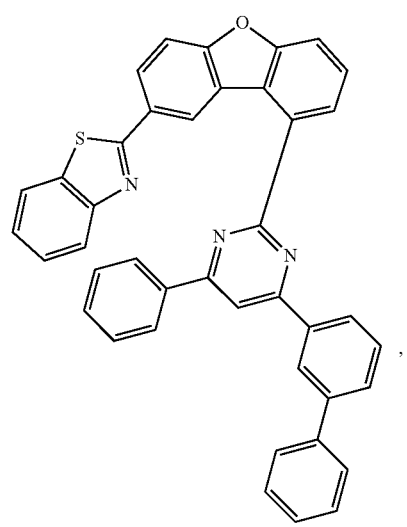
,
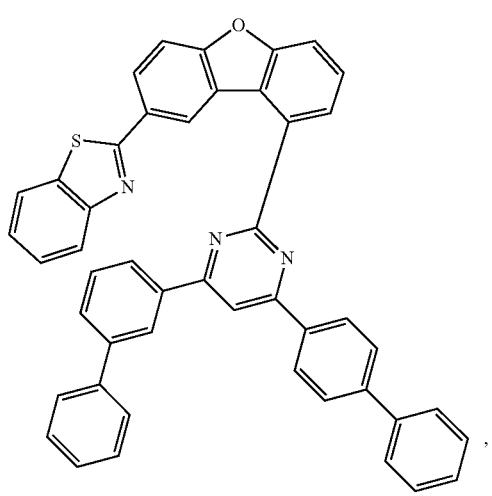
,
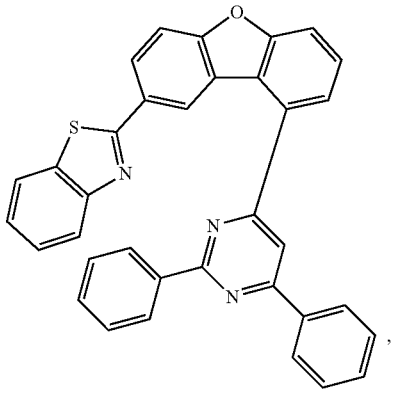
,
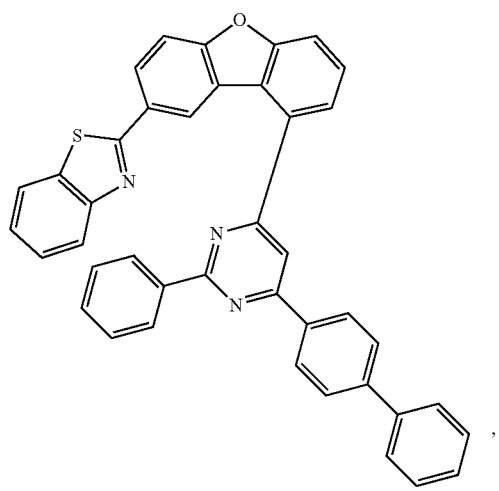
,
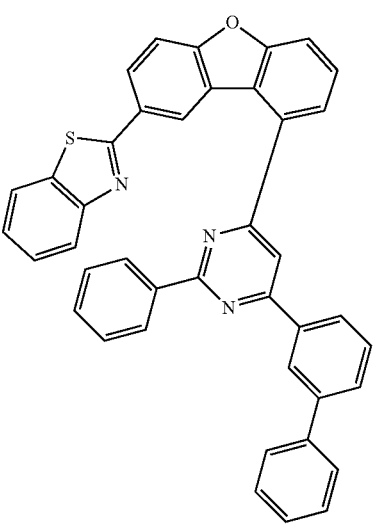
,

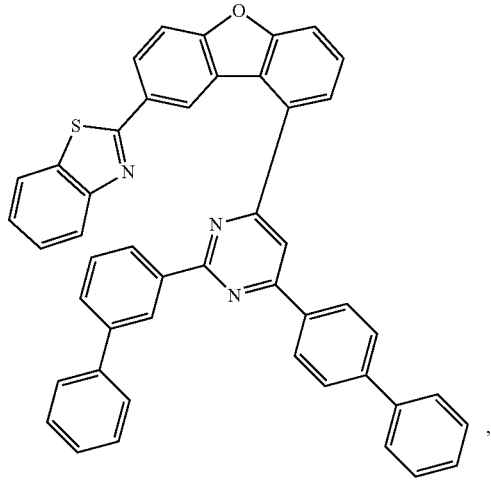
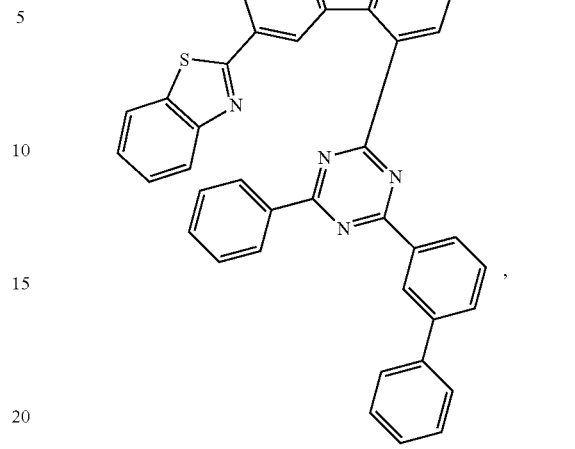
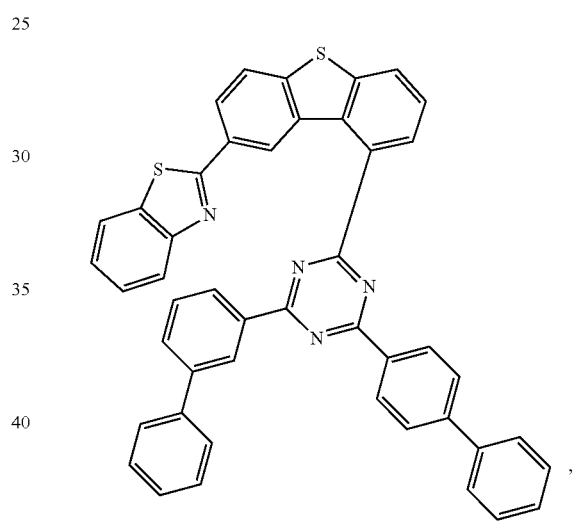
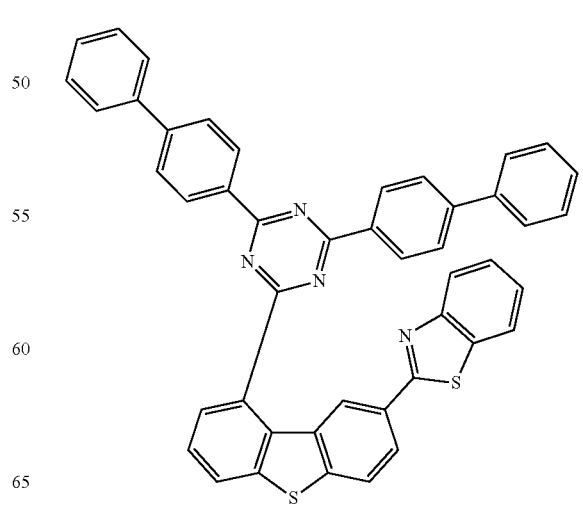

29
-continued
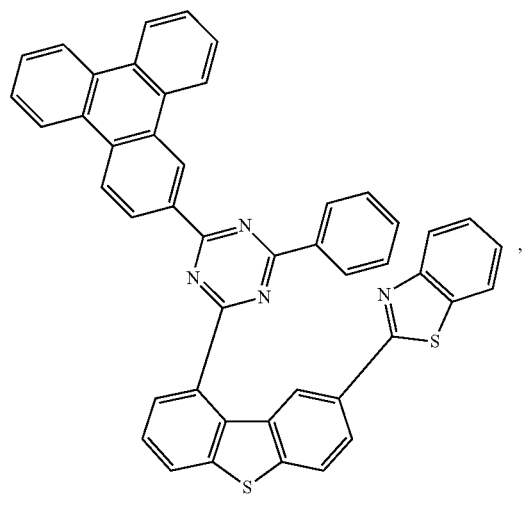
,
30
-continued
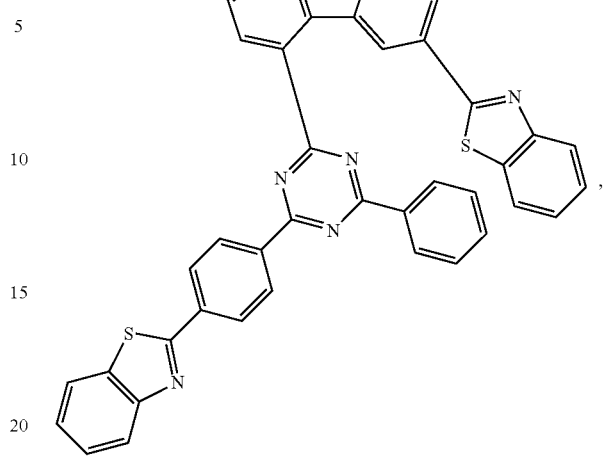
,
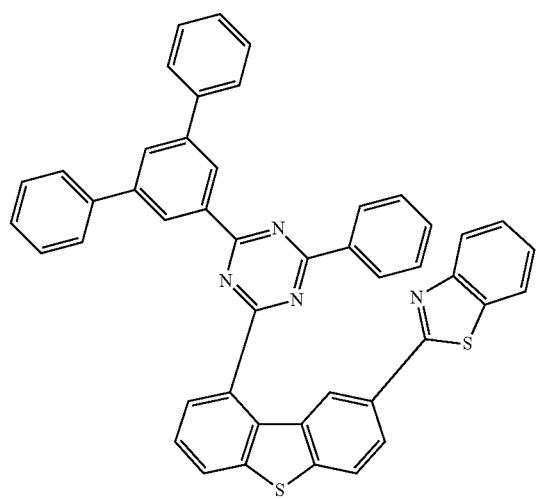
,
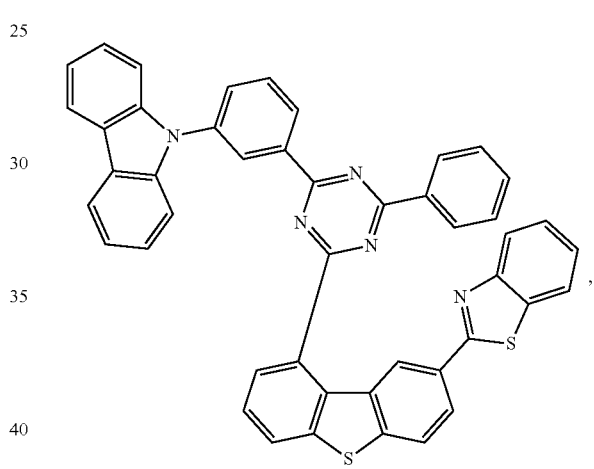
,
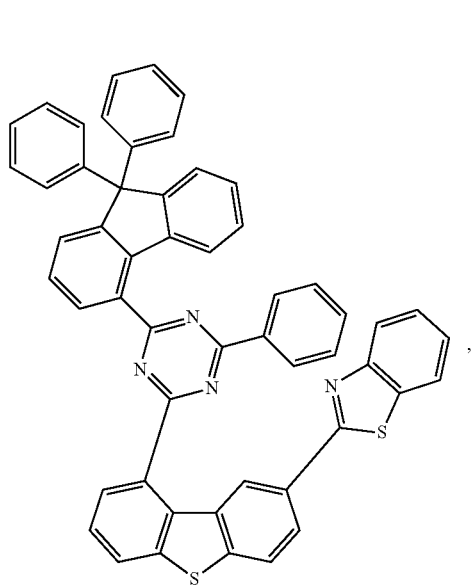
,
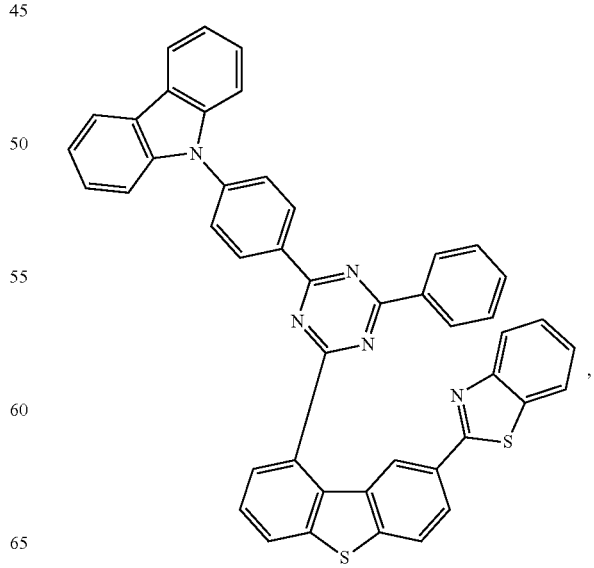
, 31
-continued
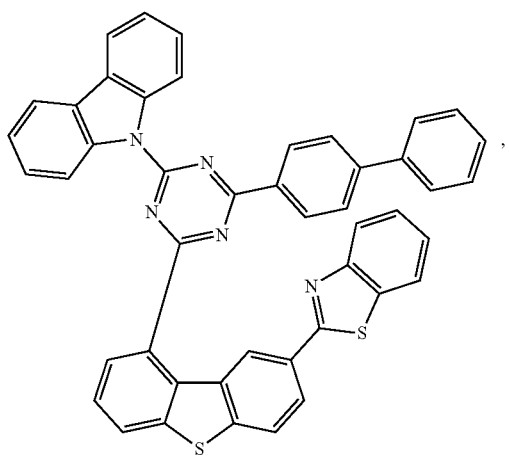
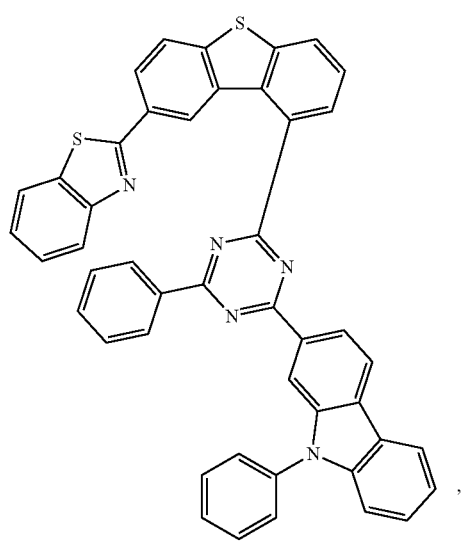
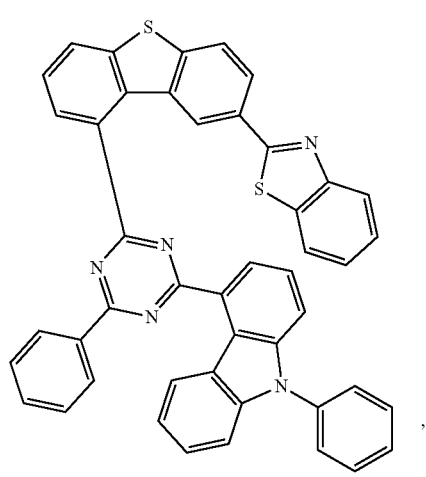
32
-continued
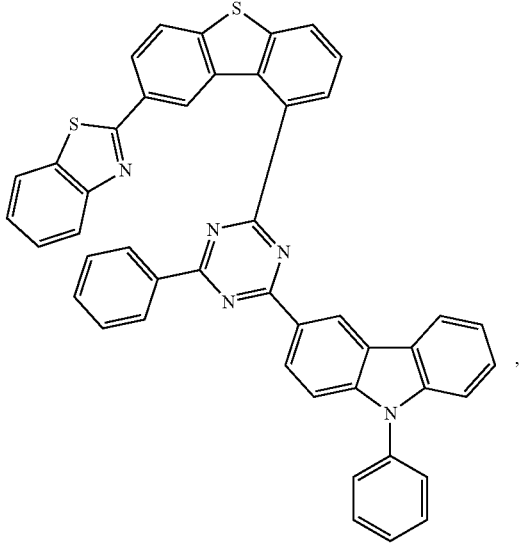
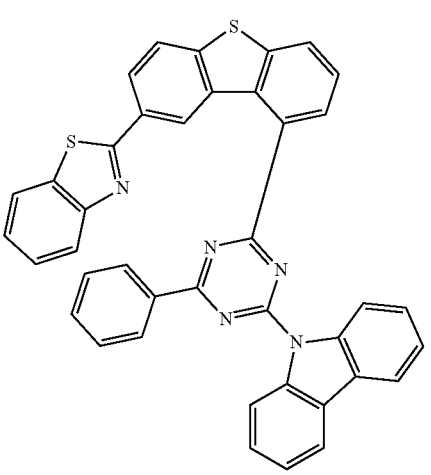
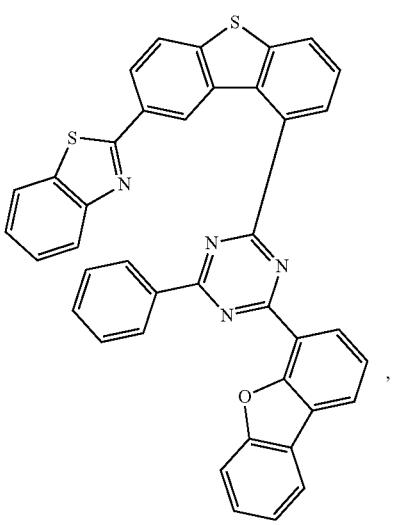

33
-continued
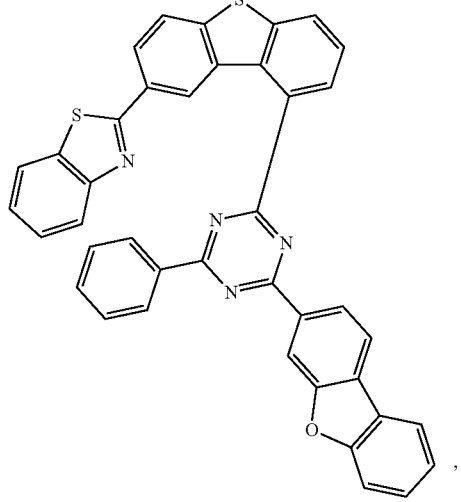
,
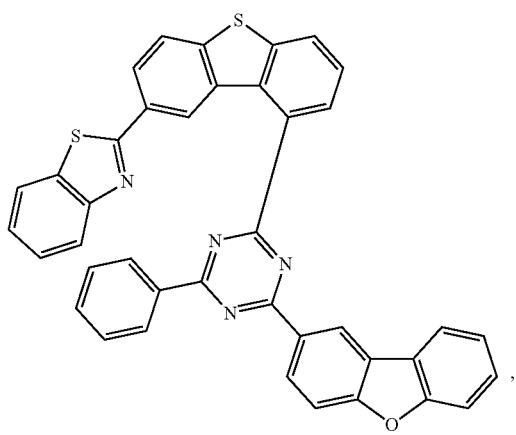
,
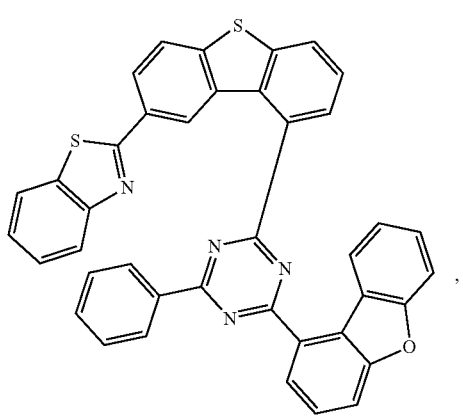
,
34
-continued
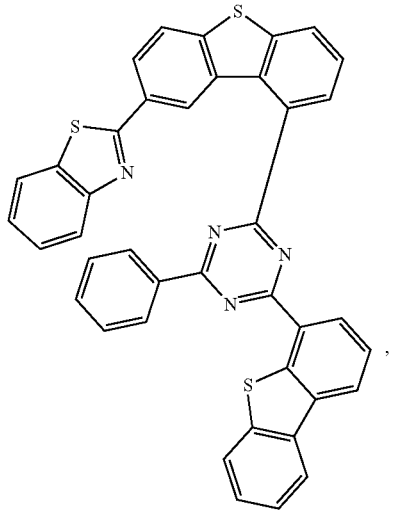
,
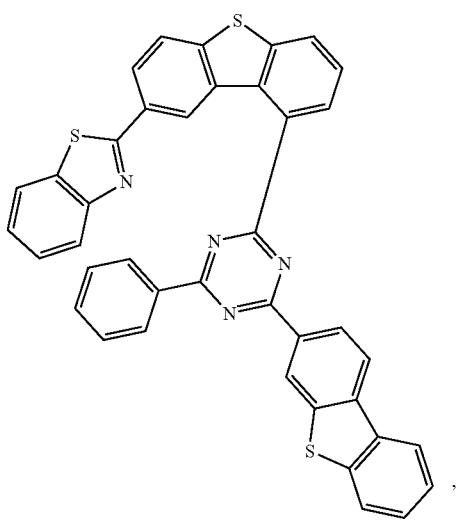
,
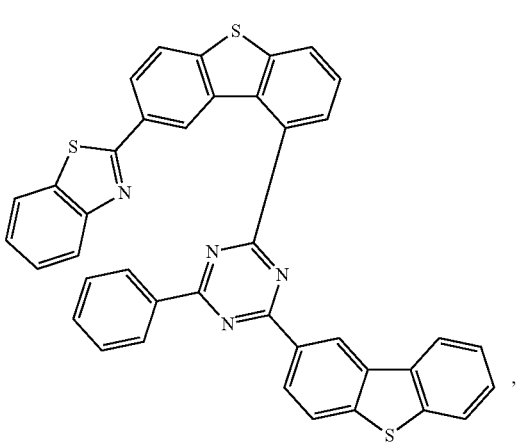
, -continued
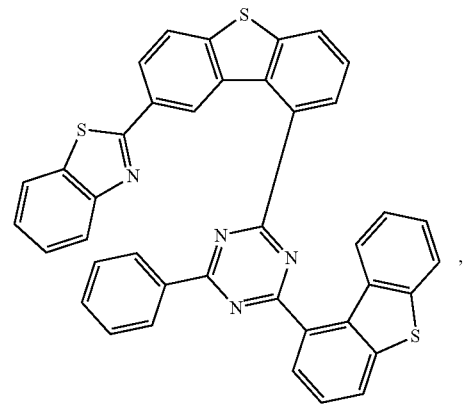
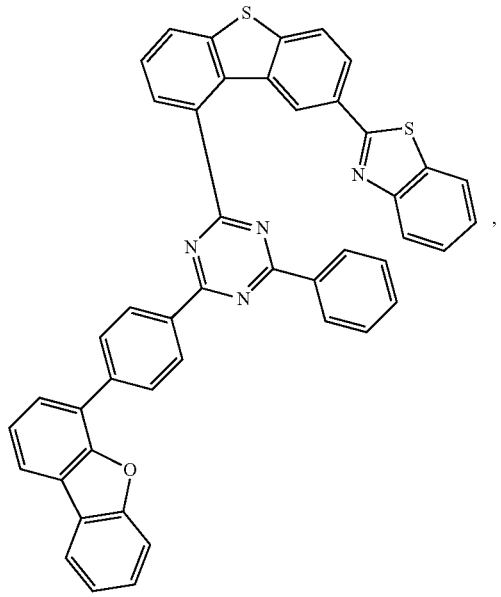
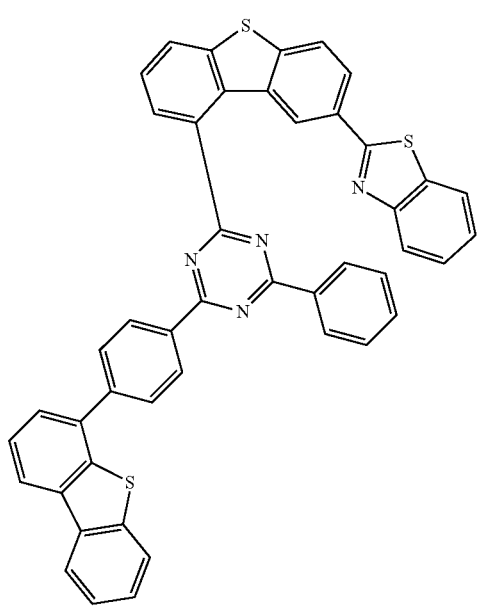
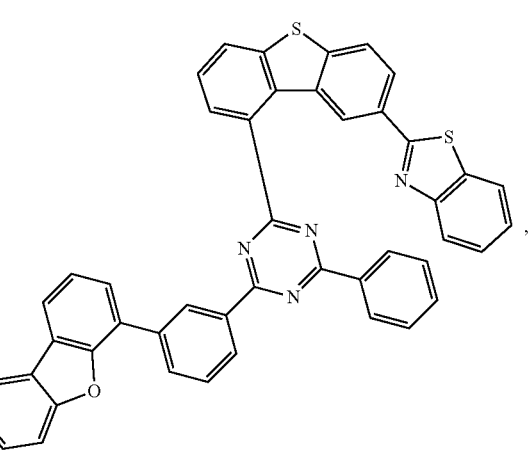
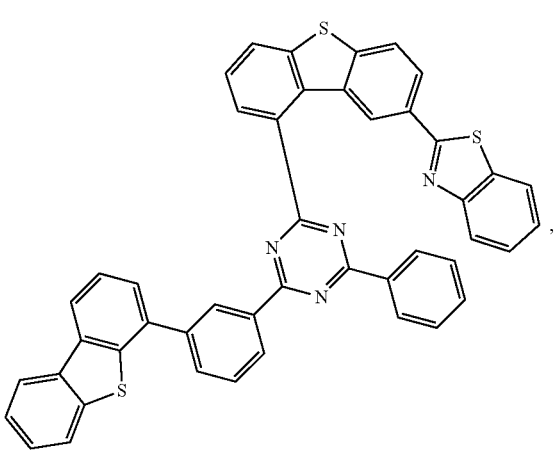
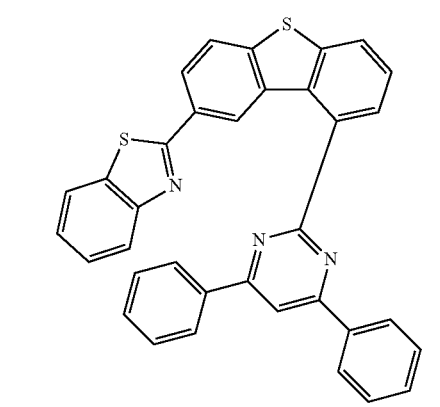

-continued
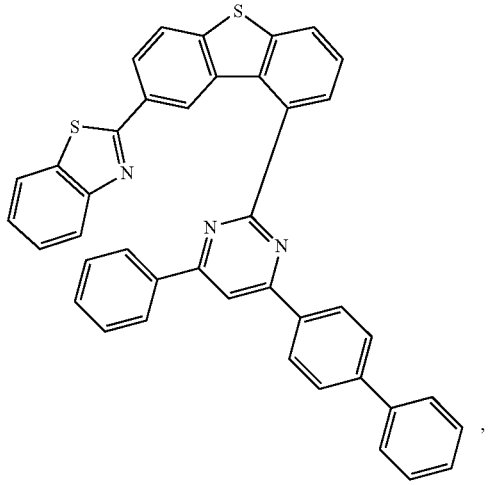
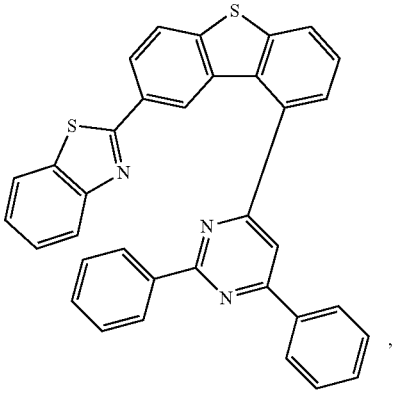
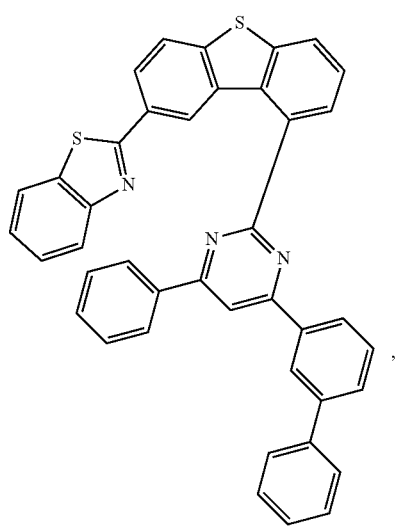
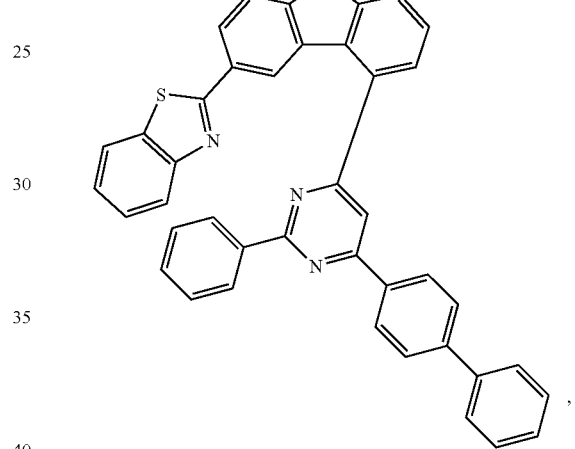
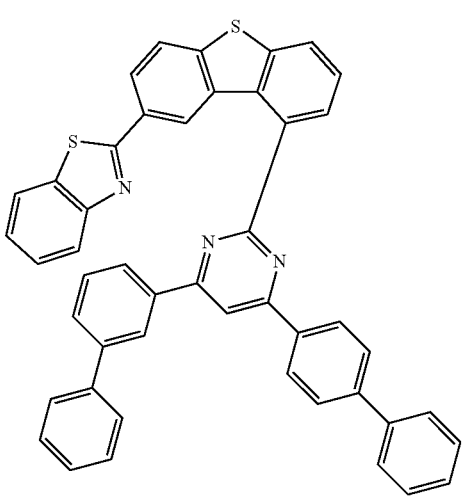
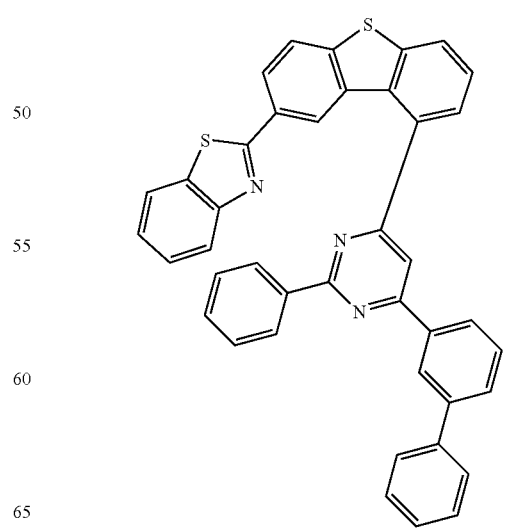

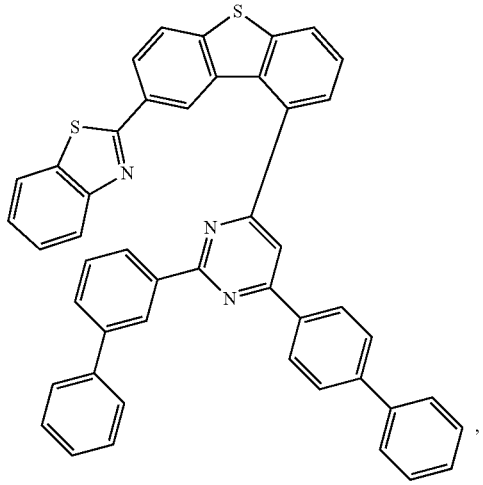
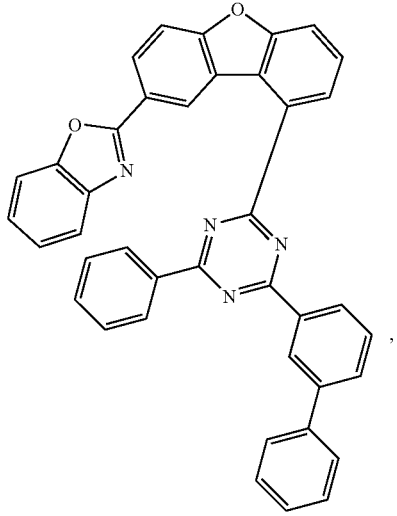
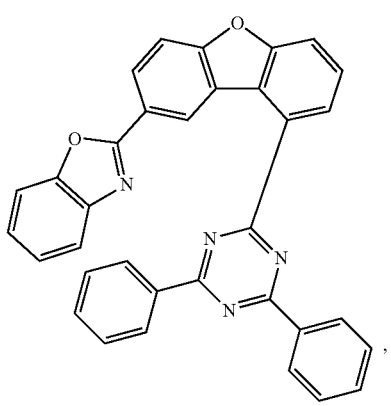
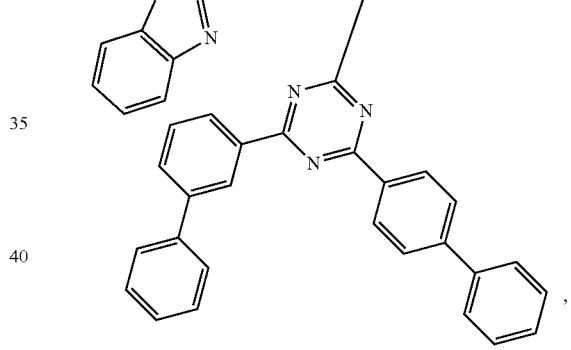
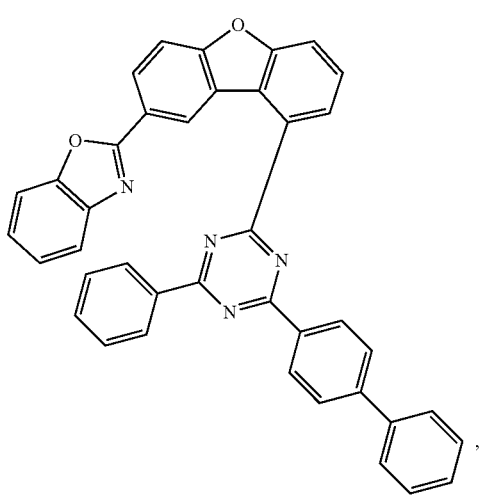
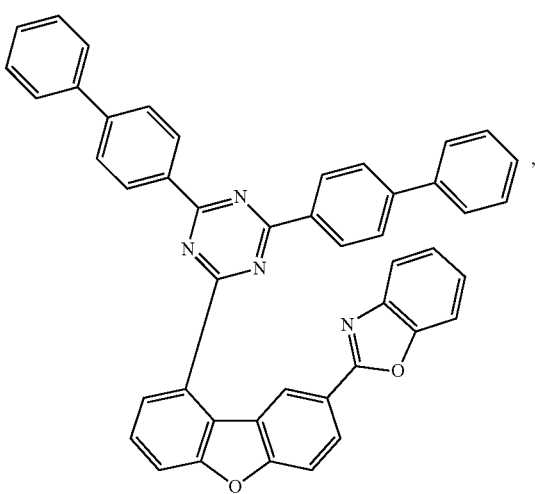

-continued
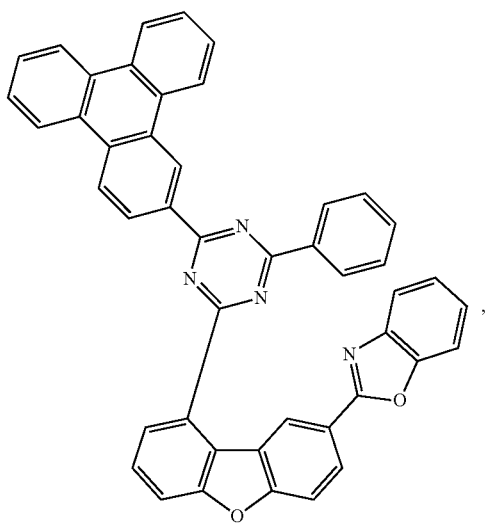
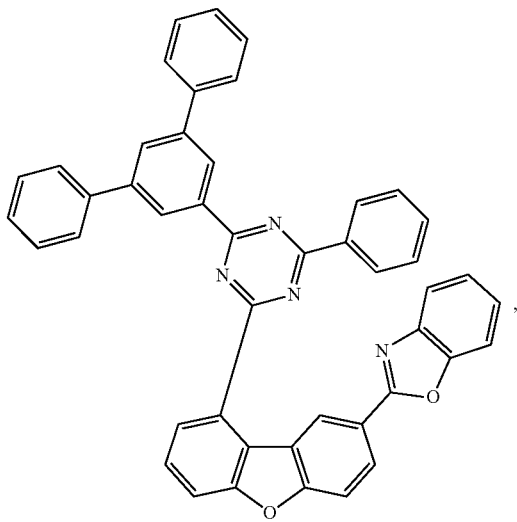
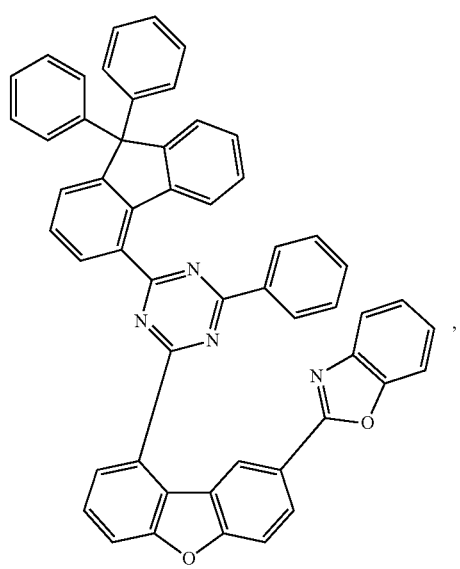
-continued
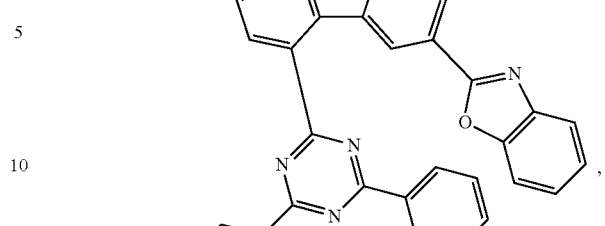
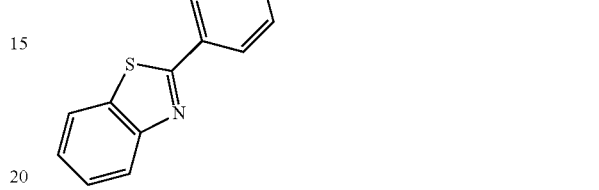
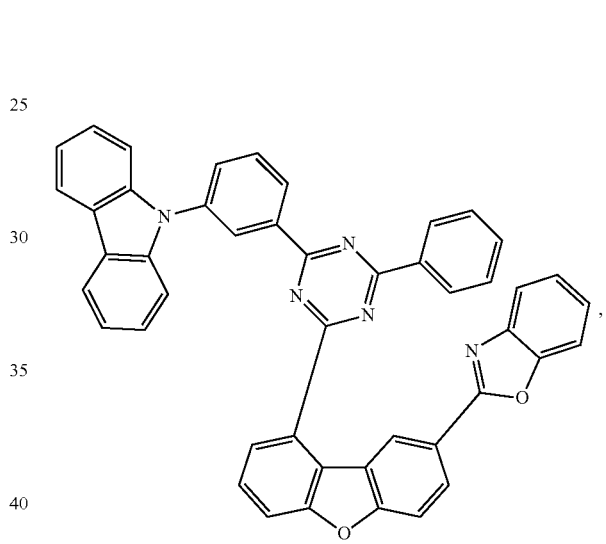
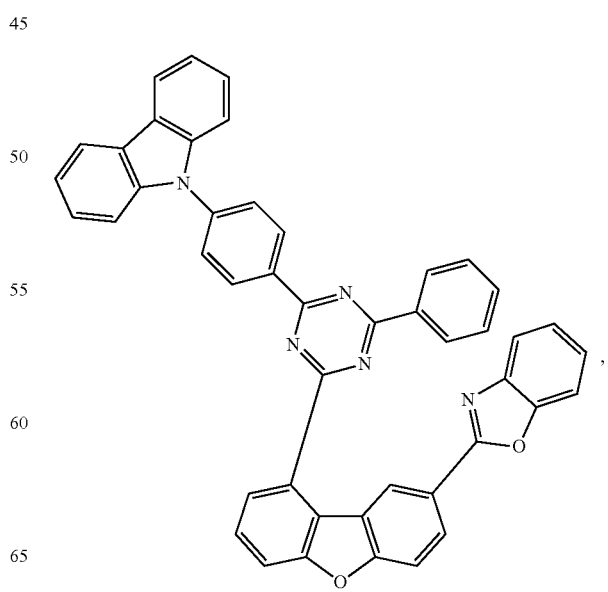

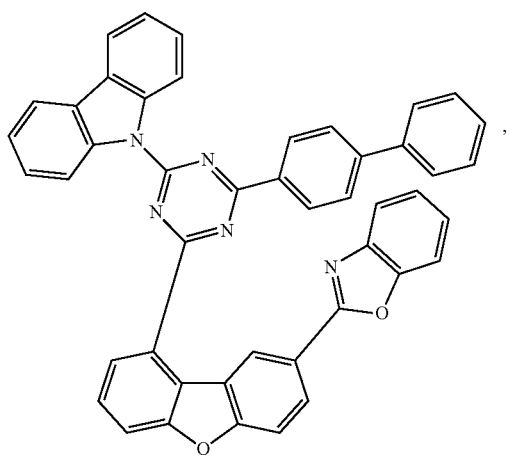
,
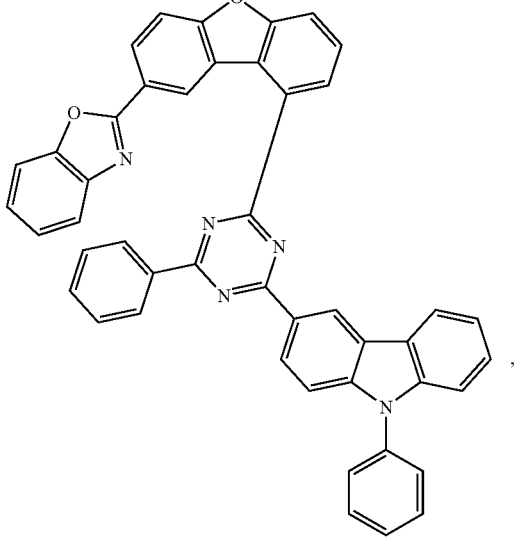
,
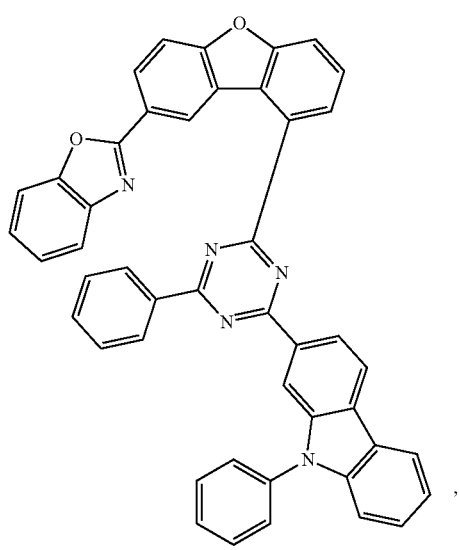
,
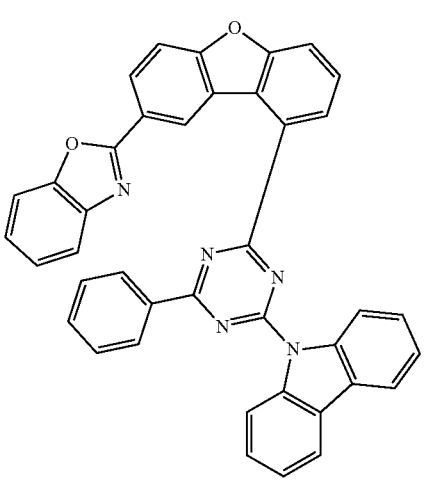
,
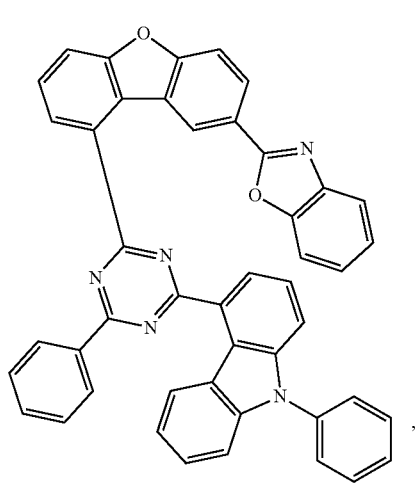
,
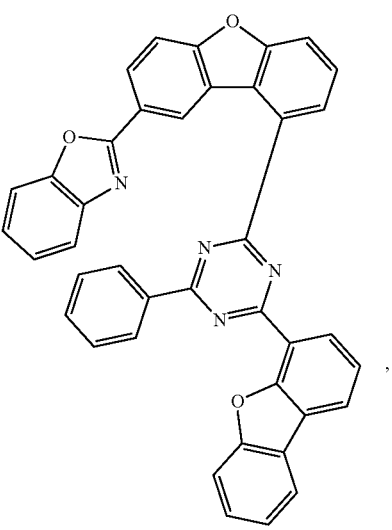
, -continued
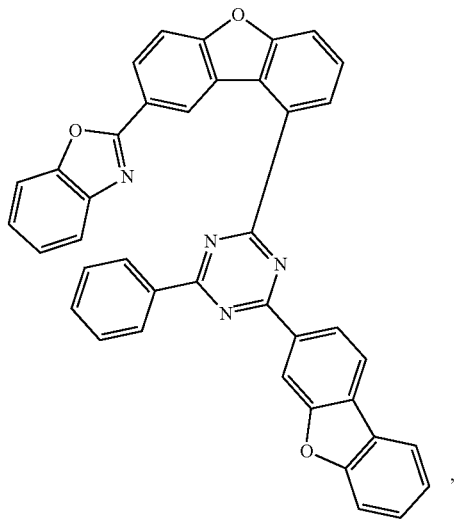
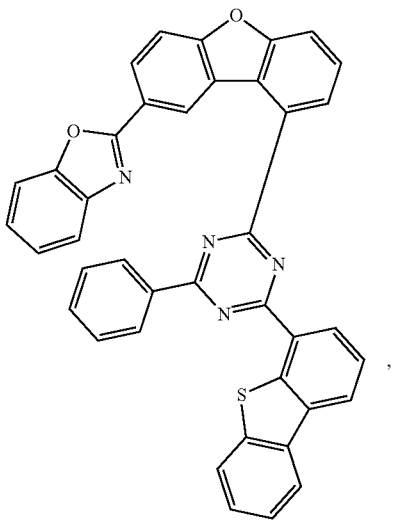
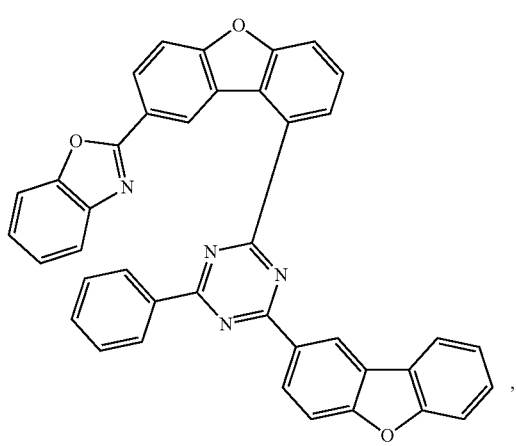
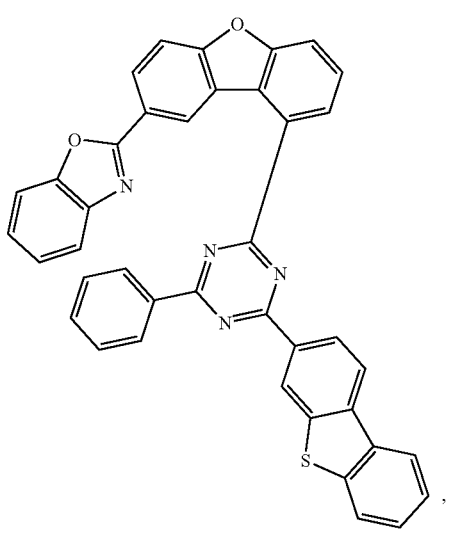
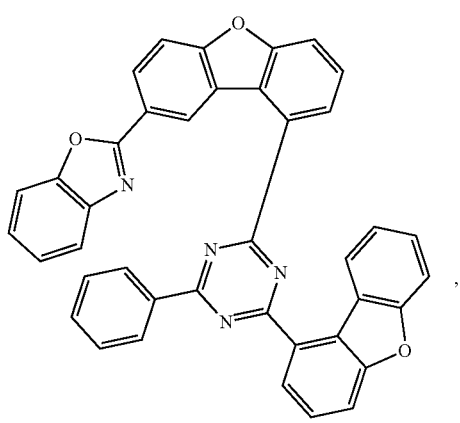
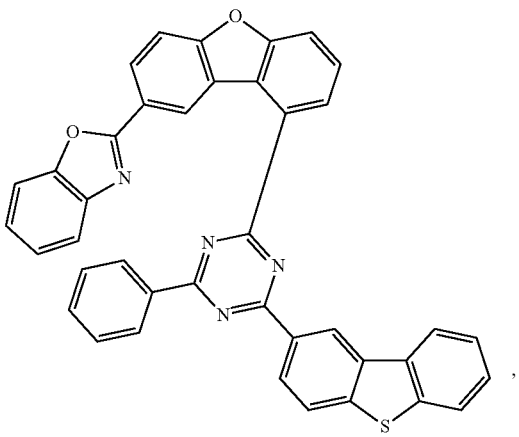

47
-continued
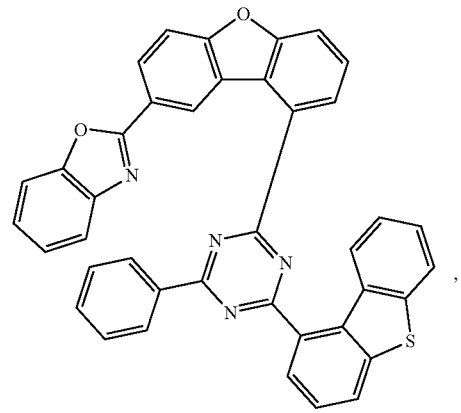
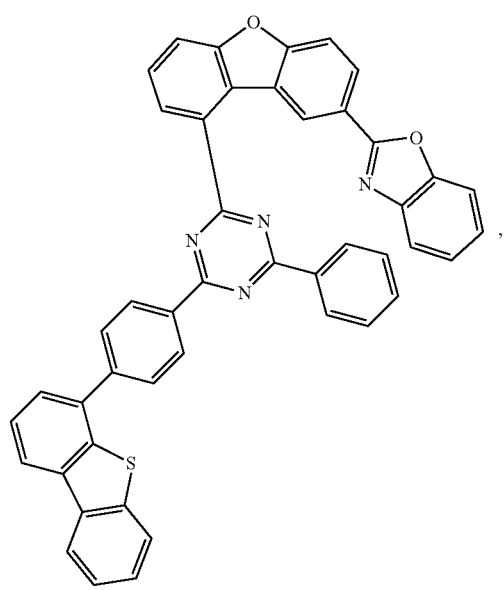
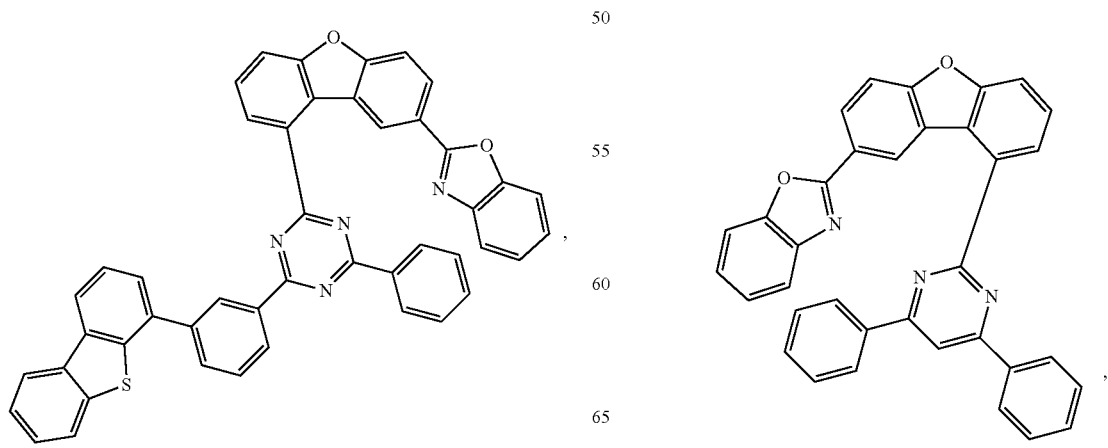
48
-continued
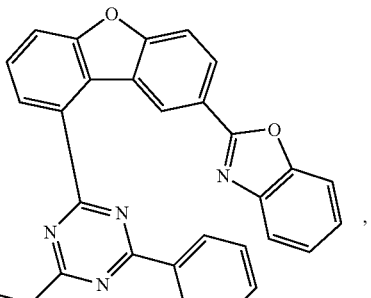
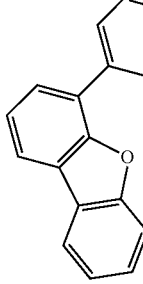
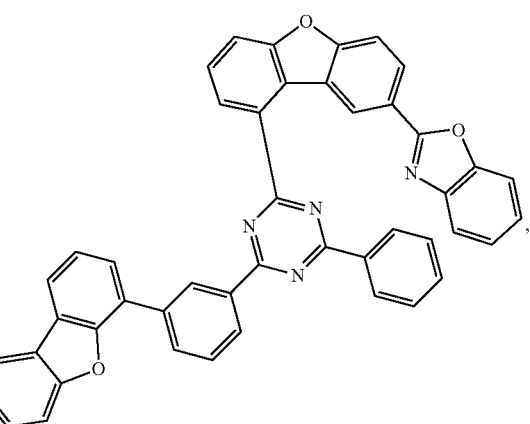
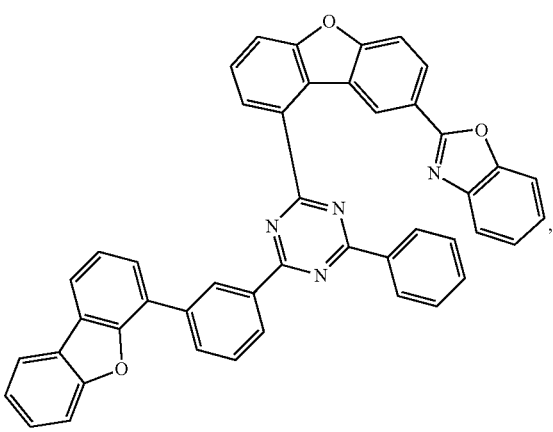

49
-continued
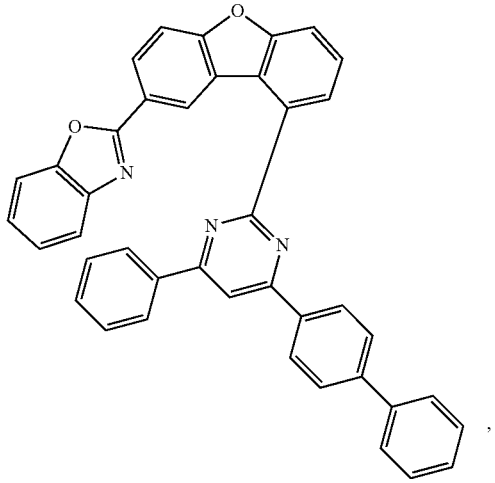
,
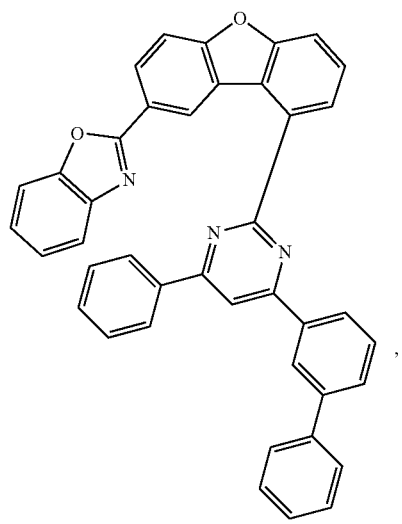
,
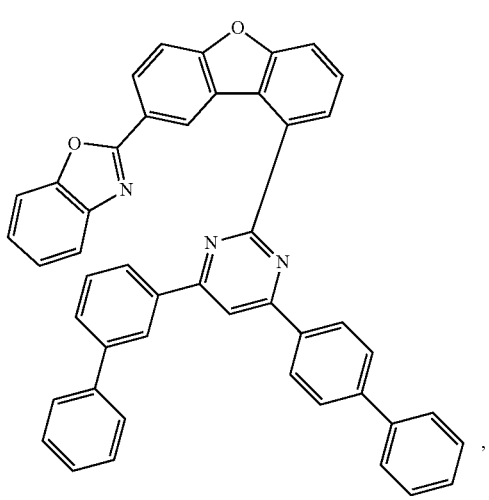
,
50
-continued
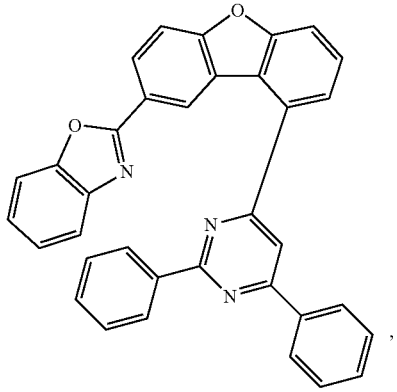
,
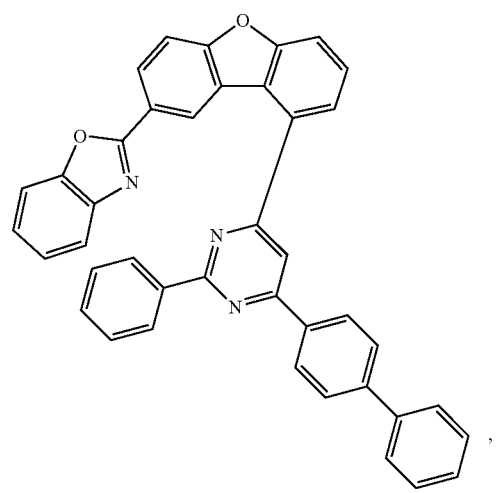
,
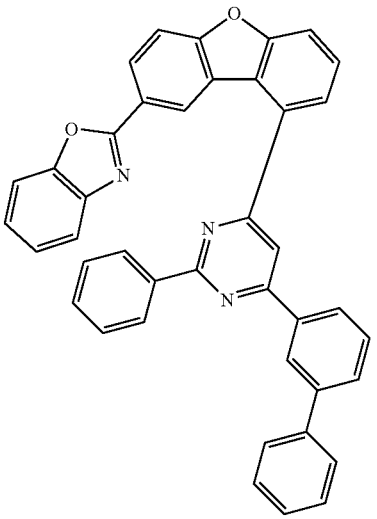
, 51
-continued
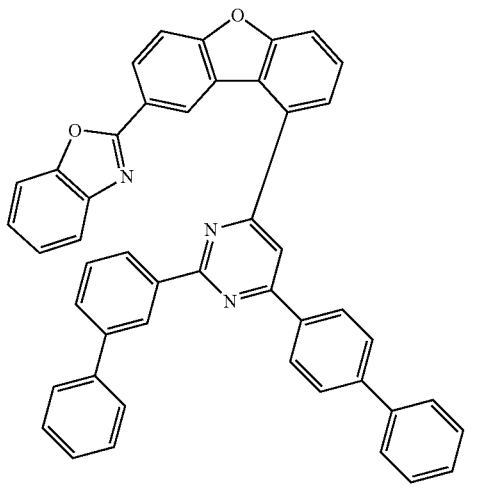
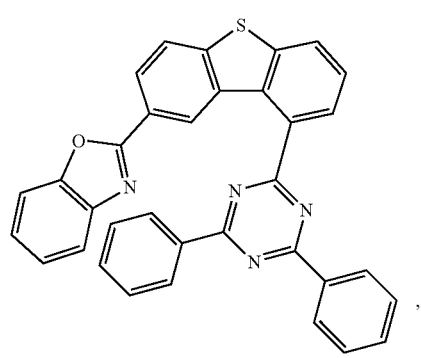
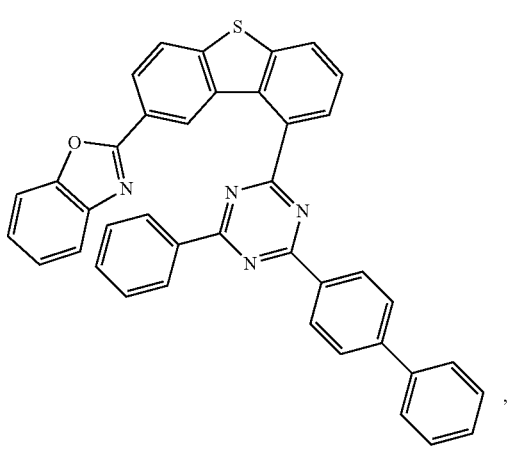
52
-continued
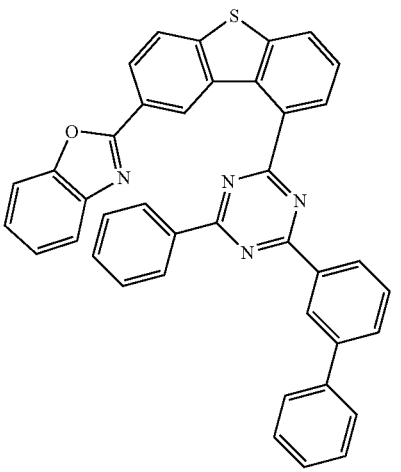
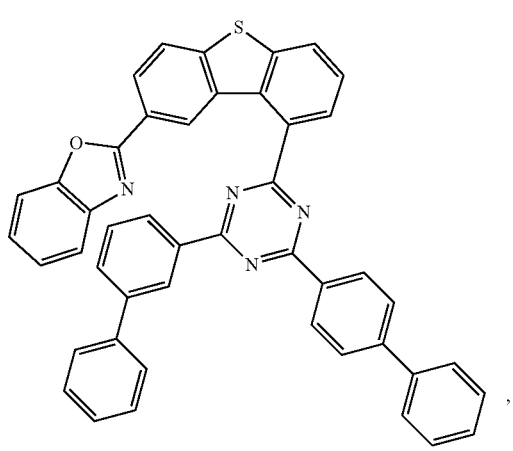
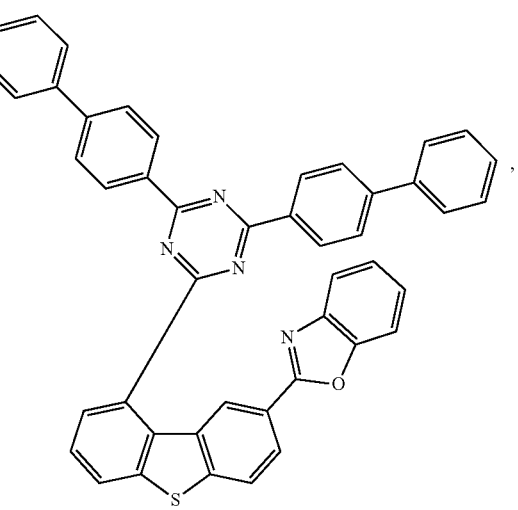

53
-continued
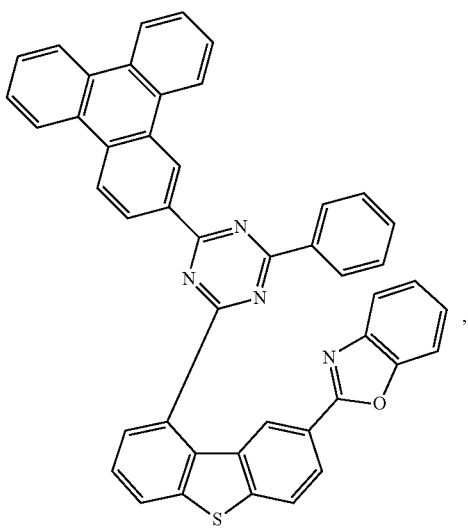
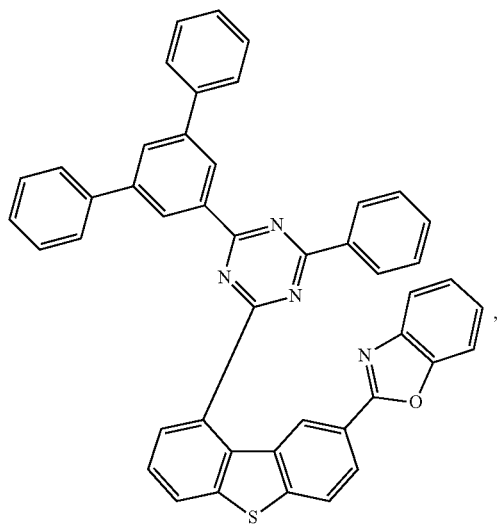
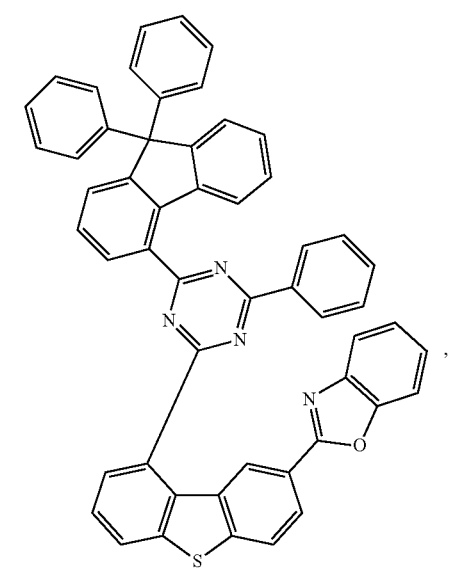
54
-continued
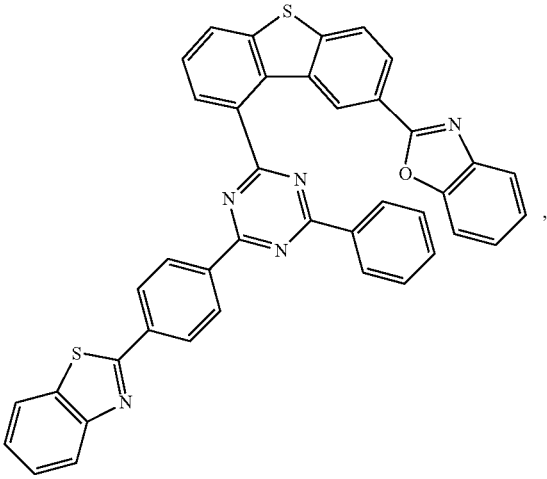
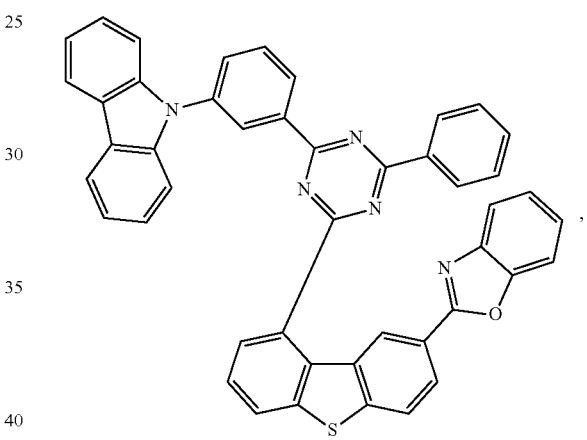
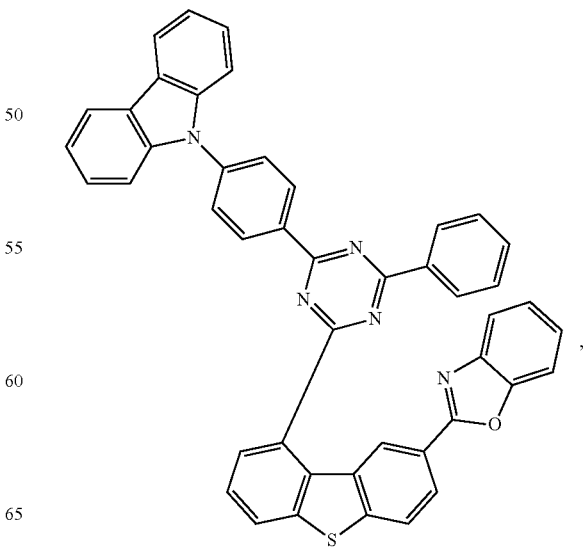

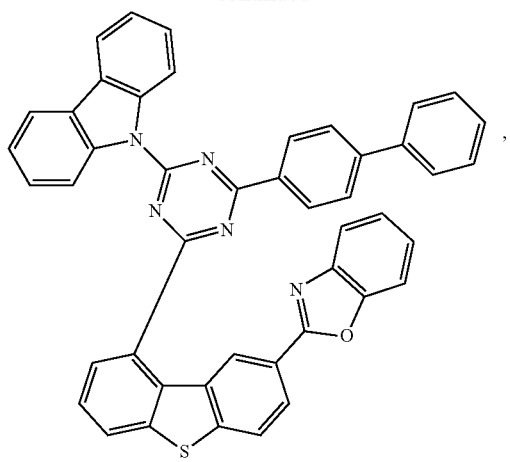
,
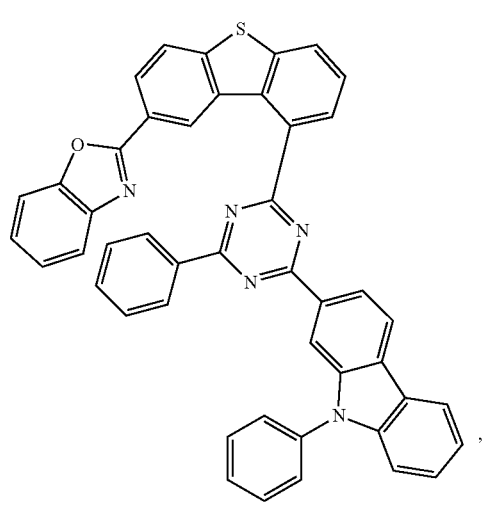
,
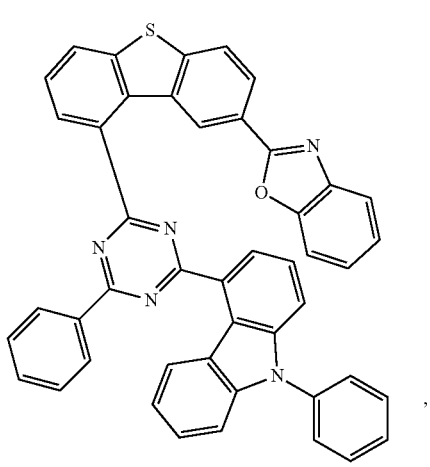
,
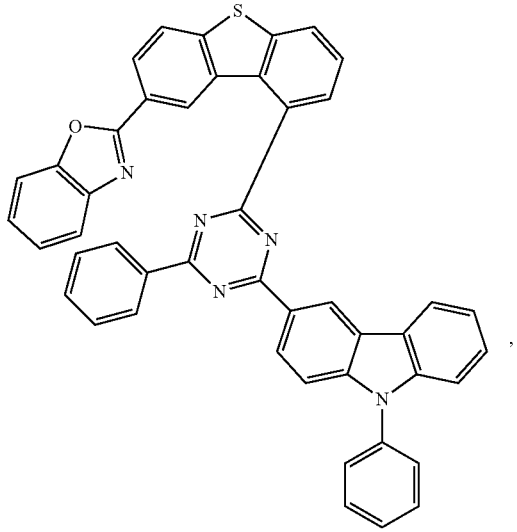
,
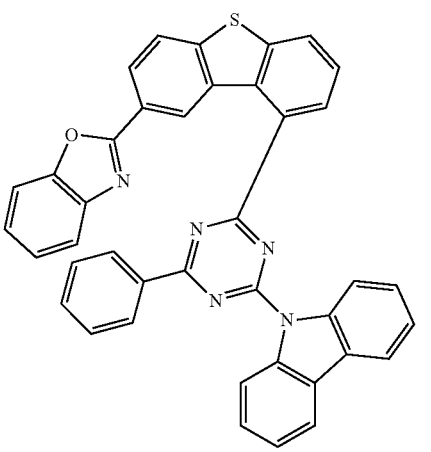
,
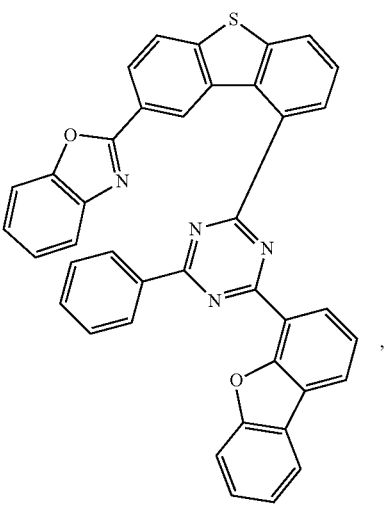
, 57
-continued
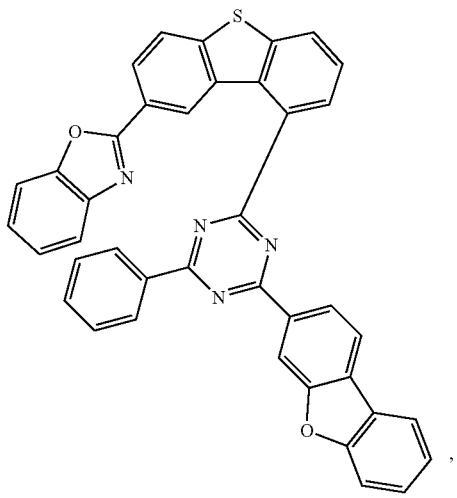
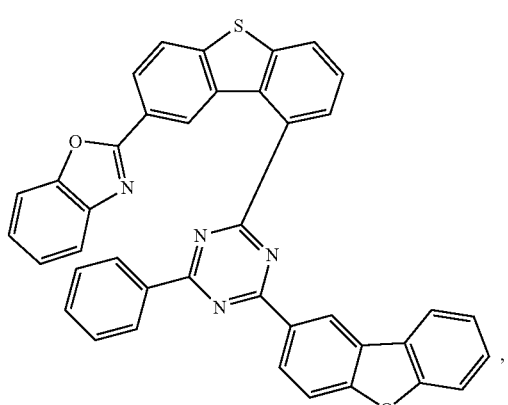
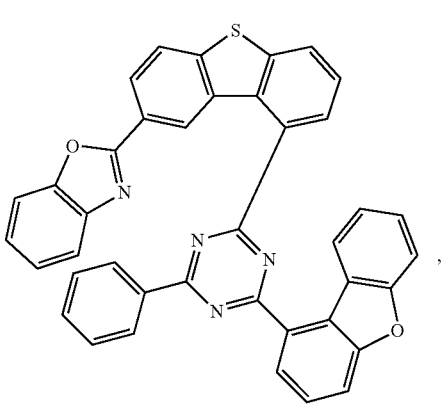
58
-continued
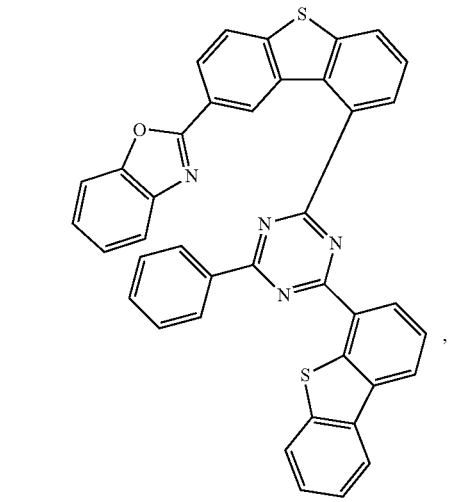
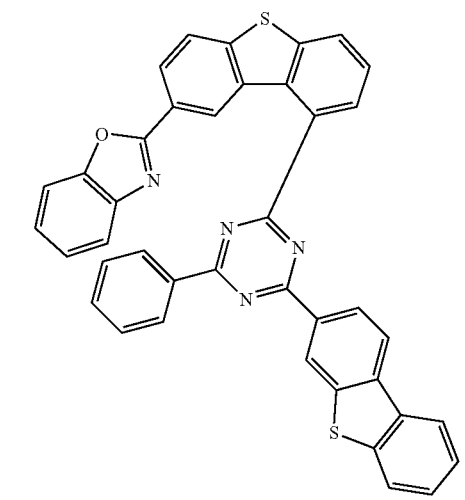
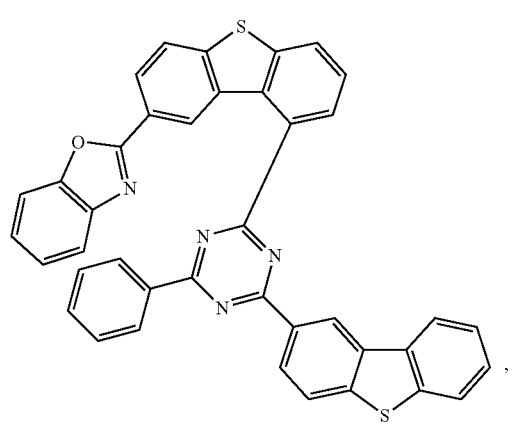

59
-continued
60
-continued
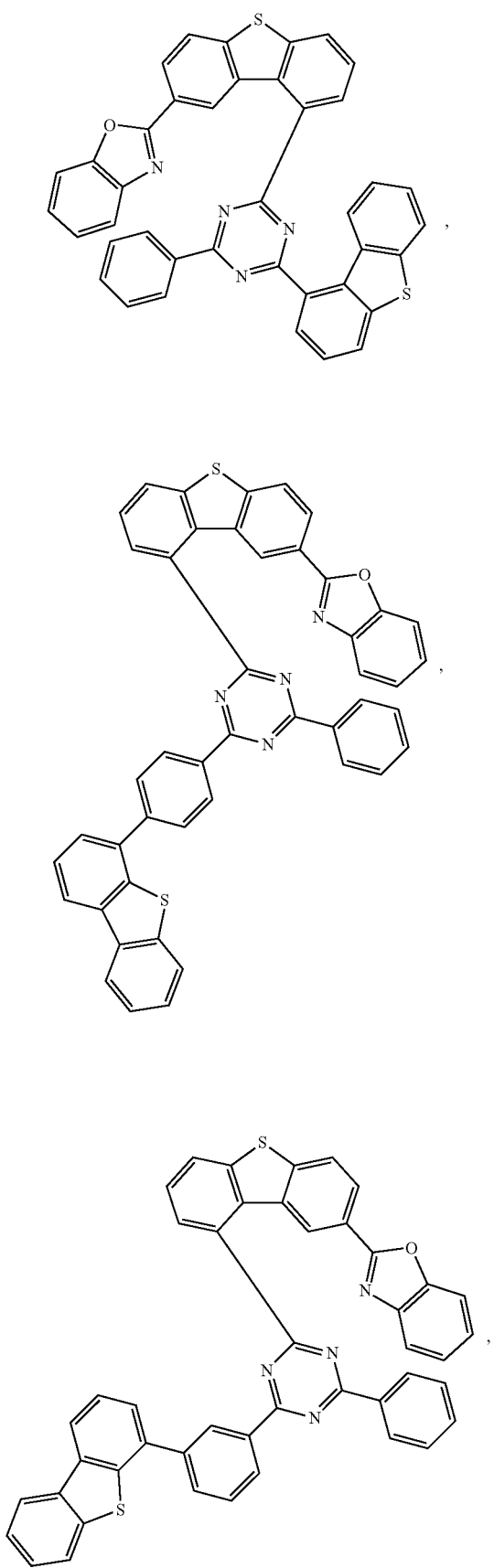
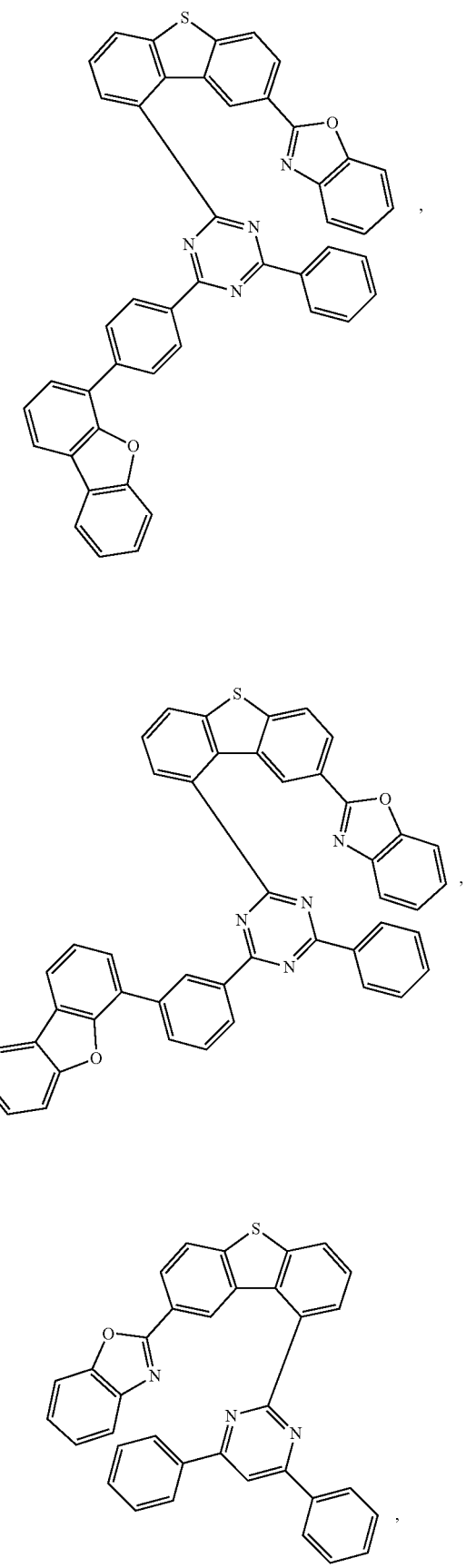

61
-continued
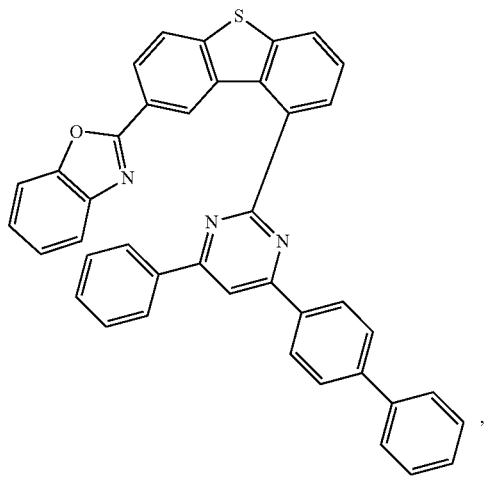
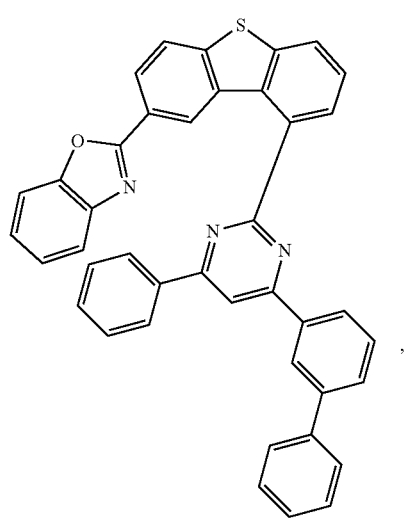
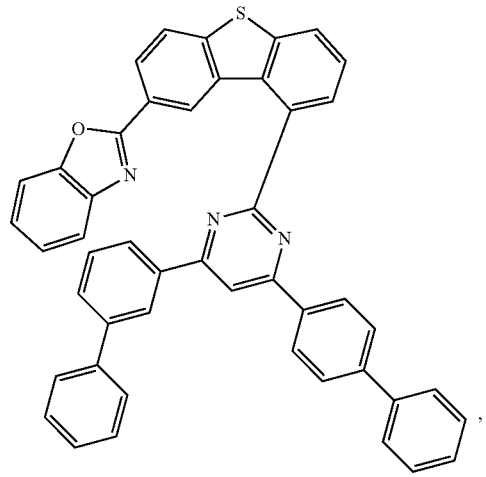
62
-continued
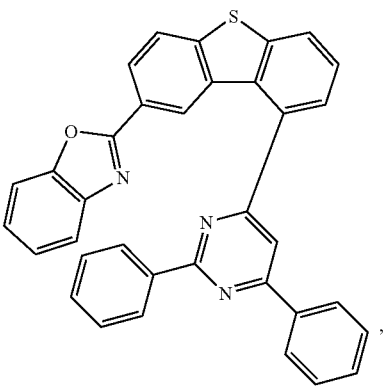
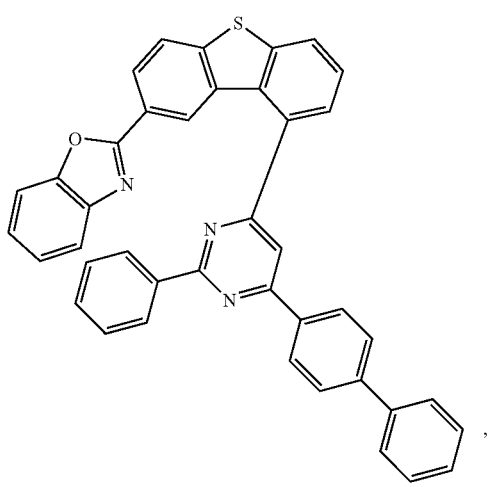
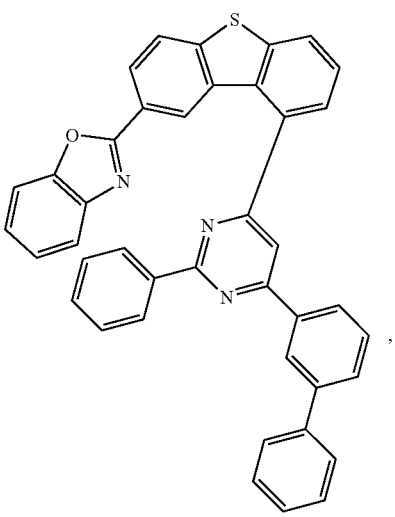

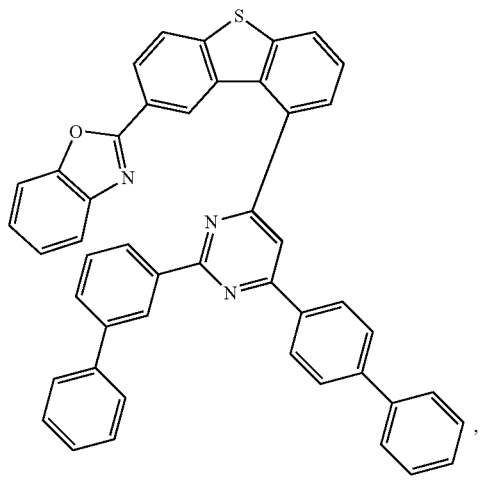
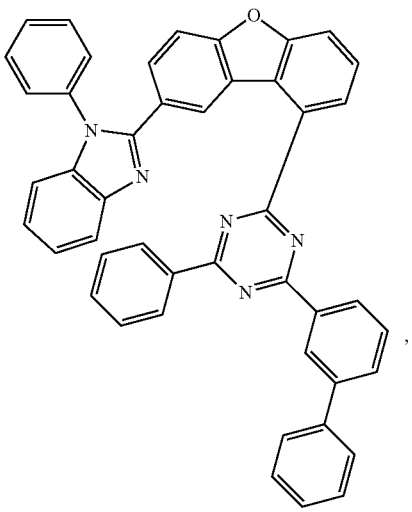
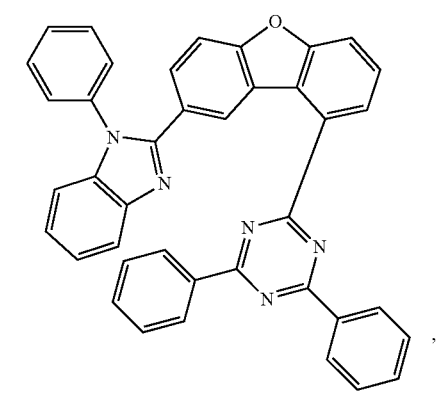
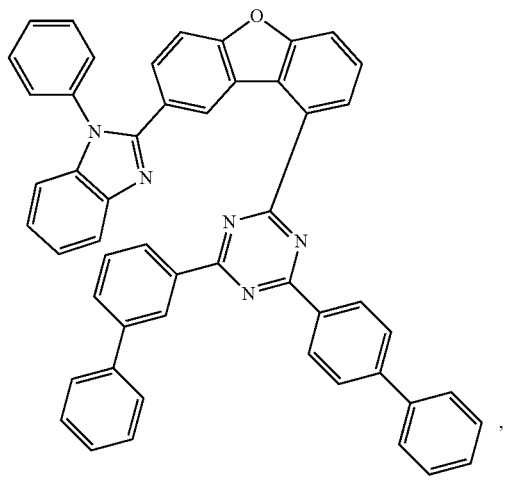
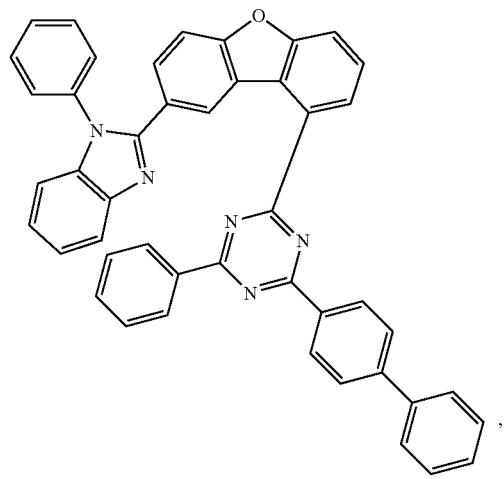
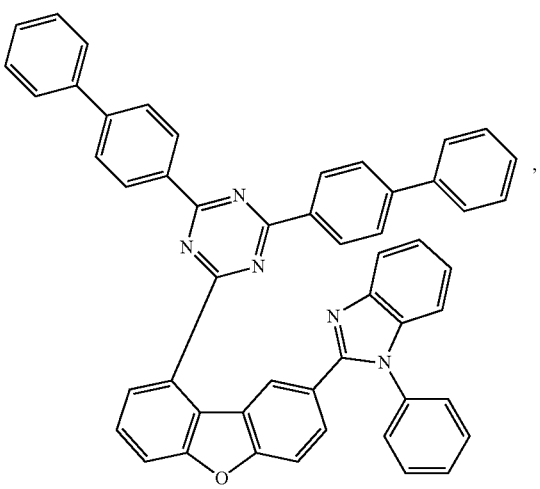

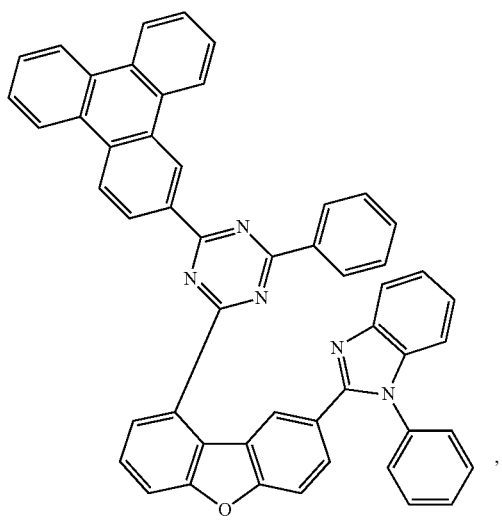
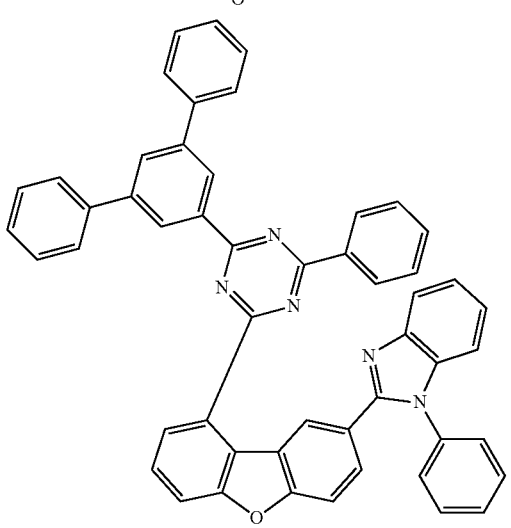
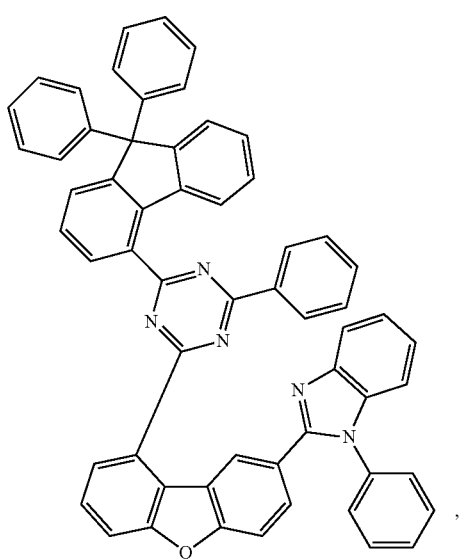
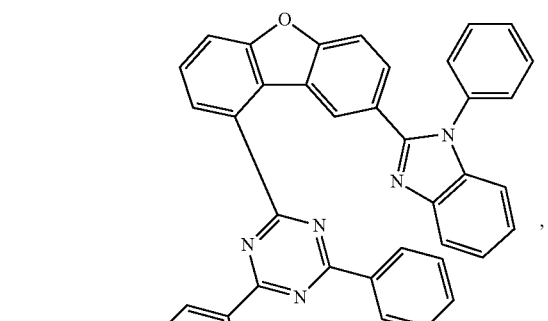
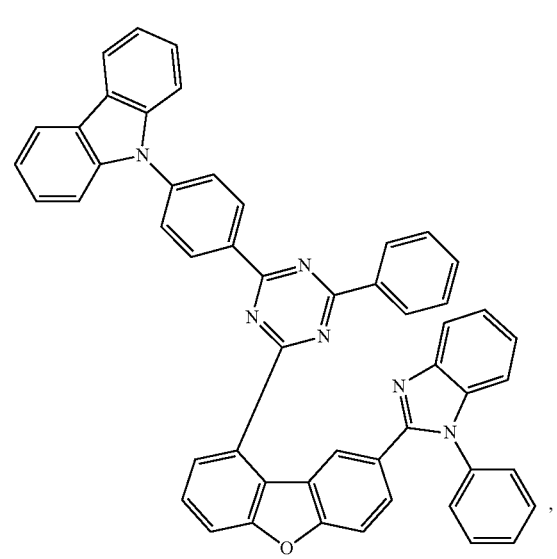

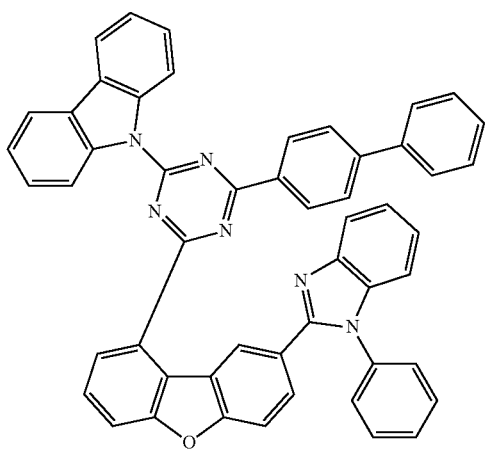
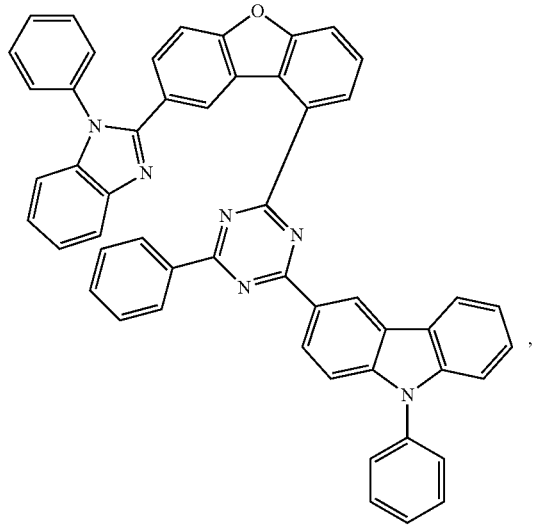
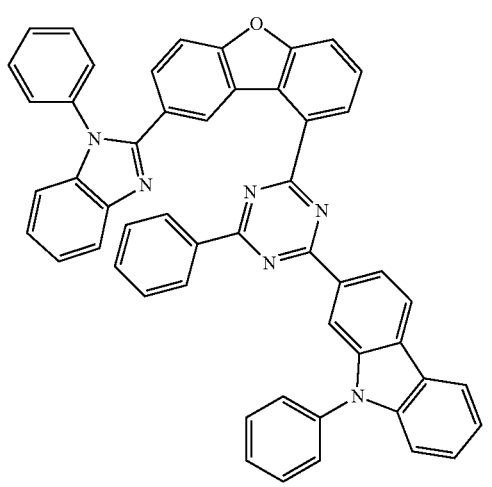
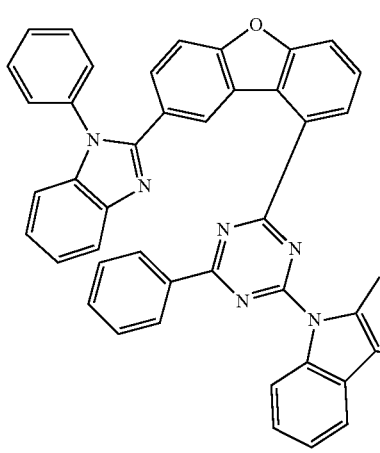
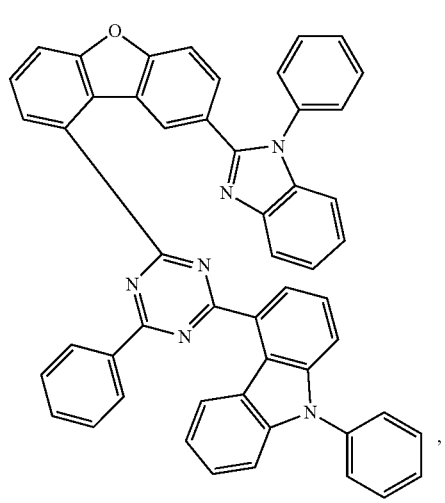
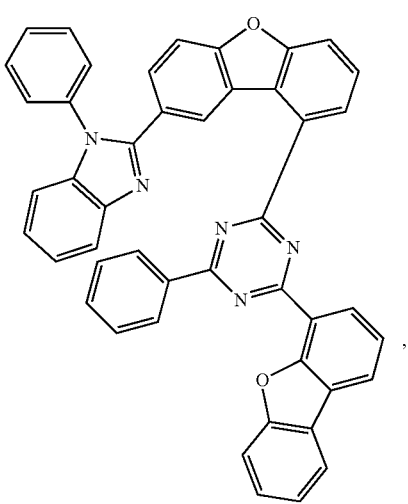

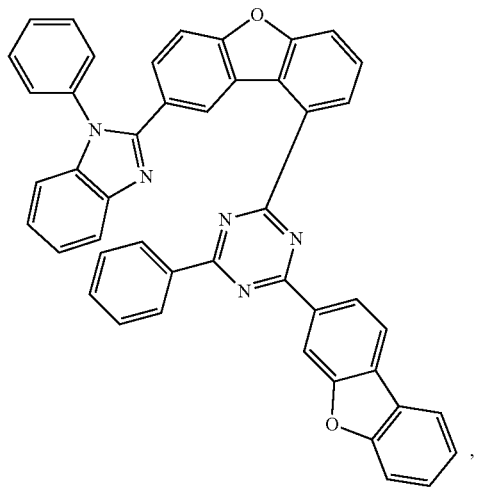
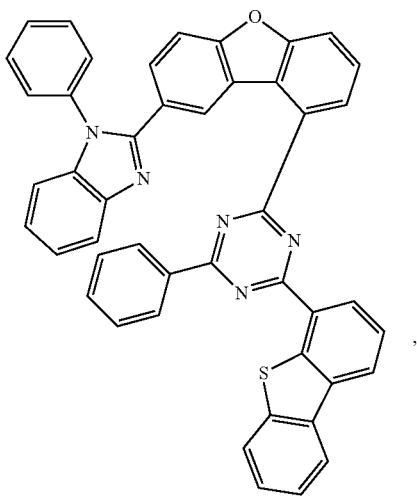
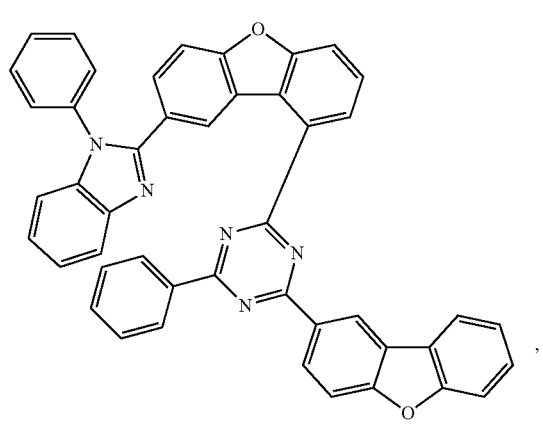
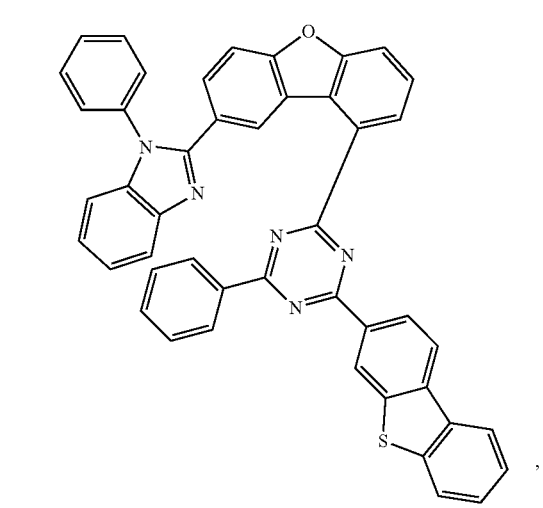
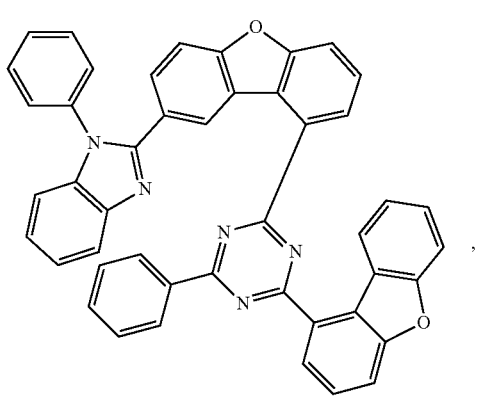
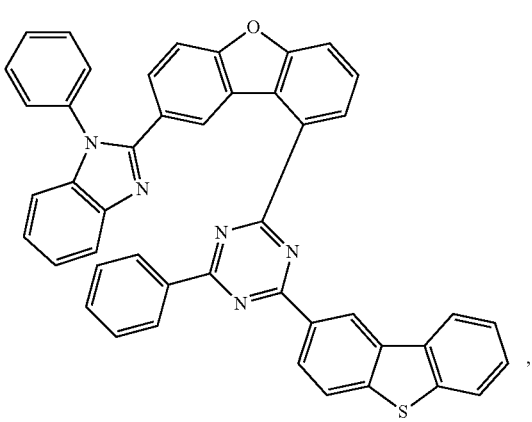

71
-continued
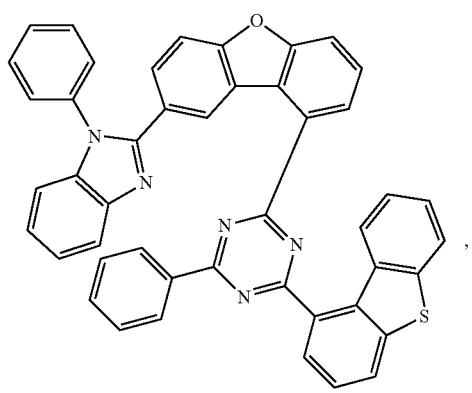
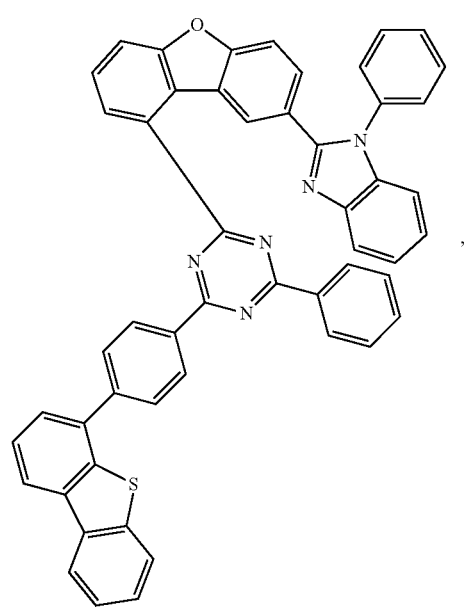
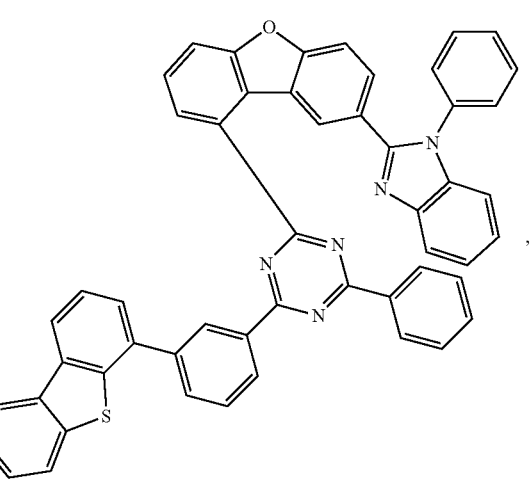
72
-continued
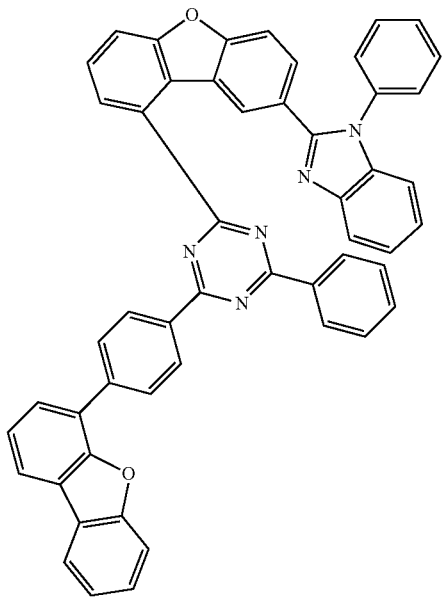
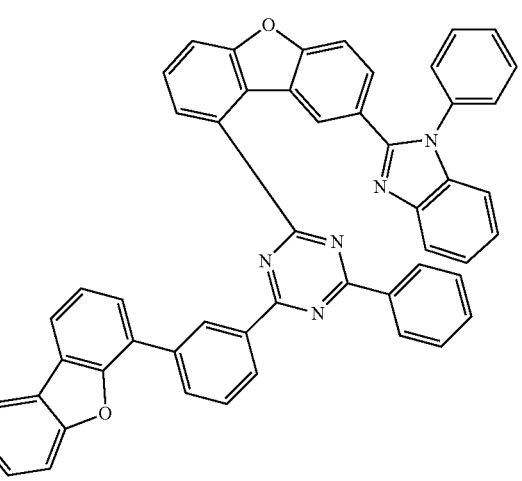
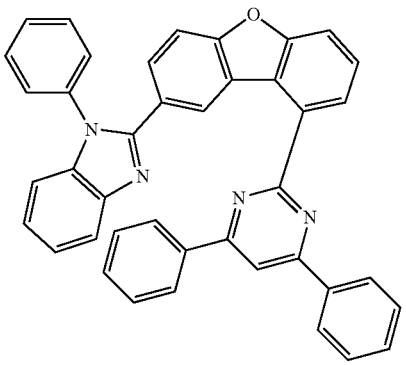

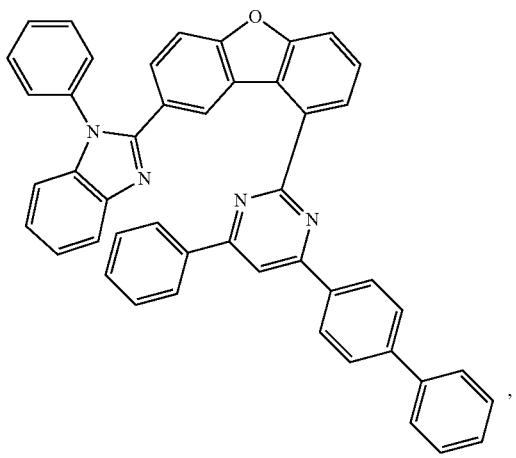
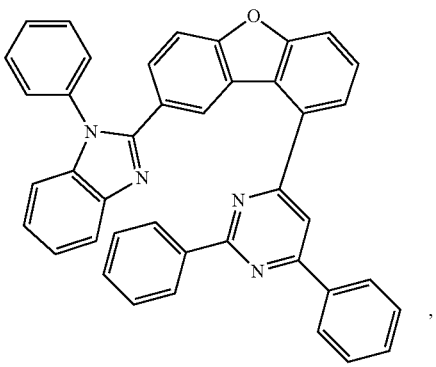
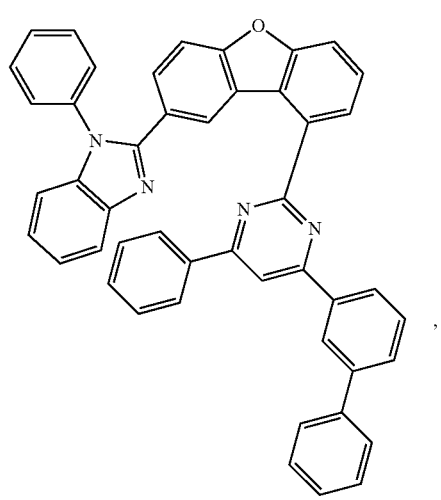
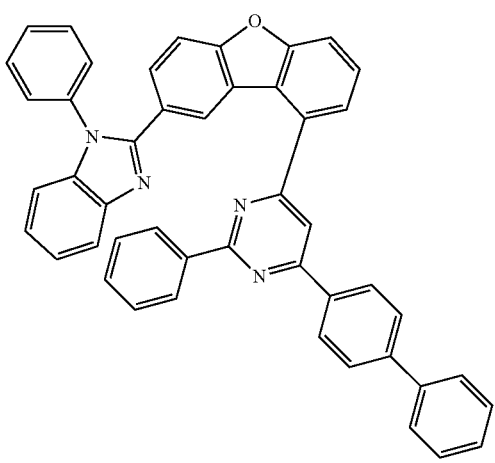
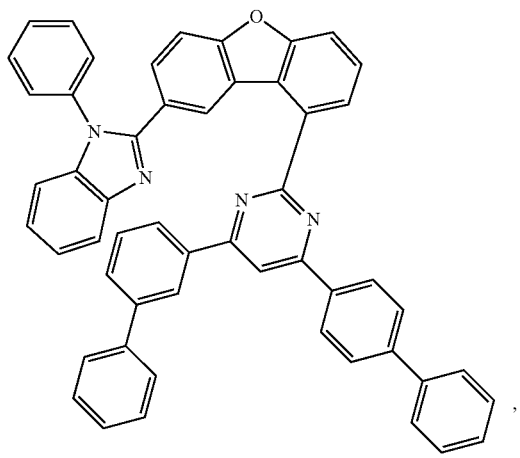
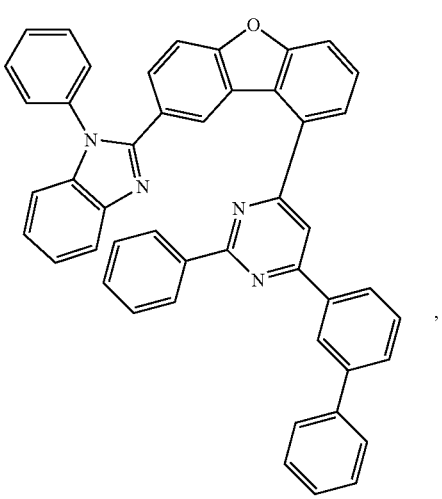

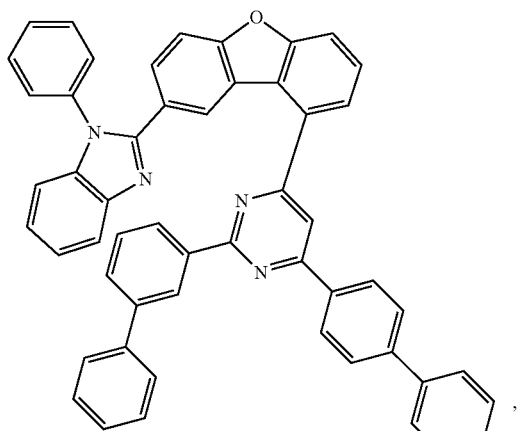,
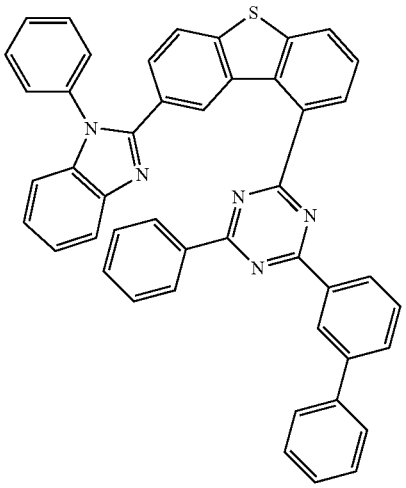,
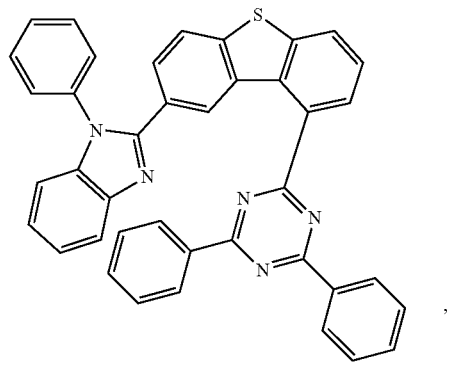,
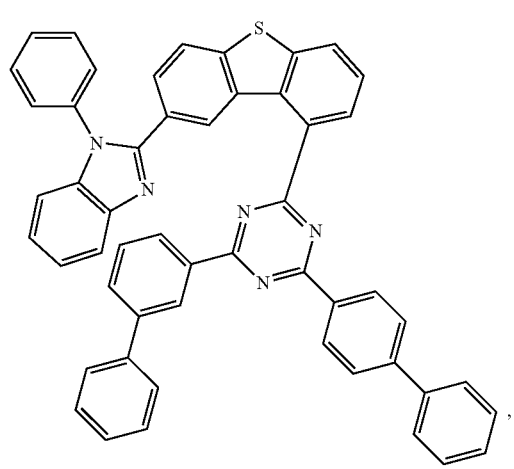,
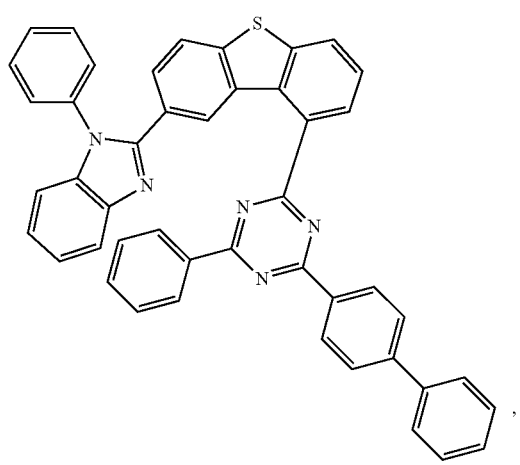,
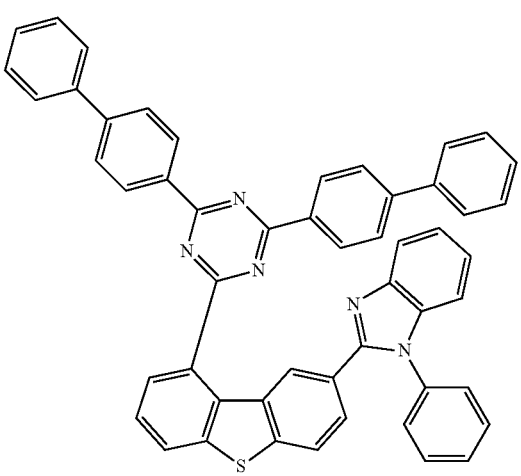,

77
-continued
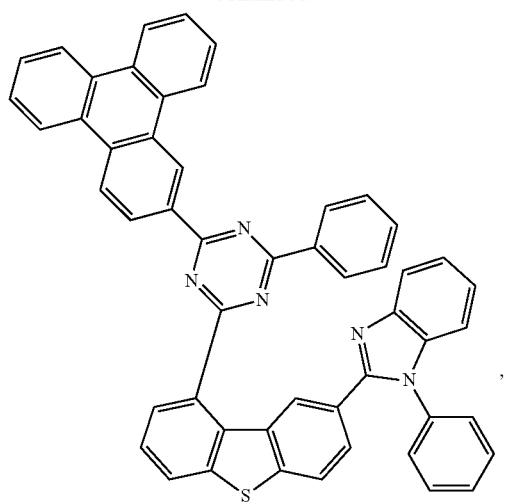
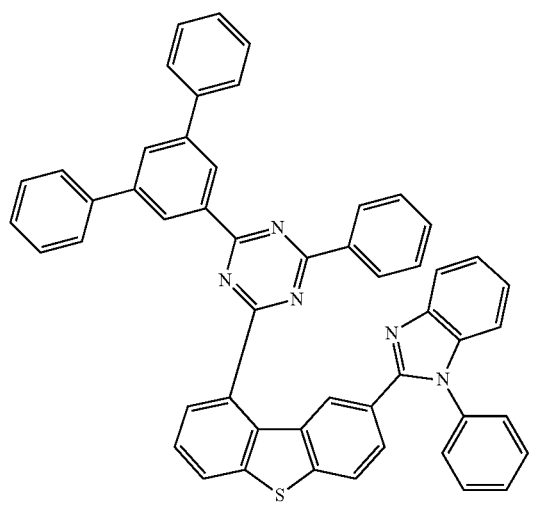
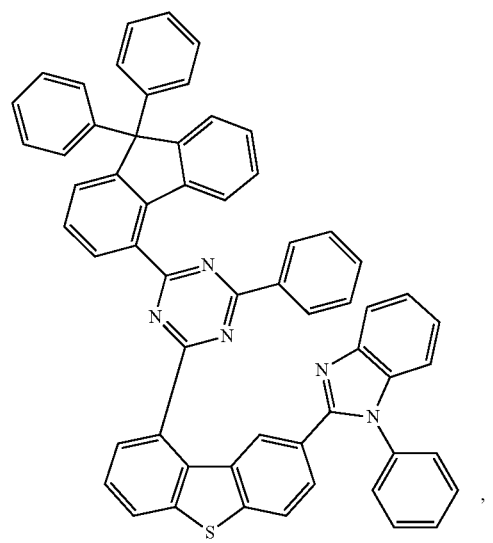
78
-continued
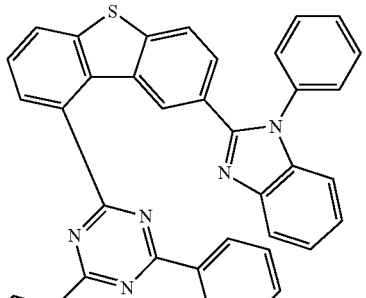
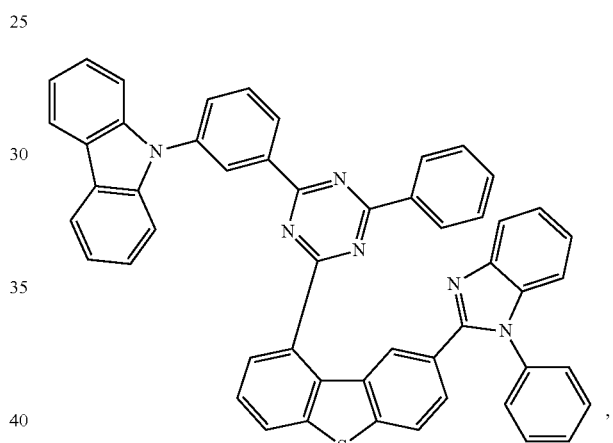
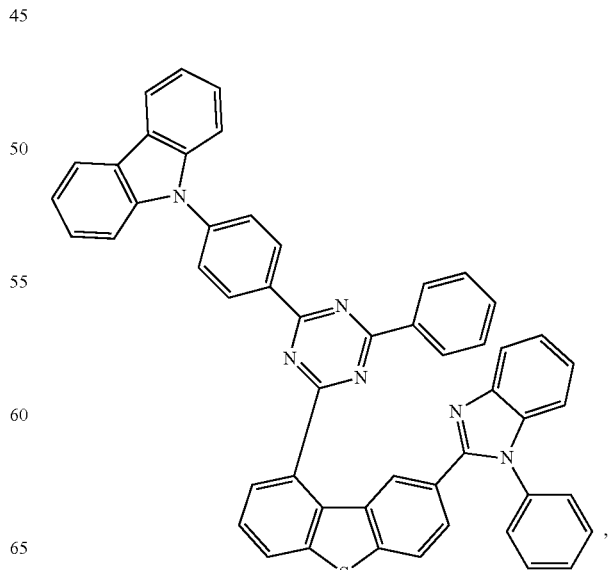

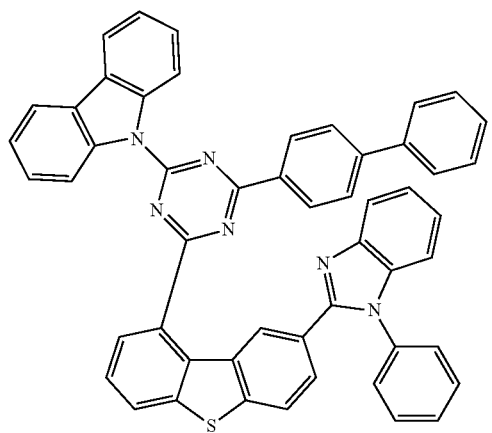
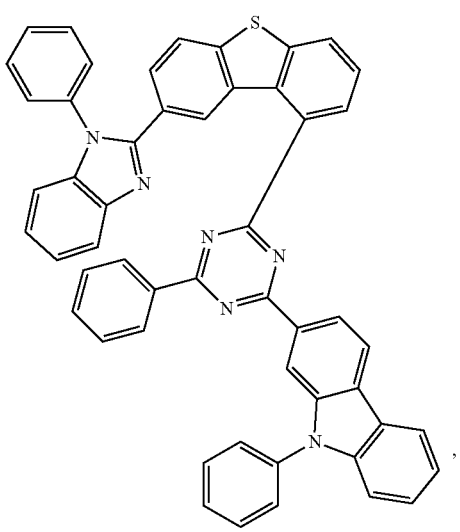
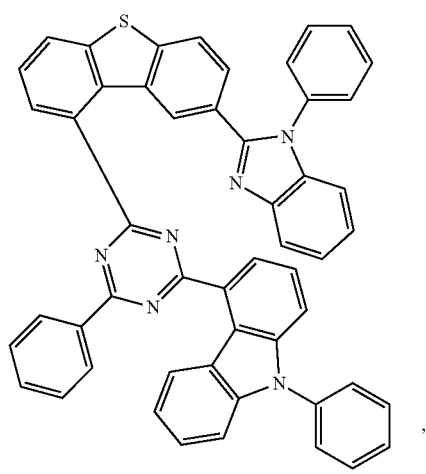
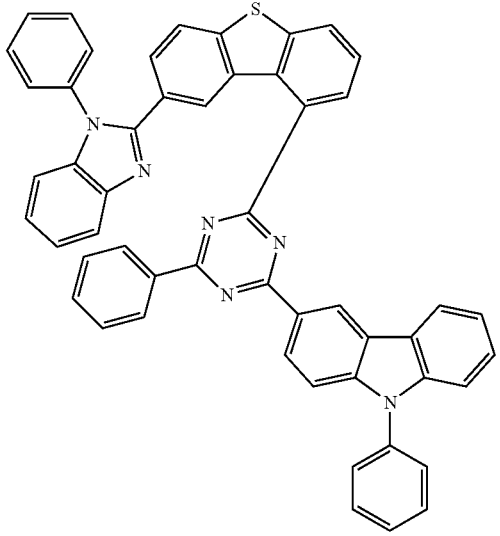
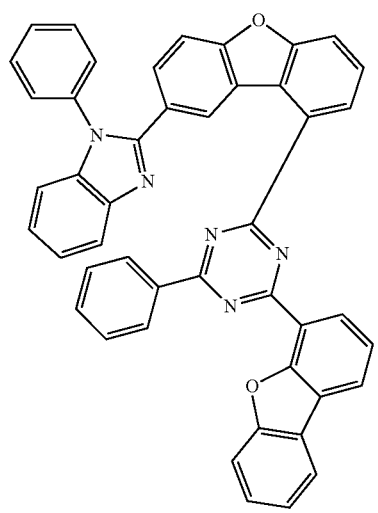

81
-continued
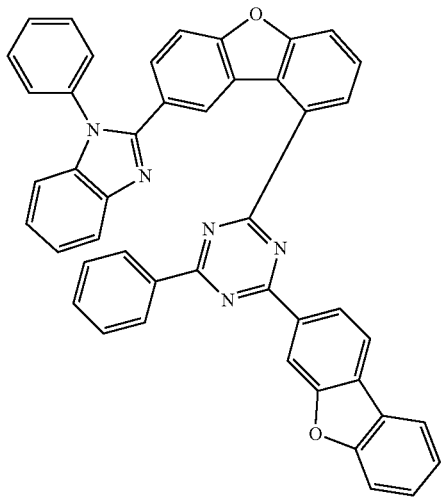
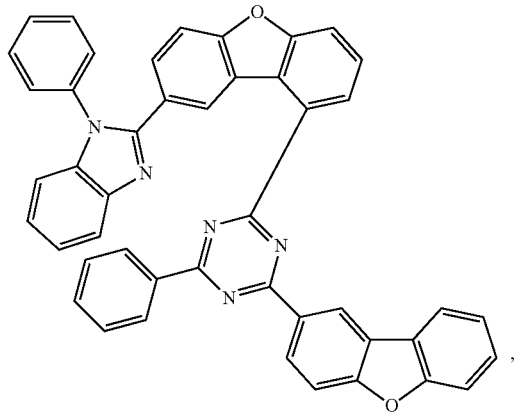
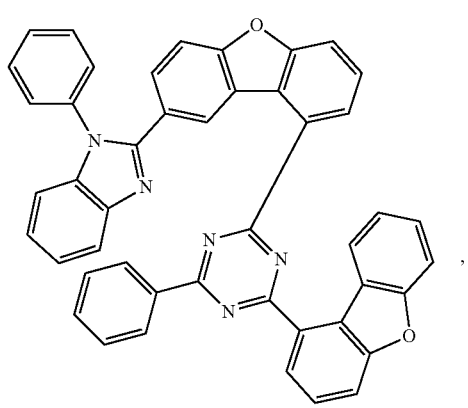
82
-continued
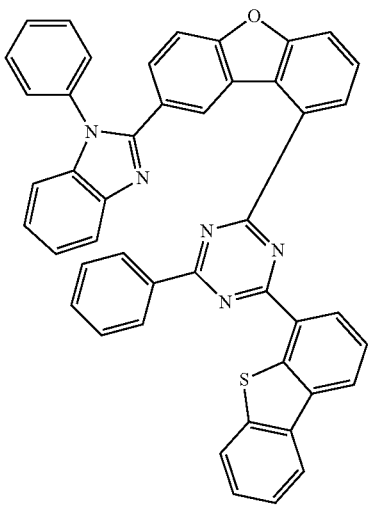
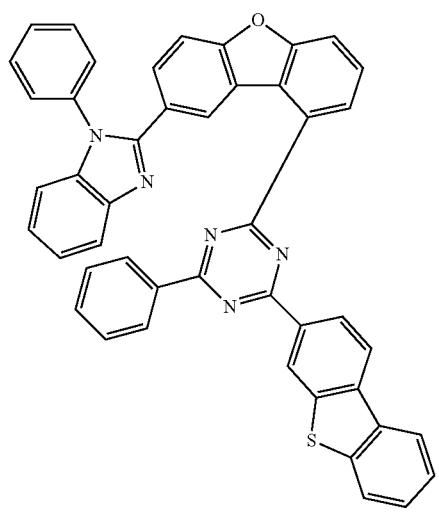
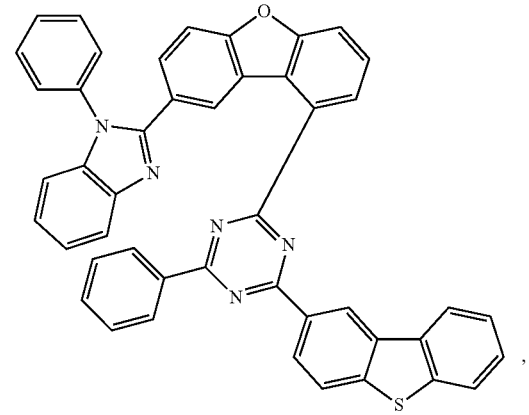

83
-continued
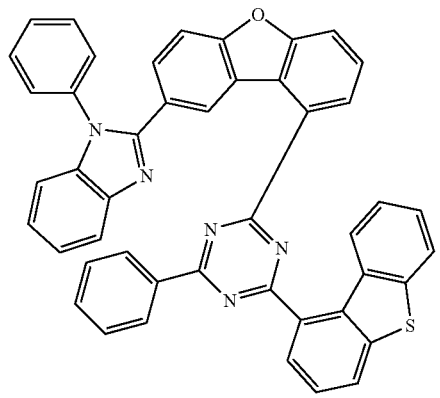
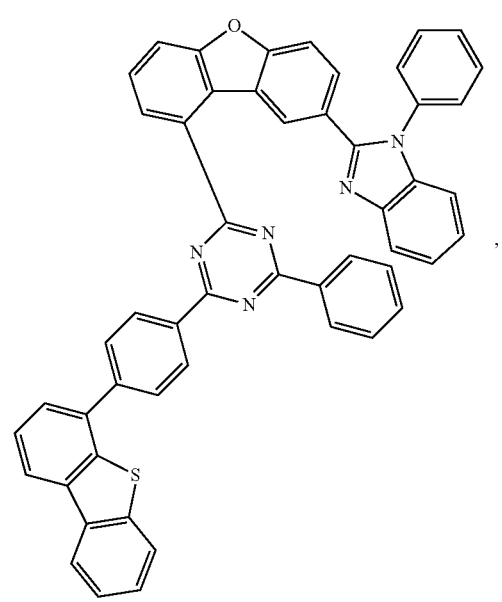
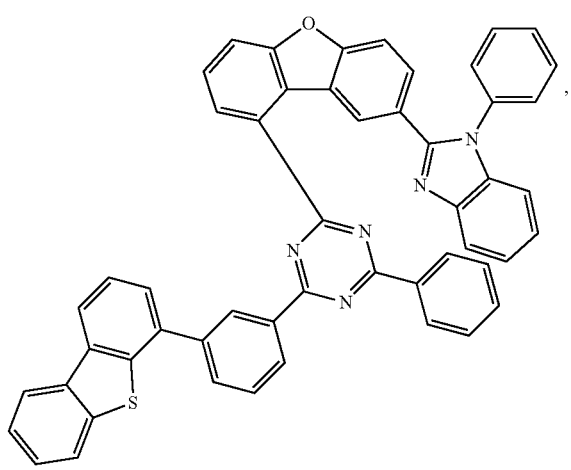
84
-continued
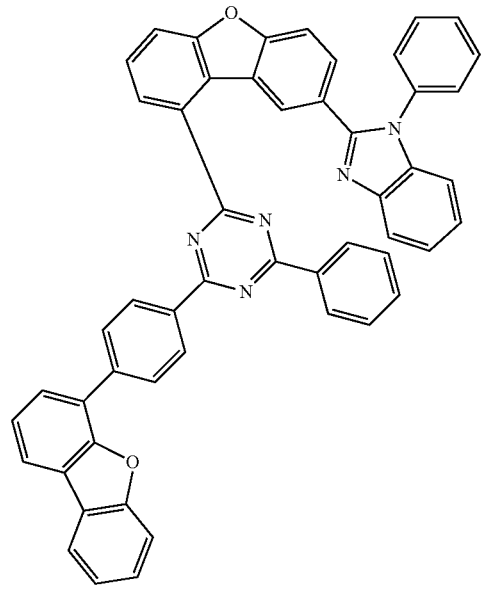
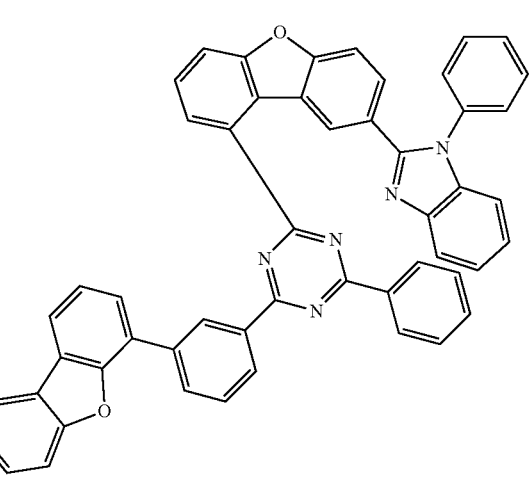
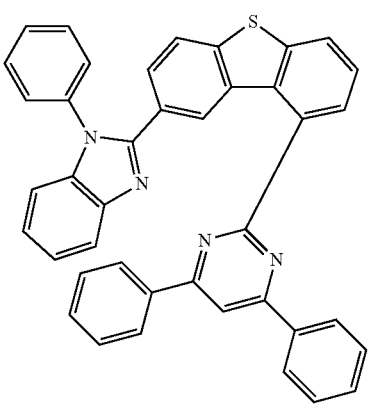

-continued
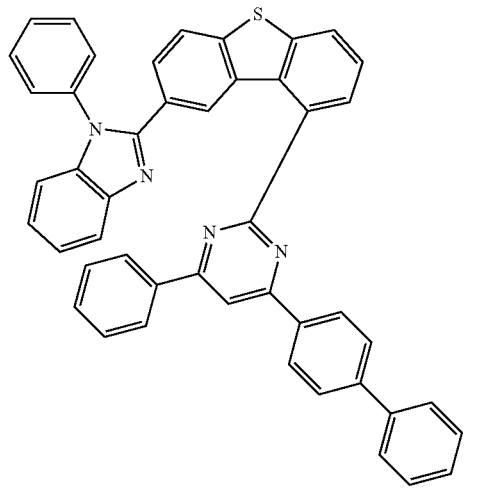
,
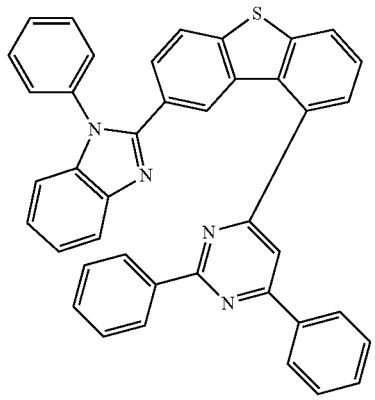
,
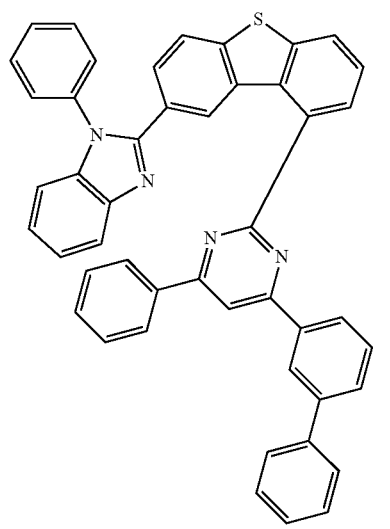
,
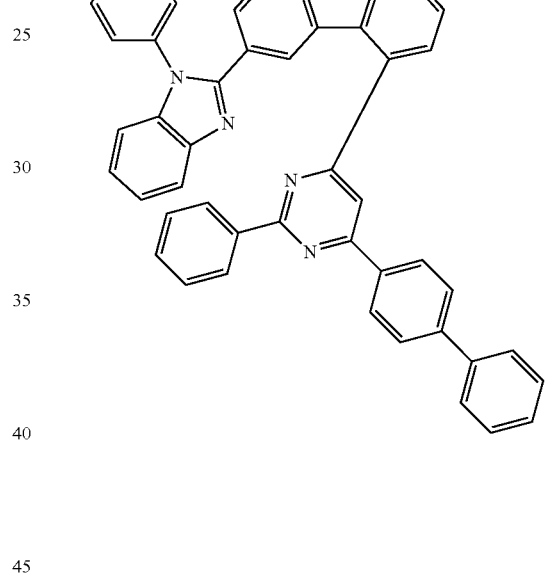
,
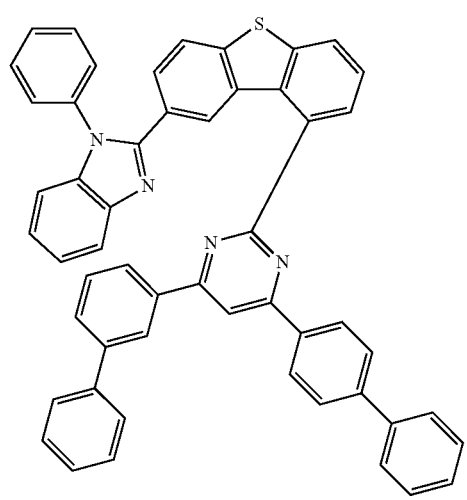
,
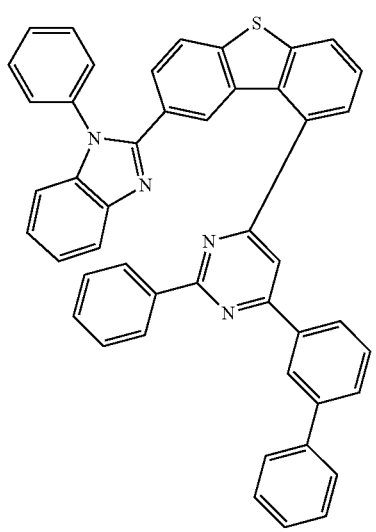
, 87
-continued
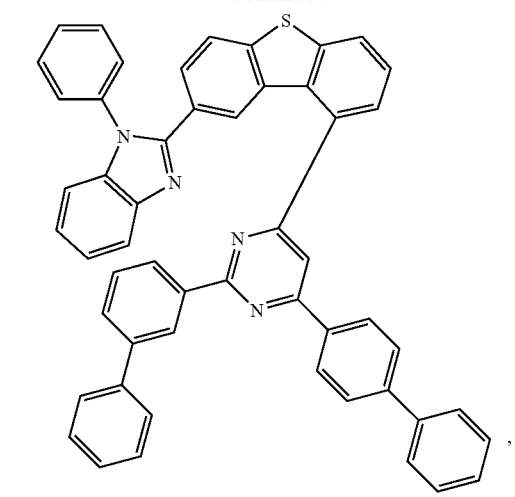
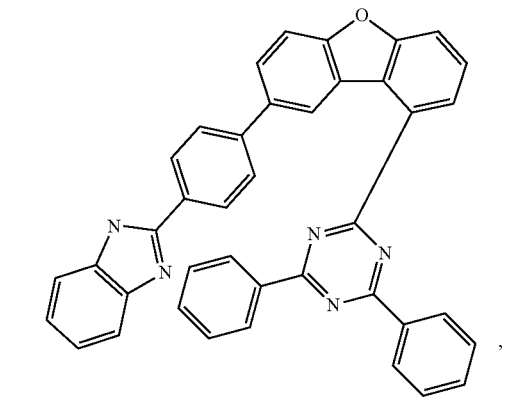
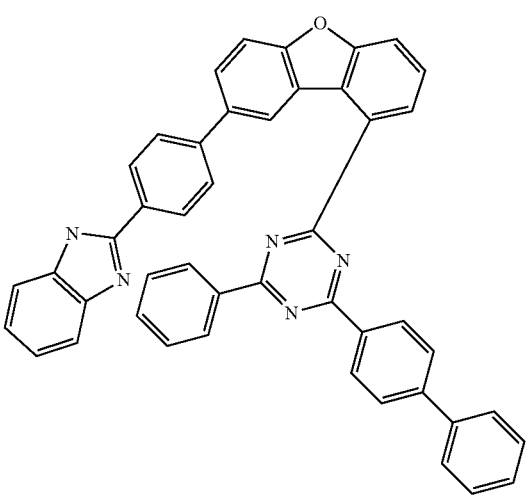
88
-continued
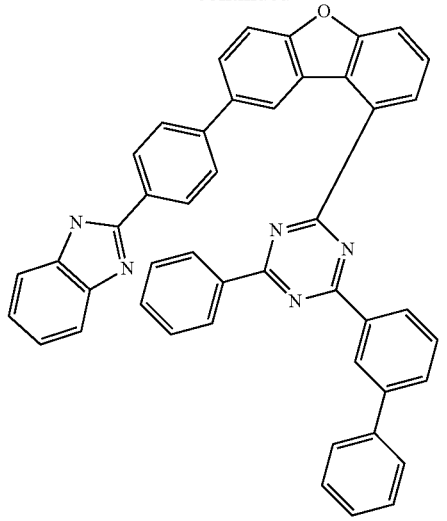
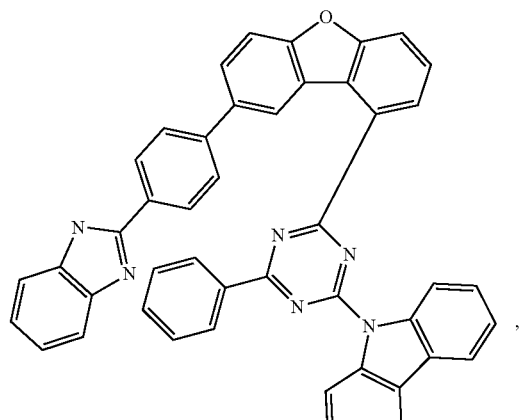
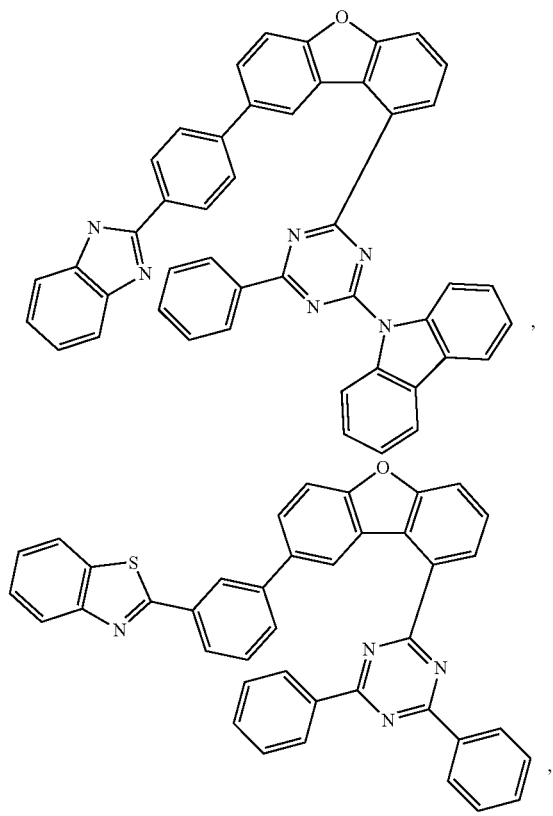

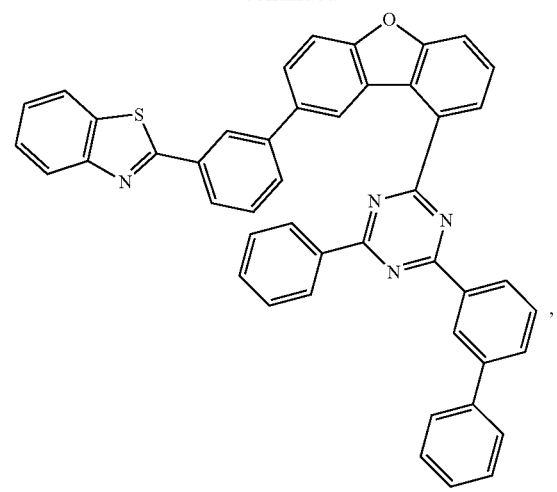
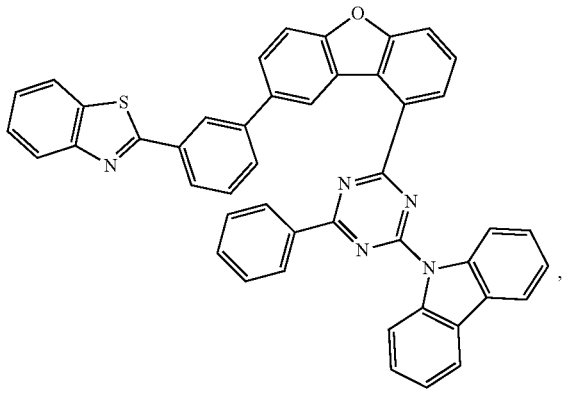
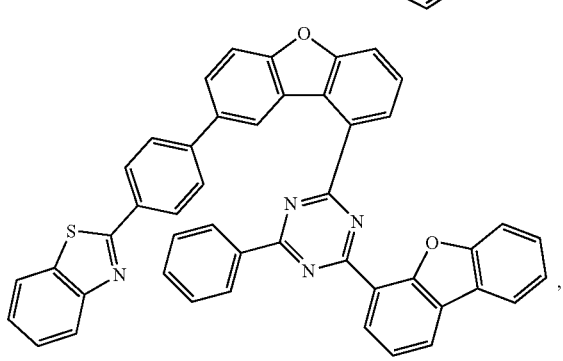
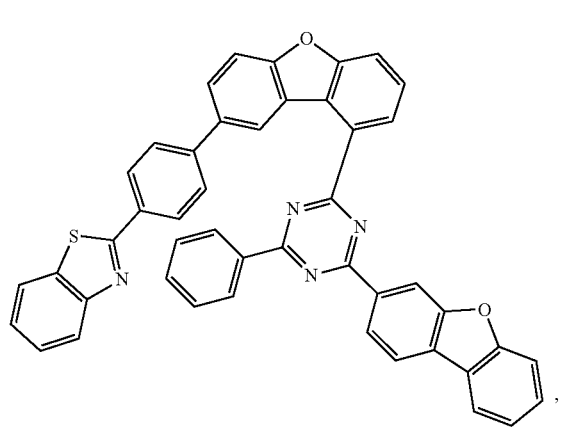
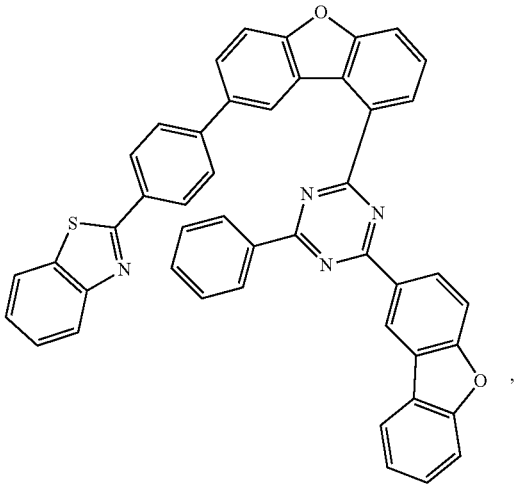
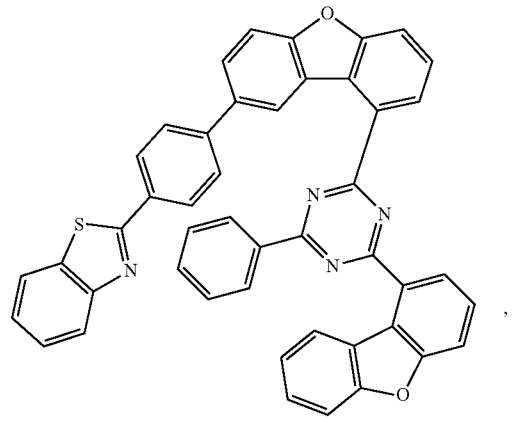
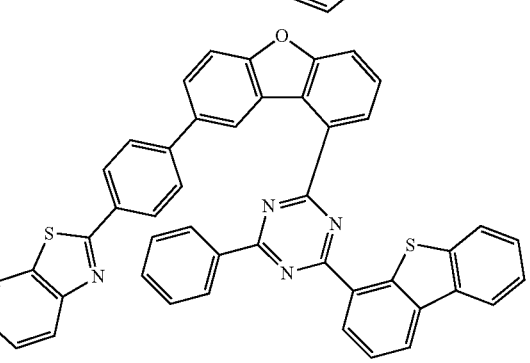
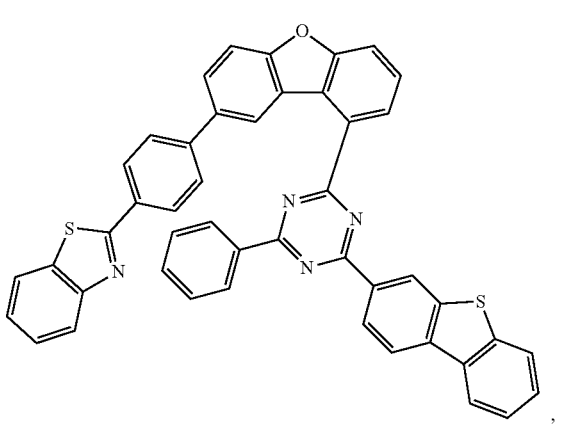

91
-continued
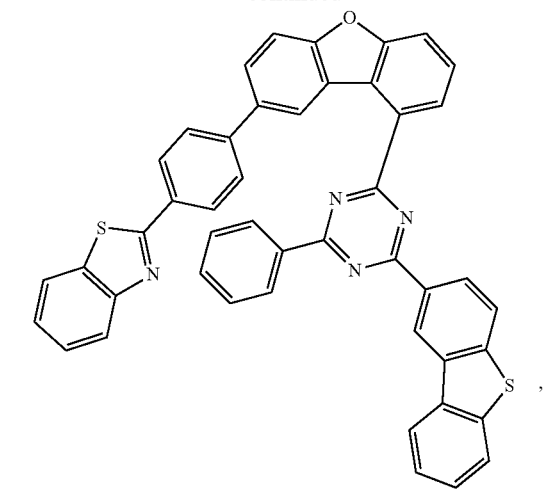
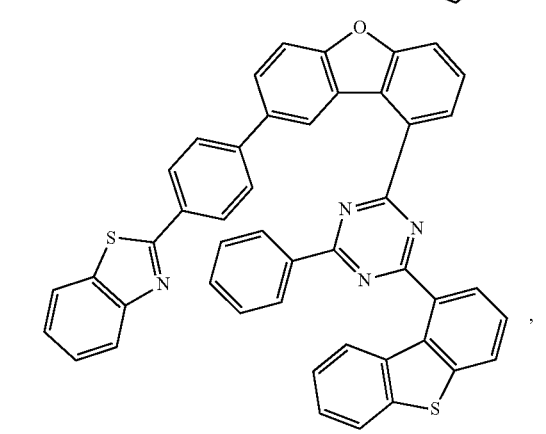
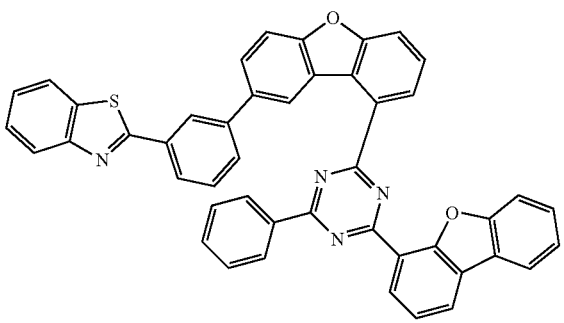
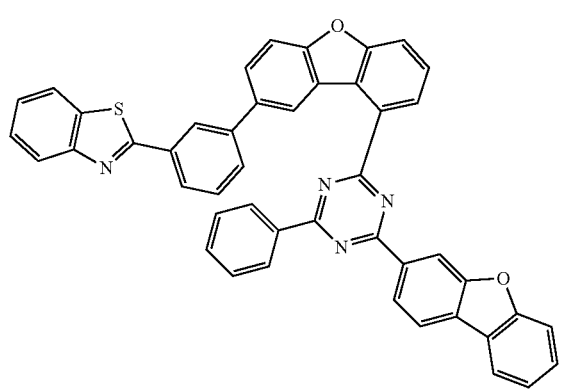
92
-continued
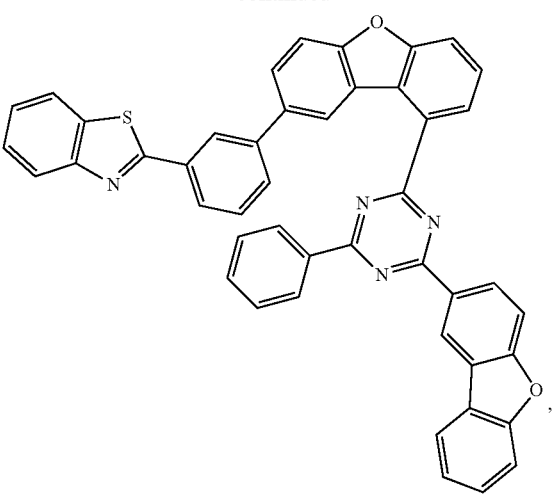
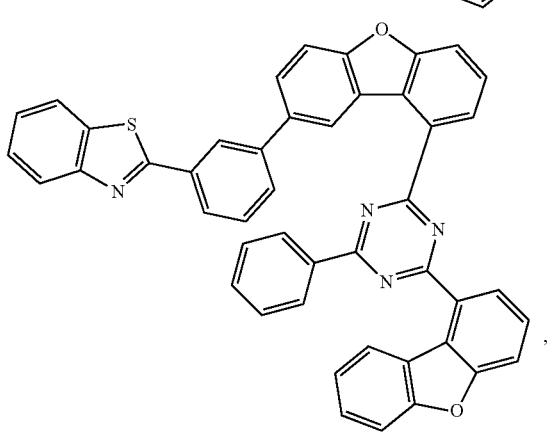
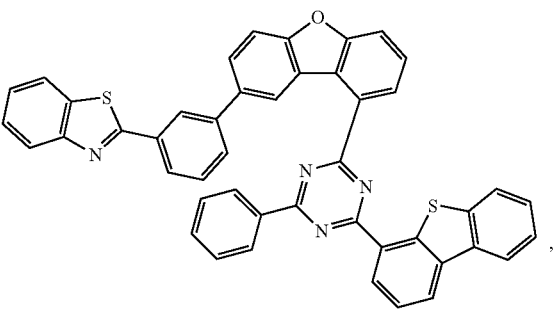
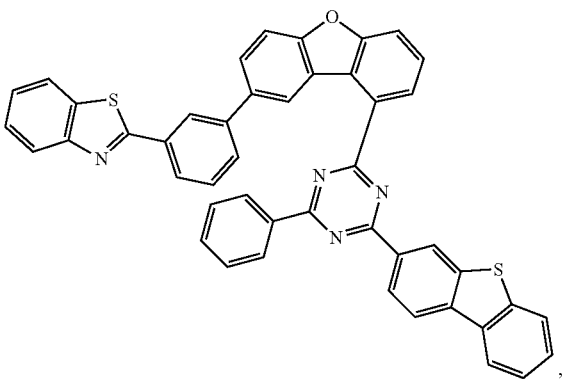

93
-continued
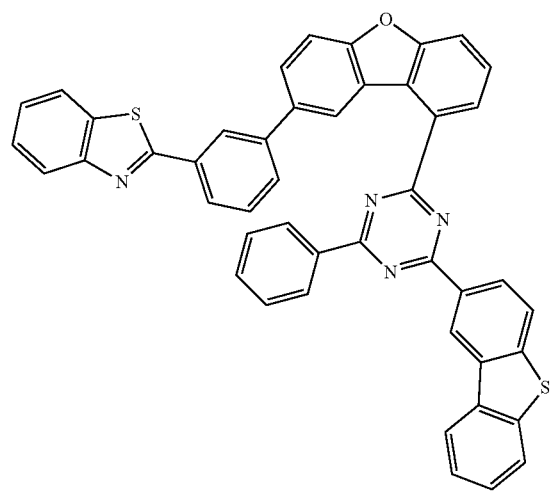
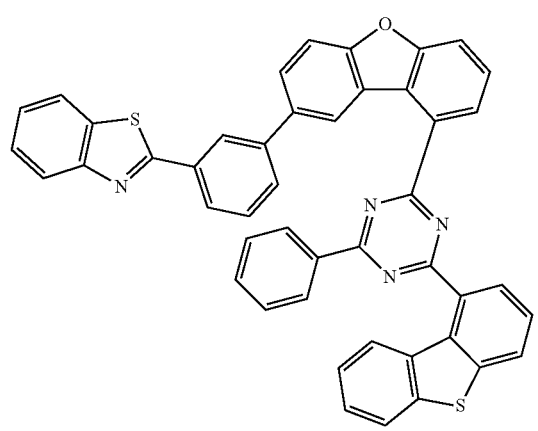
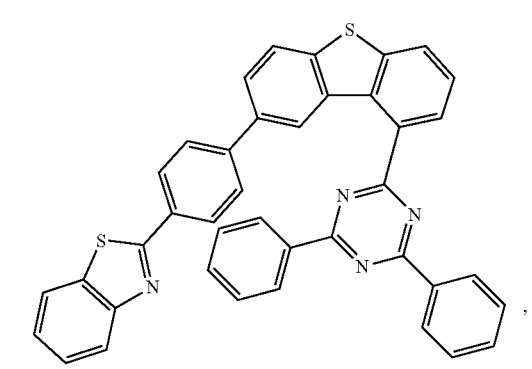
94
-continued
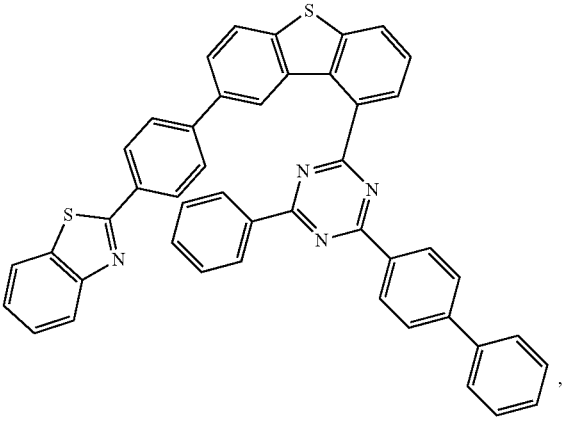
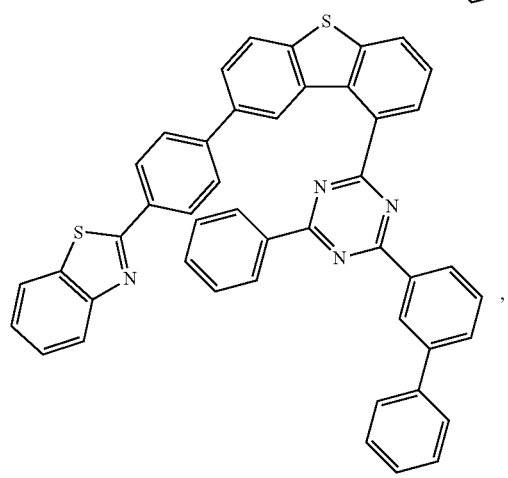
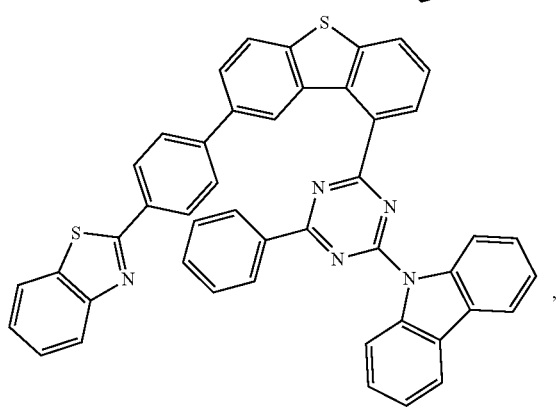
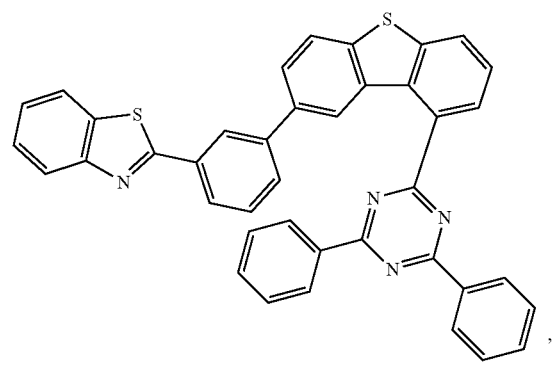

95
-continued
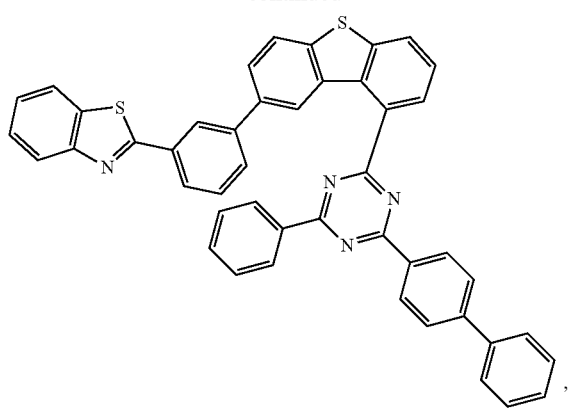
,
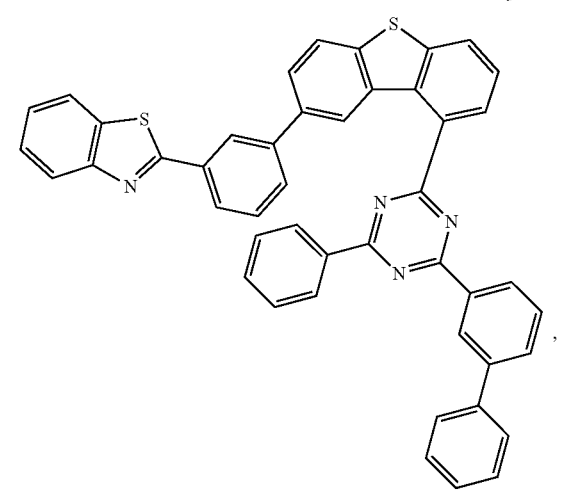
,
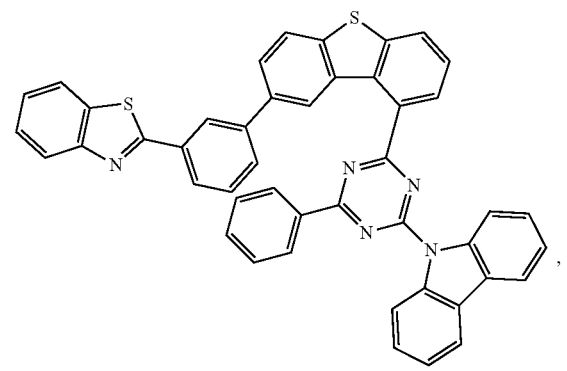
,
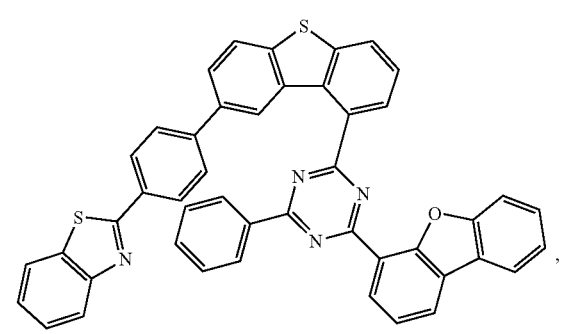
,
96
-continued
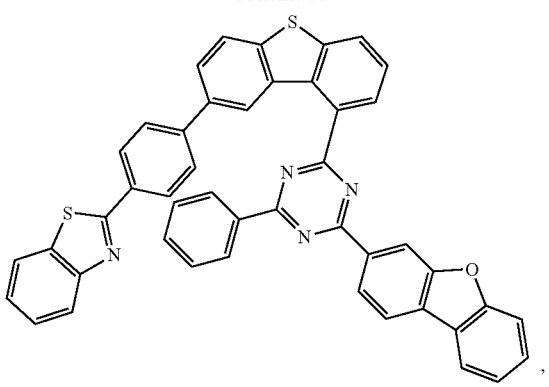
,
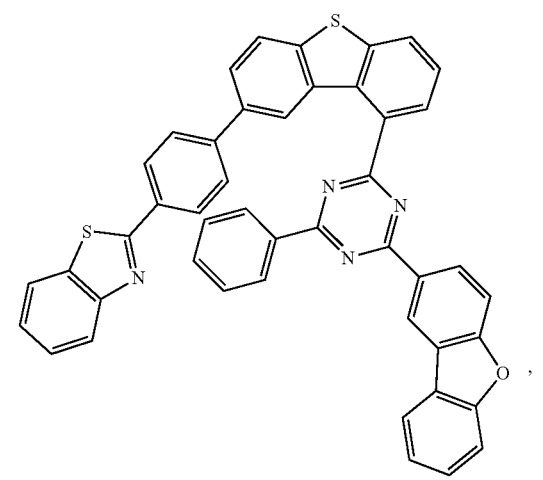
,
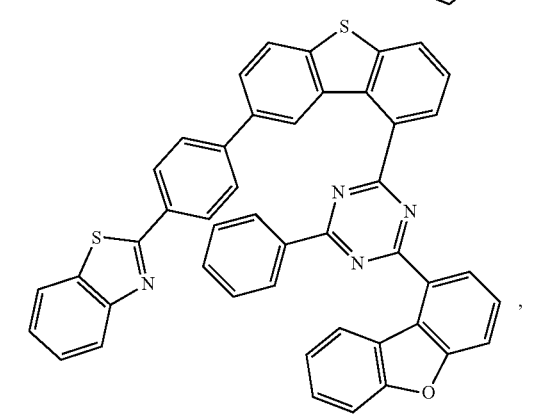
,
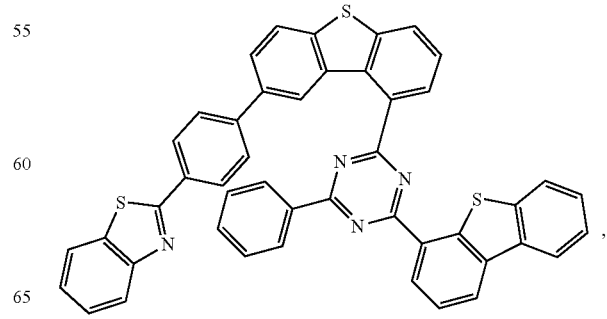
, -continued
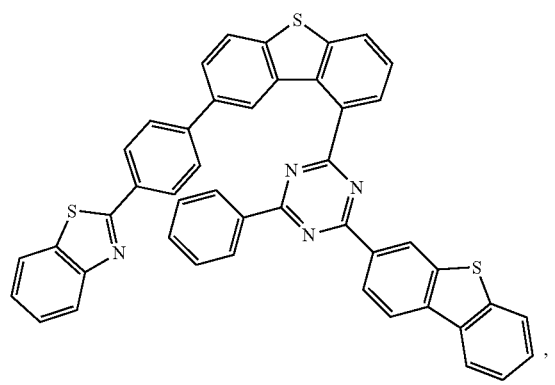
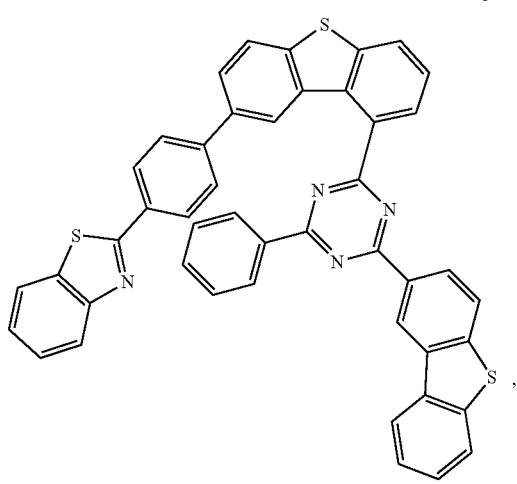
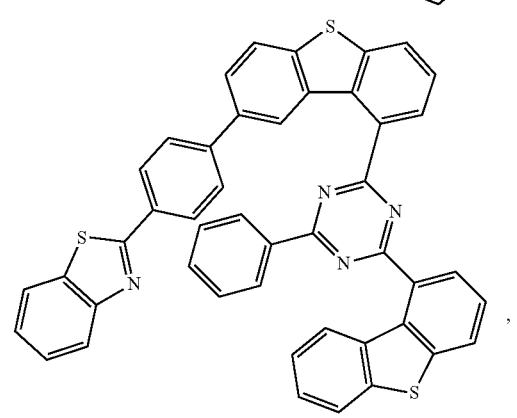
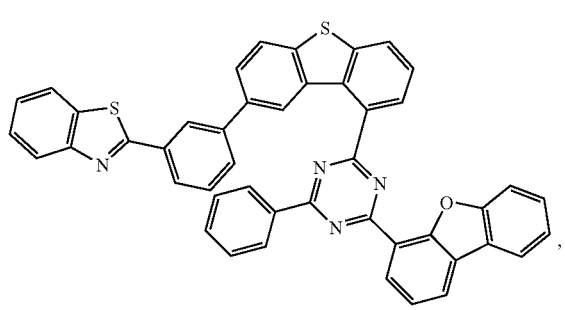
-continued
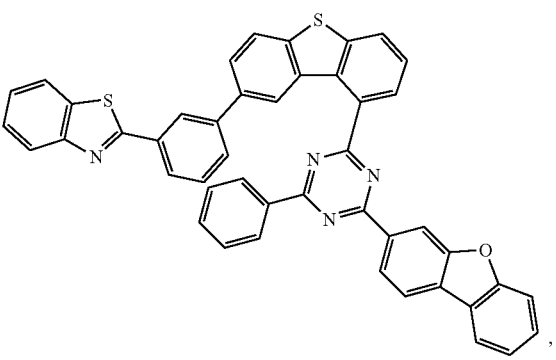
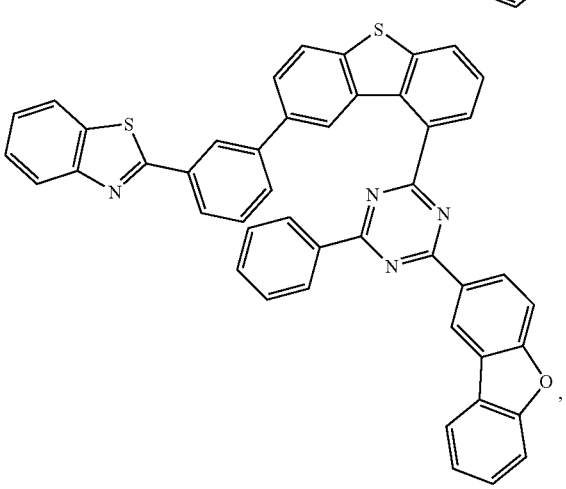
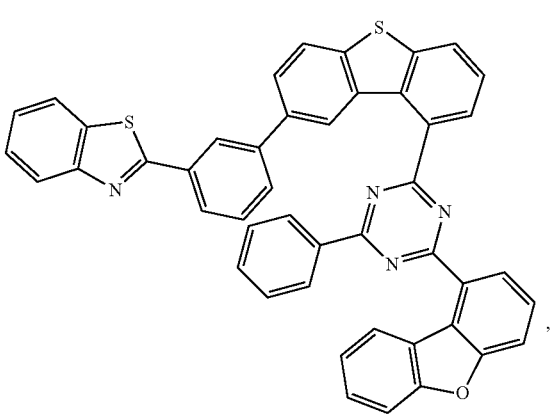
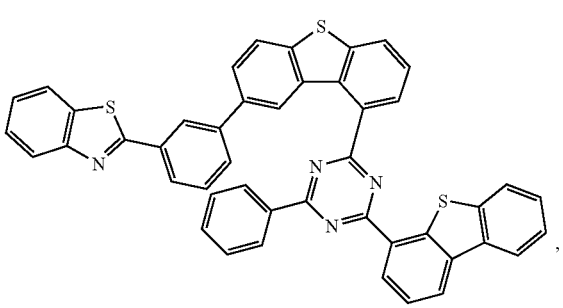

99
-continued
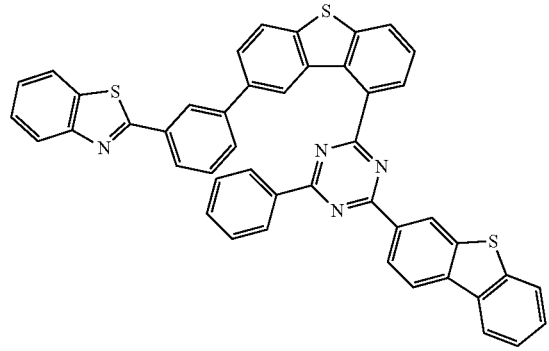
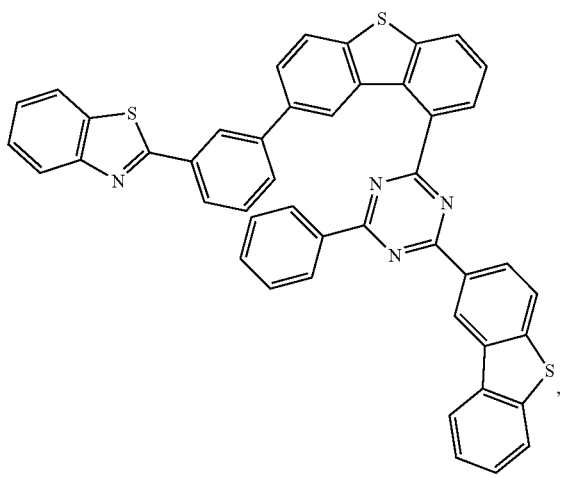
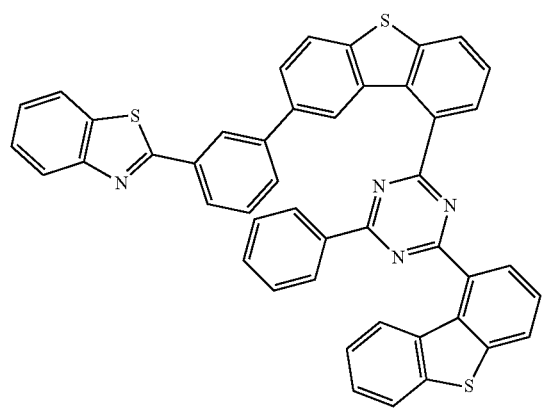
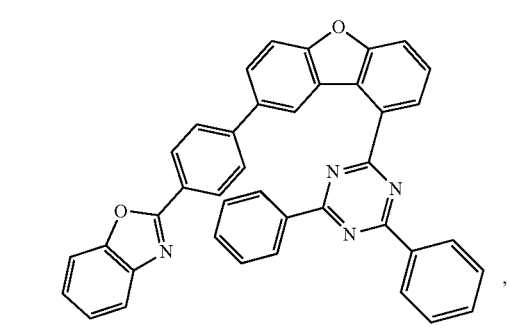
100
-continued
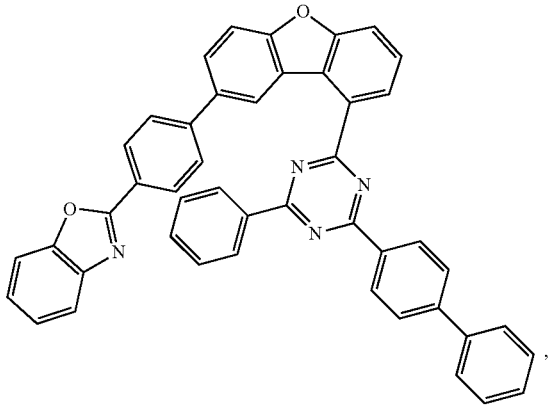
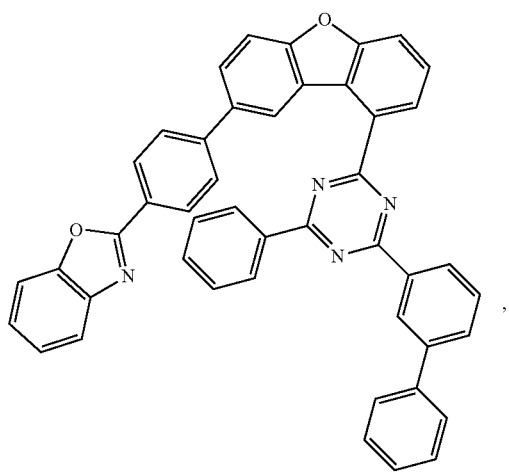
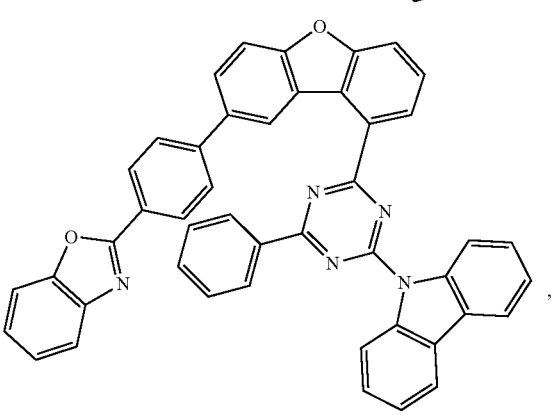
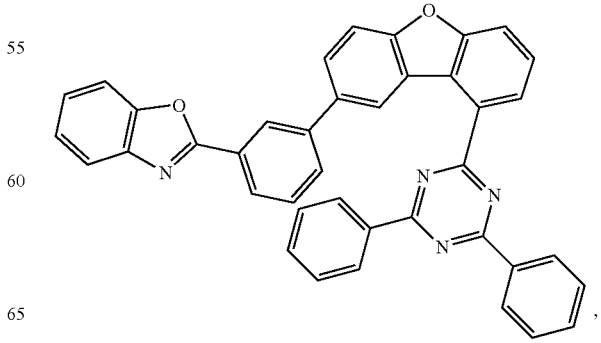

101
-continued
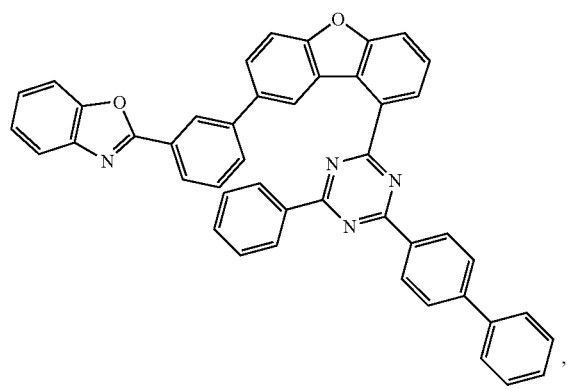
,
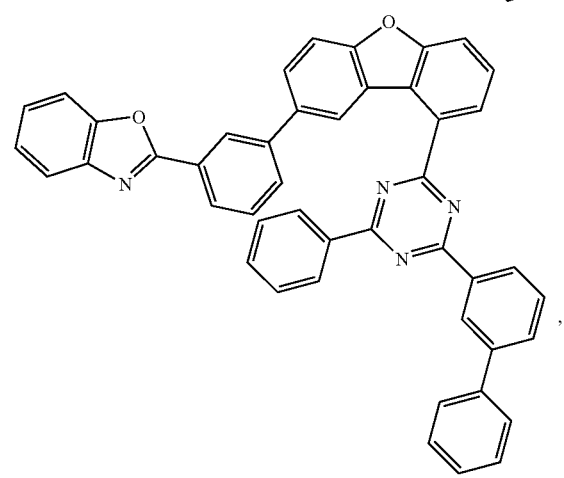
,
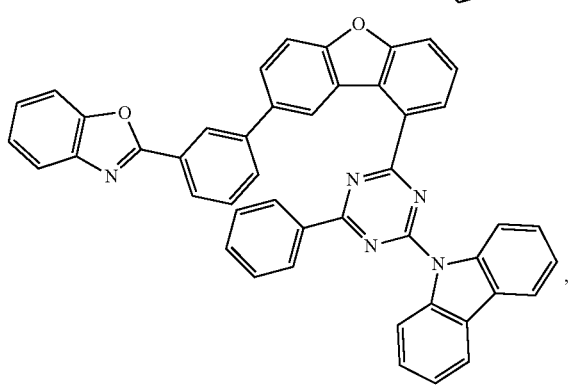
,
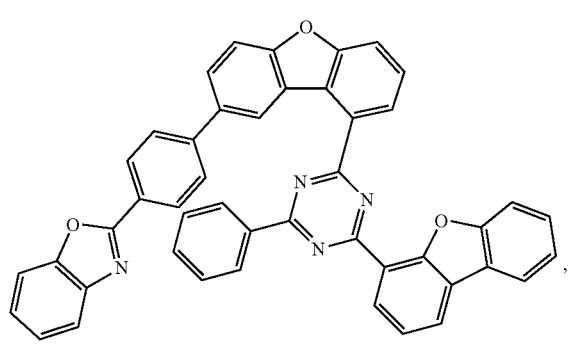
,
102
-continued
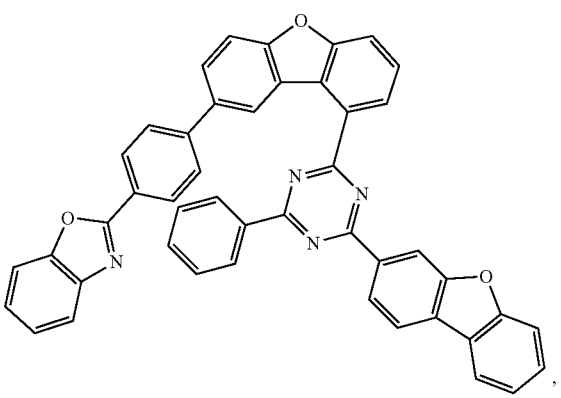
,
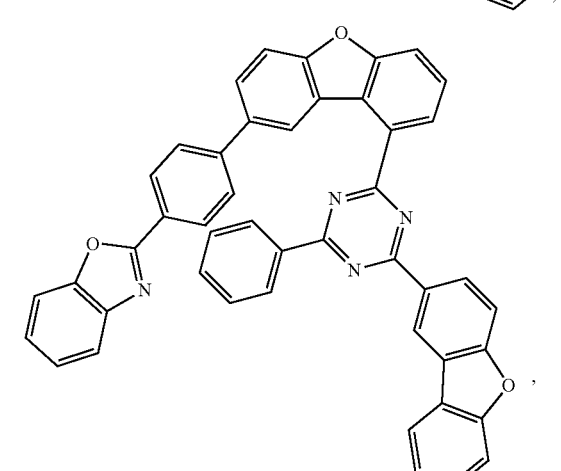
,
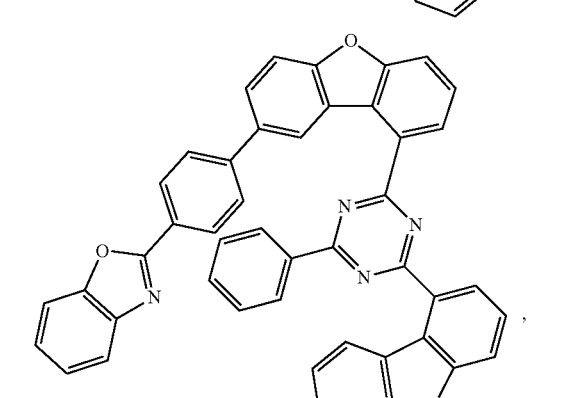
,
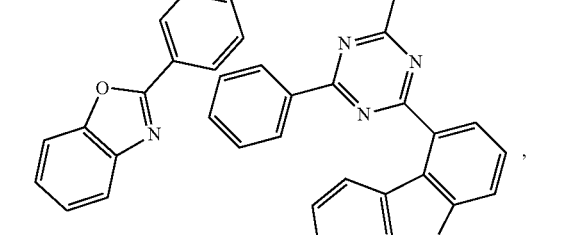
, 103
-continued
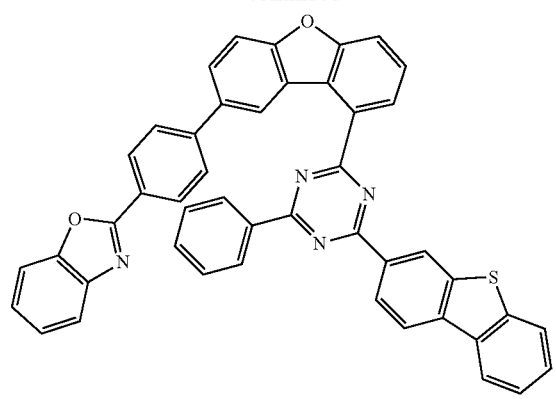
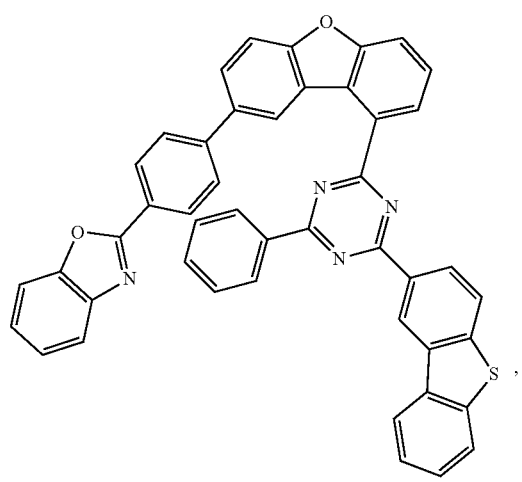
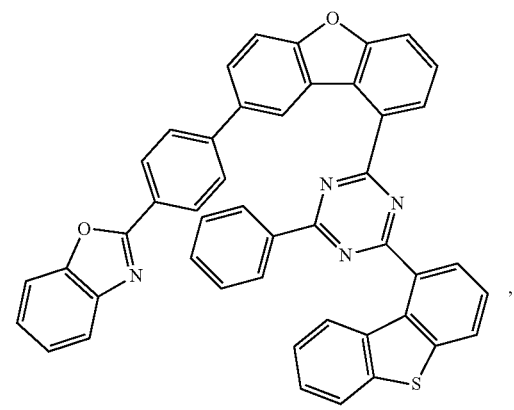
104
-continued
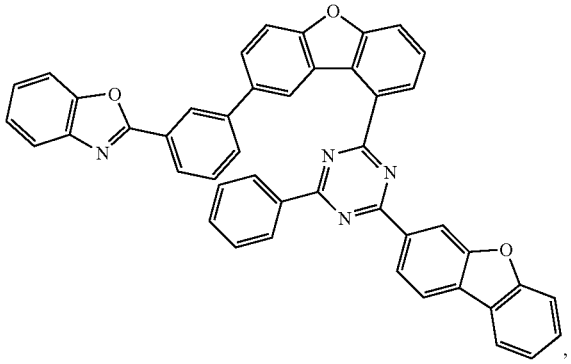
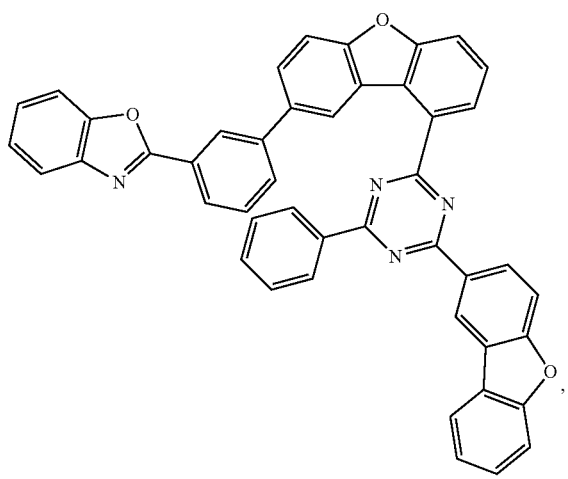
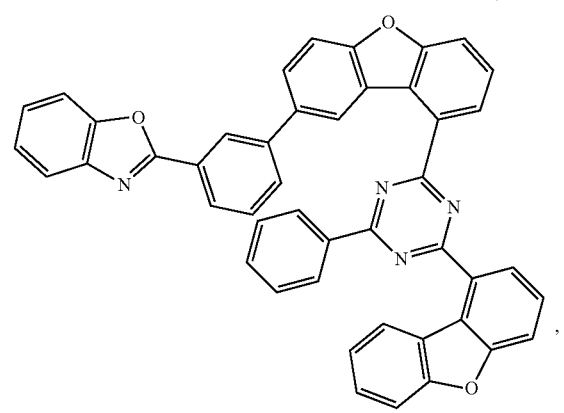
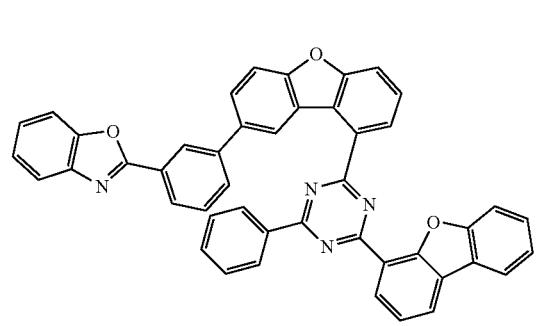
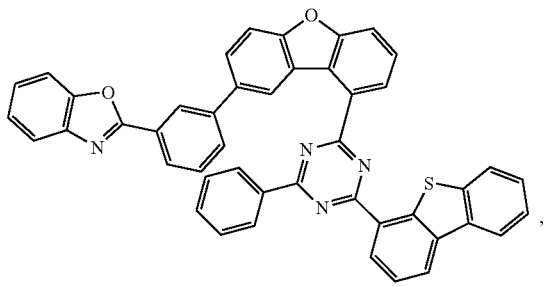

105
-continued
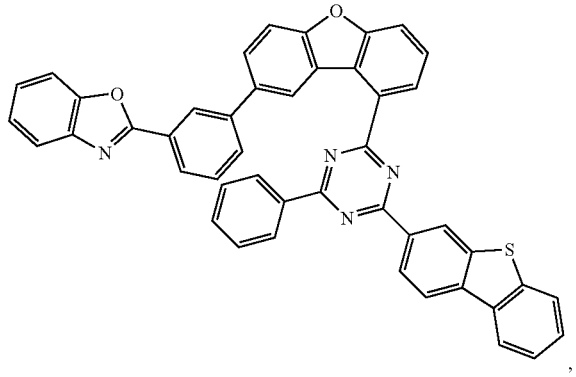
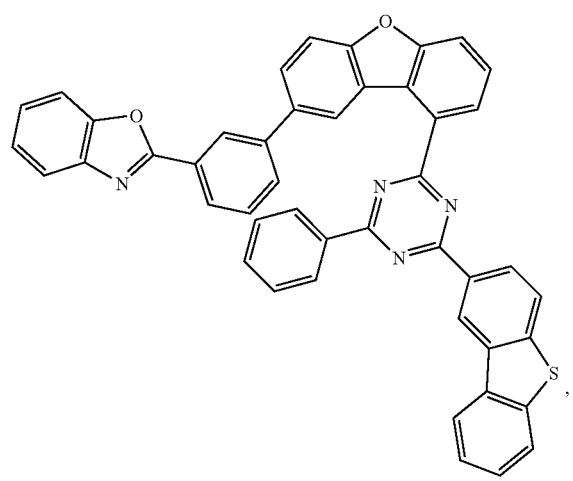
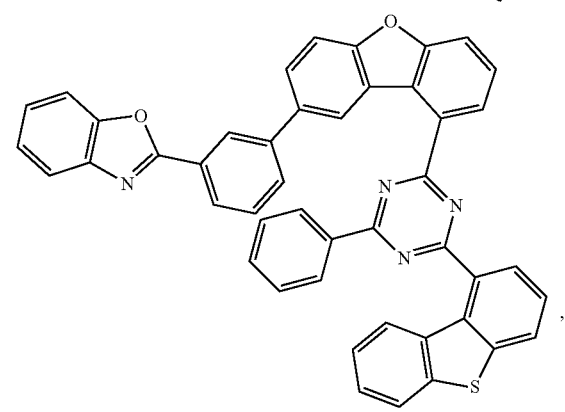
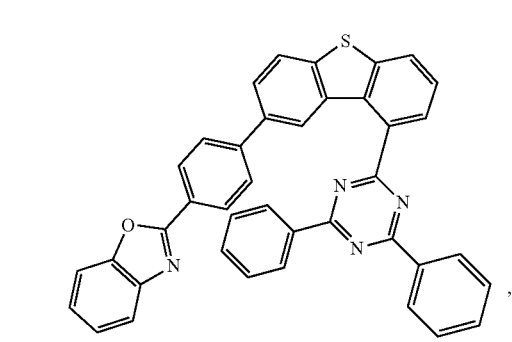
106
-continued
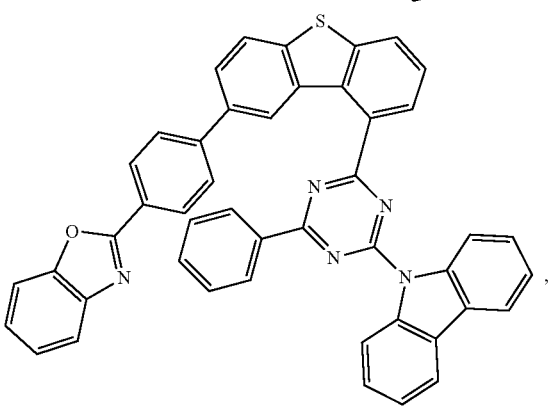
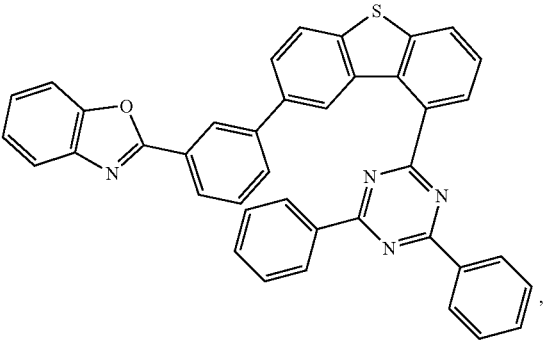

107
-continued
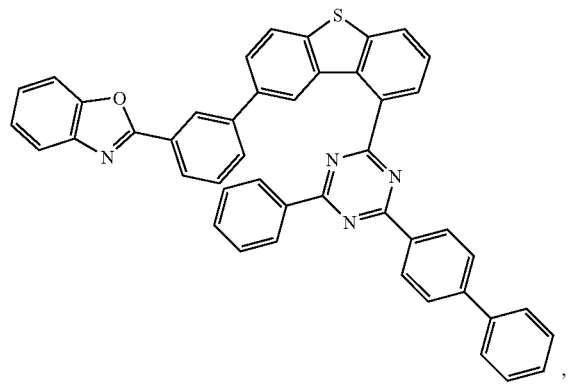
,
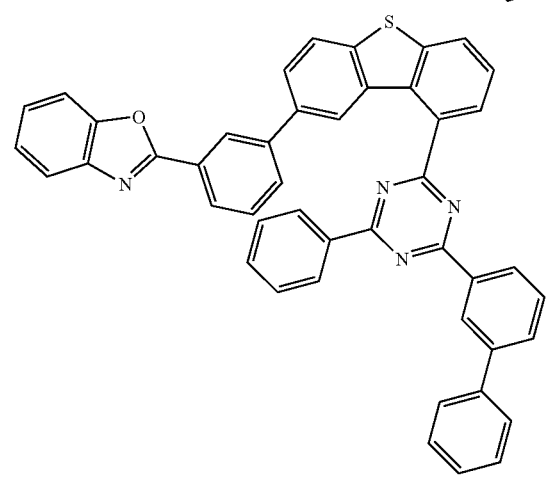
,
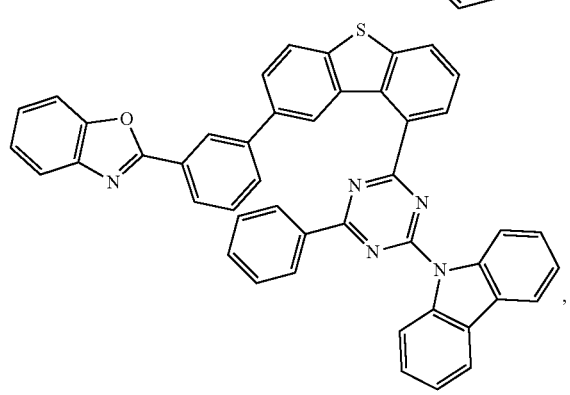
,
,
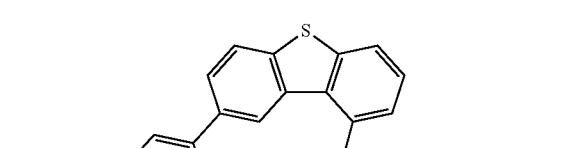
,
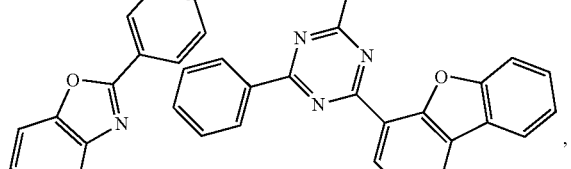
,
108
-continued
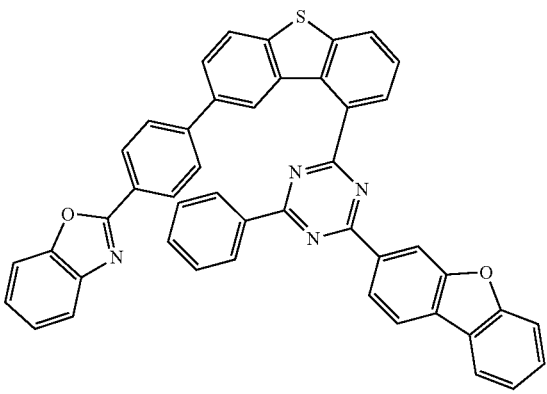
,
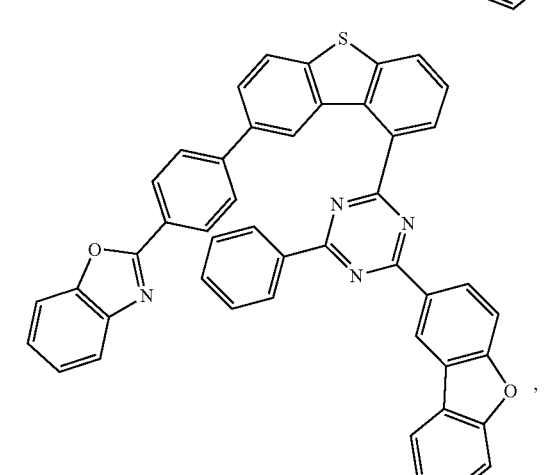
,
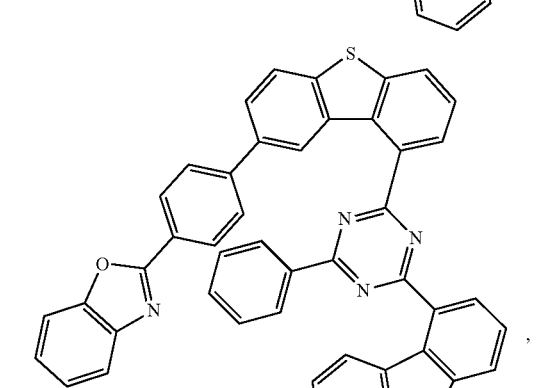
,
,
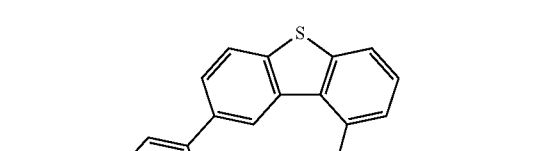
,
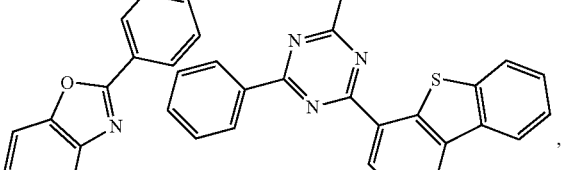
, 109
-continued
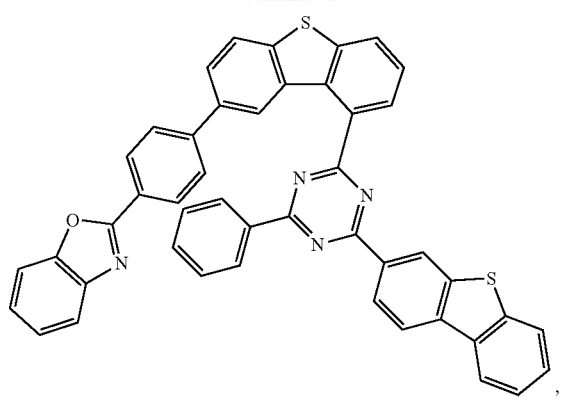,
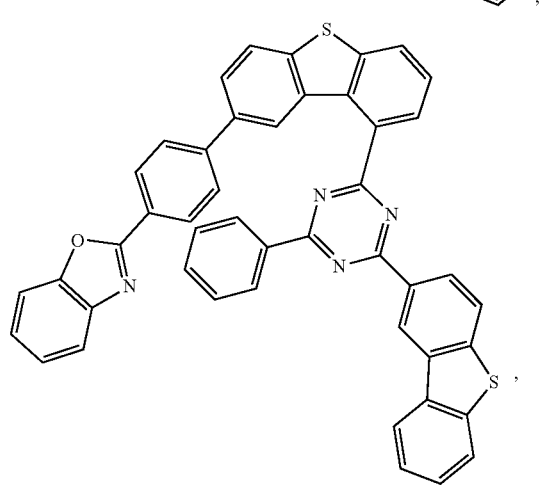,
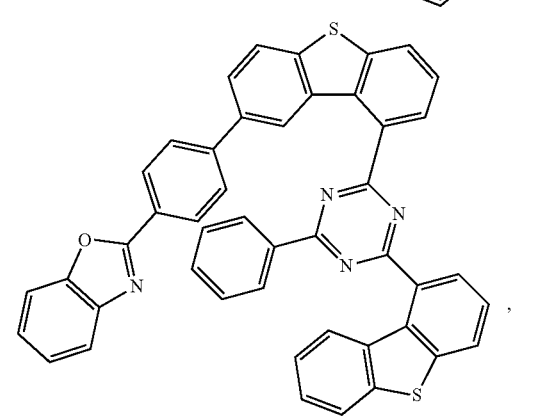,
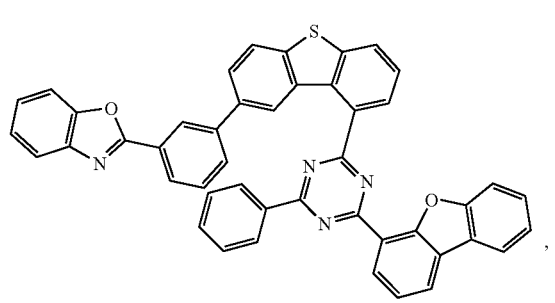,
110
-continued
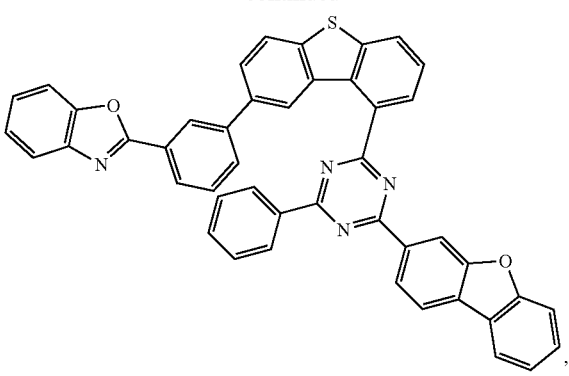,
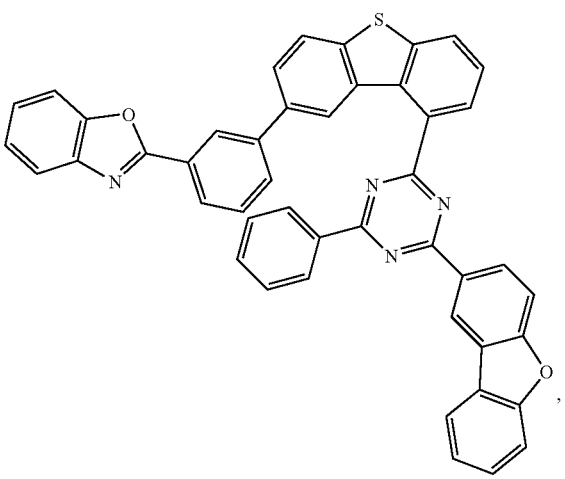,
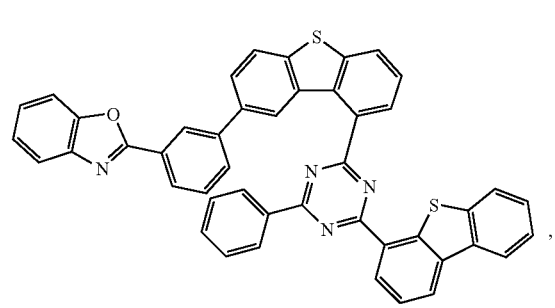, 111
-continued
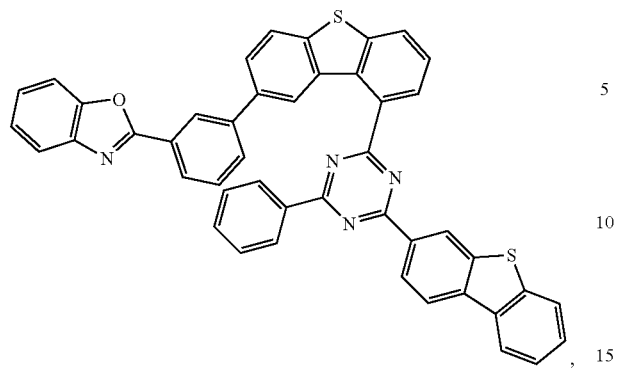
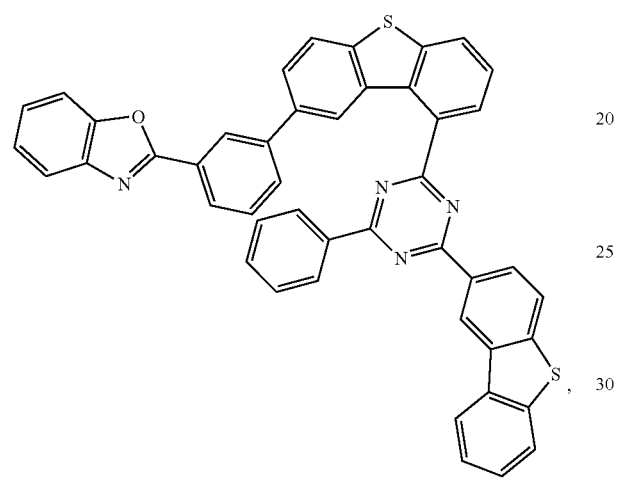
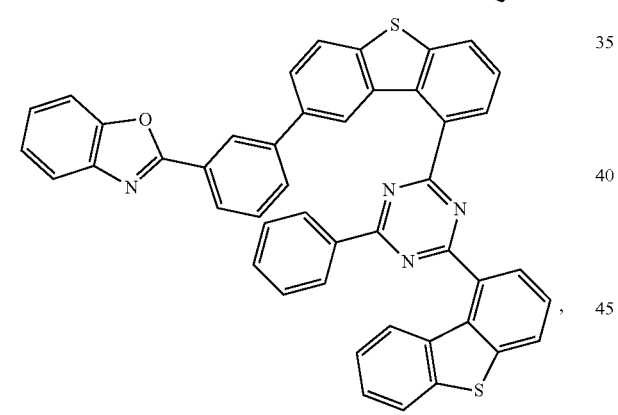
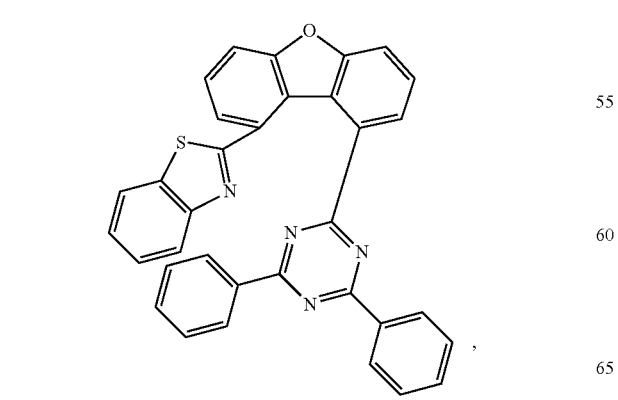
112
-continued
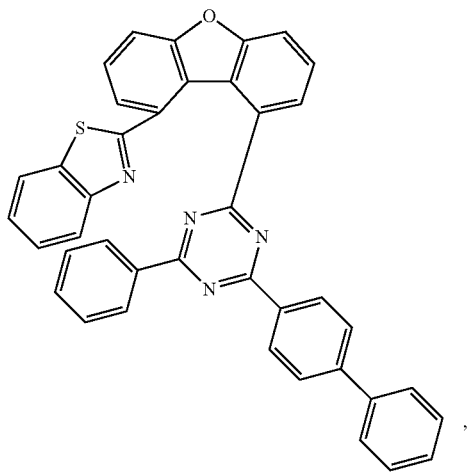
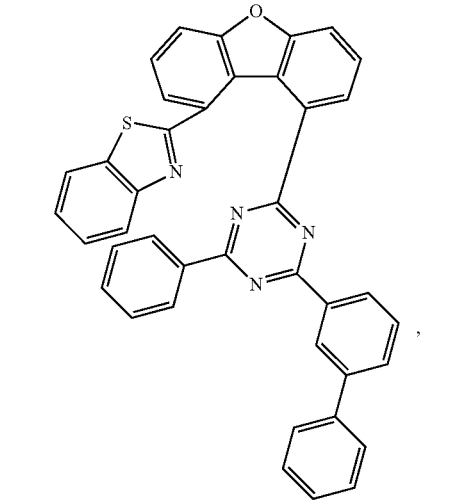
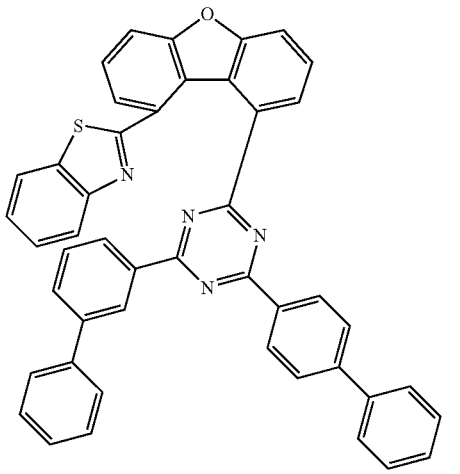

113
-continued
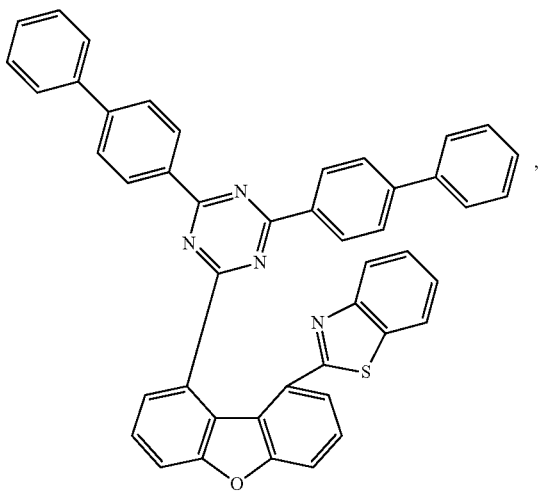
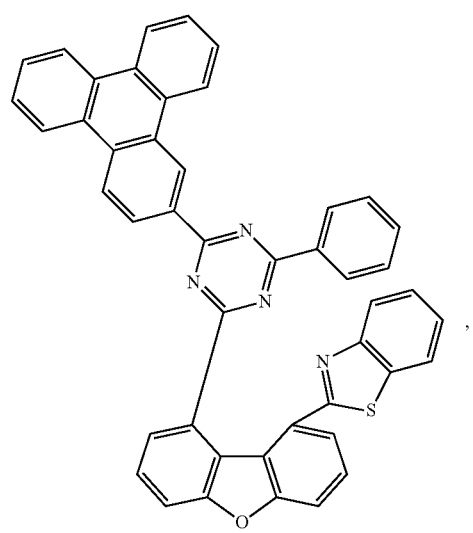
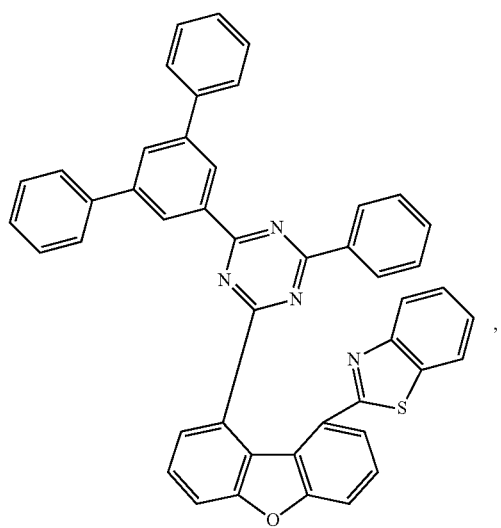
114
-continued
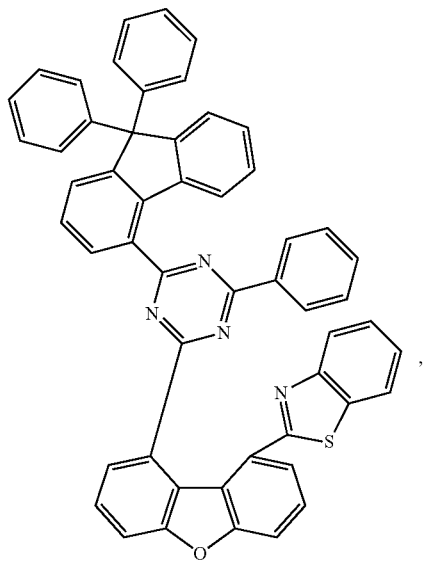
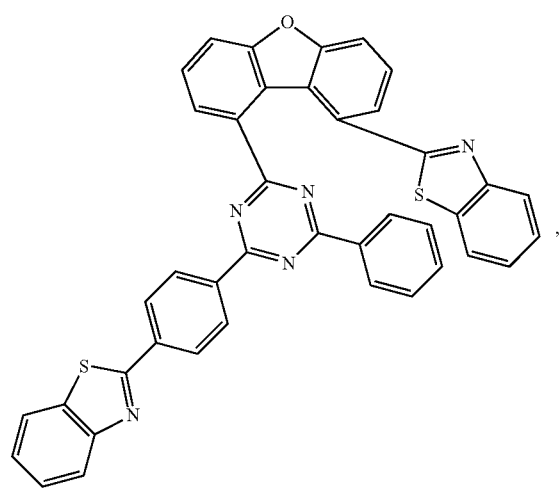
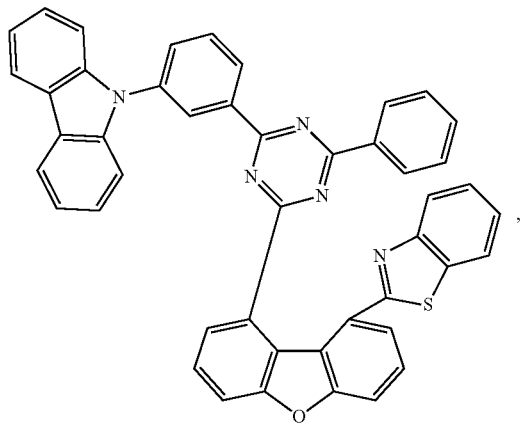

115
-continued
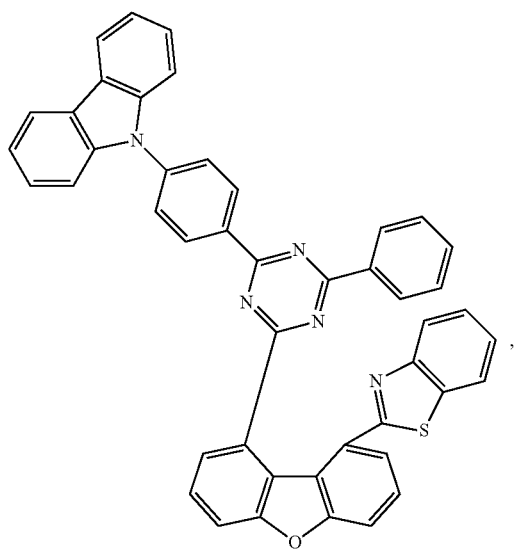
,
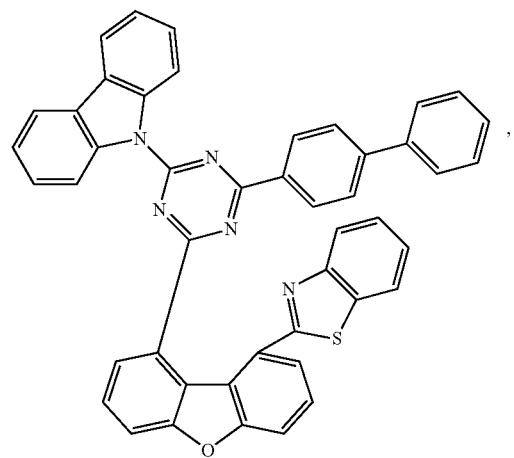
,
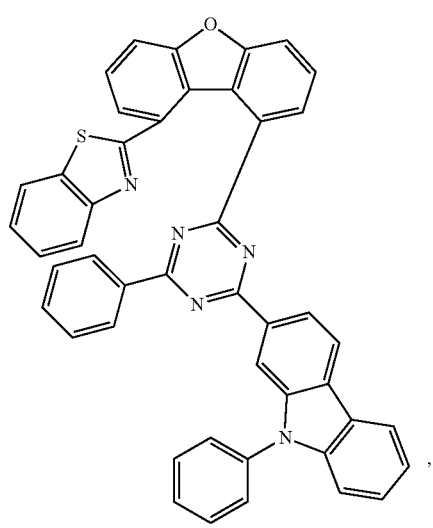
,
116
-continued
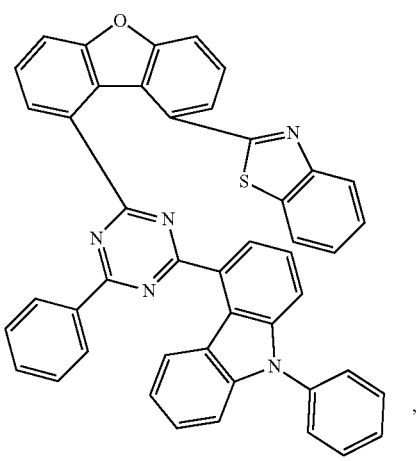
,
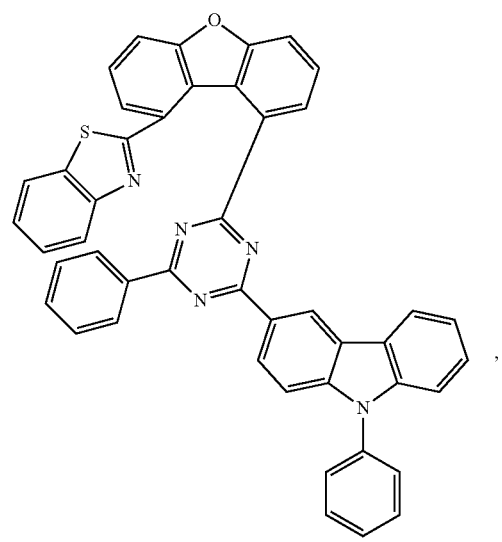
,
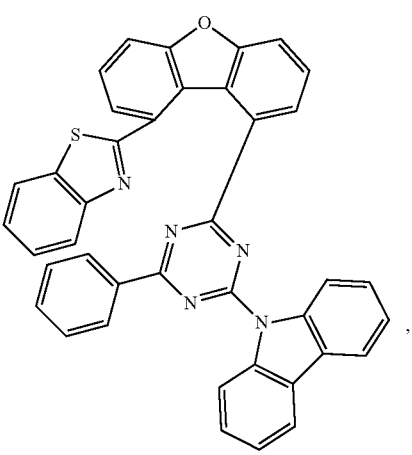
, 117
-continued
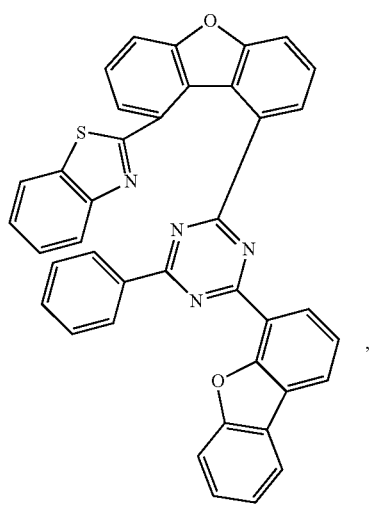
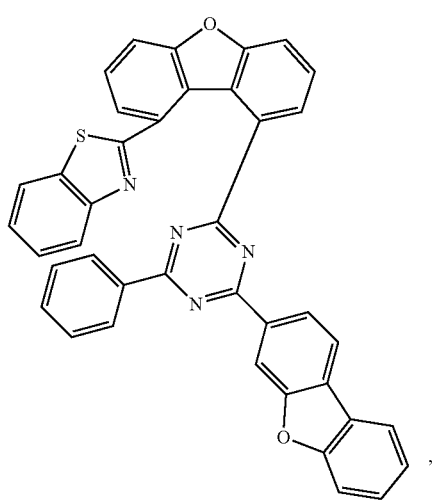
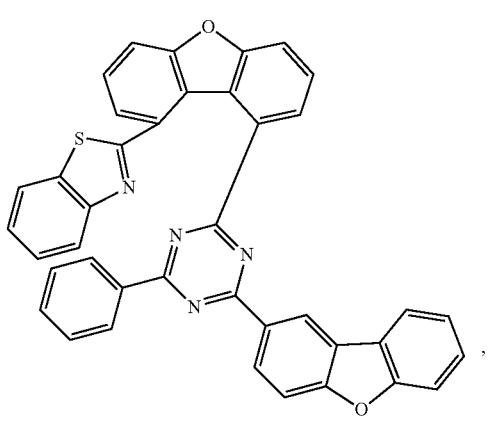
118
-continued
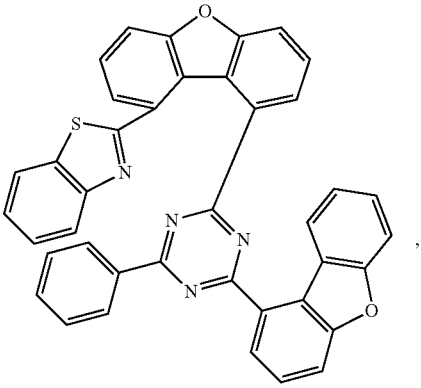
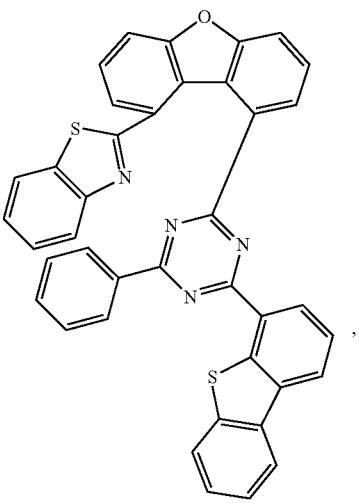
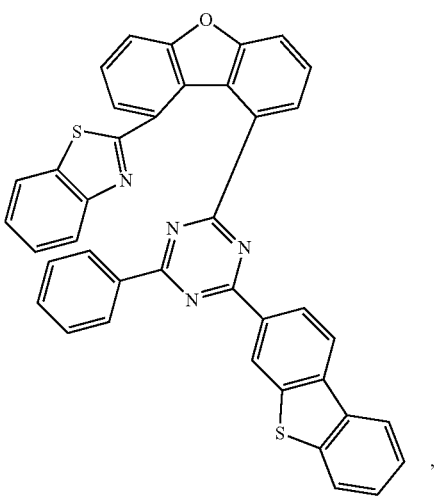

119
-continued
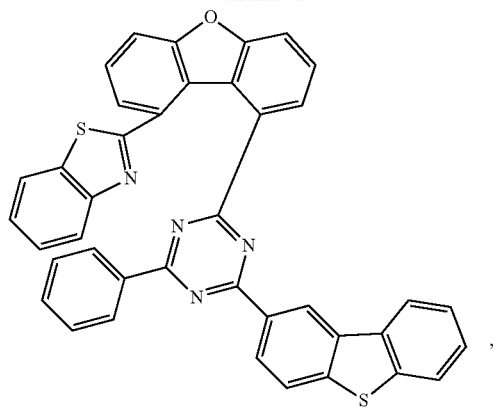
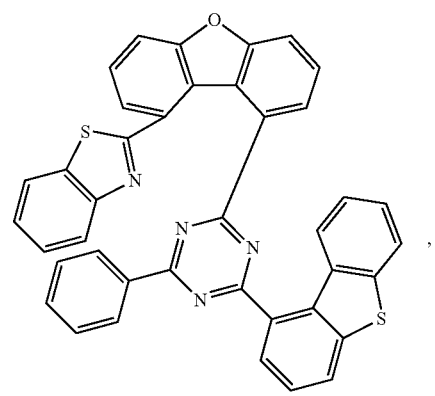
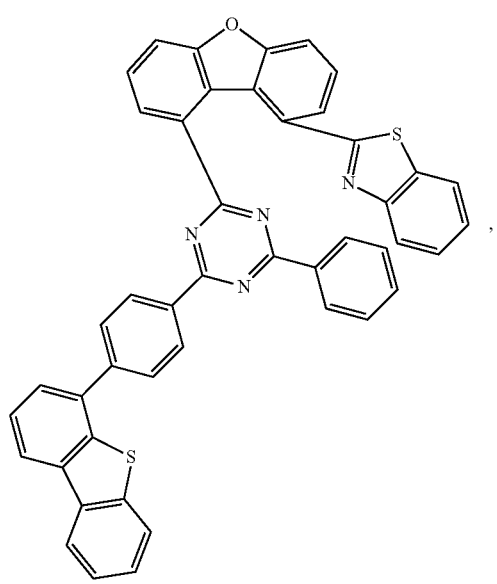
120
-continued
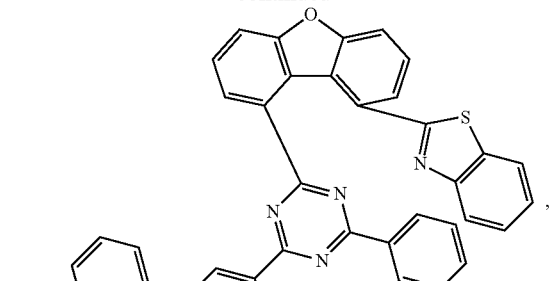
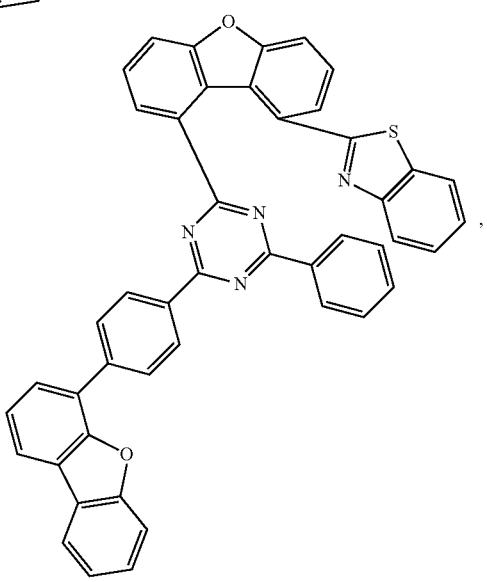
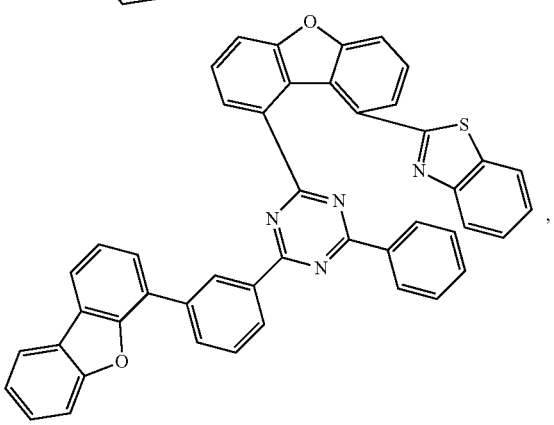
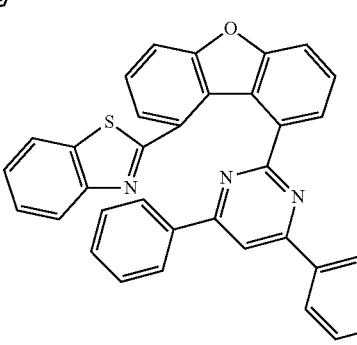

121
-continued
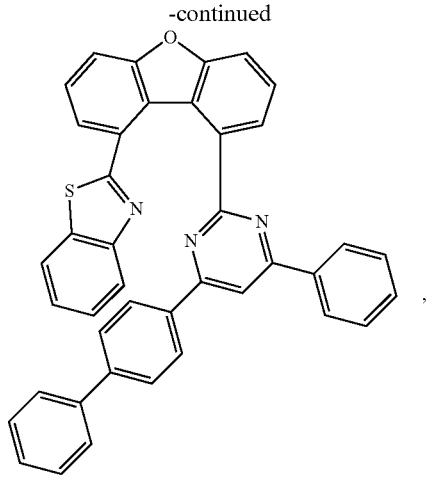,
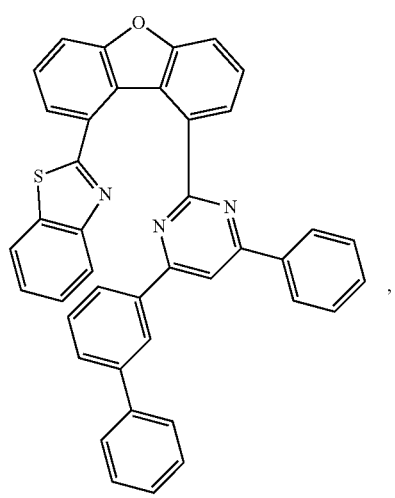,
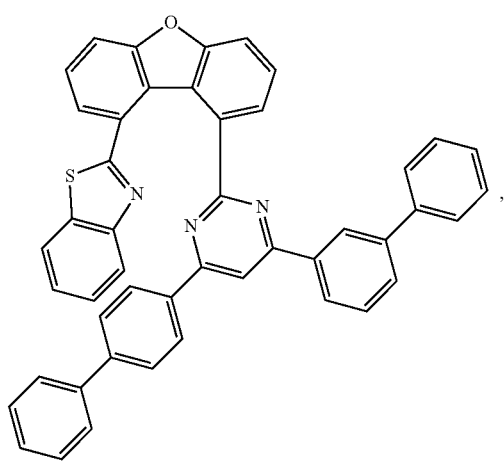,
122
-continued
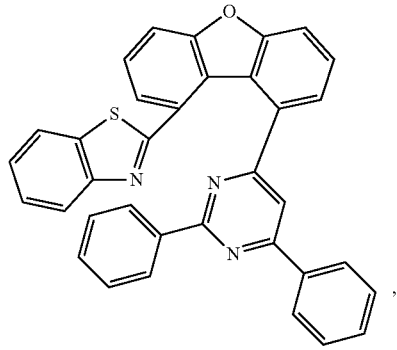,
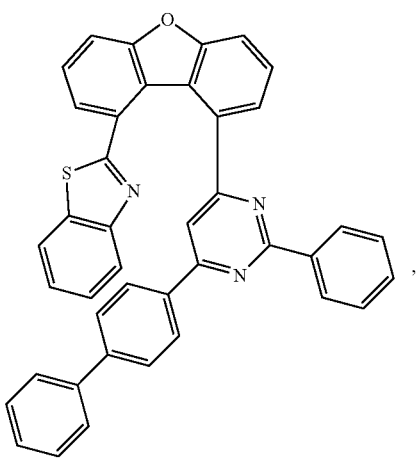,
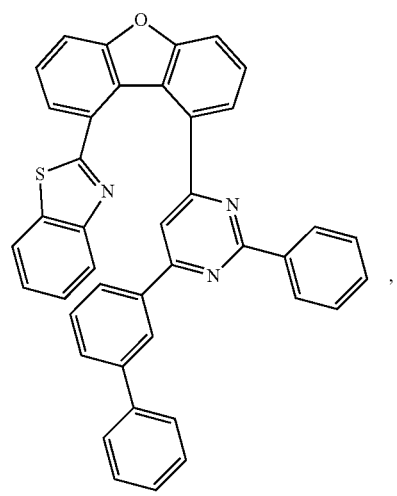,

123
-continued
124
-continued
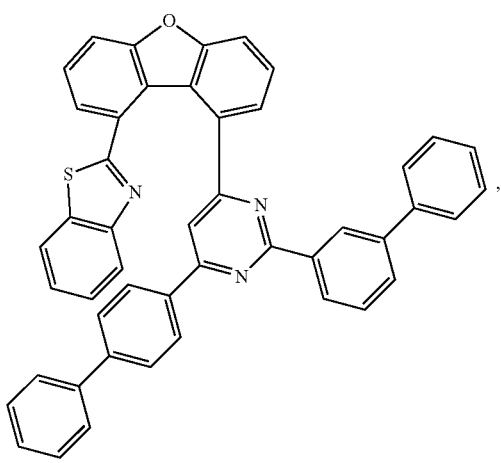 [SMILES: c1ccc(-c2ccc(-c3cc(-c4cccc5oc6cccc(-c7nc8ccccc8s7)c6c45)nc(-c4cccc(-c5ccccc5)c4)n3)cc2)cc1]
,
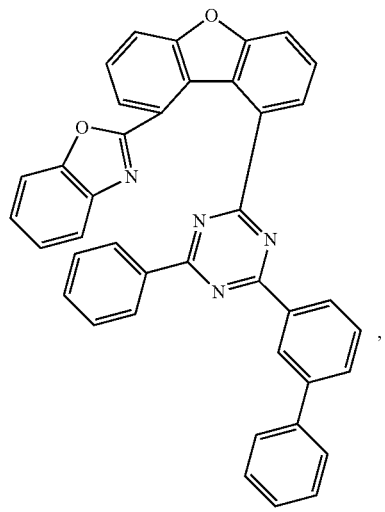
,
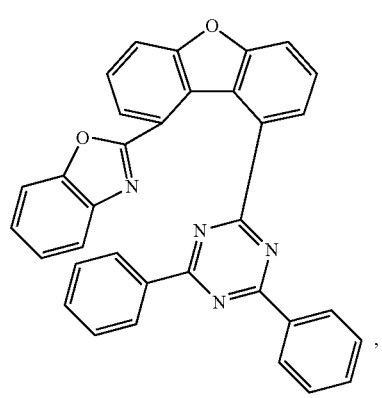
,
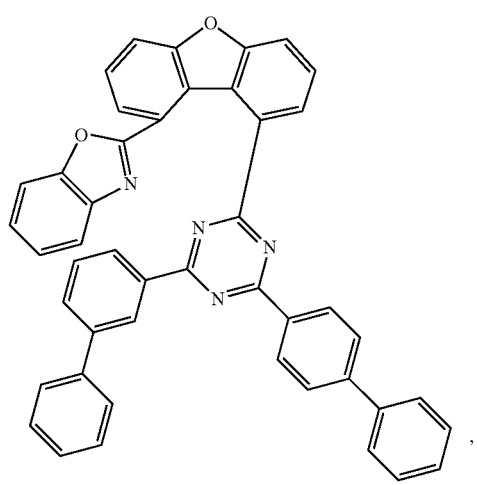
,
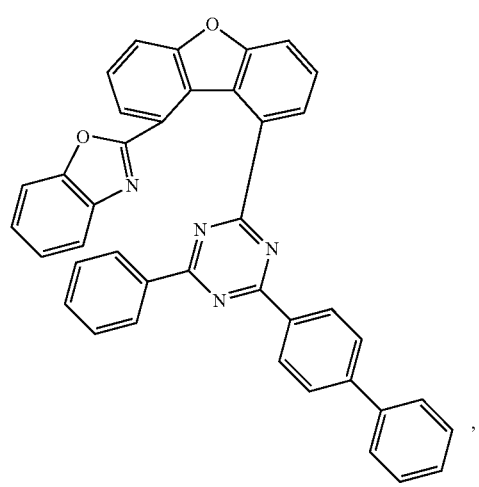
,
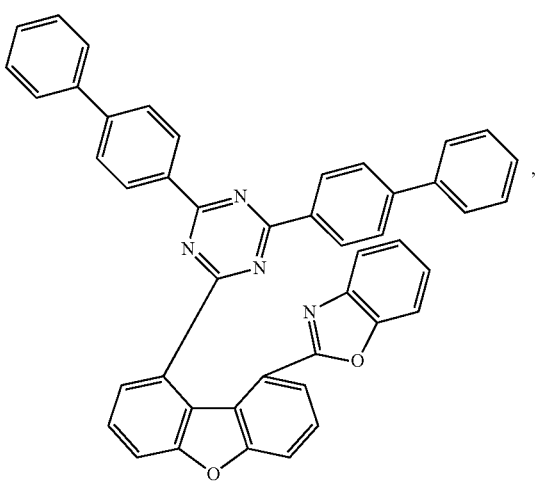
, 125
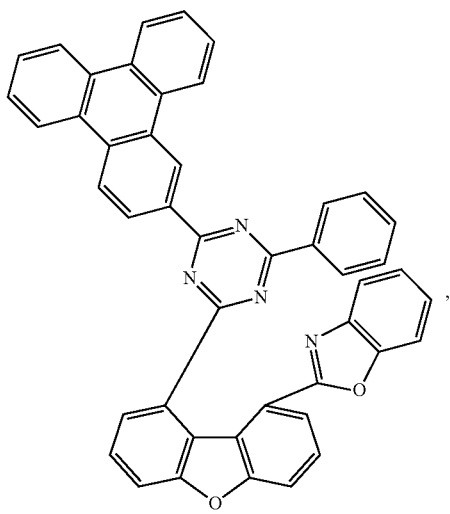
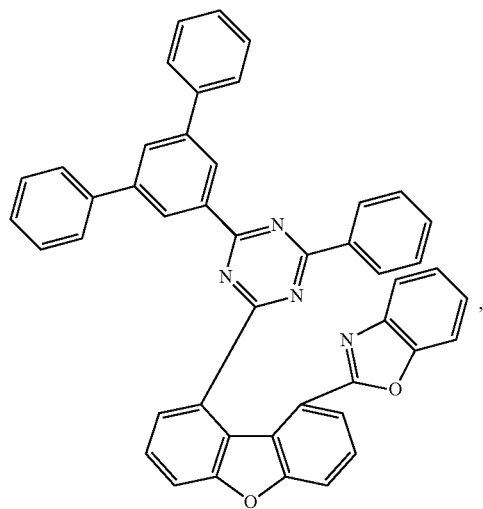
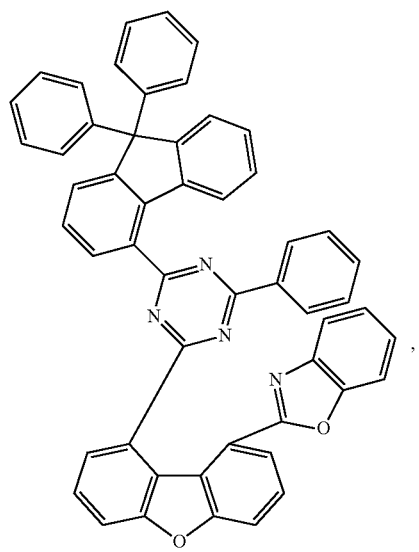
126
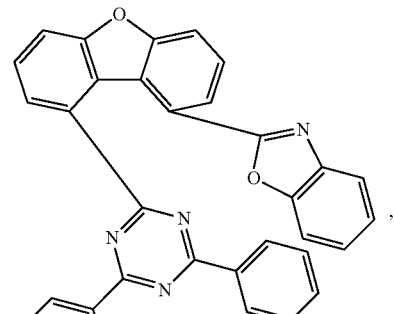
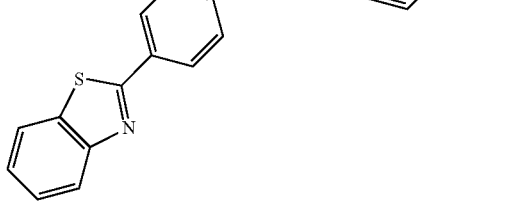
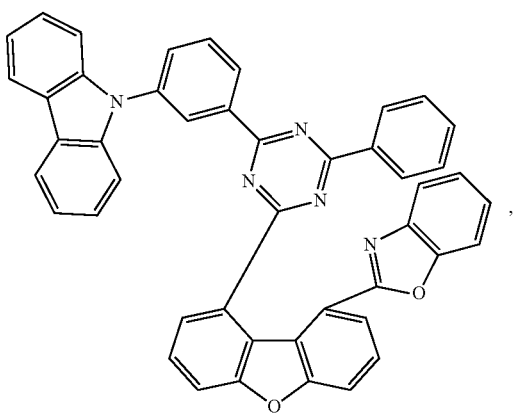
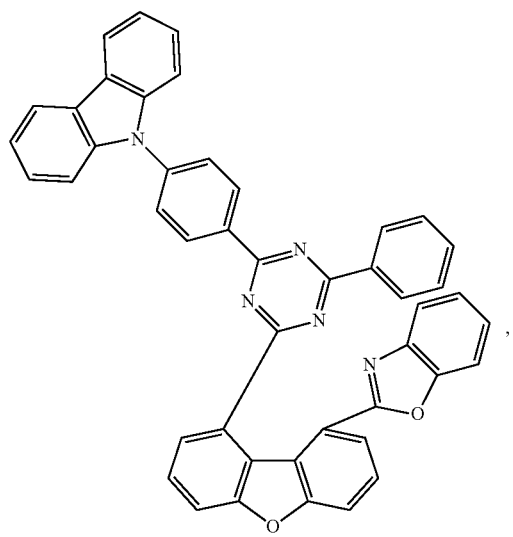

127
-continued
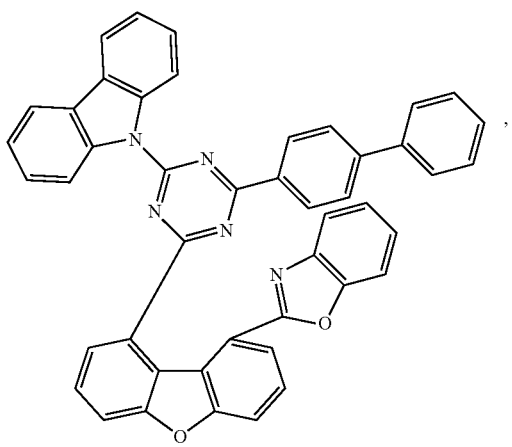,
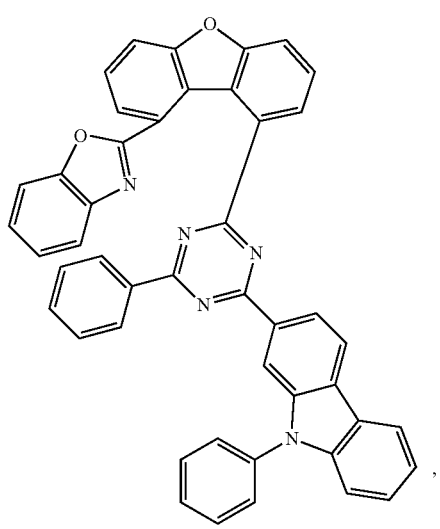,
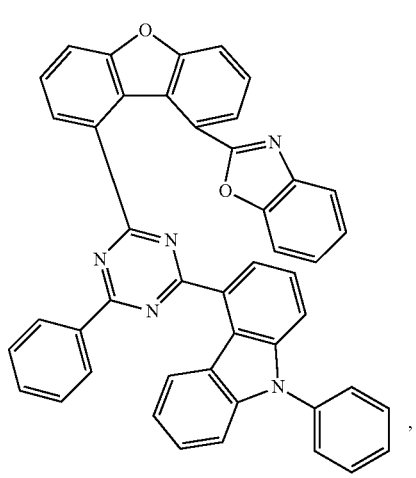,
128
-continued
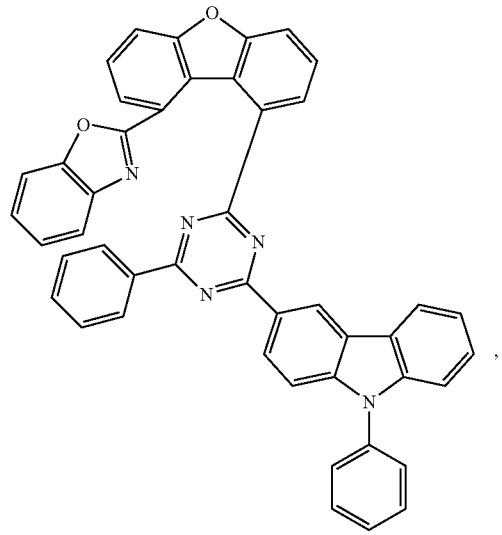,
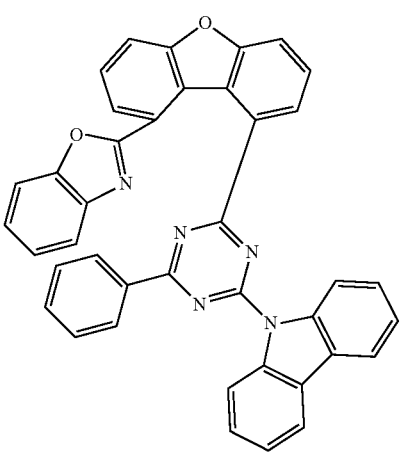,
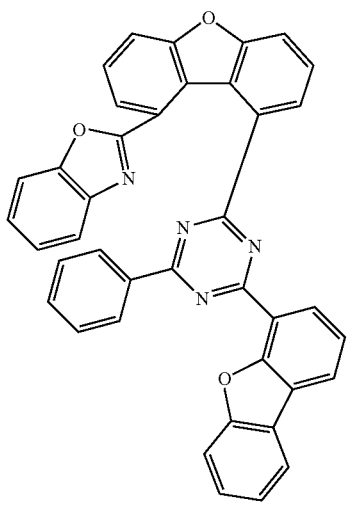,

129
-continued
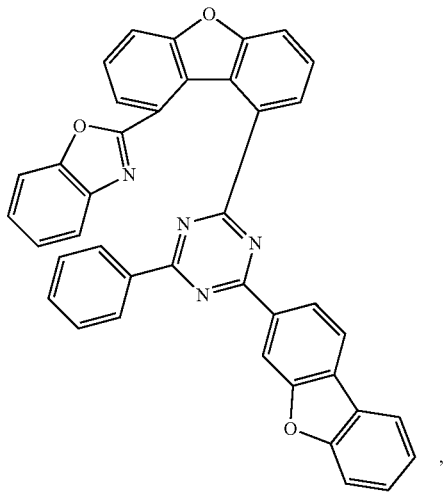
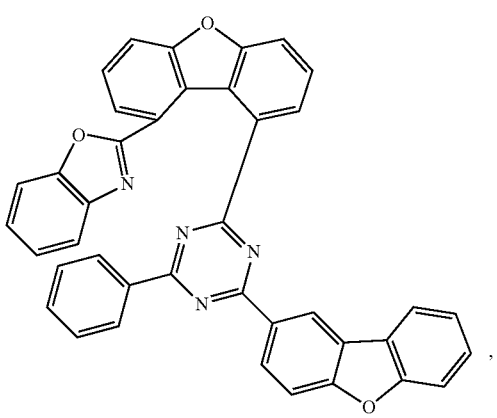
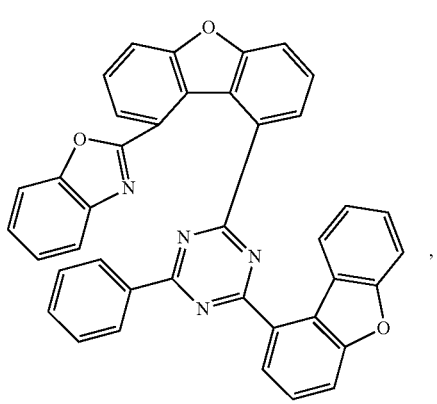
130
-continued
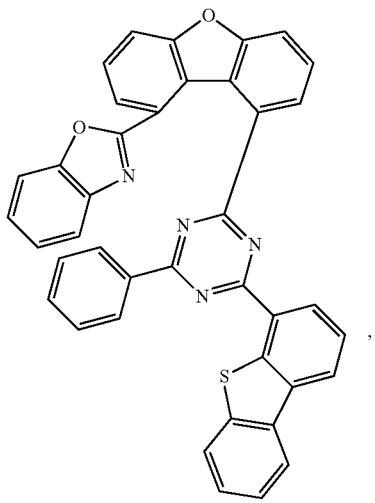
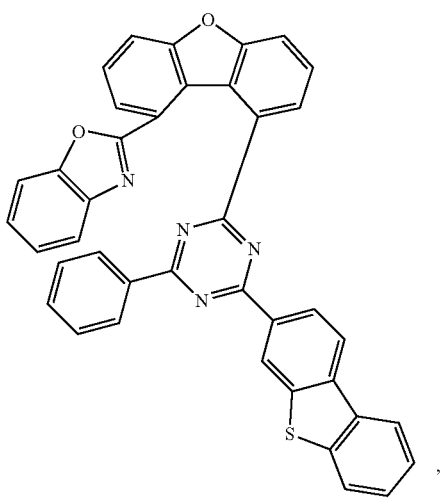
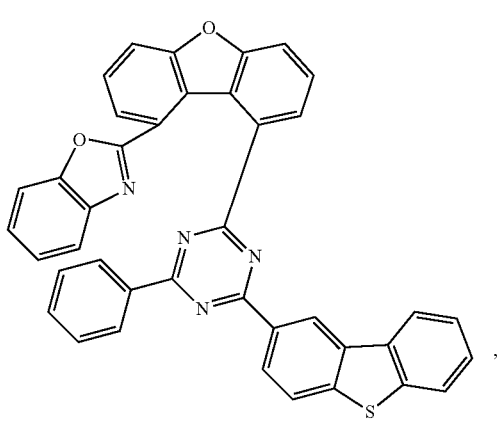

131
-continued
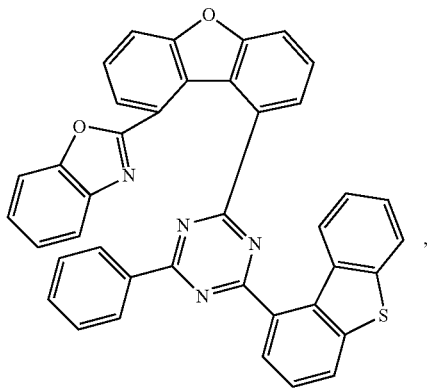
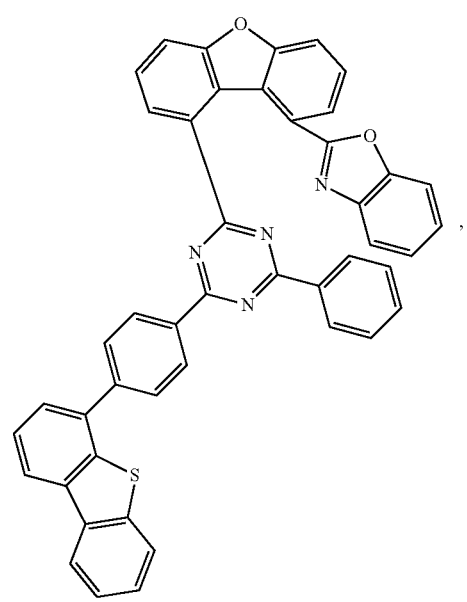
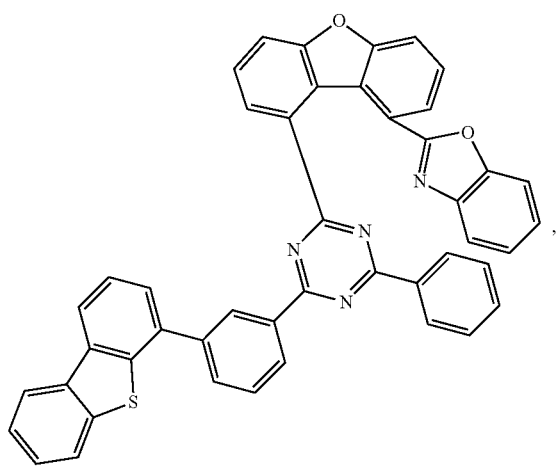
132
-continued
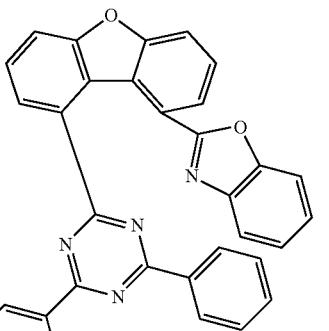
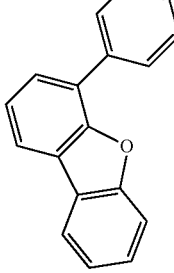
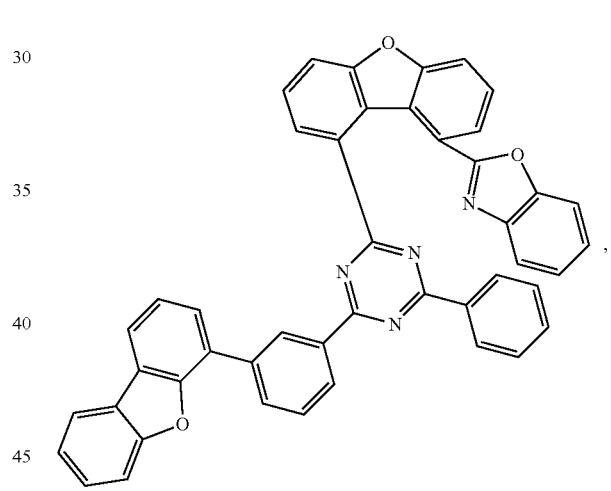
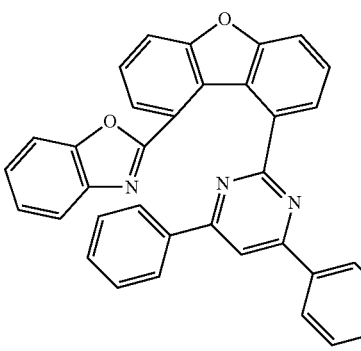

133                                    134
-continued                          -continued
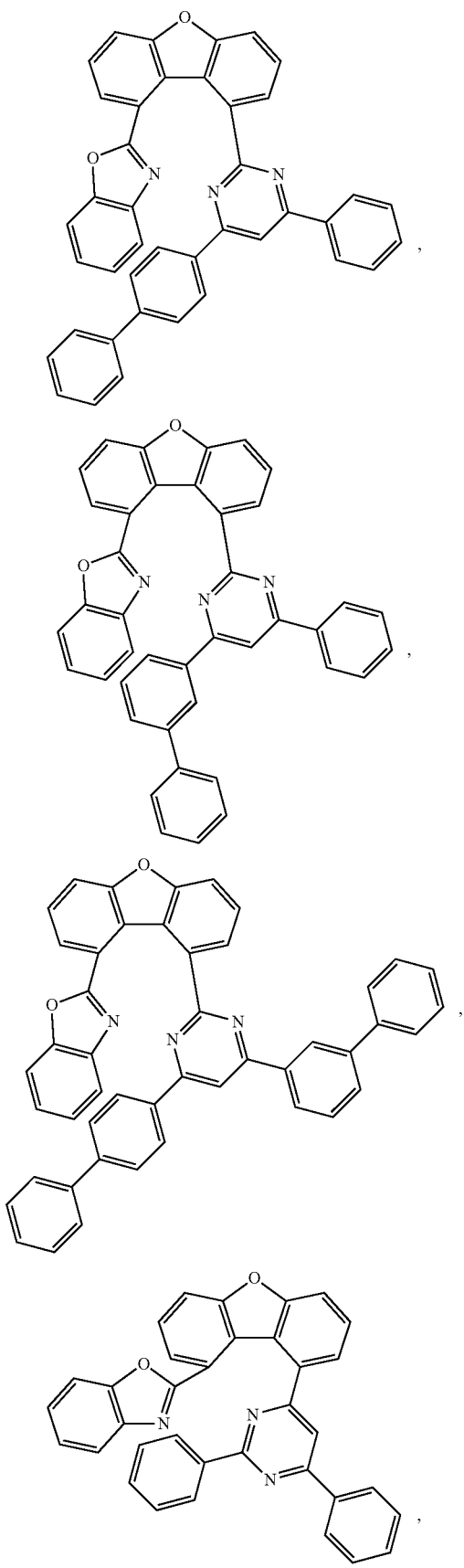

135
-continued
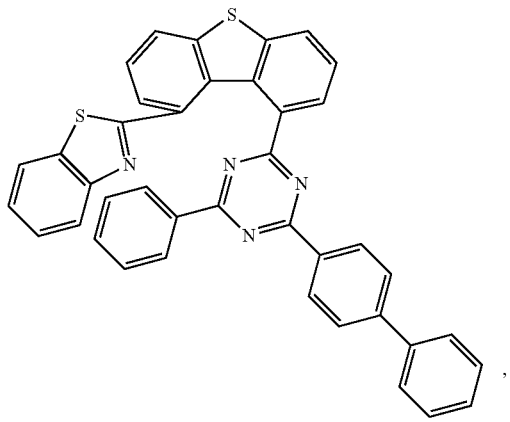
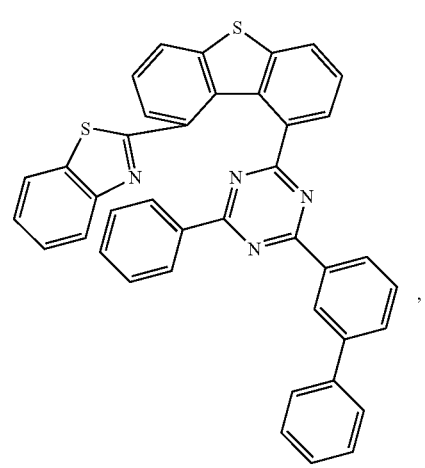
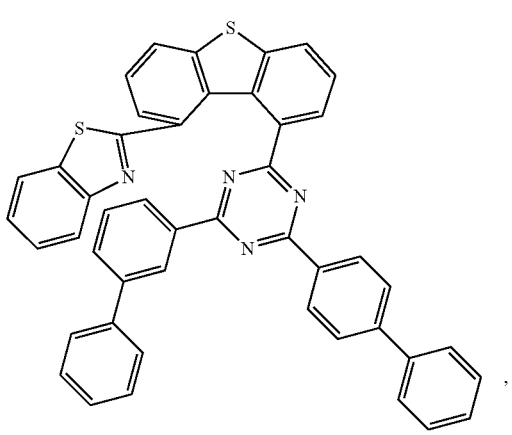
136
-continued
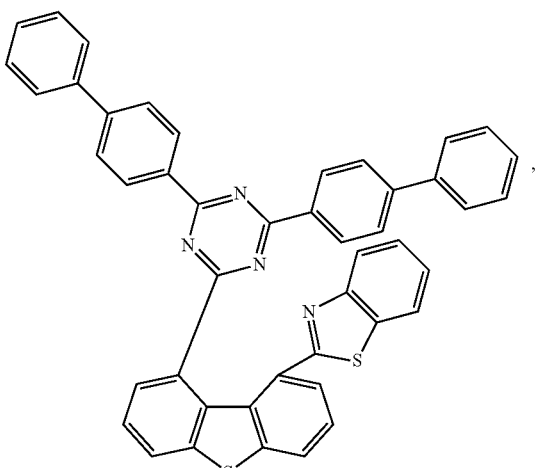
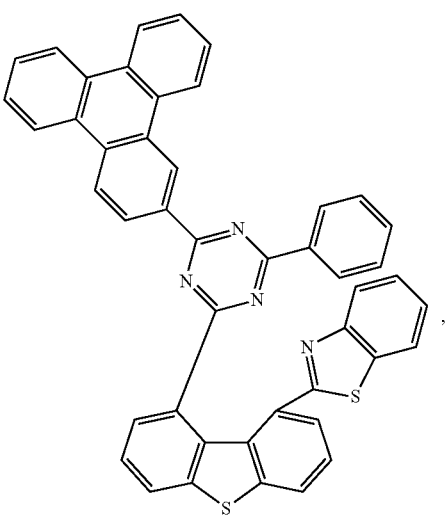
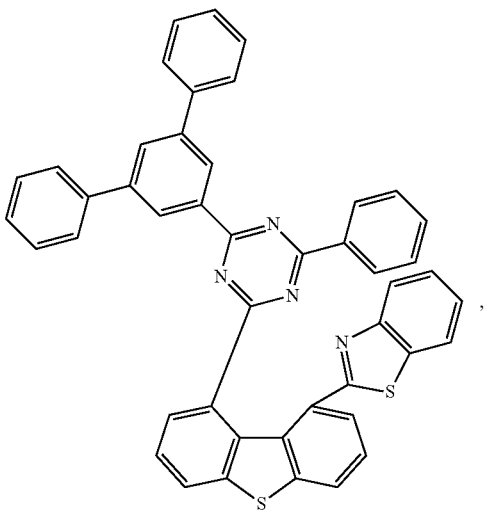

137
-continued
138
-continued
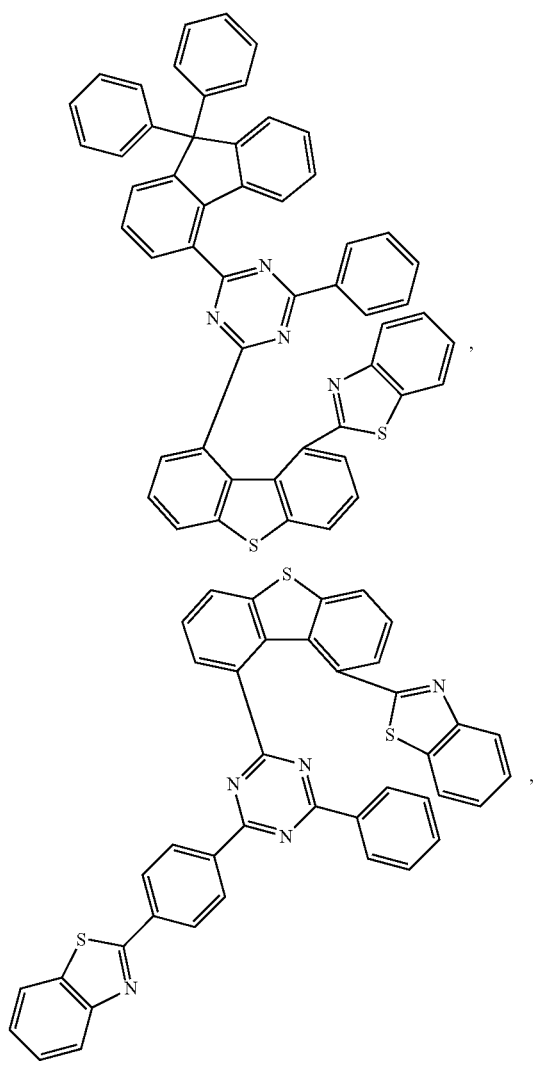
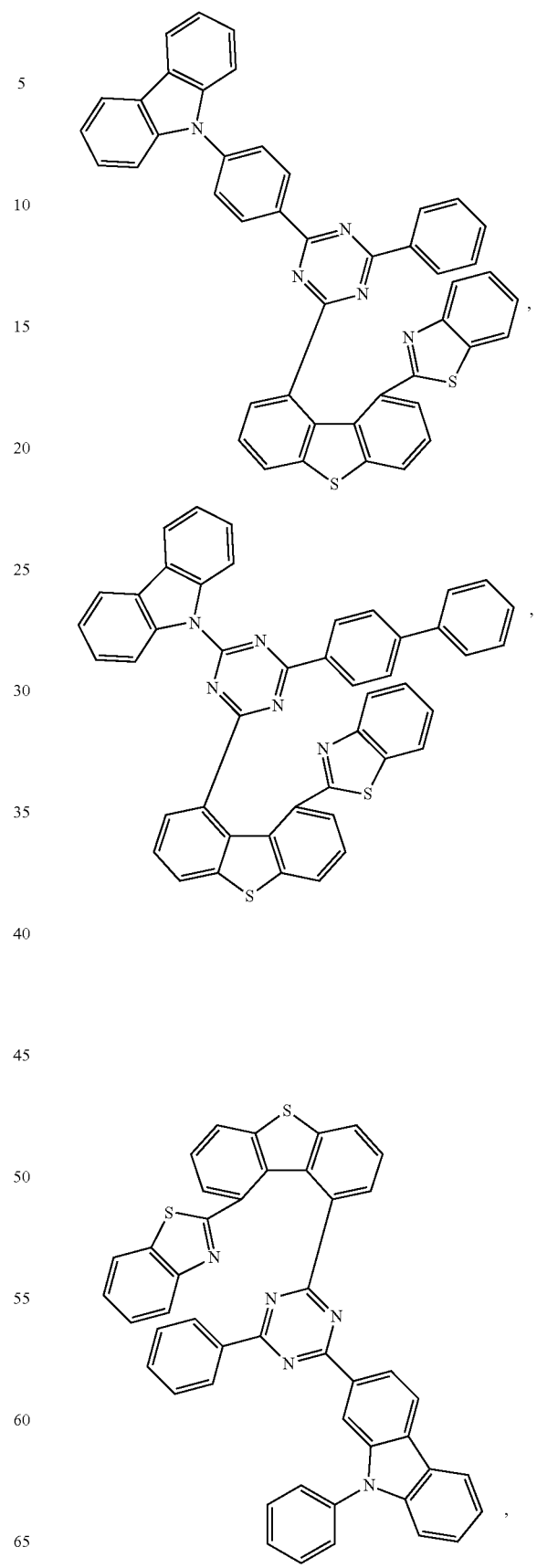

139
-continued
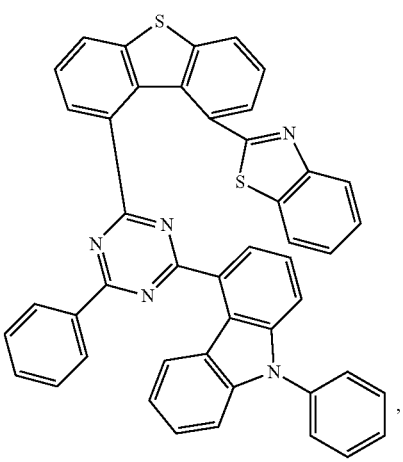
,
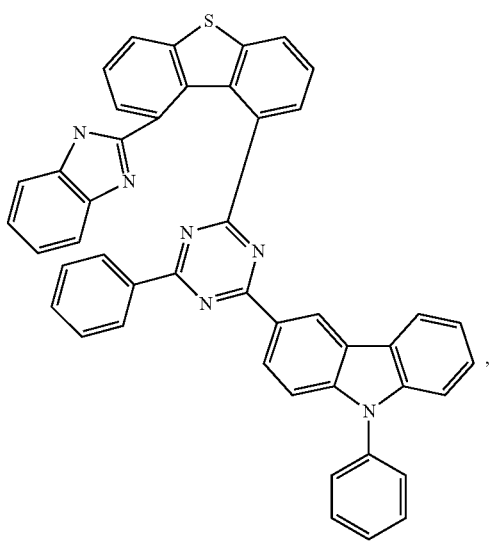
,
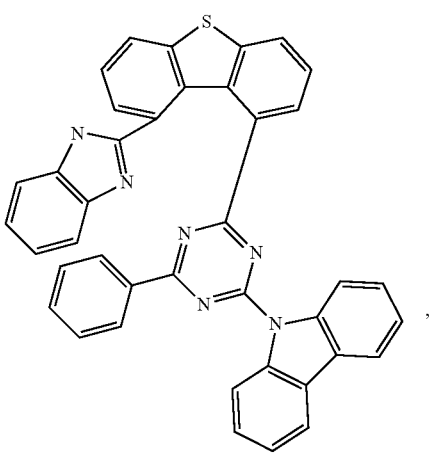
,
140
-continued
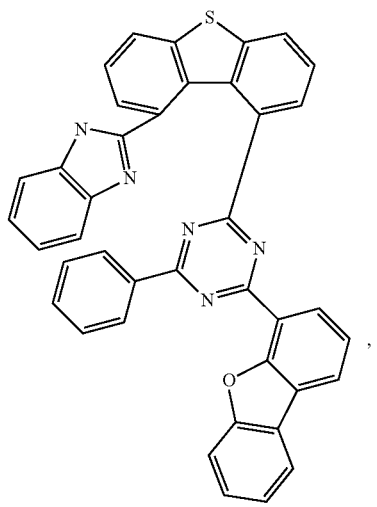
,
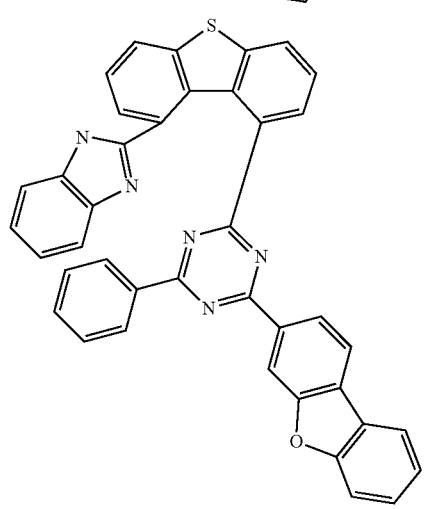
,
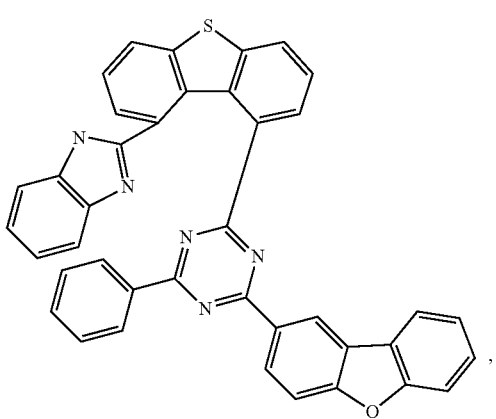
, -continued
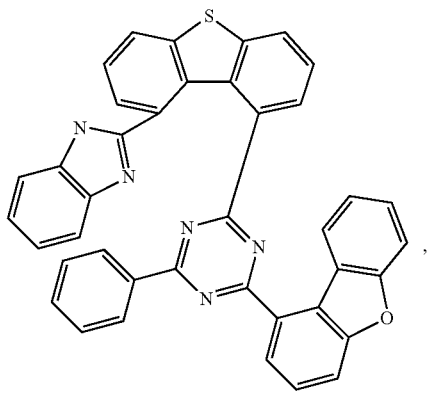
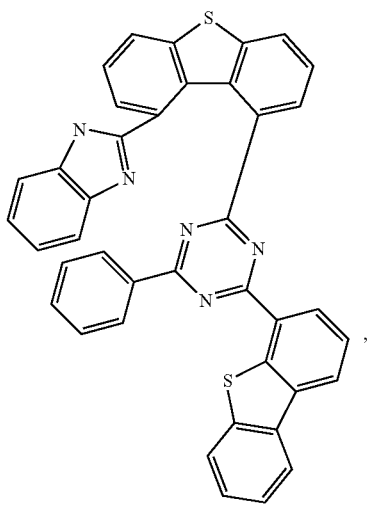
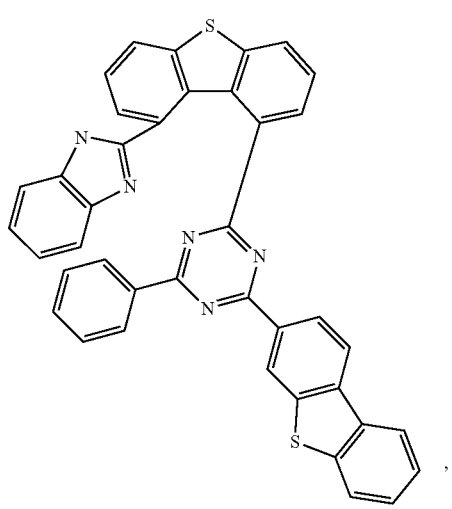
-continued
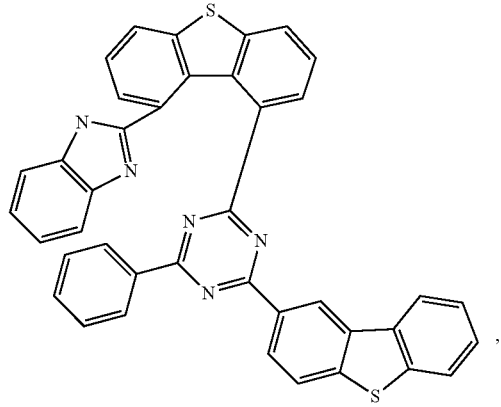
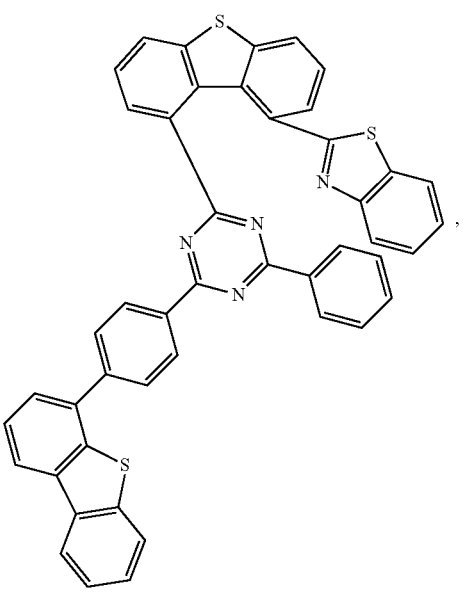

143
-continued
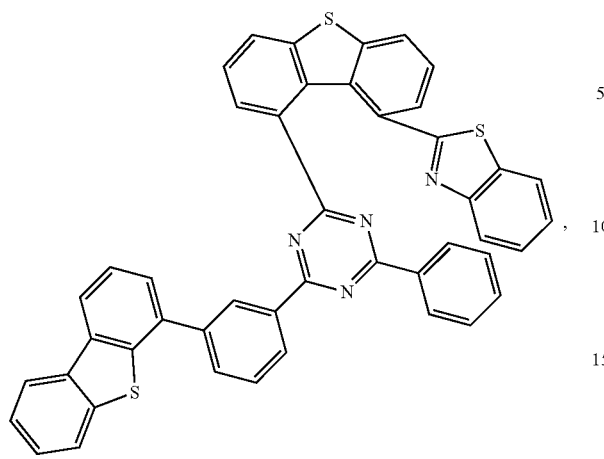
,
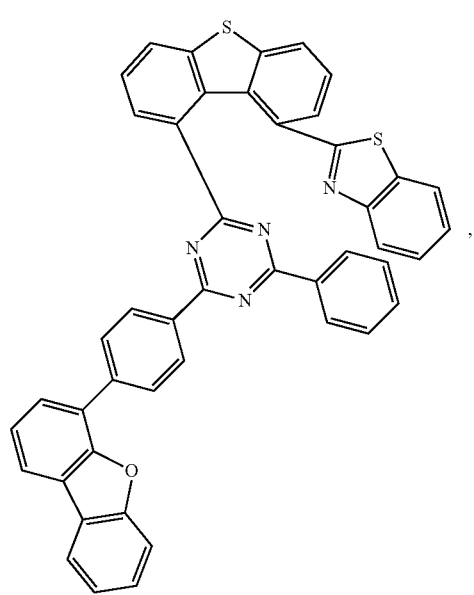
,
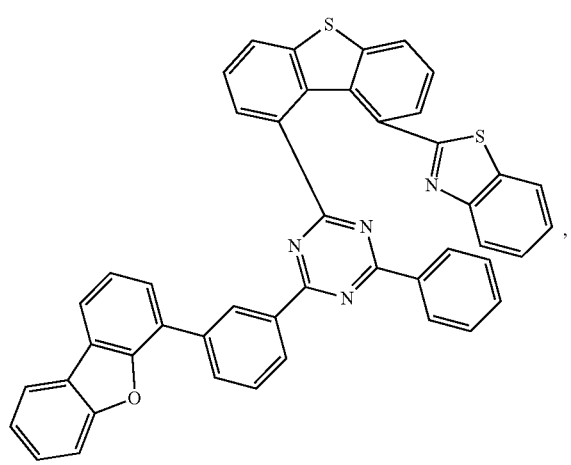
,
144
-continued
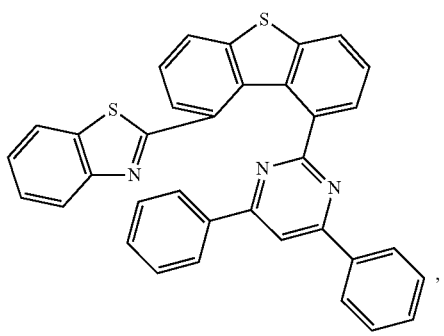
,
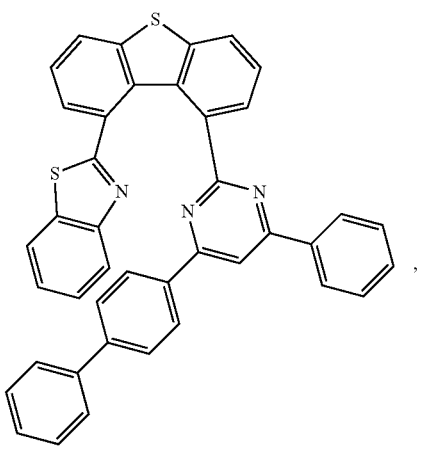
,
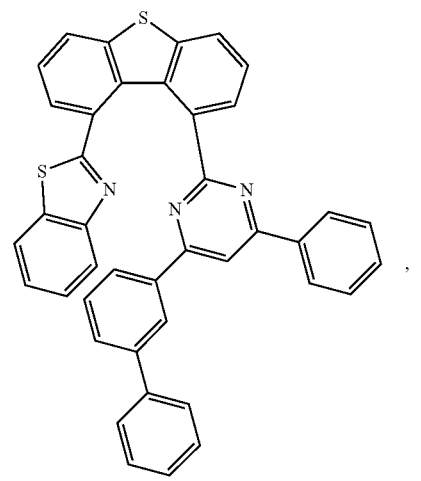
,
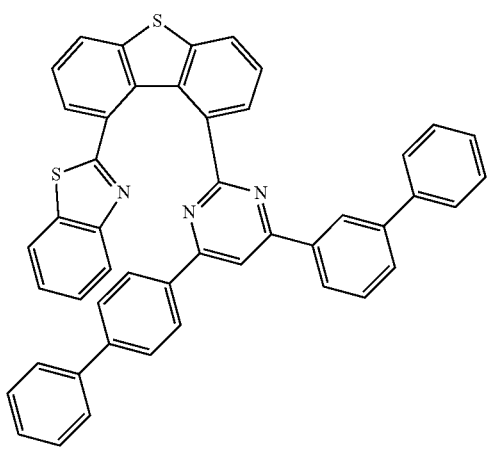
,

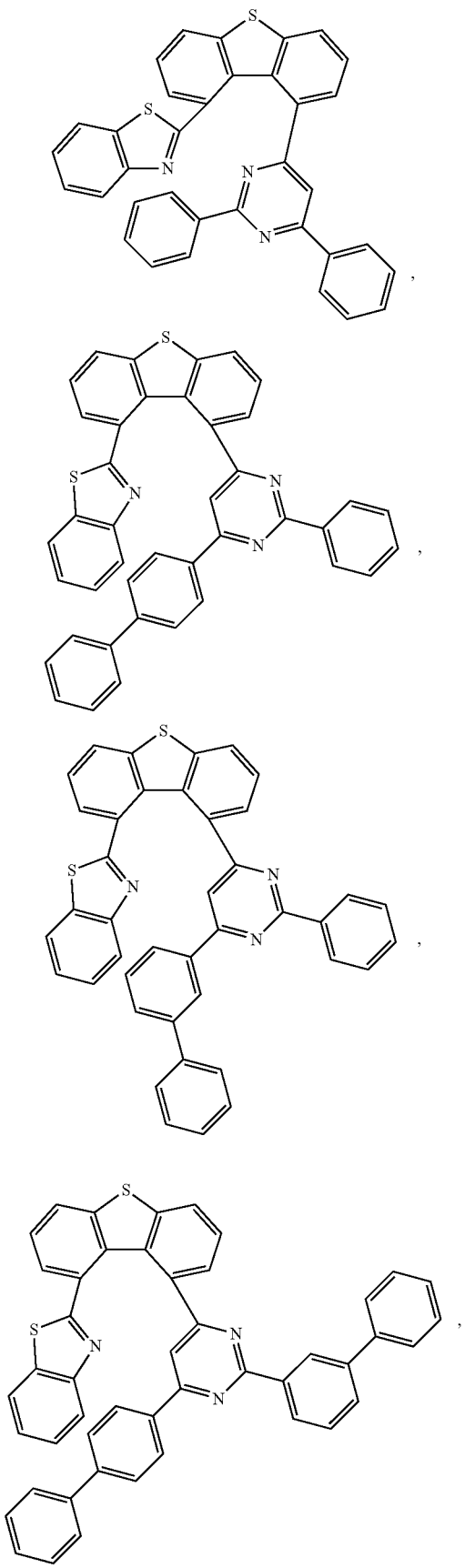

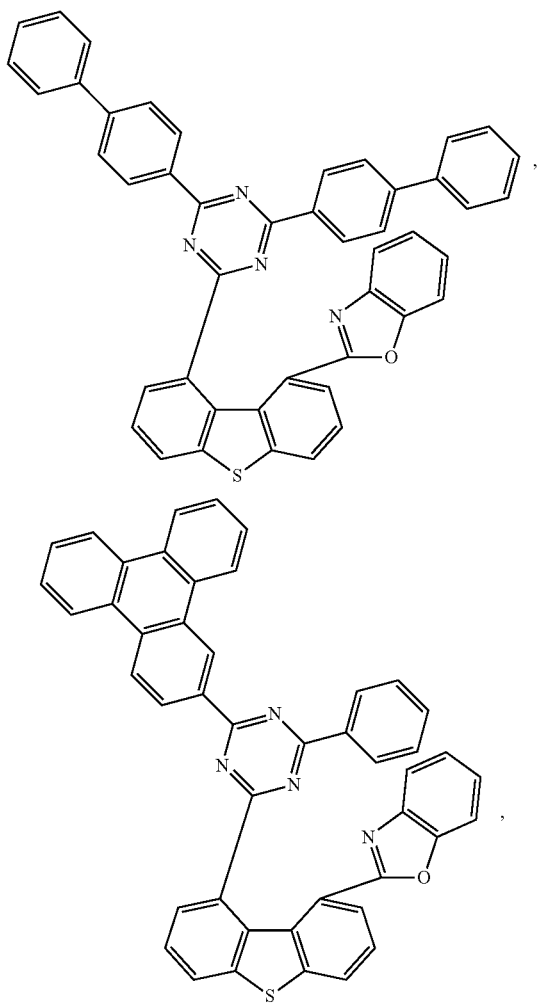
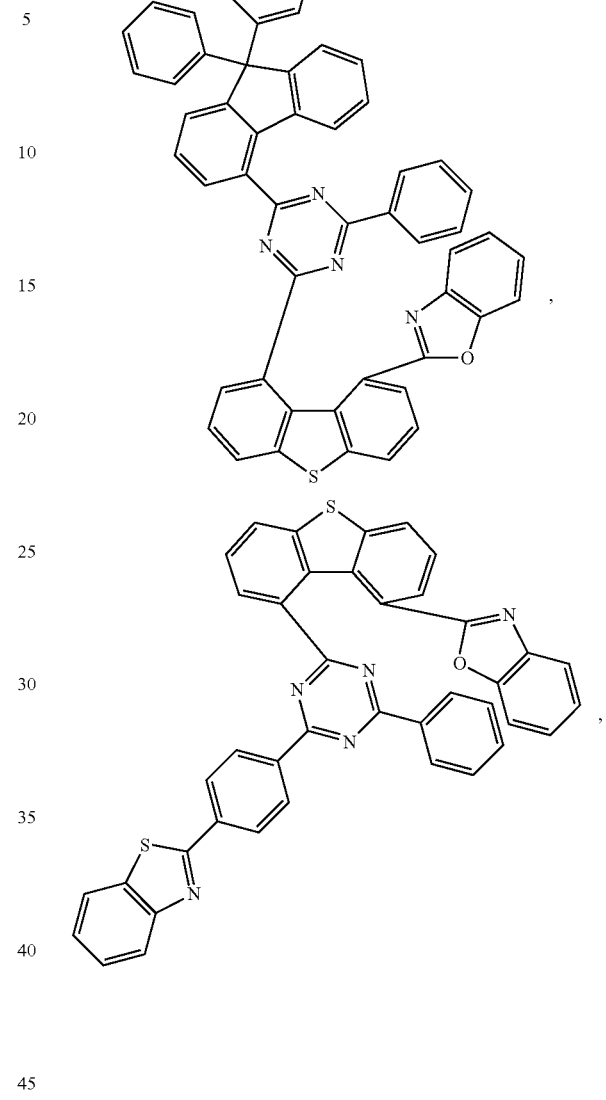
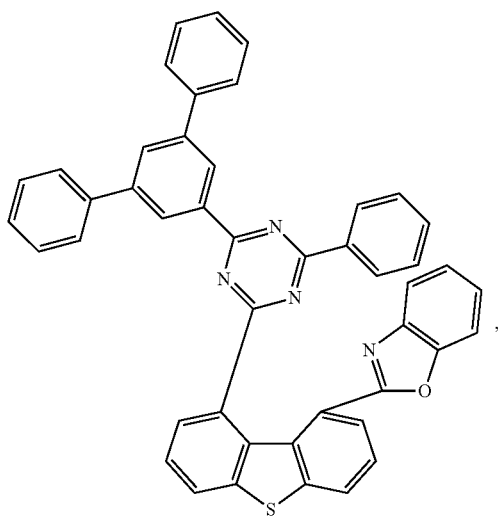
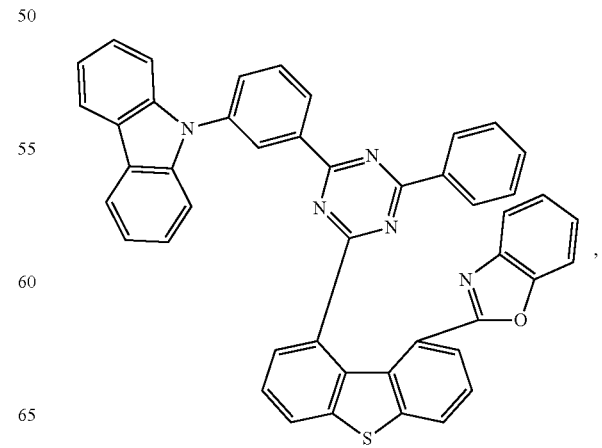

149
-continued
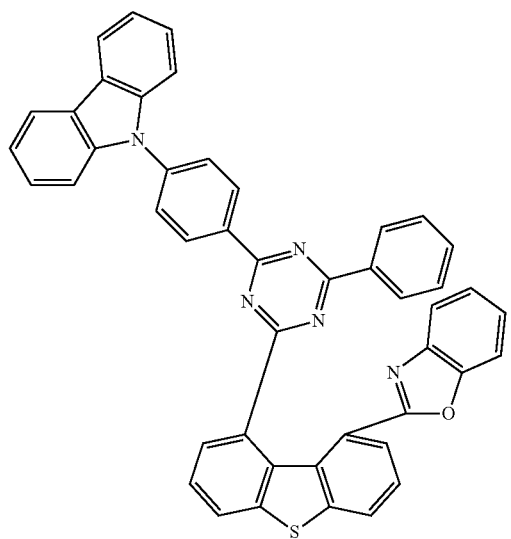
,
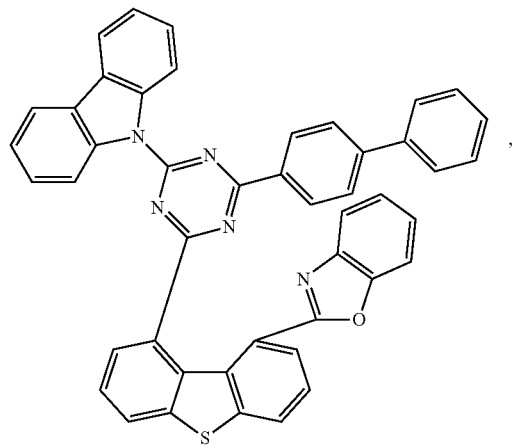
,
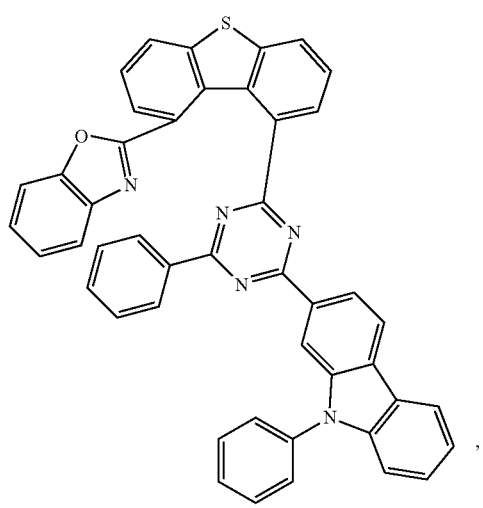
,
150
-continued
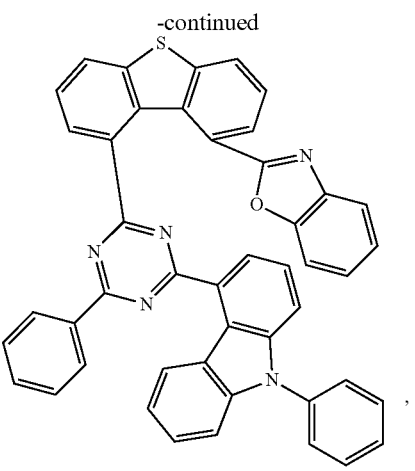
,
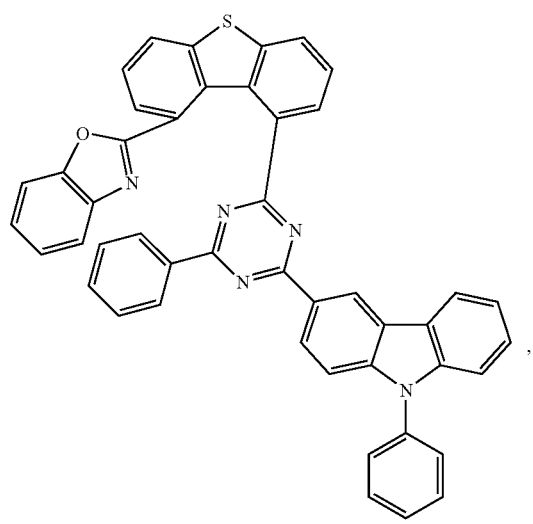
,
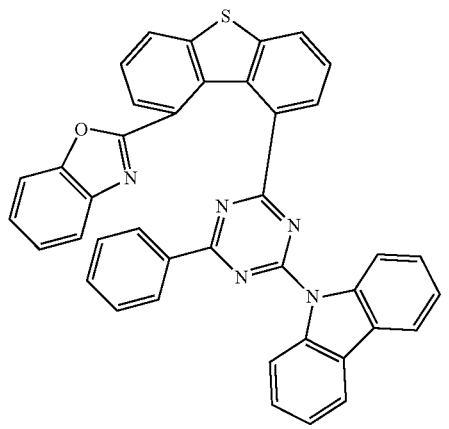
, 151
-continued

152
-continued

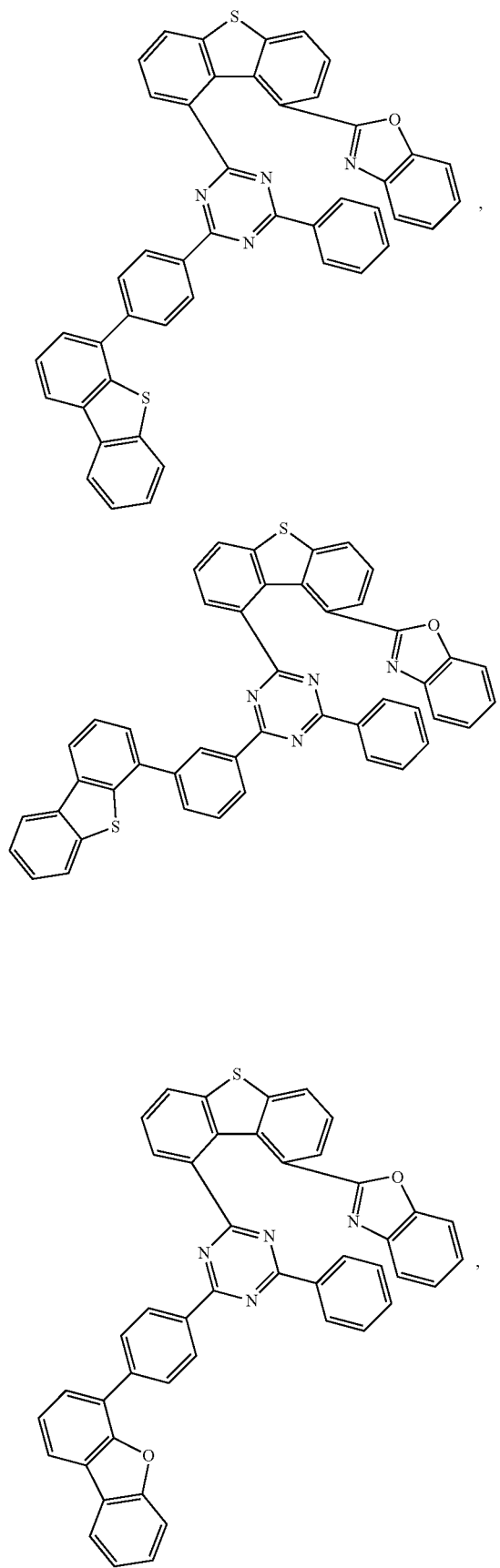

155
-continued
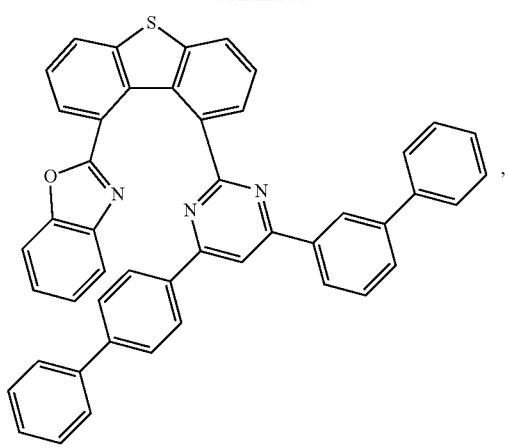
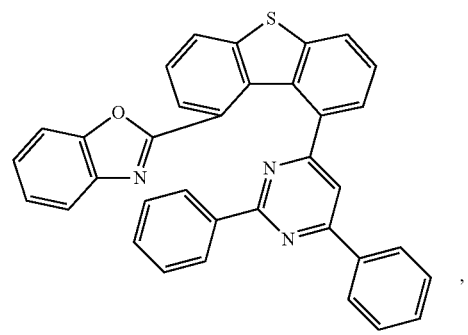
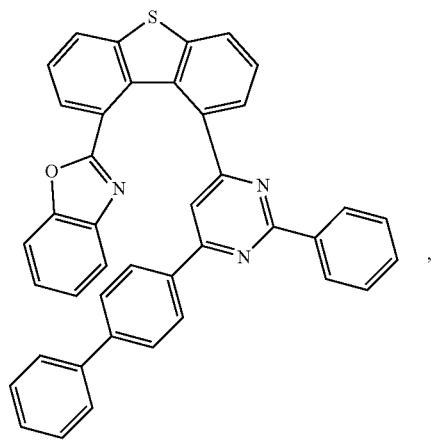
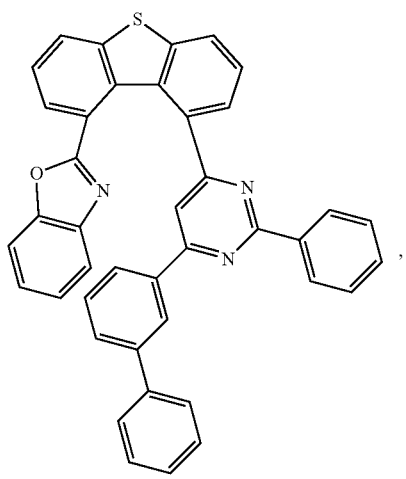
156
-continued
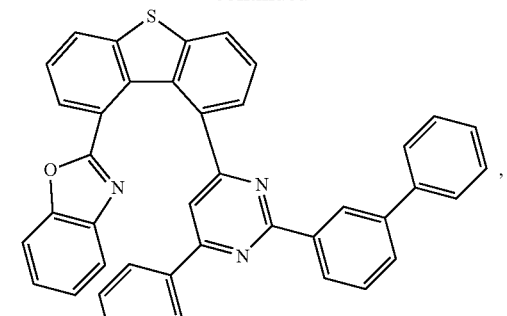
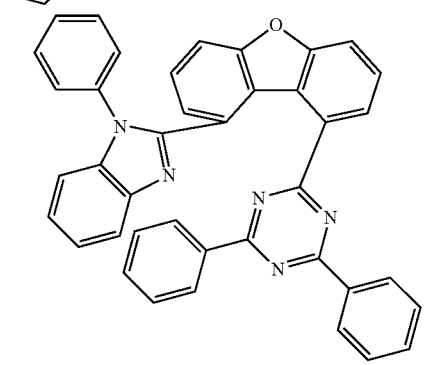
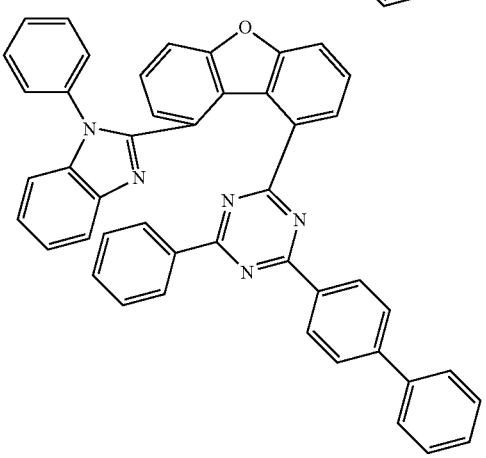
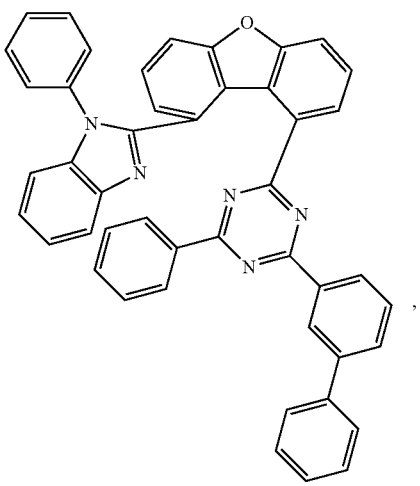

157
-continued
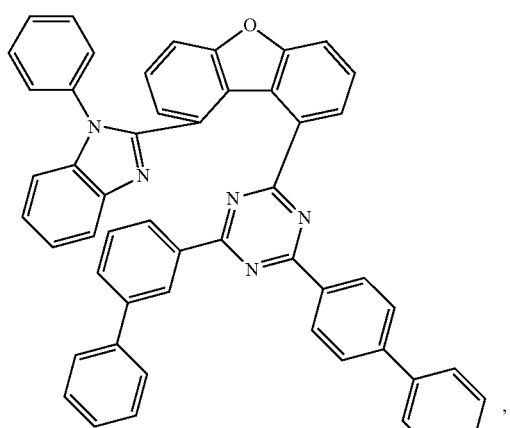
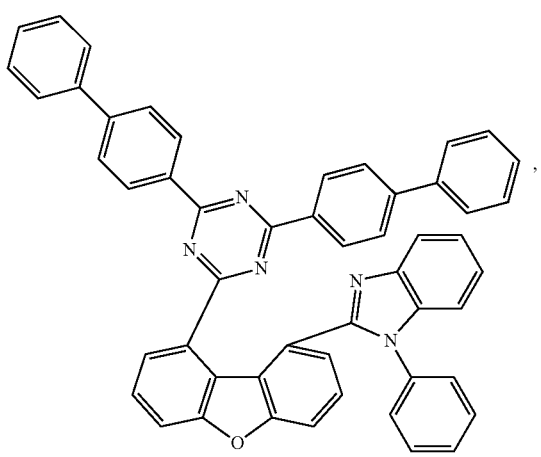
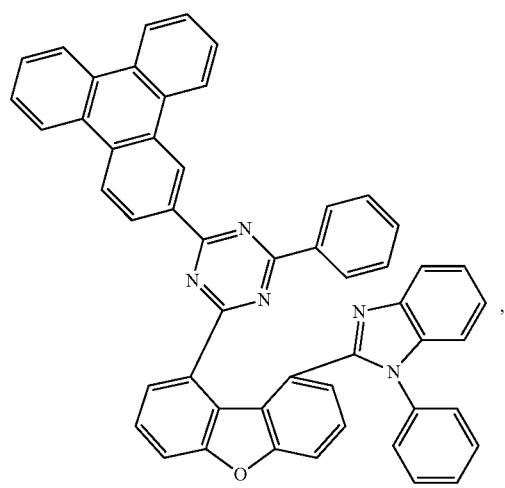
158
-continued
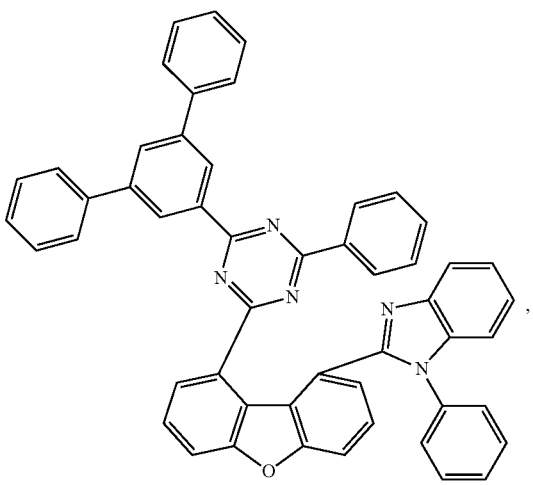
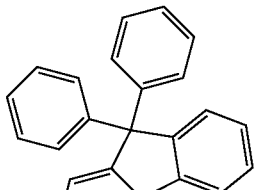
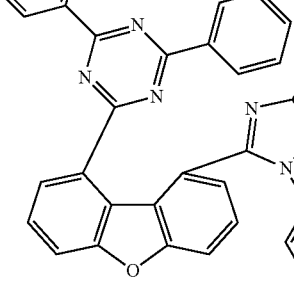
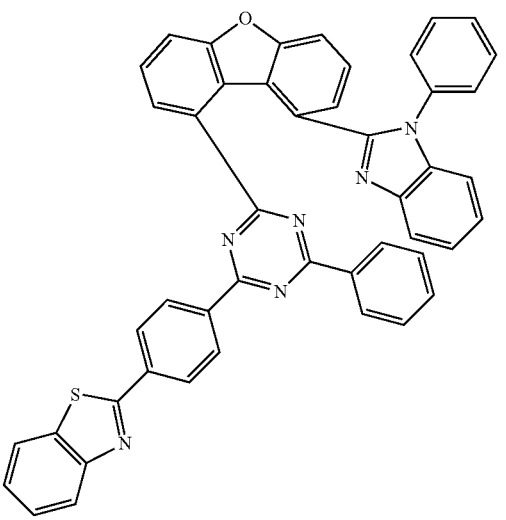

159
-continued
160
-continued
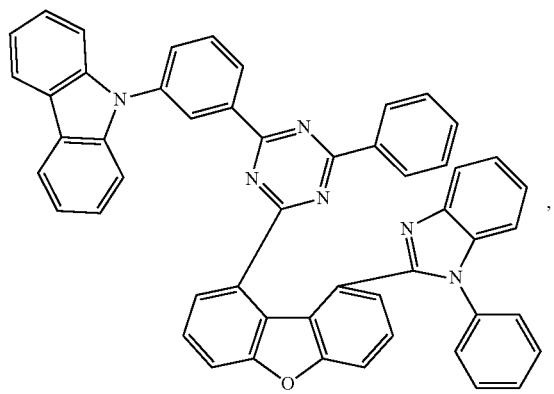
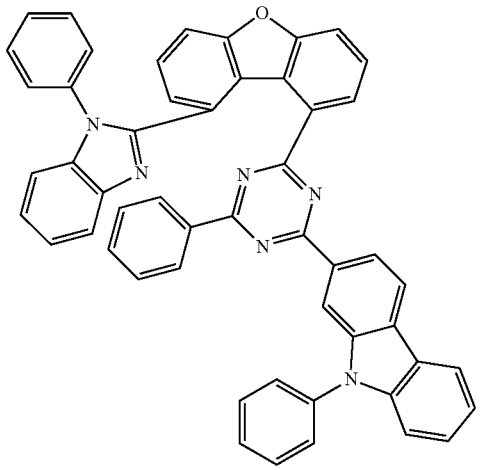
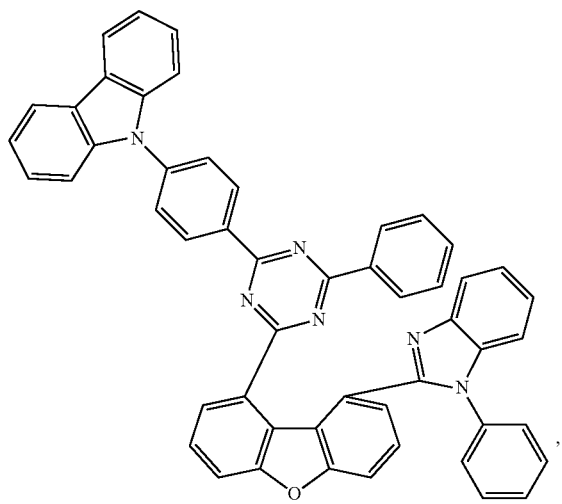
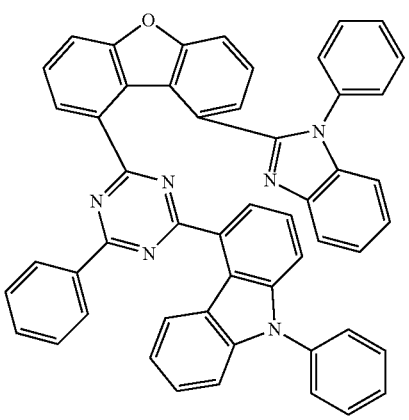
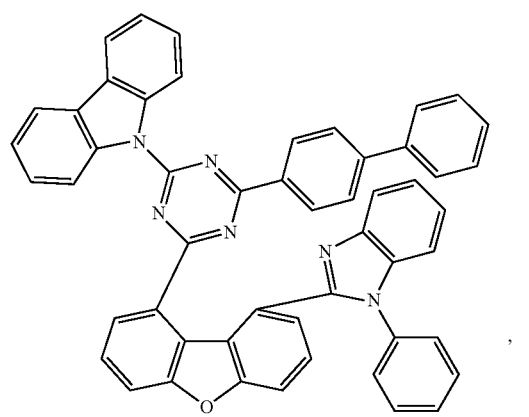
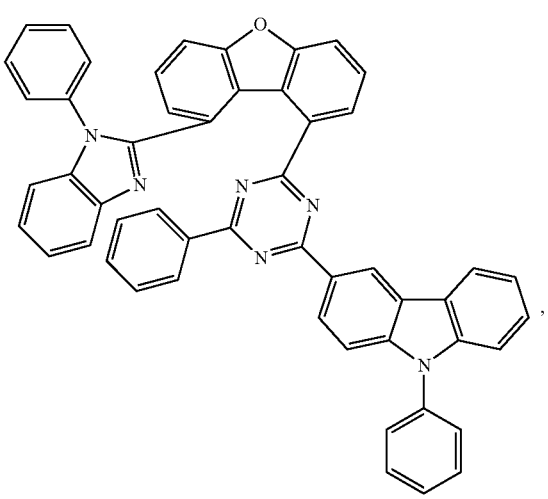

161
-continued
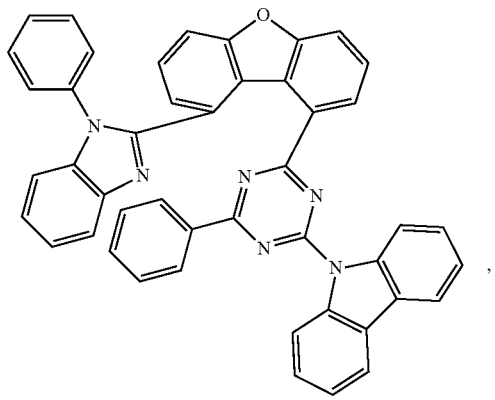
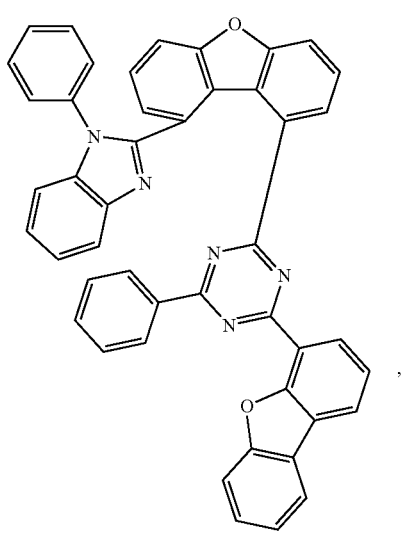
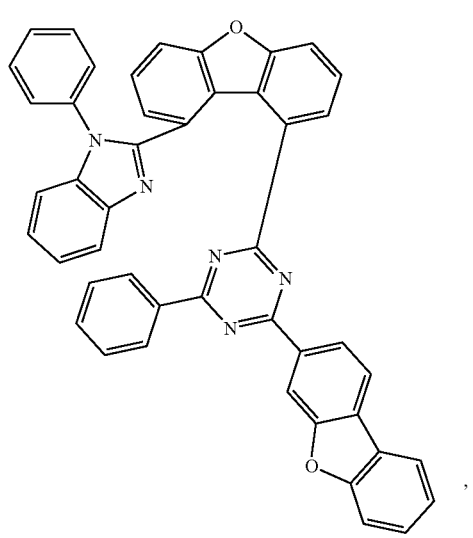
162
-continued
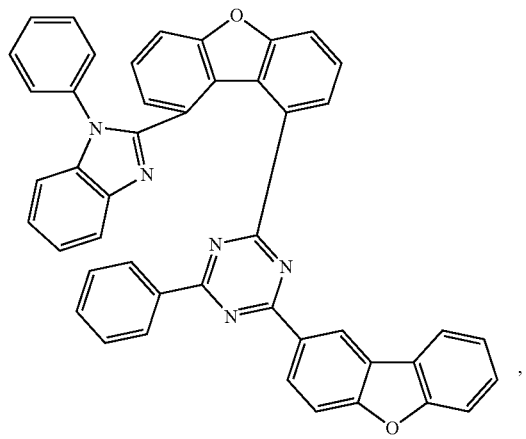
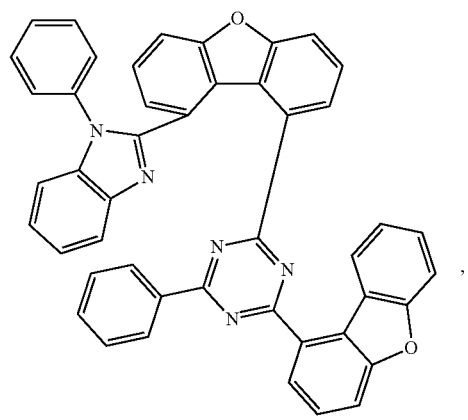
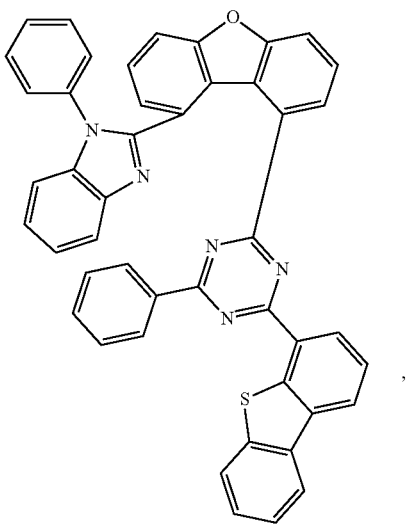

-continued
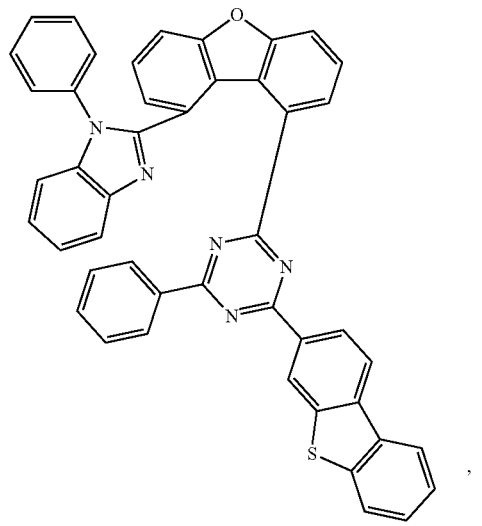
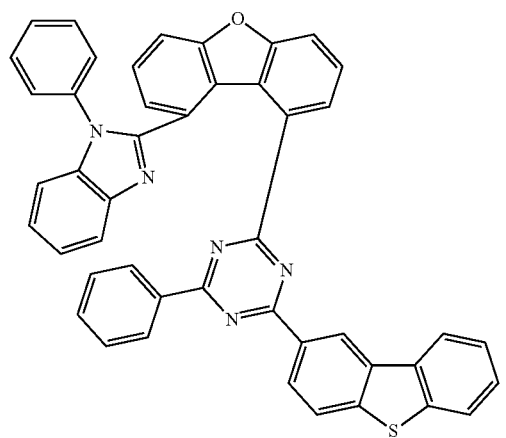
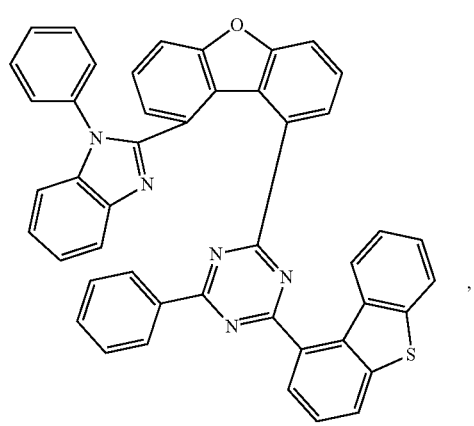
-continued
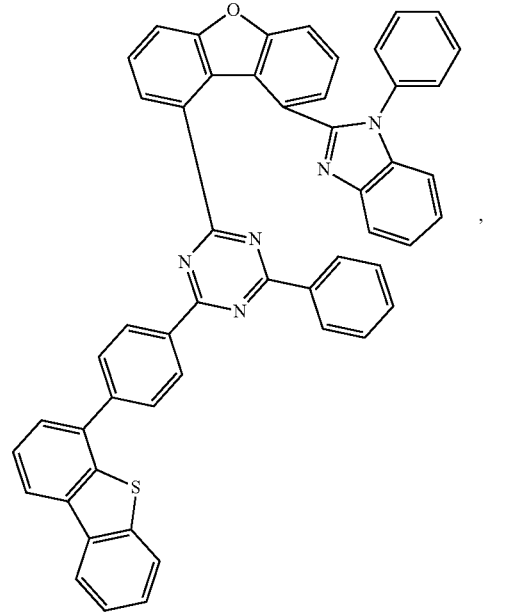
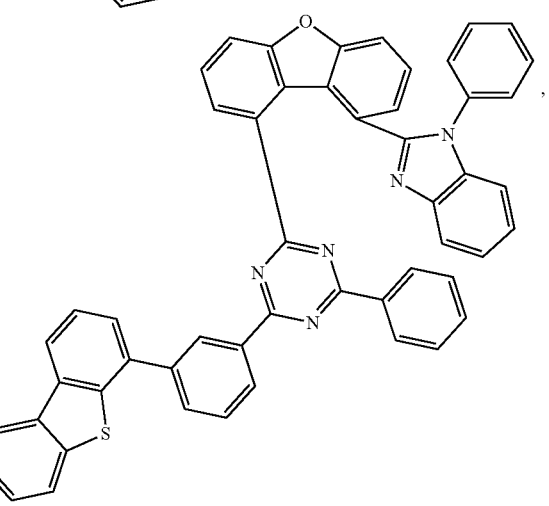
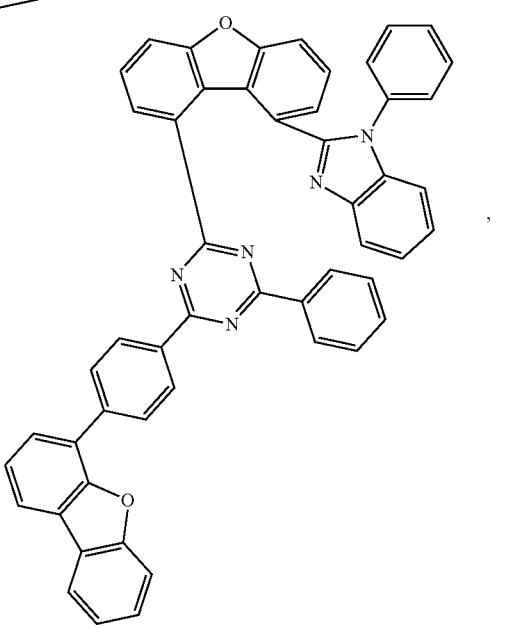

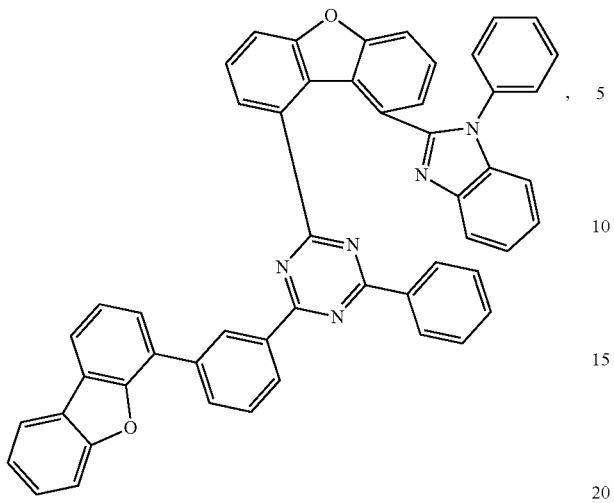
,
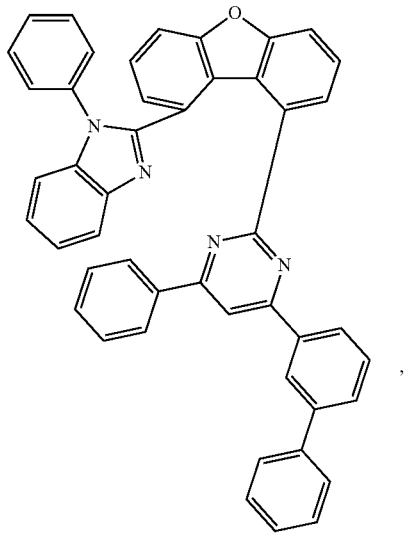
,
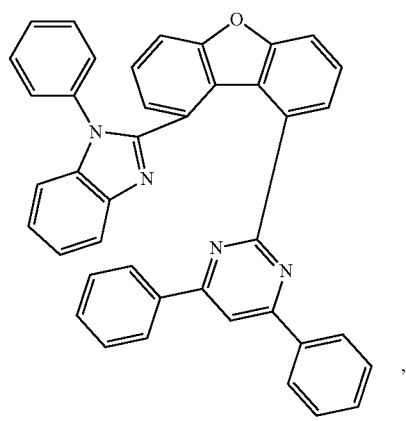
,
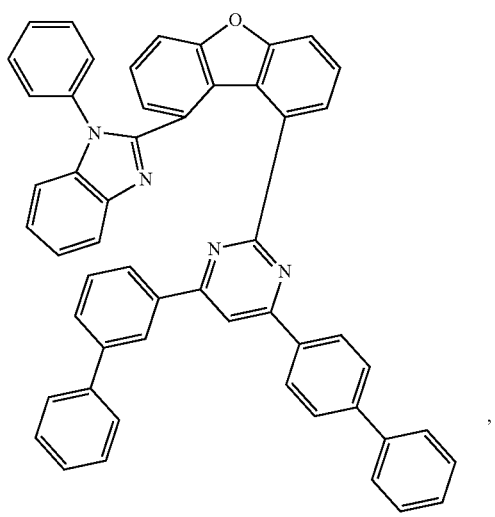
,
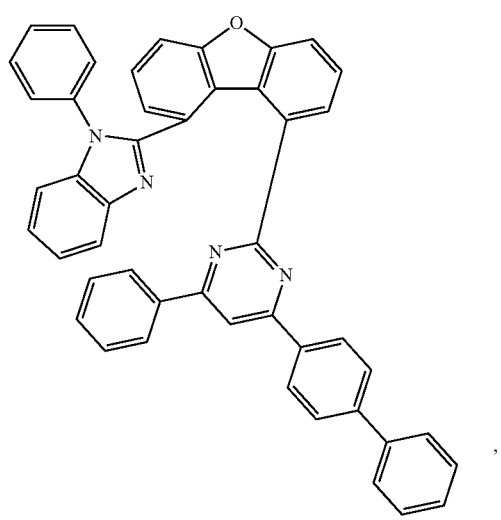
,
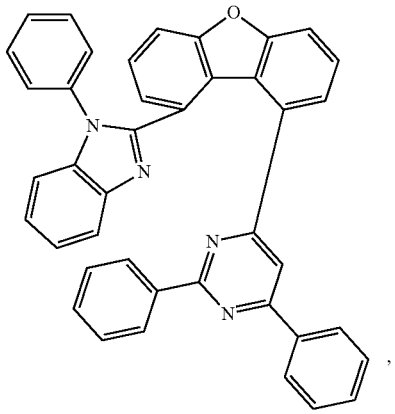
, 167
-continued
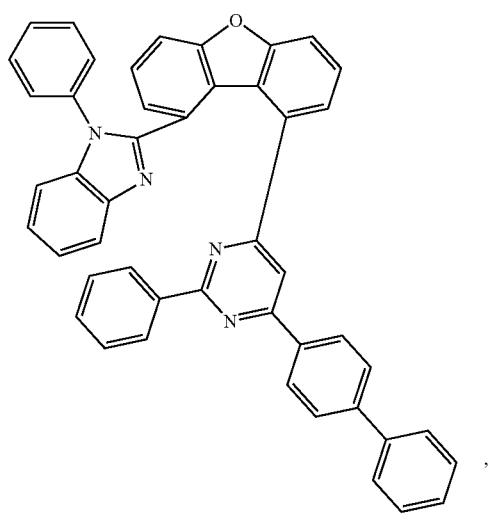
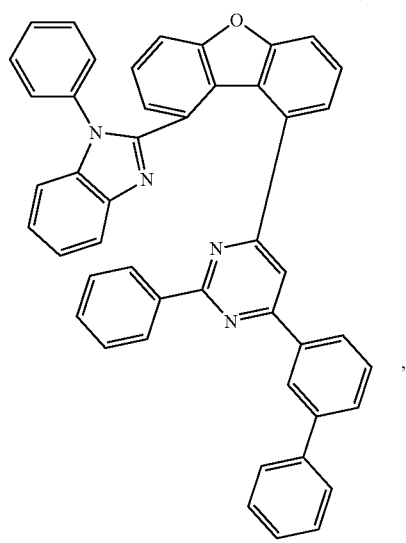
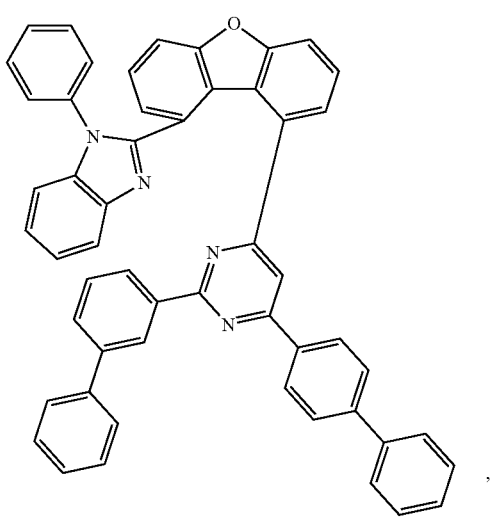
168
-continued
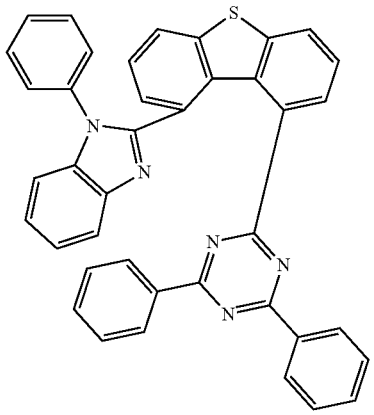
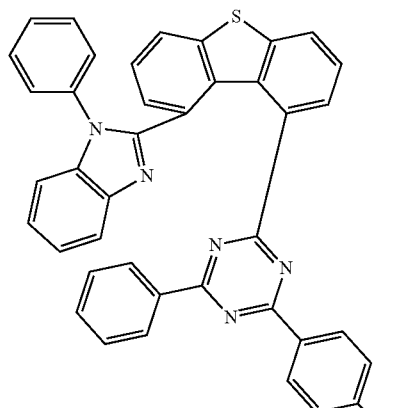
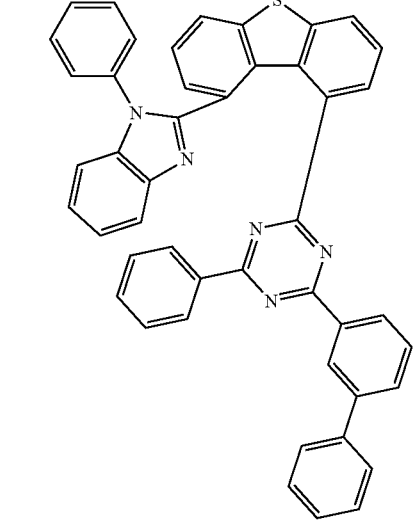

169
-continued
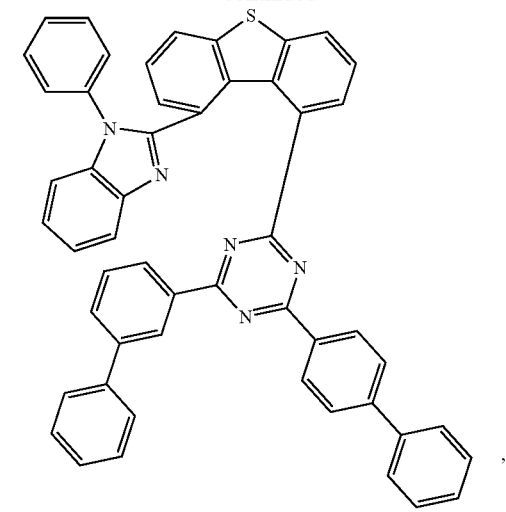
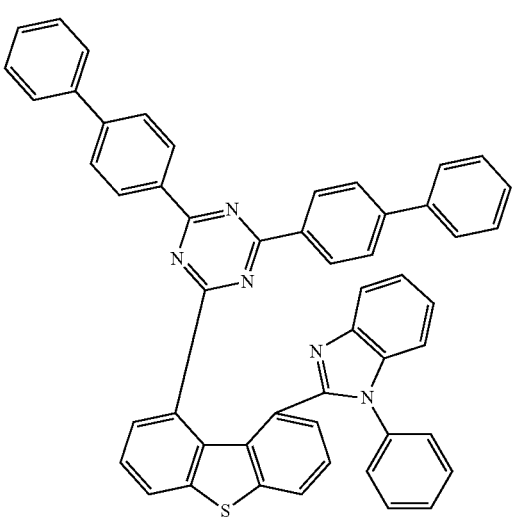
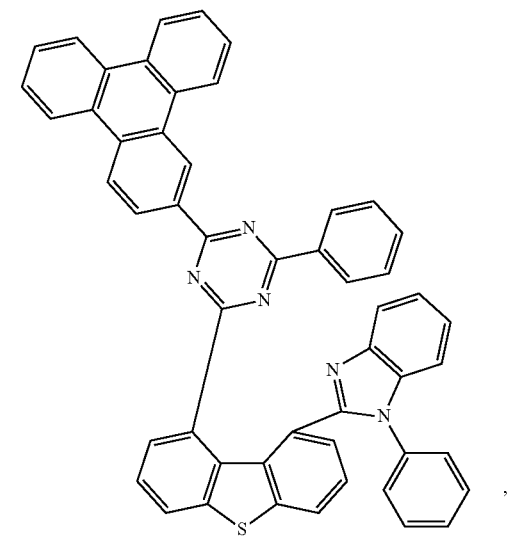
170
-continued
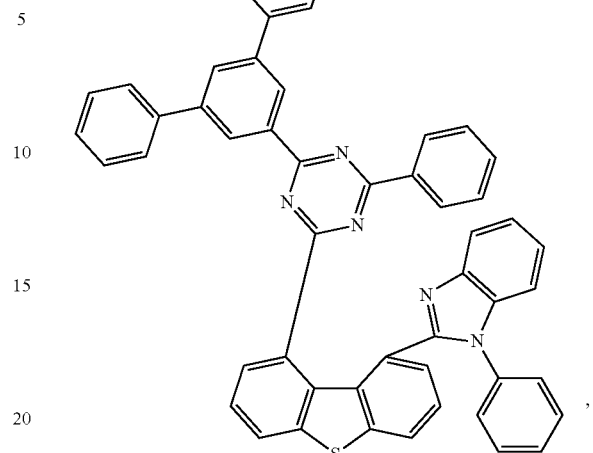
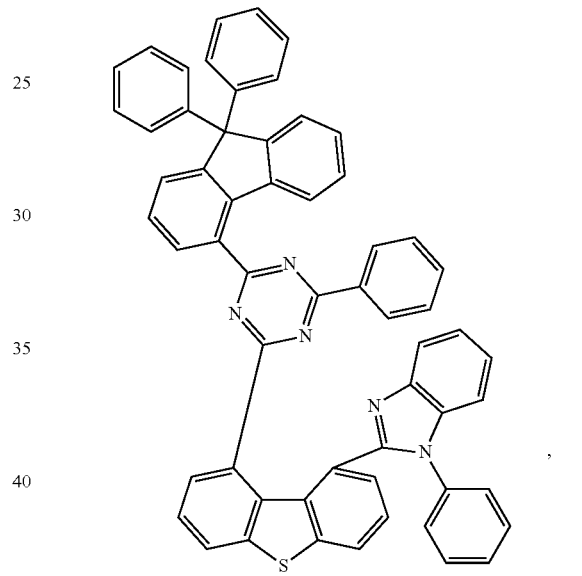
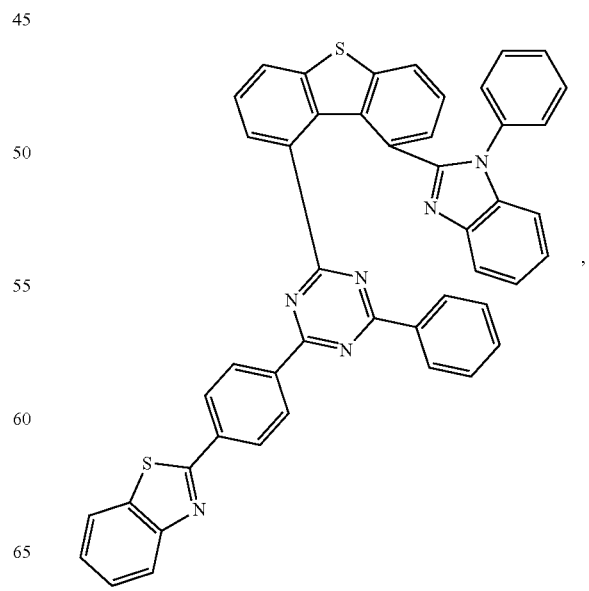

171
-continued
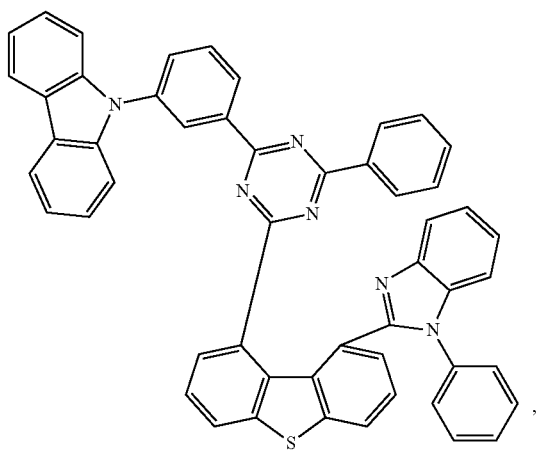
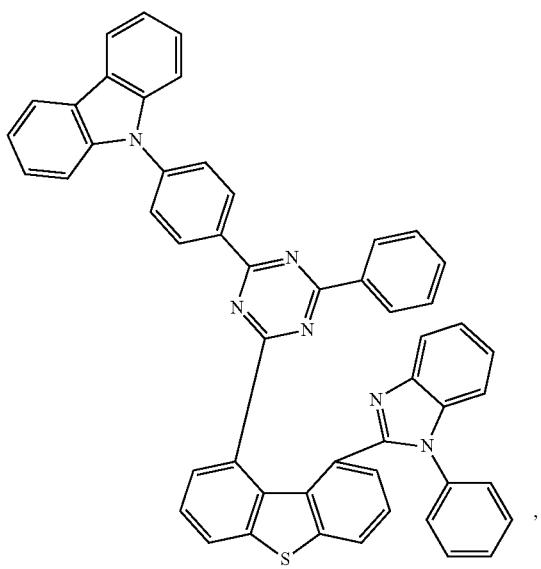
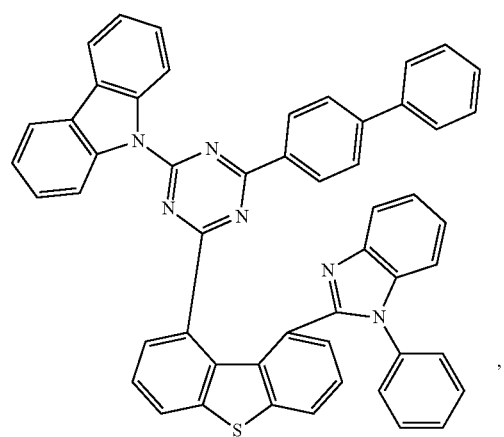
172
-continued
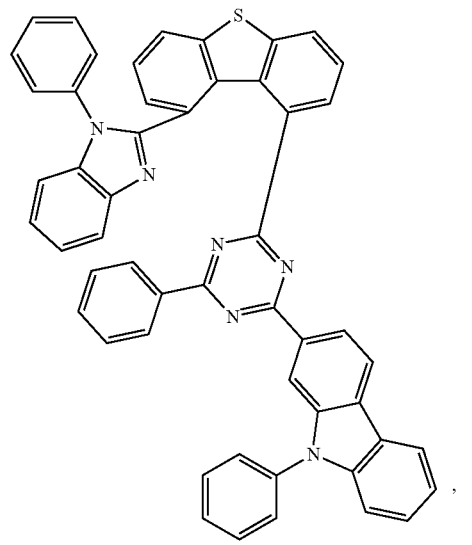
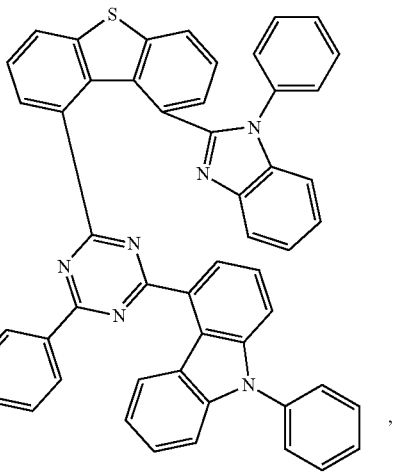
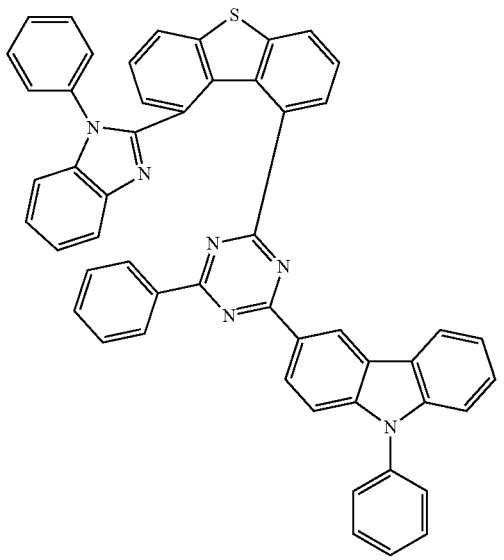

173
-continued
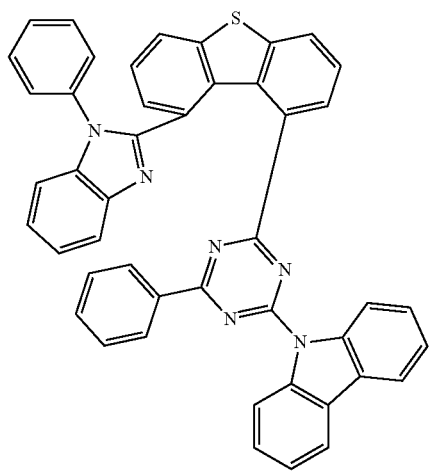
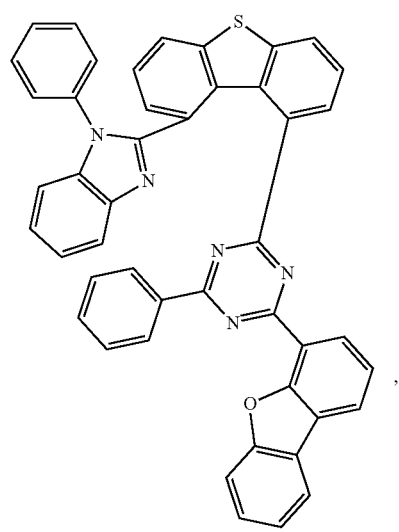
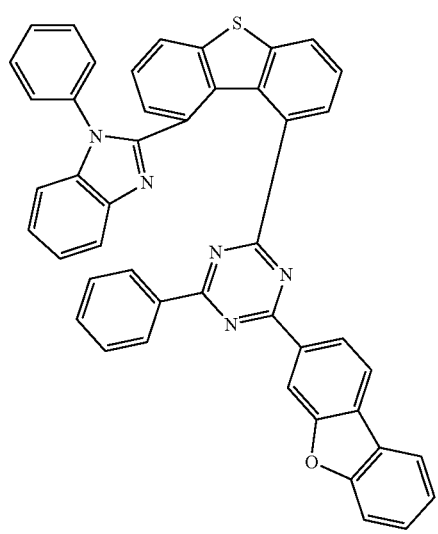
174
-continued
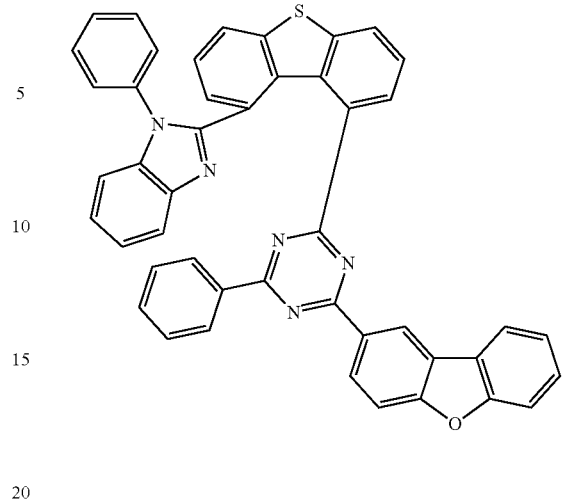
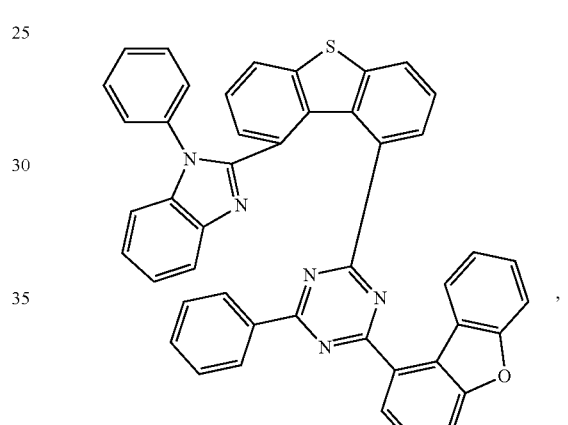
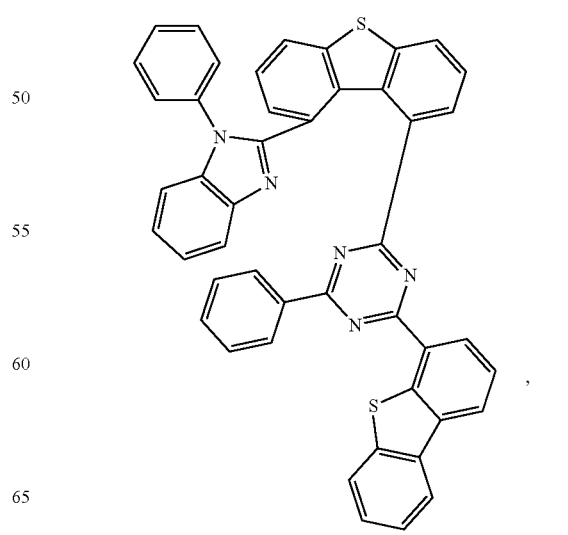

175
-continued
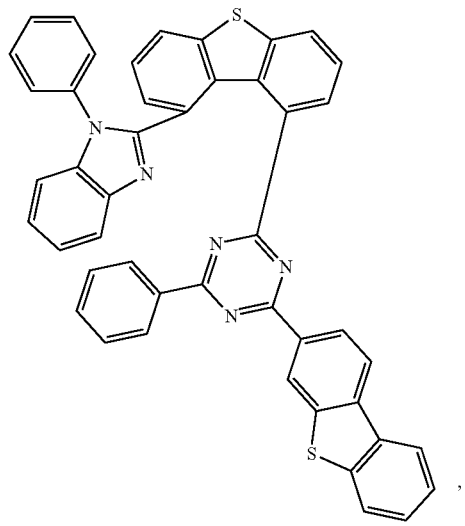
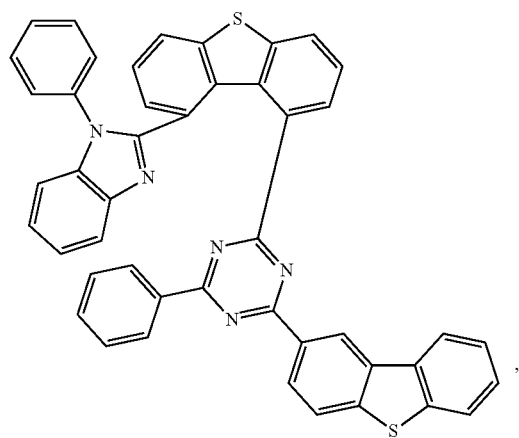
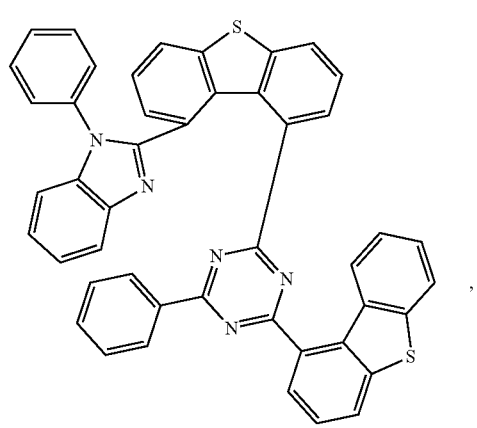
176
-continued
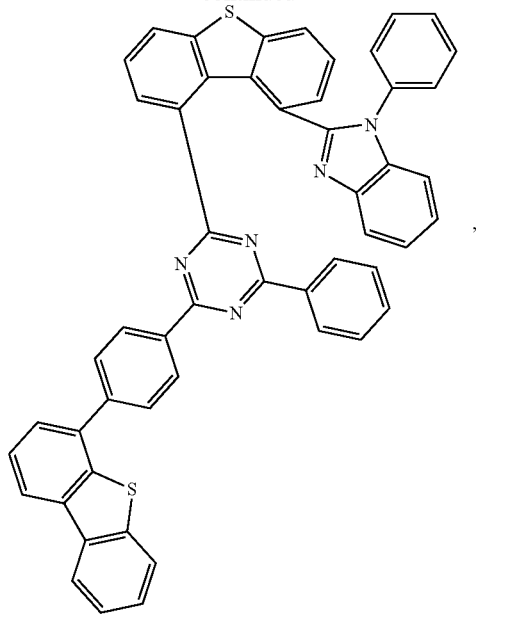
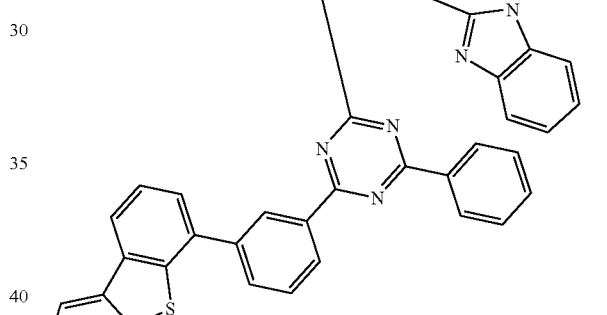
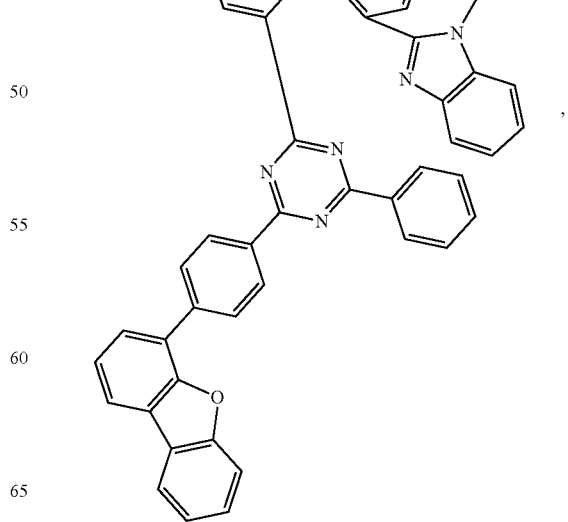

-continued
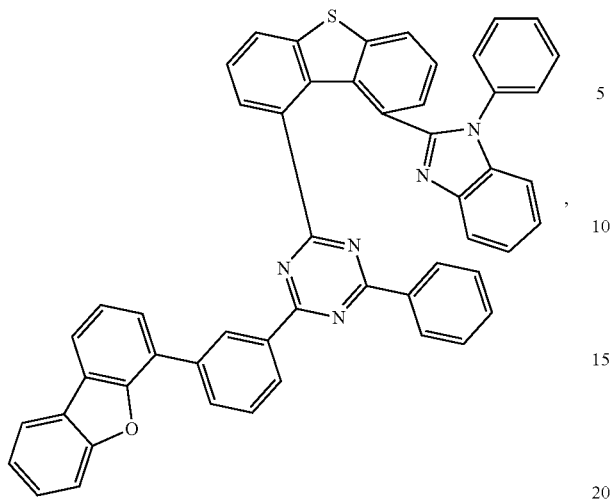
,
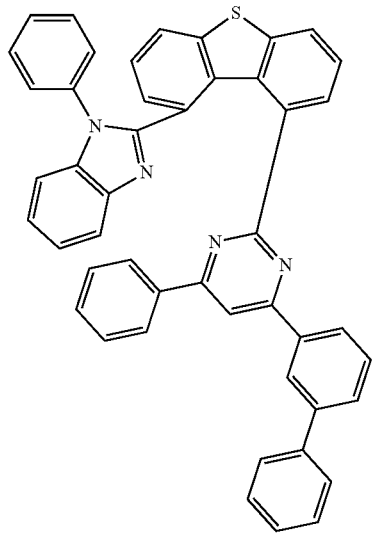
,
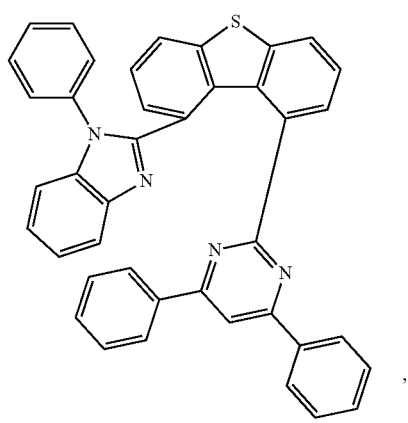
,
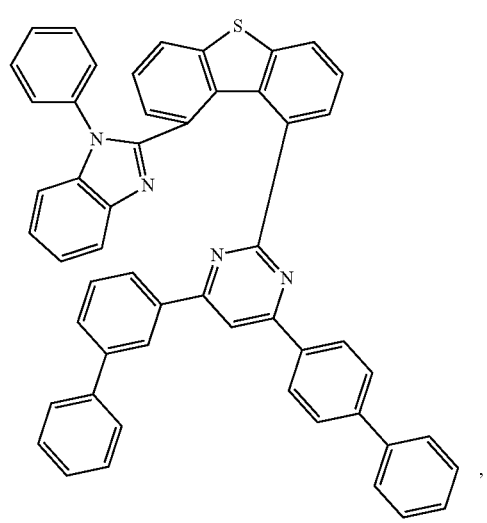
,
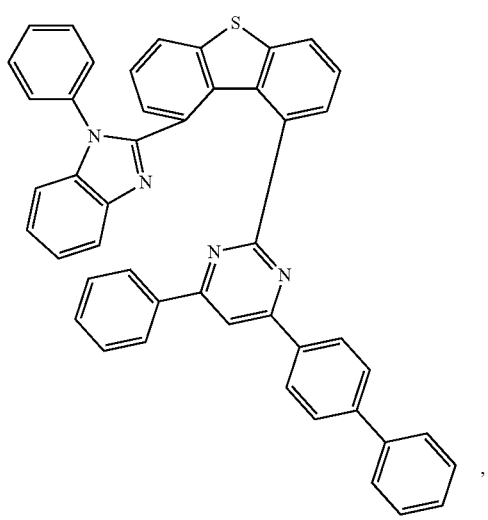
,
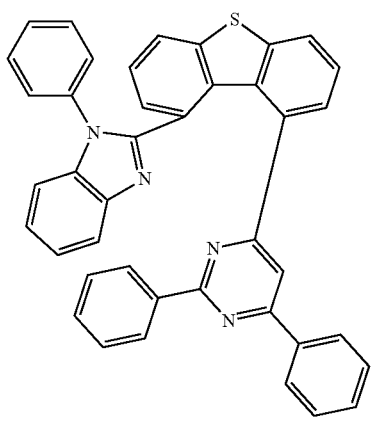
,

179
-continued
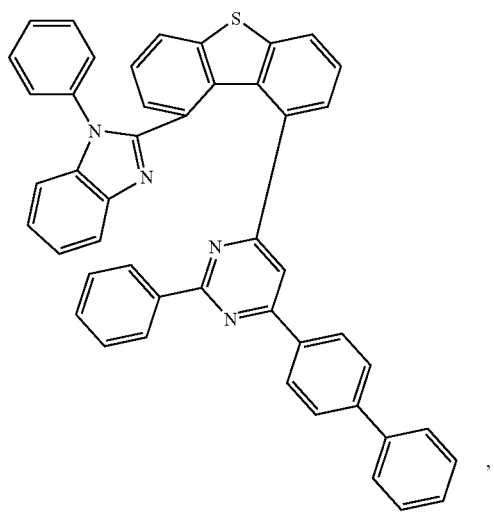
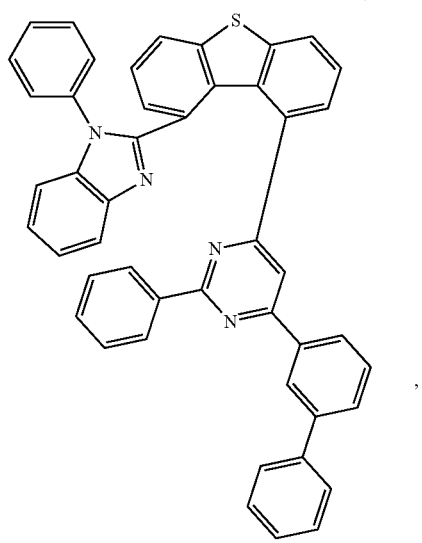
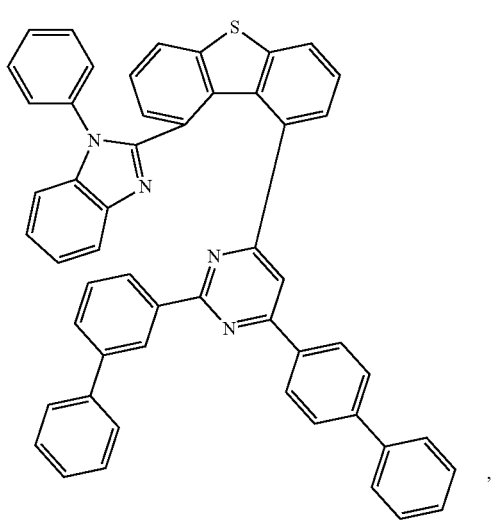
180
-continued
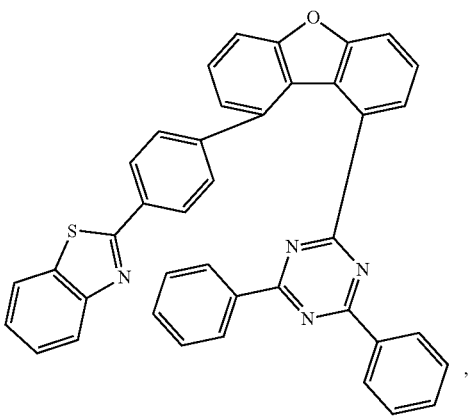
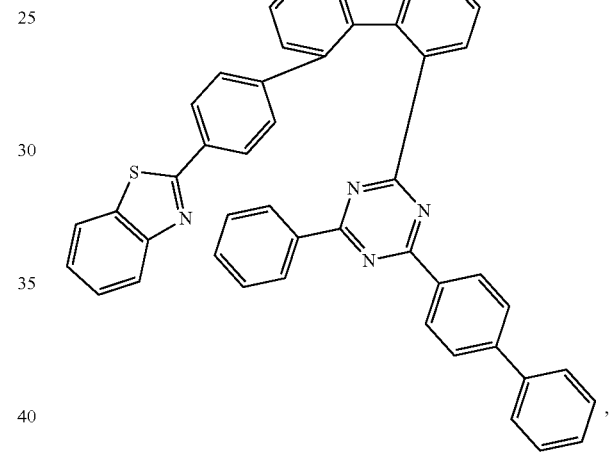
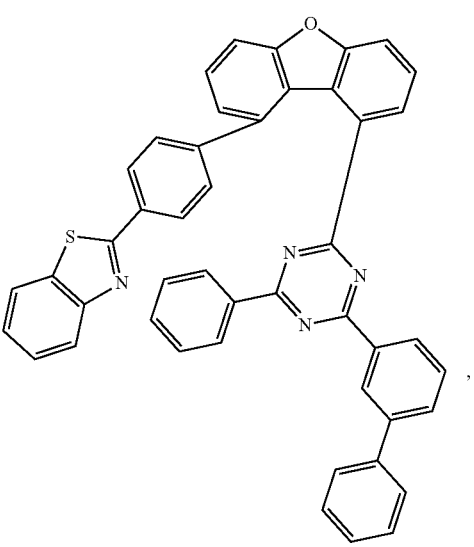

-continued
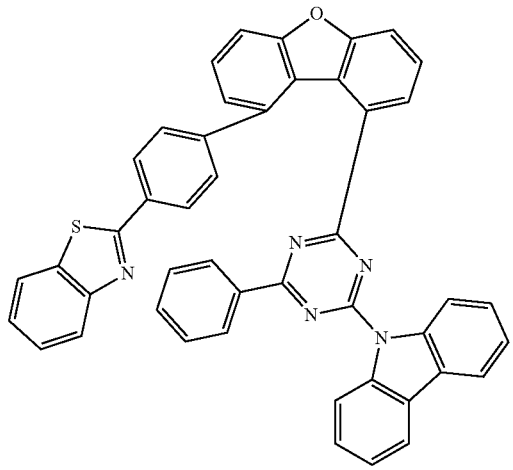
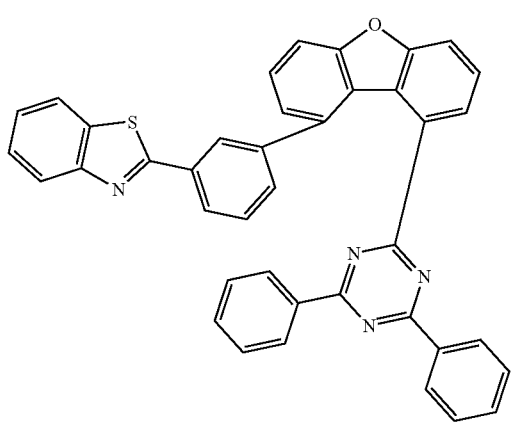
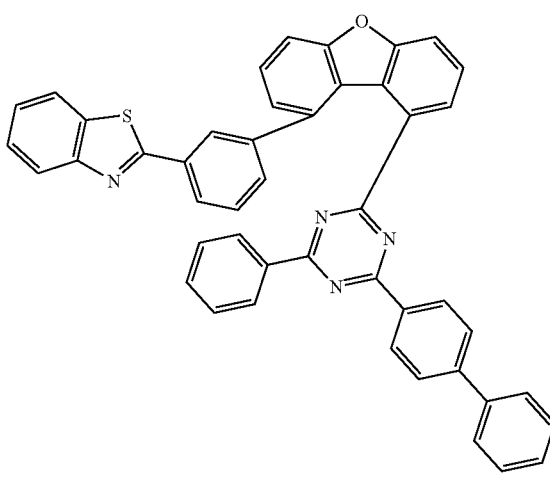
-continued
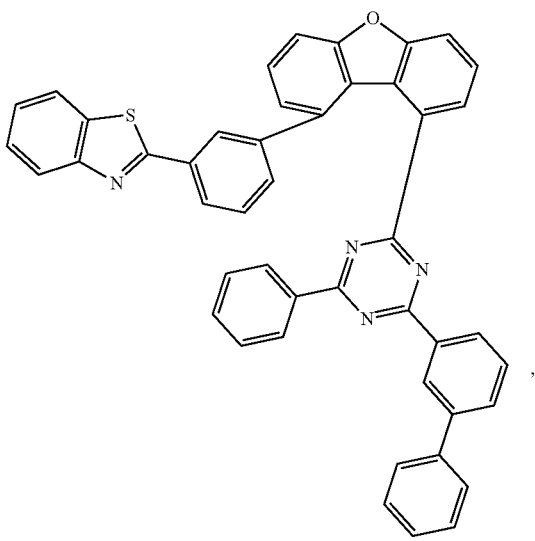
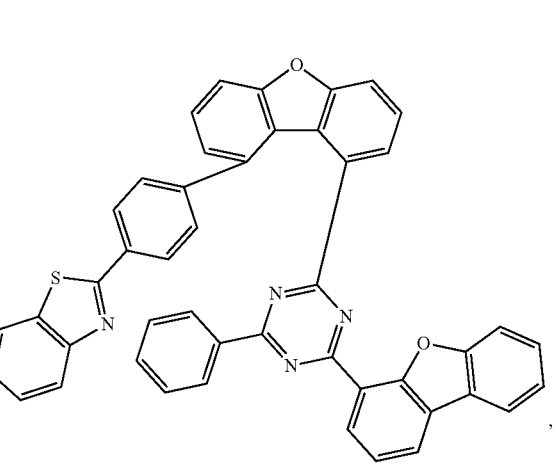

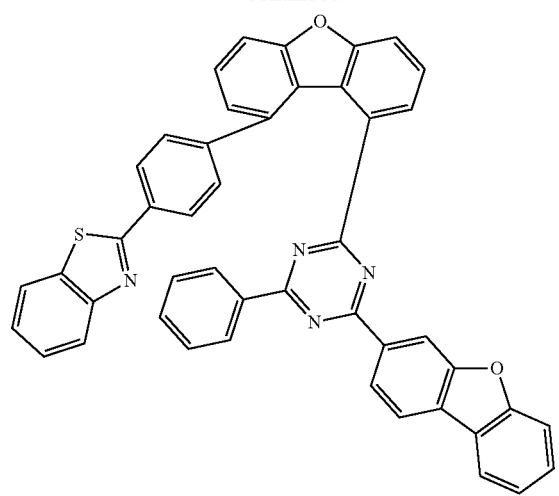
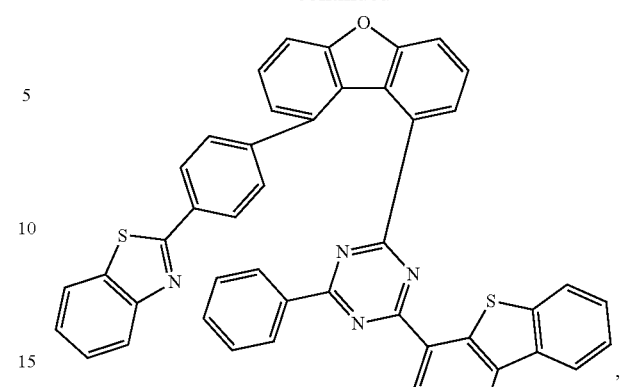
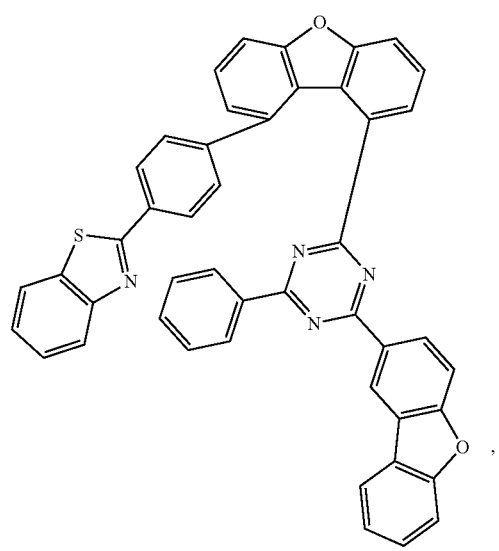
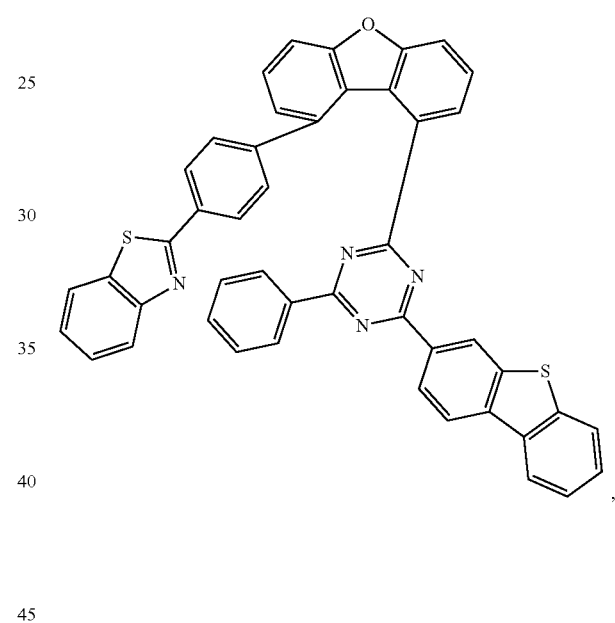
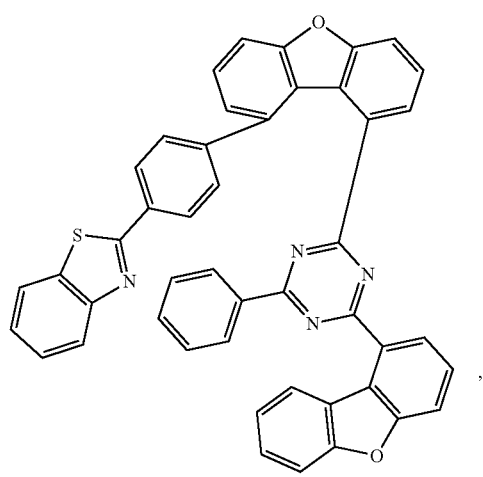
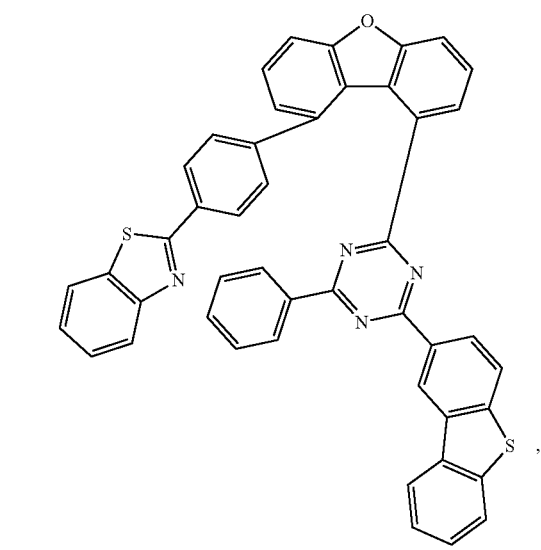

185
-continued
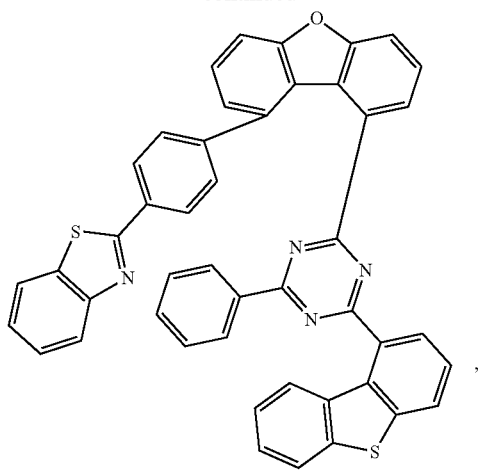
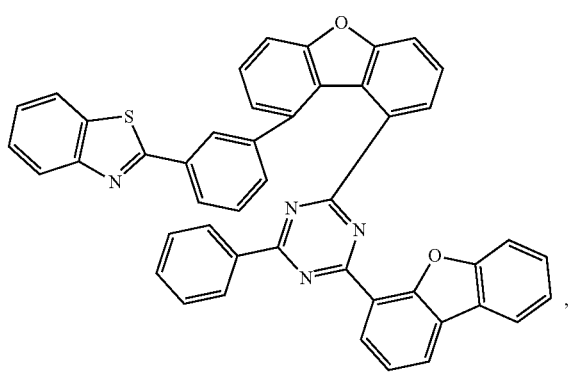
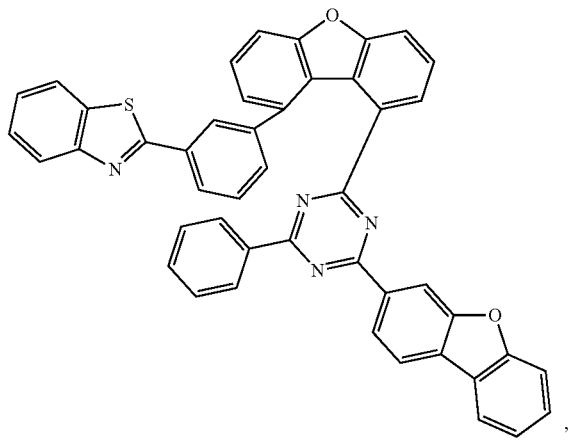
186
-continued
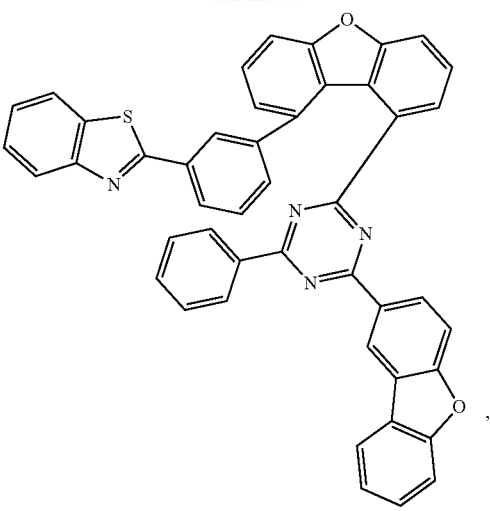
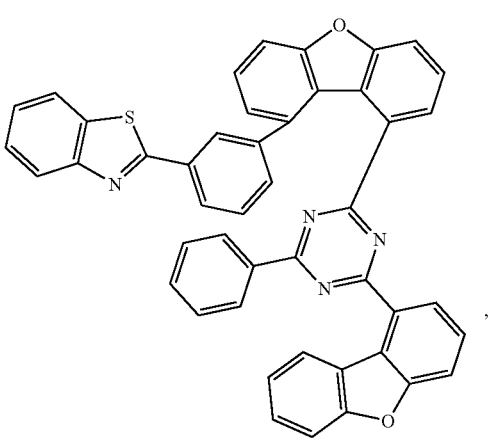
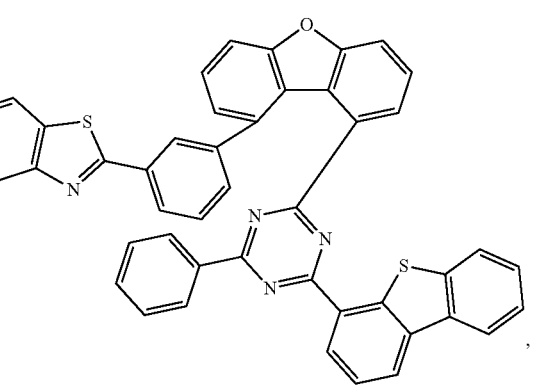

187
-continued
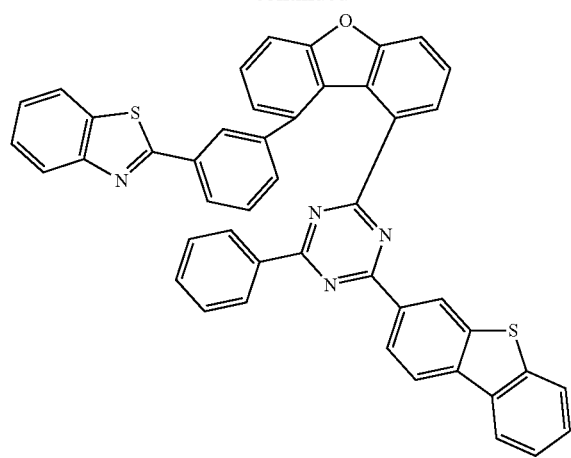
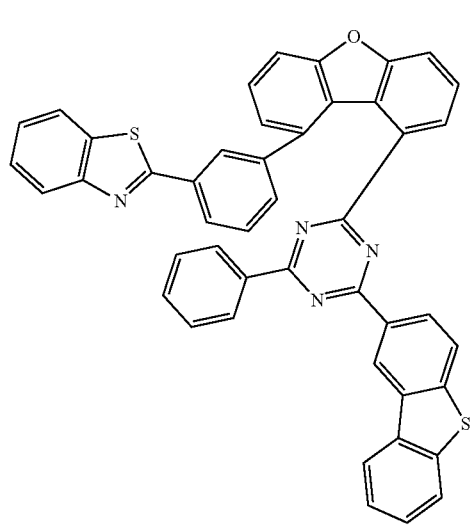
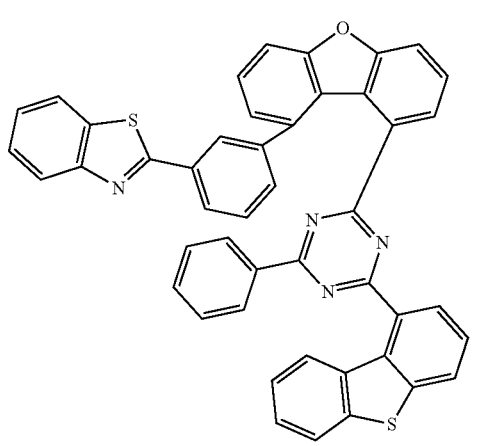
188
-continued
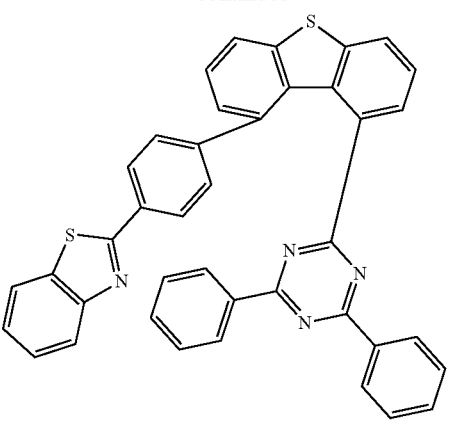
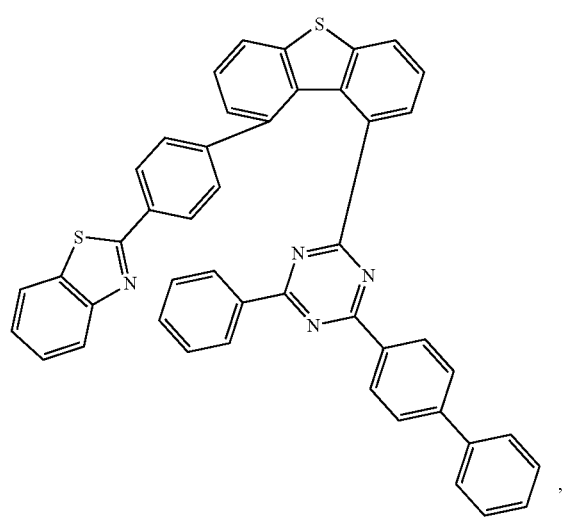
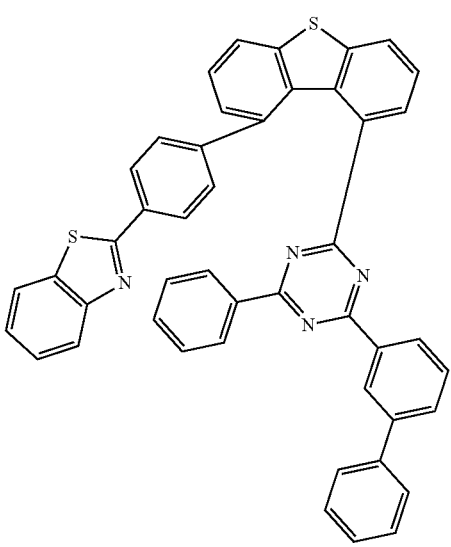

189
-continued
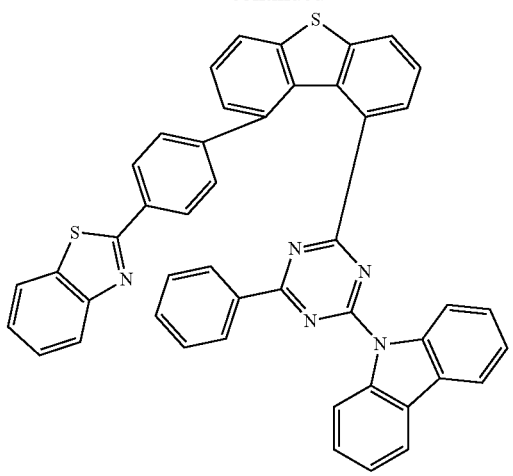
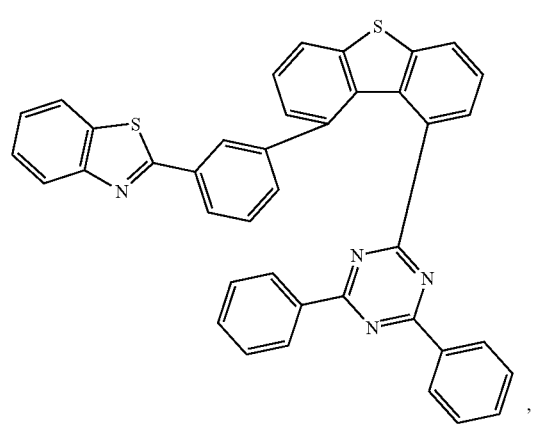
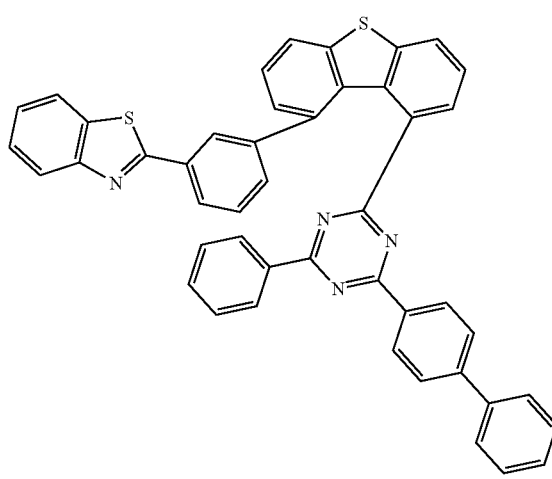
190
-continued
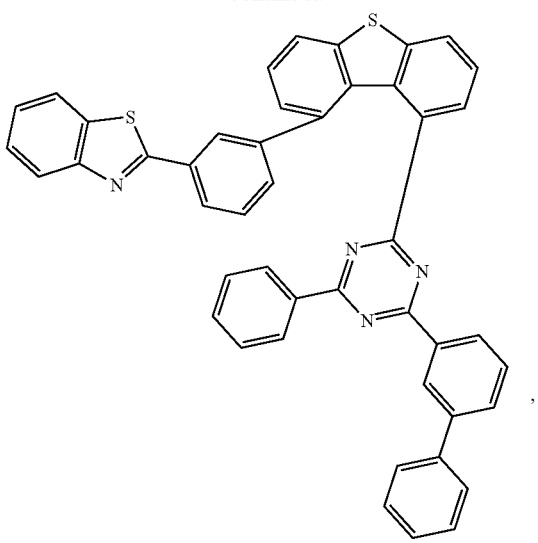
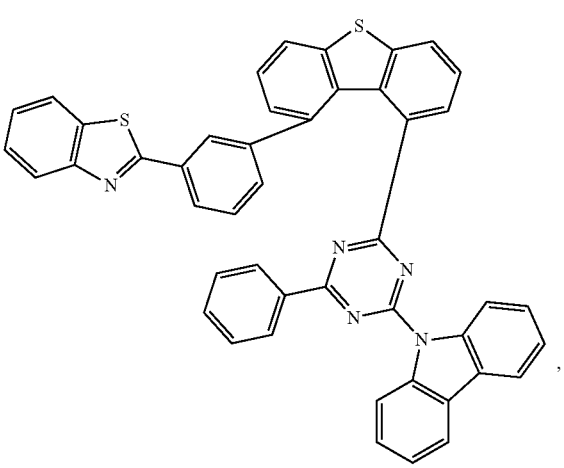
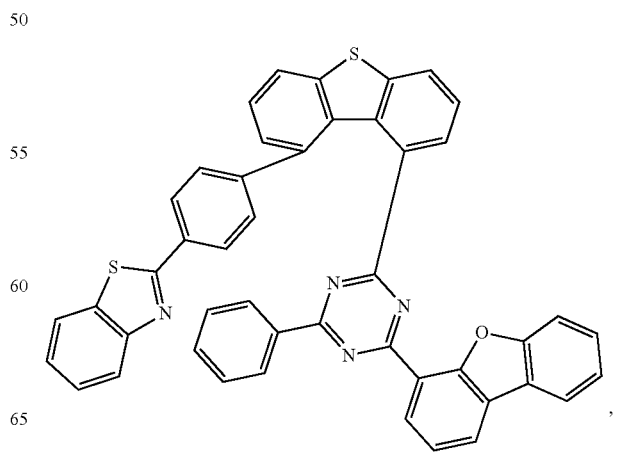

191
-continued
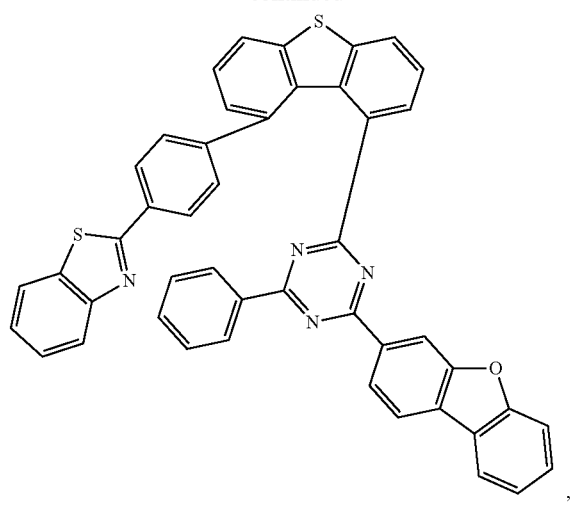
,
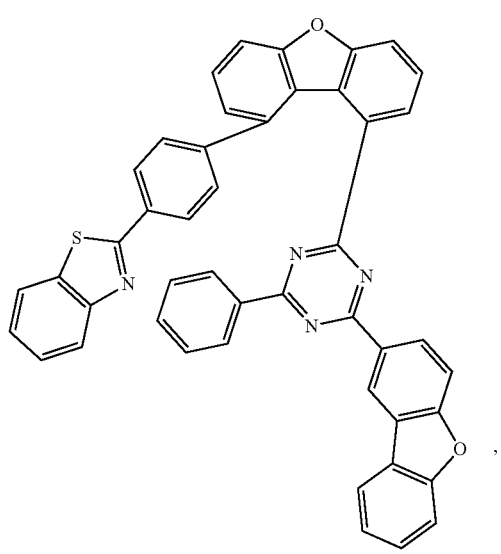
,
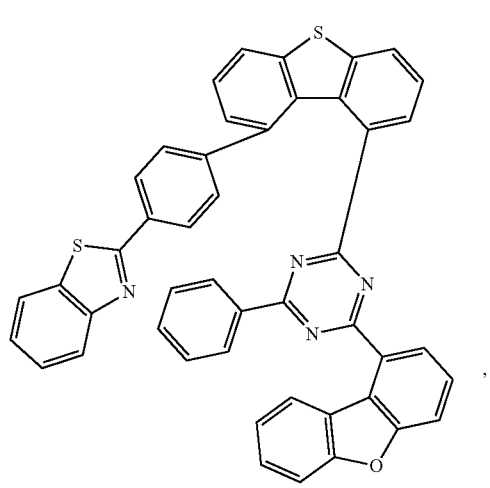
,
192
-continued
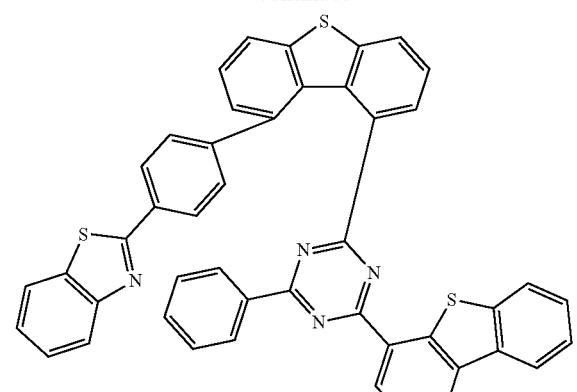
,
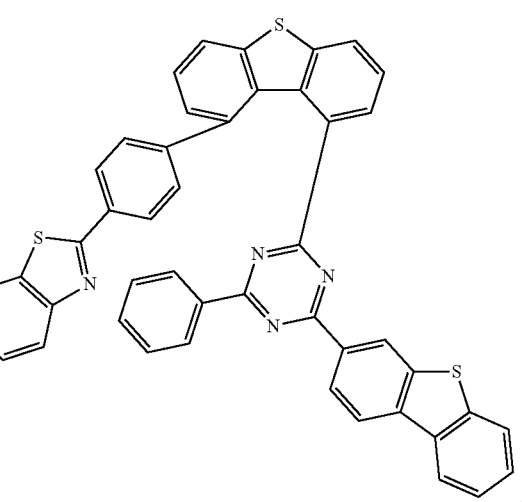
,
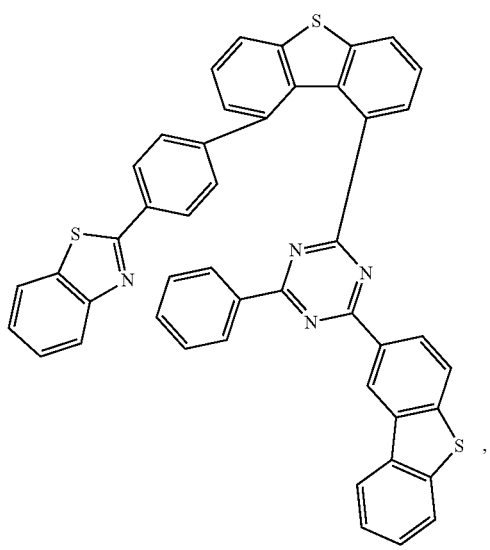
, 193
-continued
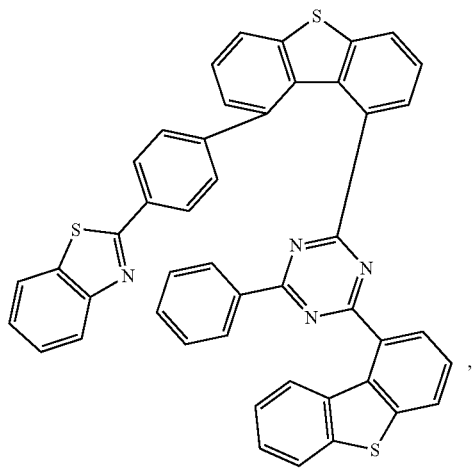
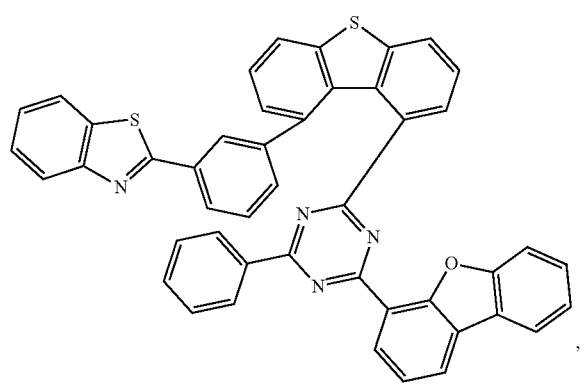
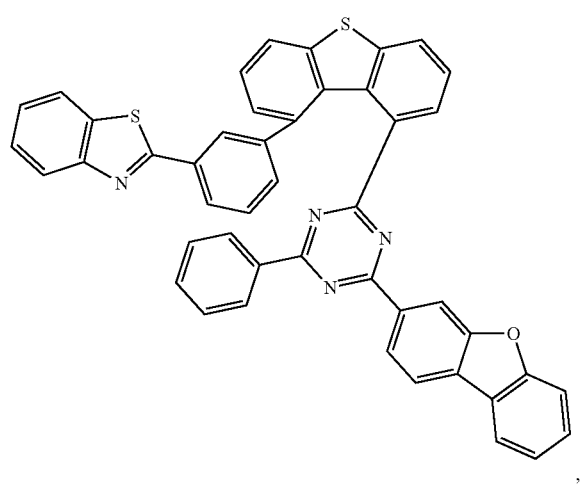
194
-continued
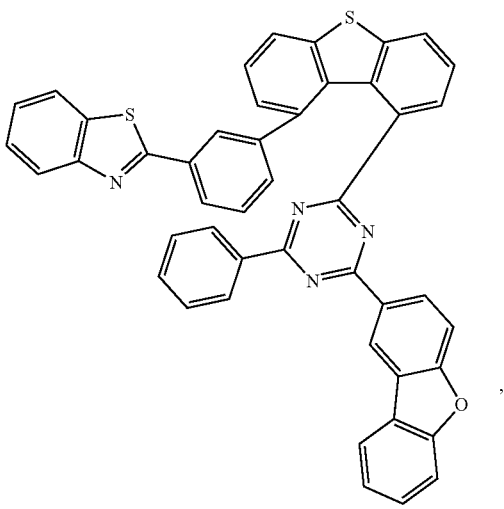
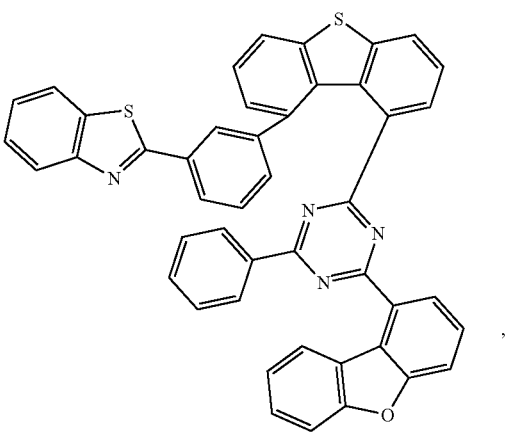
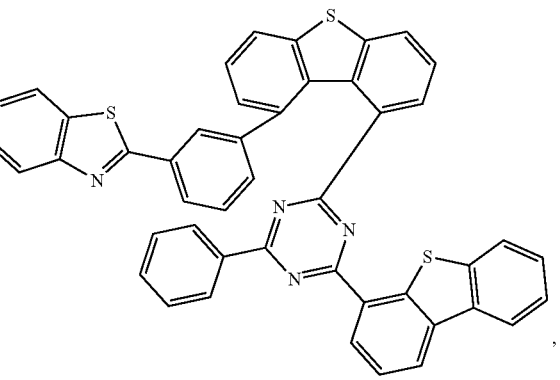

195
-continued
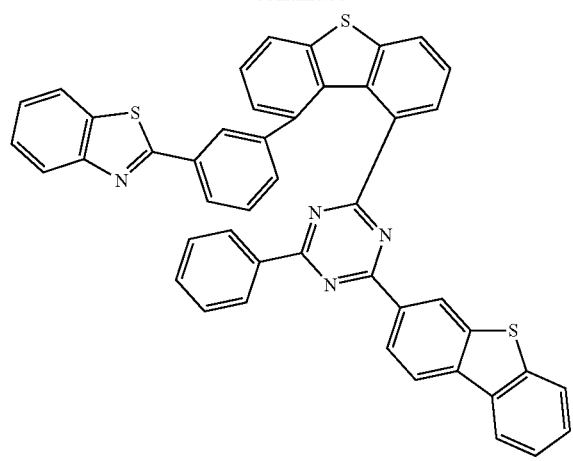
,
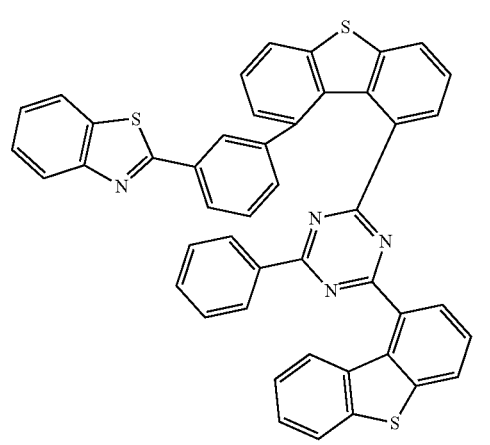
,
196
-continued
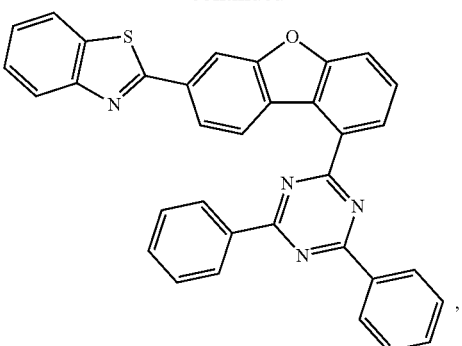
,
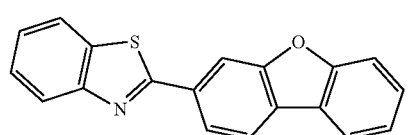
,
,
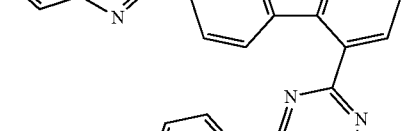
,

197
-continued
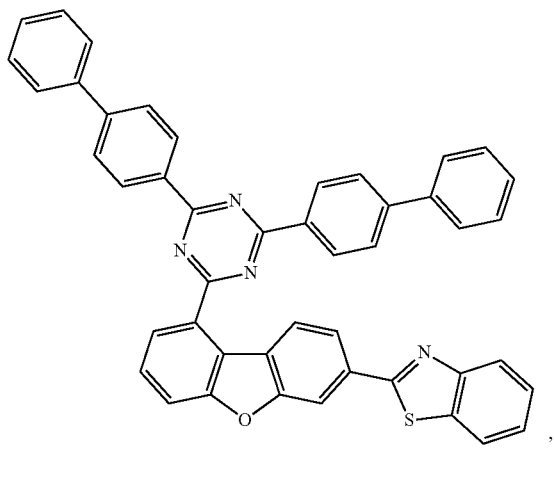
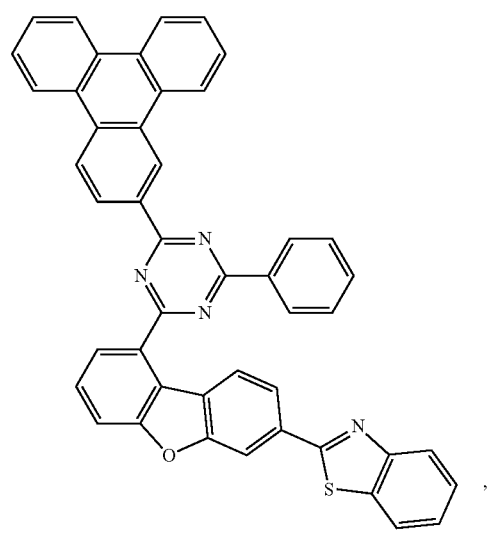
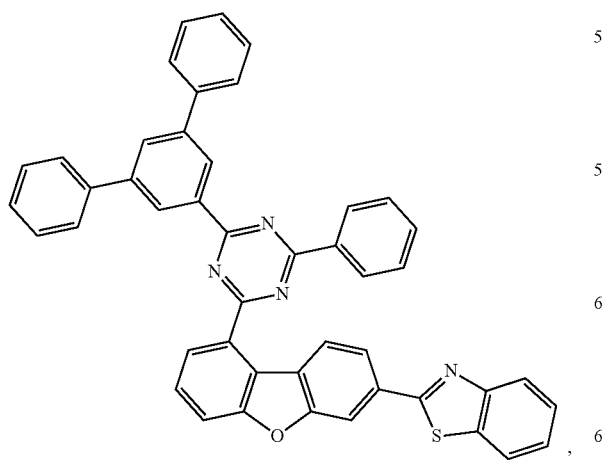
198
-continued
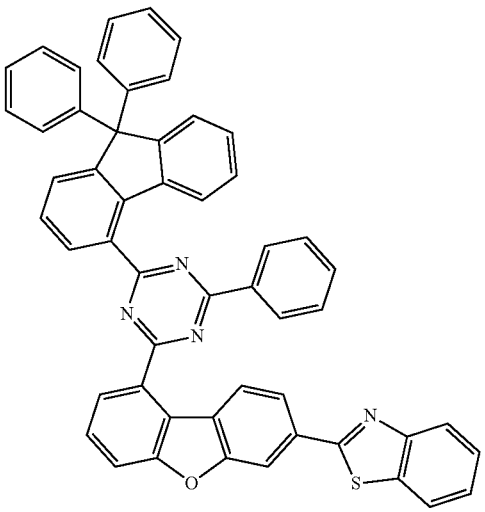
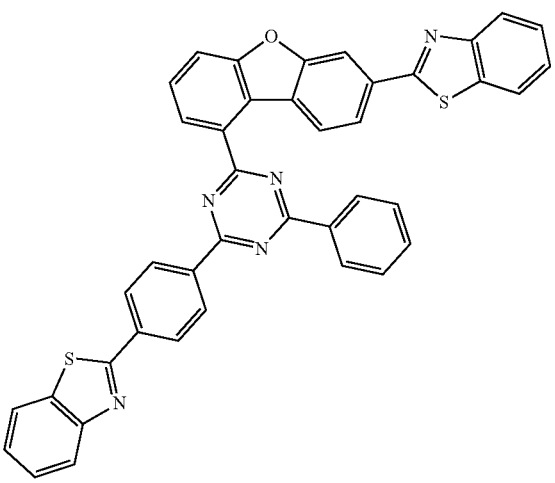
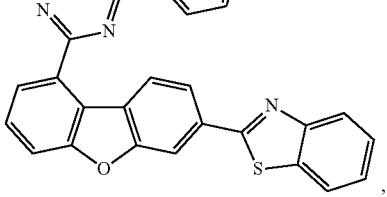

199
-continued
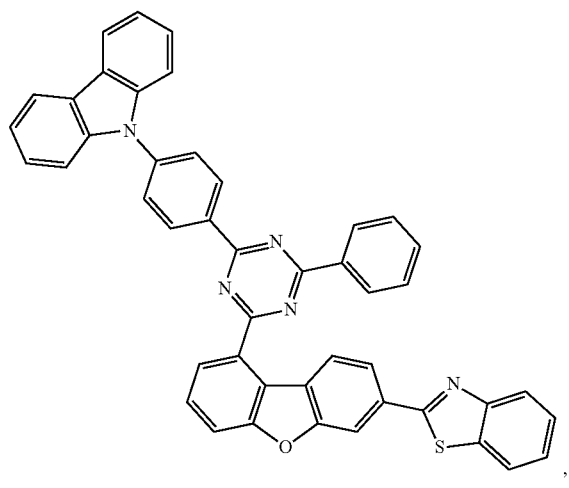
,
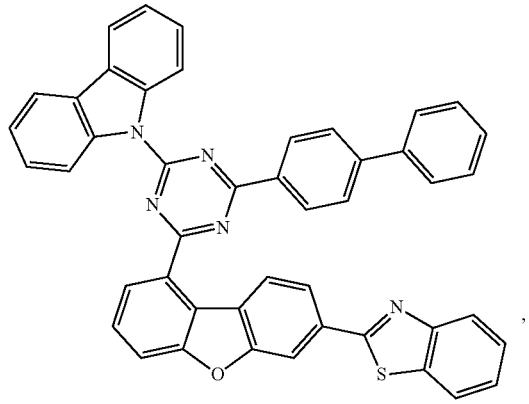
,
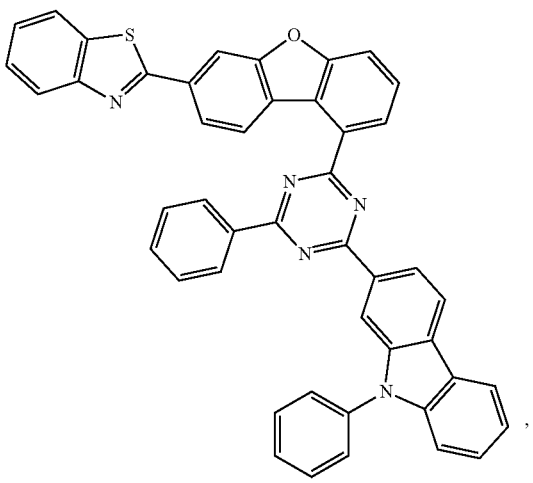
,
200
-continued
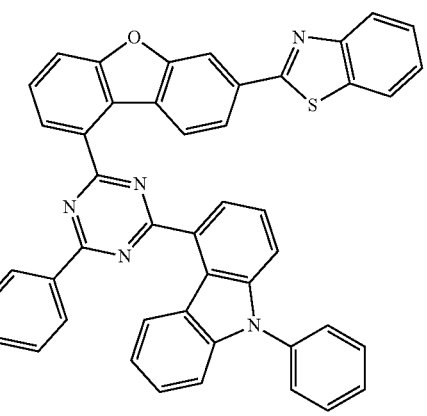
,
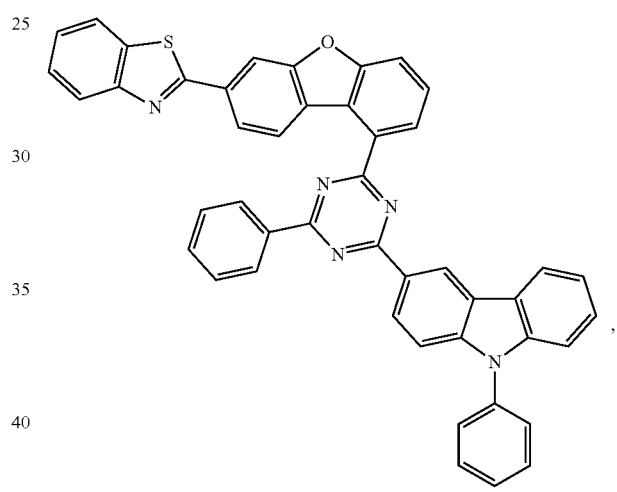
,
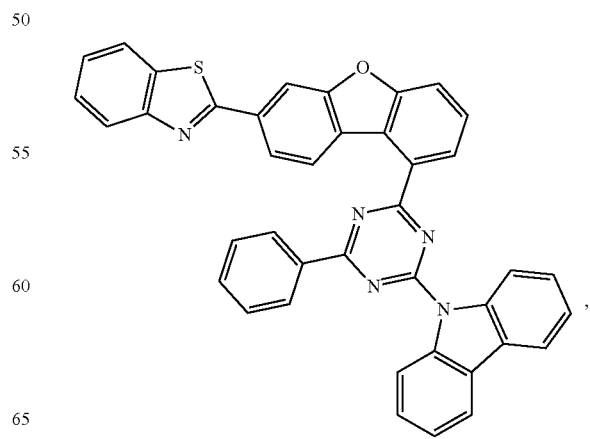
, 201
-continued
202
-continued
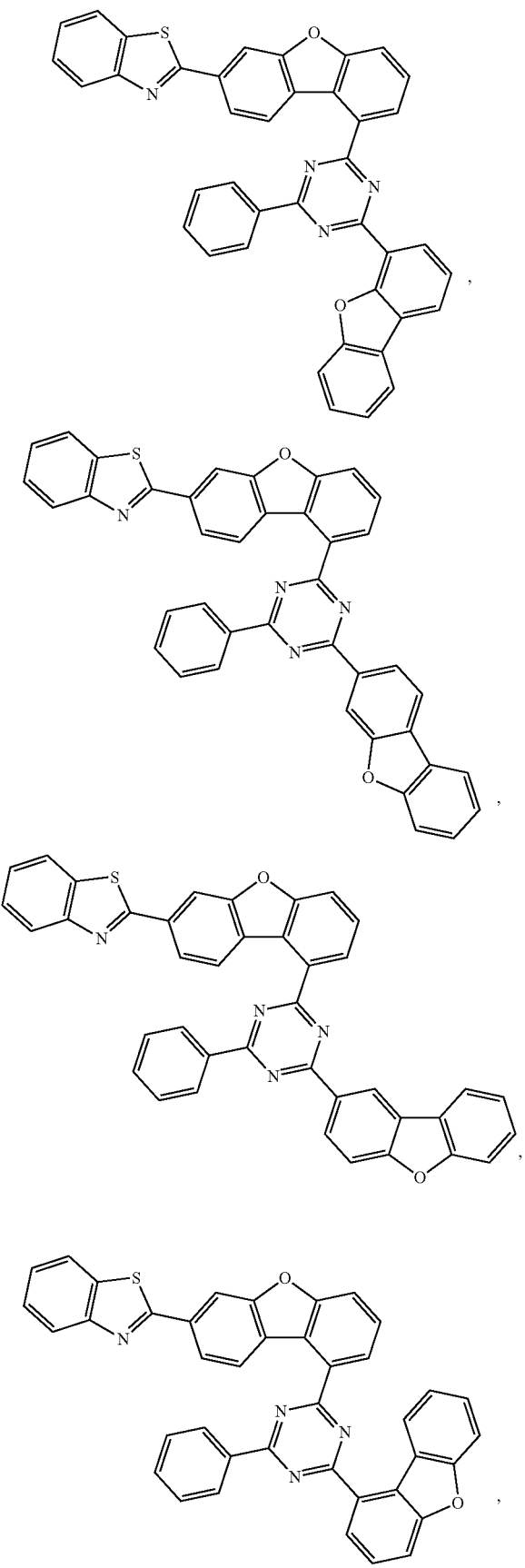
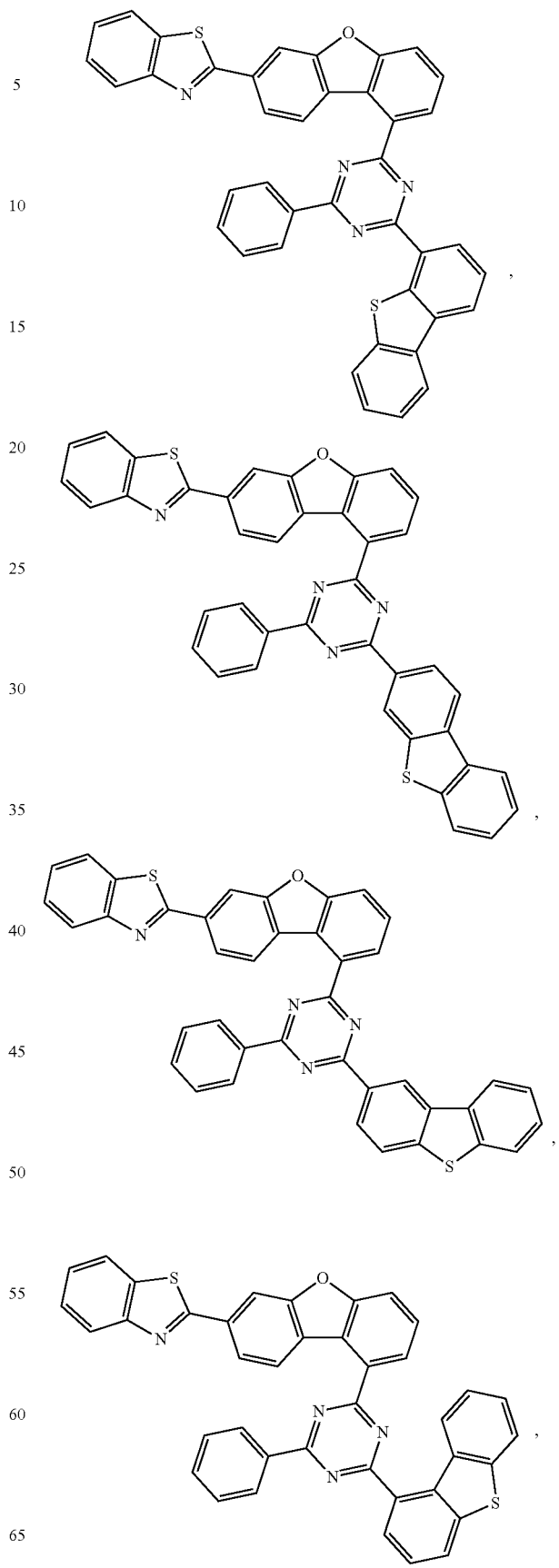

203
-continued
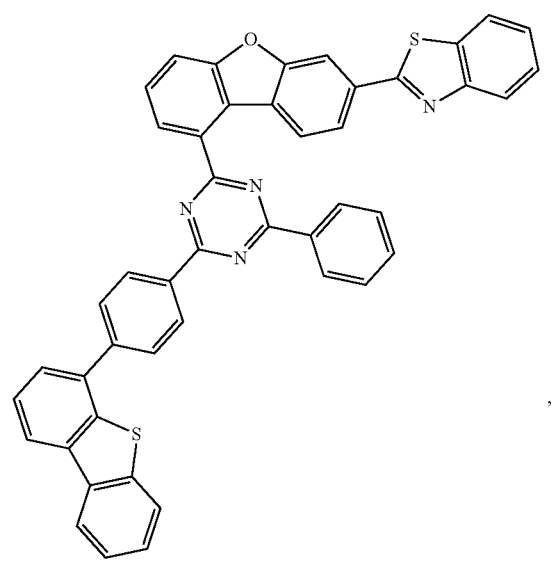
,
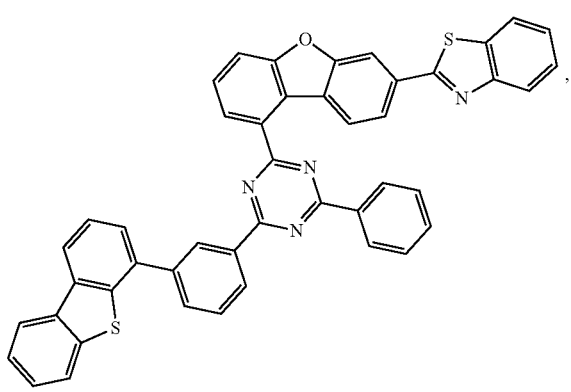
,
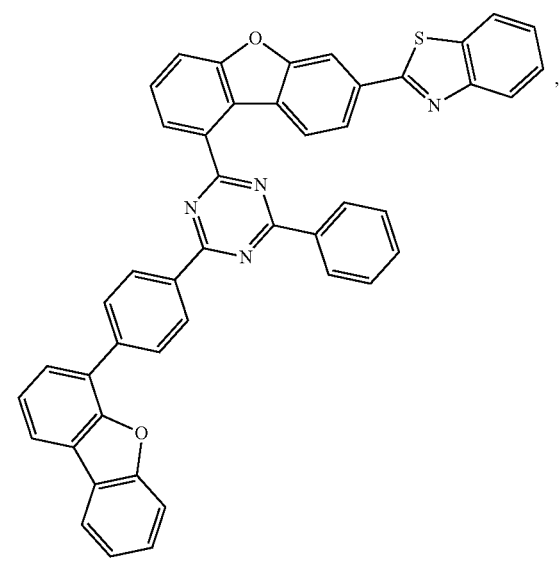
,
204
-continued
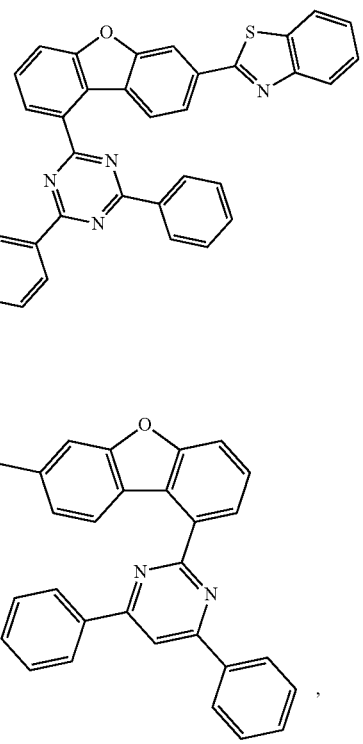
,
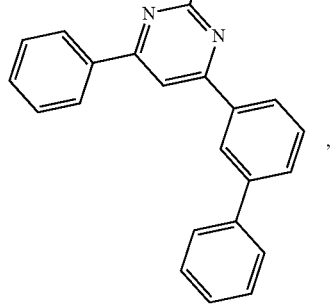
, 205
-continued
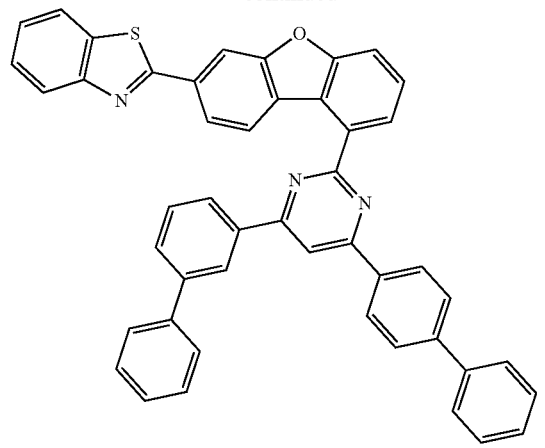
206
-continued
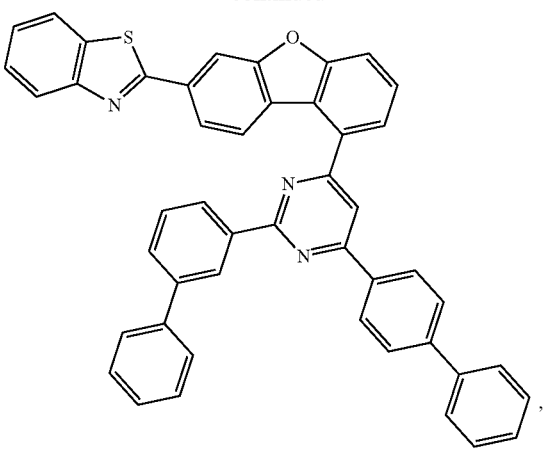
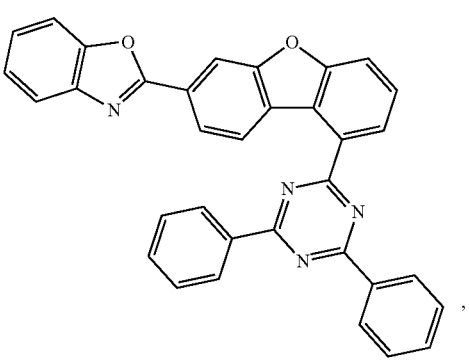
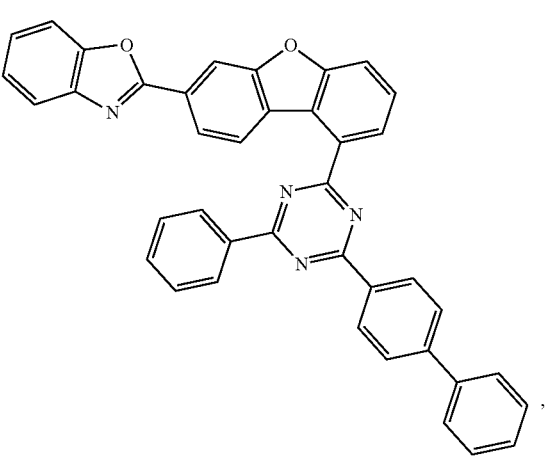

207
-continued
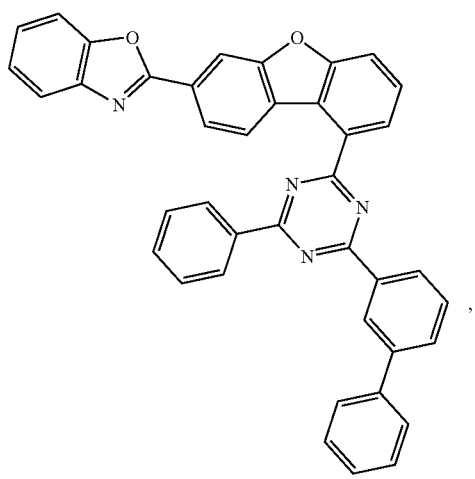
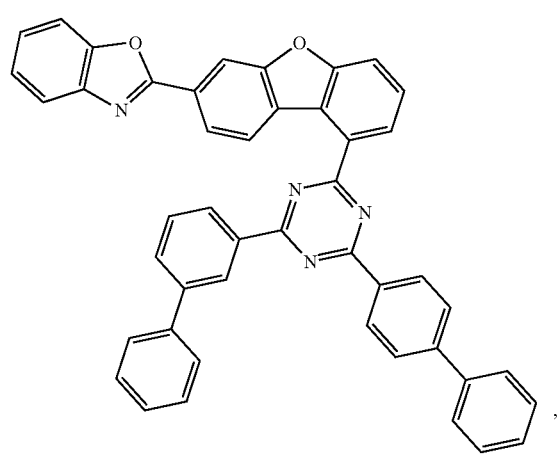
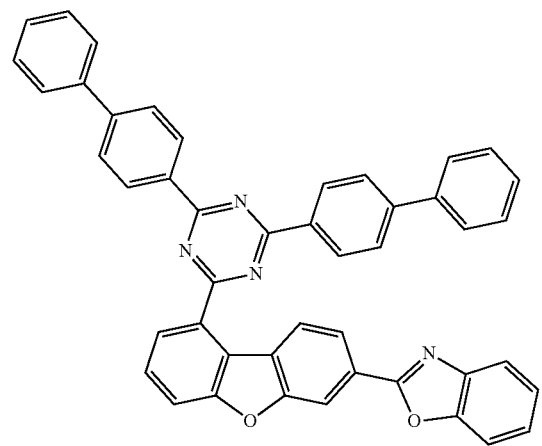
208
-continued
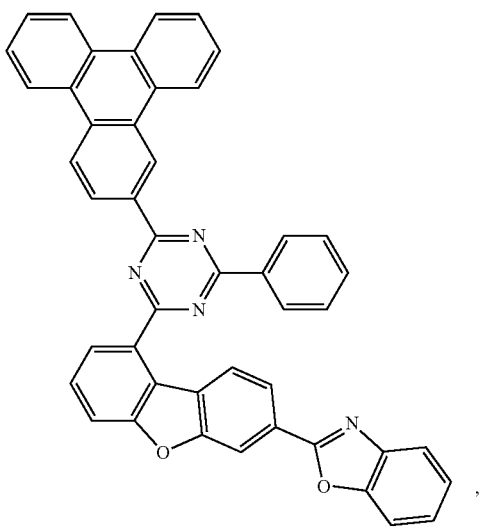
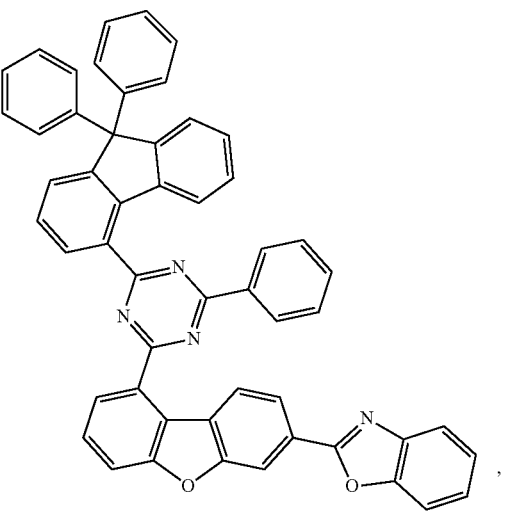

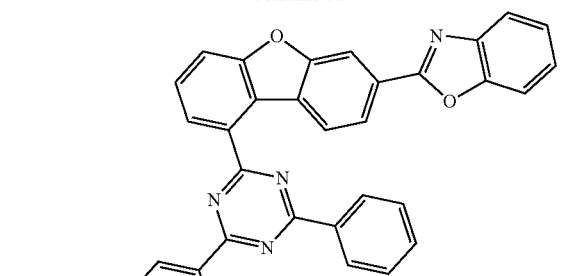
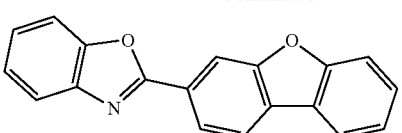
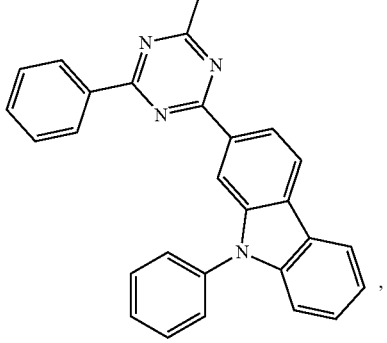
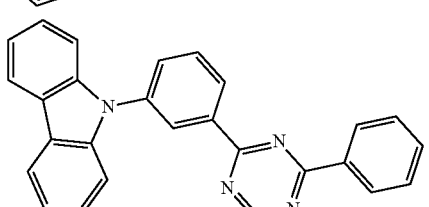
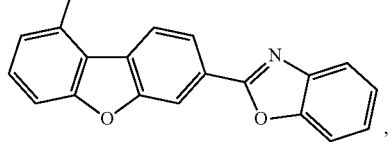
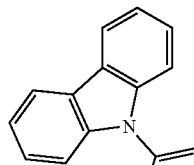
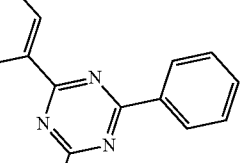
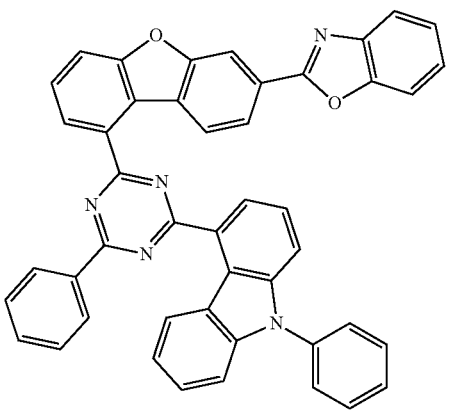
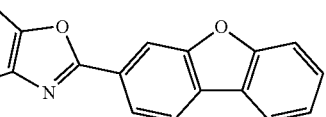
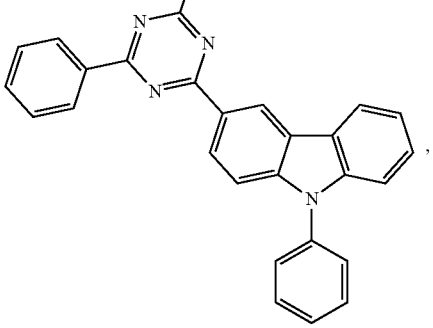

211
-continued
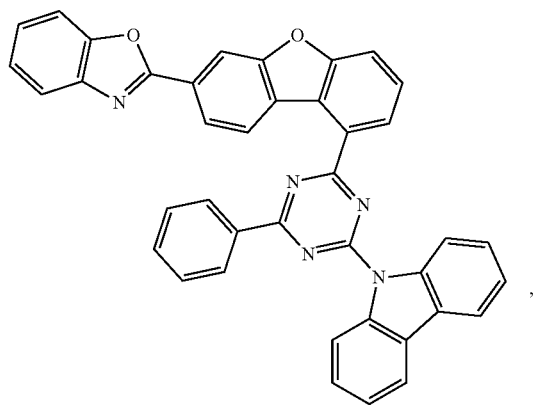
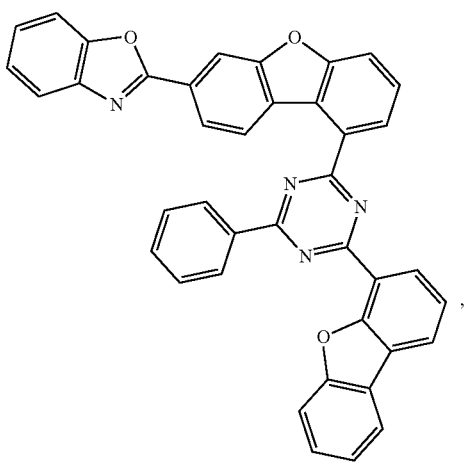
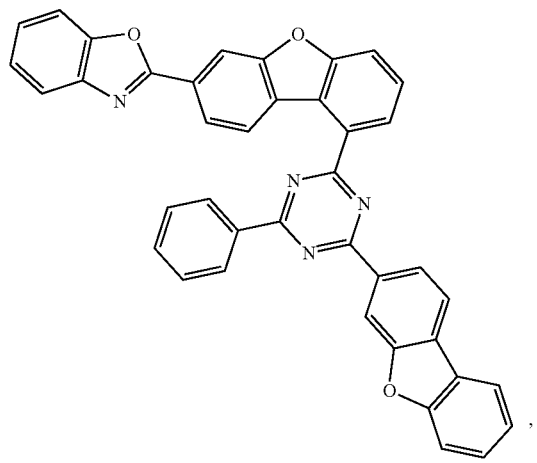
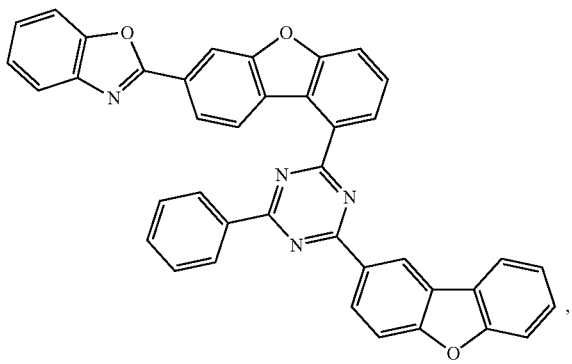
212
-continued
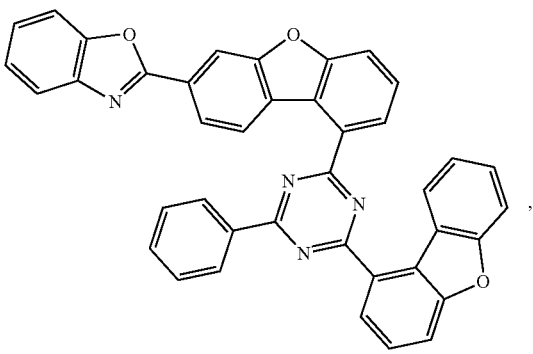
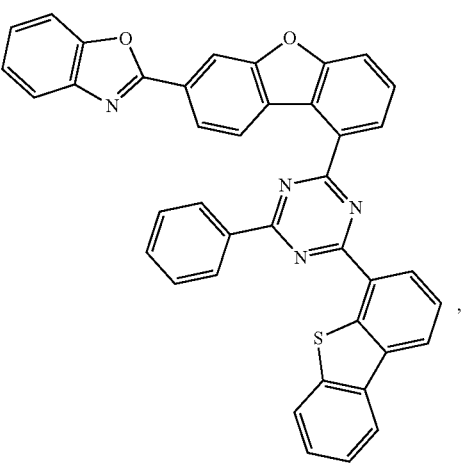
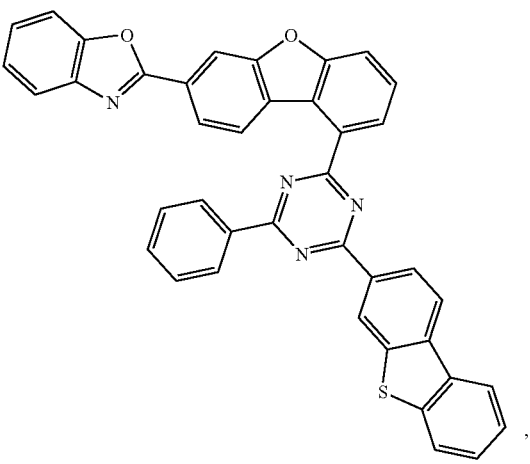
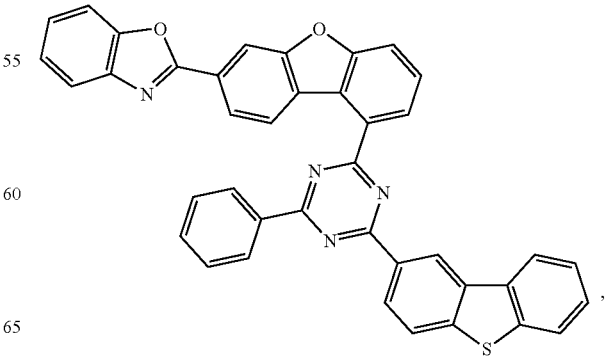

213
-continued
214
-continued
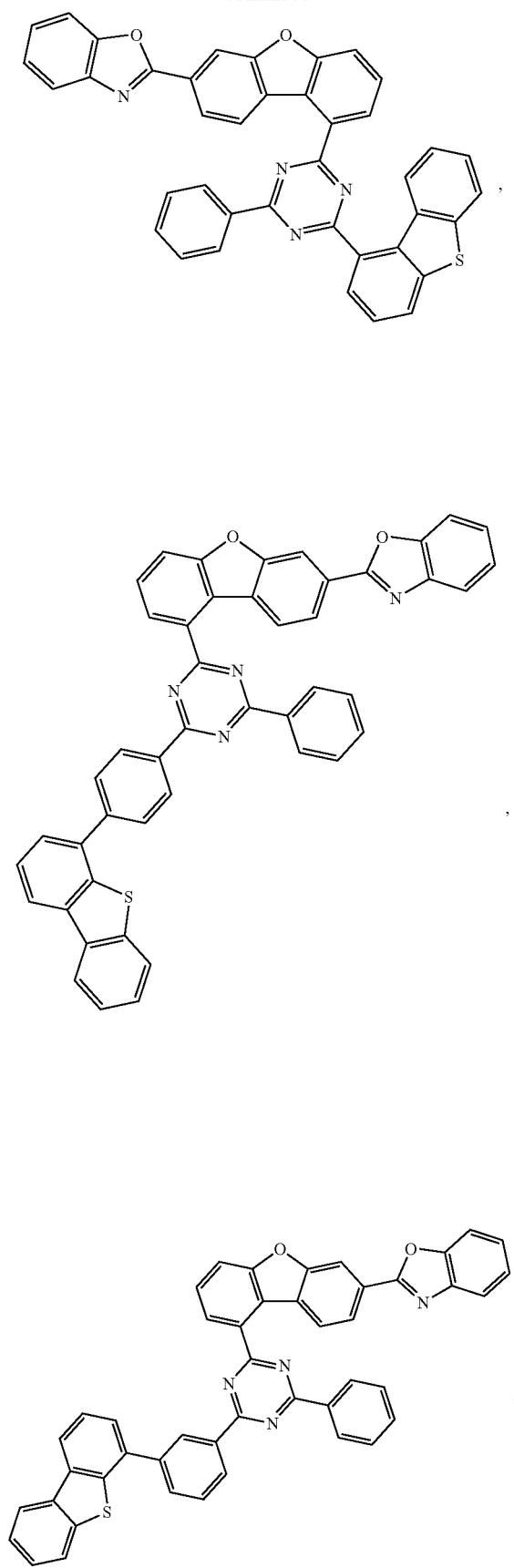
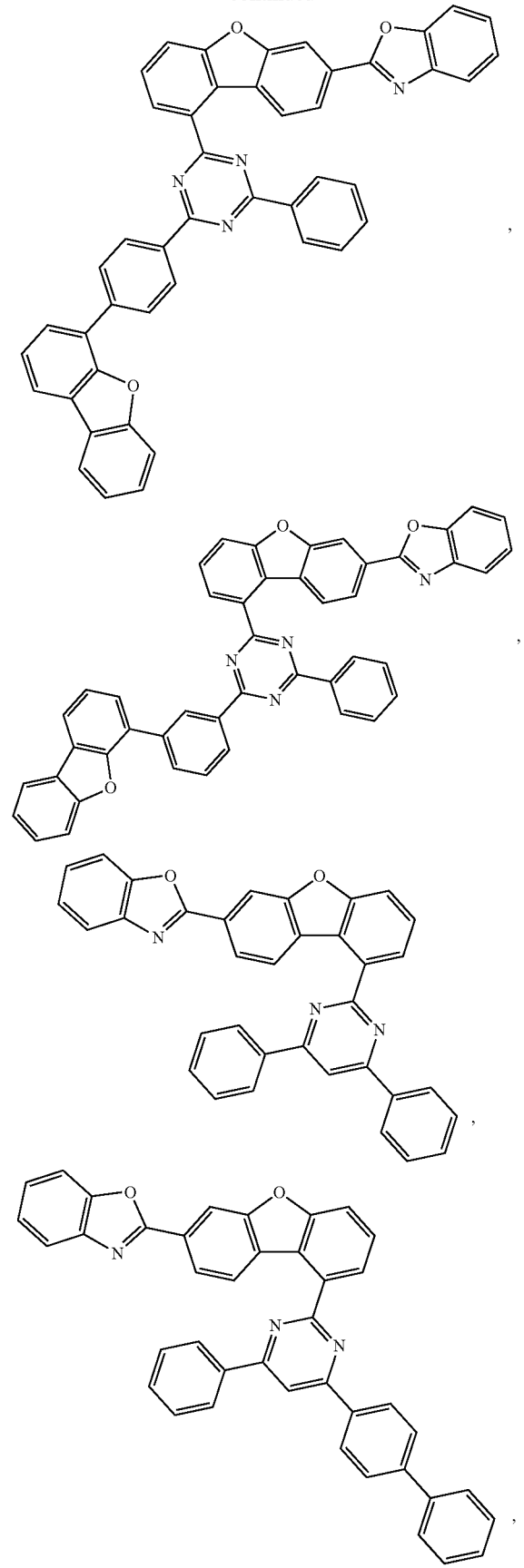

215
-continued
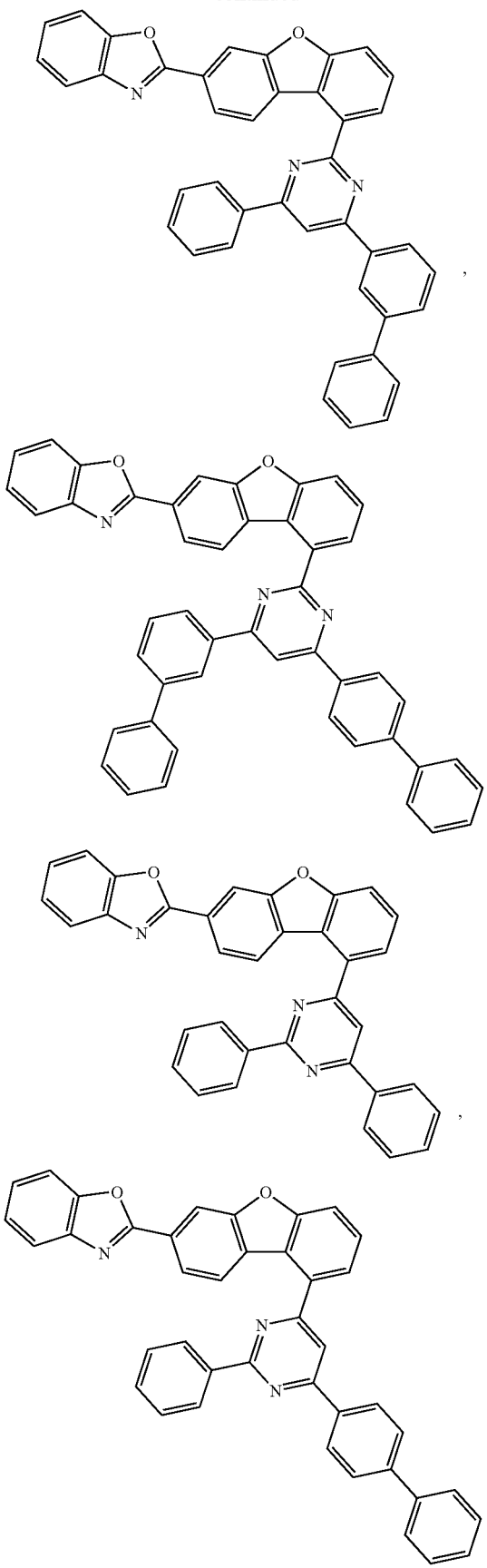
216
-continued
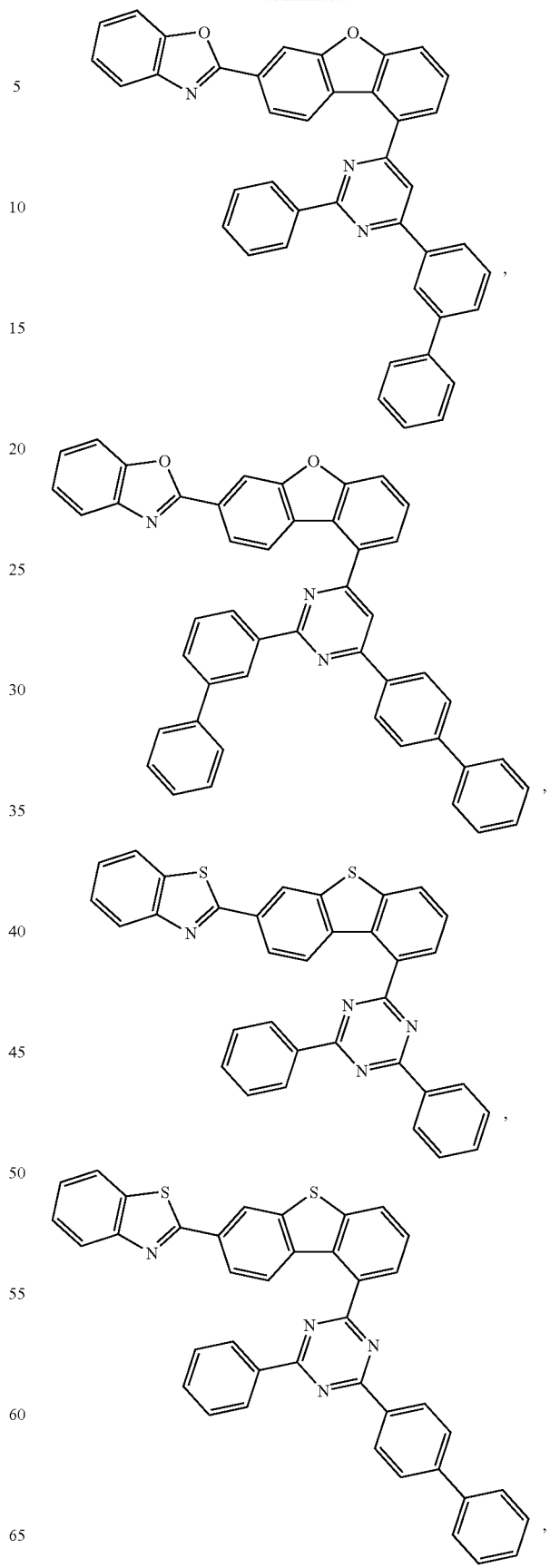

217
-continued
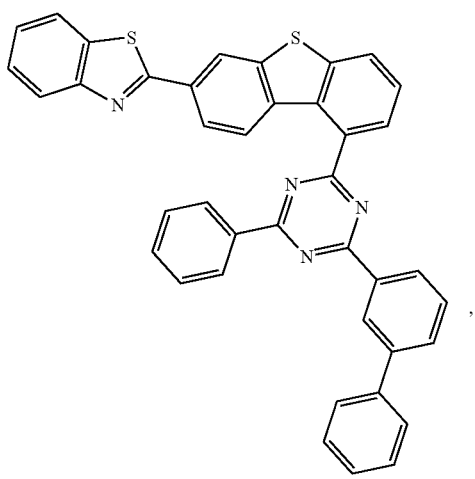
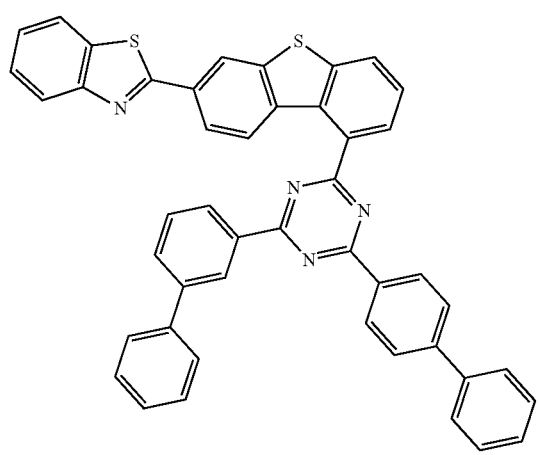
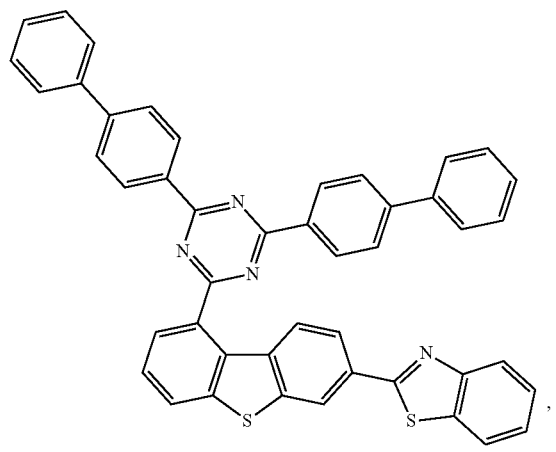
218
-continued
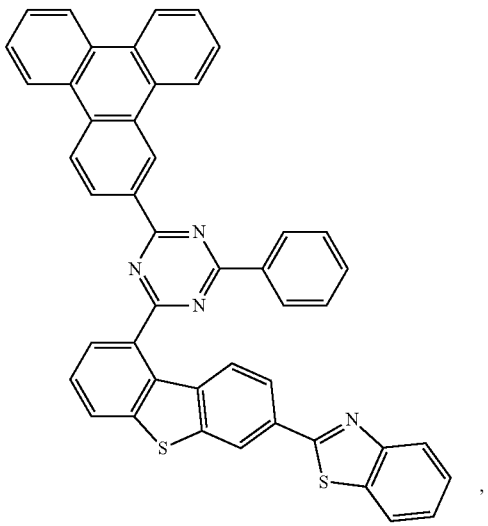
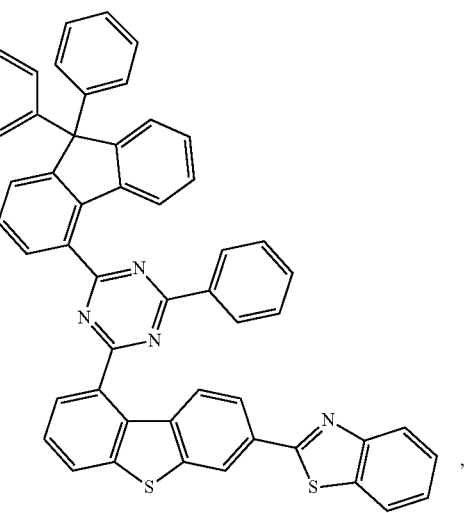

219
-continued
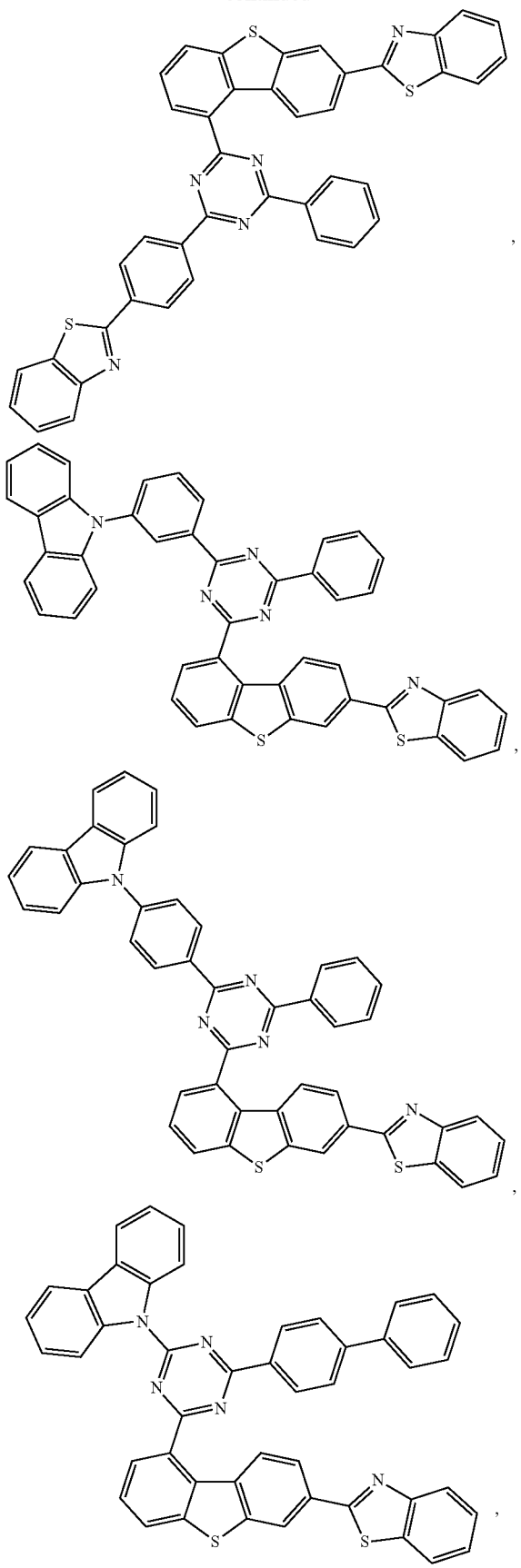
220
-continued
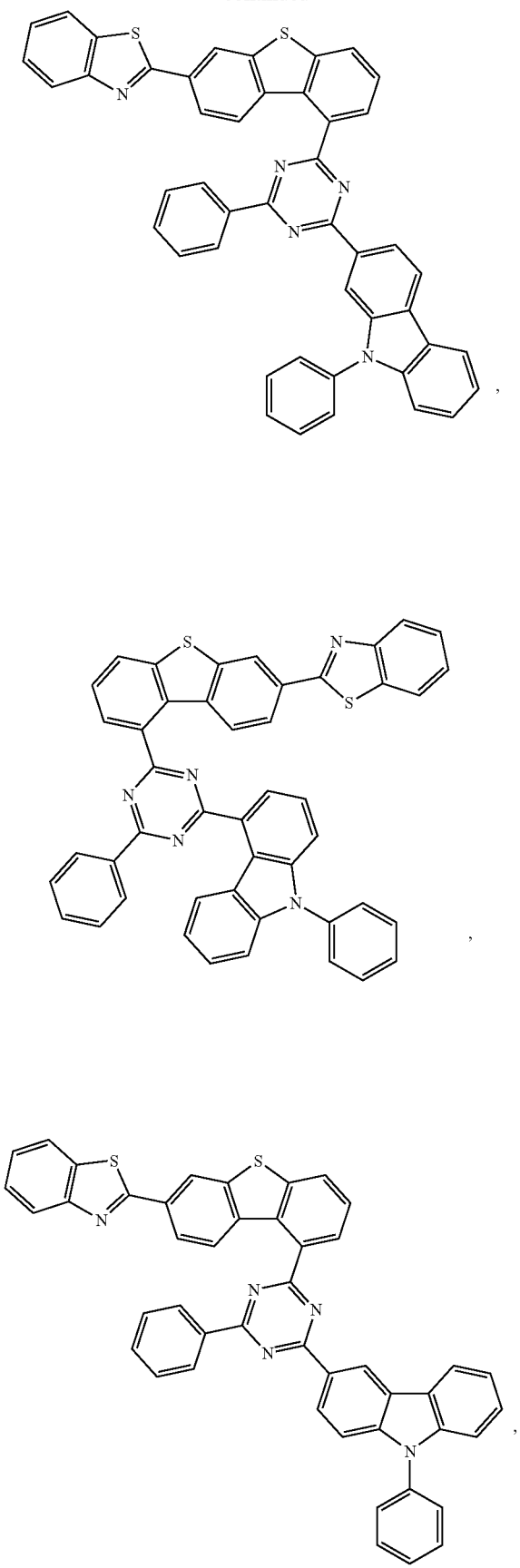

221
-continued
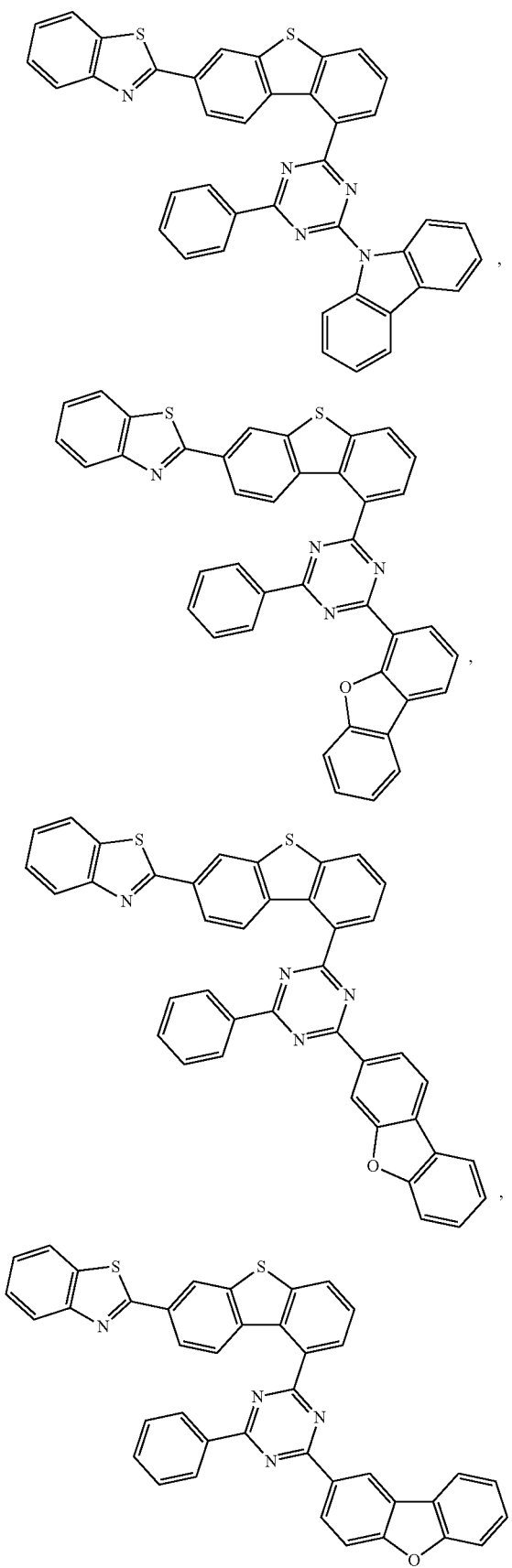
222
-continued
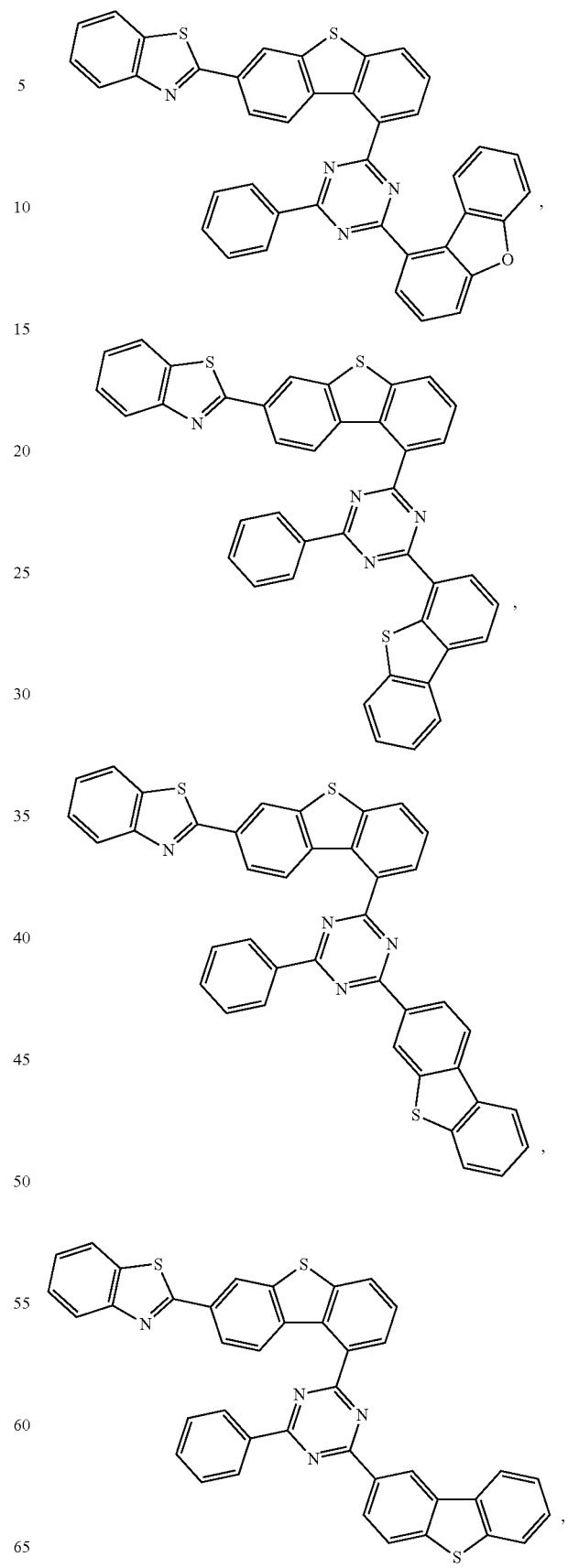

223
-continued
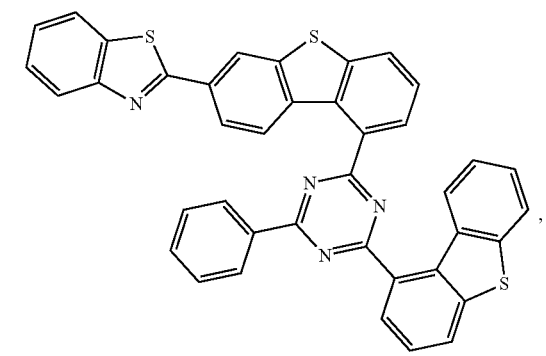
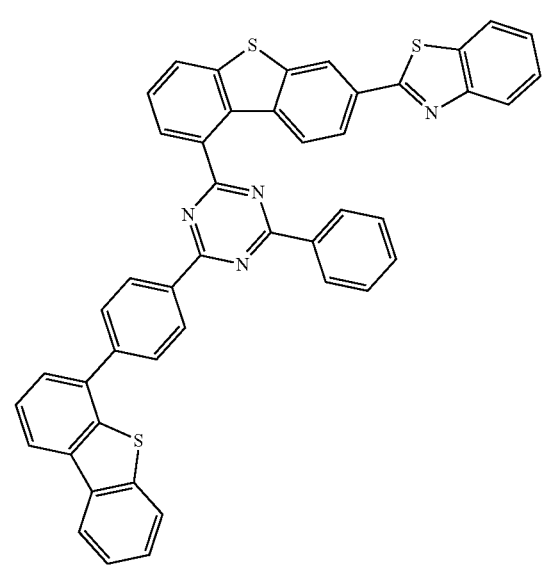
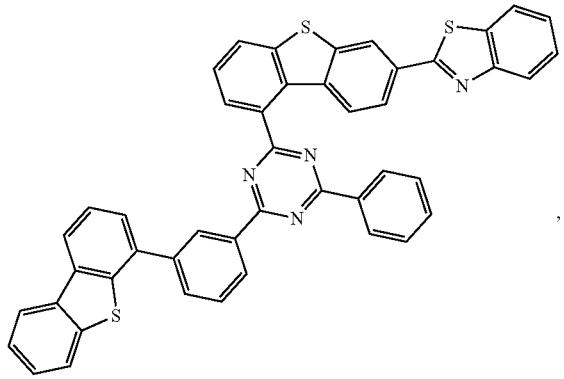
224
-continued
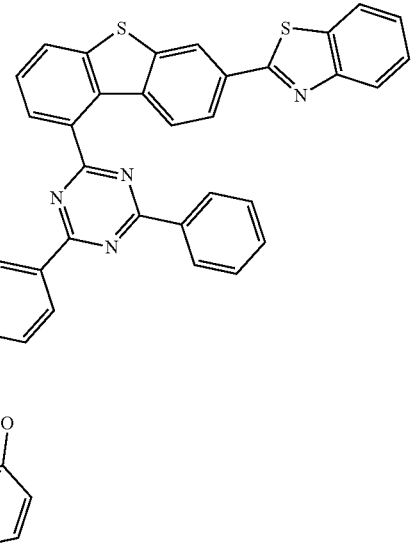
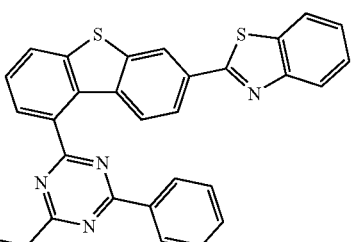
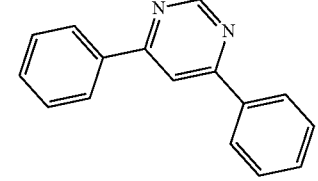
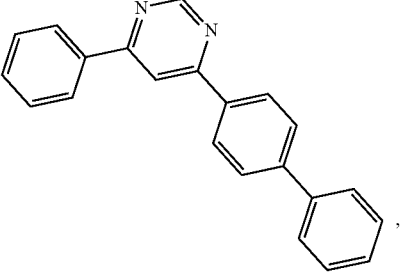

225
-continued
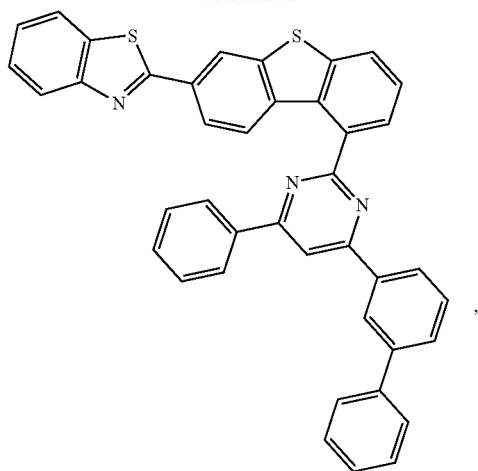
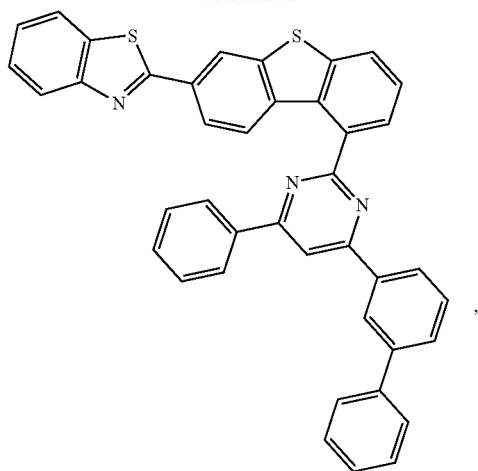
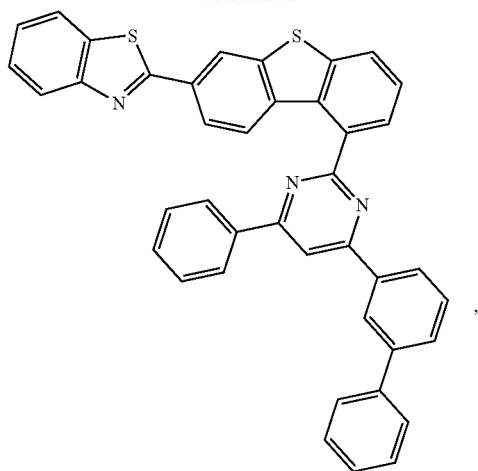
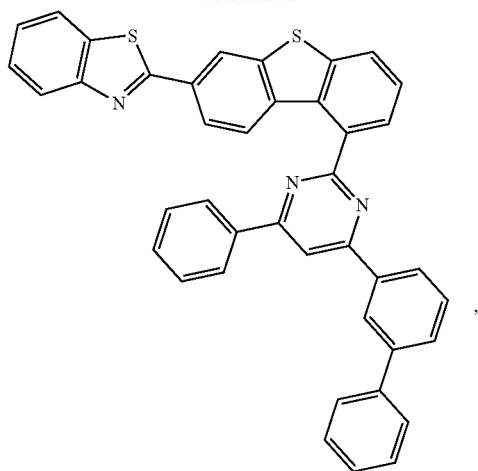
226
-continued
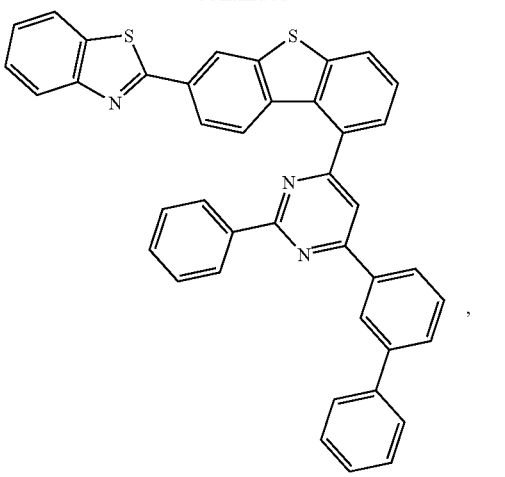
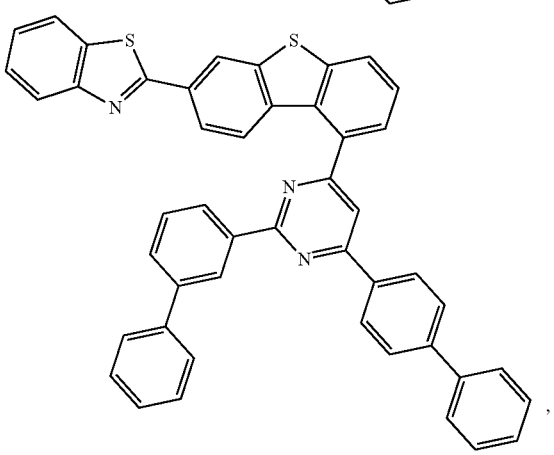
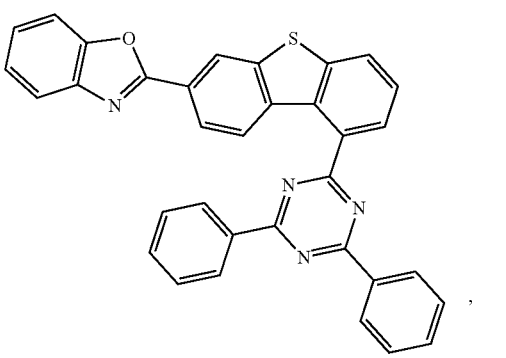
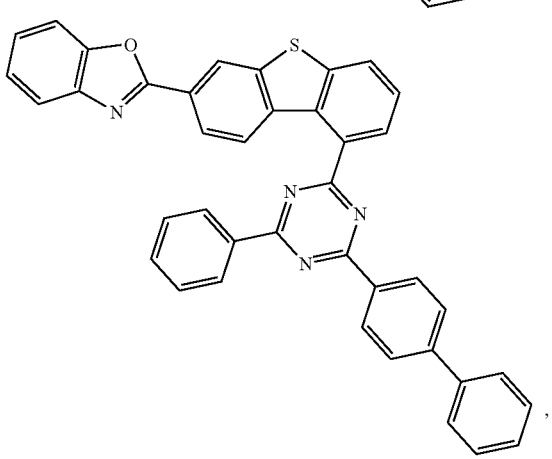

227
-continued
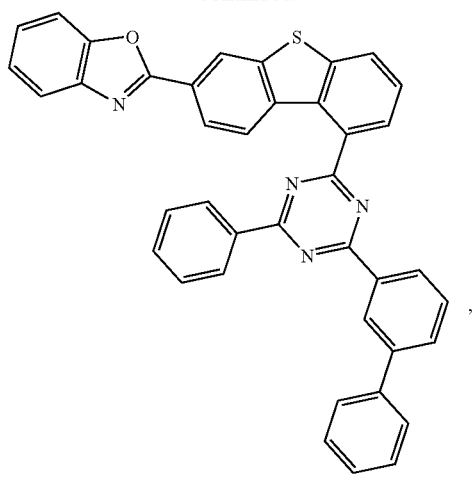
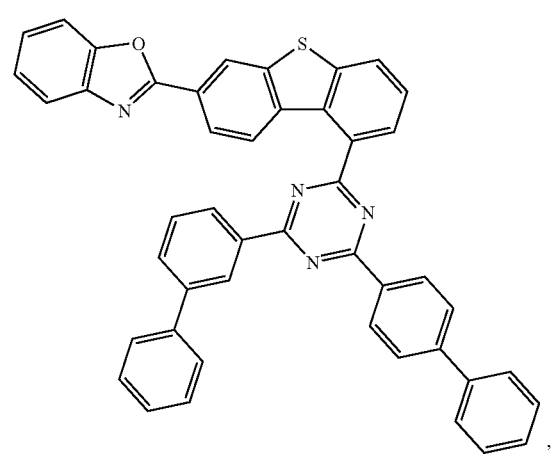
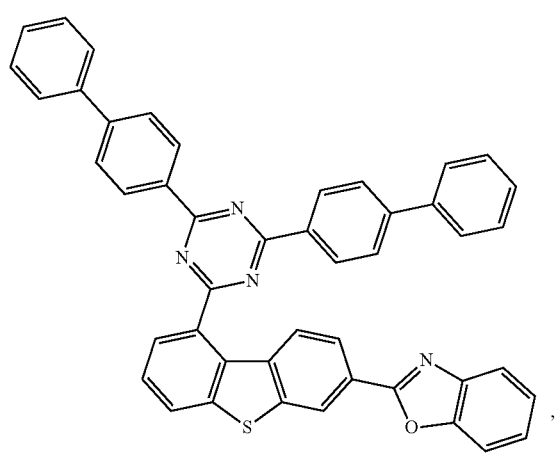
228
-continued
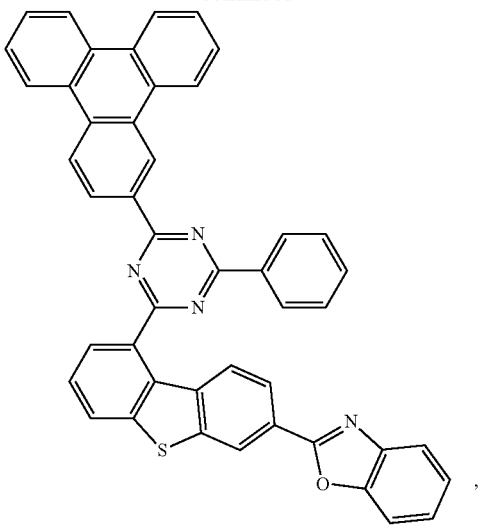
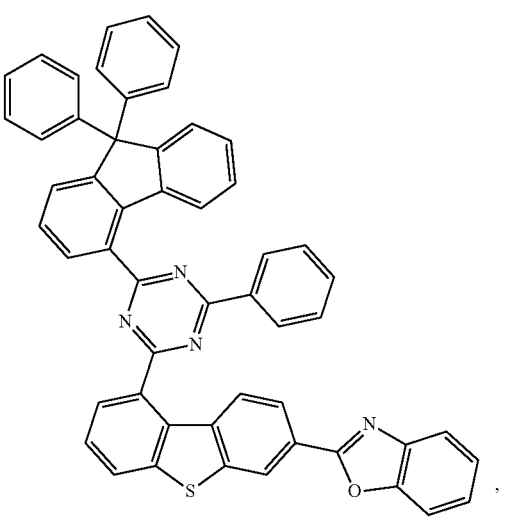

229
-continued
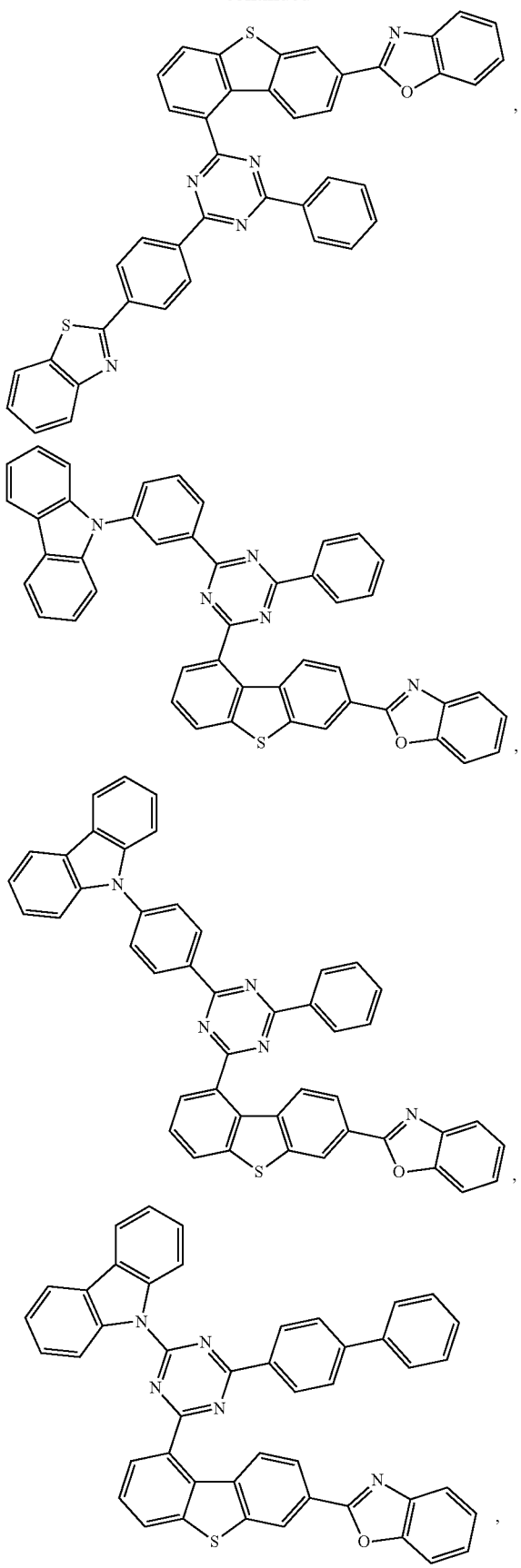
230
-continued
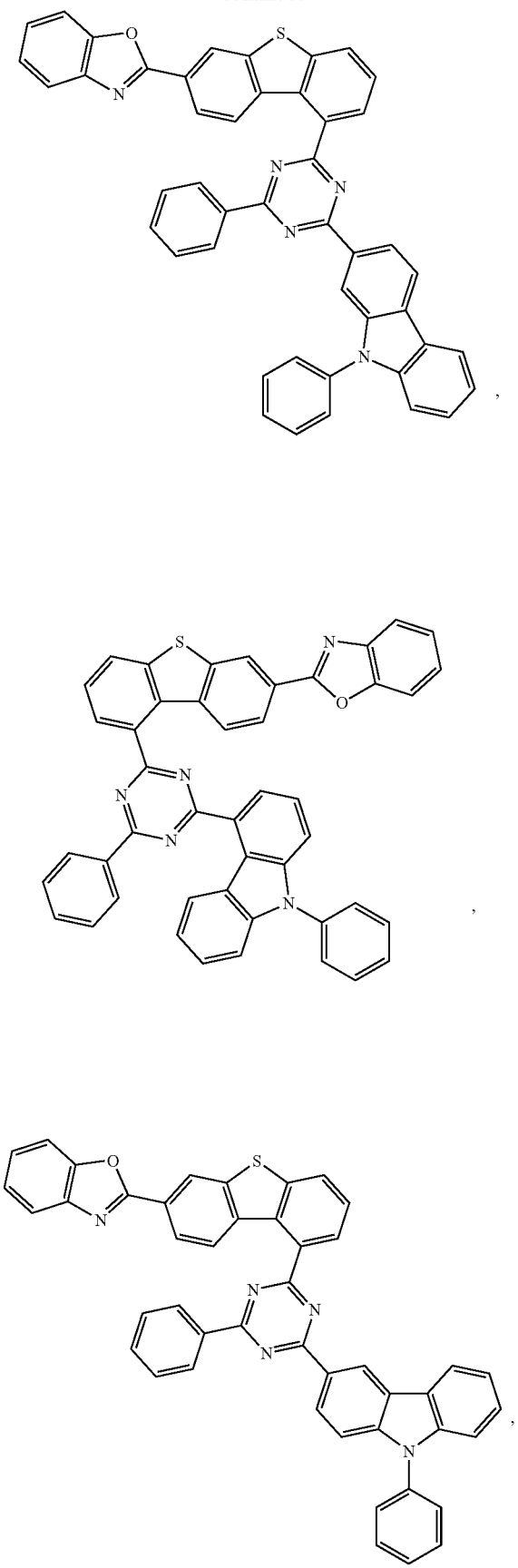

231
-continued
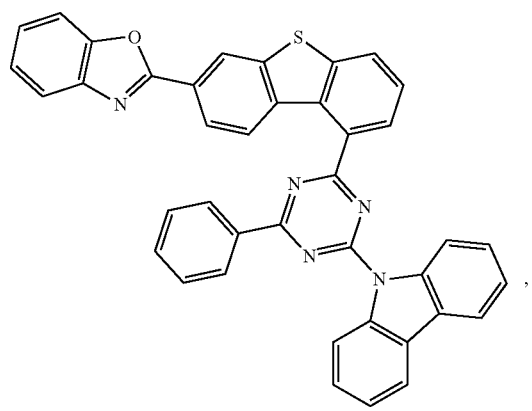
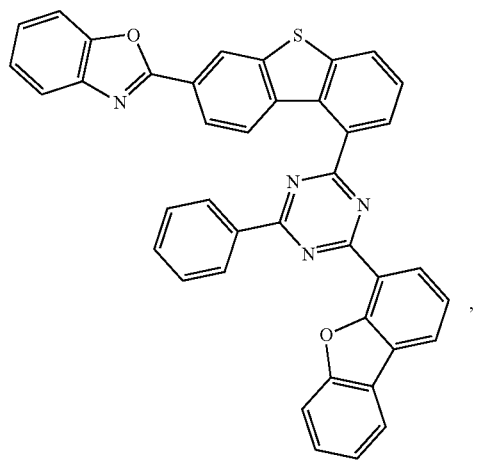
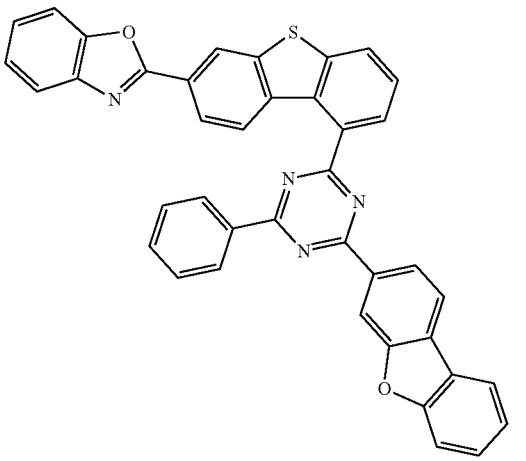
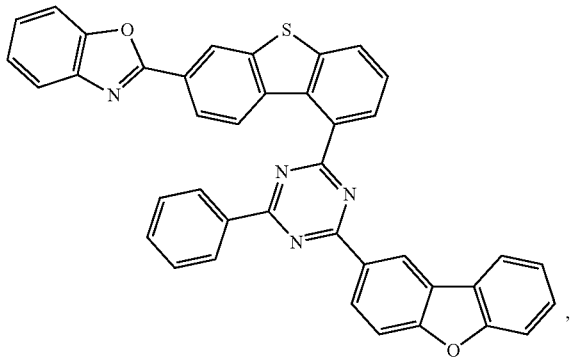
232
-continued
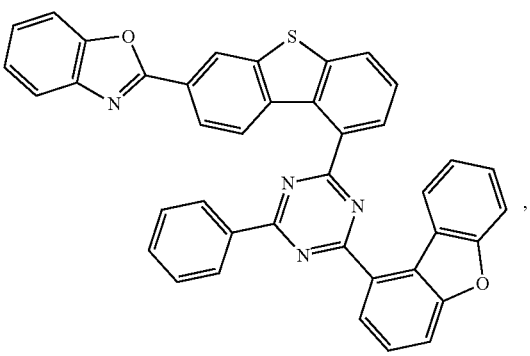
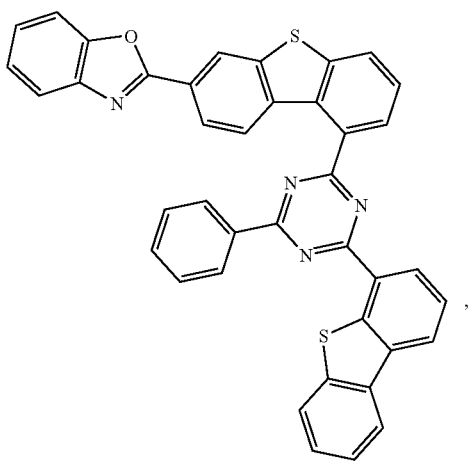
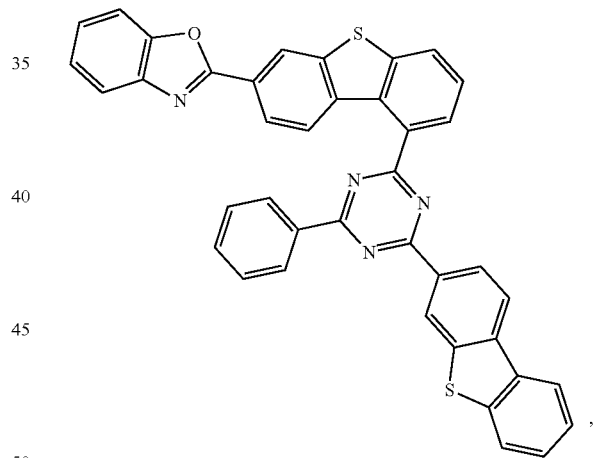
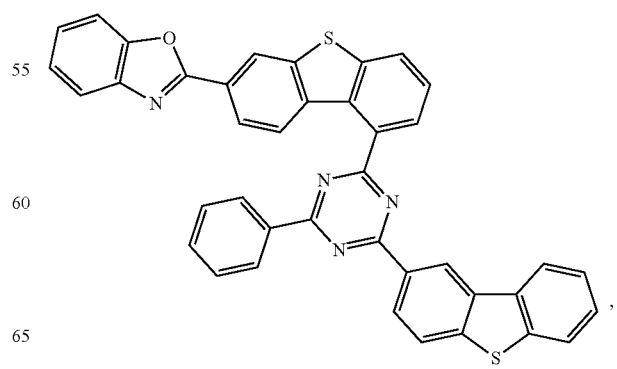

233
-continued
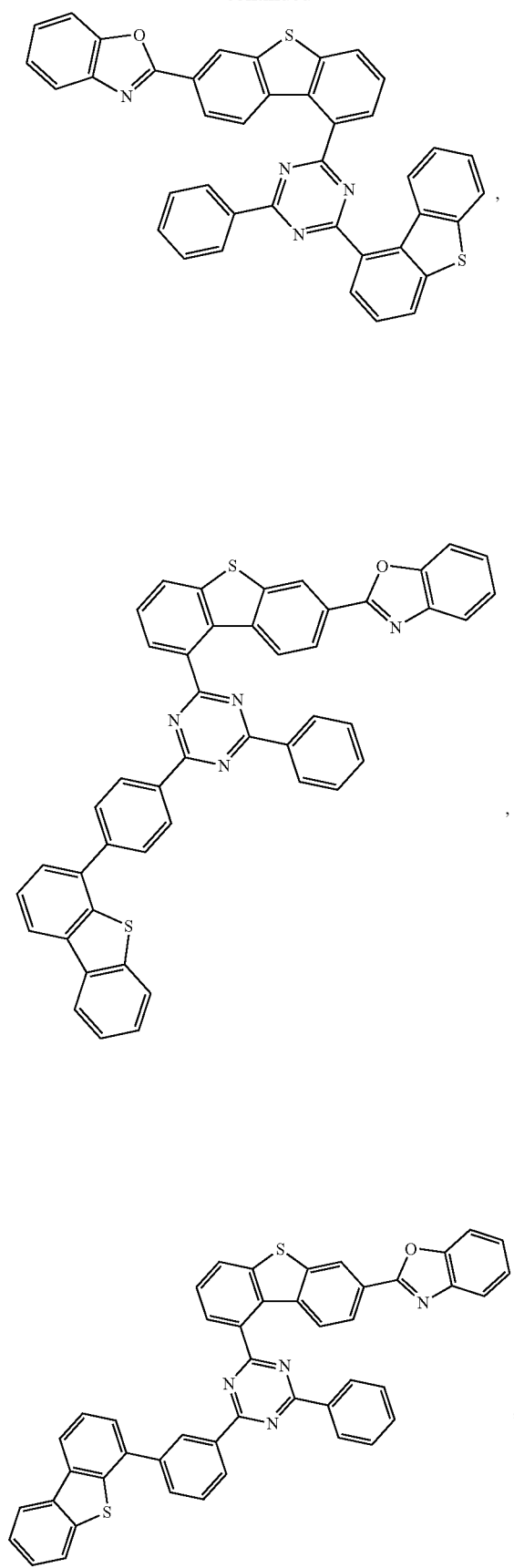
234
-continued
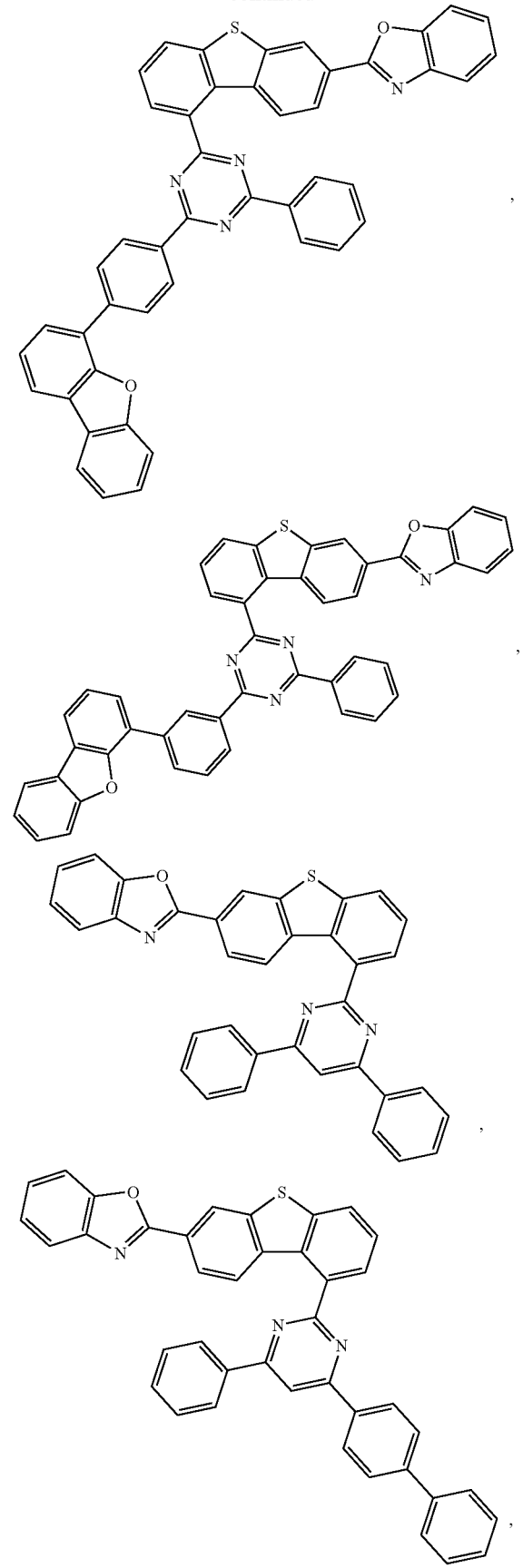

235
-continued
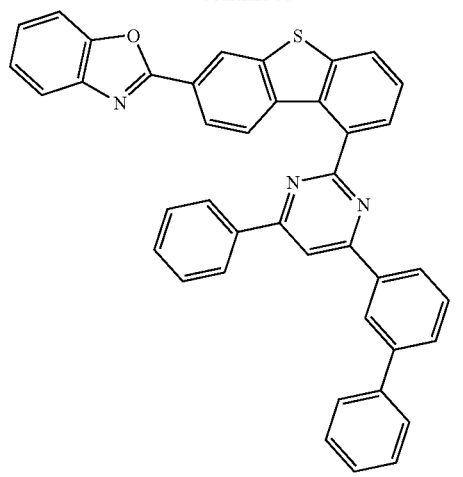
,
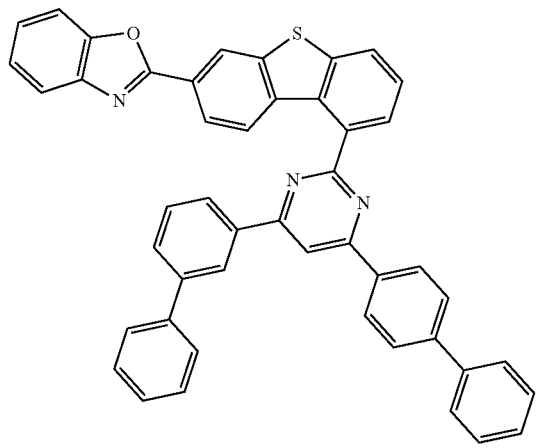
,
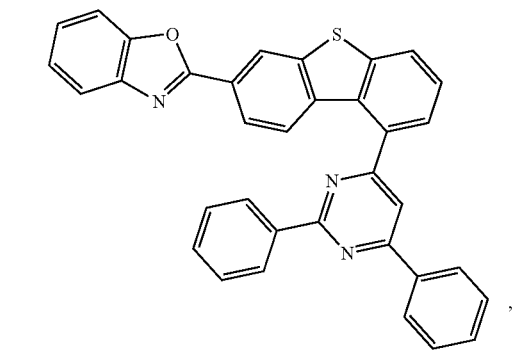
,
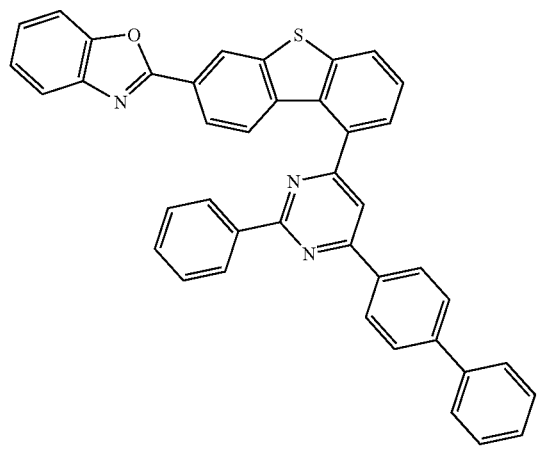
,
236
-continued
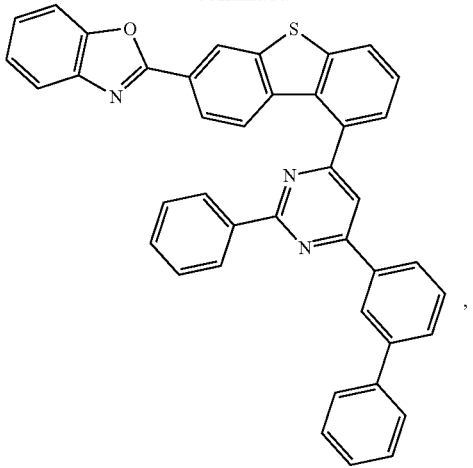
,
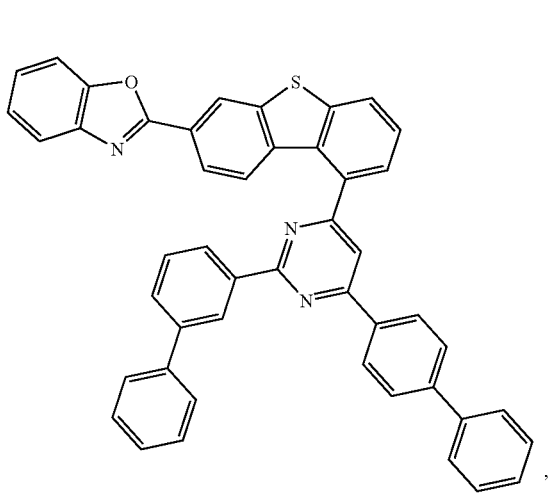
,
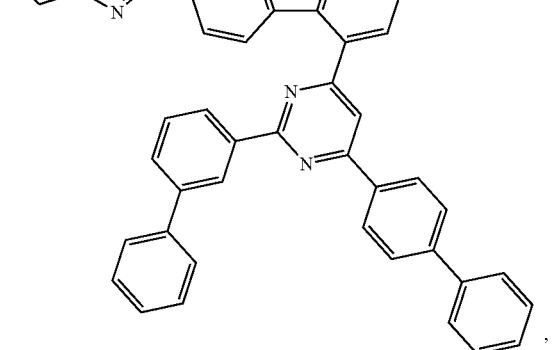
, 237
-continued
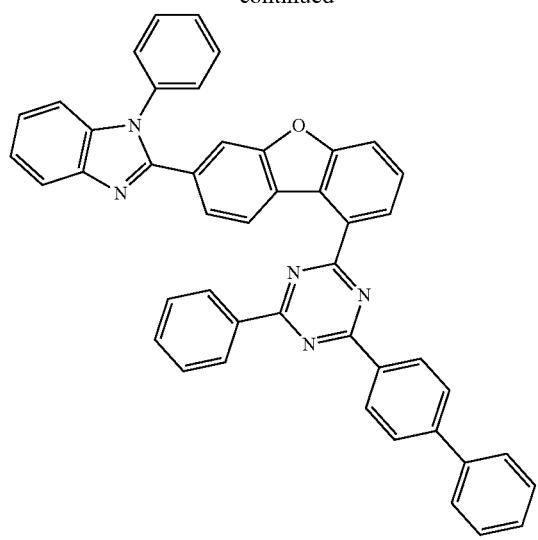
,
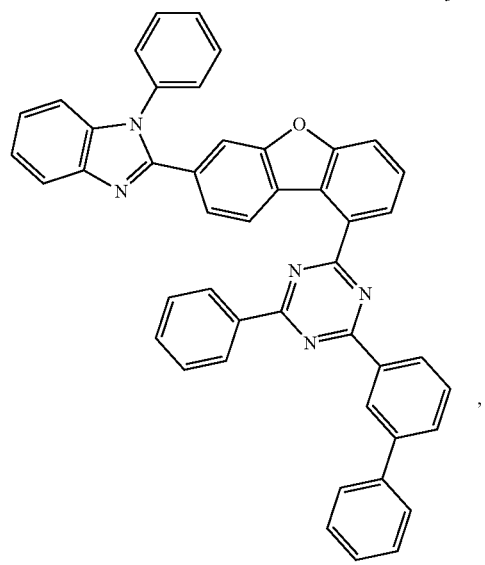
,
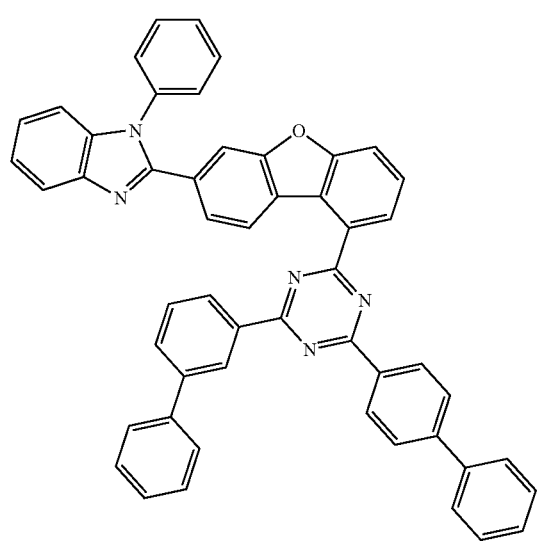
,
238
-continued
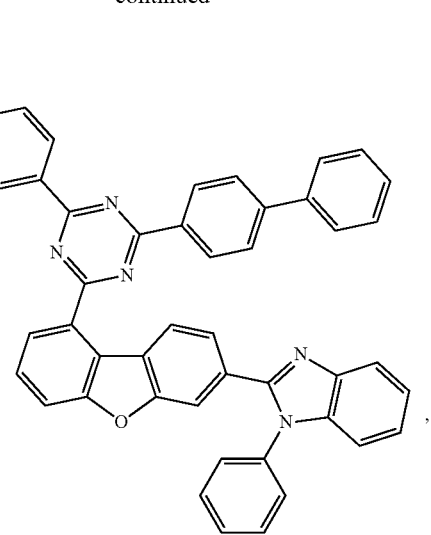
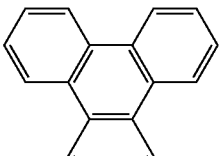
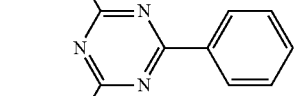
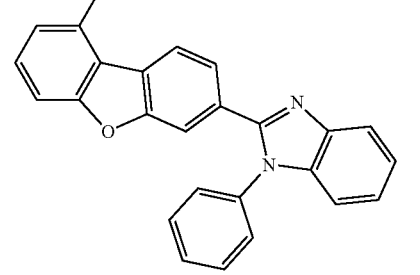
,
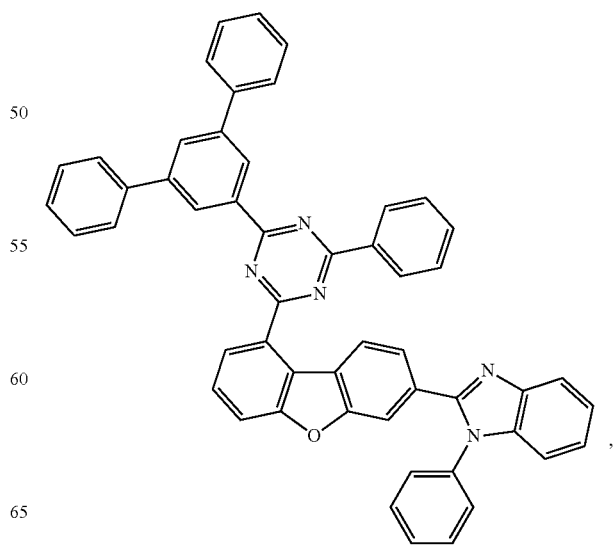
, 239
-continued
240
-continued
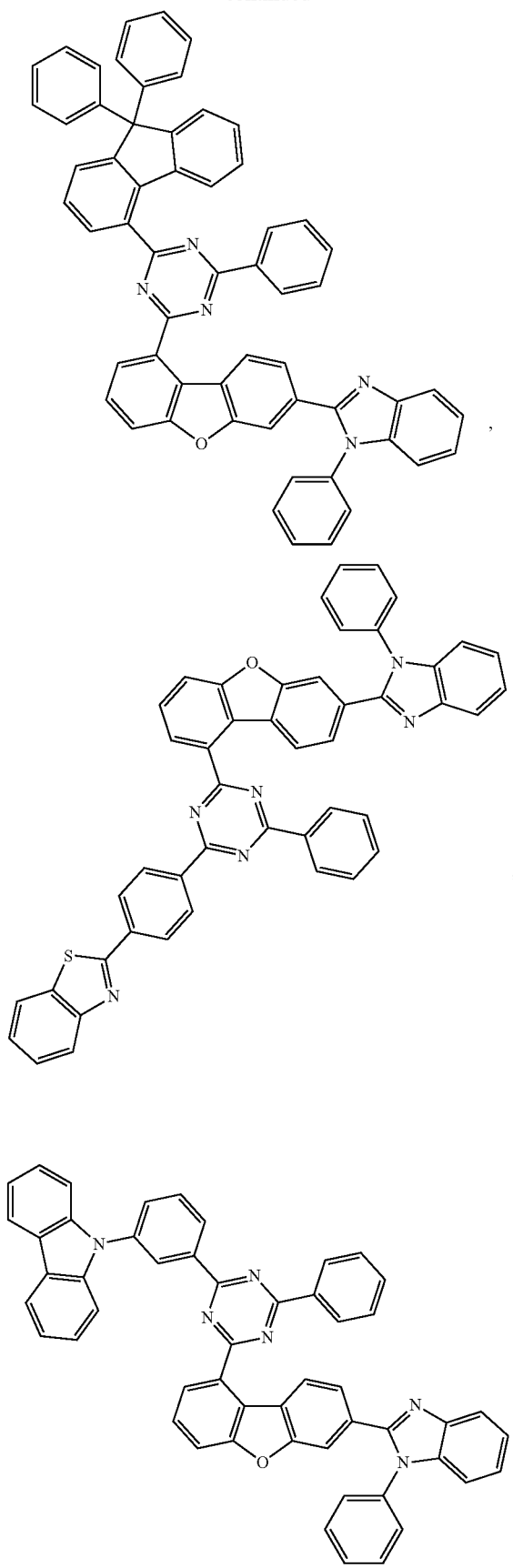
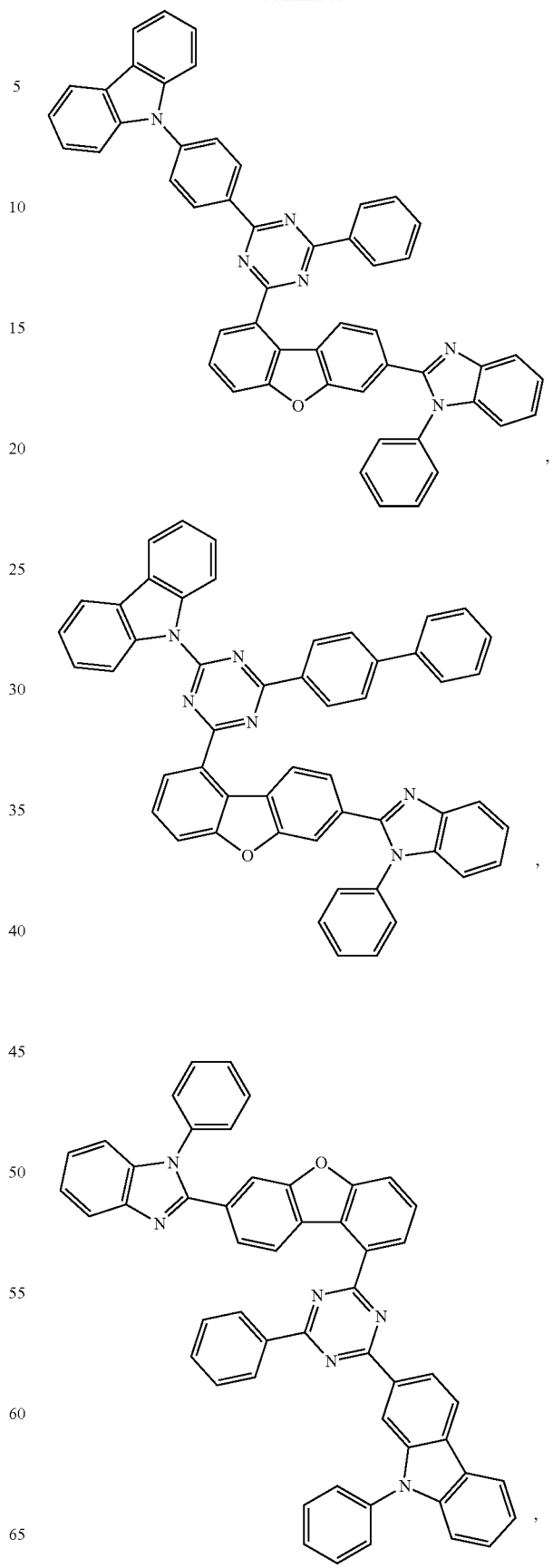

241
-continued
242
-continued
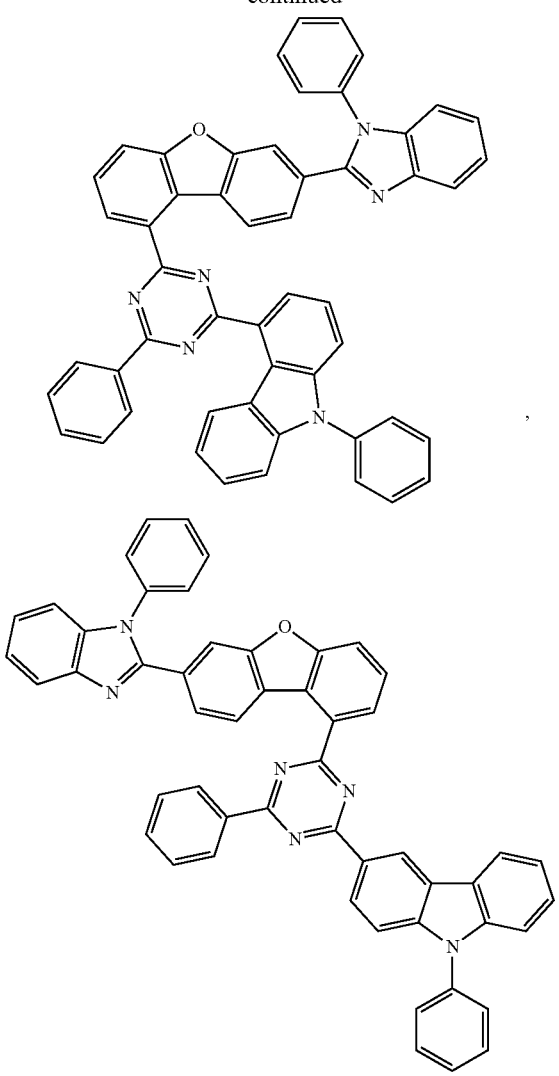
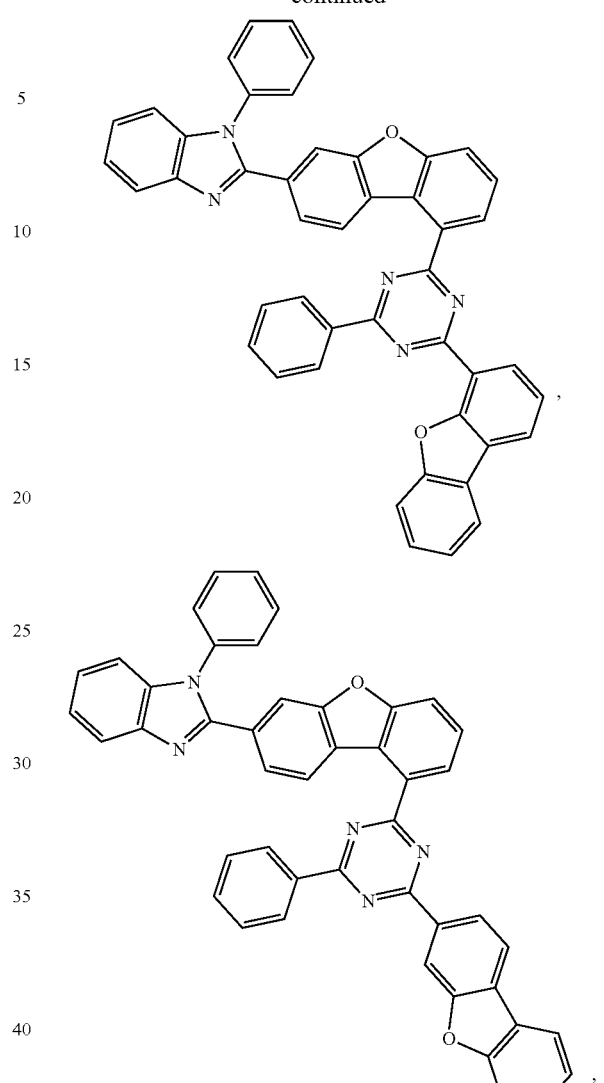
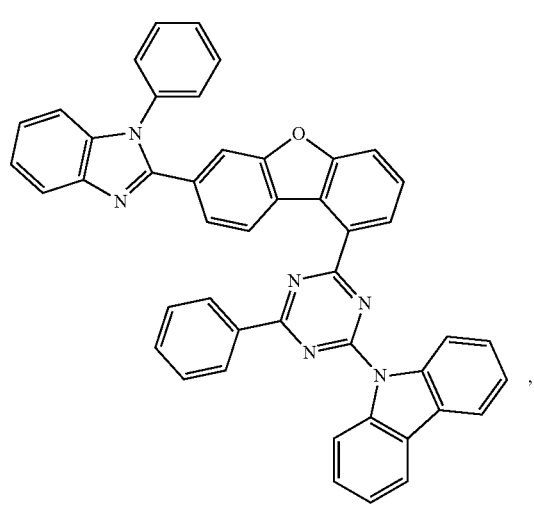
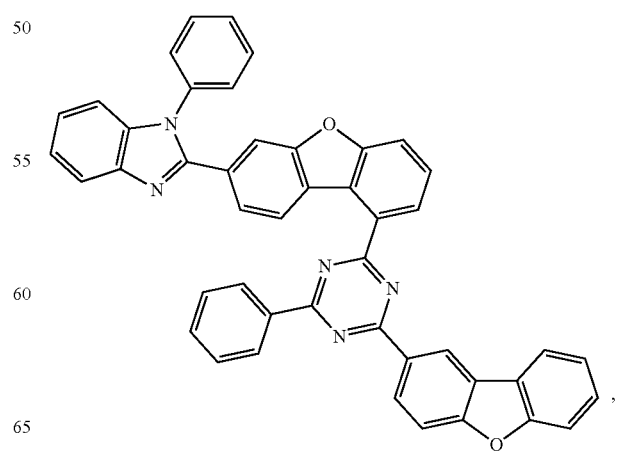

243
-continued
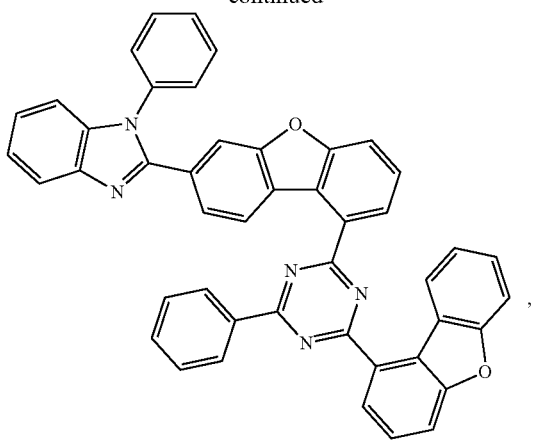
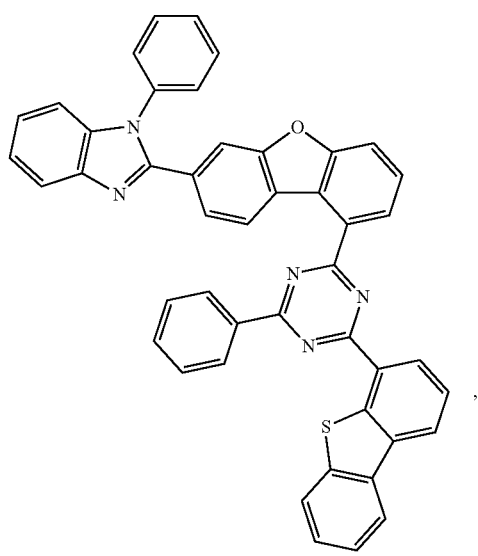
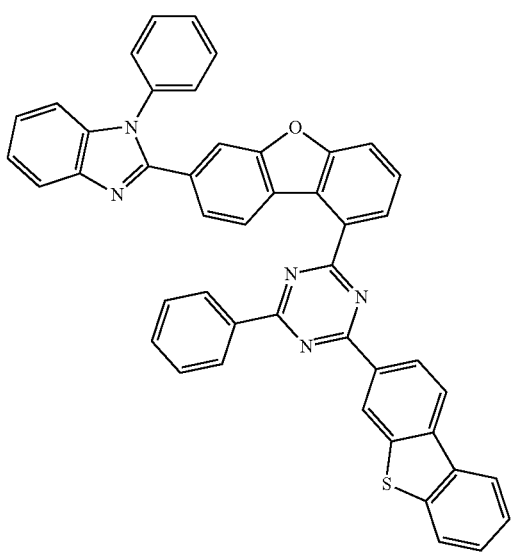
244
-continued
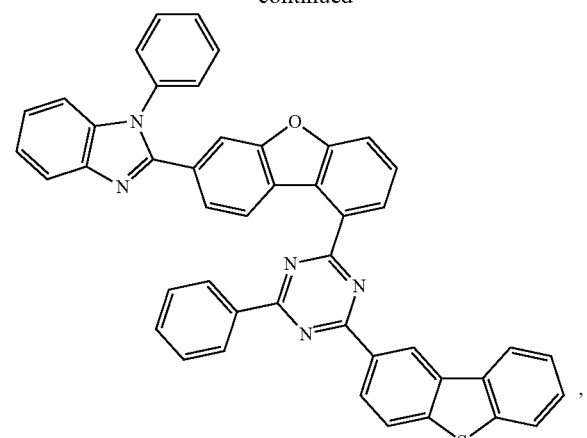
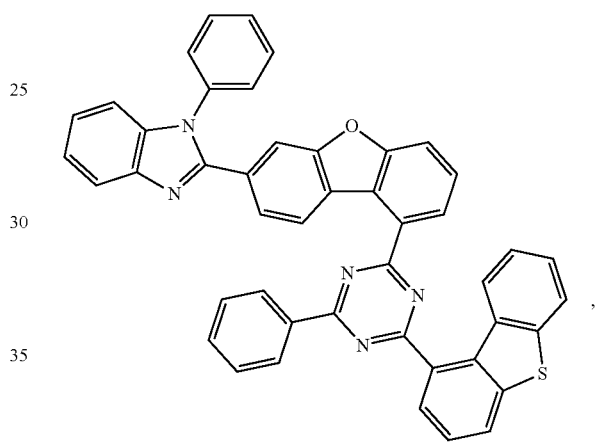
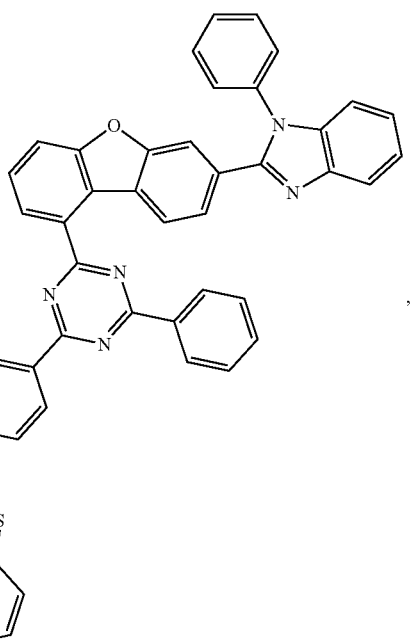

245
-continued
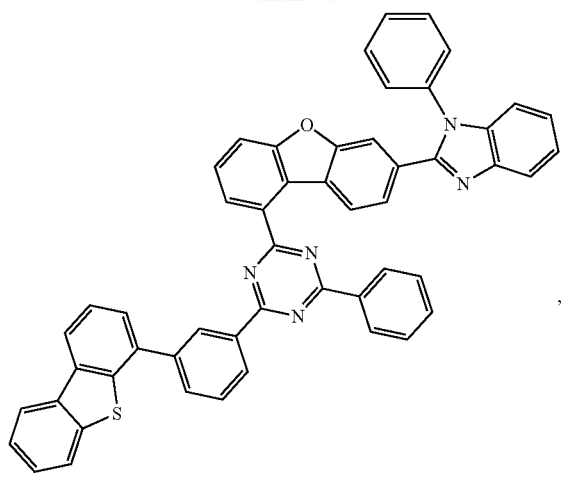
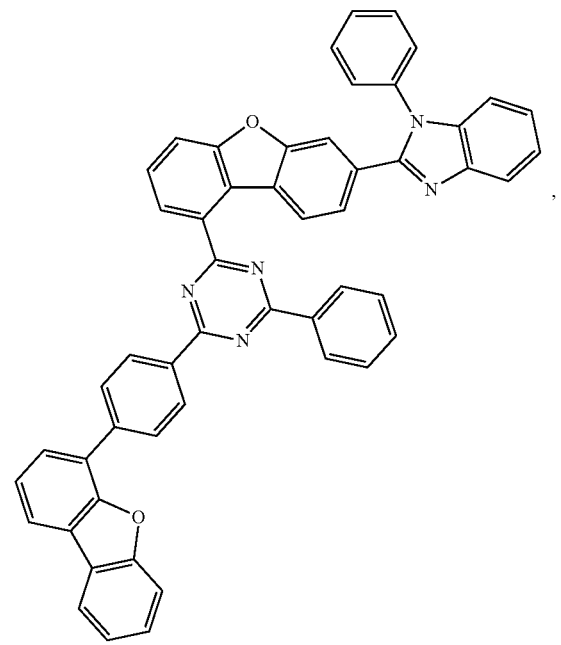
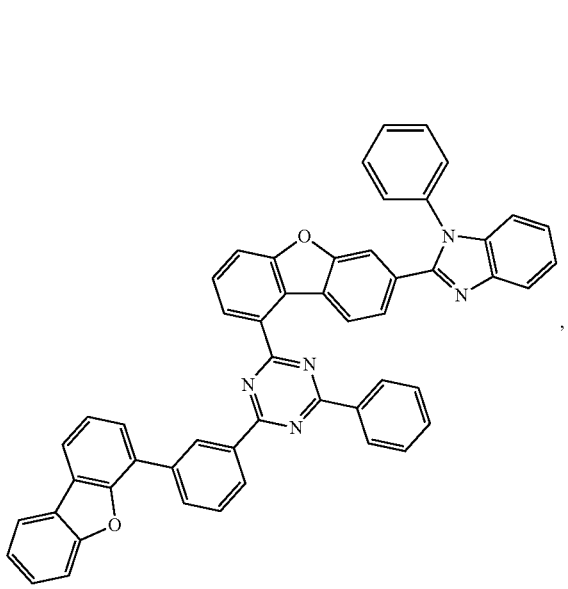
246
-continued
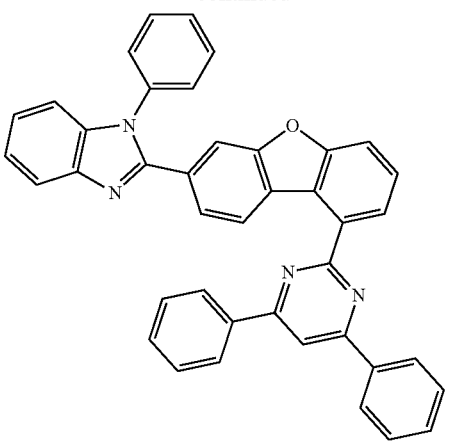
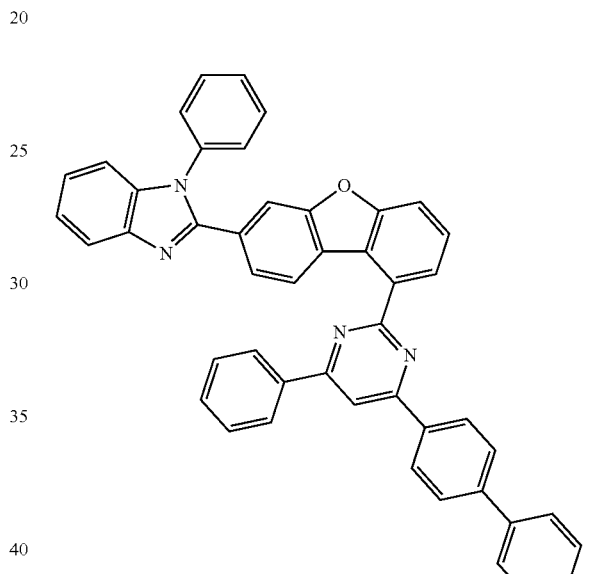
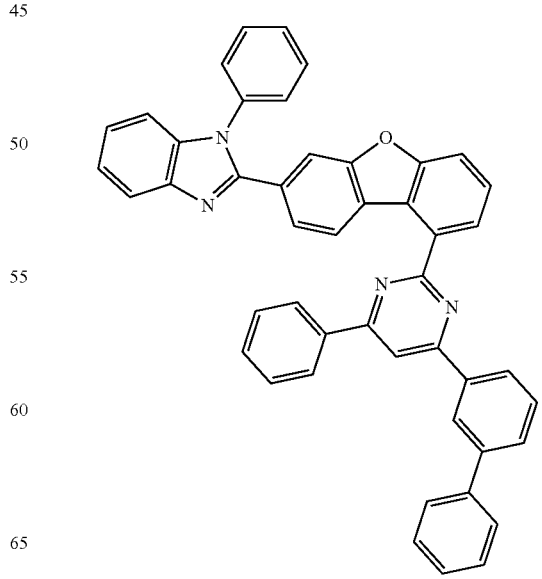

247
-continued
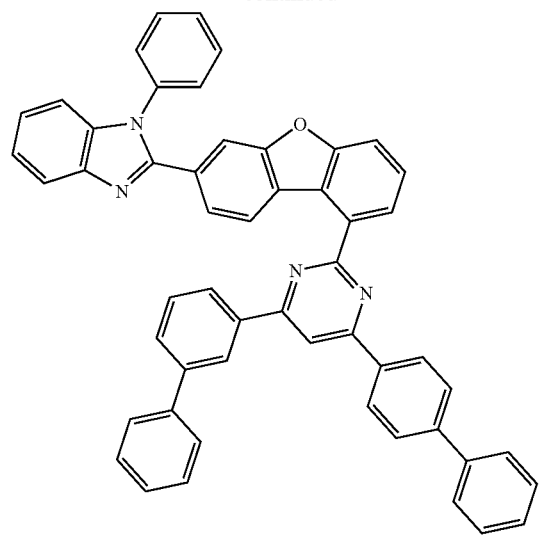
,
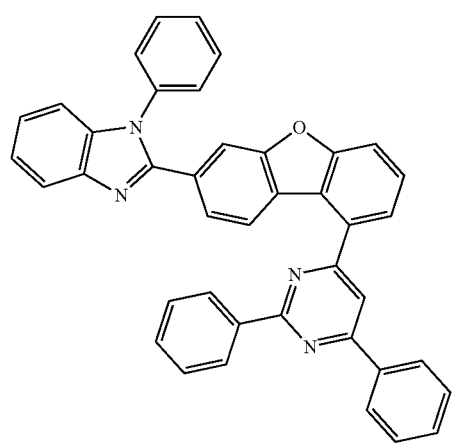
,
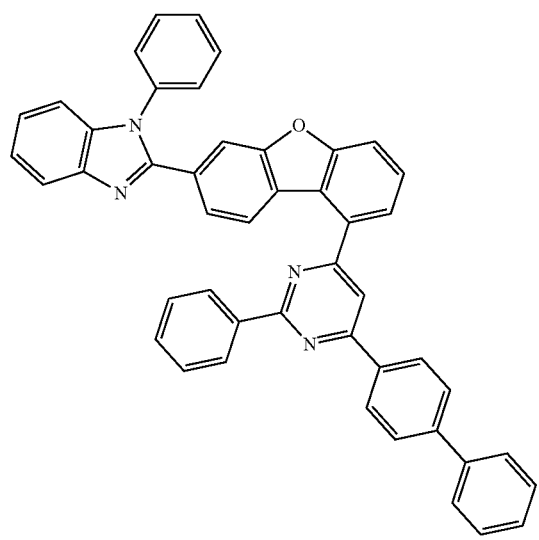
,
248
-continued
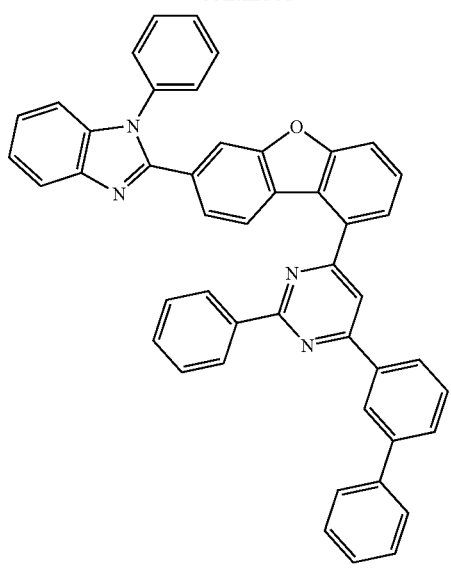
,
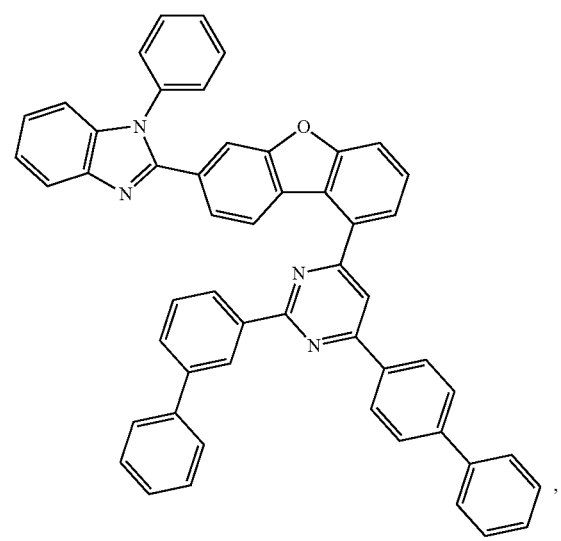
,
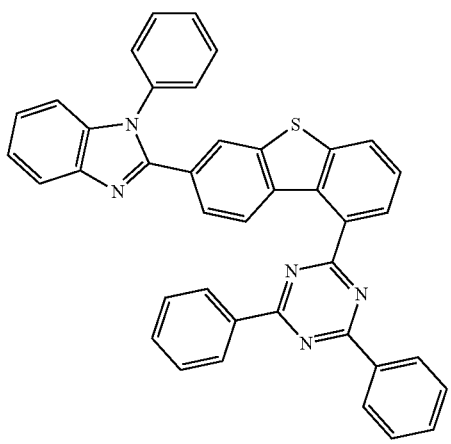
, 249
-continued
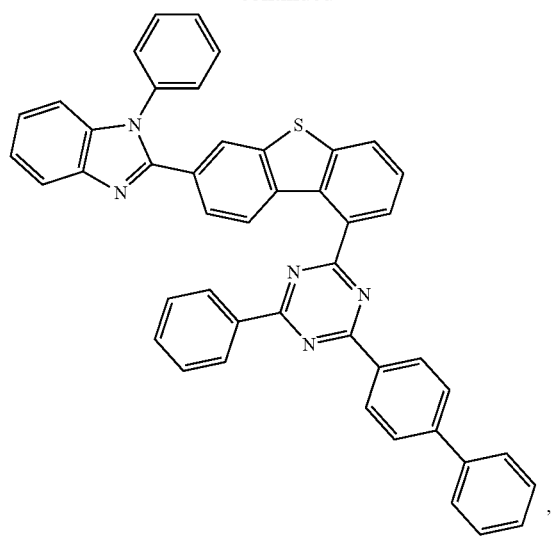
,
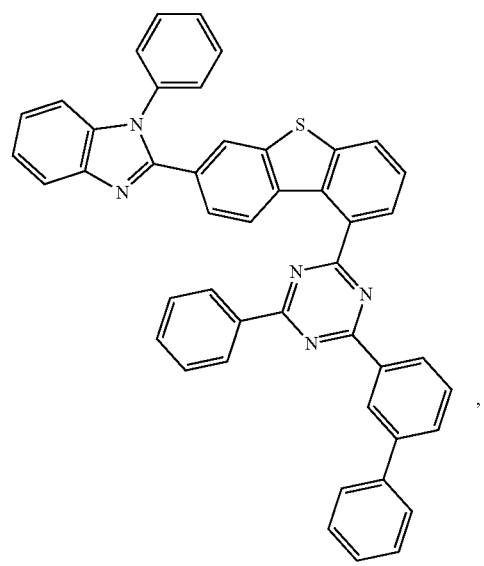
,
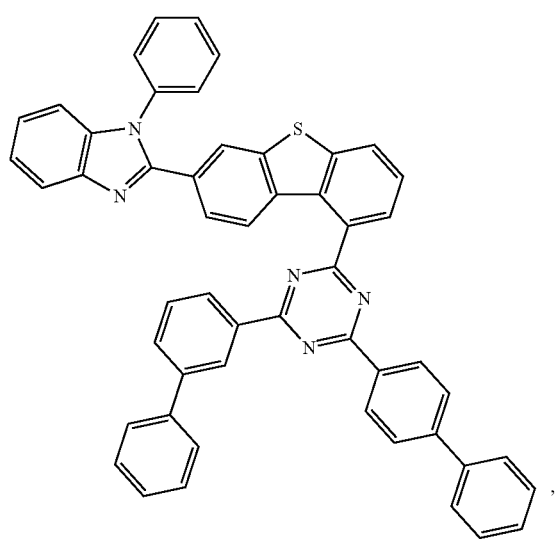
,
250
-continued
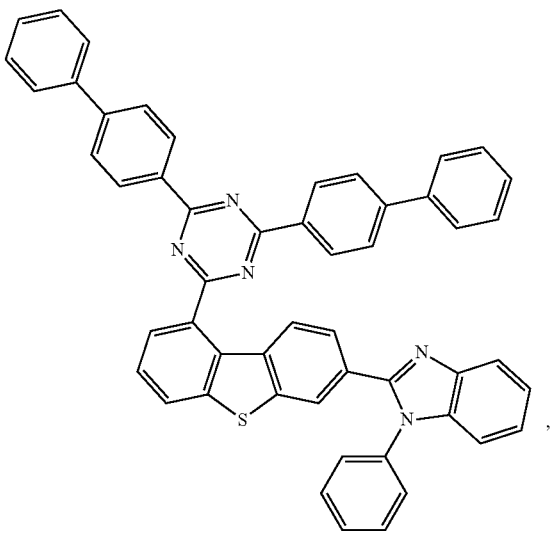
,
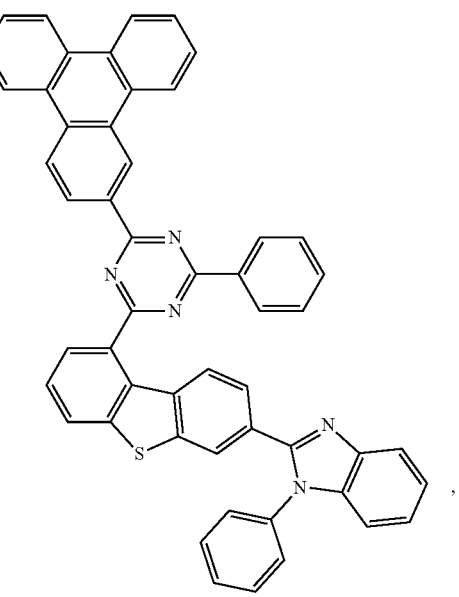
,
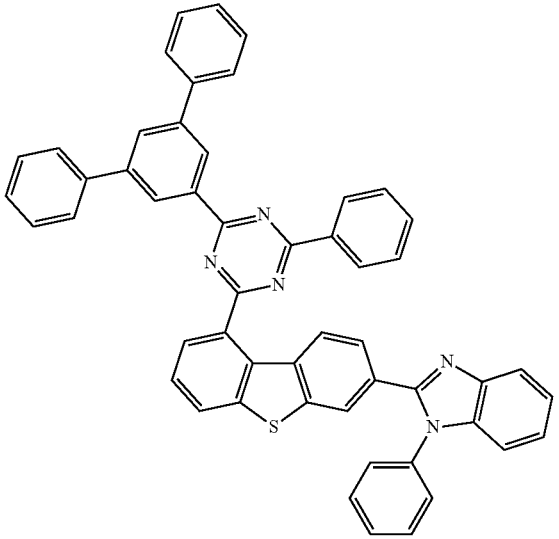
, 251
-continued
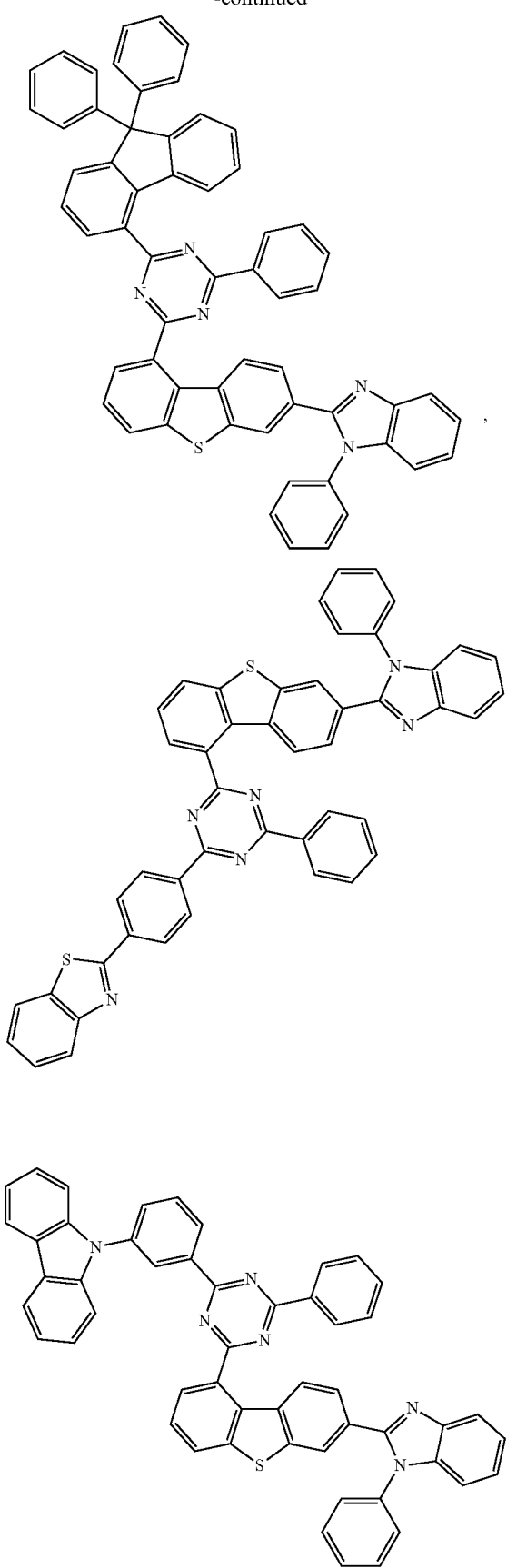
252
-continued
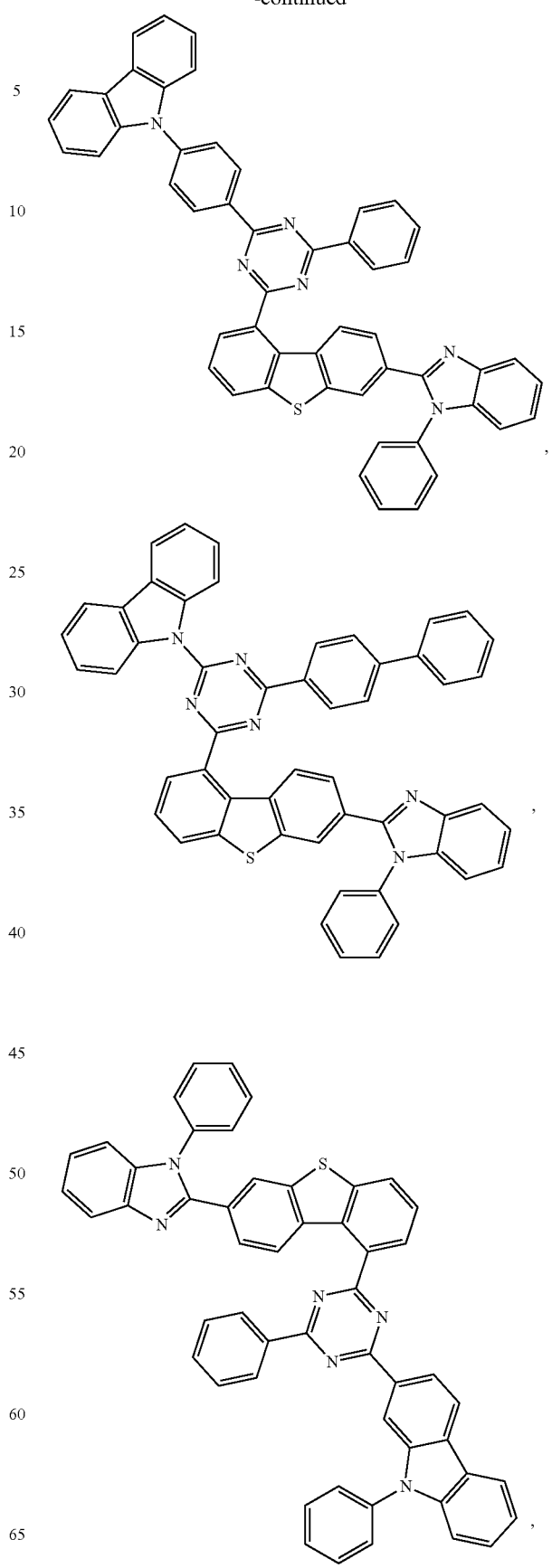

253
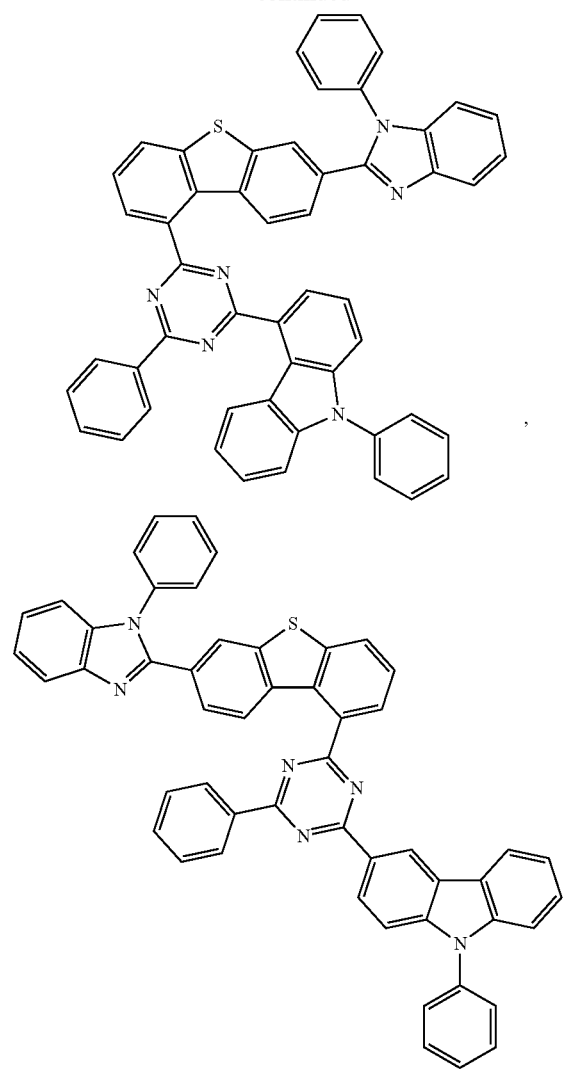
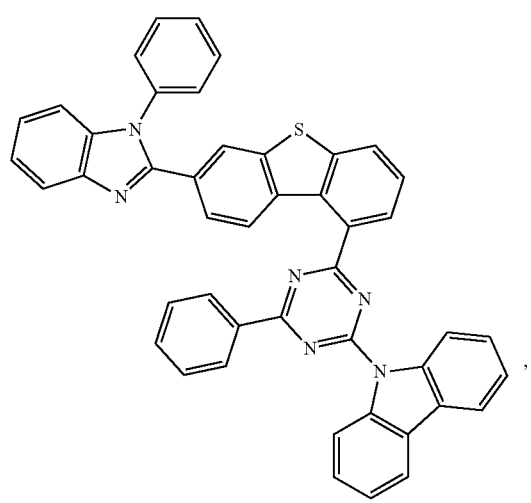
254
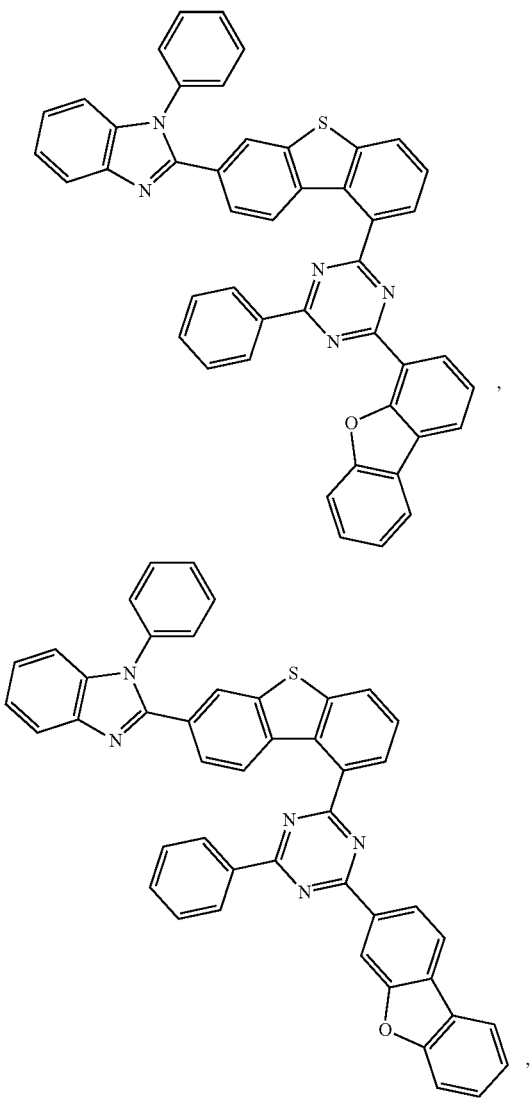
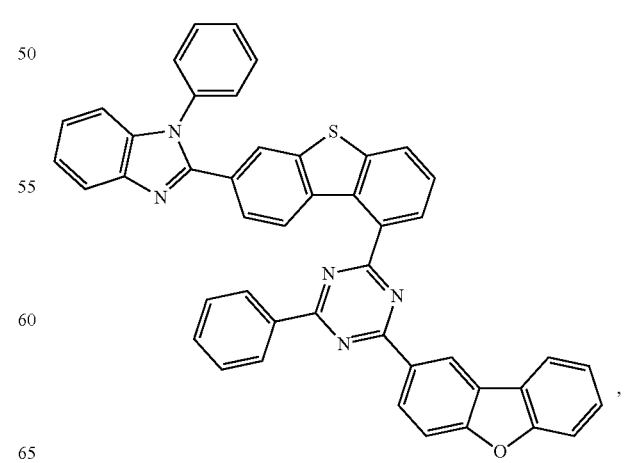

255
-continued
256
-continued
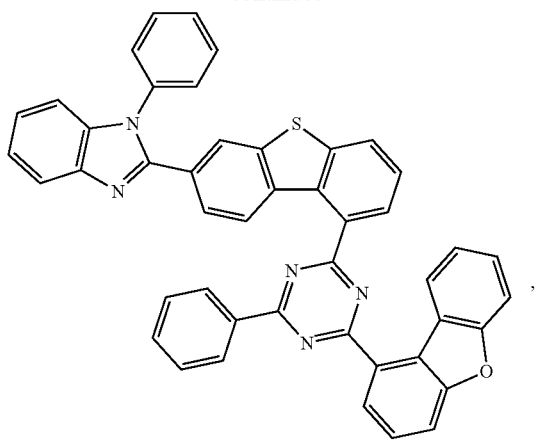
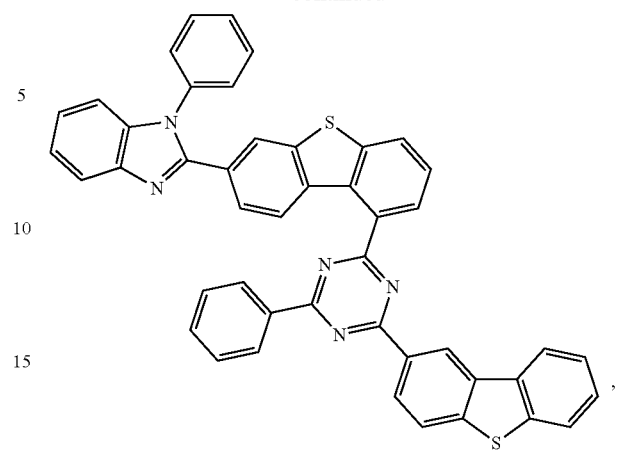

257
-continued
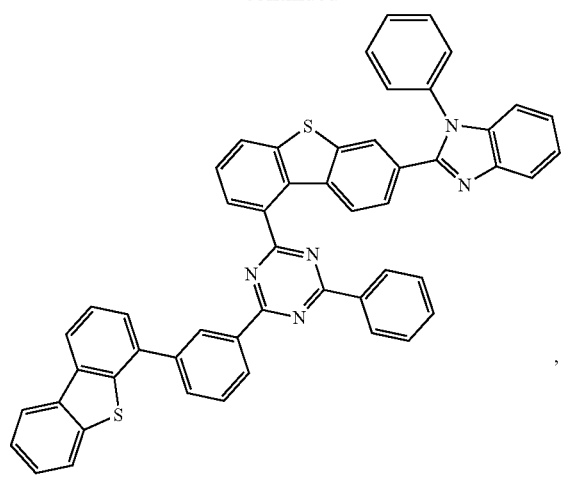
,
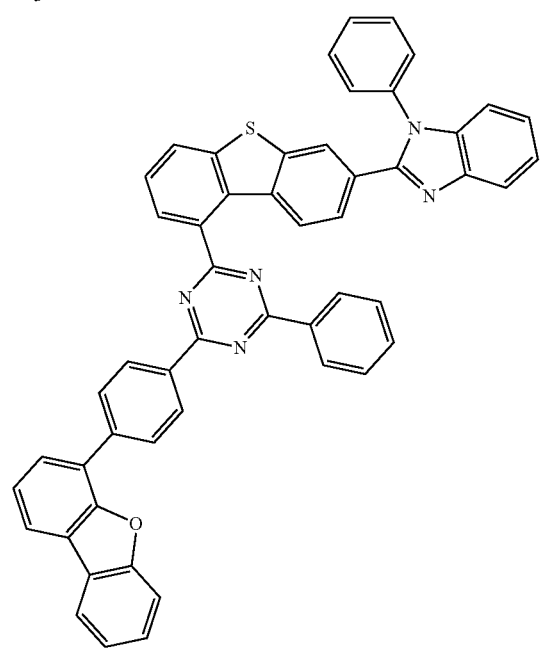
,
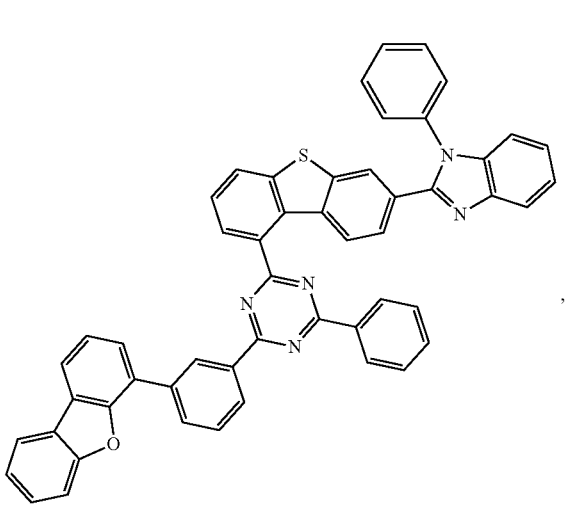
,
258
-continued
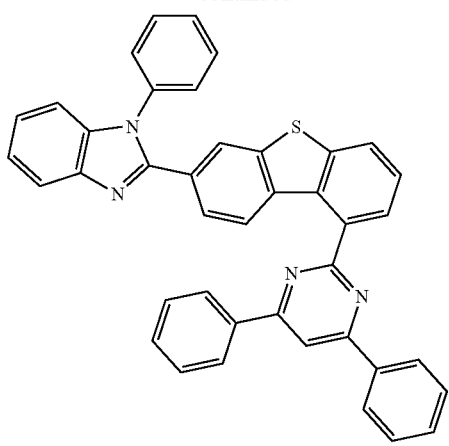
,
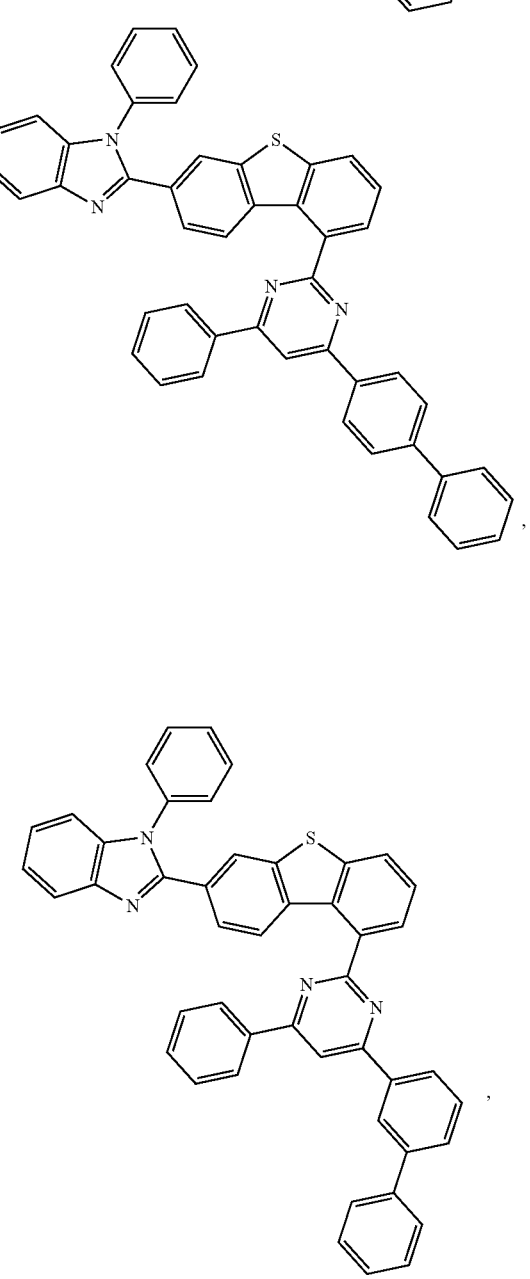

259
-continued
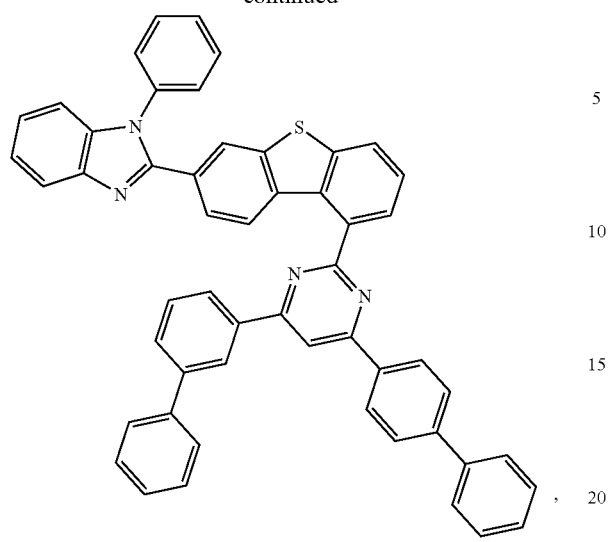
260
-continued
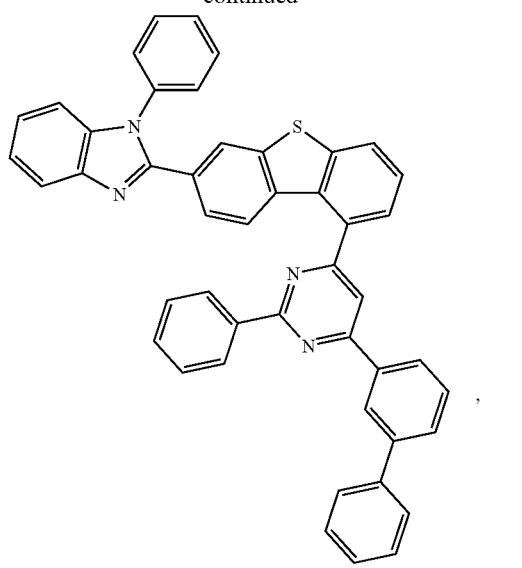
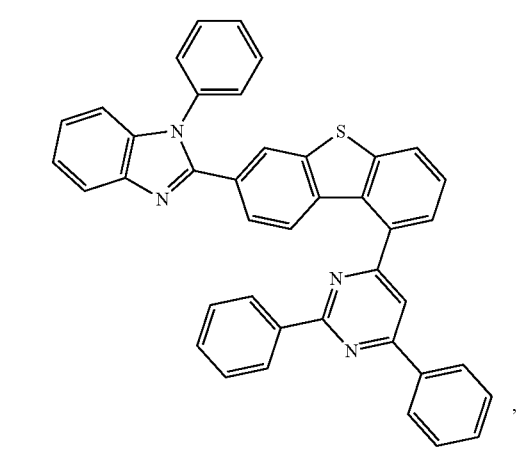
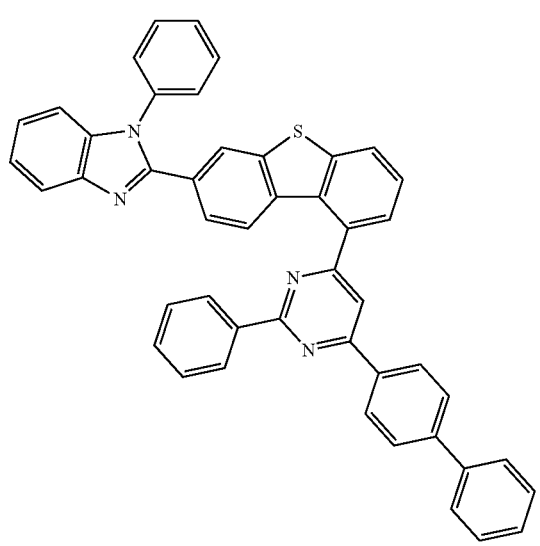
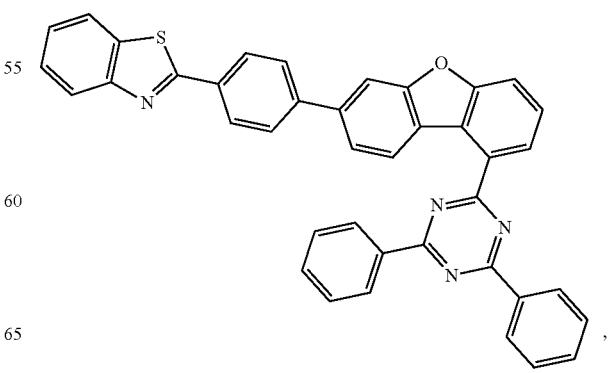

261
-continued
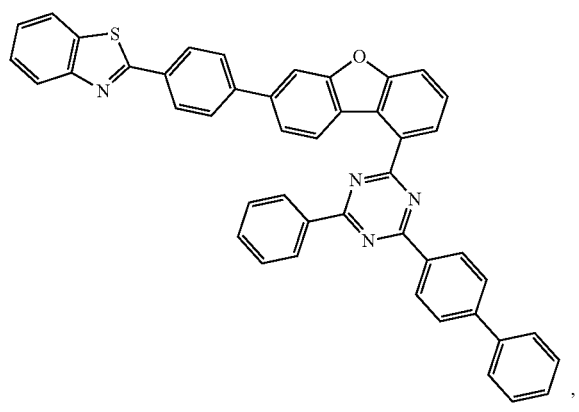
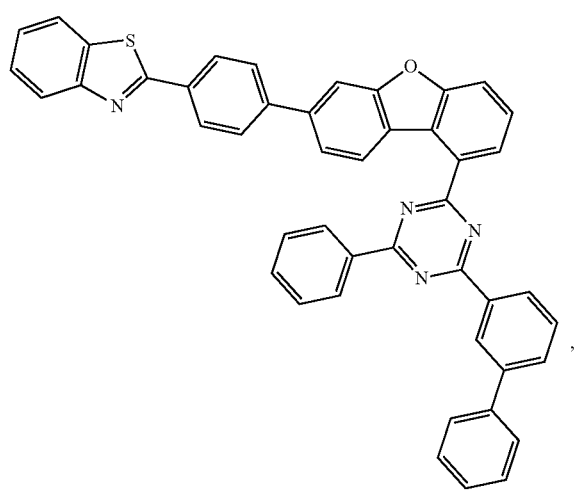
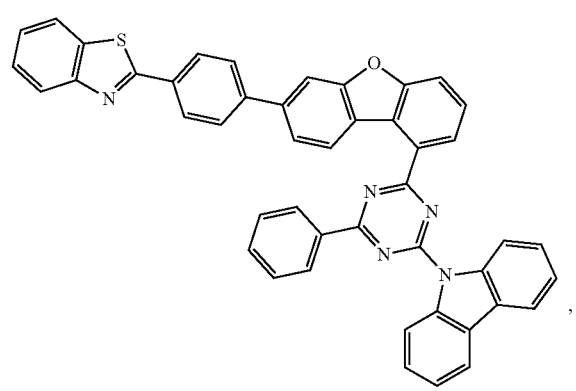
262
-continued
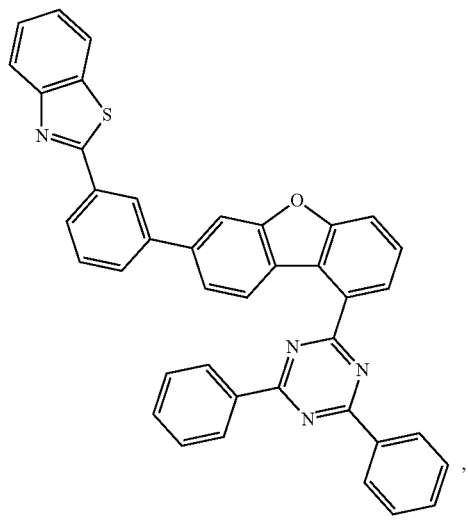
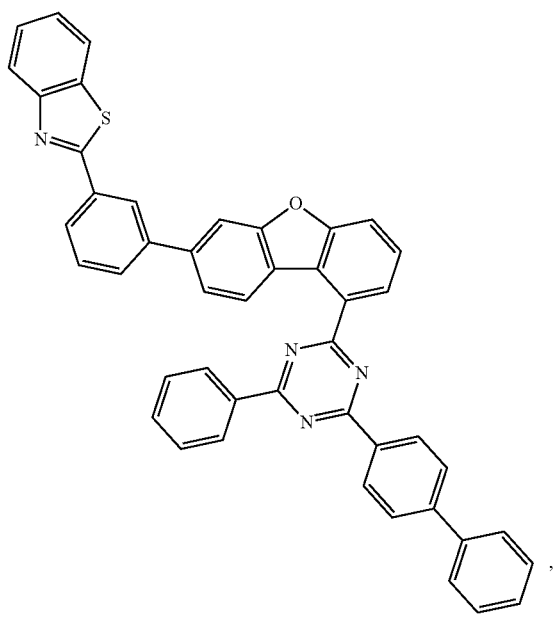

263
-continued
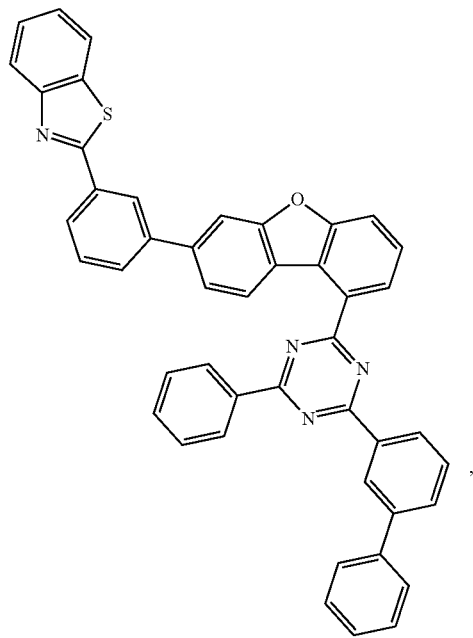
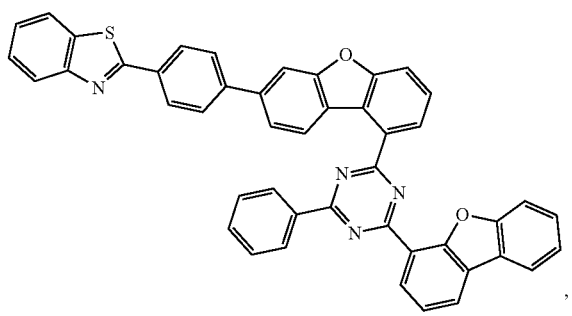
264
-continued
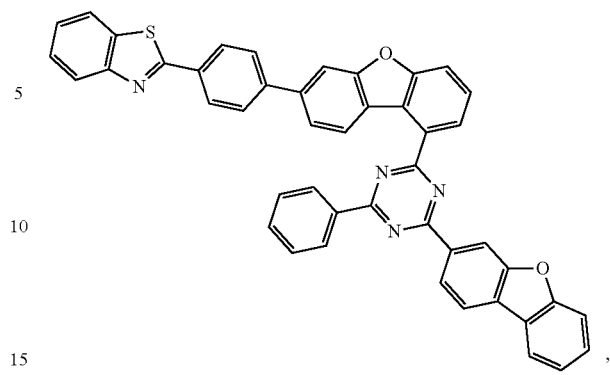
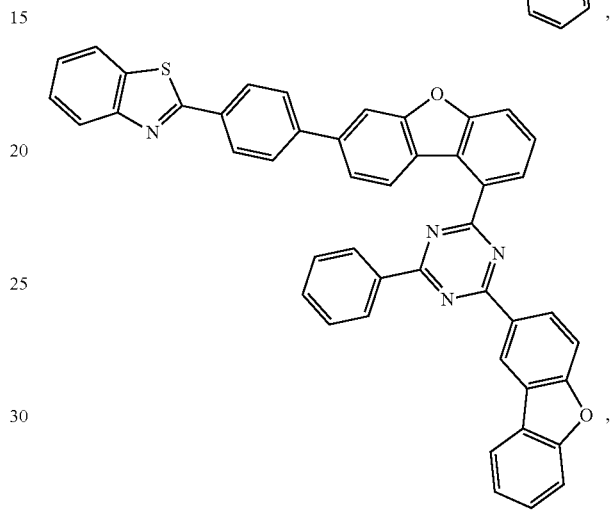
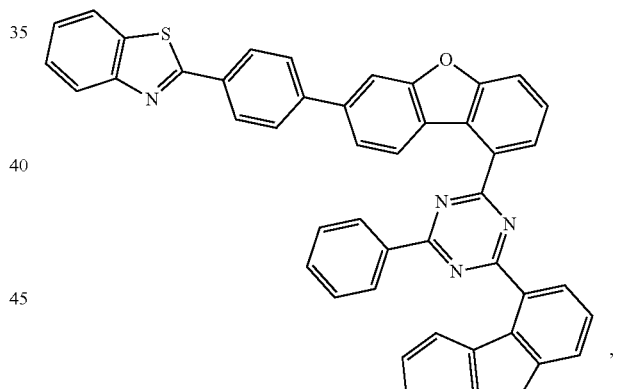
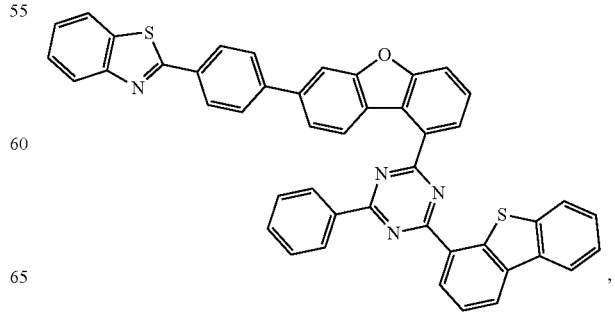

265
-continued
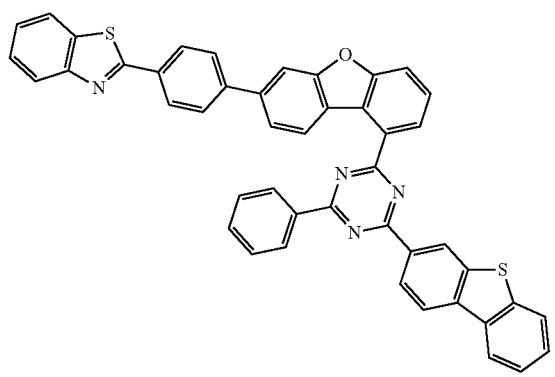
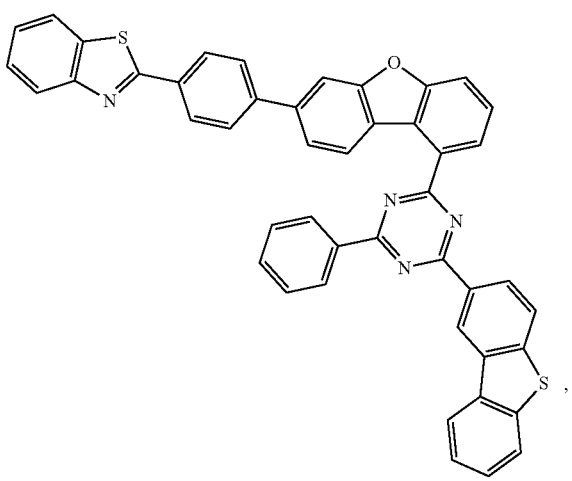
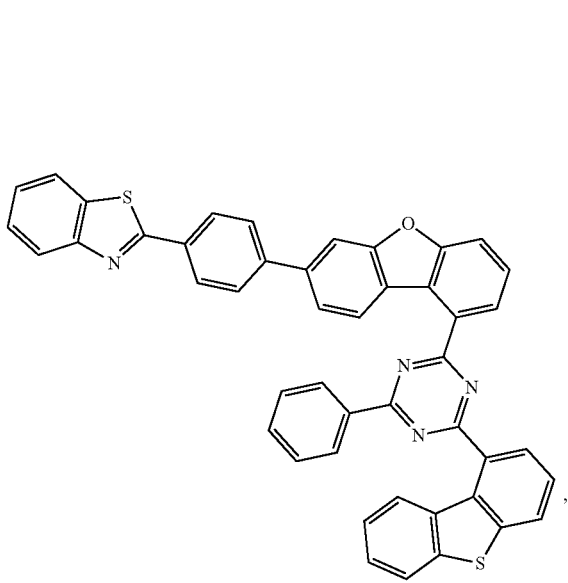
266
-continued
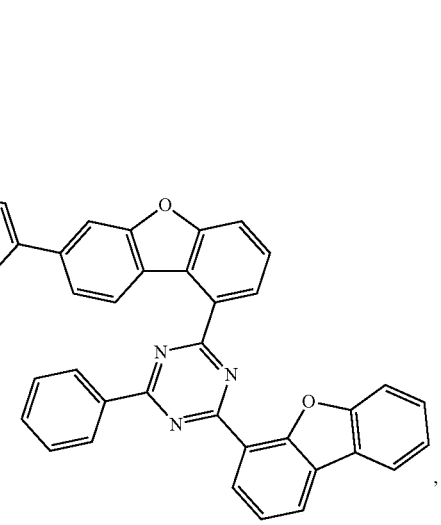
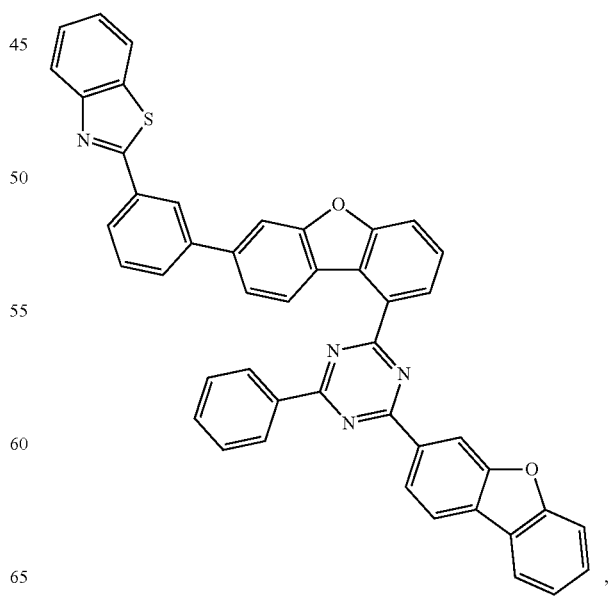

267
-continued
268
-continued
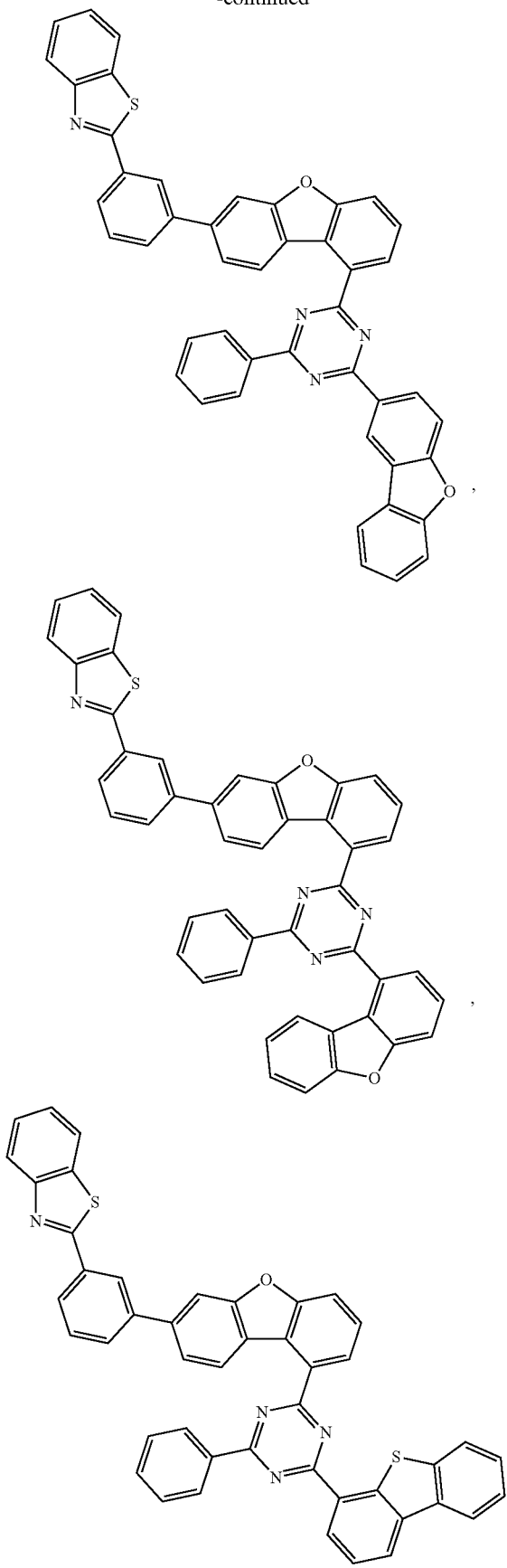
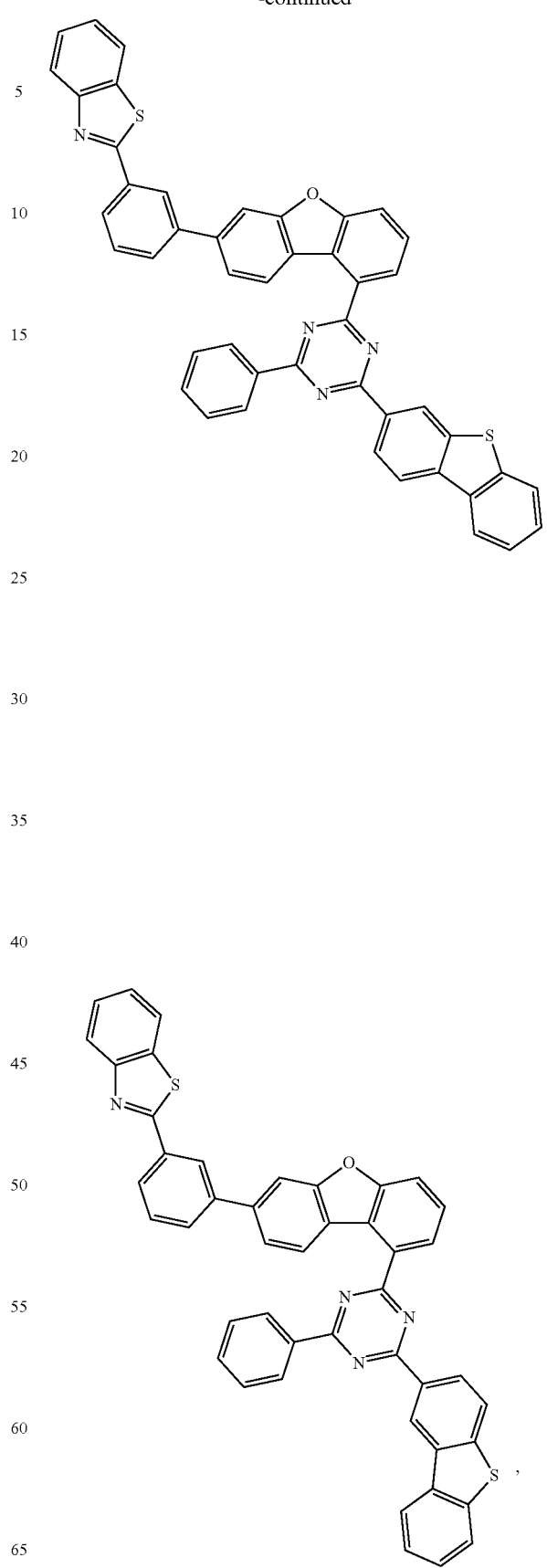

269
-continued
270
-continued
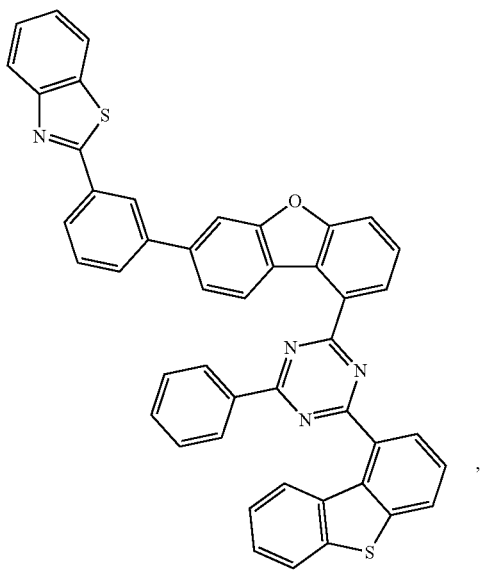
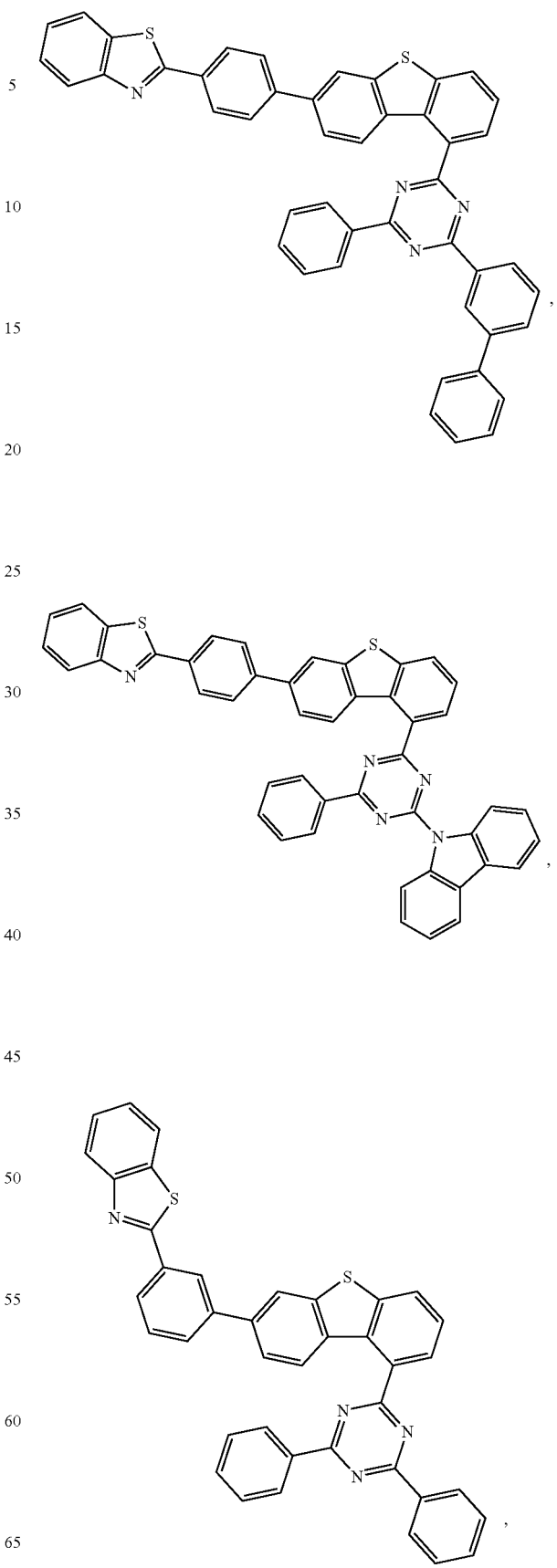

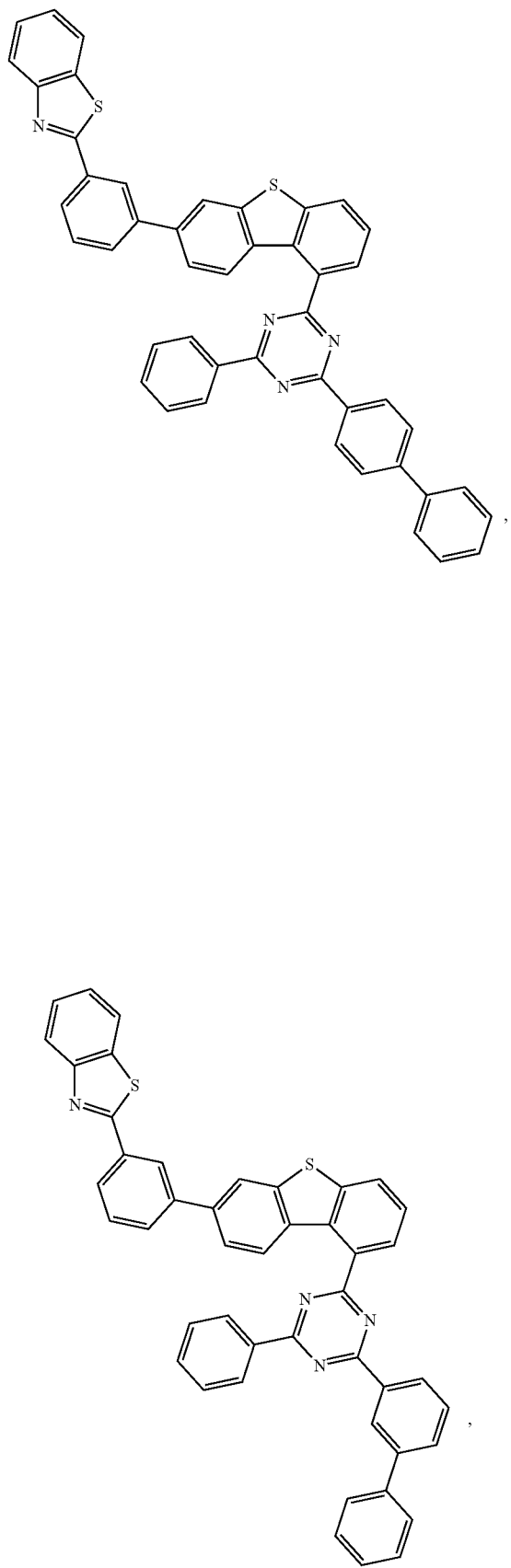
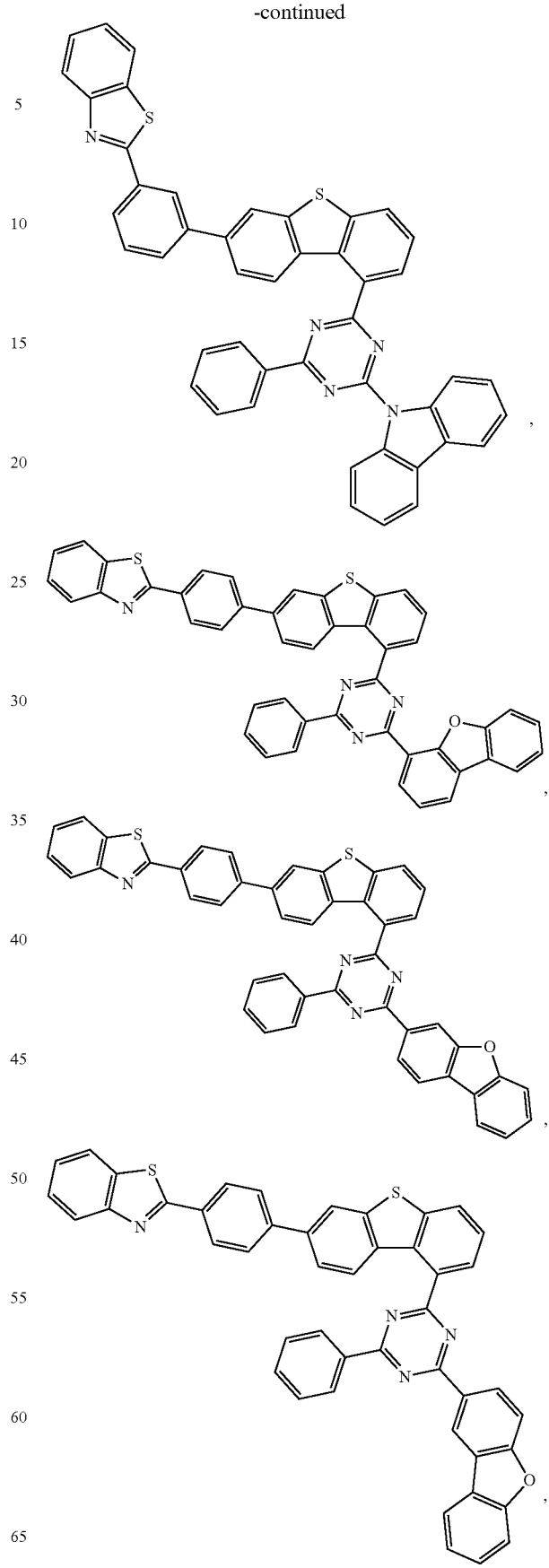

273
-continued
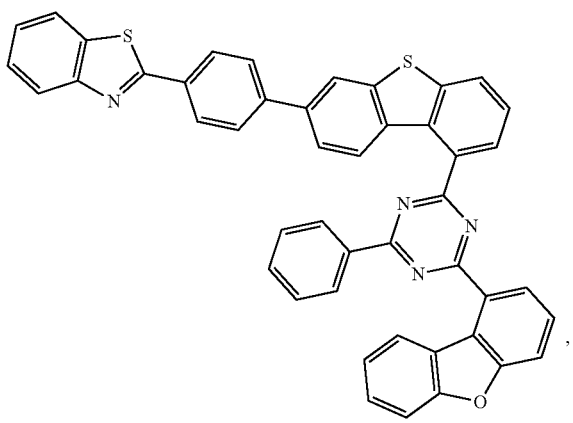
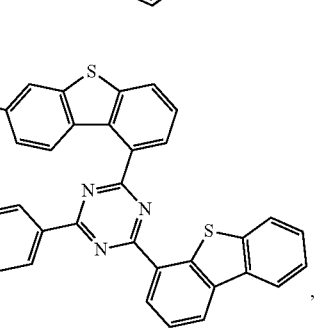
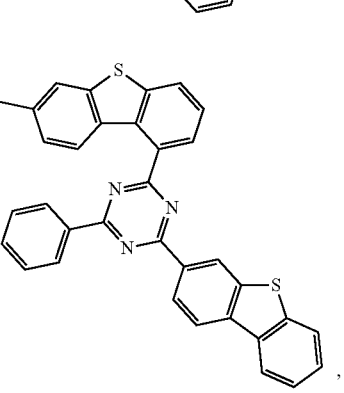
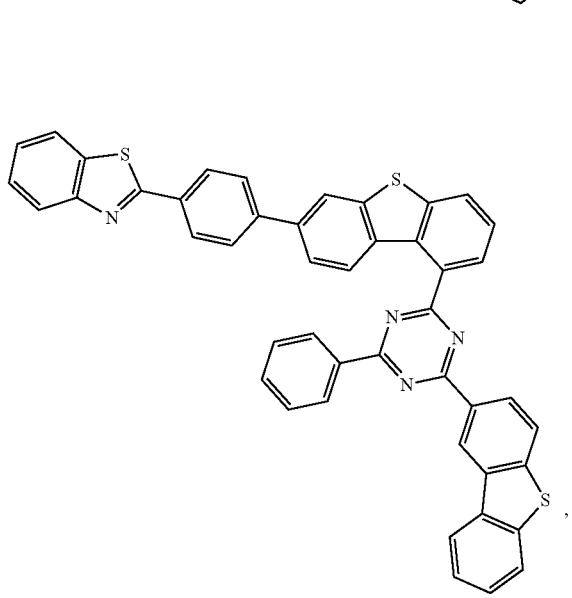
274
-continued
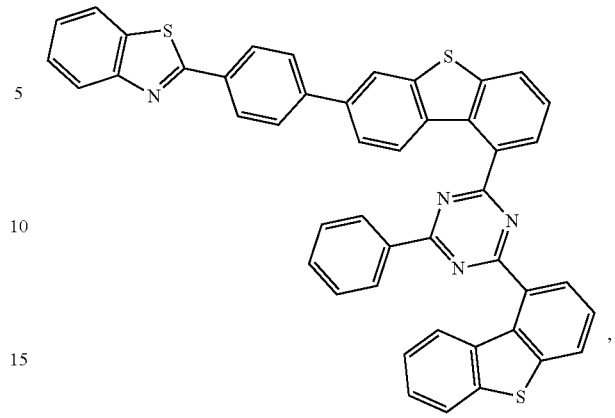
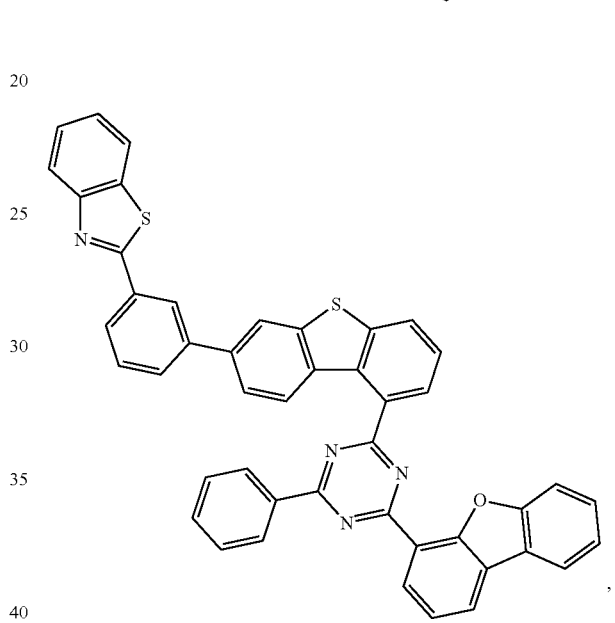
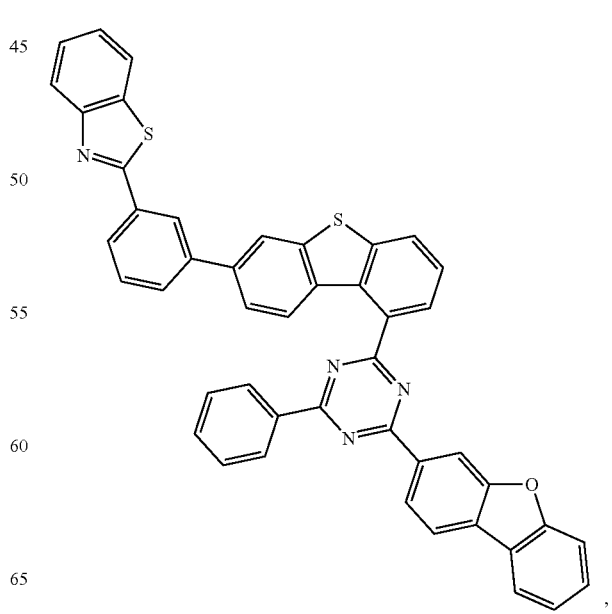

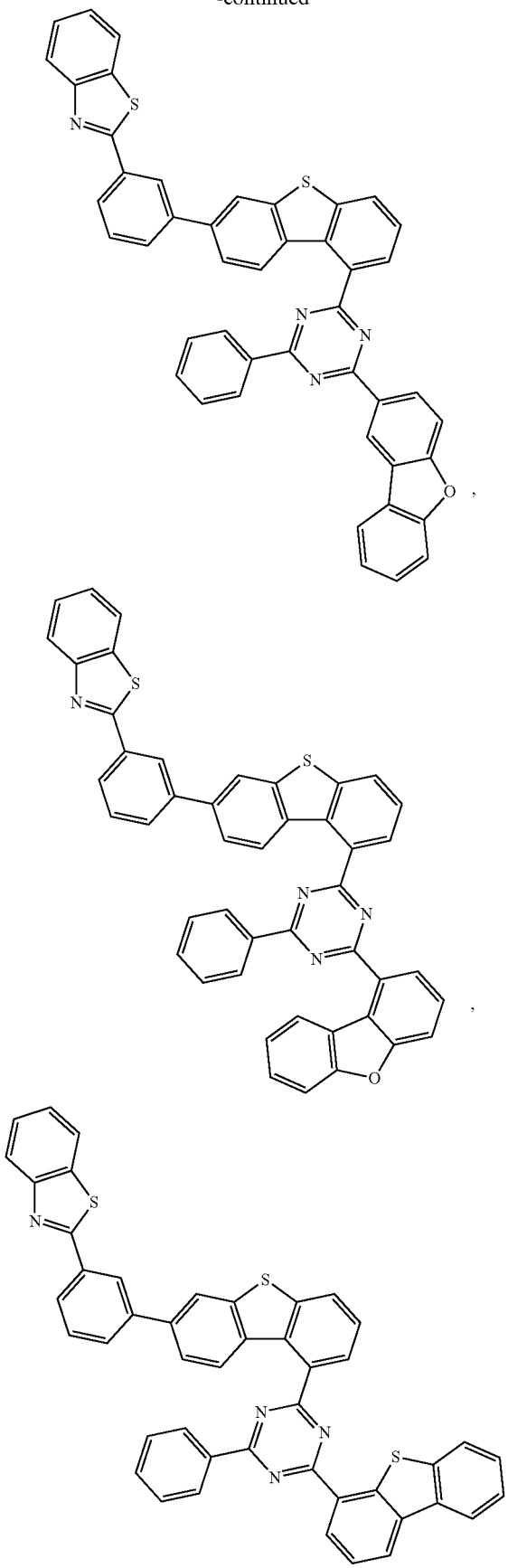

277
-continued
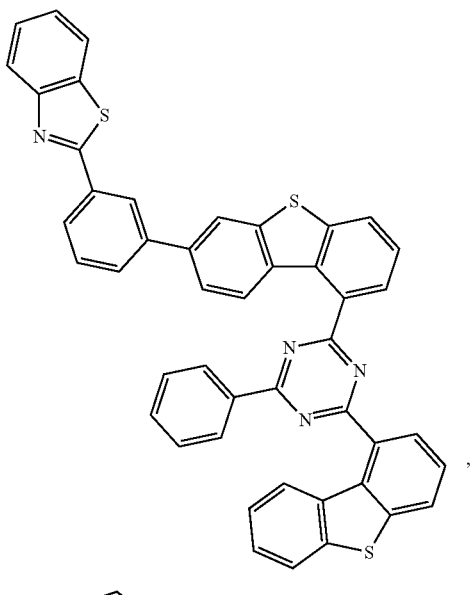
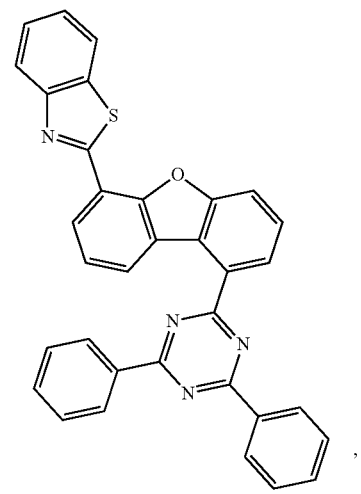
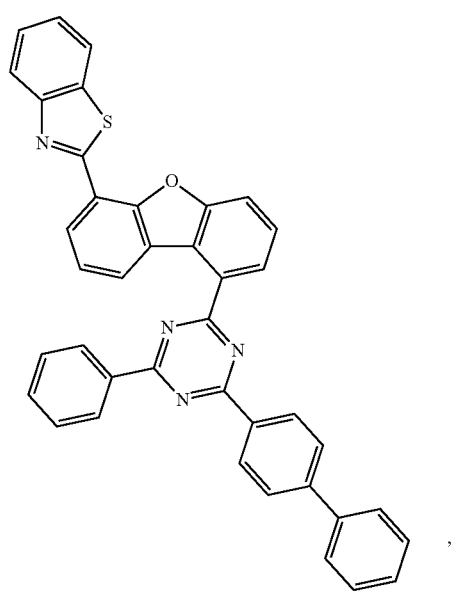
278
-continued
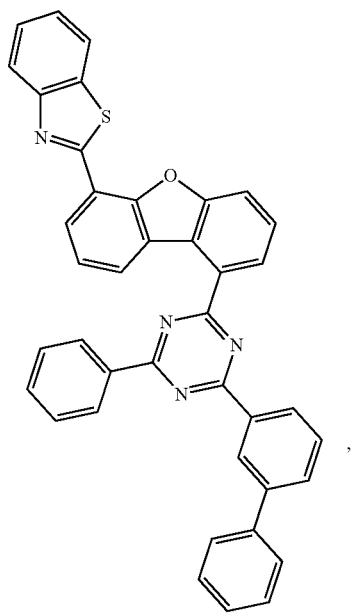
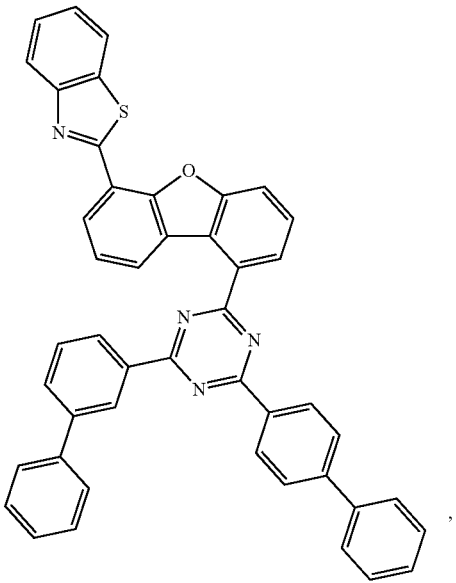

279
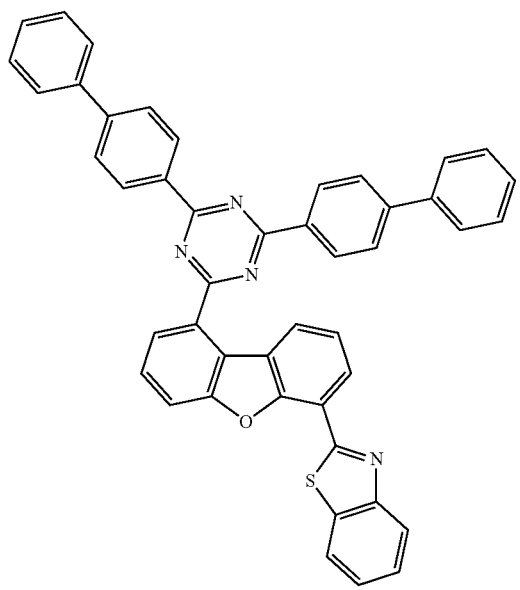
280
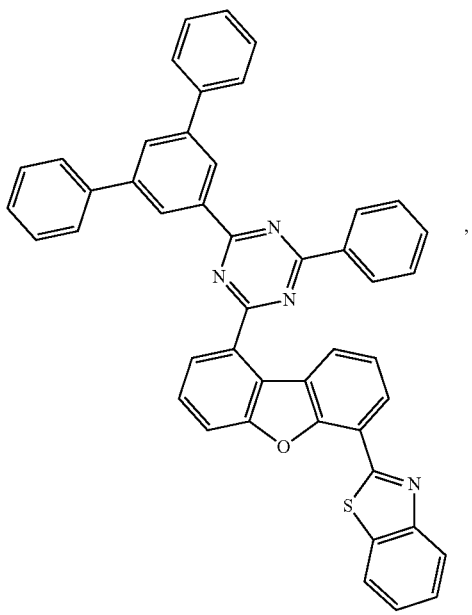
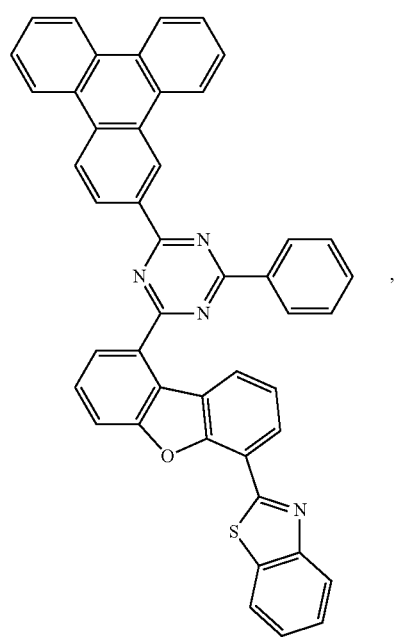
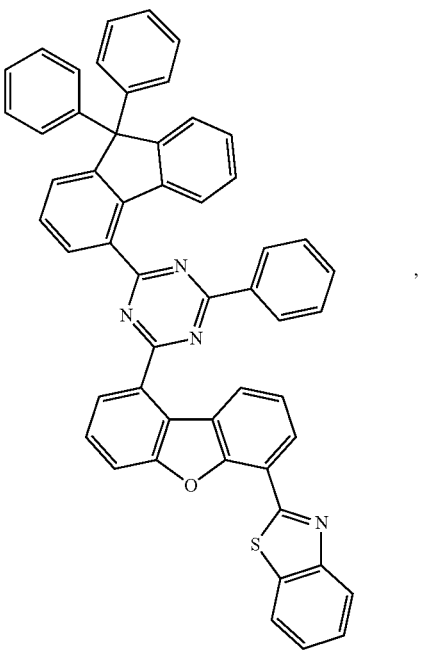

281
-continued
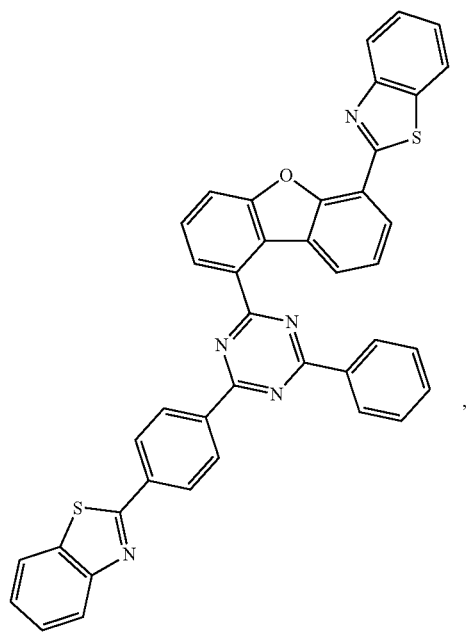
282
-continued
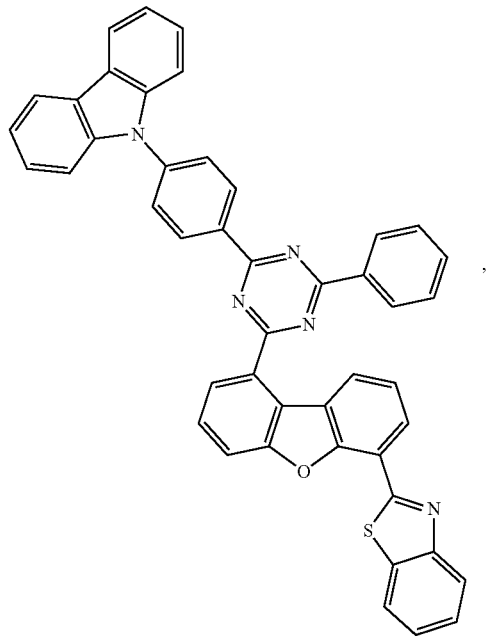,
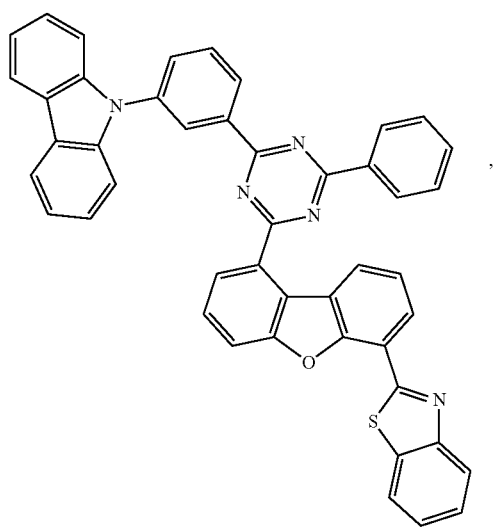,
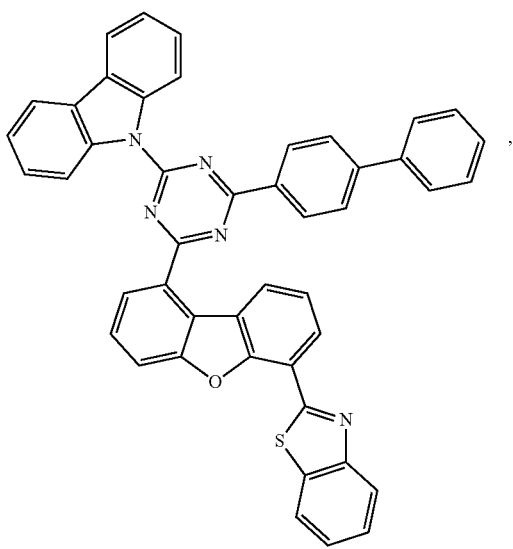, 283
-continued
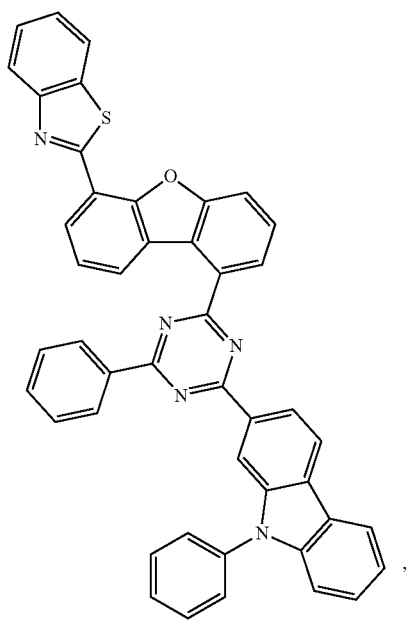
284
-continued
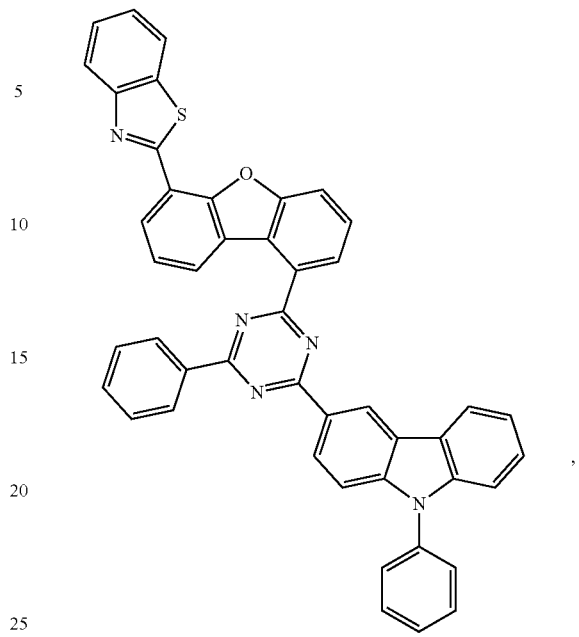
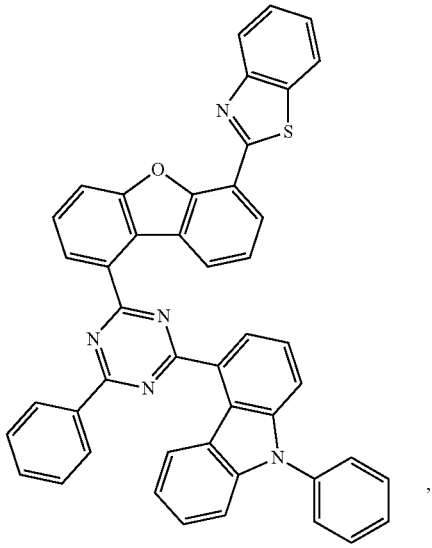
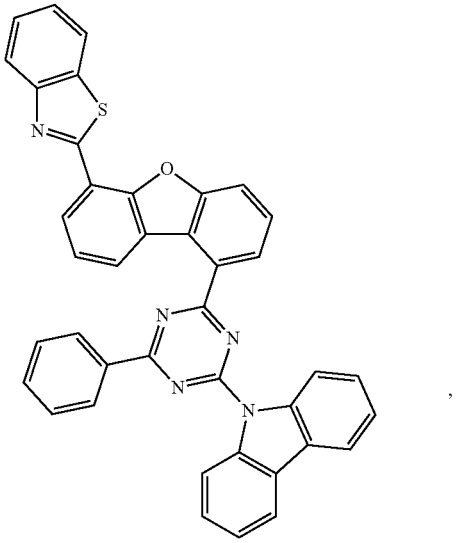

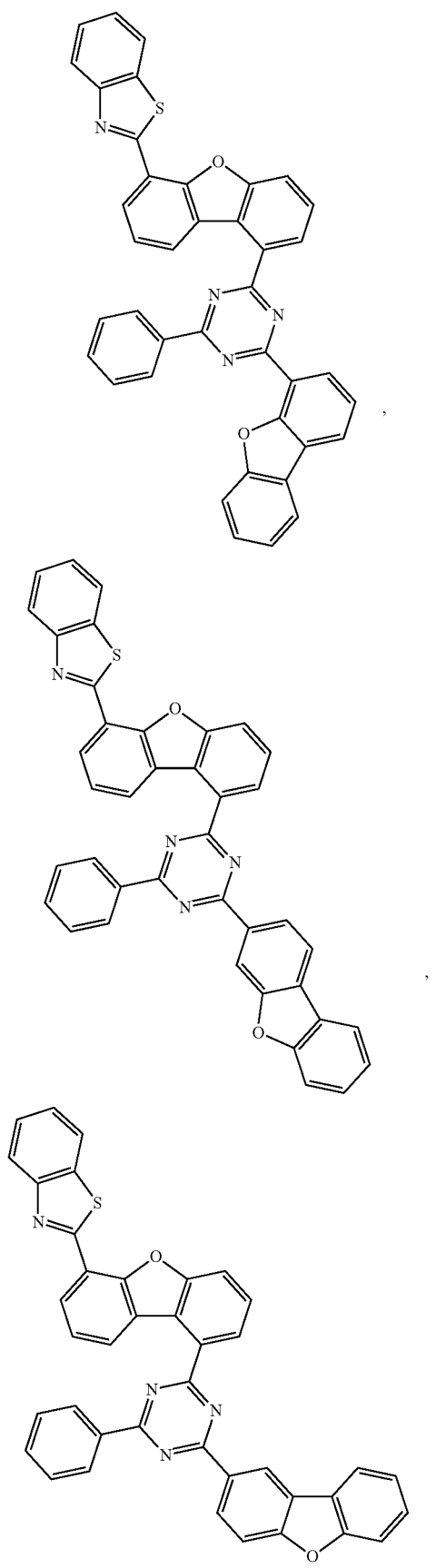

287
-continued
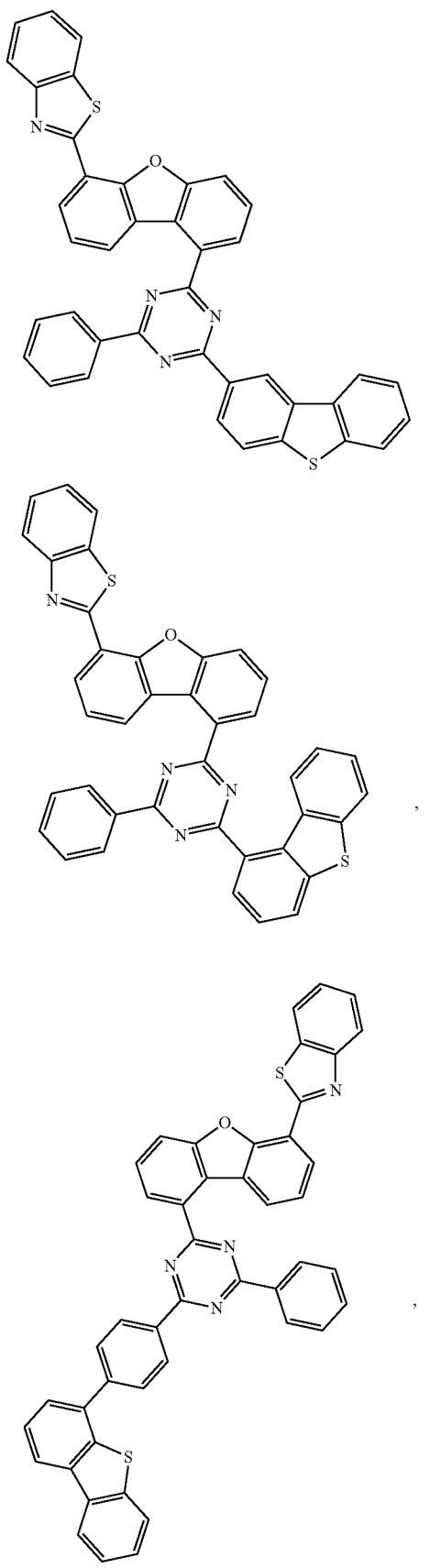
288
-continued
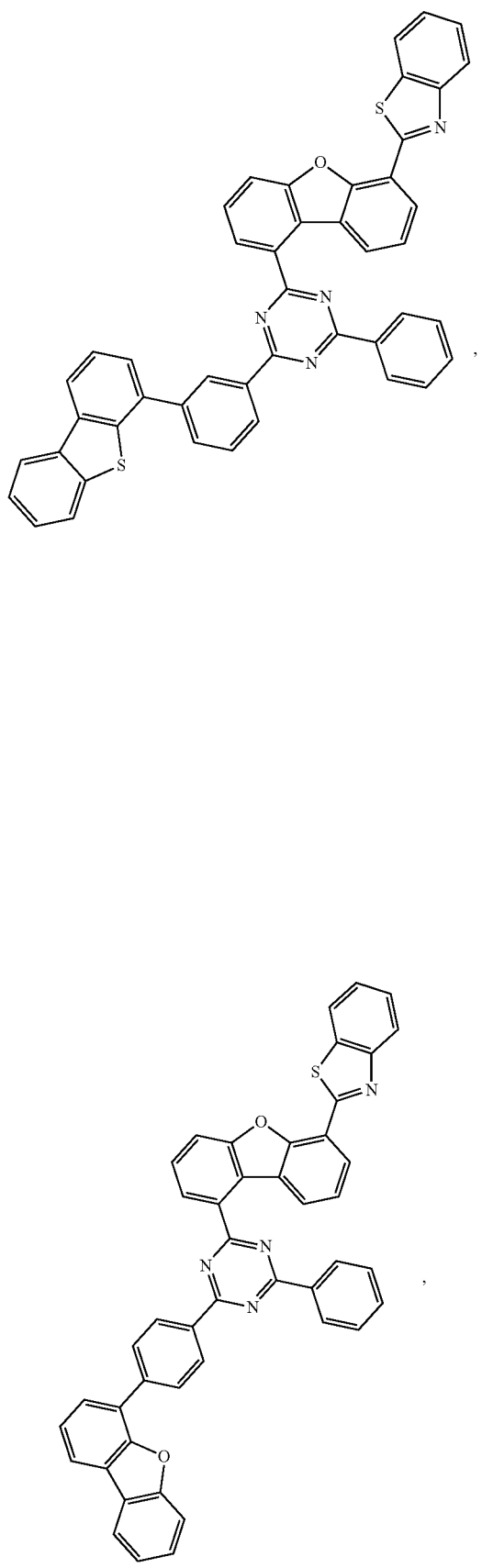

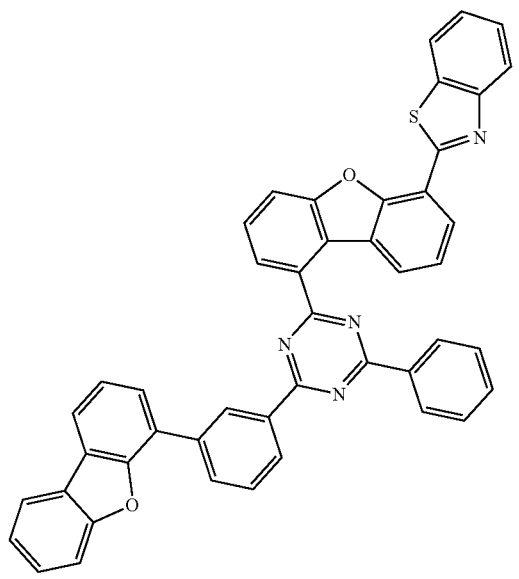
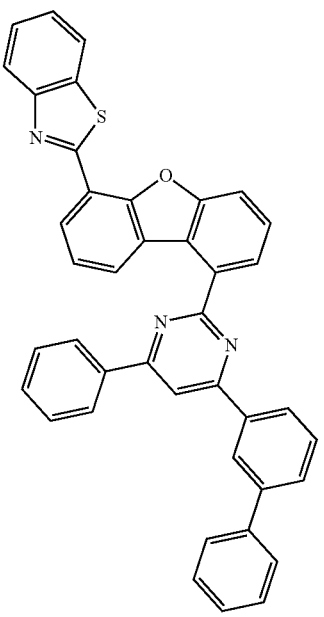
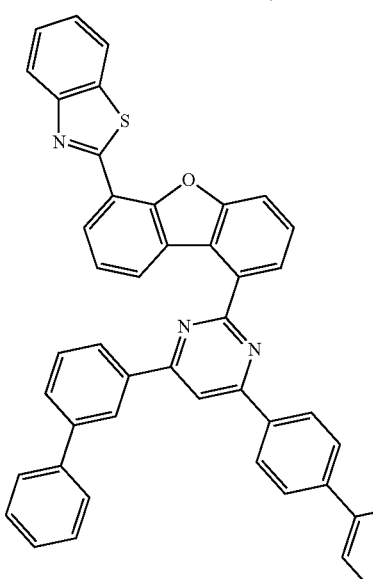
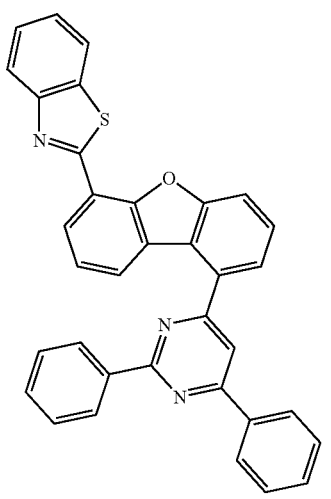

291
-continued
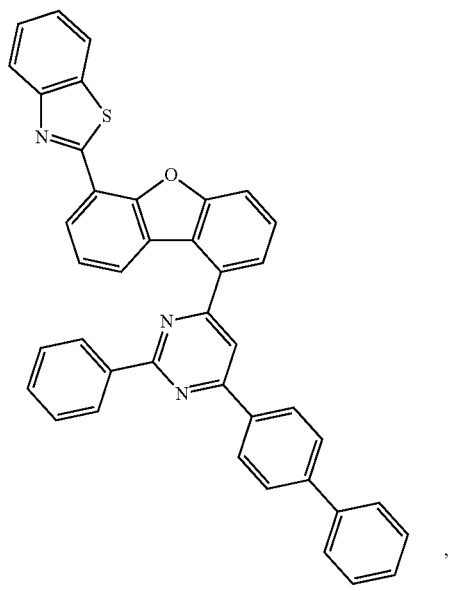
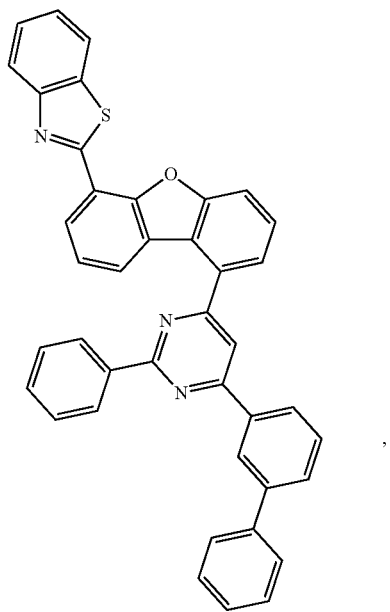
292
-continued
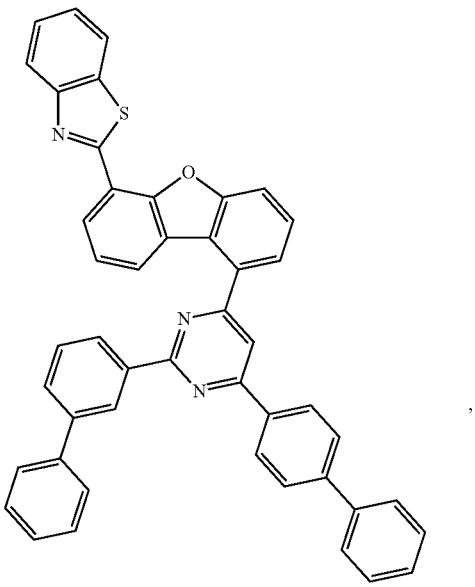
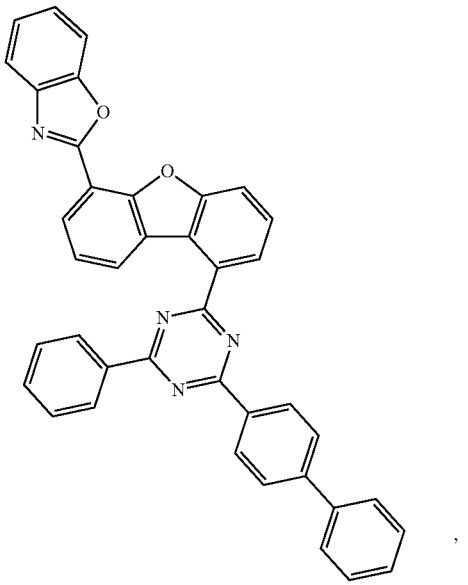

293
-continued
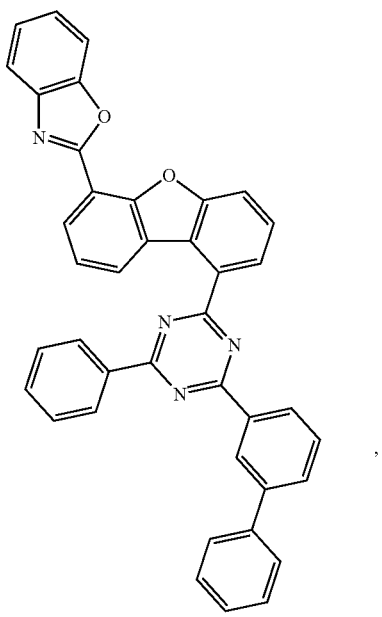
,
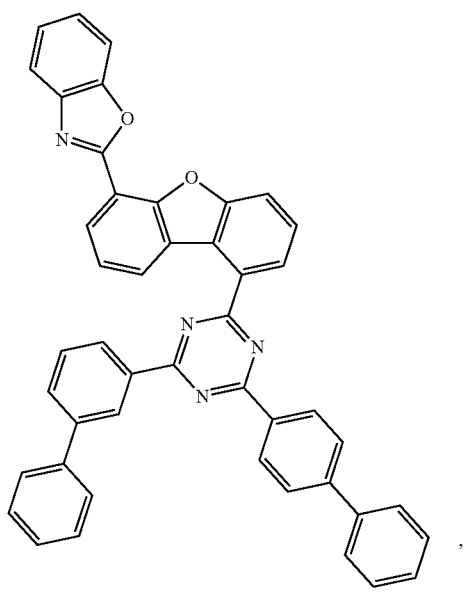
,
294
-continued
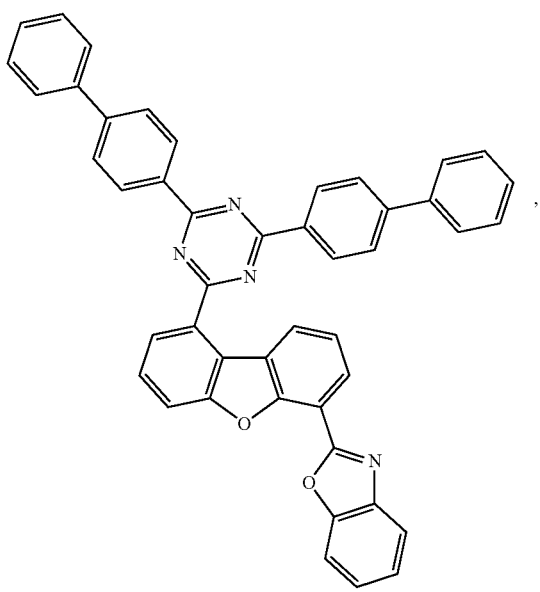
,
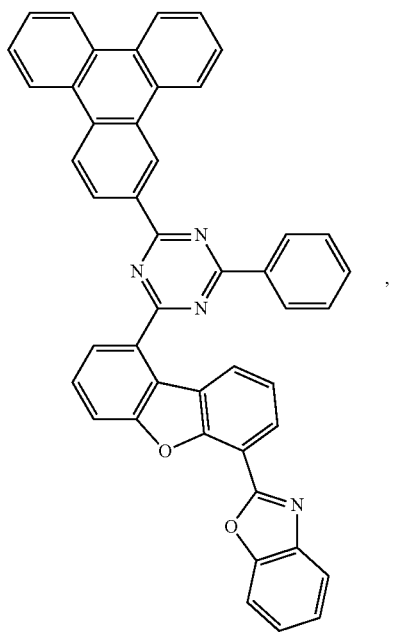

295
-continued
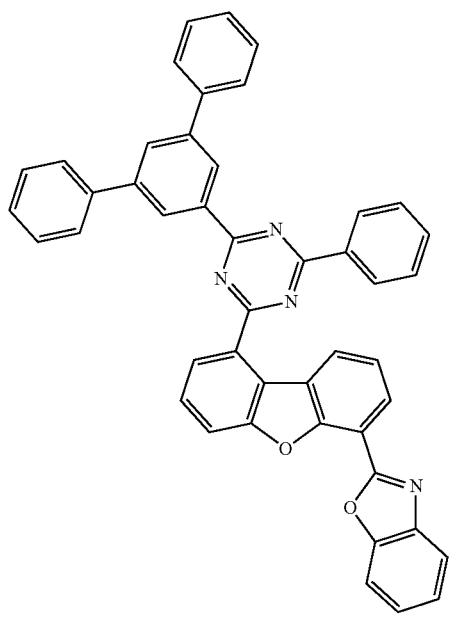
,
296
-continued
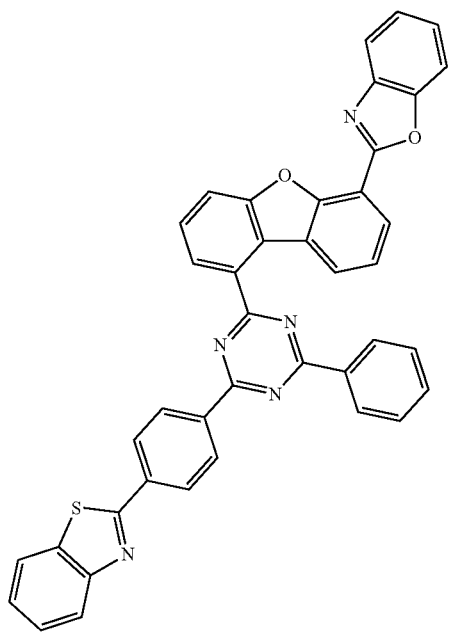
,
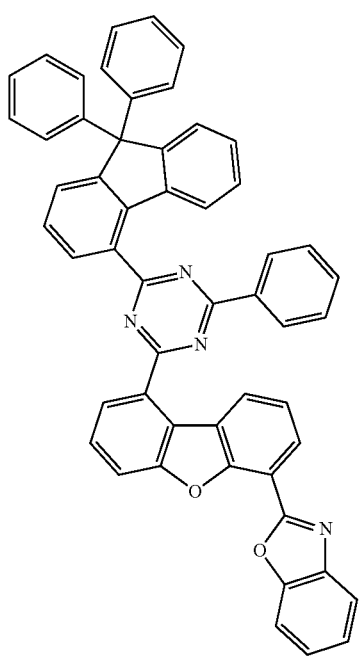
,

297
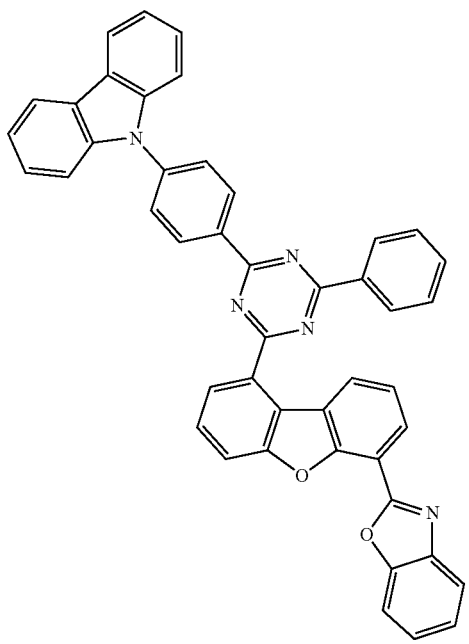
,
298
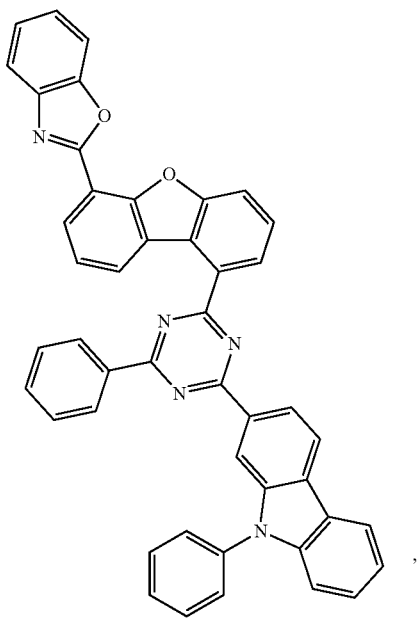
,
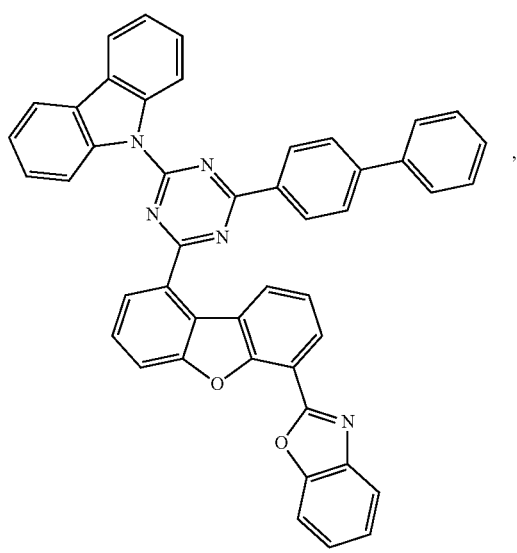
,
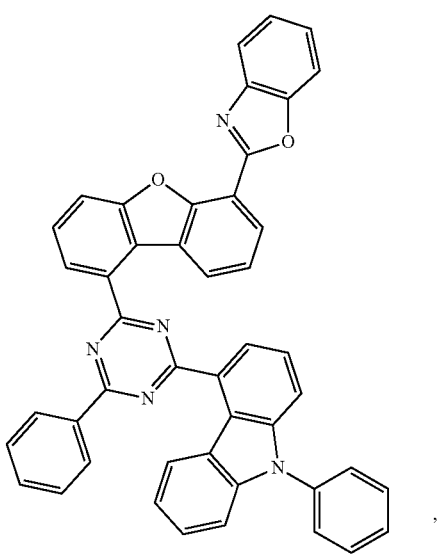
,

299
-continued
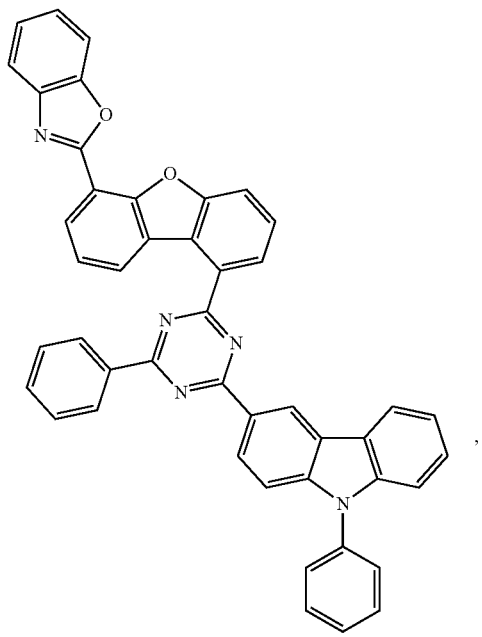
300
-continued
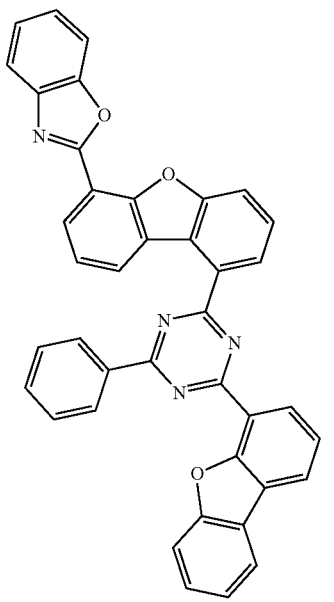
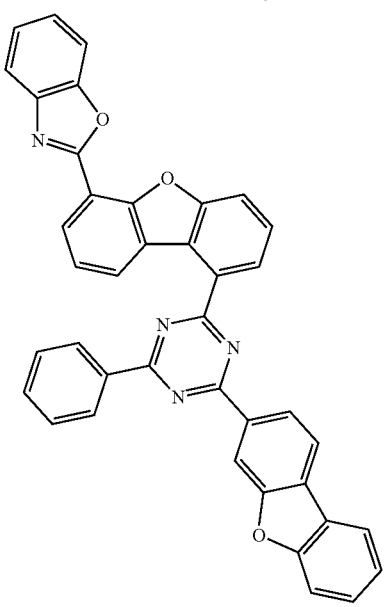
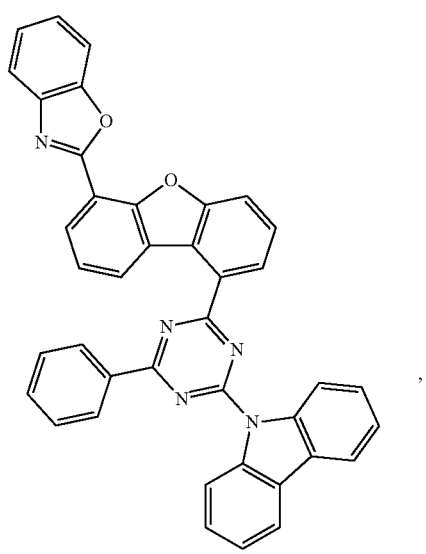
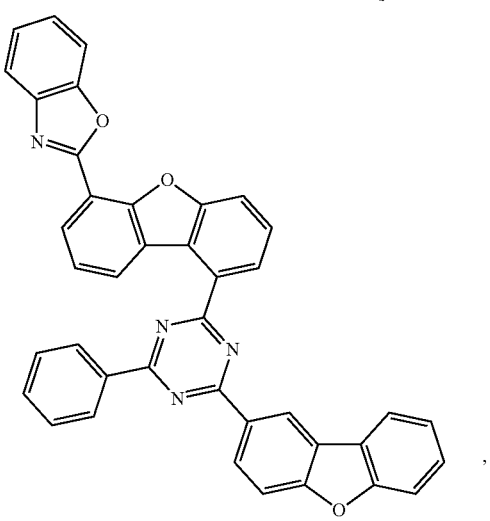

301
-continued
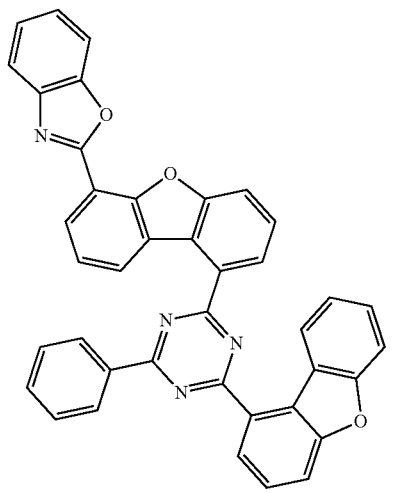
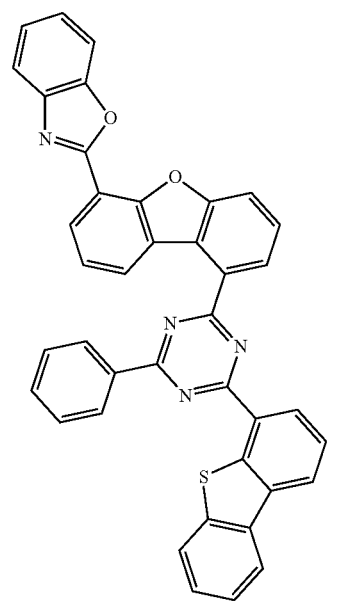
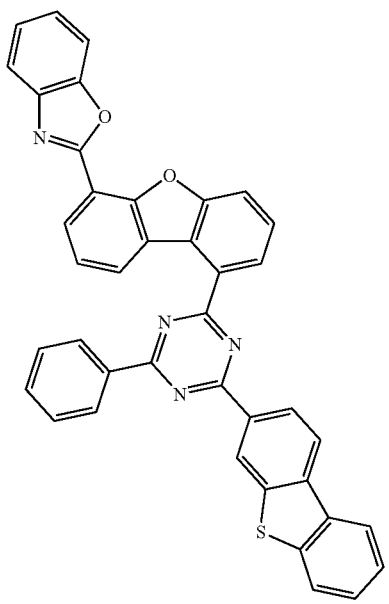
302
-continued
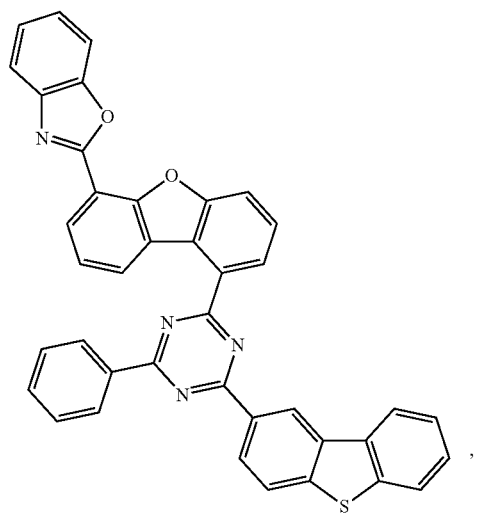
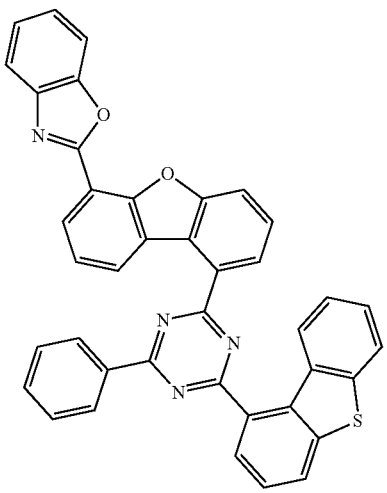

303
-continued
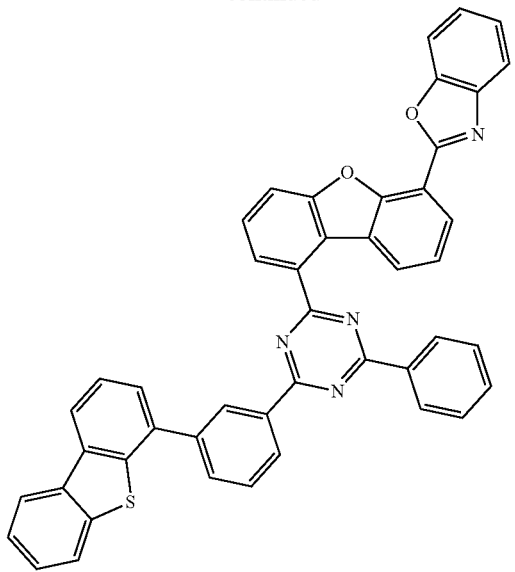
,
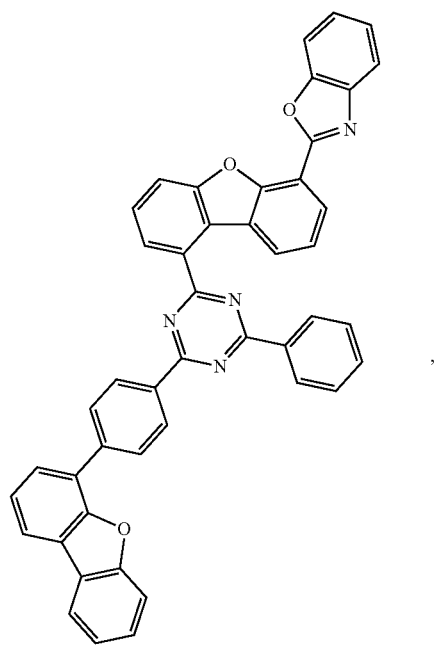
,
304
-continued
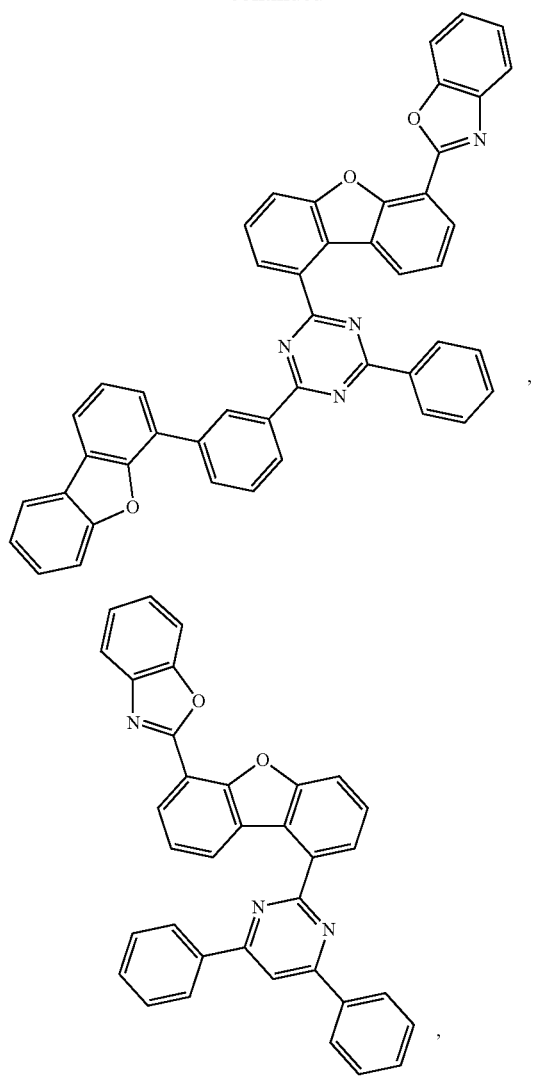

305
-continued
306
-continued
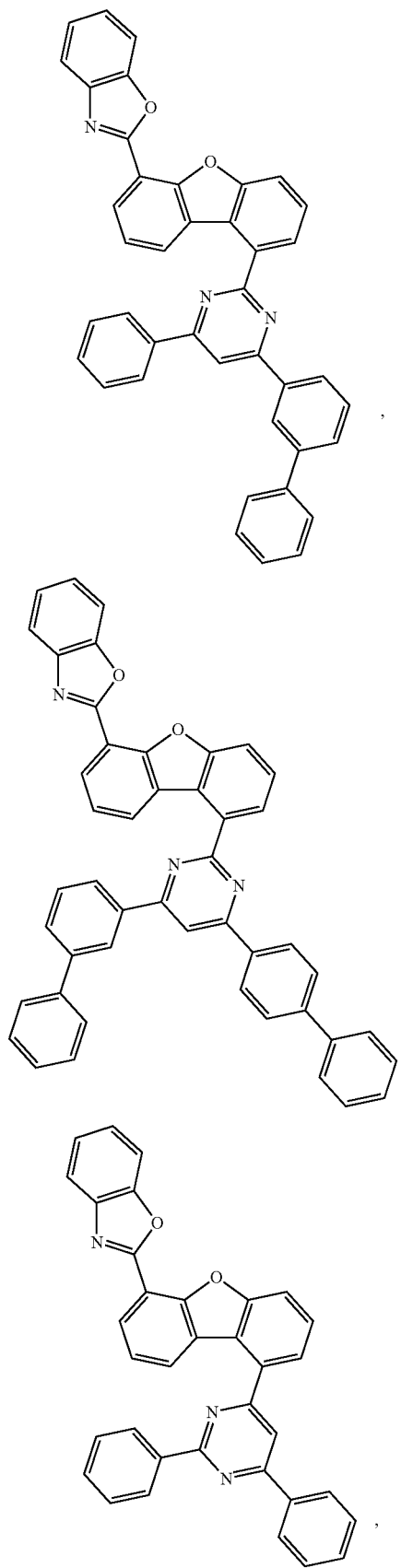

307
-continued
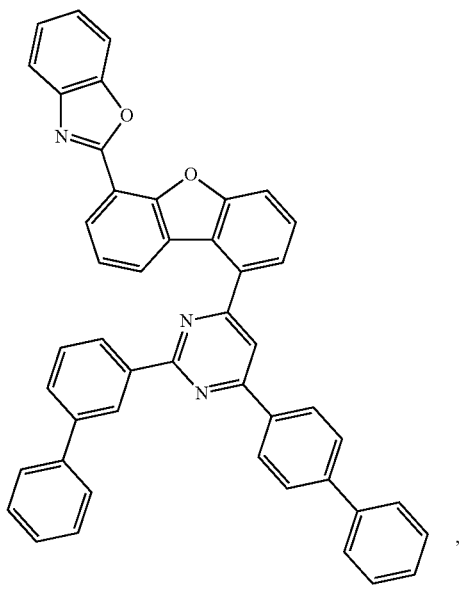
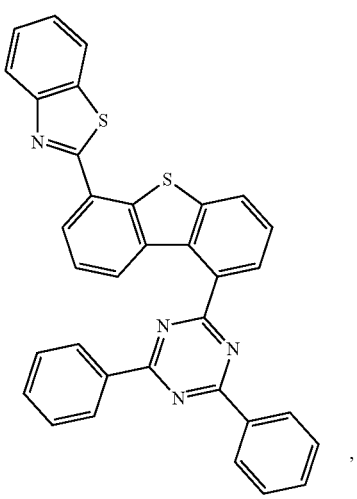
308
-continued
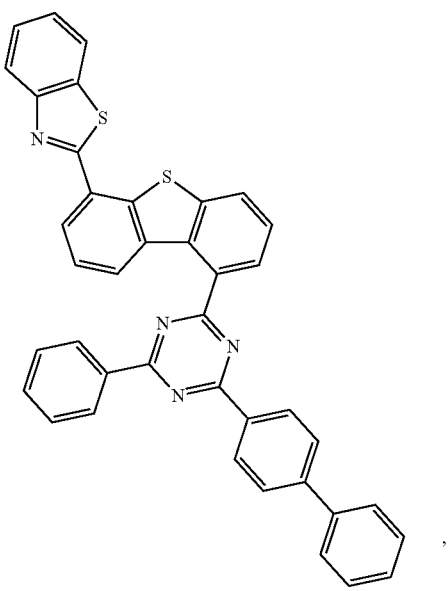
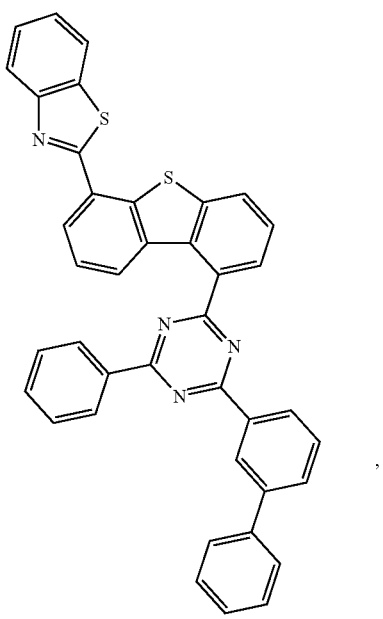

309
-continued
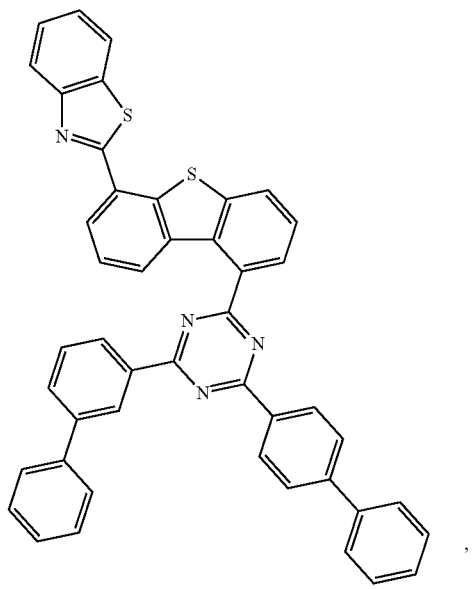
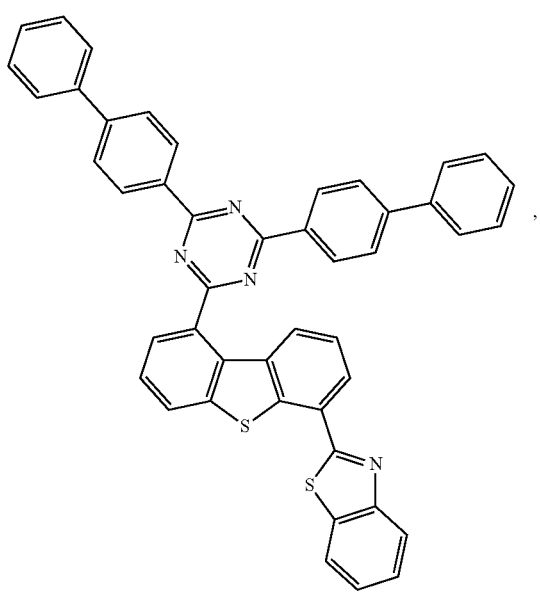
310
-continued
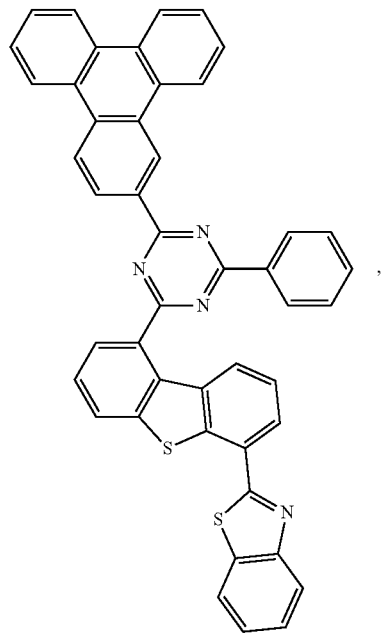
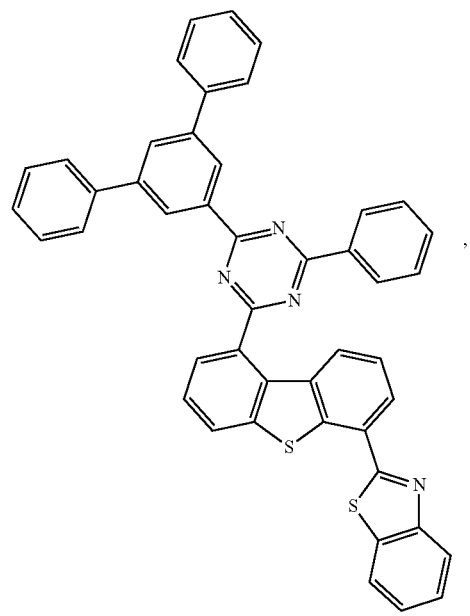

311
-continued
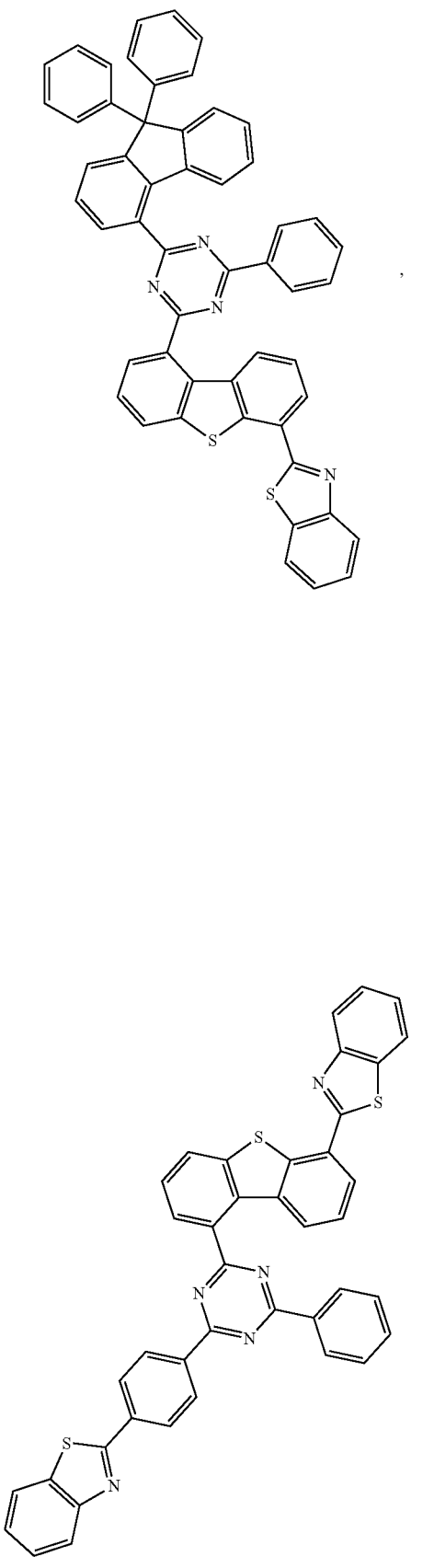
312
-continued
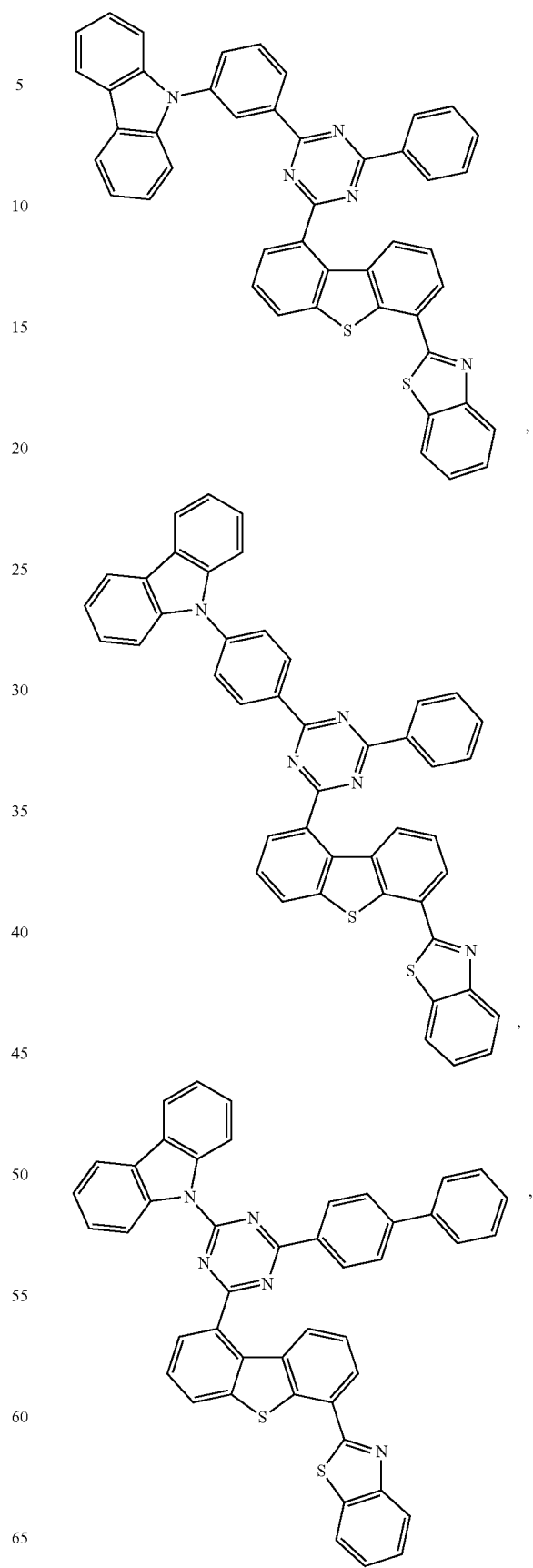

313
-continued
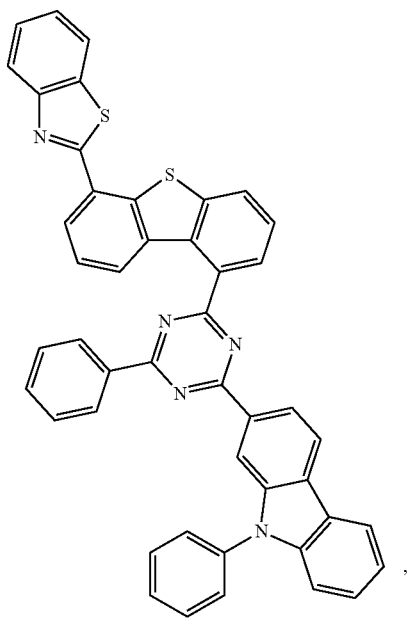
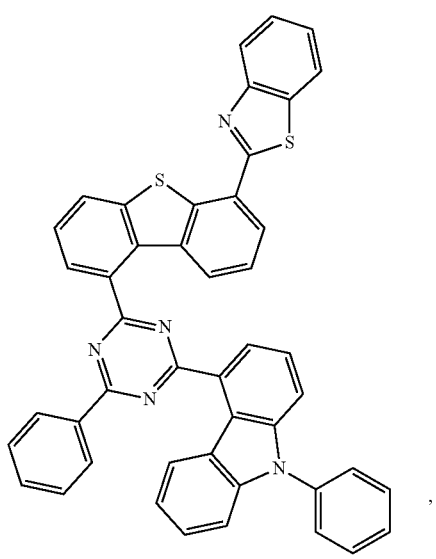
314
-continued
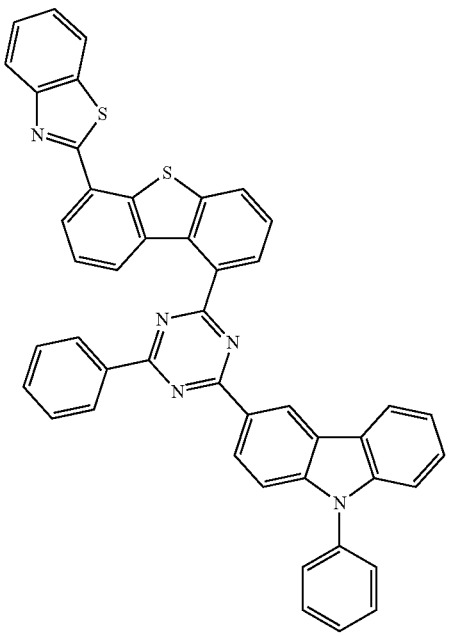
,
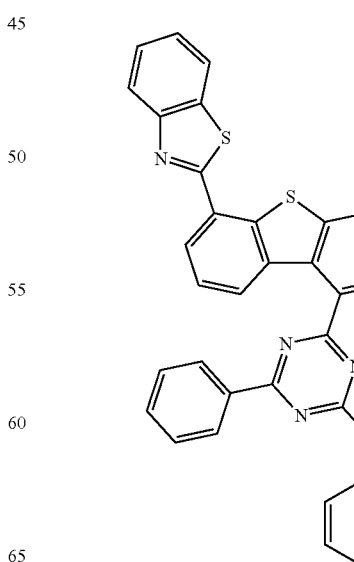
, 315
-continued
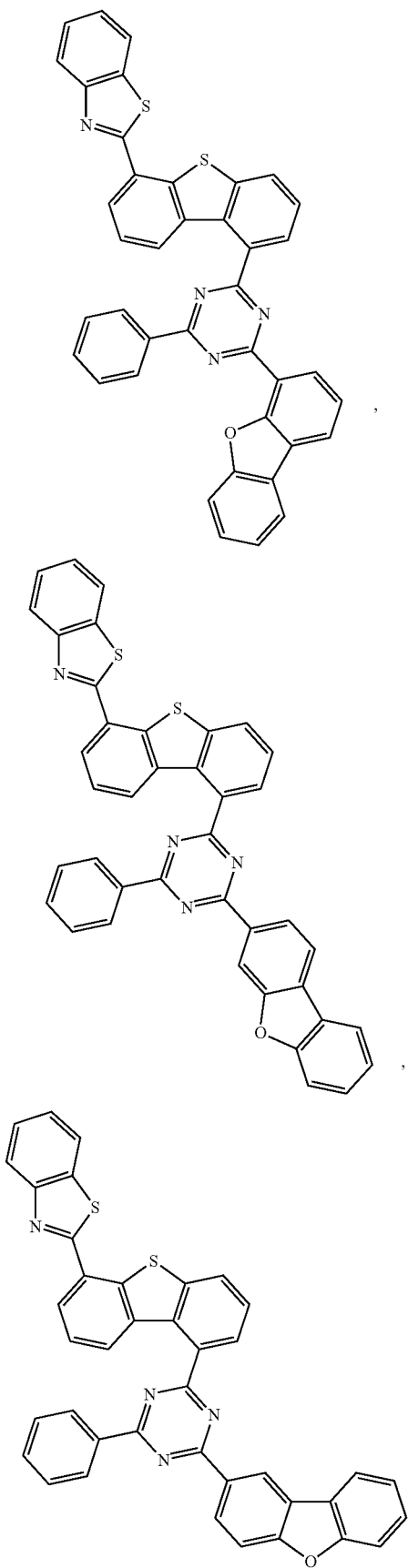
316
-continued
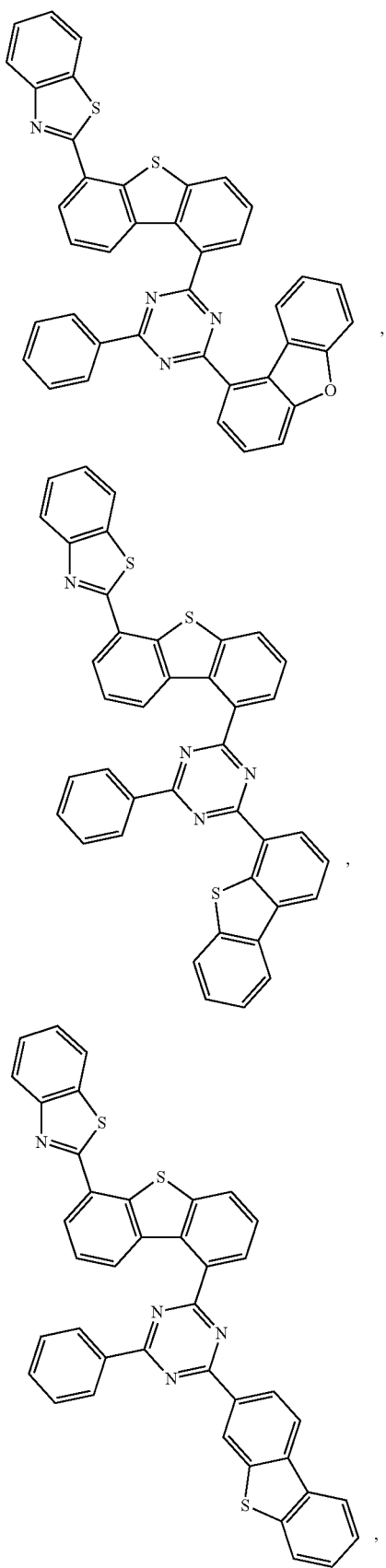

317
-continued
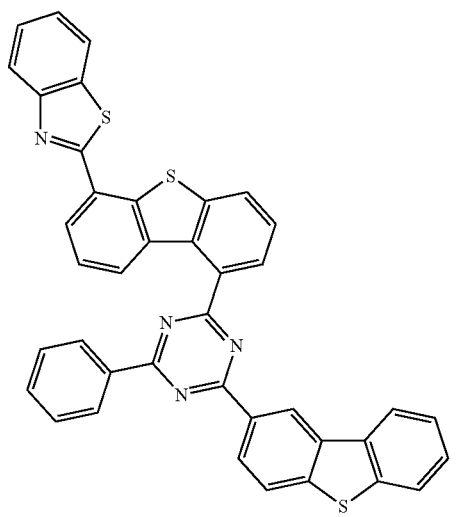
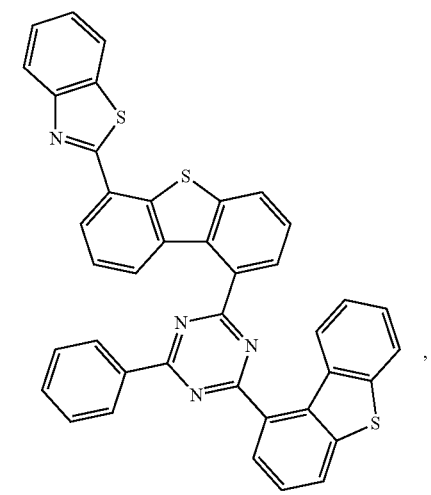
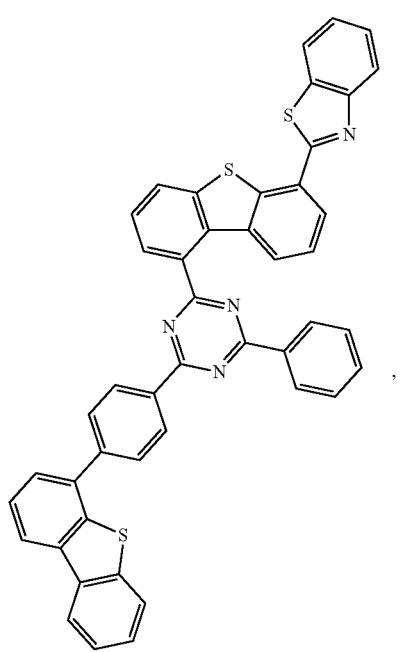
318
-continued
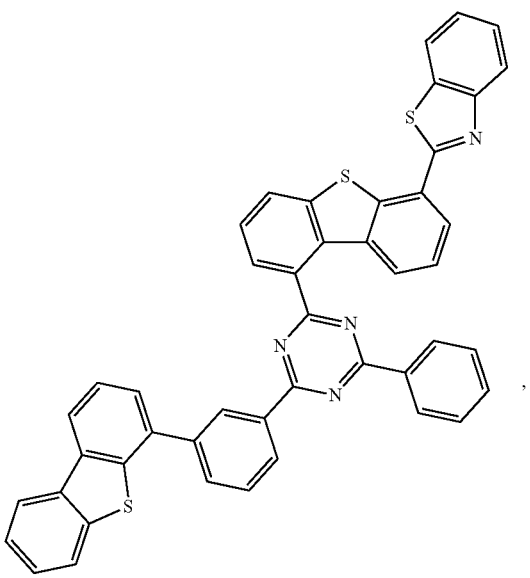
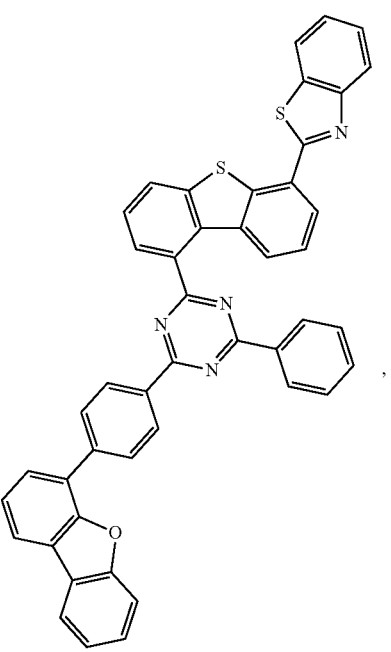

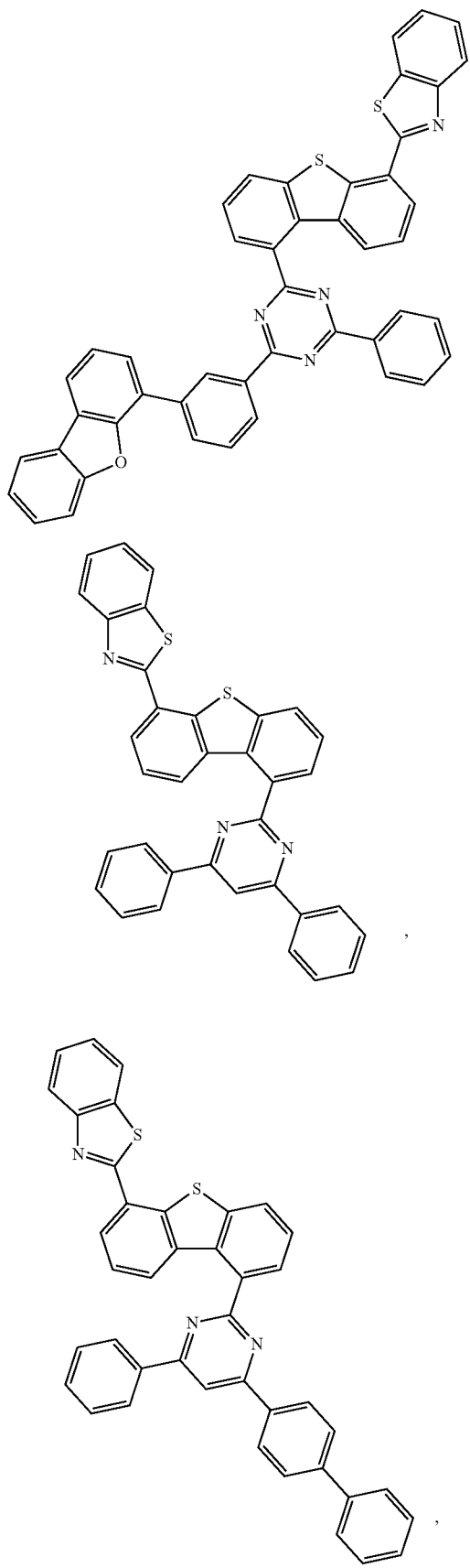
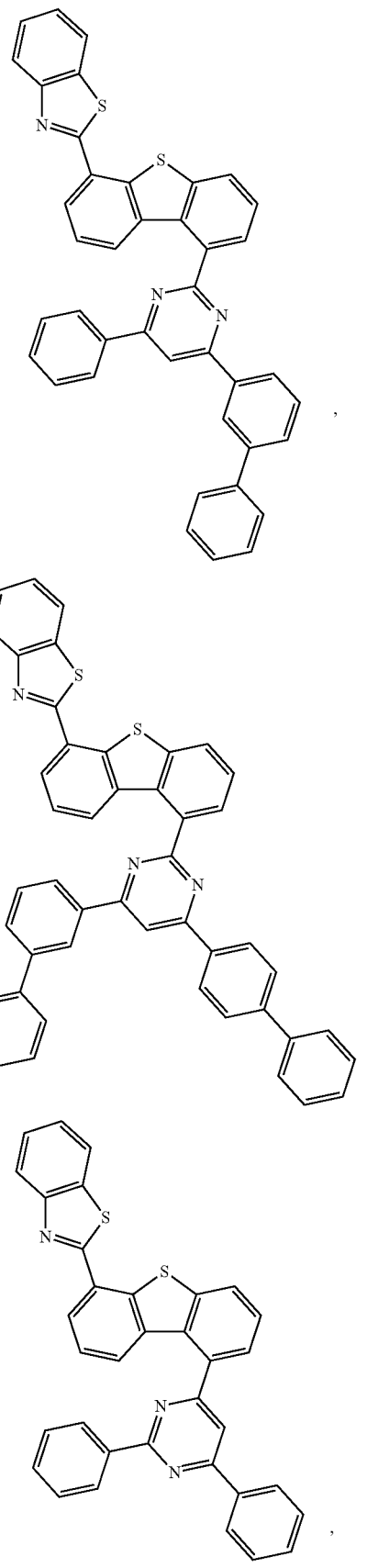

321
-continued
322
-continued
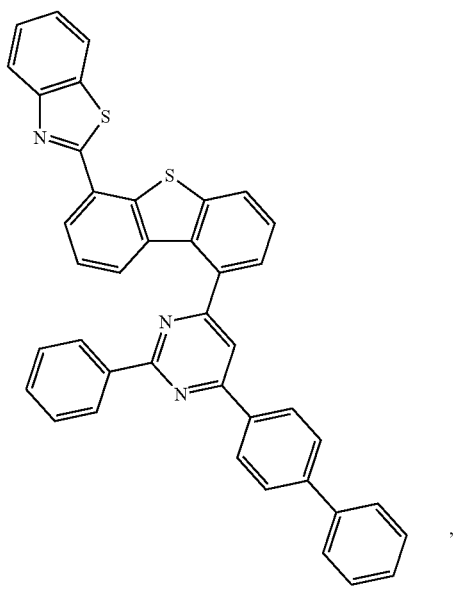

323
-continued
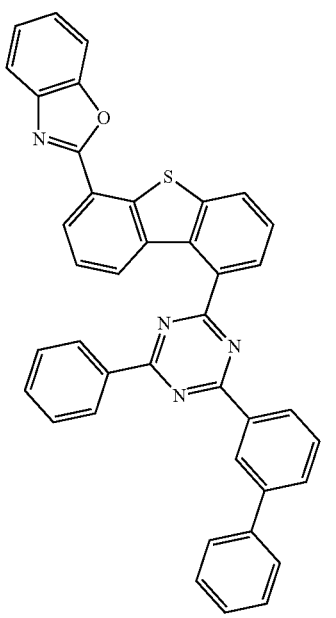
324
-continued
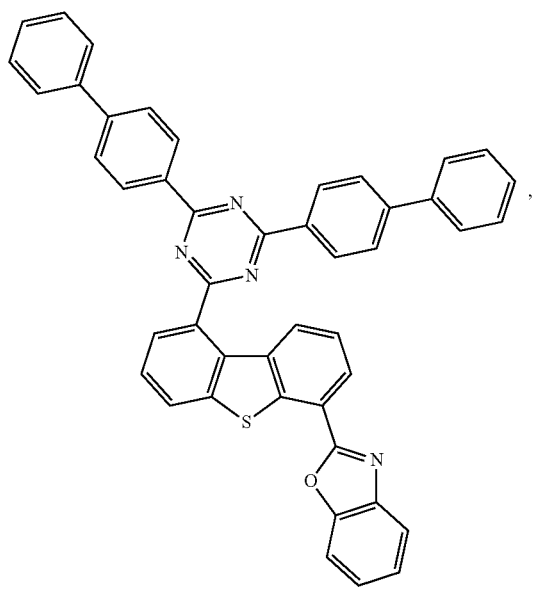
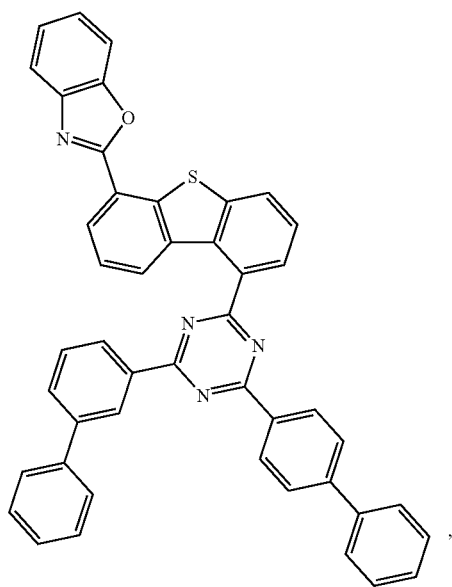
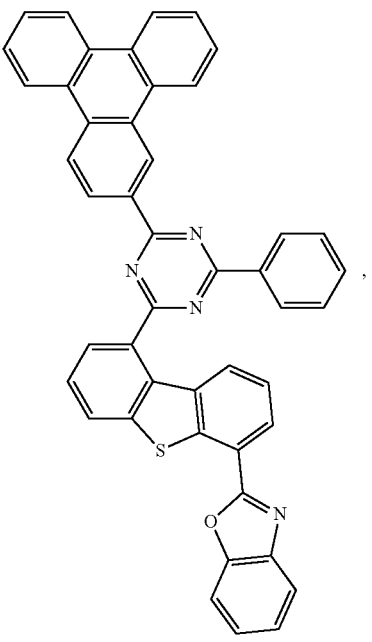

325
-continued
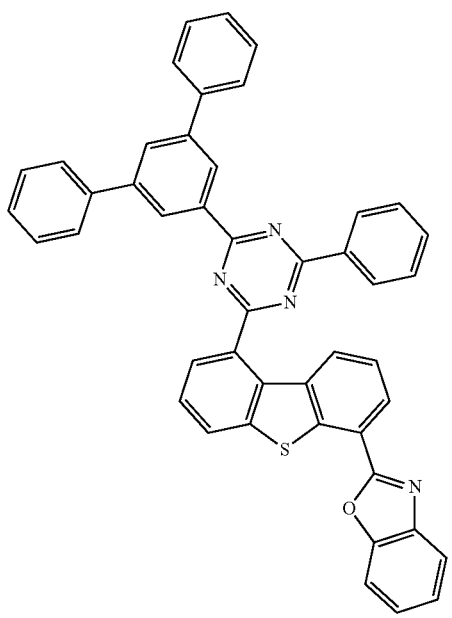
,
326
-continued
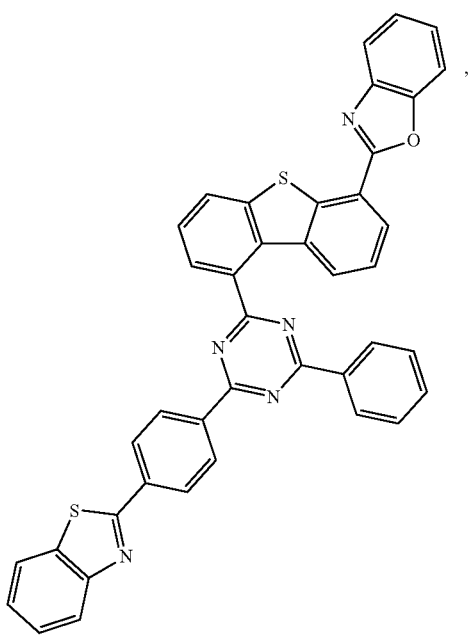
,
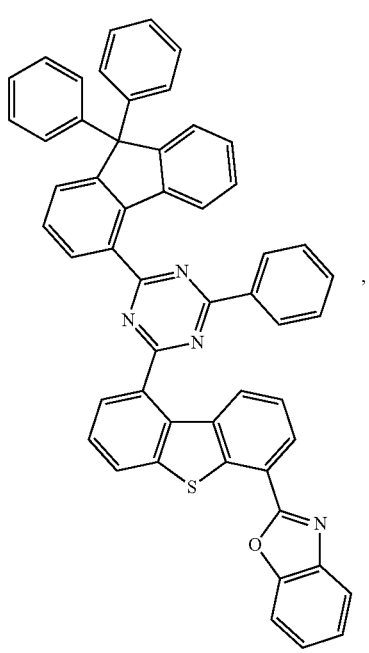
,
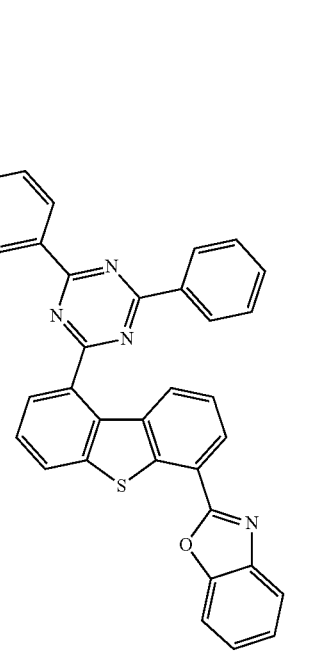
, 327
-continued
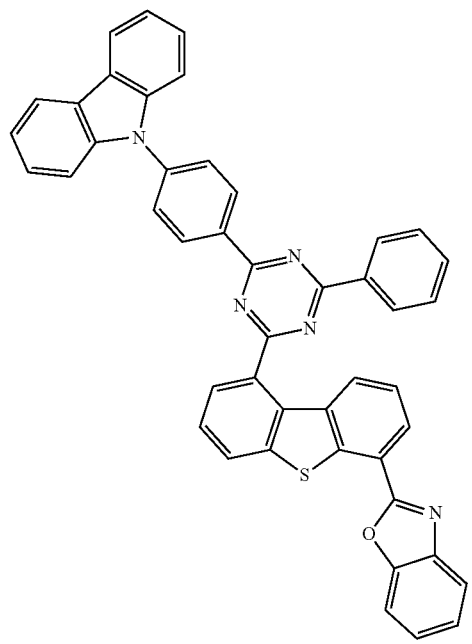
328
-continued
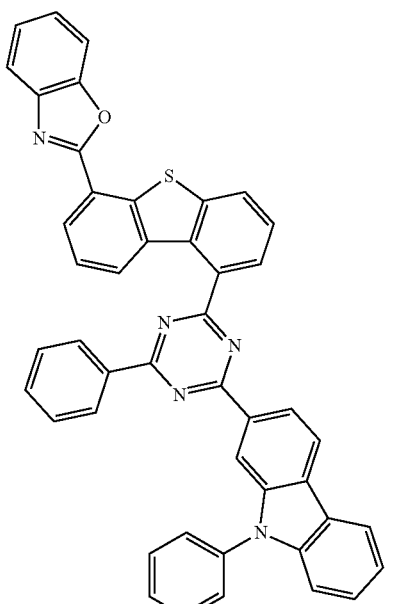
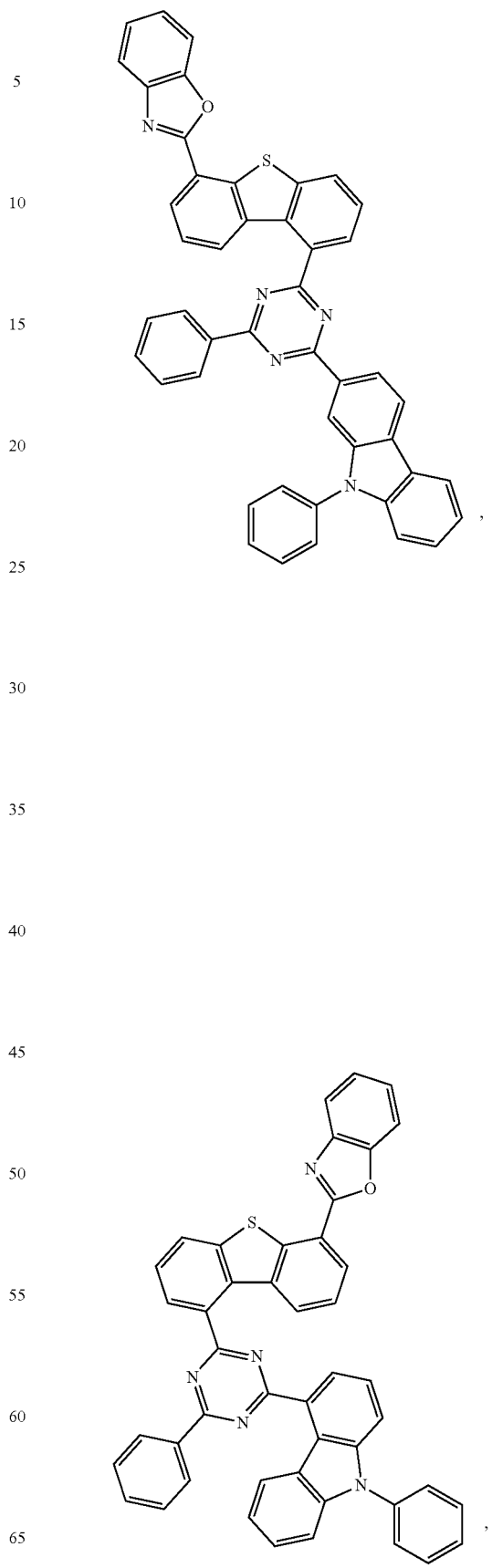

329
-continued
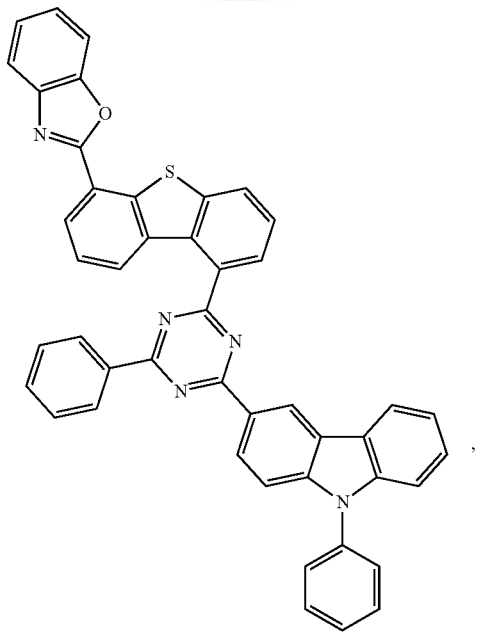
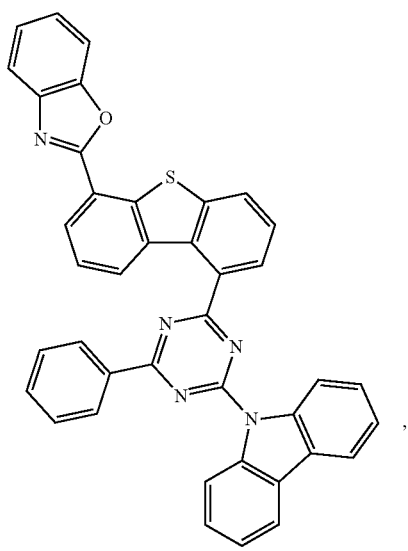
330
-continued
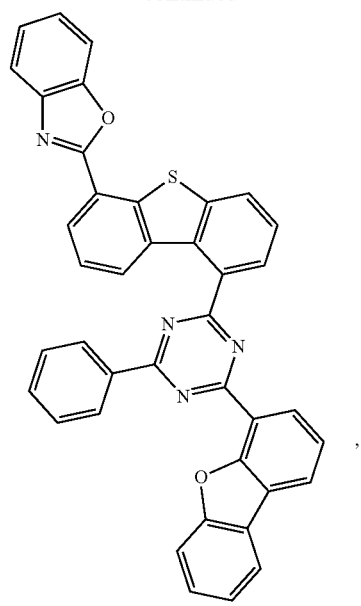
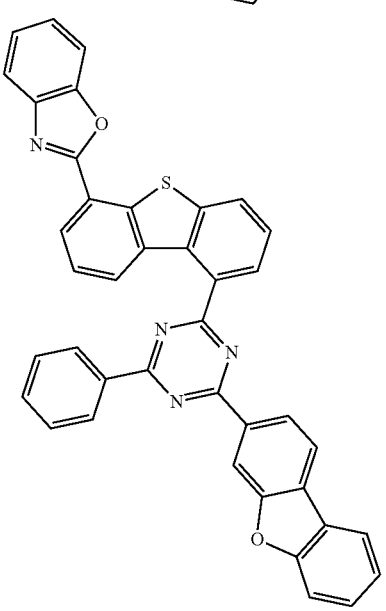

331
-continued
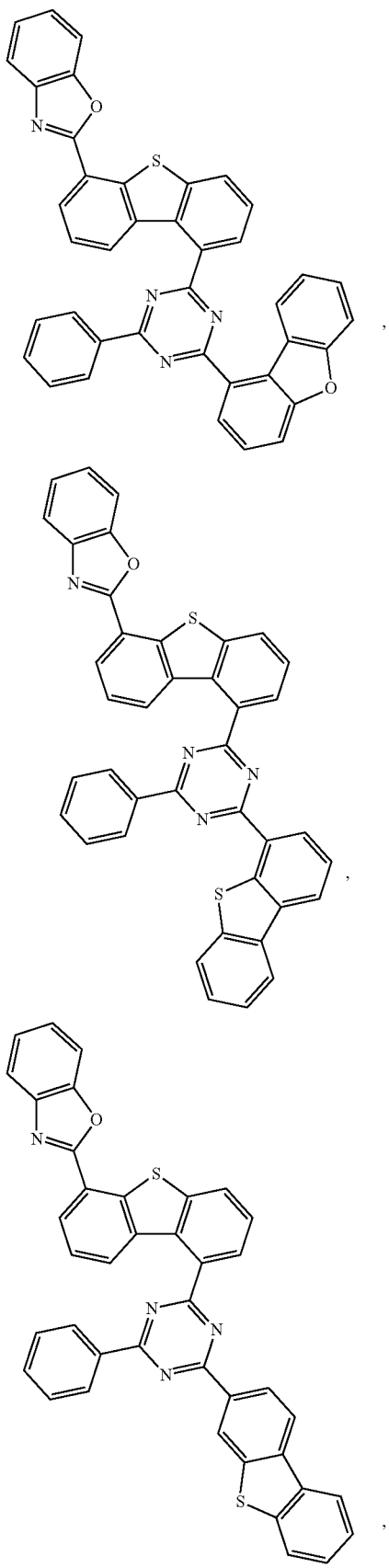
332
-continued
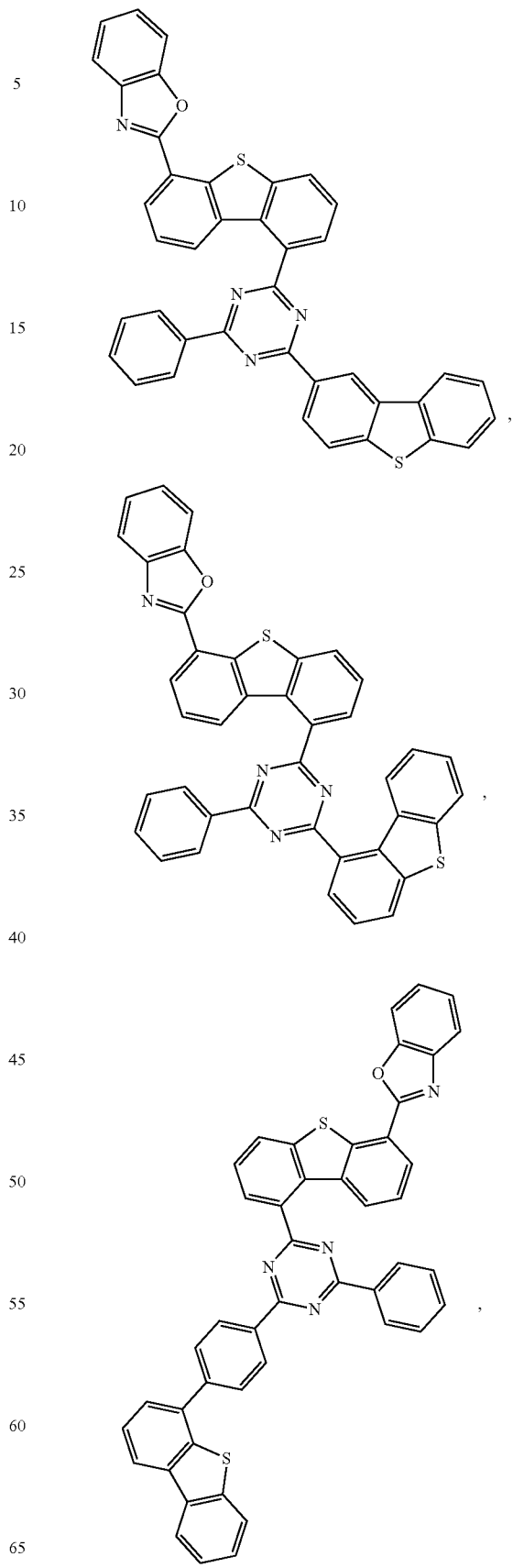

333
-continued
334
-continued
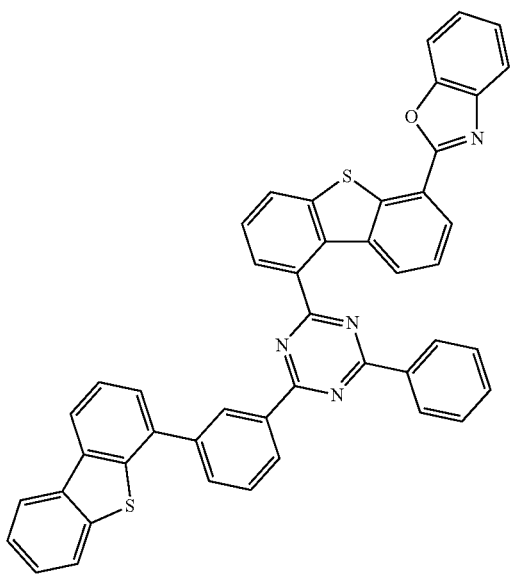
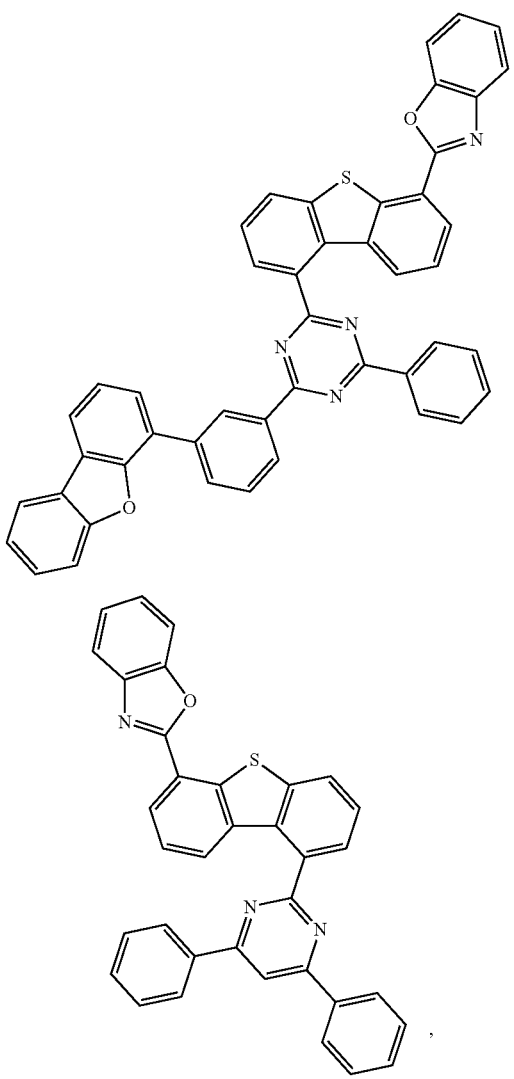
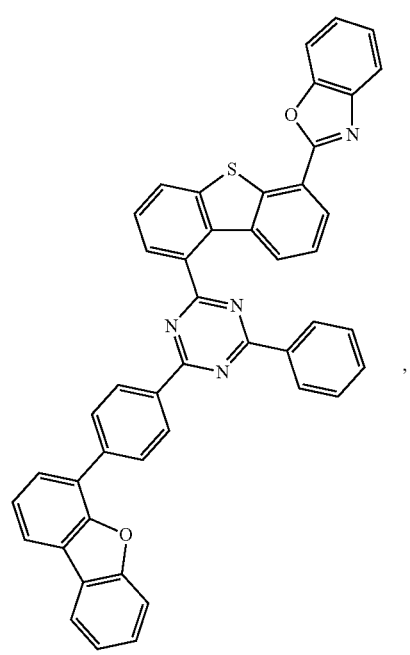

335
-continued
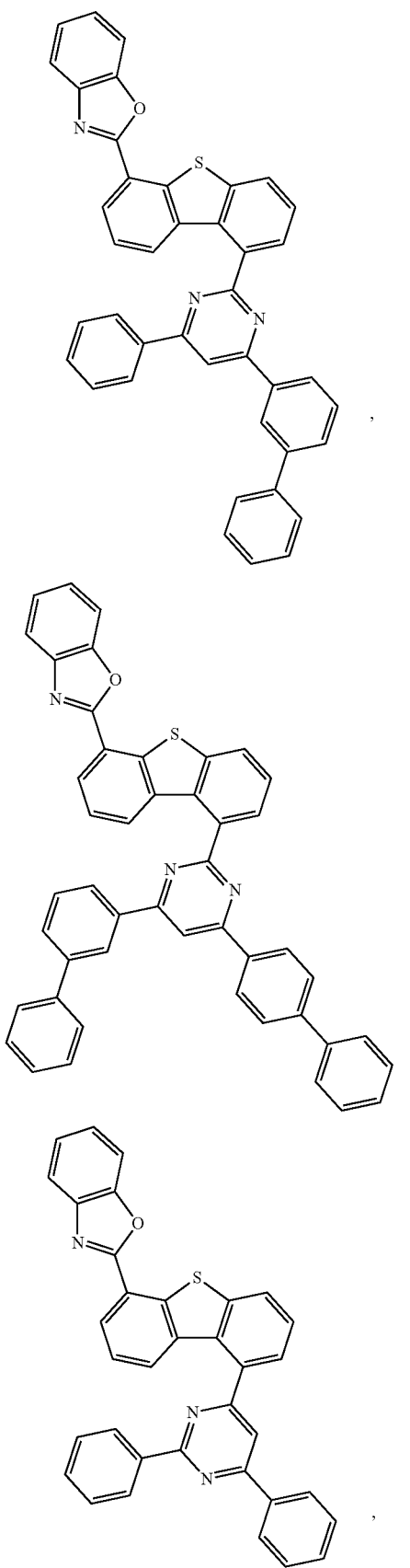
336
-continued

337
-continued
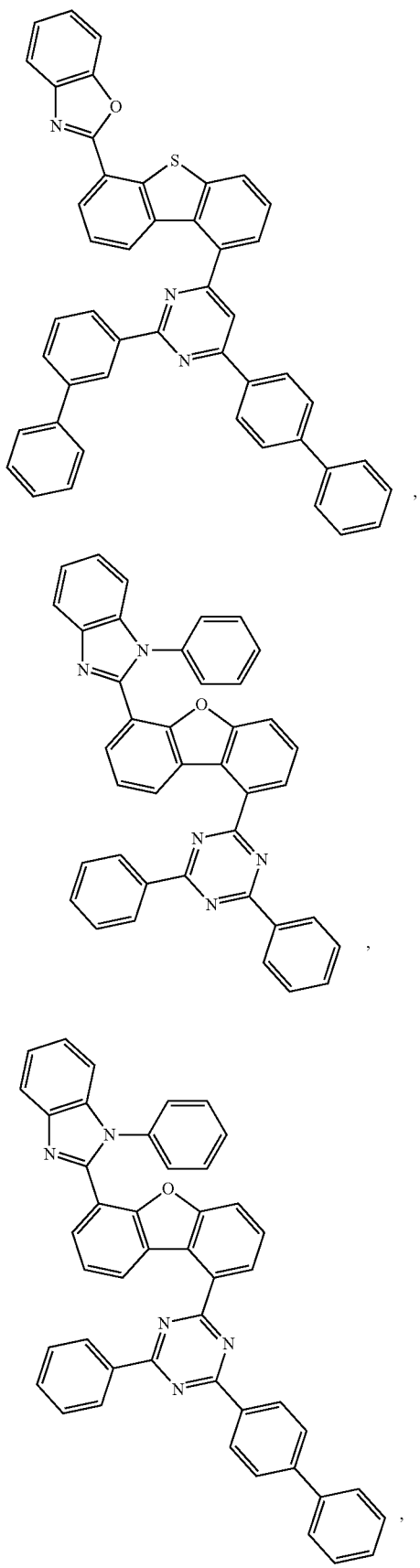
338
-continued
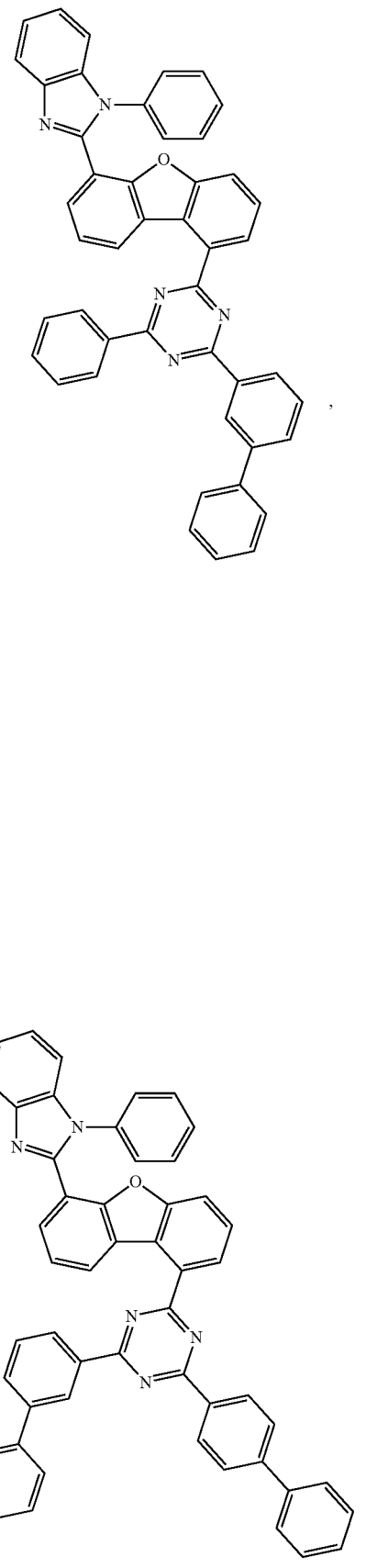

339
-continued
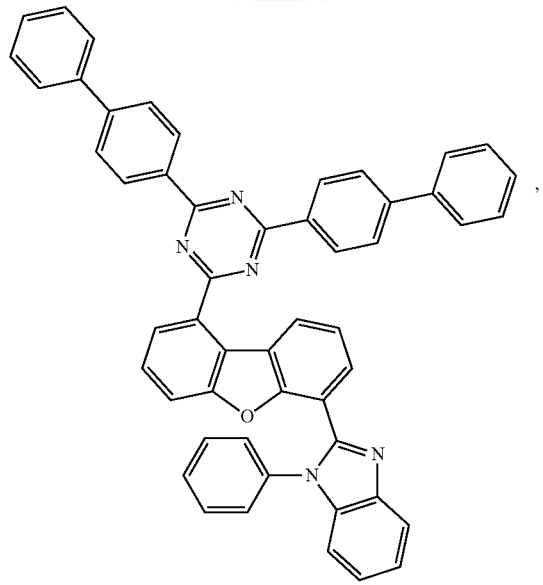
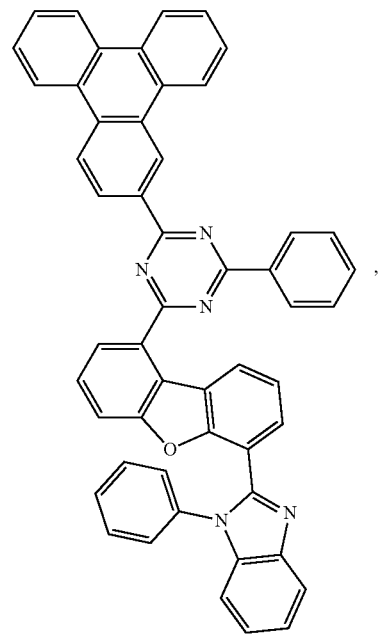
340
-continued
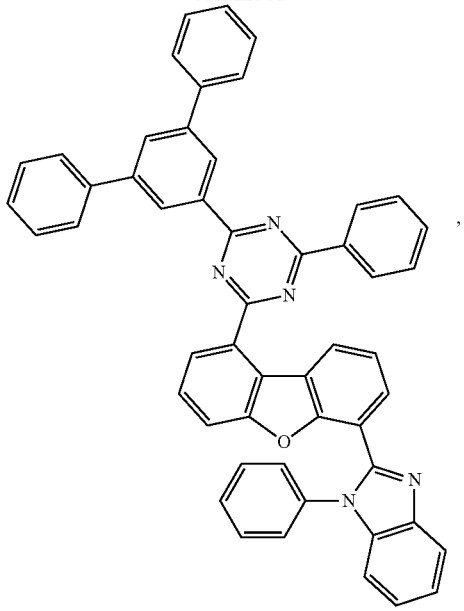
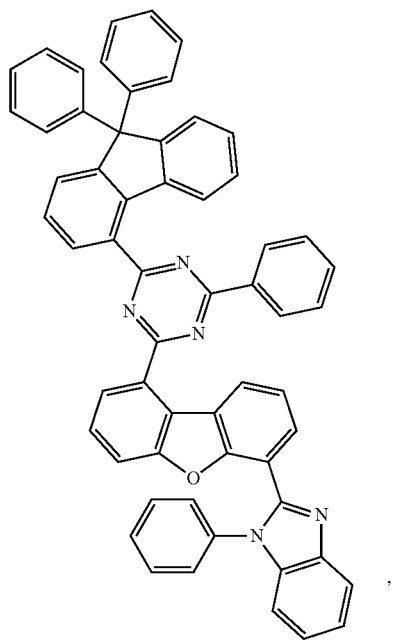

341
-continued
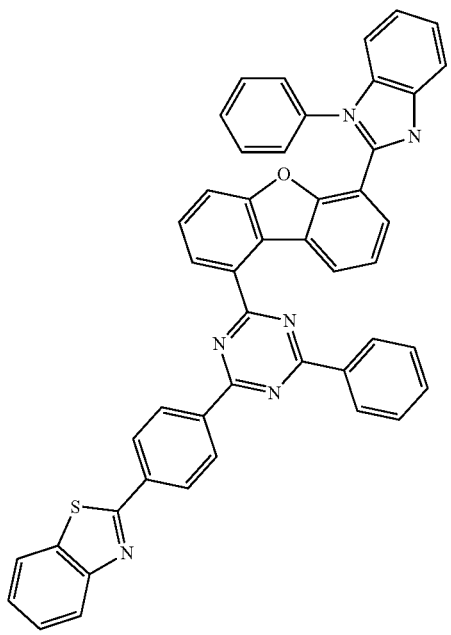
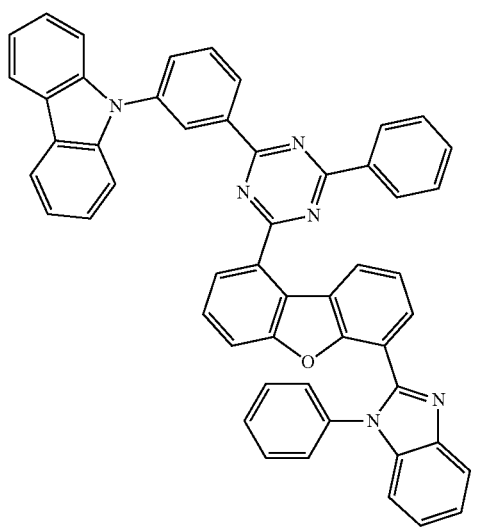
342
-continued
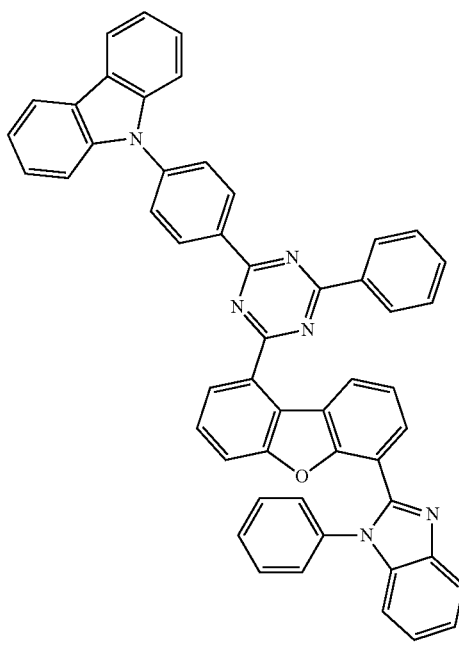
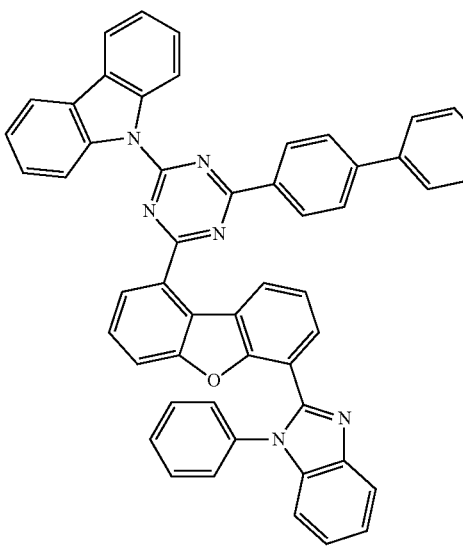

343
-continued
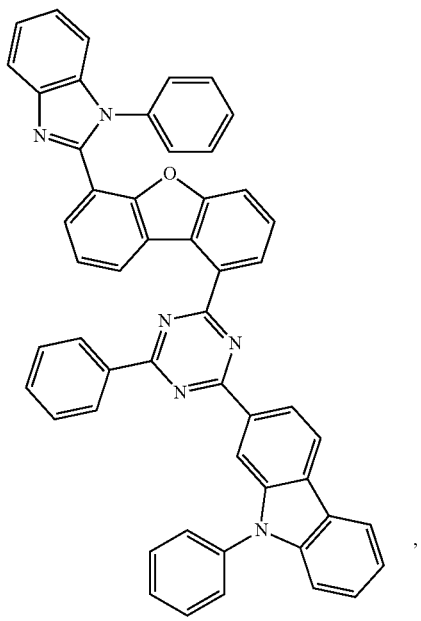
,
344
-continued
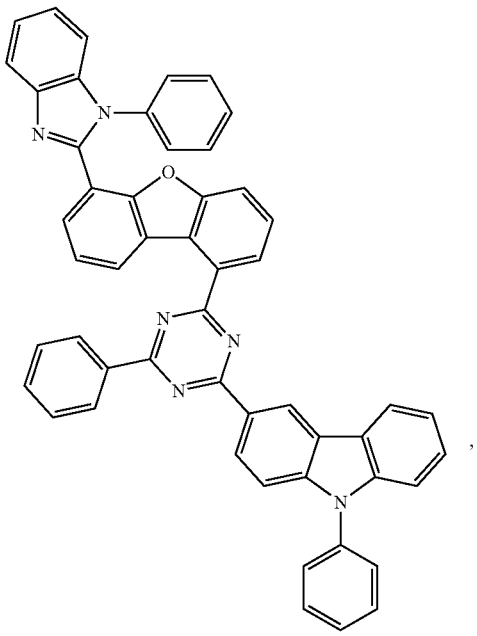
,
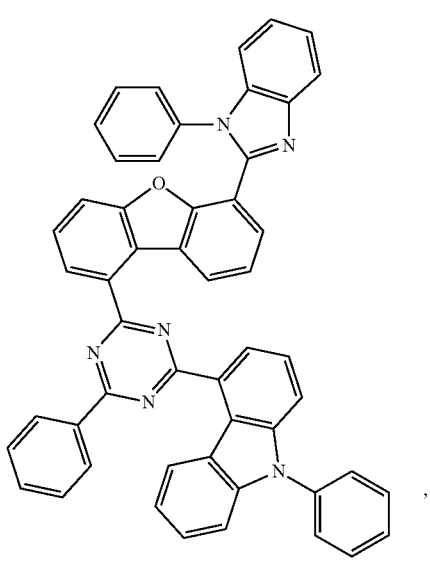
,
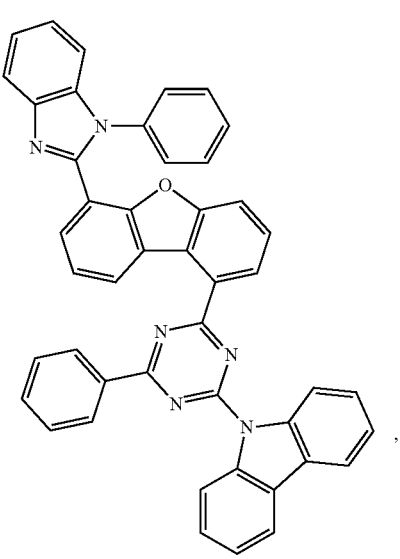 [SMILES: c1ccc(-c2nc(-c3cccc4sc5c(-c6nc7ccccc7n6-c6ccccc6)cccc5c34)nc(-n3c4ccccc4c4ccccc43)n2)cc1]
,

345
-continued
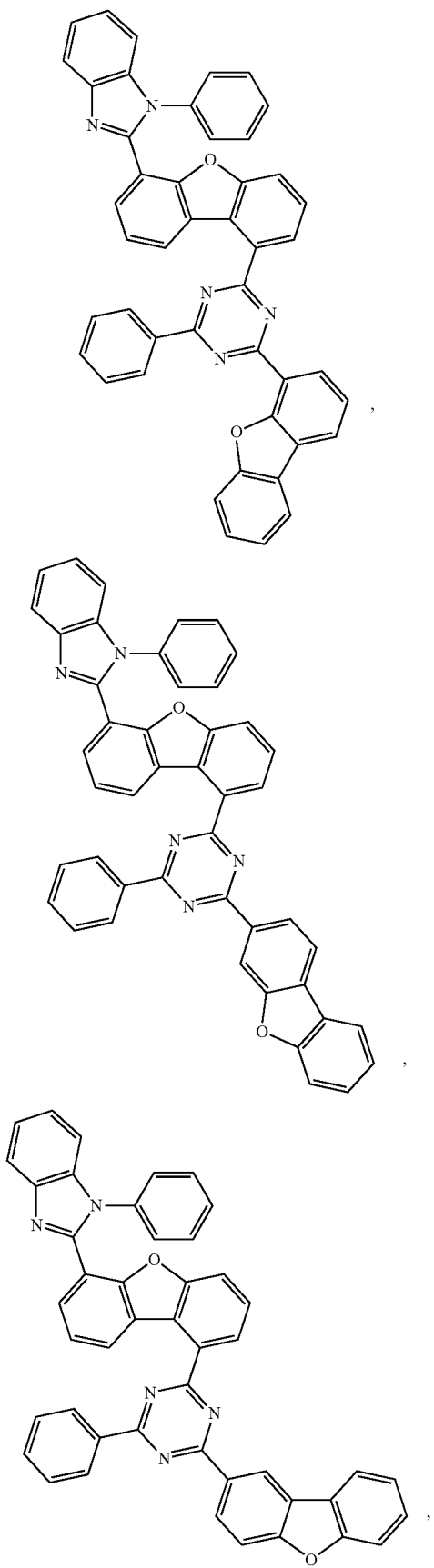
346
-continued
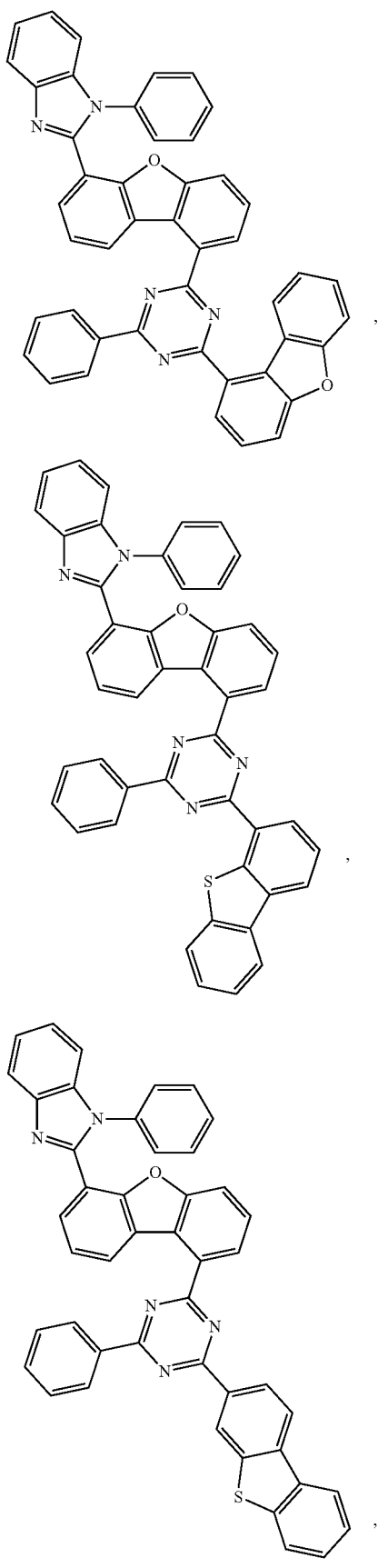

347
-continued
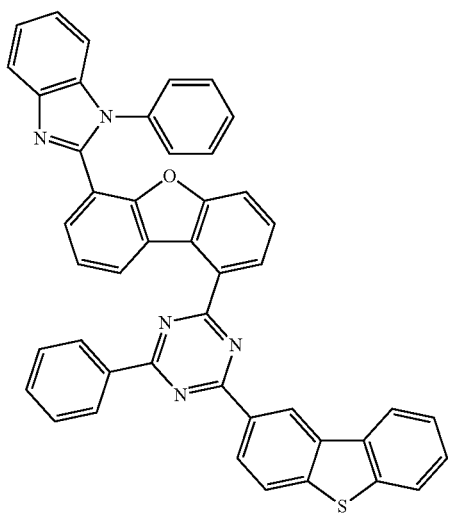
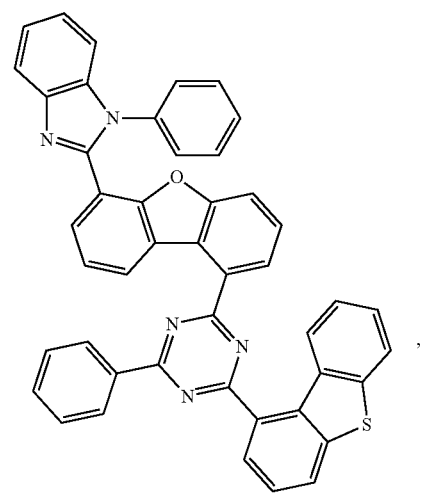
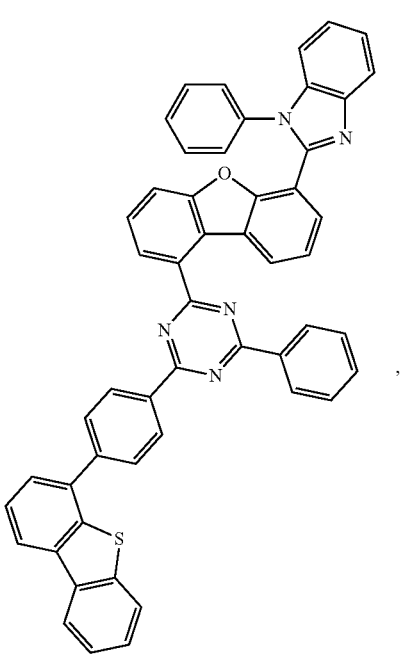
348
-continued
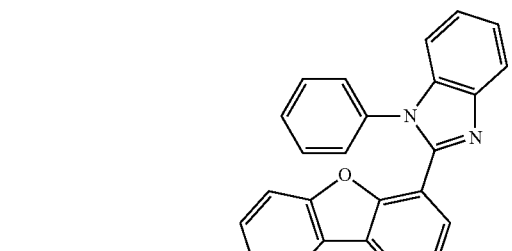
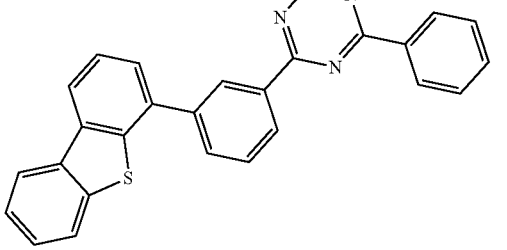
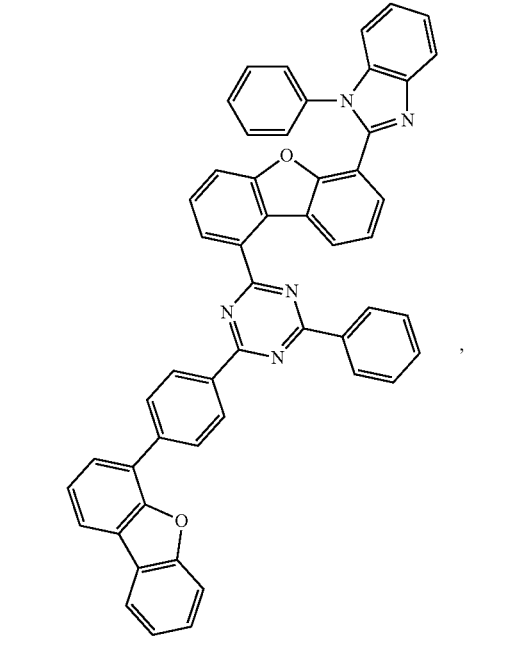

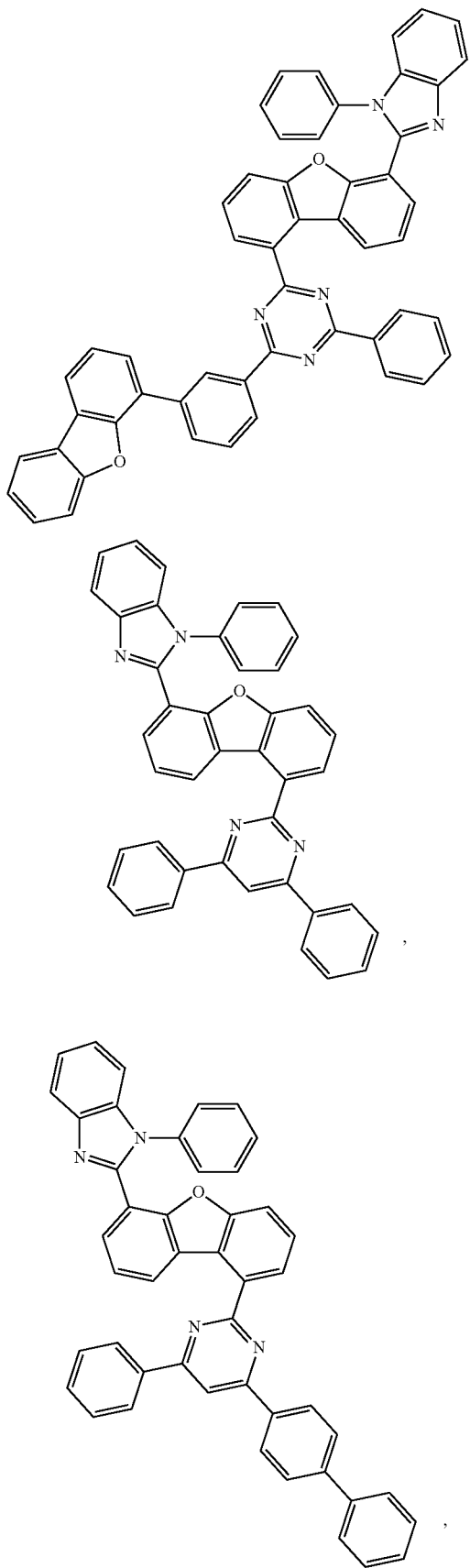
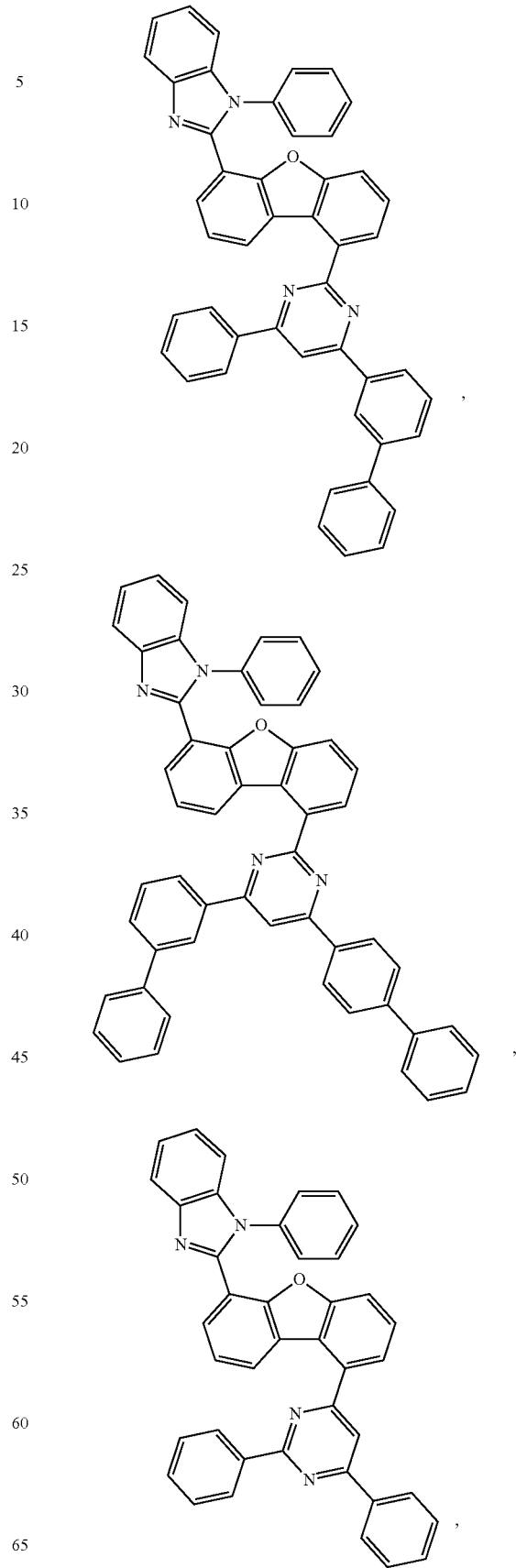

351
-continued
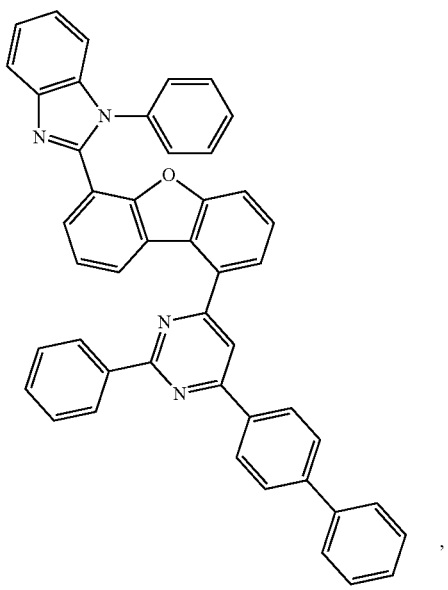
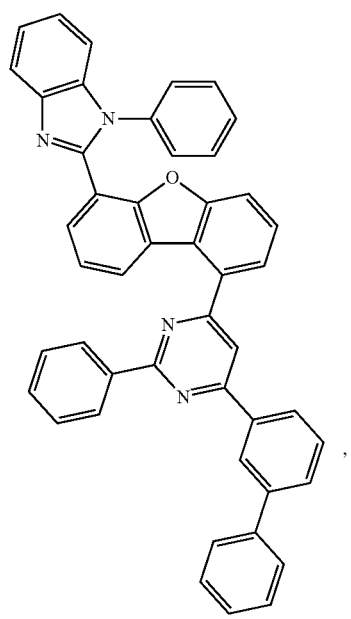
352
-continued
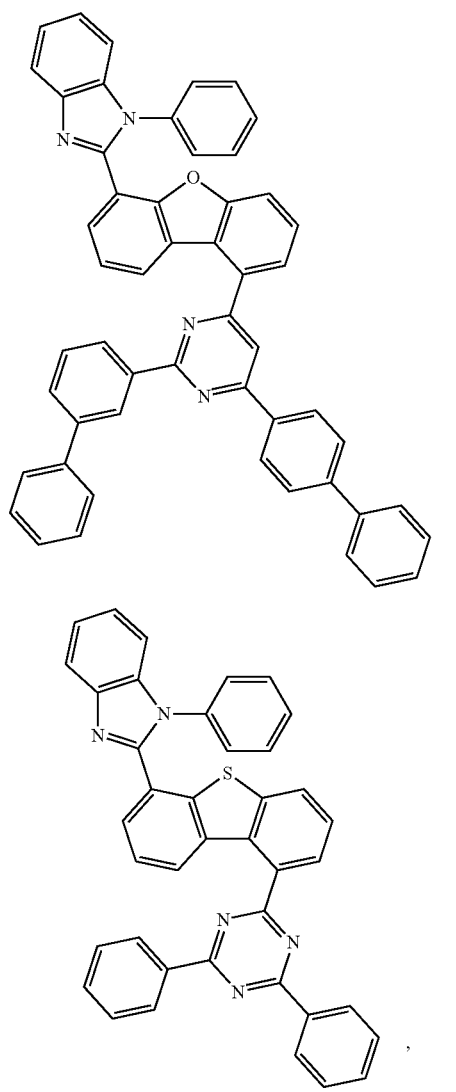
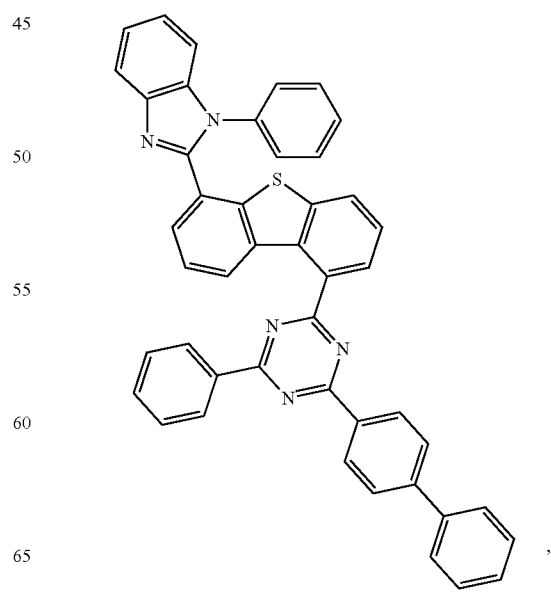

353
-continued
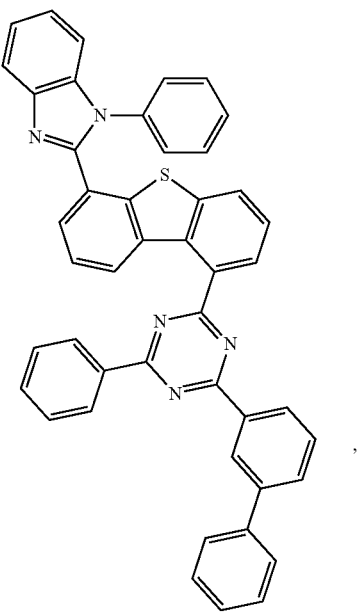
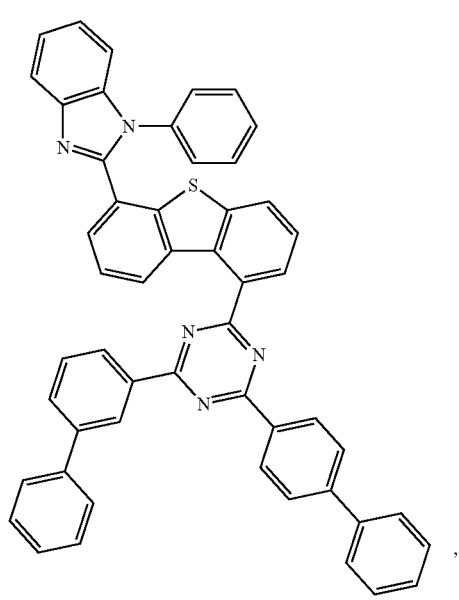
354
-continued
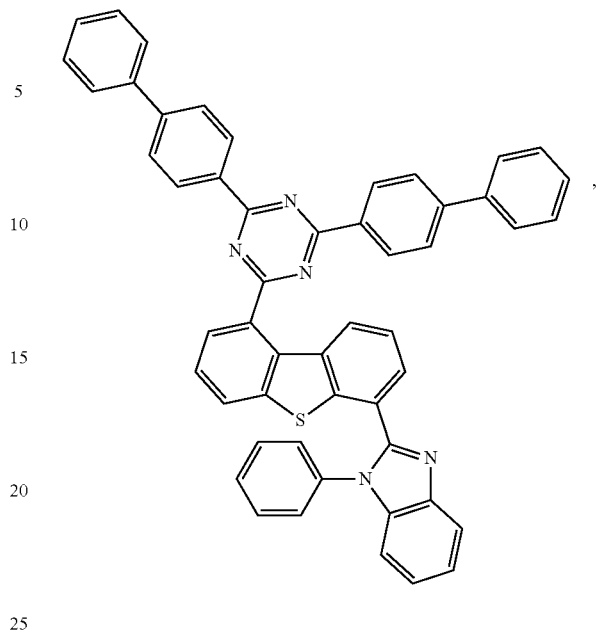
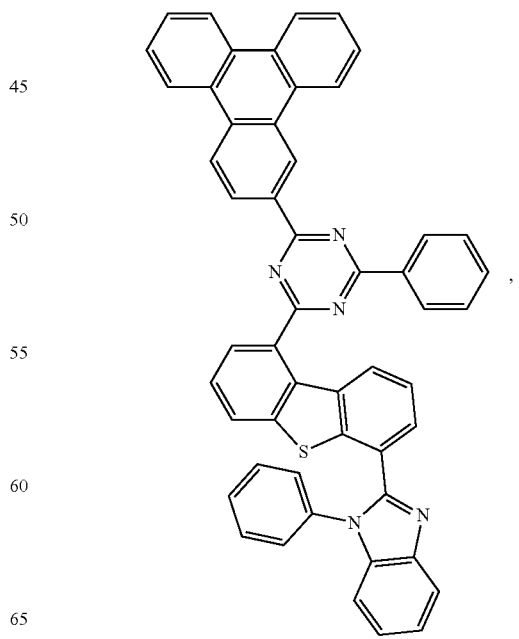

355
-continued
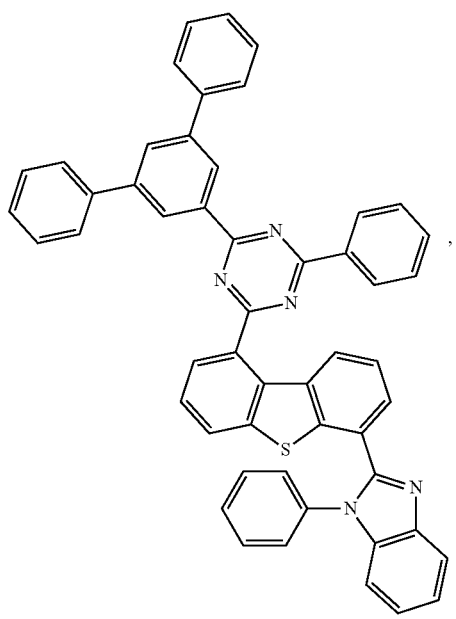
,
356
-continued
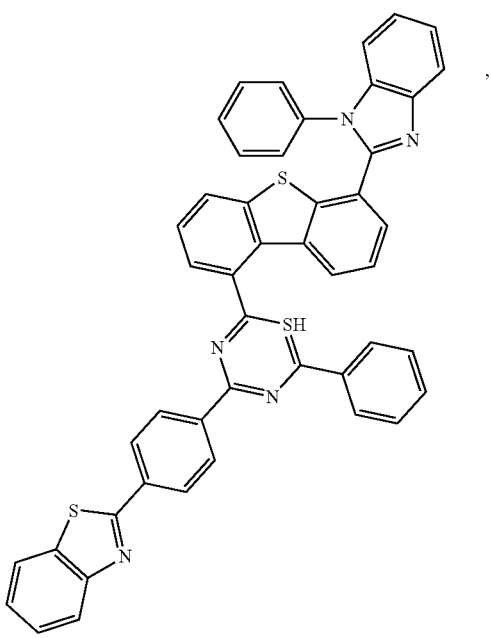
,
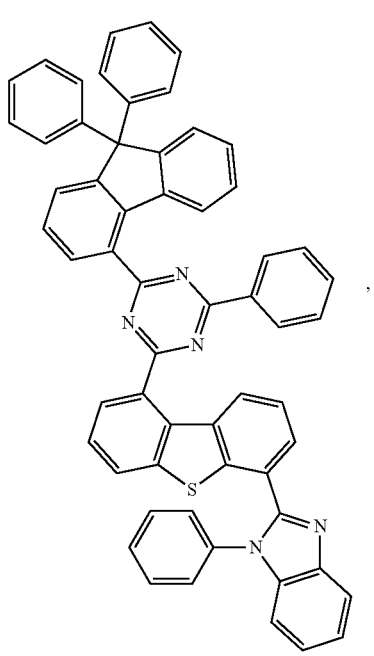
,
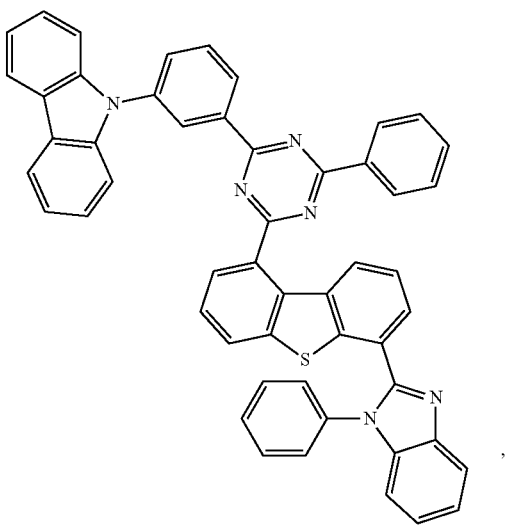
,

357
-continued
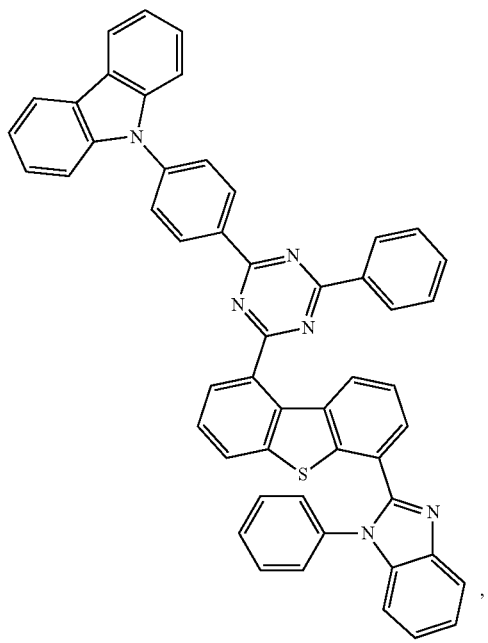
358
-continued
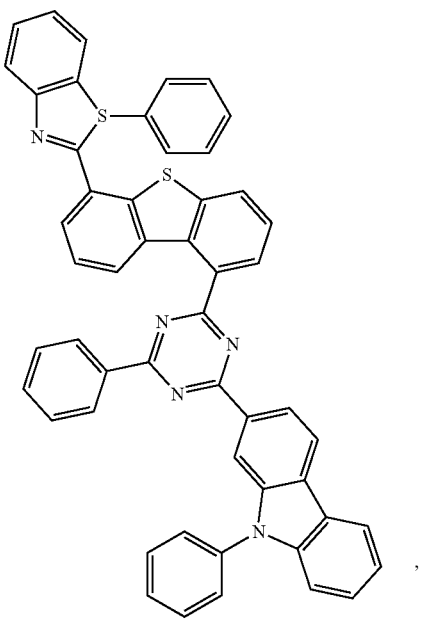
,
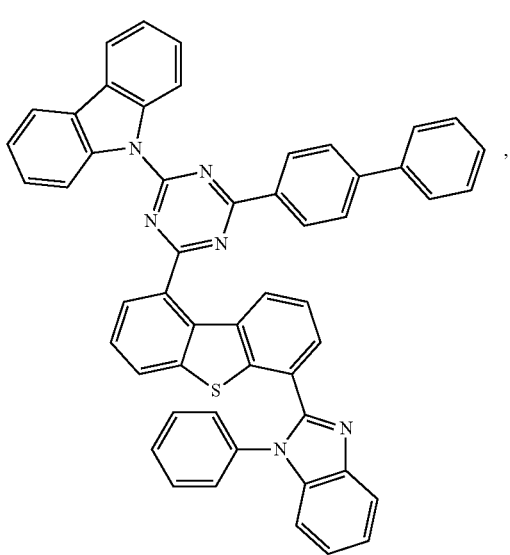
,
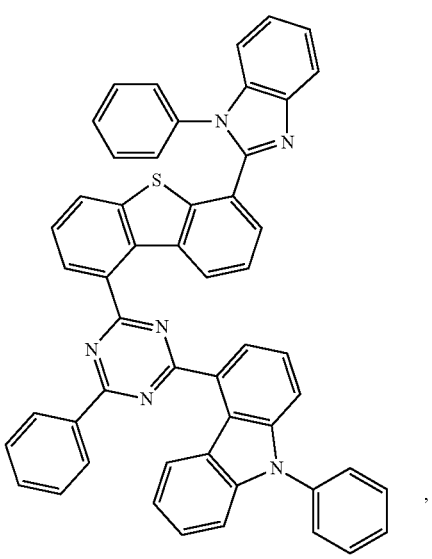
,

359
-continued
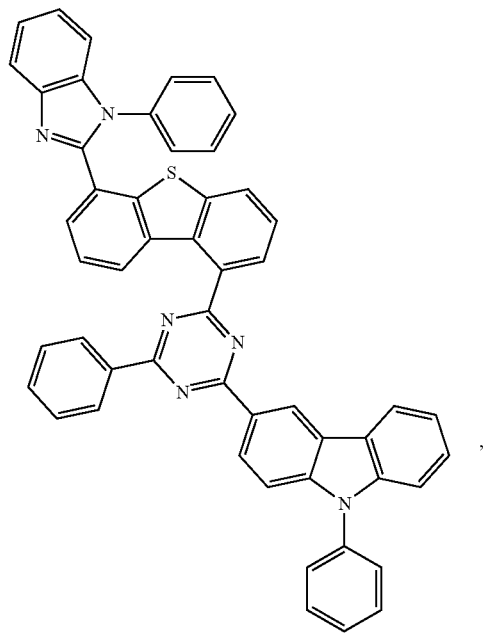
360
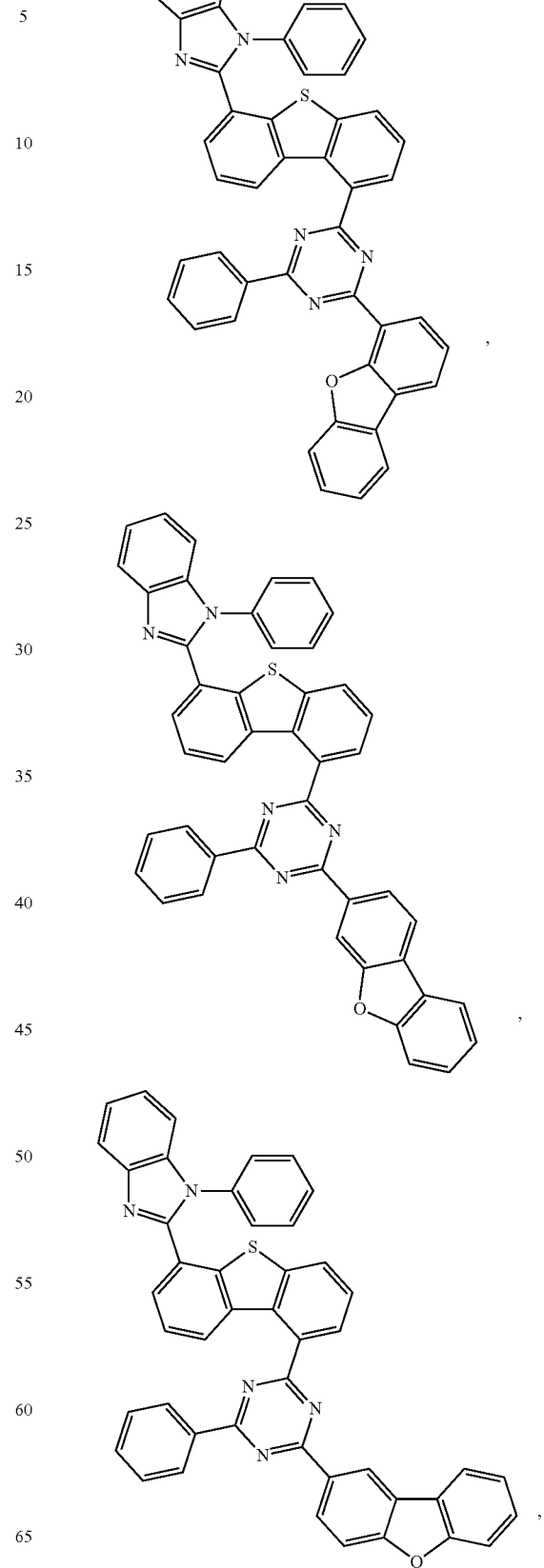

361
-continued
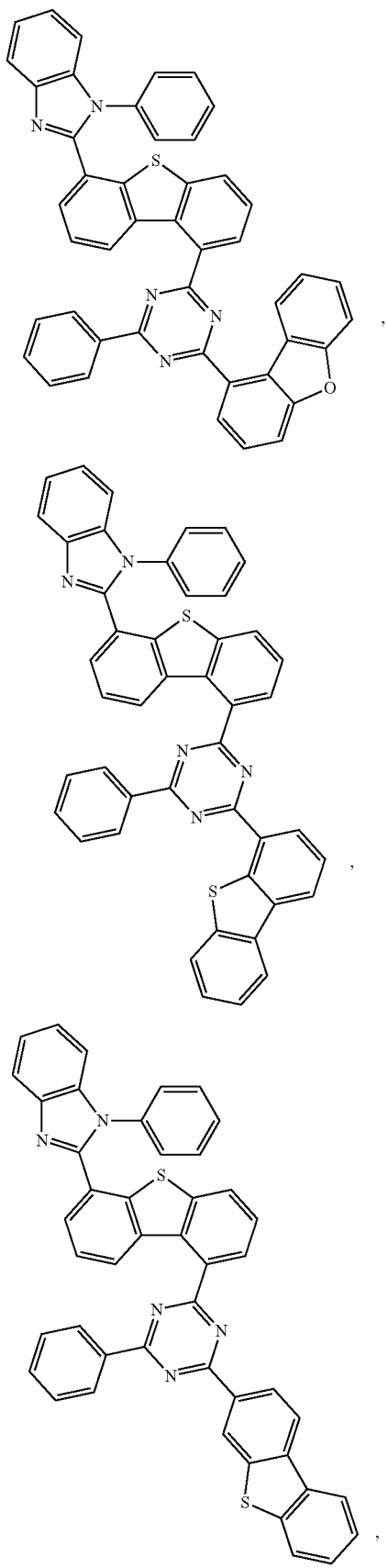
362
-continued
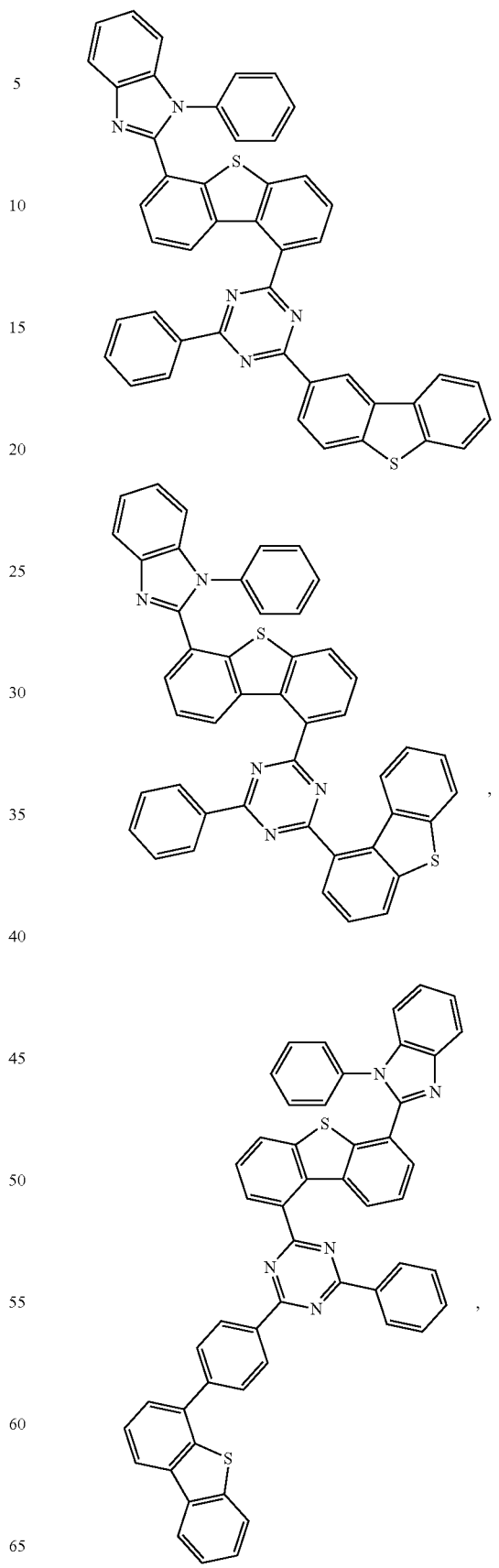

363
-continued
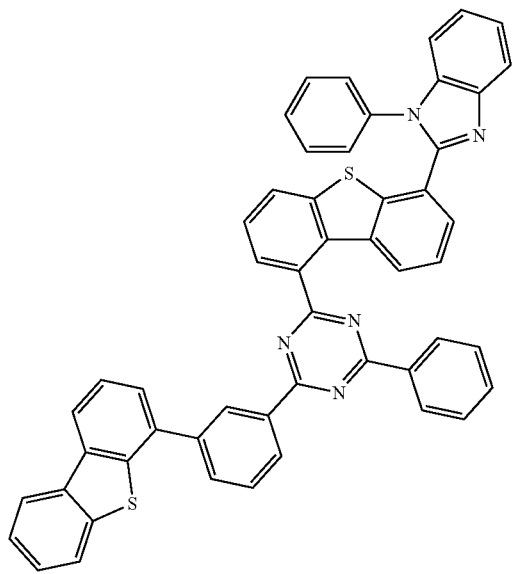
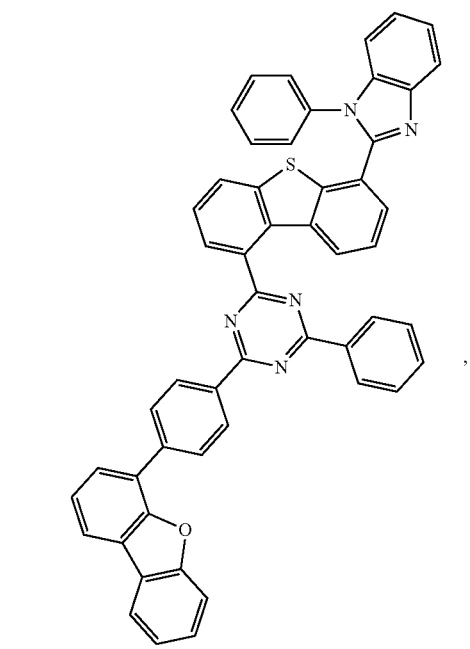
364
-continued
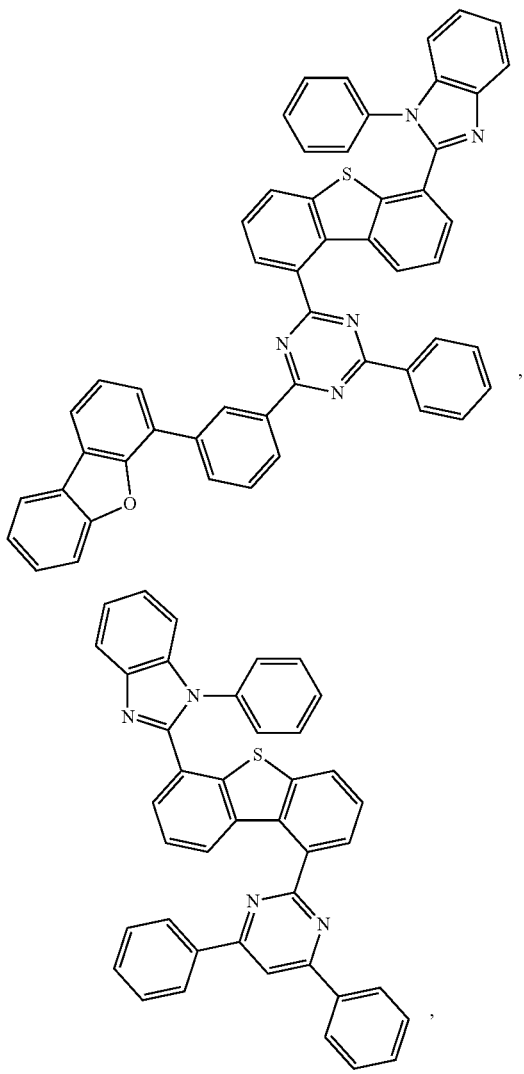
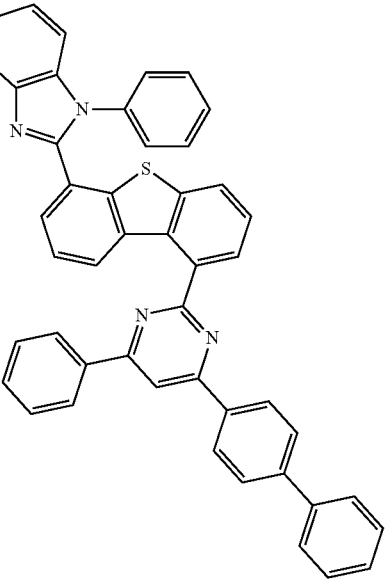

365
-continued
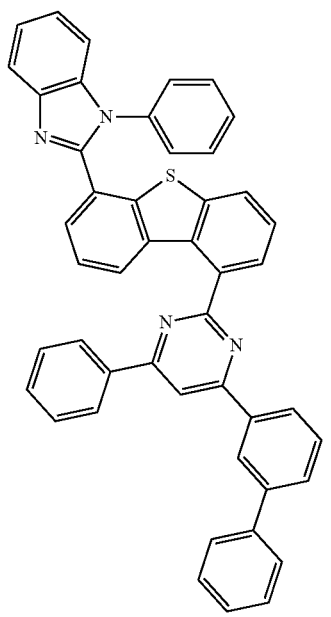
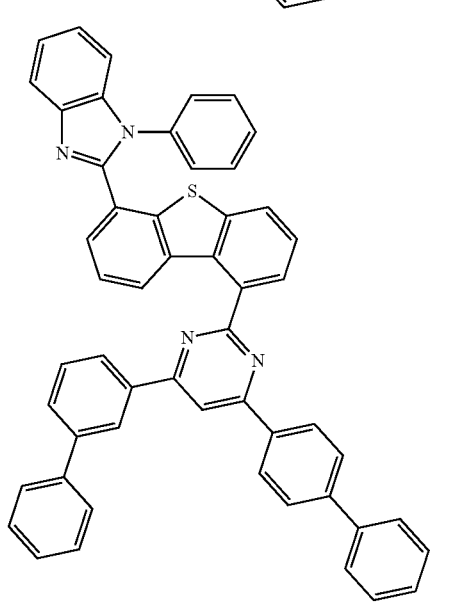
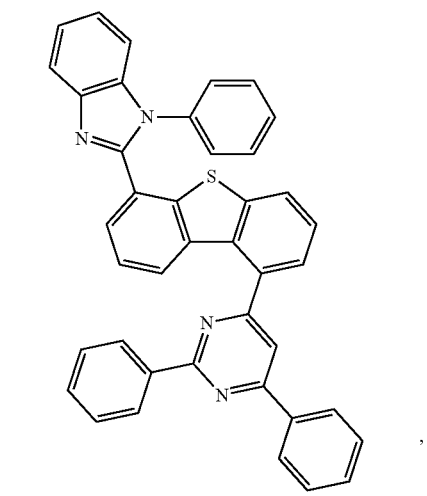
366
-continued
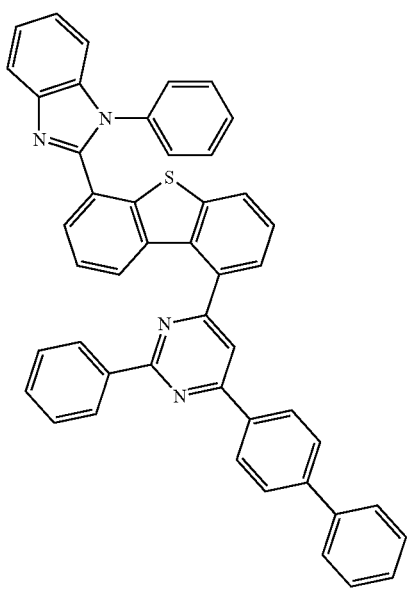
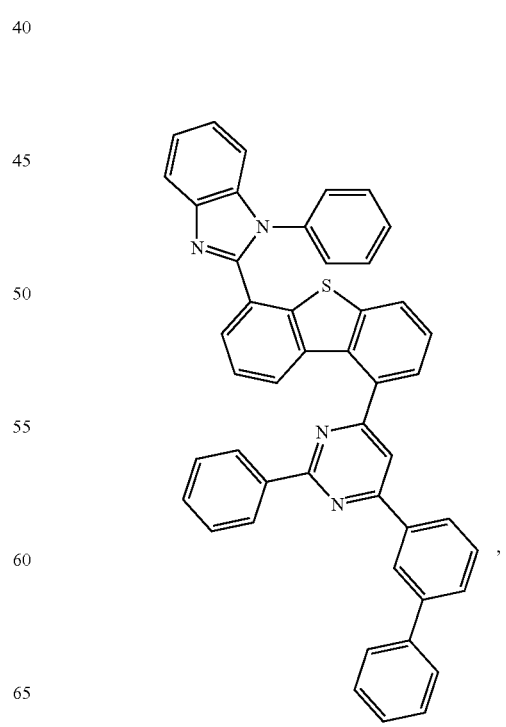

367
-continued
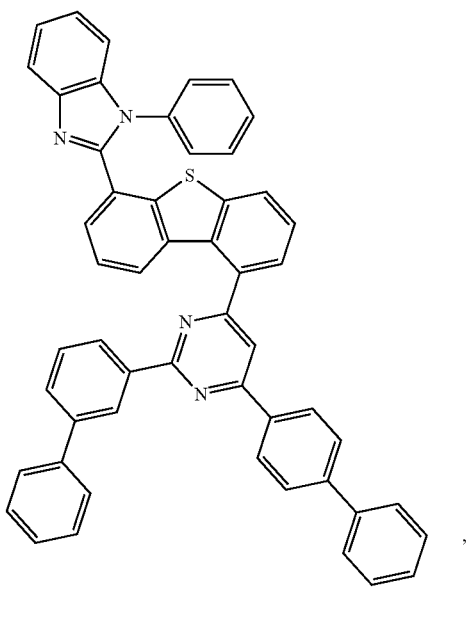
368
-continued
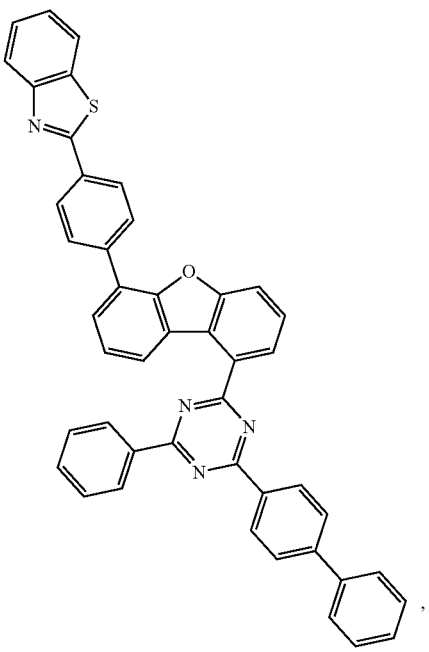
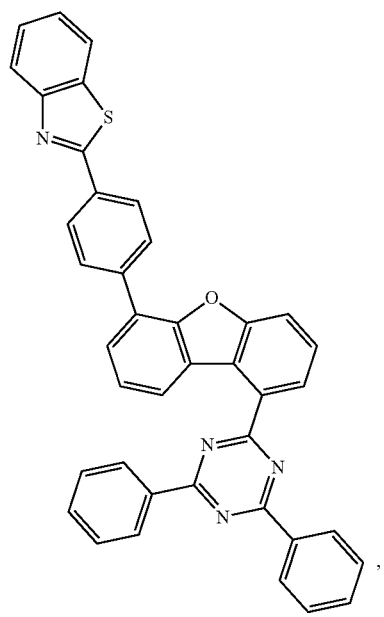
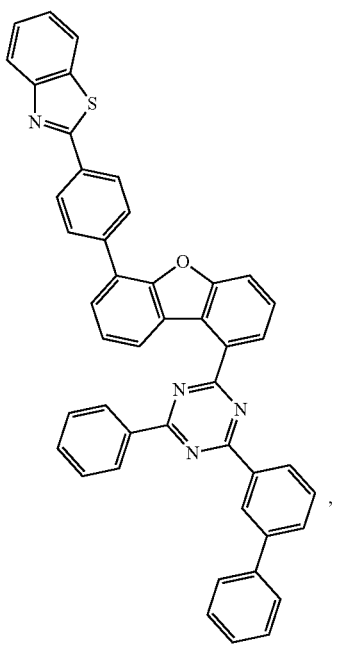

369
-continued
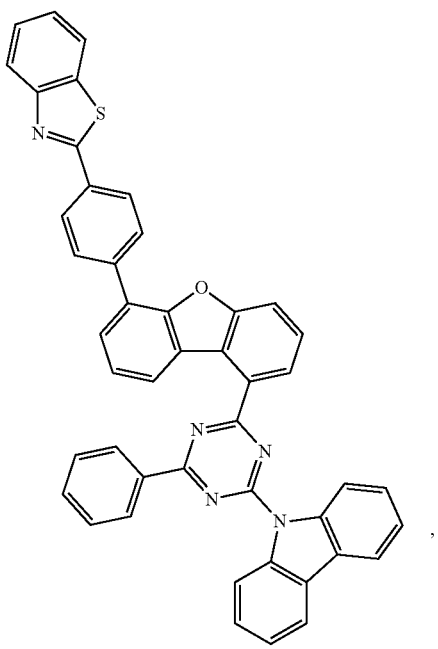
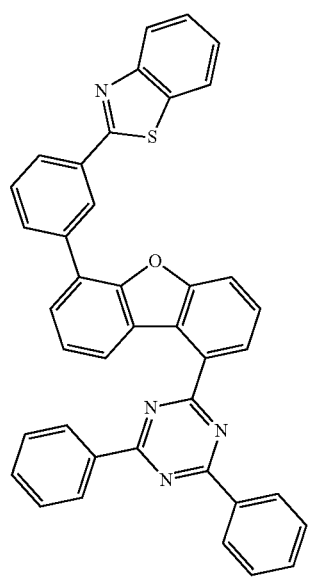
370
-continued
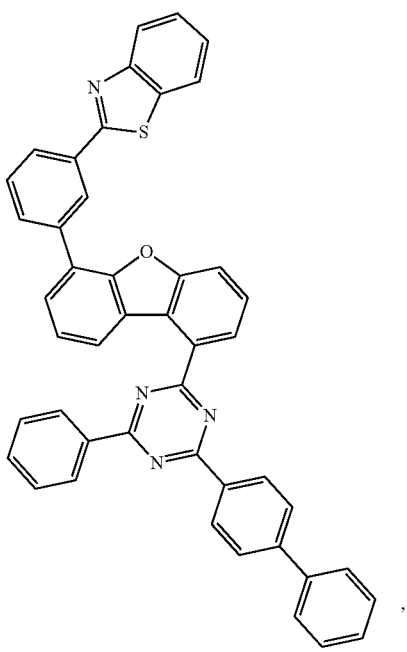
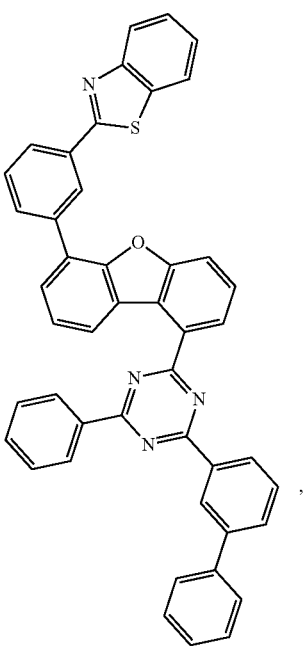

371
-continued
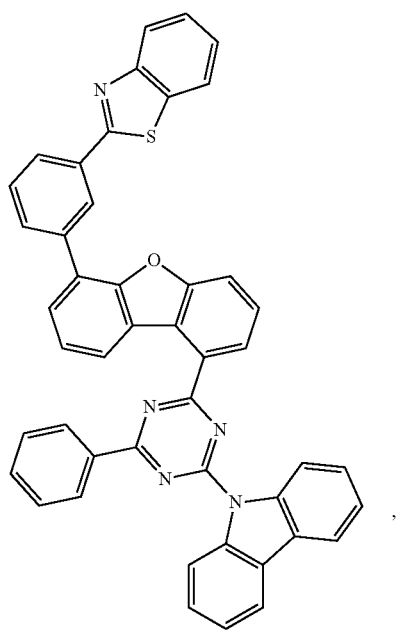
372
-continued
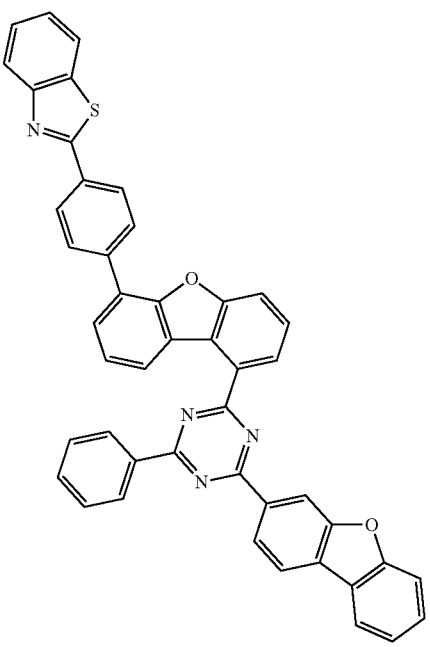
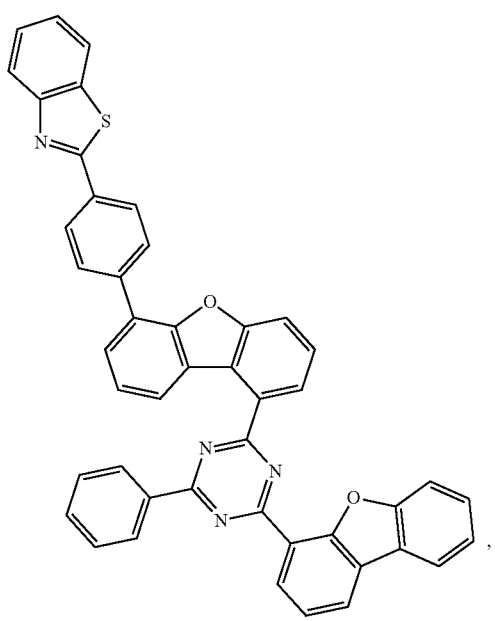
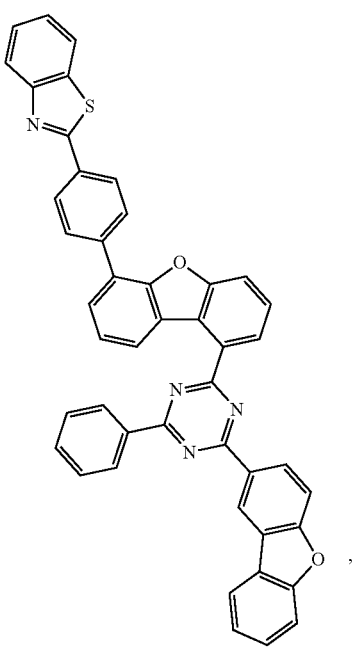

373
-continued
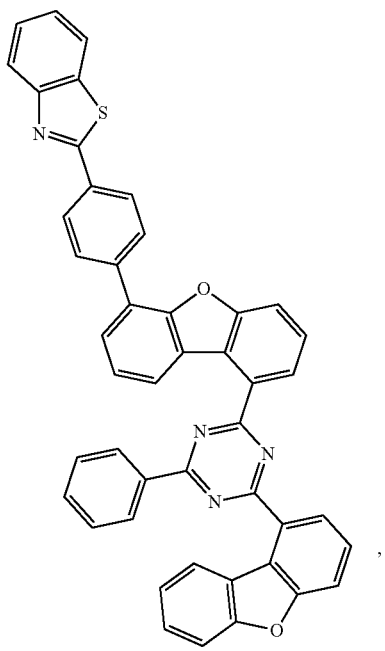
374
-continued
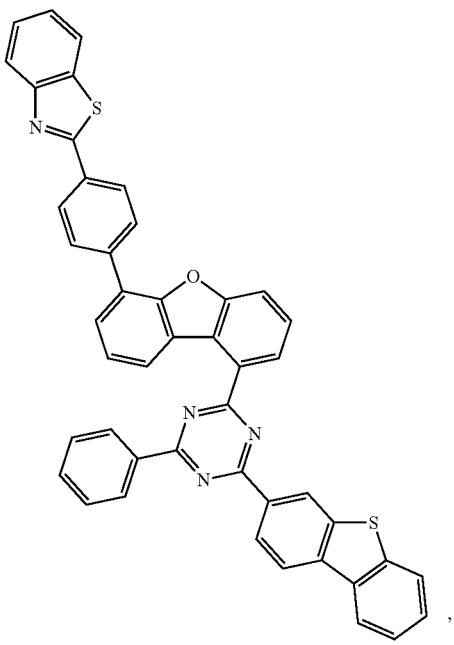
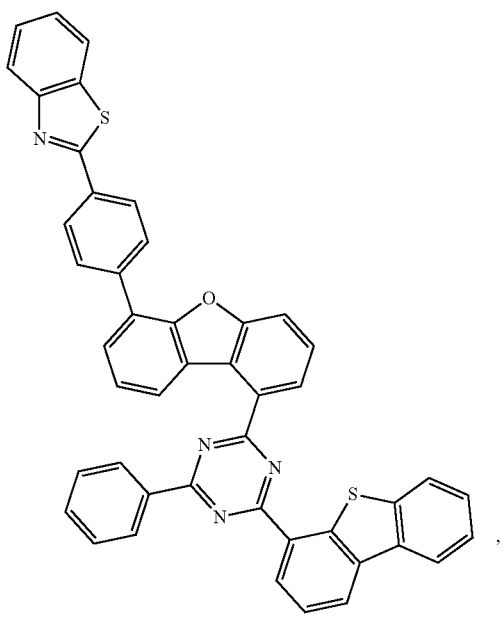
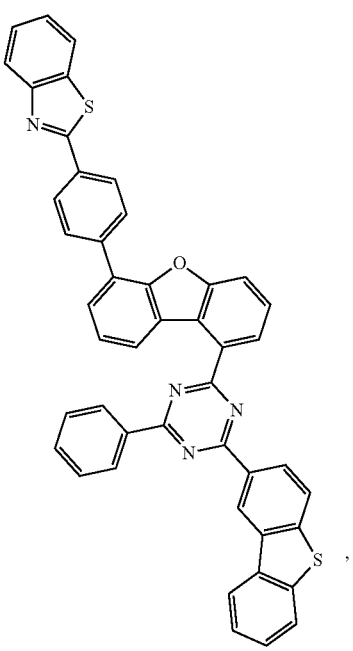

375
-continued
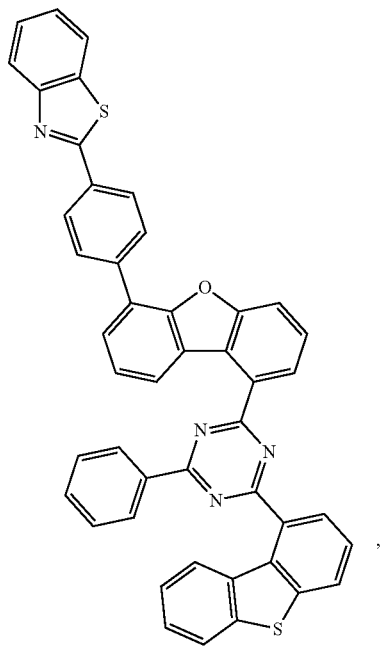
376
-continued
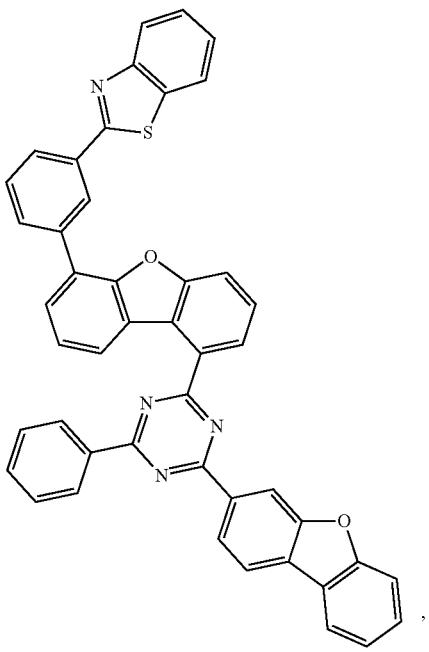
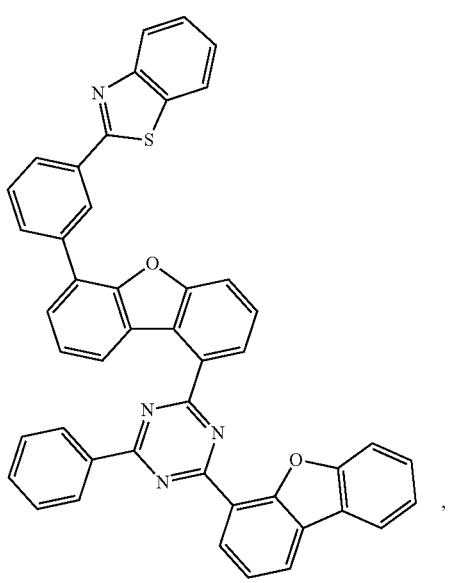
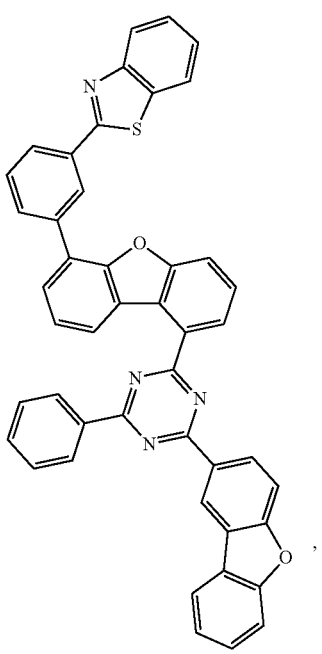

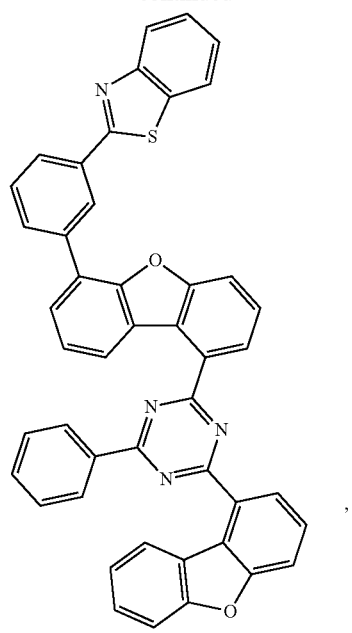
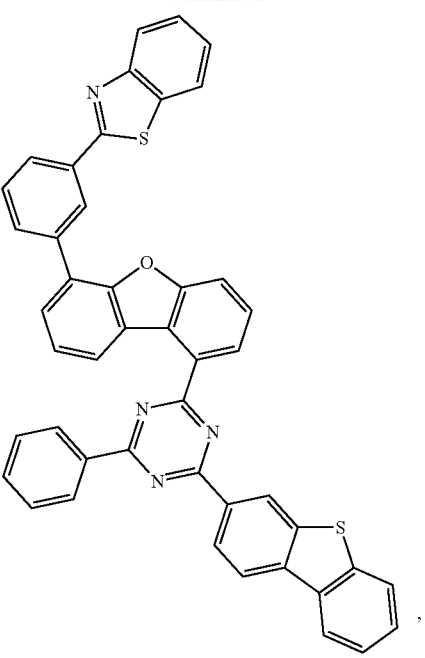
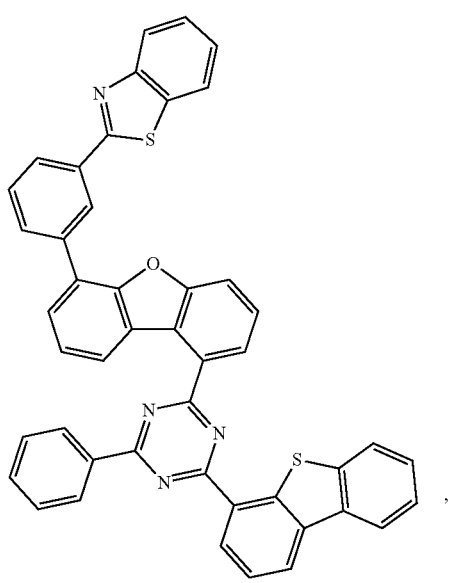
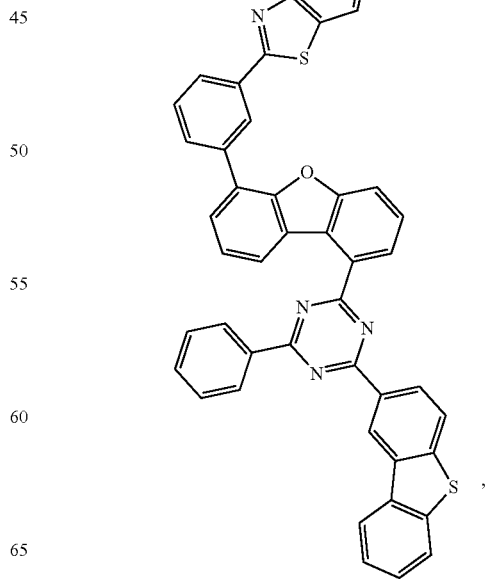

379
-continued
380
-continued
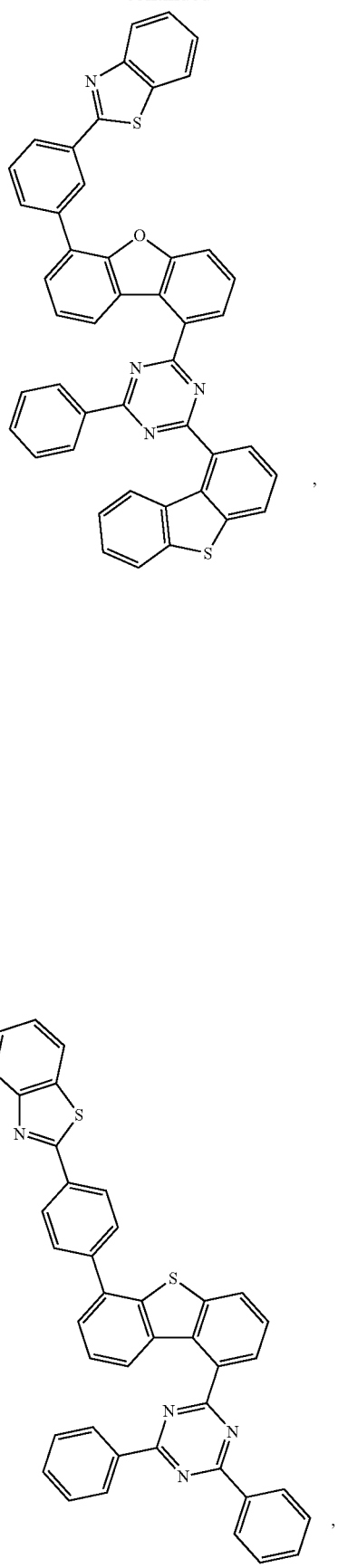
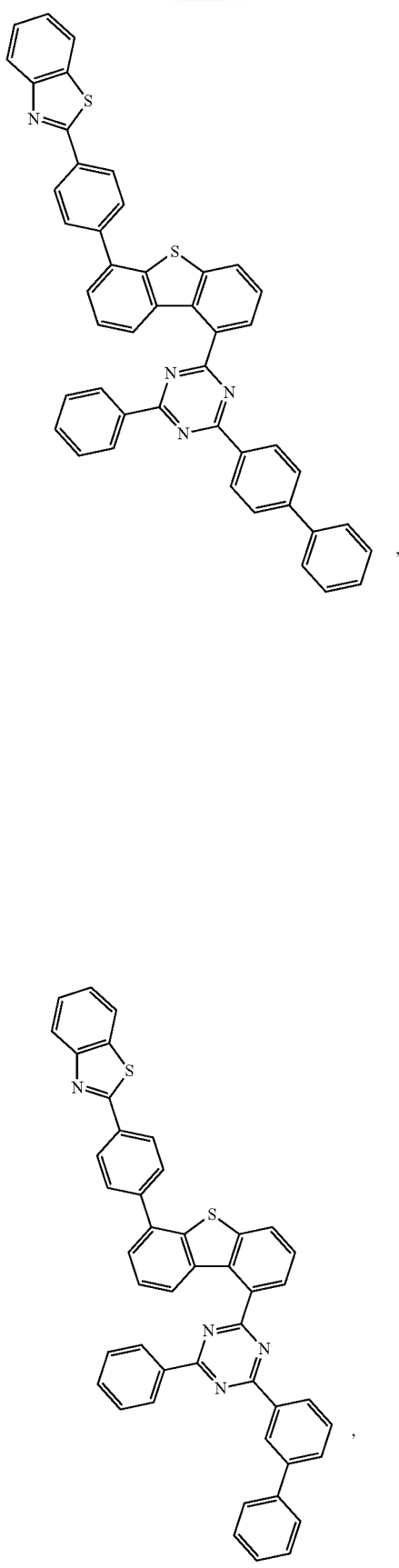

381
-continued
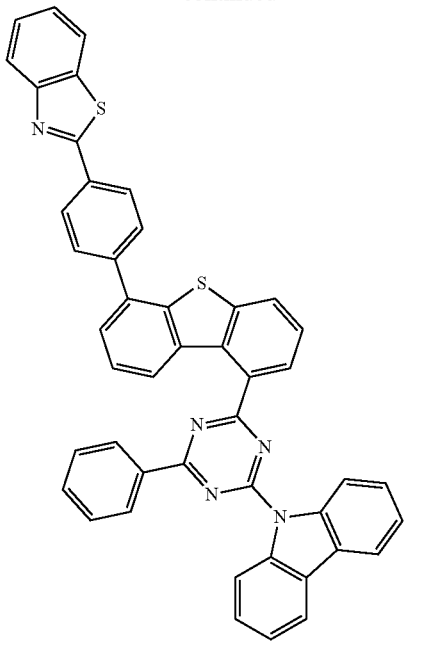
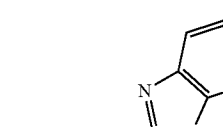
382
-continued
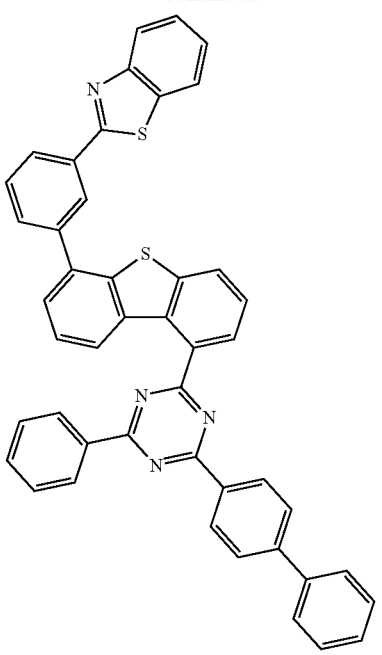

383
-continued
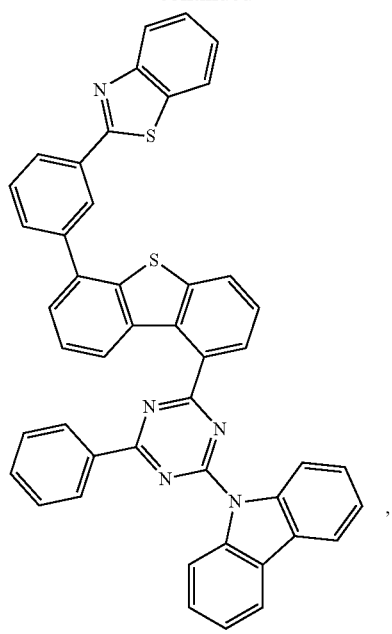
384
-continued
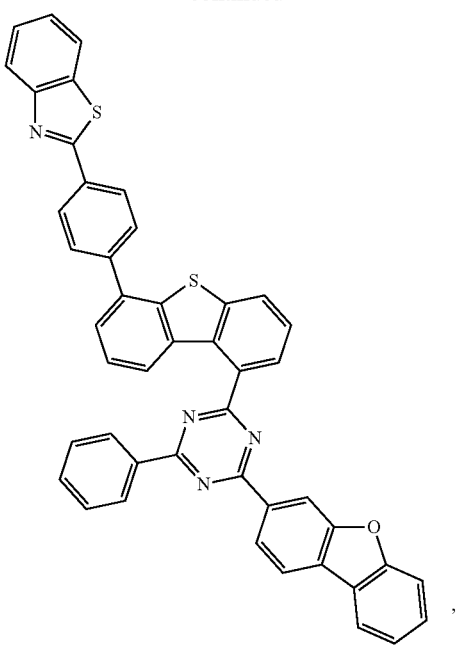
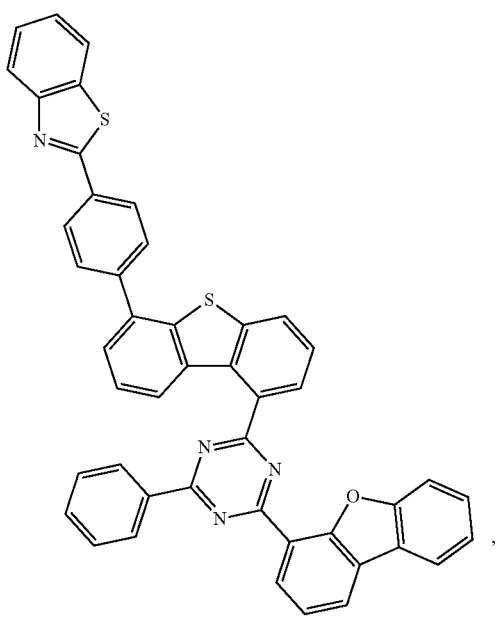
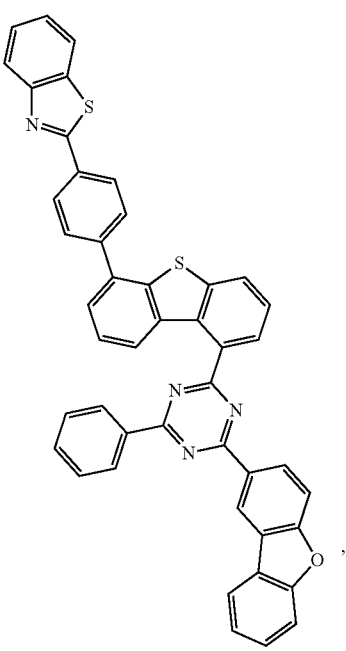

385
-continued
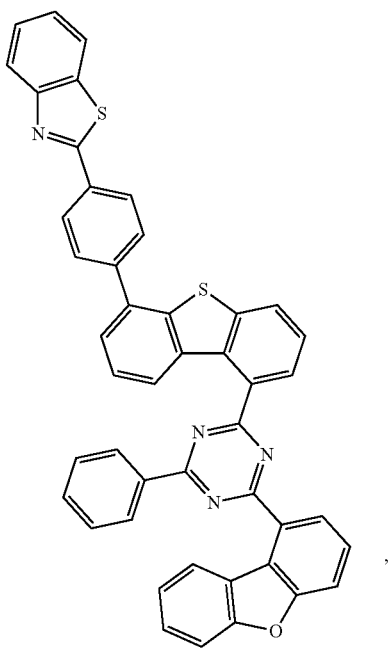
,
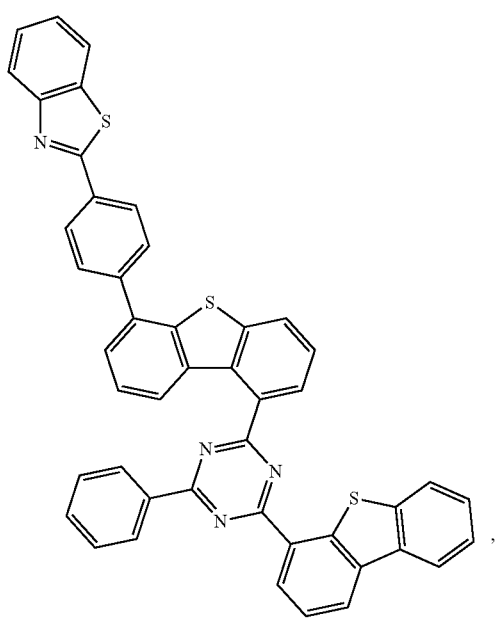
,
386
-continued
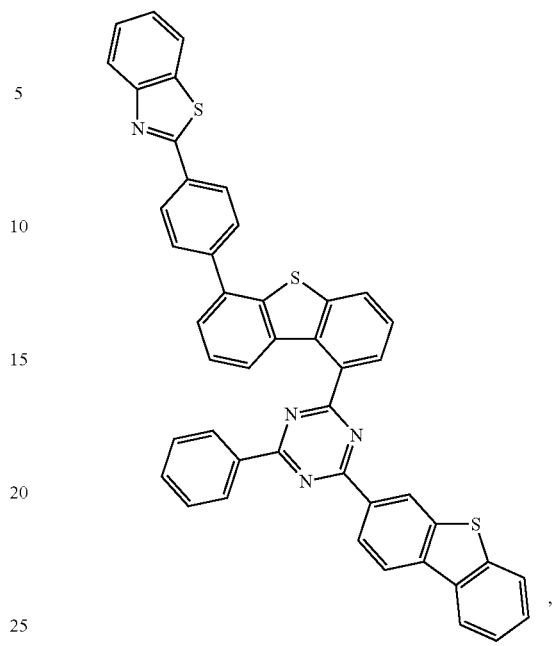
,
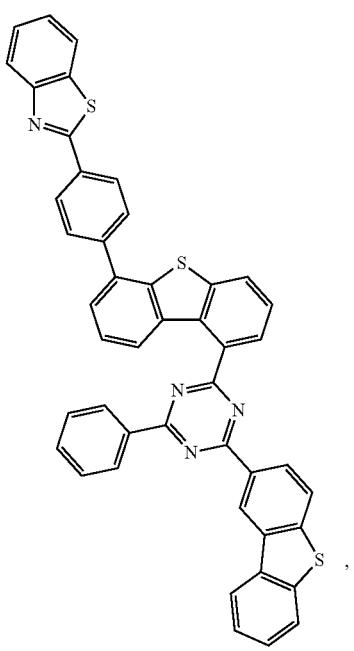
,

387
-continued
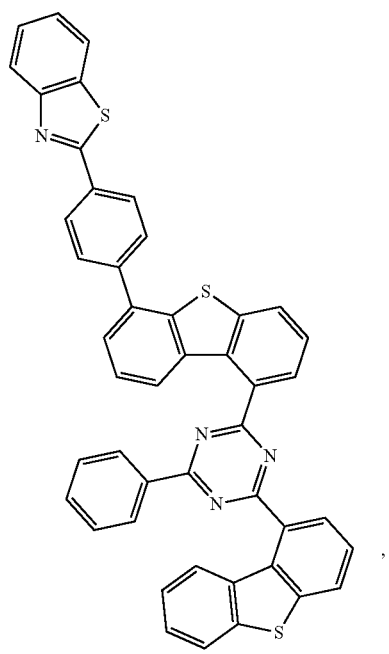
388
-continued
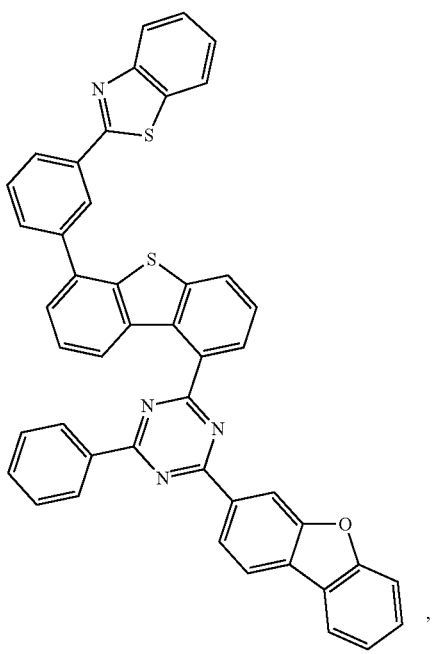
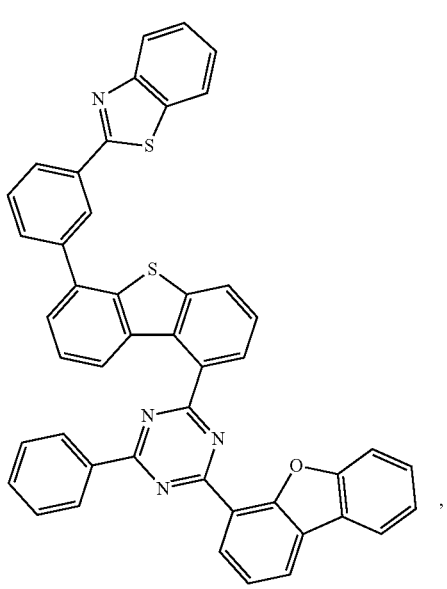
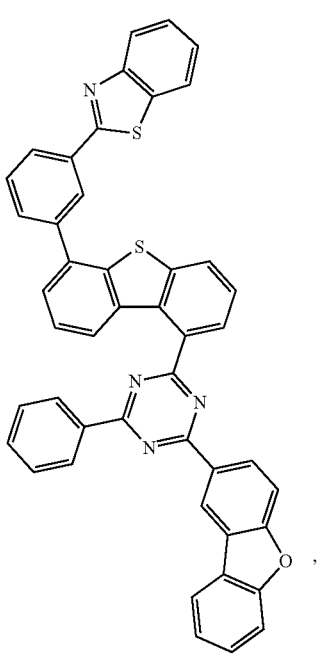

389
-continued
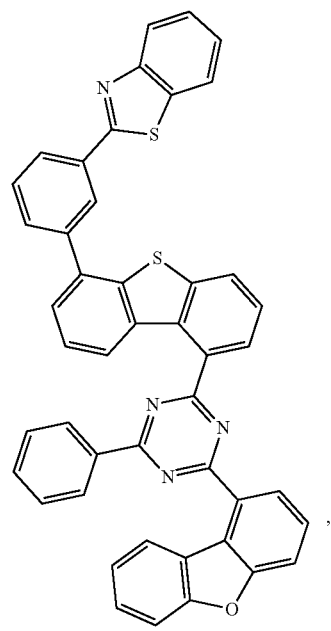
,
390
-continued
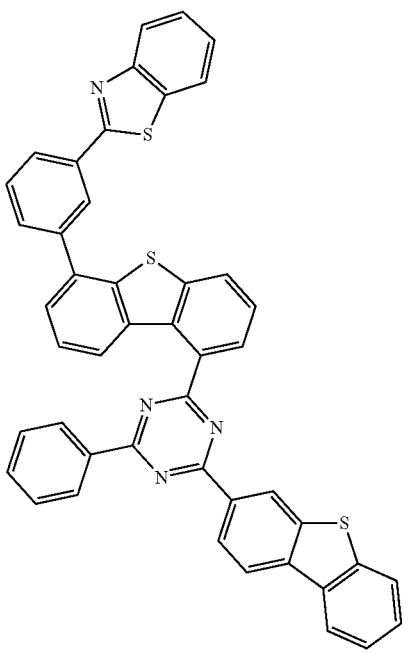
,
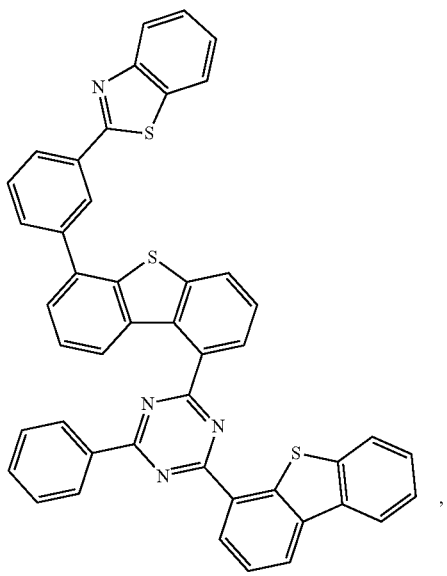
,
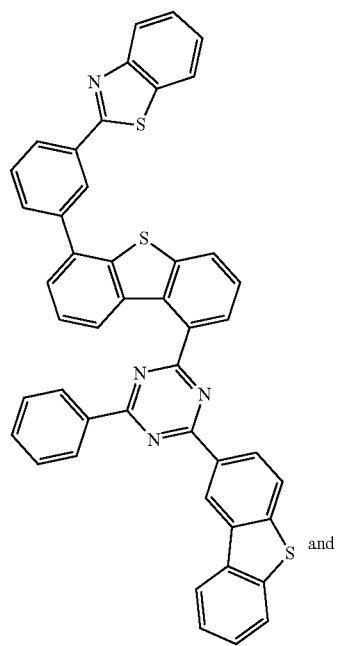 and

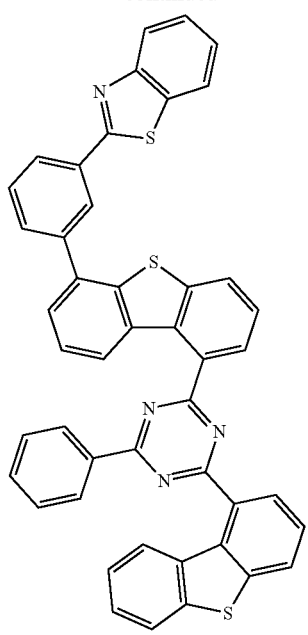

Since the compound by of Formula 1 has a structure that simultaneously has a substituent such as triazine (pyridine, pyrimidine) substituted at the 1-position of the dibenzofuran (dibenzothiophene) core and the above-described substituent Het, it is possible to exhibit excellent heat resistance and suppress crystallization during the operation of the device. Therefore, an organic light emitting device using the same can have high efficiency, a low driving voltage, high luminance, a long lifetime, and the like.

The compound of Formula 1 can be prepared according to the preparation method as shown in Reaction Scheme 1 below.

[Reaction Scheme 1]

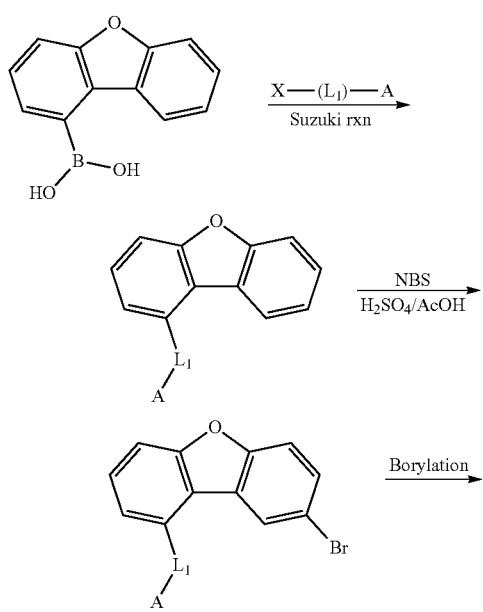

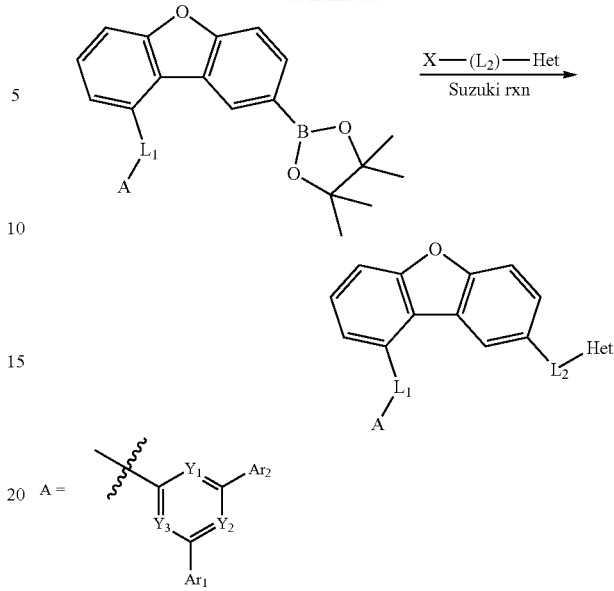

In Reaction Scheme 1, $L_1$, $L_2$, $Y_1$, $Y_2$, $Y_3$, $Ar_1$, $Ar_2$, and Het are as defined above. The type of the reactive group and the catalyst used in the above reaction scheme can be appropriately changed.

In addition, the present invention provides an organic light emitting device including the compound of Formula 1. In one example, the present invention provides an organic light emitting device including: a first electrode; a second electrode provided at a side opposite to the first electrode; and at least one organic material layer provided between the first electrode and the second electrode, wherein the at least one organic material layer includes a compound of Formula 1.

The organic material layer of the organic light emitting device of the present invention can have a single layer structure, or it can have a multilayered structure in which two or more organic material layers are stacked. For example, the organic light emitting device of the present invention can have a structure including a hole injection layer, a hole transport layer, a light emitting layer, an electron transport layer, an electron injection layer, and the like as the organic material layer. However, the structure of the organic light emitting device is not limited thereto, and it can include a smaller number of organic layers.

The organic material layer can include a hole injection layer, a hole transport layer, or a layer simultaneously performing hole injection and transport, wherein the hole injection layer, the hole transport layer, and the layer simultaneously performing hole injection and transport include a compound a Formula 1.

The organic material layer can include a light emitting layer, wherein the light emitting layer includes a compound of Formula 1.

The organic material layer can include an electron transport layer or an electron injection layer, wherein the electron transport layer or the electron injection layer includes a compound of Formula 1.

The electron transport layer, the electron injection layer, and the layer simultaneously performing electron injection and electron transport include a compound of Formula 1. In particular, the compound of Formula 1 according to one embodiment of the present invention has excellent thermal stability, a deep HOMO level of 6.0 eV or more, and high triplet energy (ET) and hole stability. Further, when the compound of Formula 1 is used for an organic material layer capable of simultaneously performing electron injection and electron transport, the n-type dopant used in the art can be mixed and used.

The organic material layer can include a light emitting layer and an electron transport layer, wherein the electron transport layer can include a compound of Formula 1.

The organic light emitting device according to the present invention can be a normal type of organic light emitting device in which an anode, at least one organic material layer, and a cathode are sequentially stacked on a substrate. Further, the organic light emitting device according to the present invention can be an inverted type of organic light emitting device in which a cathode, at least one organic material layer, and an anode are sequentially stacked on a substrate. For example, the structure of an organic light emitting device according to an embodiment of the present invention is illustrated in FIGS. 1 and 2.

FIG. 1 shows an example of an organic light emitting device including a substrate 1, an anode 2, a light emitting layer 3, and a cathode 4. In such a structure, the compound of Formula 1 can be included in the light emitting layer.

FIG. 2 shows an example of an organic light emitting device including a substrate 1, an anode 2, a hole injection layer 5, a hole transport layer 6, a light emitting layer 7, an electron transport layer 8, and a cathode 4. In such a structure, the compound of Formula 1 can be included in at least one layer of the hole injection layer, the hole transport layer, the light emitting layer, and the electron transport layer.

The organic light emitting device according to the present invention can be manufactured by materials and methods known in the art, except that at least one organic material layer includes the compound of Formula 1. In addition, when the organic light emitting device includes a plurality of organic material layers, the organic material layers can be formed of the same material or different materials.

For example, the organic light emitting device according to the present invention can be manufactured by sequentially stacking a first electrode, an organic material layer, and a second electrode on a substrate. In this case, the organic light emitting device can be manufactured by depositing a metal, metal oxides having conductivity, or an alloy thereof on the substrate by using a PVD (physical vapor deposition) method such as a sputtering method or an e-beam evaporation method to form the anode, forming an organic material layer including the hole injection layer, the hole transport layer, the light emitting layer, and the electron transport layer thereon, and then depositing a material that can be used as the cathode thereon. In addition to such a method, the organic light emitting device can be manufactured by sequentially depositing a cathode material, an organic material layer, and an anode material on a substrate.

In addition, the compound of Formula 1 can be formed into an organic layer by a solution coating method as well as a vacuum deposition method at the time of manufacturing an organic light emitting element. Herein, the solution coating method means spin coating, dip coating, doctor blading, inkjet printing, screen printing, a spray method, roll coating, or the like, but is not limited thereto.

In addition to such a method, the organic light emitting device can be manufactured by sequentially depositing a cathode material, an organic material layer, and an anode material on a substrate (International Publication WO 2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy) thiophene](PEDOT), polypyrrole, and polyaniline; and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has an ability to transport the holes, a hole injecting effect in the anode, and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrile-hexaazatriphenylene-based organic material, a quinacridone-based organic material, a perylene-based organic material, anthraquinone, a polyaniline and polythiophene-based conductive polymer, and the like, but are not limited thereto.

The hole transport layer is a layer that receives holes from the hole injection layer and transports the holes to the light emitting layer. The hole transport material is suitably a material having large mobility to the holes, which can receive holes from the anode or the hole injection layer, and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is a material capable of emitting light in the visible light region by combining holes and electrons respectively transported from the hole transport layer and the electron transport layer, and having good quantum efficiency for fluorescence or phosphorescence. Specific examples include an 8-hydroxy-quinoline aluminum ($Alq_3$) complex; carbazole-based compounds; dimerized styryl compounds; BAlq; 10-hydroxybenzoquinoline-metal compounds; benzoxazole, benzothiazole, and benzimidazole-based compounds; poly(p-phenylene vinylene) (PPV)-based polymers; spiro compounds; and polyfluorene, rubrene, and the like, but are not limited thereto.

The light emitting layer can include a host material and a dopant material, and the compound of the present invention can be included as a host material in the light emitting layer. The host material can be a fused aromatic ring derivative, a heterocycle-containing compound, or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, and examples thereof include pyrene, anthracene, chrysene, and periflanthene having the arylamino group, and the like. The styrylamine compound is a compound where at least one arylvinyl group is substituted in a substituted or unsubstituted arylamine, in which one or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, and the electron transport material is a material that can receive the electrons well from the cathode and transport the electrons to the light emitting layer, wherein a material having large mobility to the electrons is suitable. Specific examples thereof include an 8-hydroxyquinoline Al complex, a complex including Alq$_3$, an organic radical compound, a hydroxyflavone-metal complex, and the like, but are not limited thereto. The electron transport layer can be used together with a predetermined desired cathode material as used according to the prior art. Particularly, an example of an appropriate cathode material is a general material having the low work function and followed by an aluminum layer or a silver layer, Specific examples thereof include cesium, barium, calcium, ytterbium, and samarium, and each case is followed by the aluminum layer or the silver layer.

The electron injection layer is a layer which injects the electrons from the electrode, and is preferably a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium, and the like, but are not limited thereto.

The organic light emitting device according to the present invention can be a front side emission type, a back side emission type, or a double side emission type according to the material used.

In addition, the compound of Formula 1 can be included in an organic solar cell or an organic transistor in addition to an organic light emitting device.

The preparation of the compound of Formula 1 and the organic light emitting device including the same will be described in detail in the following examples. However, these examples are presented for illustrative purposes only, and the scope of the present invention is not limited thereto.

Preparation Example 1

Preparation Example 1-1: Synthesis of Intermediate Compound A-4

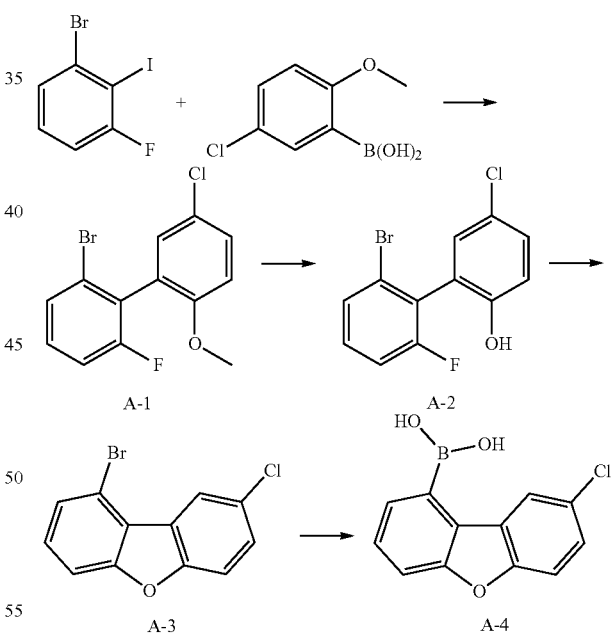

1) Preparation of Compound A-1

1-bromo-3-fluoro-2-iodobenzene (75 g, 249.3 mmol), and (5-chloro-2-methoxyphenyl)boronic acid (51.1 g, 249.3 mmol) were dissolved in 550 mL of tetrahydrofuran. A 2 M sodium carbonate (Na$_2$CO$_3$) solution (350 mL) and tetrakis (triphenylphosphine)palladium(0) (2.88 g, 2.49 mmol) were added thereto and refluxed for 11 hours. After the reaction was completed, the reaction mixture was cooled to room temperature. The aqueous layer was separated and removed, dried over anhydrous magnesium sulfate, and concentrated under reduced pressure. The resulting mixture was recrystallized using chloroform and ethanol to obtain Compound A-1 (63.2 g, yield 80%; MS:[M+H]$^+$=314).

2) Preparation of Compound A-2

Compound A-1 (63.2 g, 200.3 mmol) was dissolved in 750 mL of dichloromethane and then cooled to 0° C. Boron tribromide (20.0 mL, 210.3 mmol) was slowly added dropwise and then stirred for 12 hours. After the reaction was completed, the reaction mixture was washed three times with water, dried over magnesium sulfate, and filtered. The filtrate was distilled under reduced pressure and purified by column chromatography to obtain Compound A-2 (57.9 g, yield 96%; MS: [M+H]$^+$=300).

3) Preparation of Compound A-3

Compound A-2 (57.9 g, 192.0 mmol) and calcium carbonate (79.6 g, 576.0 mol) were dissolved in 350 mL of N-methyl-2-pyrrolidone and then heated and stirred for 2 hours. After lowering the temperature to room temperature, the reaction mixture was subjected to reverse precipitation in water and filtered. The mixture was completely dissolved in dichloromethane, washed with water, dried over anhydrous magnesium sulfate, concentrated under reduced pressure, recrystallized using ethanol and dried to obtain Compound A-3 (42.1 g, yield 78%; MS: [M+H]$^+$=280).

4) Preparation of Compound A-4

After Compound A-3 (42.1 g, 149.5 mmol) was dissolved in tetrahydrofuran (330 mL), the temperature was lowered to −78° C. and 2.5 M tert-butyllithium (t-BuLi) (60.4 mL, 151.0 mmol) was added slowly. The mixture was stirred at the same temperature for 1 hour, and then triisopropylborate (51.8 mL, 224.3 mmol) was added thereto, and stirred for 3 hours while gradually raising the temperature to room temperature. To the reaction mixture was added a 2N aqueous hydrochloric acid solution (300 mL) and the mixture was stirred at room temperature for 1.5 hours. The resulting precipitate was filtered, washed with water and ethyl ether, and then vacuum dried to obtain Compound A-4 (34.3 g, yield 93%; MS:[M+H]$^+$=247).

Preparation Example 1-2: Synthesis of Intermediate Compound B-5

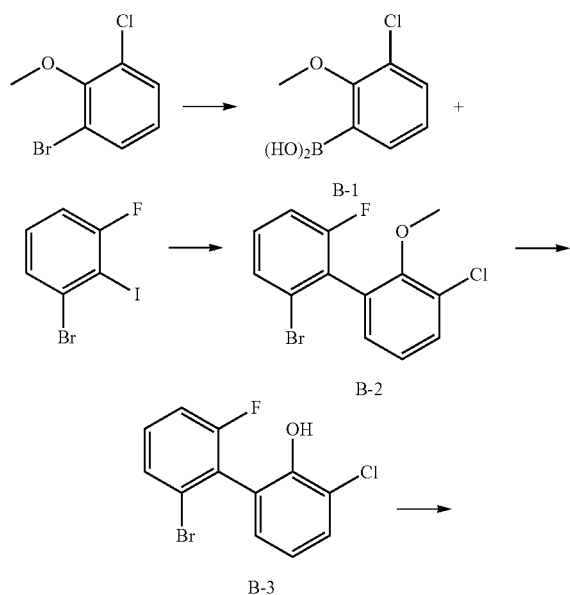

1) Preparation of Compound B-1

After 1-bromo-3-fluoro-2-methoxybenzene (100.0 g, 451.5 mmol) was dissolved in tetrahydrofuran (1000 mL), the temperature was lowered to −78° C. and 2.5 M tert-butyl lithium (t-BuLi) (182.4 mL, 456.0 mmol) was slowly added dropwise. The mixture was stirred at the same temperature for 1 hour, and triisopropylborate (B(OiPr)$_3$) (156.3 mL, 677.3 mmol) was added thereto and stirred for 3 hours while gradually raising the temperature to room temperature. A 2N aqueous hydrochloric acid solution (150 mL) was added to the reaction mixture and the mixture was stirred at room temperature for 1.5 hours. The resulting precipitate was filtered, washed sequentially with water and ethyl ether, and then vacuum dried. After drying, it was recrystallized with chloroform and ethyl acetate and dried to produce Compound B-1 (84.2 g, yield 90%; MS: [M+H]$^+$=230).

2) Preparation of Compound B-2

Compound B-2 (74.6 g, yield 52%; MS:[M+H]$^+$=314) was prepared in the same manner as in the preparation of Compound A-1 of Preparation Example 1, except that Compound B-1 (84.2 g, 451.7 mmol) was used instead of (5-chloro-2-methoxyphenyl) boronic acid.

3) Preparation of Compound B-3

Compound B-3 (60.3 g, yield 85%; MS:[M+H]$^+$=300) was prepared in the same manner as in the preparation of Compound A-2, except that Compound B-2 (74.6 g, 236.4 mmol) was used instead of Compound A-1.

4) Preparation of Compound B-4

Compound B-4 (48.1 g, yield 85%; MS:[M+H]$^+$=280) was prepared in the same manner as in the preparation of Compound A-3, except that Compound B-3 (60.3 g, 199.9 mmol) was used instead of Compound A-2.

5) Preparation of Compound B-5

Compound B-5 (40.1 g, yield 95%; MS: [M+H]$^+$=247 was prepared in the same manner as in the preparation of Compound A-4, except that Compound B-4 (48.1 g, 170.9 mmol) was used instead of Compound A-3.

Preparation Example 1-3: Synthesis of Intermediate Compound C-4

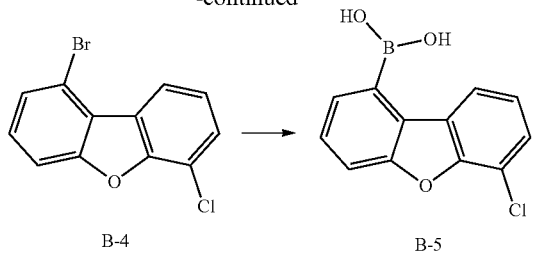

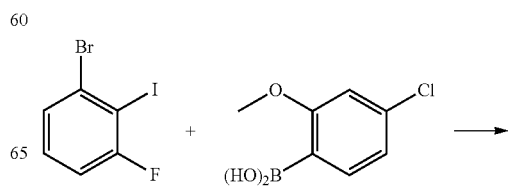

399

-continued

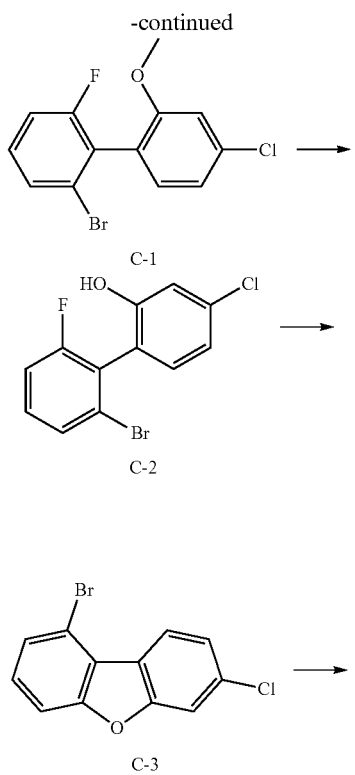

C-1

C-2

C-3

C-4

Preparation Example 1-4: Synthesis of Intermediate Compound D-4

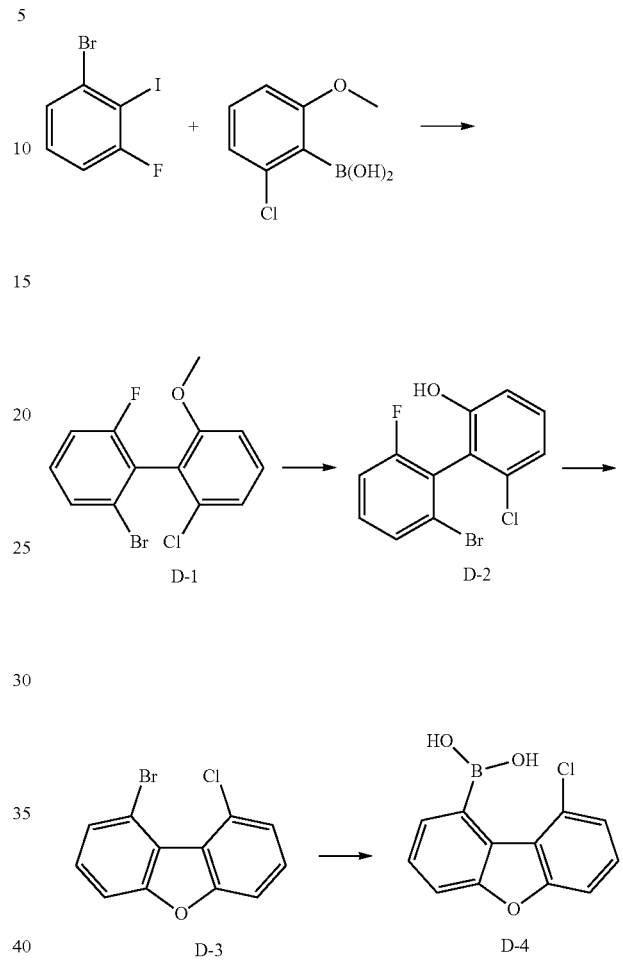

D-1

D-2

D-3

D-4

1) Preparation of Compound C-1

Compound C-1 (60.1 g, yield 76%; MS:[M+H]$^+$=314) was prepared in the same manner as in the preparation of Compound A-1 of Preparation Example 1, except that (4-chloro-2-methoxyphenyl)boronic acid (51.1 g, 249.3 mmol) was used instead of (5-chloro-2-methoxyphenyl) boronic acid.

2) Preparation of Compound C-2

Compound C-2 (54.0 g, yield 94%; MS:[M+H]$^+$=300) was prepared in the same manner as in the preparation of Compound A-2, except that Compound C-1 (60.1 g, 190.4 mmol) was used instead of Compound A-1.

3) Preparation of Compound C-3

Compound C-3 (42.2 g, yield 83%; MS: [M+H]$^+$=280) was prepared in the same manner as in the preparation of Compound A-3, except that Compound C-2 (54.0 g, 179.1 mmol) was used instead of Compound A-2.

4) Preparation of Compound C-4

Compound C-4 (34.1 g, yield 92%; MS:[M+H]$^+$=247) was prepared in the same manner as in the preparation of Compound A-4, except that Compound C-3 (42.2 g, 170.9 mmol) was used instead of Compound A-3.

1) Preparation of Compound D-1

Compound D-1 (63.5 g, yield 81%; MS:[M+H]$^+$=314) was prepared in the same manner as in the preparation of Compound A-1 of Preparation Example 1, except that (2-chloro-6-methoxyphenyl)boronic acid (51.1 g, 249.3 mmol) was used instead of (5-chloro-2-methoxyphenyl) boronic acid.

2) Preparation of Compound D-2

Compound D-2 (55.1 g, yield 91%; MS:[M+H]$^+$=300) was prepared in the same manner as in the preparation of Compound A-2, except that Compound D-1 (63.5 g, 201.2 mmol) was used instead of Compound A-1.

3) Preparation of Compound D-3

Compound D-3 (42.0 g, yield 82%; MS:[M+H]$^+$=280) was prepared in the same manner as in the preparation of Compound A-3, except that Compound D-2 (55.1 g, 182.7 mmol) was used instead of Compound A-2.

4) Preparation of Compound D-4

Compound D-4 (35.7 g, yield 85%; MS:[M+H]$^+$=247) was prepared in the same manner as in the preparation of Compound A-4, except that Compound D-3 (42.0 g, 149.2 mmol) was used instead of Compound A-3.

Preparation Example 2

Preparation Example 2-1: Synthesis of Intermediate Compound A-6

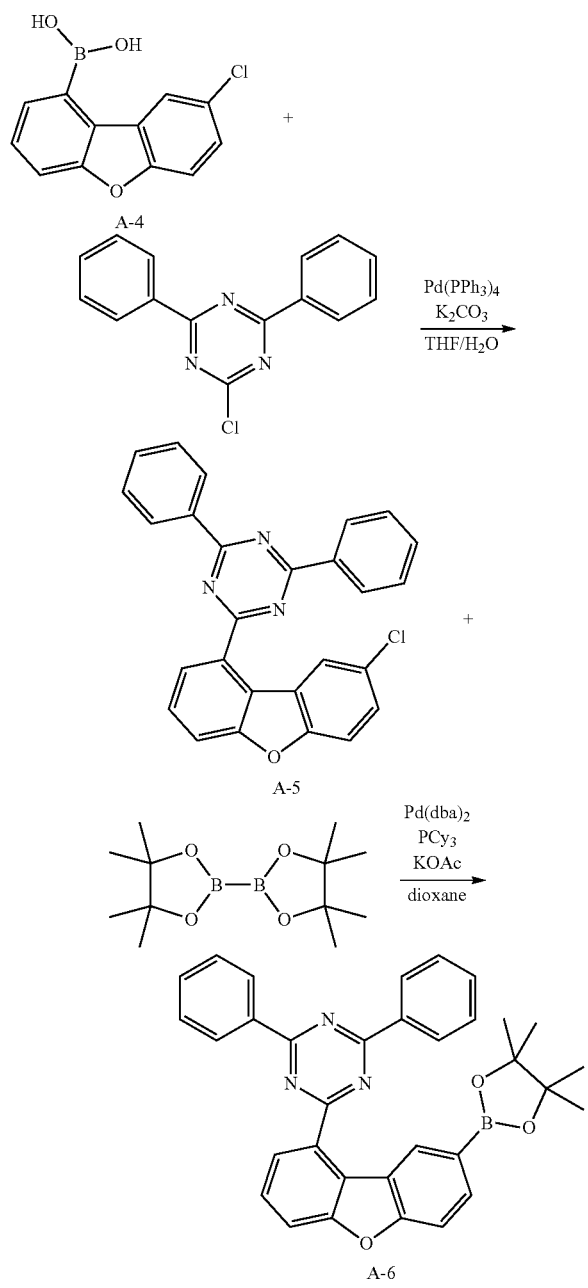

1) Preparation of Compound A-5

Compound A-4 (20.0 g, 61 mmol) and 2-chloro-4,6-diphenyltriazine (16.3 g, 61 mmol) were dissolved in 200 mL of tetrahydrofuran in a 500 mL round bottom flask under a nitrogen atmosphere. Then, 1.5 M or a potassium carbonate aqueous solution (100 mL) and tetrakis(triphenylphosphine)palladium (0.93 g, 1.8 mmol) were added thereto, and then stirred while heating for 7 hours. The temperature of the mixture was lowered to room temperature, the aqueous layer was separated and removed dried over anhydrous magnesium sulfate, and concentrated under reduced pressure. The resulting material was recrystallized using a mixed solution of tetrahydrofuran and ethyl acetate and dried to produce Compound A-5 (20.5 g, yield 78%, MS: $[M+H]^+=434$).

2) Preparation of Compound A-6

Under nitrogen atmosphere, Compound A-5 (20.5 g, 47 mmol), bis(pinacolato)diboron (13.2 g, 52 mmol) and potassium acetate (16.2 g, 165 mmol) were mixed and added to 250 ml of dioxane and heated with stirring. Bis(dibenzylideneacetone)palladium (0.81 g, 1 mmol) and tricyclohexylphosphine (0.8 g, 2 mmol) were added thereto under reflux and stirred while heating for 13 hours. After the reaction was completed, the reaction solution was cooled to room temperature and then filtered. The filtrate was poured into water, extracted with chloroform, and the organic layer was dried over anhydrous magnesium sulfate. The resulting material was distilled under reduced pressure and recrystallized with ethyl acetate to produce Compound A-6 (20.7 g, 83%).

Preparation Example 2-2: Synthesis of Intermediate Compound A-8

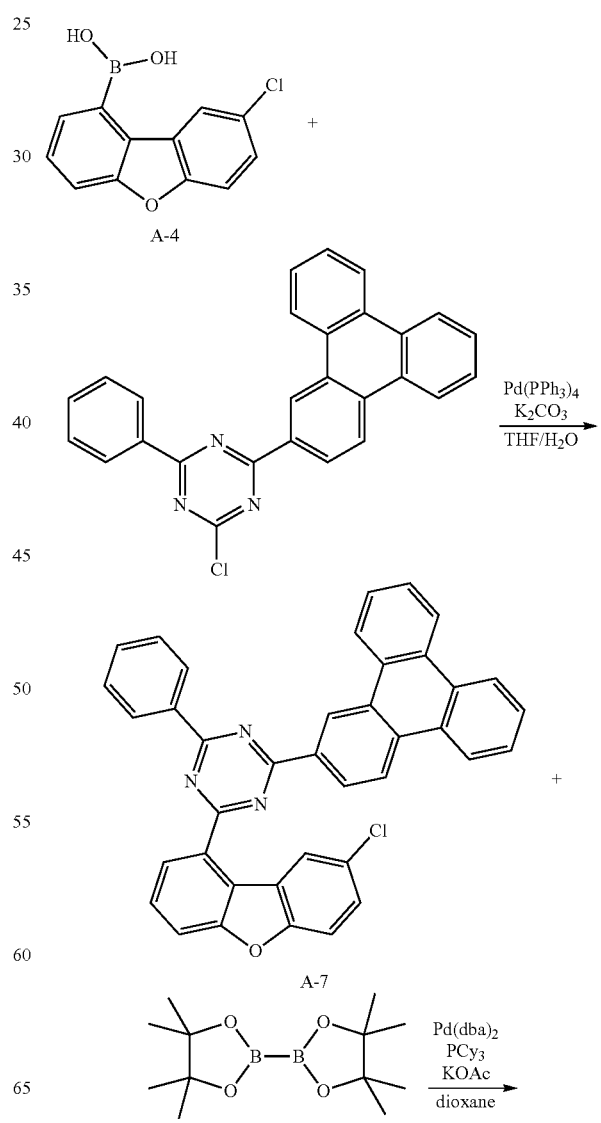

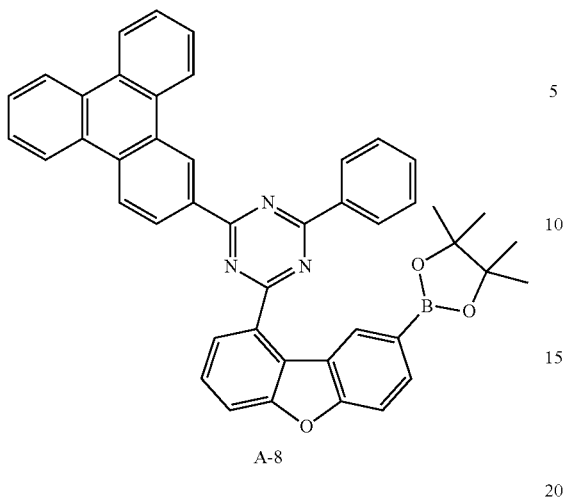

A-8

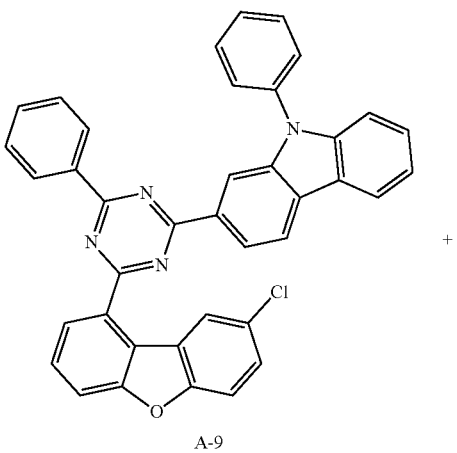

A-9

1) Preparation of Compound A-7

Compound A-7 (17.3 g, yield 86%, MS: [M+H]$^+$=584) was prepared in the same manner as in the preparation of Compound A-5, except that 2-chloro-4-phenyl-6-(triphenylene-2)-1,3,5-triazine was used instead of 2-chloro-4,6-diphenyltriazine.

2) Preparation of Compound A-8

Compound A-8 (16.9 g, yield 84%, MS: [M+H]$^+$=676) was prepared in the same manner as in the preparation of Compound A-6, except that Compound A-7 was used instead of Compound A-5.

Preparation Example 2-3: Synthesis of Intermediate Compound A-10

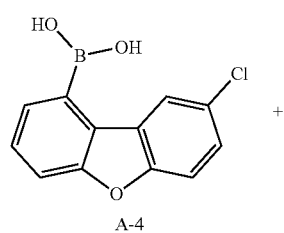

A-4

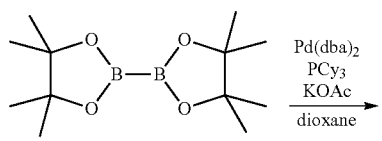

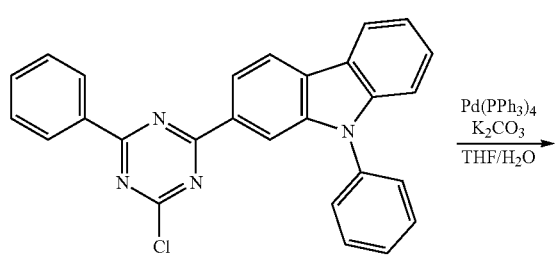

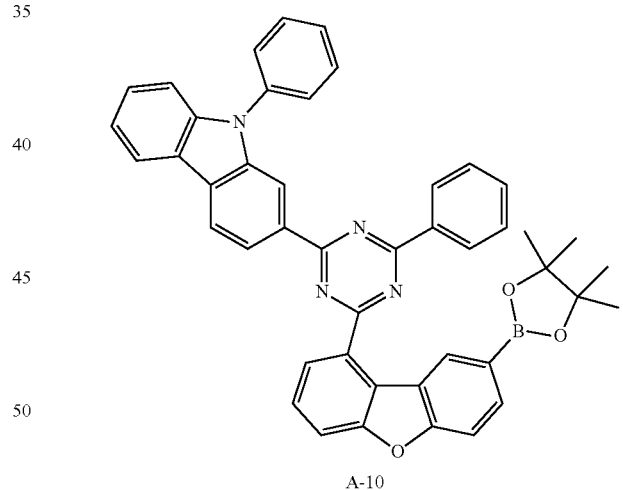

A-10

1) Preparation of Compound A-9

Compound A-9 (15.1 g, yield 82%, MS: [M+H]$^+$=599) was prepared in the same manner as in the preparation of Compound A-5, except that 2-(4-chloro-6-phenyl-1,3,5-triazine 2-yl)9-phenyl-9H-carbazole was used instead of 2-chloro-4,6-diphenyltriazine.

2) Preparation of Compound A-10

Compound A-10 (14.5 g, yield 83%, MS:[M+H]$^+$=691) was prepared in the same manner as in the preparation of Compound A-6, except that Compound A-9 was used instead of Compound A-5.

Preparation Example 2-4: Synthesis of Intermediate Compound A-12

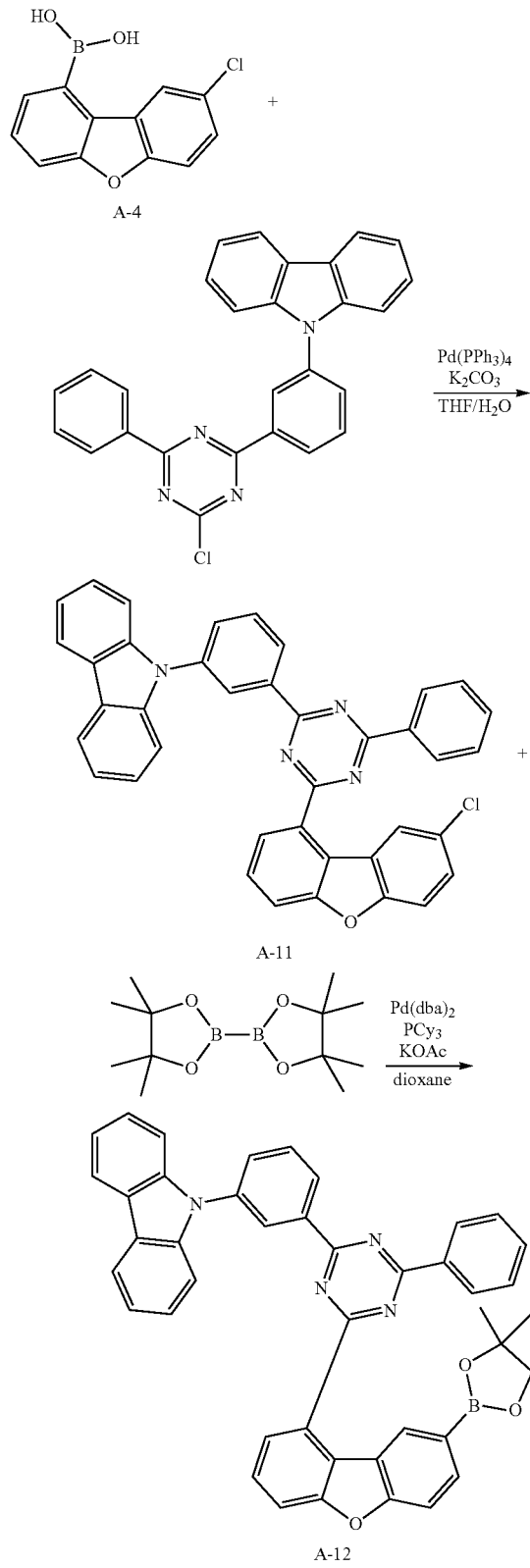

1) Preparation of Compound A-11

Compound A-11 (18.4 g, yield 82%, MS: [M+H]⁺=599) was prepared in the same manner as in the preparation of Compound A-5, except that 9-(3-(4-chloro-6-phenyl-1,3,5-triazin-2-yl)phenyl)9H-carbazole was used instead of 2-chloro-4,6-diphenyltriazine.

2) Preparation of Compound A-12

Compound A-12 (17.7 g, yield 83%, MS: [M+H]⁺=691) was prepared in the same manner as in the preparation of Compound A-6, except that Compound A-11 was used instead of Compound A-5.

Preparation Example 2-5: Synthesis of Intermediate Compound A-14

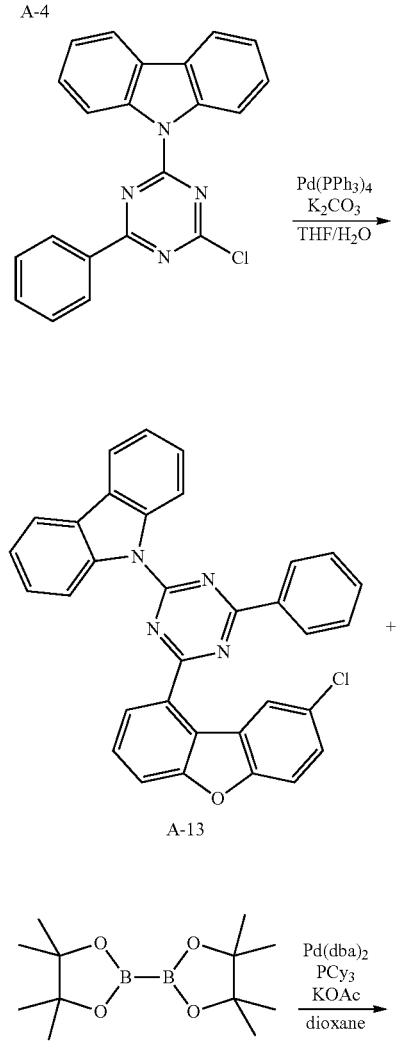

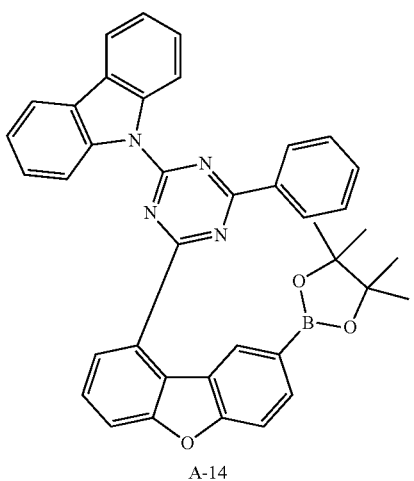

A-14

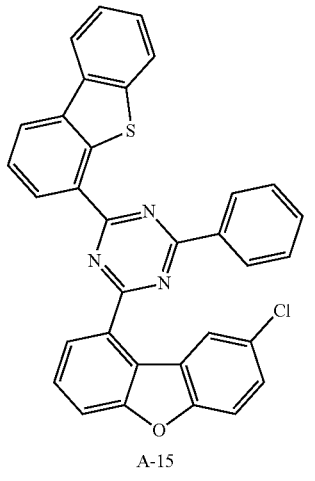

A-15

1) Preparation of Compound A-13

Compound A-13 (16.8 g, yield 82%, MS: [M+H]⁺=523) was prepared in the same manner as in the preparation of Compound A-5, except that 9-(4-chloro-6-phenyl-1,3,5-triazin-2-yl)-9H-carbazole was used instead of 2-chloro-4,6-diphenyltriazine.

2) Preparation of Compound A-14

Compound A-14 (16.3 g, yield 82%, MS: [M+H]⁺=615) was prepared in the same manner as in the preparation of Compound A-6, except that Compound A-13 was used instead of Compound A-5.

Preparation Example 2-6: Synthesis of Intermediate Compound A-16

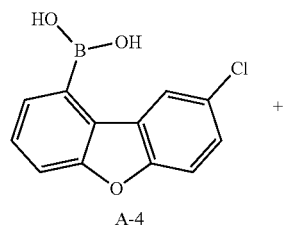

A-4

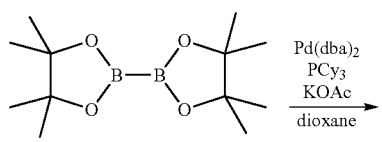

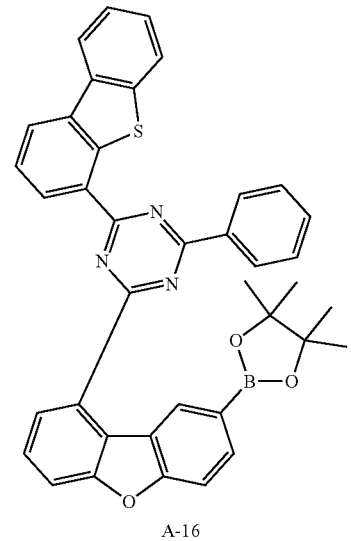

A-16

1) Preparation of Compound A-15

Compound A-15 (16.0 g, yield 85%, MS: [M+H]⁺=540) was prepared in the same manner as in the preparation of Compound A-5, except that 2-chloro-4-(dibenzothiophen-4-yl)-6-phenyl-1,3,5-triazine was used instead of 2-chloro-4,6-diphenyltriazine.

2) Preparation of Compound A-16

Compound A-16 (15.6 g, yield 86%, MS:[M+H]⁺=632 was prepared in the same manner as in the preparation of Compound A-6, except that Compound A-15 was used instead of Compound A-5.

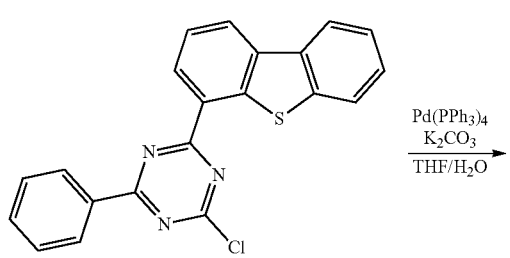

Preparation Example 2-7: Synthesis of Intermediate Compound A-18

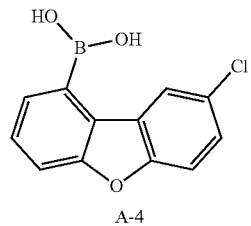

A-4

+

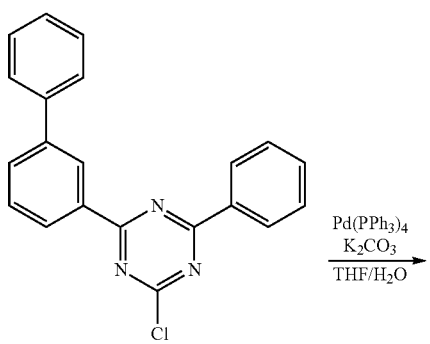

Pd(PPh₃)₄
K₂CO₃
THF/H₂O

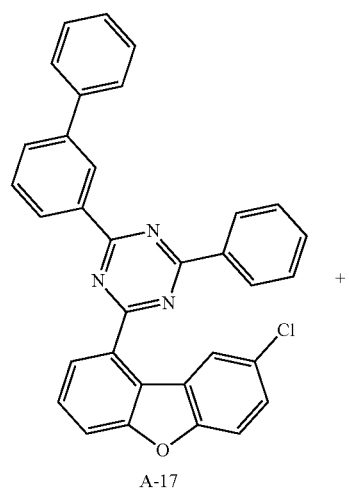

A-17

Pd(dba)₂
PCy₃
KOAc
dioxane

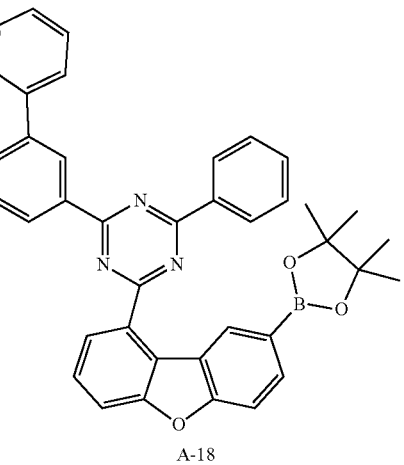

A-18

1) Preparation of Compound A-17

Compound A-17 (14.2 g, yield 77%, MS: [M+H]⁺=510) was prepared in the same manner as in the preparation of Compound A-5, except that 2-([1,1'-biphenyl]-3-yl)-4-chloro-6-phenyl-1,3,5-triazine was used instead of 2-chloro-4,6-diphenyltriazine.

2) Preparation of Compound A-18

Compound A-18 (13.9 g, yield 83%, MS: [M+H]⁺=602) was prepared in the same manner as in the preparation of Compound A-6, except that Compound A-17 was used instead of Compound A-5.

Preparation Example 3-1: Synthesis of Intermediate Compound B-7

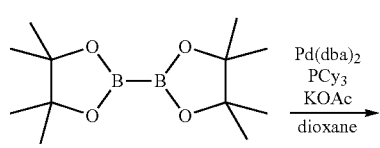

B-5

+

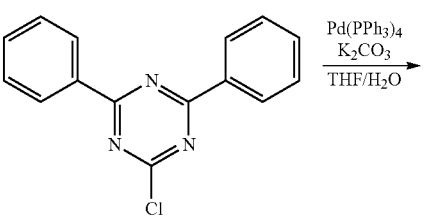

Pd(PPh₃)₄
K₂CO₃
THF/H₂O

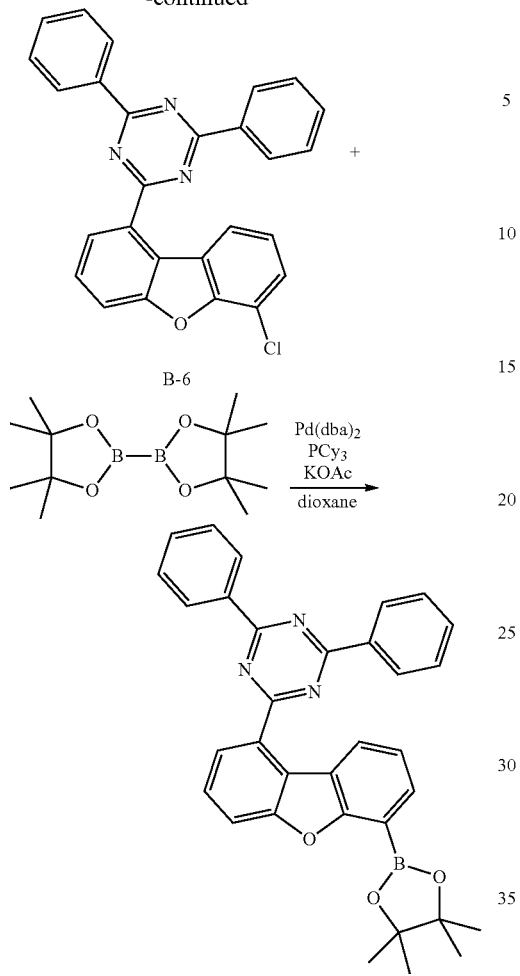

B-6

B-7

1) Preparation of Compound B-6

Compound B-6 (14.2 g, yield 82%, MS: [M+H]⁺=434) was prepared in the same manner as in the preparation of Compound A-5, except that Compound B-5 was used instead of Compound A-4.

2) Preparation of Compound B-7

Compound B-7 (15.0 g, yield 82%, MS: [M+H]⁺=526) was prepared in the same manner as in the preparation of Compound A-6, except that Compound B-6 was used instead of Compound A-5.

Preparation Example 3-2: Synthesis of Intermediate Compound B-9

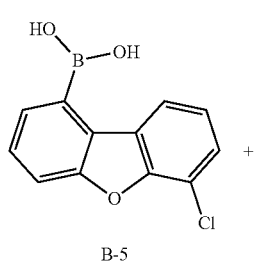

B-5

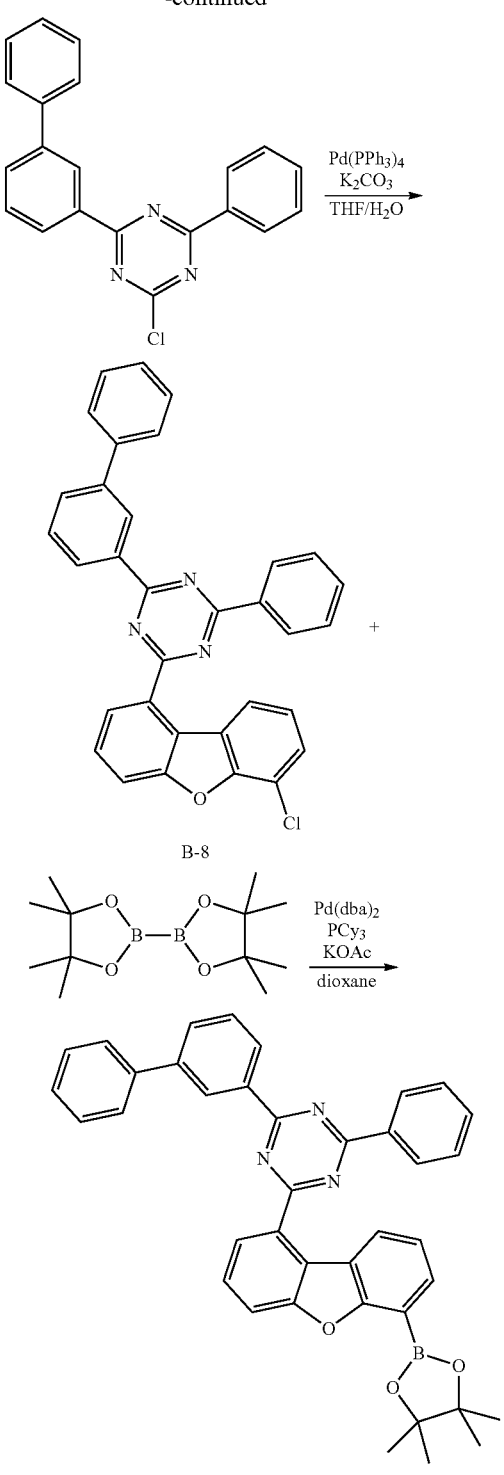

B-8

B-9

1) Preparation of Compound B-8

Compound B-8 (17.5 g, yield 80%, MS: [M+H]⁺=510) was prepared in the same manner as in the preparation of Compound A-5, except that Compound B-5 and 2-([1,1'-biphenyl]-3-yl)-4-chloro-6-phenyl-1,3,5-triazine were used instead of Compound A-4 and 2-chloro-4,6-diphenyltriazine.

2) Preparation of Compound B-9

Compound B-9 (16.2 g, yield 78%, MS:[M+H]⁺=602 was prepared in the same manner as in the preparation of Compound A-6, except that Compound B-8 was used instead of Compound A-5.

Preparation Example 3-3: Synthesis of Intermediate Compound B-11

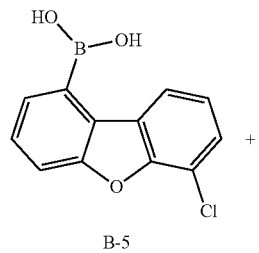

B-5

+

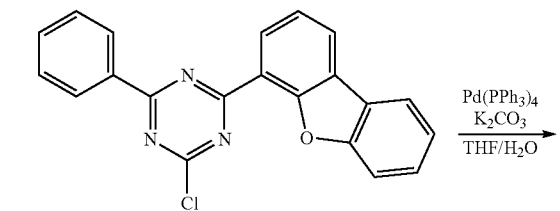

B-10

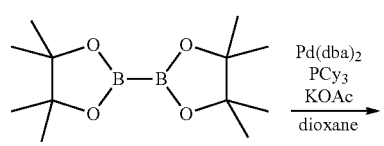

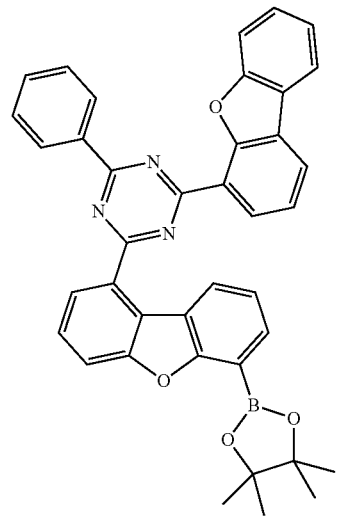

B-11

1) Preparation of Compound B-10

Compound B-10 (15.0 g, yield 79%, MS: [M+H]⁺=524) was prepared in the same manner as in the preparation of Compound A-5, except that B-5 and 2-chloro-4-(dibenzofuran-4-yl)-6-phenyl-1,3,5-triazine were used instead of Compound A-4 and 2-chloro-4,6-diphenyltriazine.

2) Preparation of Compound B-11

Compound B-11 (14.1 g, yield 80%, MS: [M+H]⁺=616) was prepared in the same manner as in the preparation of Compound A-6, except that Compound B-10 was used instead of Compound A-5.

Preparation Example 3-4: Synthesis of Intermediate Compound B-13

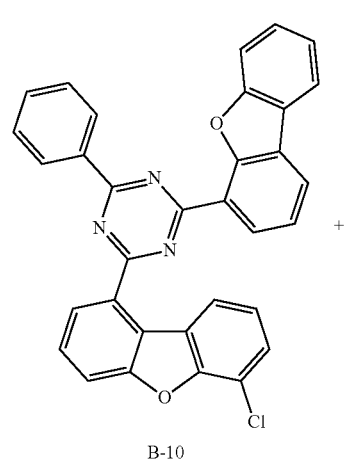

B-5

+

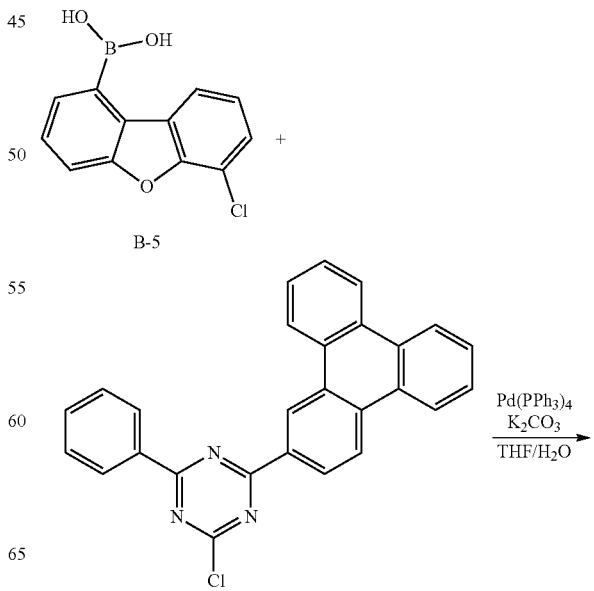

-continued

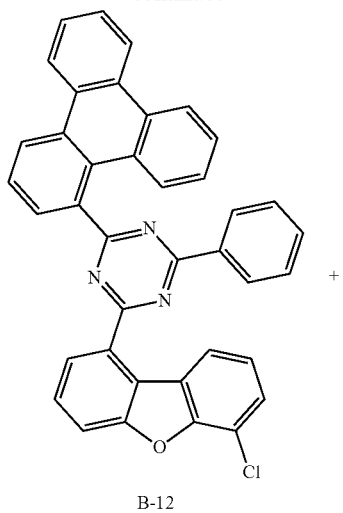

B-12

+

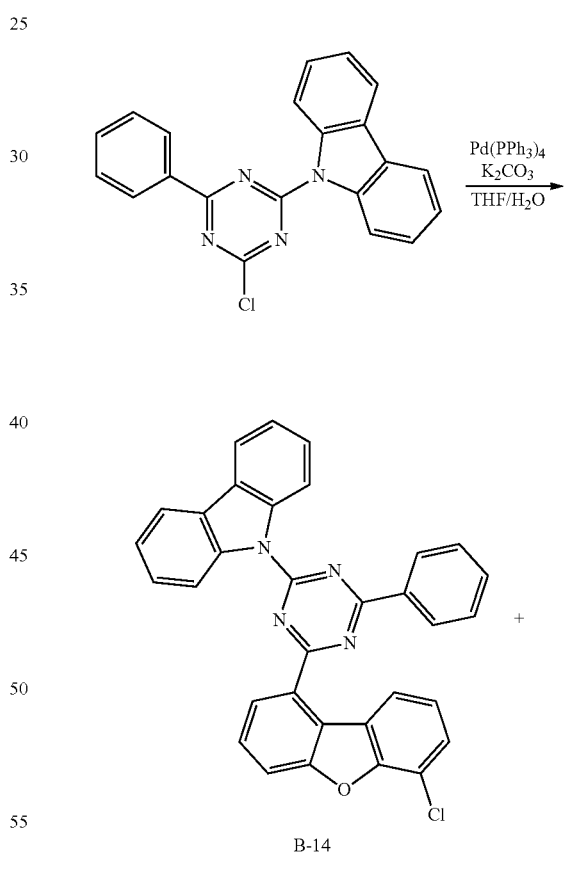

2) Preparation of Compound B-13

Compound B-13 (20.1 g, yield 89%, MS:[M+H]⁺=676 was prepared in the same manner as in the preparation of Compound A-6, except that Compound B-12 was used instead of Compound A-5.

Preparation Example 3-5: Synthesis of Intermediate Compound B-15

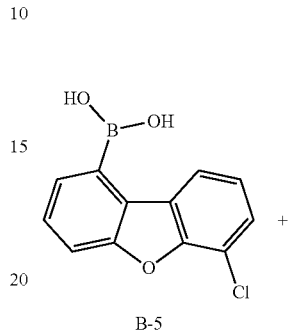

B-5

+

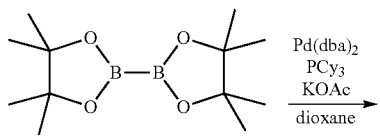

1) Preparation of Compound B-12

Compound B-12 (19.5 g, yield 86%, MS: [M+H]⁺=584) was prepared in the same manner as in the preparation of Compound A-5, except that Compound B-5 and 2-chloro-4-phenyl-6-(triphenylene-2)-1,3,5-triazine were used instead of Compound A-4 and 2-chloro-4,6-diphenyltriazine.

417

-continued

B-15

1) Preparation of Compound B-14

Compound B-14 (14.4 g, yield 76%, MS: [M+H]⁺=523) was prepared in the same manner as in the preparation of Compound A-5, except that Compound B-5 and 9-(4-chloro-6-phenyl-1,3,5-triazin-2-yl)-9H-carbazole were used instead of Compound A-4 and 2-chloro-4,6-diphenyltriazine.

2) Preparation of Compound B-15

Compound B-15 (12.2 g, yield 72%, MS: [M+H]⁺=615) was prepared in the same manner as in the preparation of Compound A-6, except that Compound B-14 was used instead of Compound A-5.

Preparation Example 3-6: Synthesis of Intermediate Compound B-17

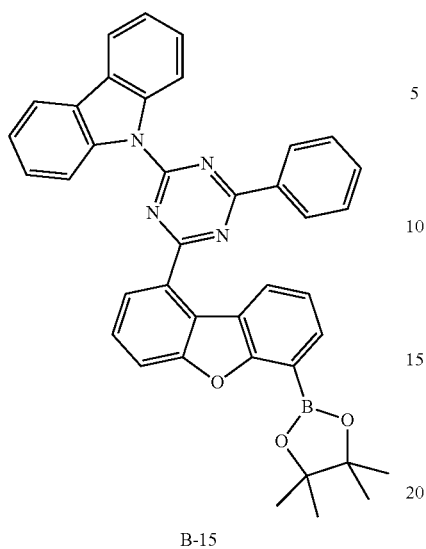

B-5

418

-continued

B-16

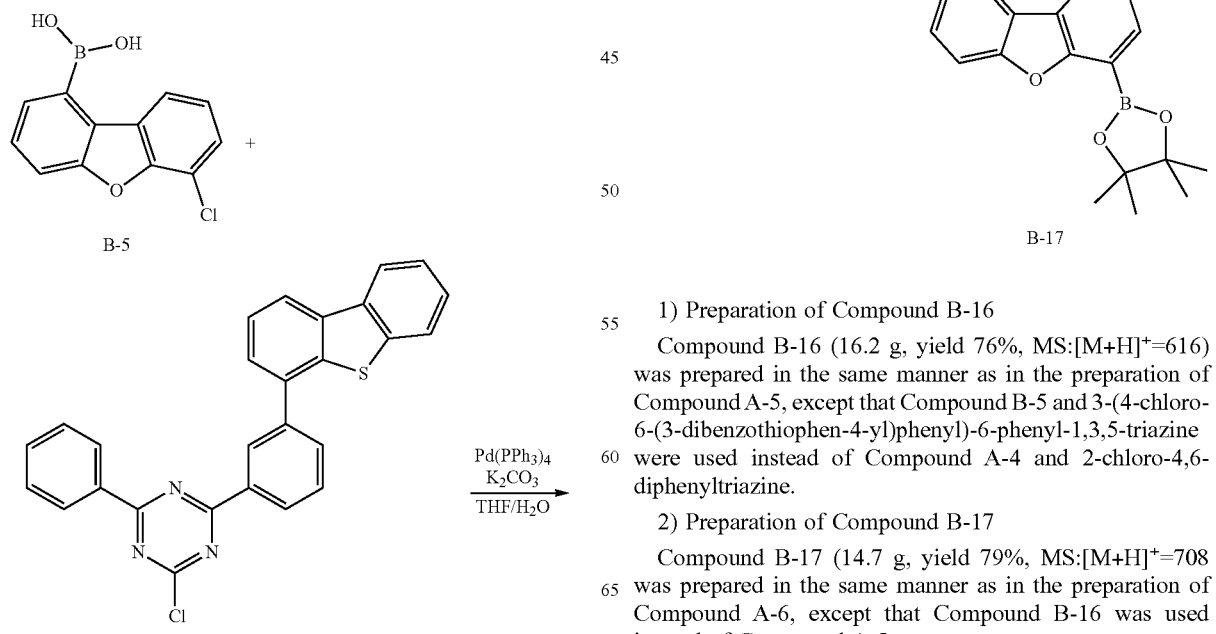

B-17

1) Preparation of Compound B-16

Compound B-16 (16.2 g, yield 76%, MS:[M+H]⁺=616) was prepared in the same manner as in the preparation of Compound A-5, except that Compound B-5 and 3-(4-chloro-6-(3-dibenzothiophen-4-yl)phenyl)-6-phenyl-1,3,5-triazine were used instead of Compound A-4 and 2-chloro-4,6-diphenyltriazine.

2) Preparation of Compound B-17

Compound B-17 (14.7 g, yield 79%, MS:[M+H]⁺=708 was prepared in the same manner as in the preparation of Compound A-6, except that Compound B-16 was used instead of Compound A-5.

Preparation Example 4-1: Synthesis of Intermediate Compound C-6

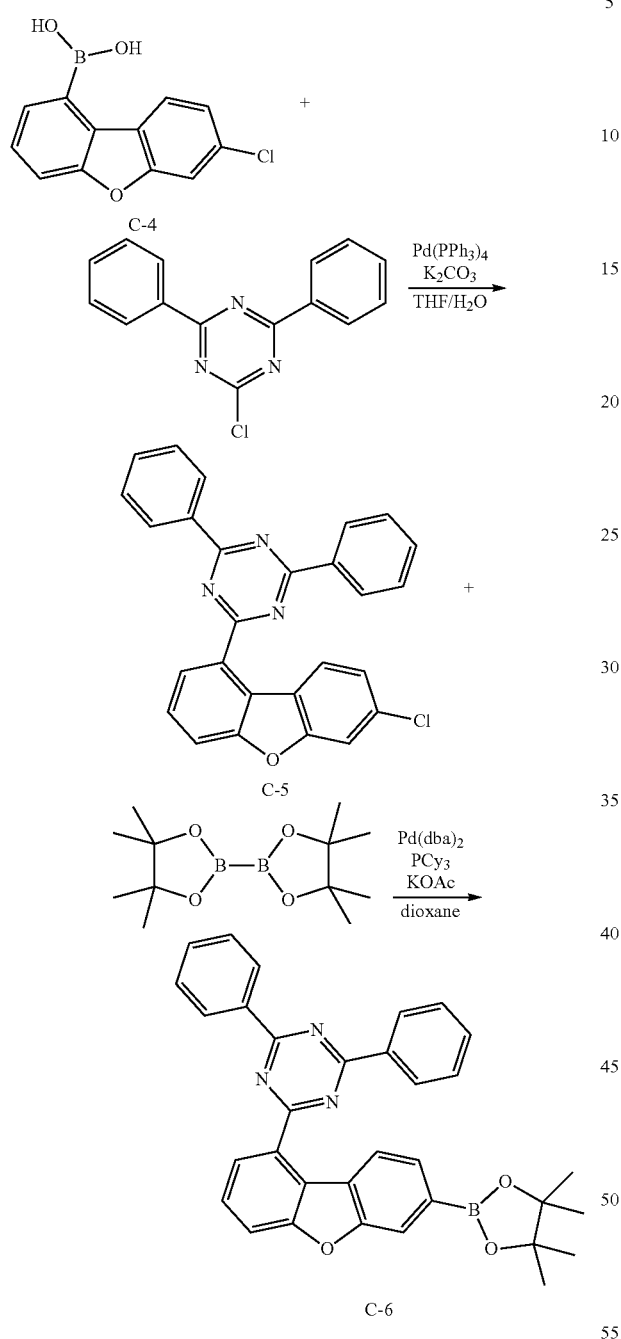

Preparation Example 4-2: Synthesis of Intermediate Compound C-8

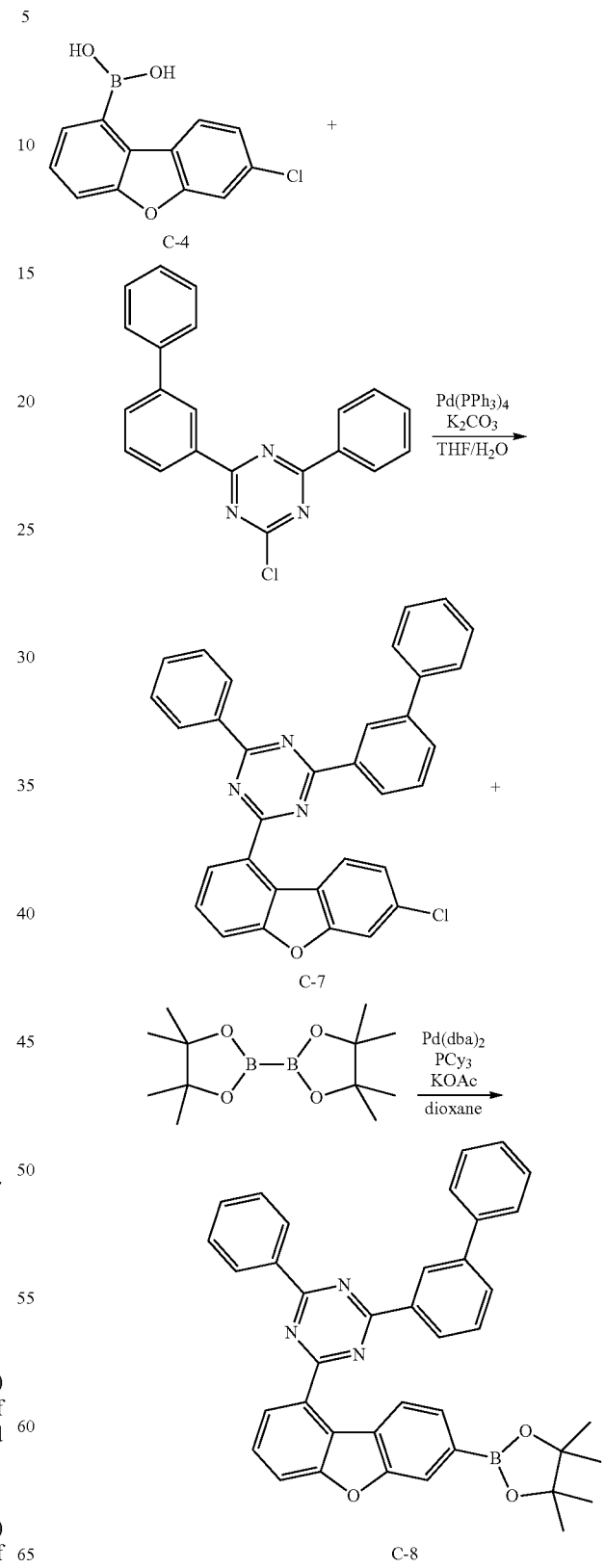

1) Preparation of Compound C-5

Compound C-5 (13.0 g, yield 77%, MS: [M+H]⁺=434) was prepared in the same manner as in the preparation of Compound A-5, except that Compound C-4 was used instead of Compound A-4.

2) Preparation of Compound C-6

Compound C-6 (12.8 g, yield 82%, MS: [M+H]⁺=526) was prepared in the same manner as in the preparation of Compound A-6, except that Compound C-5 was used instead of Compound A-5.

1) Preparation of Compound C-7

Compound C-7 (14.0 g, yield 76%, MS: [M+H]$^+$=510) was prepared in the same manner as in the preparation of Compound A-5, except that Compound C-4 and 2-([1,1'-biphenyl]-3-yl)-4-chloro-6-phenyl-1,3,5-triazine were used instead of Compound A-4 and 2-chloro-4,6-diphenyltriazine.

2) Preparation of Compound C-8

Compound C-8 (12.2 g, yield 74%, MS:[M+H]$^+$=602) was prepared in the same manner as in the preparation of Compound A-6, except that Compound C-7 was used instead of Compound A-5.

Preparation Example 4-3: Synthesis of Intermediate Compound C-10

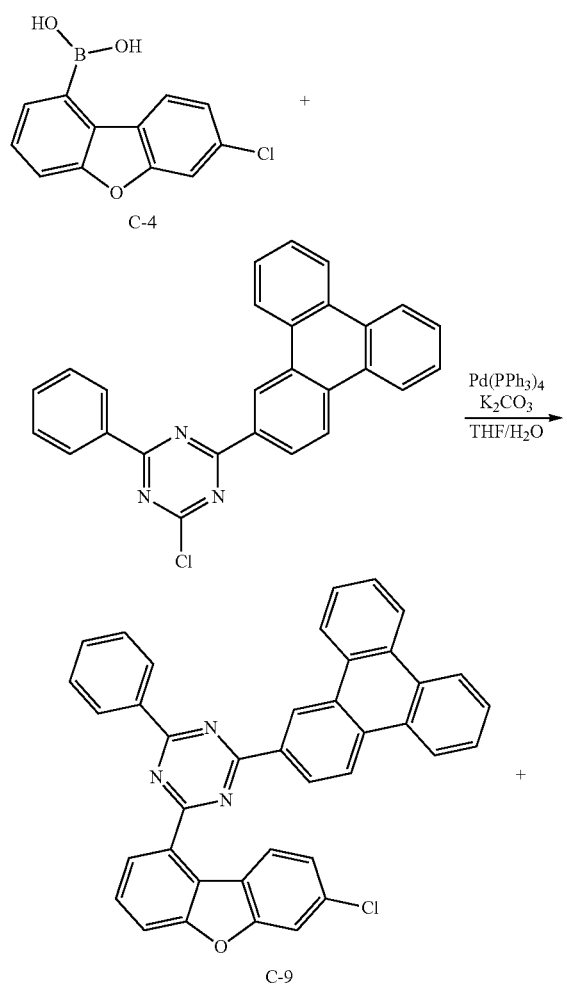

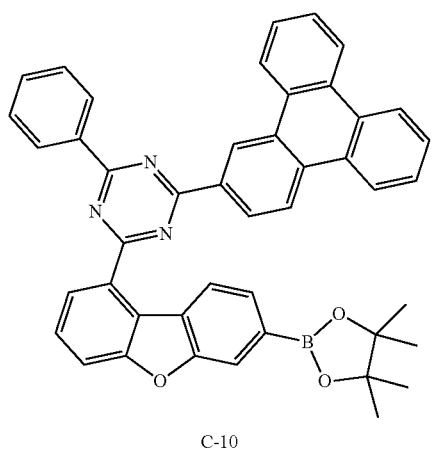

C-10

1) Preparation of Compound C-9

Compound C-9 (16.6 g, yield 82%, MS: [M+H]$^+$=584) was prepared in the same manner as in the preparation of Compound A-5, except that Compound C-4 and 2-chloro-4-phenyl-6-(triphenylene-2)-1,3,5-triazine were used instead of Compound A-4 and 2-chloro-4,6-diphenyltriazine.

2) Preparation of Compound C-10

Compound C-10 (16.5 g, yield 85%, MS: [M+H]$^+$=676) was prepared in the same manner as in the preparation of Compound A-6, except that Compound C-9 was used instead of Compound A-5.

Preparation Example 4-4: Synthesis of Intermediate Compound C-12

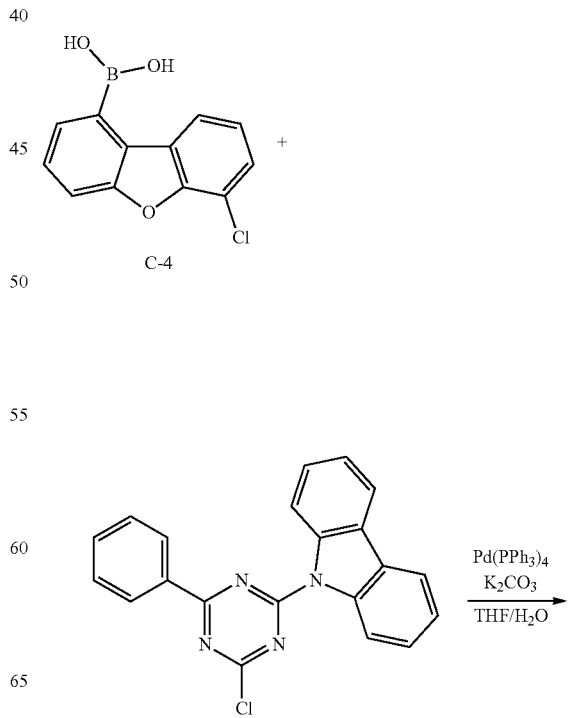

-continued

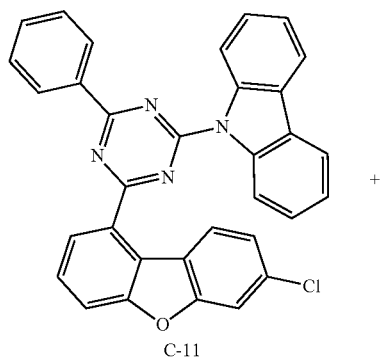
C-11

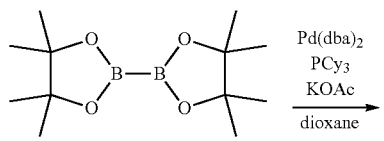

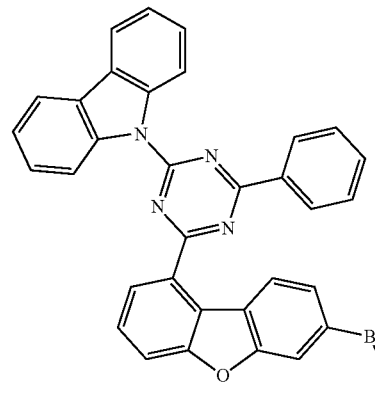
C-12

1) Preparation of Compound C-11

Compound C-11 (11.9 g, yield 76%, MS:[M+H]$^+$=523) was prepared in the same manner as in the preparation of Compound A-5, except that Compound C-4 and 9-(4-chloro-6-phenyl-1,3,5-triazin-2-yl)-9H-carbazole were used instead of Compound A-4 and 2-chloro-4,6-diphenyltriazine.

2) Preparation of Compound C-12

Compound C-12 (10.8 g, yield 77%, MS: [M+H]$^+$=615) was prepared in the same manner as in the preparation of Compound A-6, except that Compound C-11 was used instead of Compound A-5.

Preparation Example 4-5: Synthesis of Intermediate Compound C-14

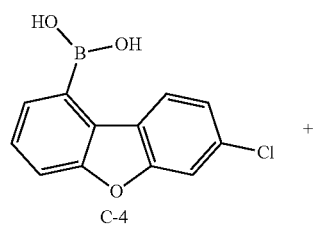
C-4

-continued

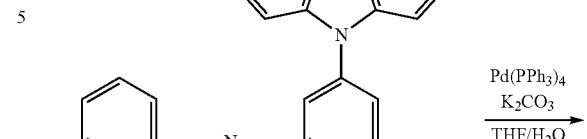

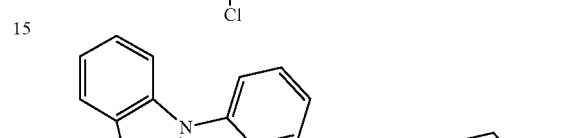
C-13

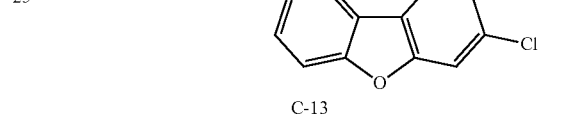

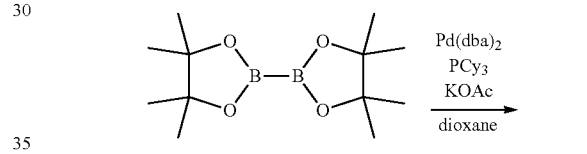

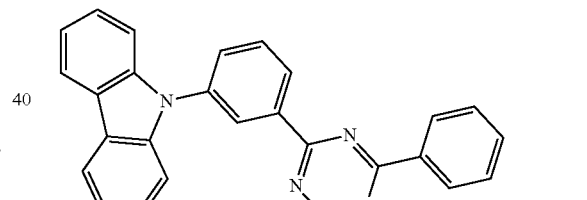

C-14

1) Preparation of Compound C-13

Compound C-13 (13.6 g, yield 77%, MS: [M+H]$^+$=599) was prepared in the same manner as in the preparation of Compound A-5, except that Compound C-4 and 9-(3-(4-chloro-6-phenyl-1,3,5-triazin-2-yl)phenyl)9H-carbazole were used instead of Compound A-4 and 2-chloro-4,6-diphenyltriazine.

2) Preparation of Compound C-14

Compound C-14 (11.8 g, yield 75%, MS:[M+H]$^+$=691 was prepared in the same manner as in the preparation of Compound A-6, except that Compound C-13 was used instead of Compound A-5.

Preparation Example 4-6: Synthesis of Intermediate Compound C-16

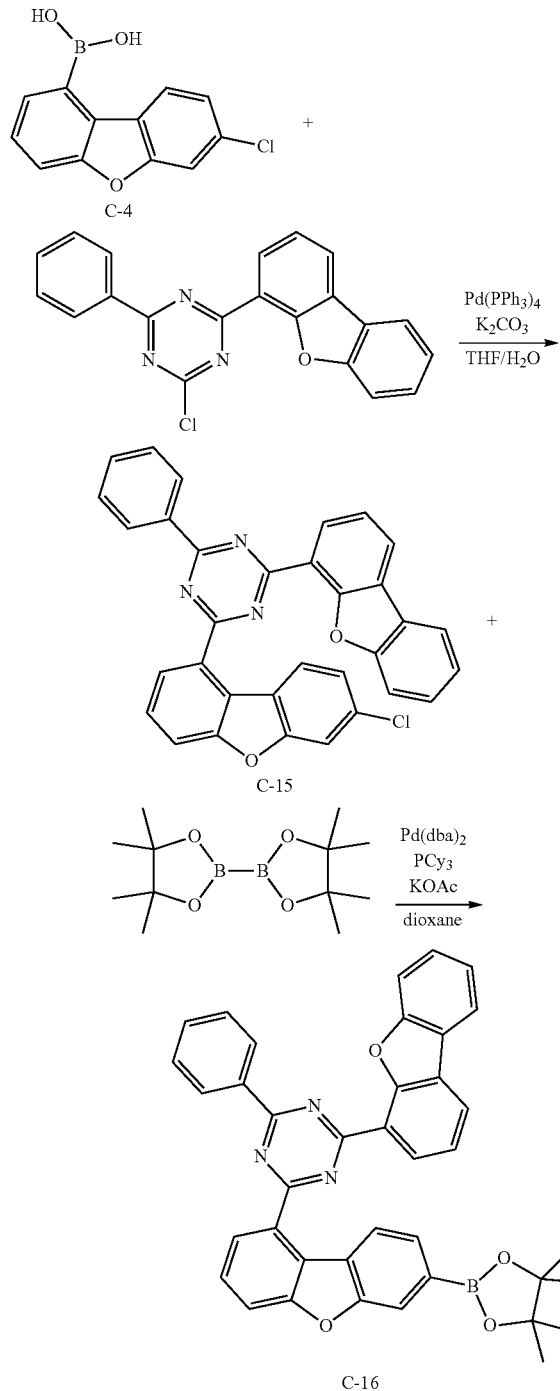

C-16

1) Preparation of Compound C-15

Compound C-15 (12.1 g, yield 74%, MS: [M+H]⁺=524) was prepared in the same manner as in the preparation of Compound A-5, except that Compound C-4 and 2-chloro-4-(dibenzofuran-4-yl)-6-phenyl-1,3,5-triazine were used instead of Compound A-4 and 2-chloro-4,6-diphenyltriazine.

2) Preparation of Compound C-16

Compound C-16 (12.5 g, yield 73%, MS: [M+H]⁺=616) was prepared in the same manner as in the preparation of Compound A-6, except that Compound C-15 was used instead of Compound A-5.

Preparation Example 5-1: Synthesis of Intermediate Compound D-6

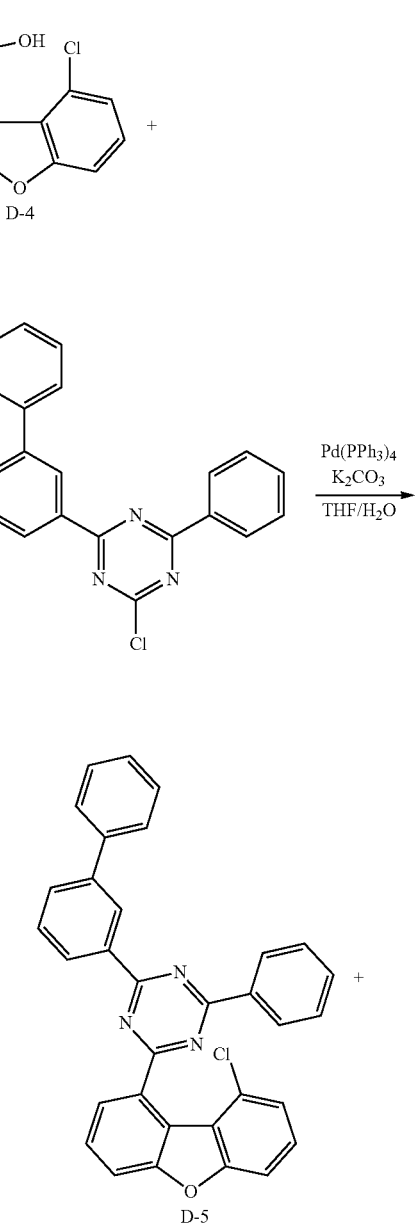

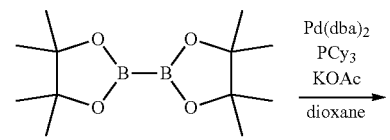

-continued

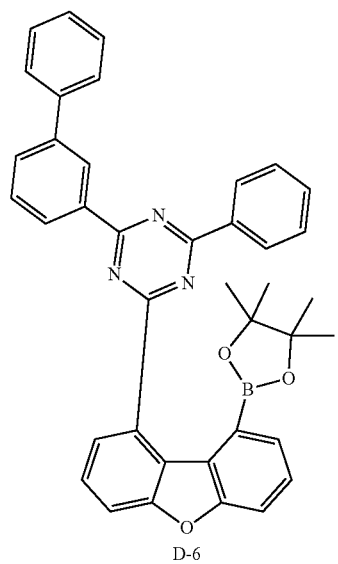

D-6

1) Preparation of Compound D-5

Compound D-5 (10.6 g, yield 76%, MS:[M+H]⁺=510) was prepared in the same manner as in the preparation of Compound A-5, except that Compound D-4 and 2-([1,1'-biphenyl]-3-yl)-4-chloro-6-phenyl-1,3,5-triazine were used instead of Compound A-4 and 2-chloro-4,6-diphenyltriazine.

2) Preparation of Compound D-6

Compound D-6 (10.0 g, yield 80%, MS: [M+H]⁺=602) was prepared in the same manner as in the preparation of Compound A-6, except that Compound D-5 was used instead of Compound A-5.

Preparation Example 5-2: Synthesis of Intermediate Compound D-8

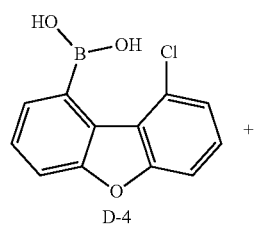

D-4

+

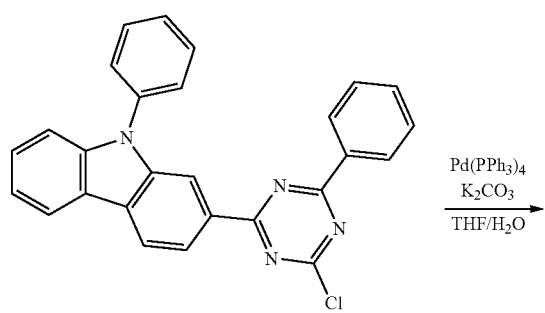

-continued

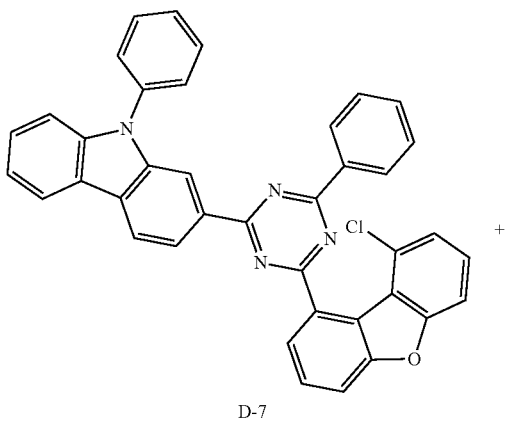

D-7

+

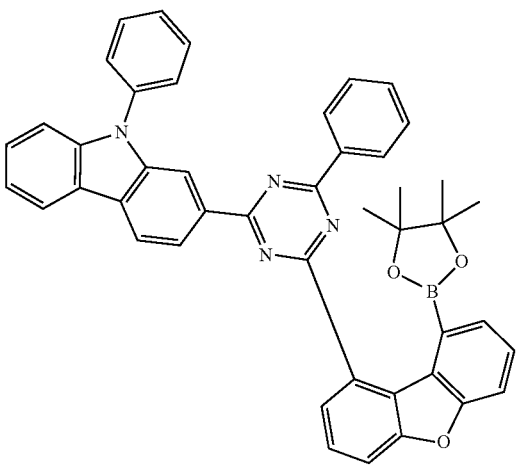

D-8

1) Preparation of Compound D-7

Compound D-7 (12.7 g, yield 77%, MS:[M+H]⁺=599 was prepared in the same manner as in the preparation of Compound A-5, except that Compound D-4 and 2-(4-chloro-6-phenyl-1,3,5-triazin-2-yl)9-phenyl-9H-carbazole were used instead of Compound A-4 and 2-chloro-4,6-diphenyltriazine.

2) Preparation of Compound D-8

Compound D-8 (11.3 g, yield 77%, MS:[M+H]⁺=691) was prepared in the same manner as in the preparation of Compound A-6, except that Compound D-7 was used instead of Compound A-5.

EXAMPLES

Example 1: Preparation of Compound 1

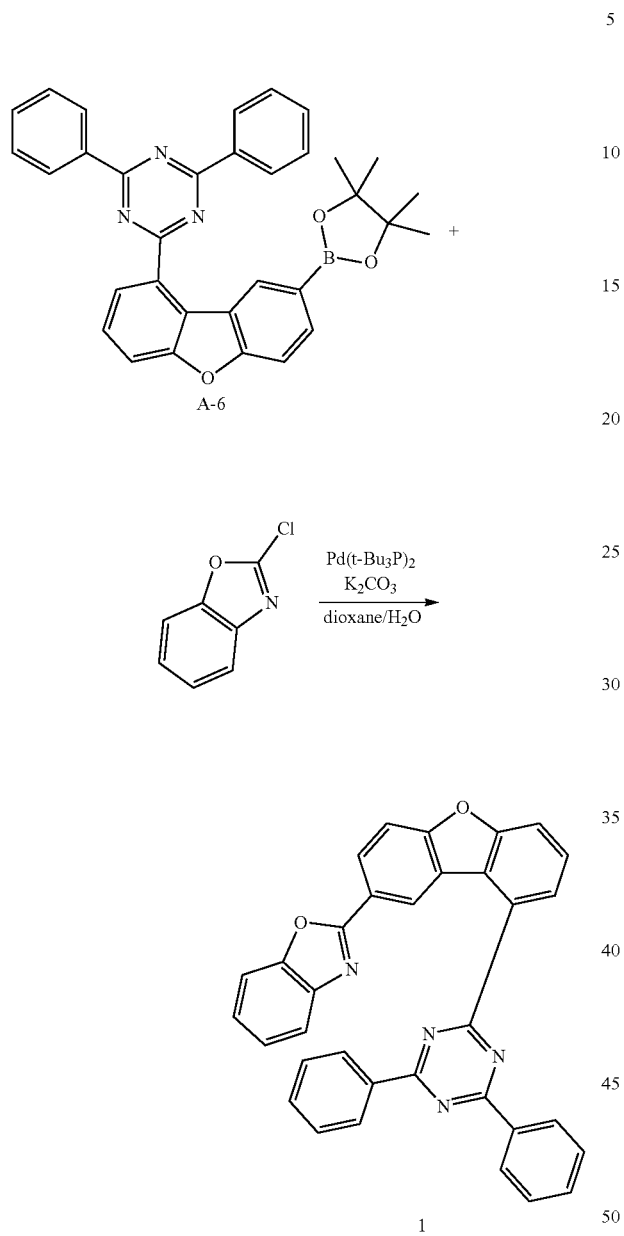

Compound A-6 (10 g, 19 mmol) and 2-chloro-oxazole (3.51 g, 23 mmol) were added to 100 ml of dioxane under a nitrogen atmosphere and stirred and refluxed. Then, potassium carbonate (7.89 g, 57 mmol) was dissolved in 50 ml of water and added thereto. After thoroughly stirring, bis(tri-t-butylphosphine)palladium(0) (0.1 g, 0.2 mmol) was added. After reaction for 20 hours, the temperature of the mixture was lowered to room temperature and filtered. The filtrate was extracted with chloroform and water, and then the organic layer was dried with magnesium sulfate. After that, the organic layer was distilled under reduced pressure and recrystallized using a mixed solution of tetrahydrofuran and ethyl acetate. The resulting solid was filtered and dried to produce Compound 1 (6.6 g, 67%, MS:[M+H]$^+$=517).

Example 2: Preparation of Compound 2

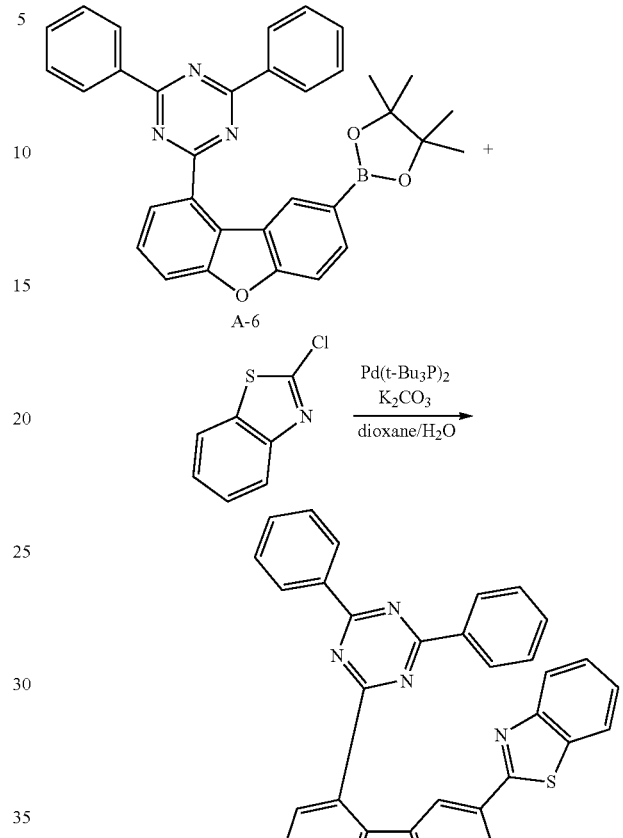

Compound 2 (6.7 g, yield 66%, MS:[M+H]$^+$=533) was prepared in the same manner as in the preparation of Compound 1 of Example 1, except that 2-chloro-thiazole was used instead of 2-chloro-oxazole.

Example 3: Preparation of Compound 3

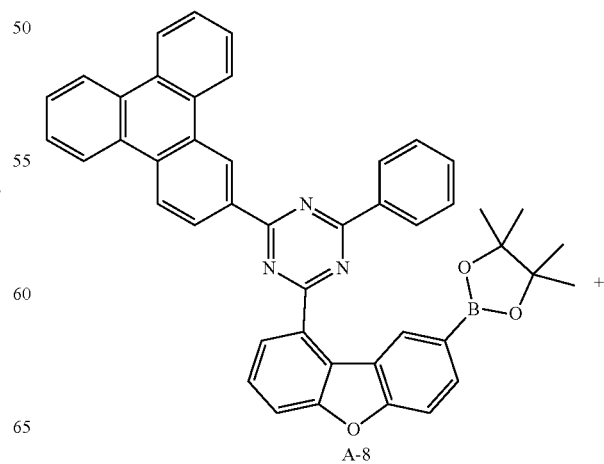

-continued

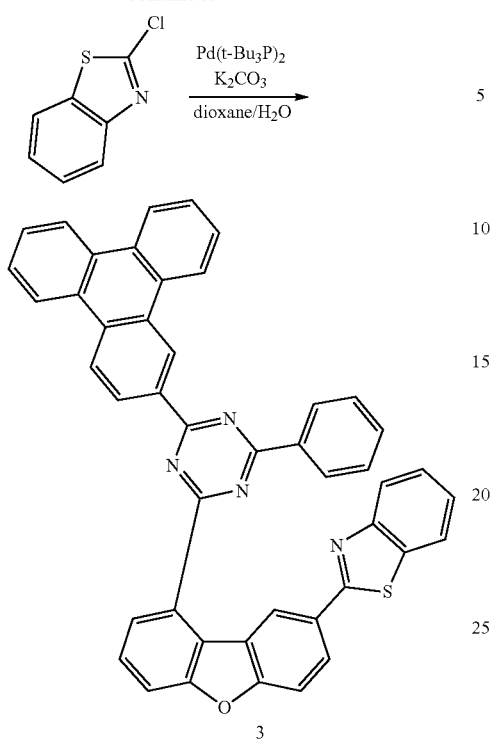

3

Compound 3 (7.3 g, yield 72%, MS: [M+H]⁺=683) was prepared in the same manner as in the preparation of Compound 1 of Example 1, except that Compound A-8 and 2-chloro-thiazole were used instead of Compound A-6 and 2-chloro-oxazole.

Example 4: Preparation of Compound 4

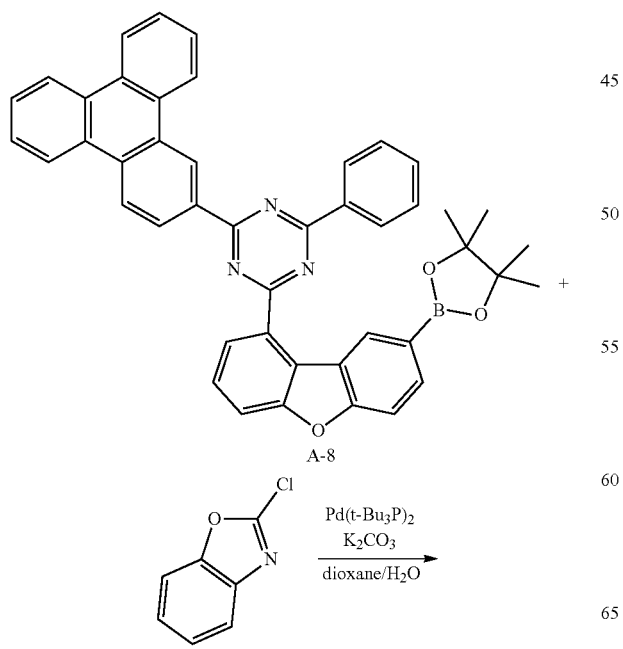

A-8

-continued

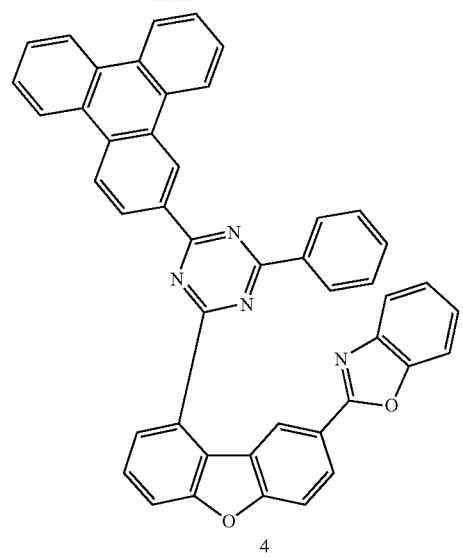

4

Compound 4 (7.4 g, yield 75%, MS:[M+H]⁺=683) was prepared in the same manner as in the preparation of Compound 1 of Example 1, except that Compound A-8 was used instead of Compound A-6.

Example 5: Preparation of Compound 5

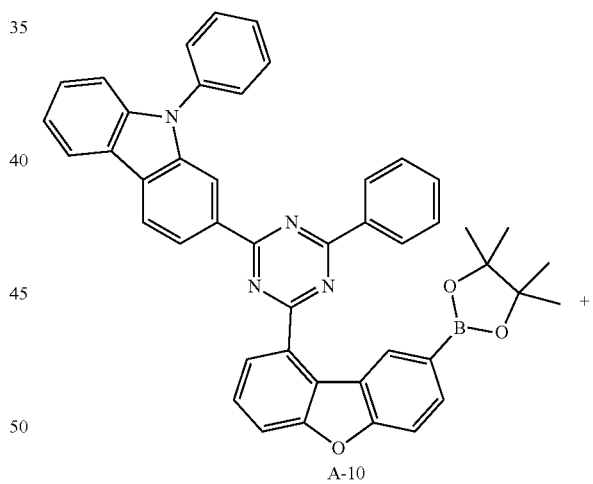

A-10

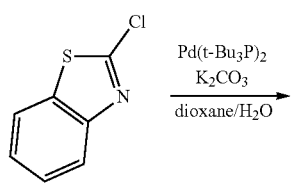

433

-continued

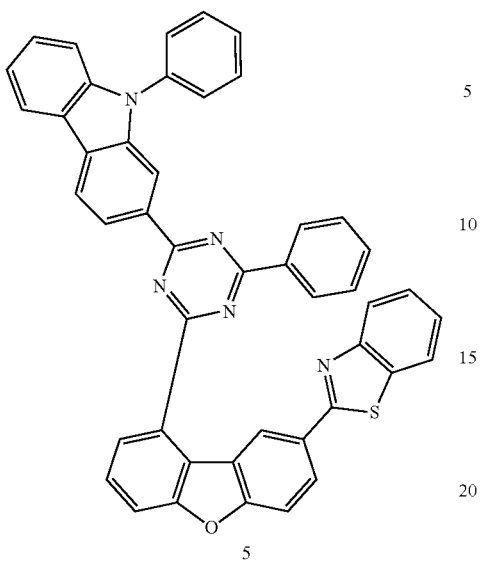

5

Compound 5 (6.5 g, yield 64%, MS:[M+H]⁺=698) was prepared in the same manner as in the preparation of Compound 1 of Example 1, except that Compound A-10 and 2-chloro-thiazole were used instead of Compound A-6 and 2-chloro-oxazole.

Example 6: Preparation of Compound 6

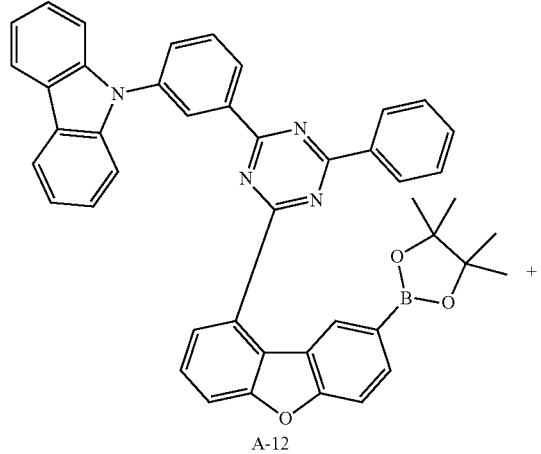

A-12

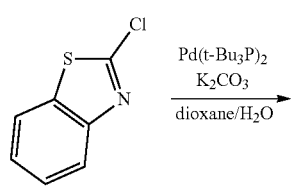

434

-continued

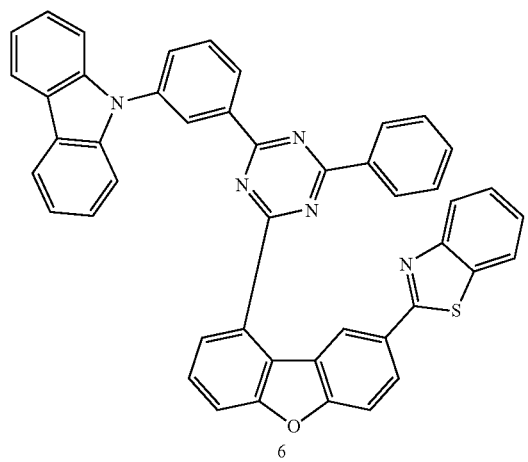

6

Compound 6 (6.1 g, yield 60%, MS: [M+H]⁺=698) was prepared in the same manner as in the preparation of Compound 1 of Example 1, except that Compound A-12 and 2-chloro-thiazole were used instead of Compound A-6 and 2-chloro-oxazole.

Example 7: Preparation of Compound 7

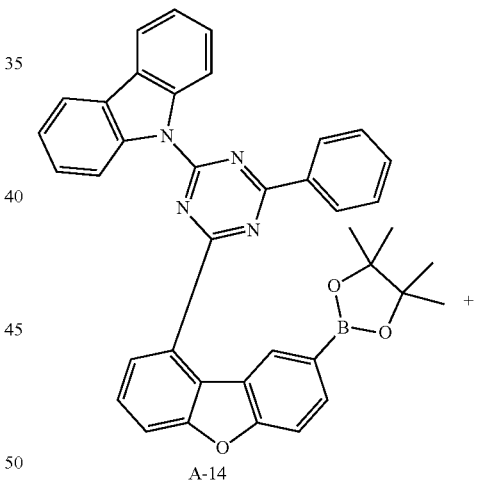

A-14

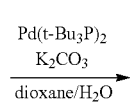

435
-continued

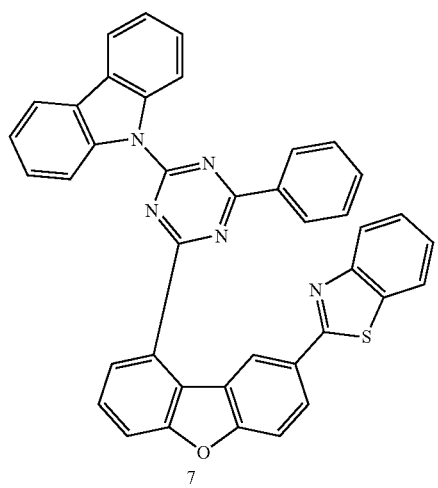

7

436
-continued

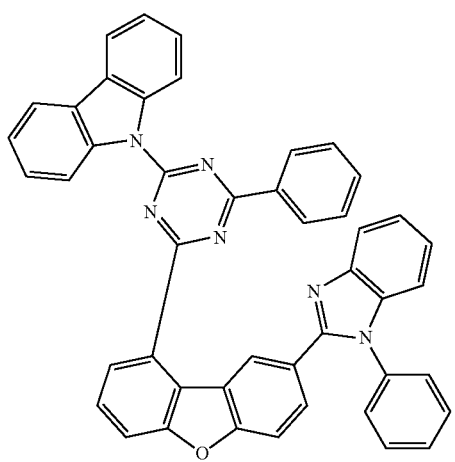

8

Compound 7 (5.9 g, yield 58%, MS: [M+H]⁺=622) was prepared in the same manner as in the preparation of Compound 1 of Example 1, except that Compound A-14 and 2-chloro-thiazole were used instead of Compound A-6 and 2-chloro-oxazole.

Compound 8 (7.0 g, yield 63%, MS: [M+H]⁺=681) was prepared in the same manner as in the preparation of Compound 1 of Example 1, except that Compound A-14 and 2-chloro-1-phenyl-1H-benzoimidazole were used instead of Compound A-6 and 2-chloro-oxazole.

Example 8: Preparation of Compound 8

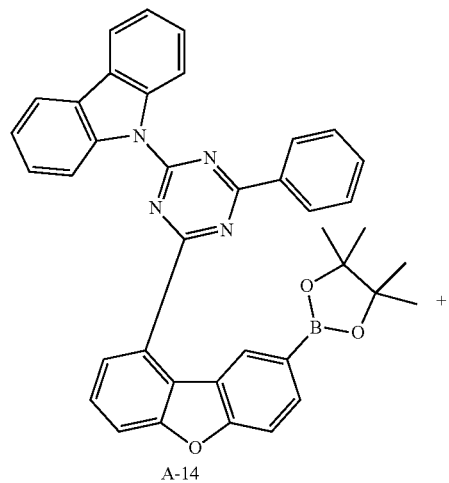

A-14

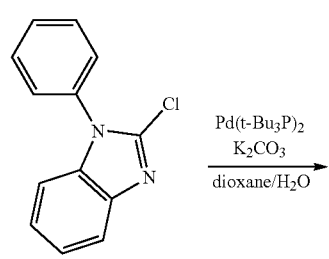

Example 9: Preparation of Compound 9

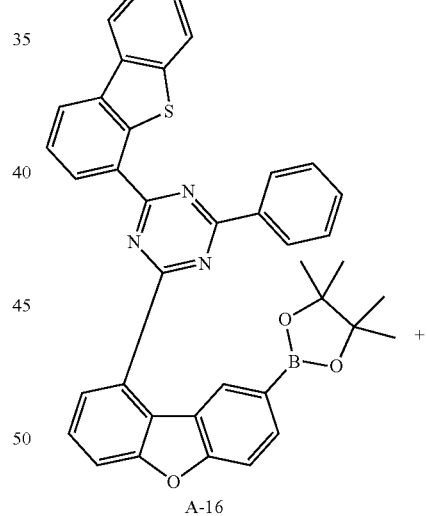

A-16

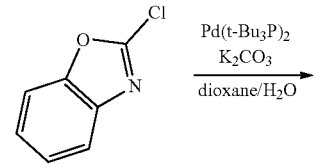

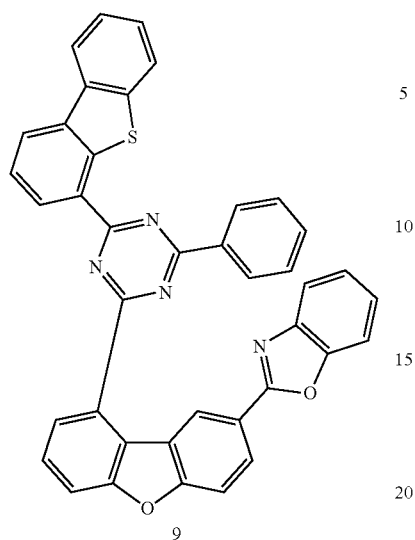

9

Compound 9 (6.7 g, yield 68%, MS: [M+H]$^+$=623) was prepared in the same manner as in the preparation of Compound 1 of Example 1, except that Compound A-16 was used instead of Compound A-6.

Example 10: Preparation of Compound 10

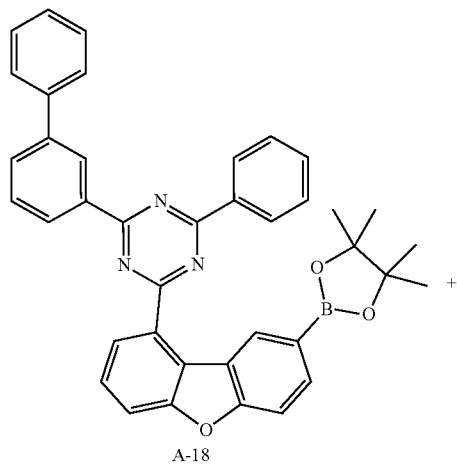

A-18

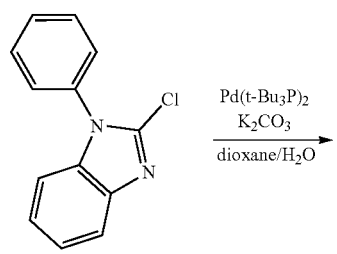

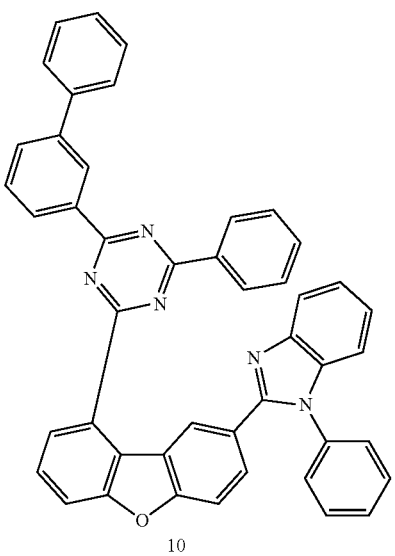

10

Compound 10 (6.8 g, yield 61%, MS: [M+H]$^+$=668) was prepared in the same manner as in the preparation of Compound 1 of Example 1, except that Compound A-18 and 2-chloro-1-phenyl-1H-benzoimidazole were used instead of Compound A-6 and 2-chloro-oxazole.

Example 11: Preparation of Compound 11

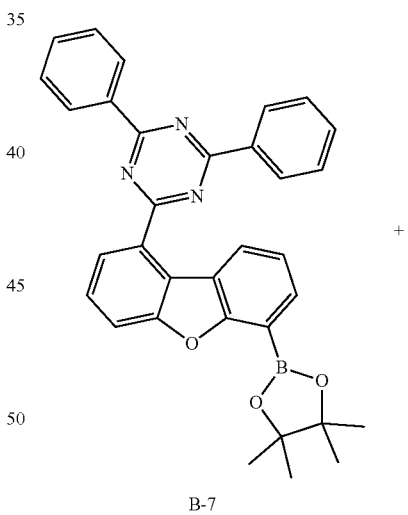

B-7

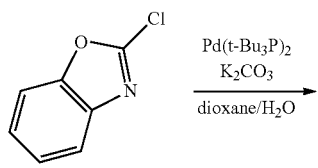

-continued

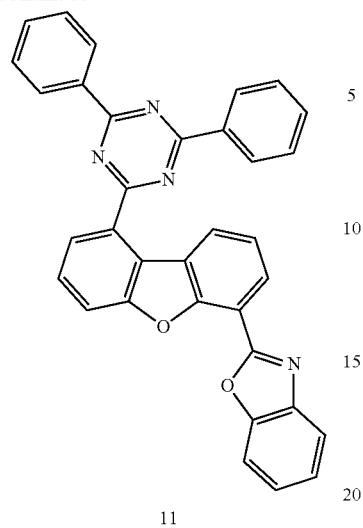

11

Compound 11 (6.7 g, yield 68%, MS: [M+H]⁺=517) was prepared in the same manner as in the preparation of Compound 1 of Example 1, except that Compound B-7 was used instead of Compound A-6.

Example 12: Preparation of Compound 12

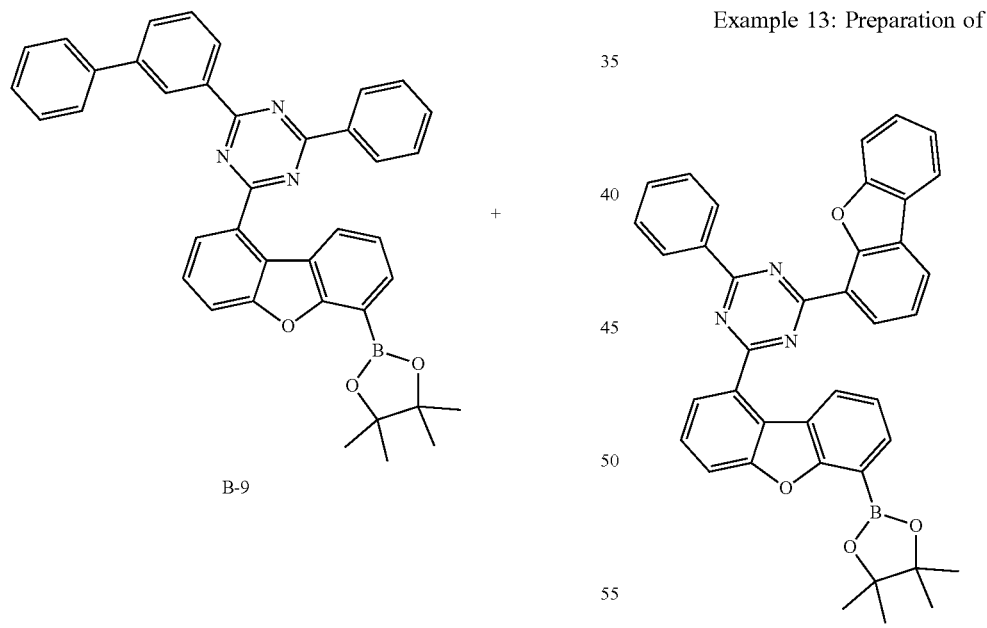

B-9

-continued

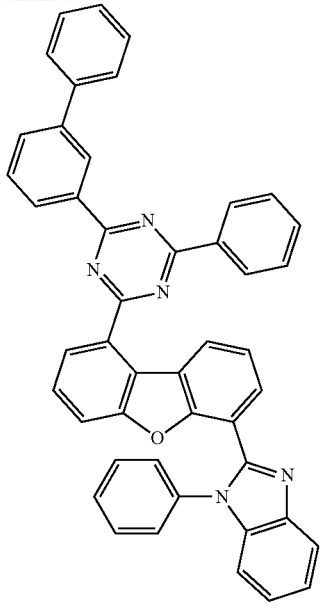

12

Compound 12 (6.9 g, yield 62%, MS: [M+H]⁺=668) was prepared in the same manner as in the preparation of Compound 1 of Example 1, except that Compound B-9 and 2-chloro-1-phenyl-1H-benzoimidazole were used instead of Compound A-6 and 2-chloro-oxazole.

Example 13: Preparation of Compound 13

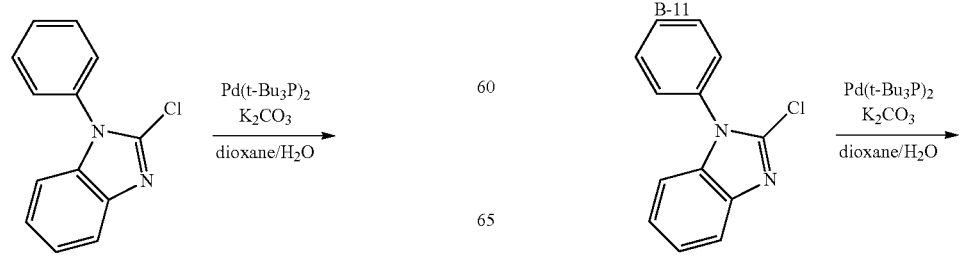

-continued

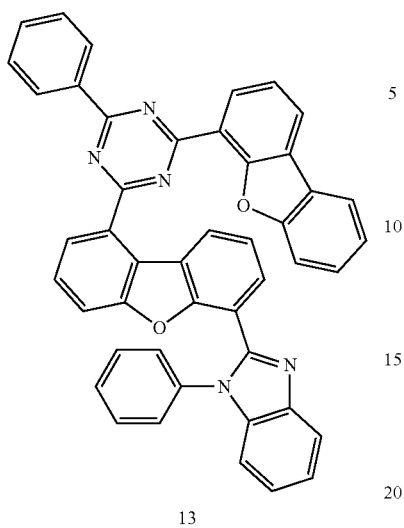

13

Compound 13 (7.3 g, yield 66%, MS: [M+H]$^+$=682) was prepared in the same manner as in the preparation of Compound 1 of Example 1, except that Compound B-11 and 2-chloro-1-phenyl-1H-benzoimidazole were used instead of Compound A-6 and 2-chloro-oxazole.

Example 14: Preparation of Compound 14

-continued

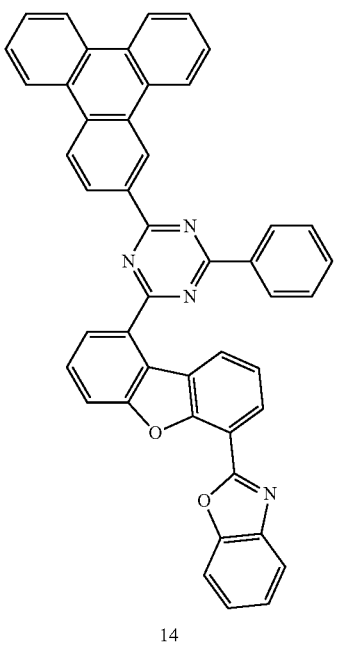

14

Compound 14 (6.9 g, yield 70%, MS: [M+H]$^+$=667) was prepared in the same manner as in the preparation of Compound 1 of Example 1, except that Compound B-13 was used instead of Compound A-6.

Example 15: Preparation of Compound 15

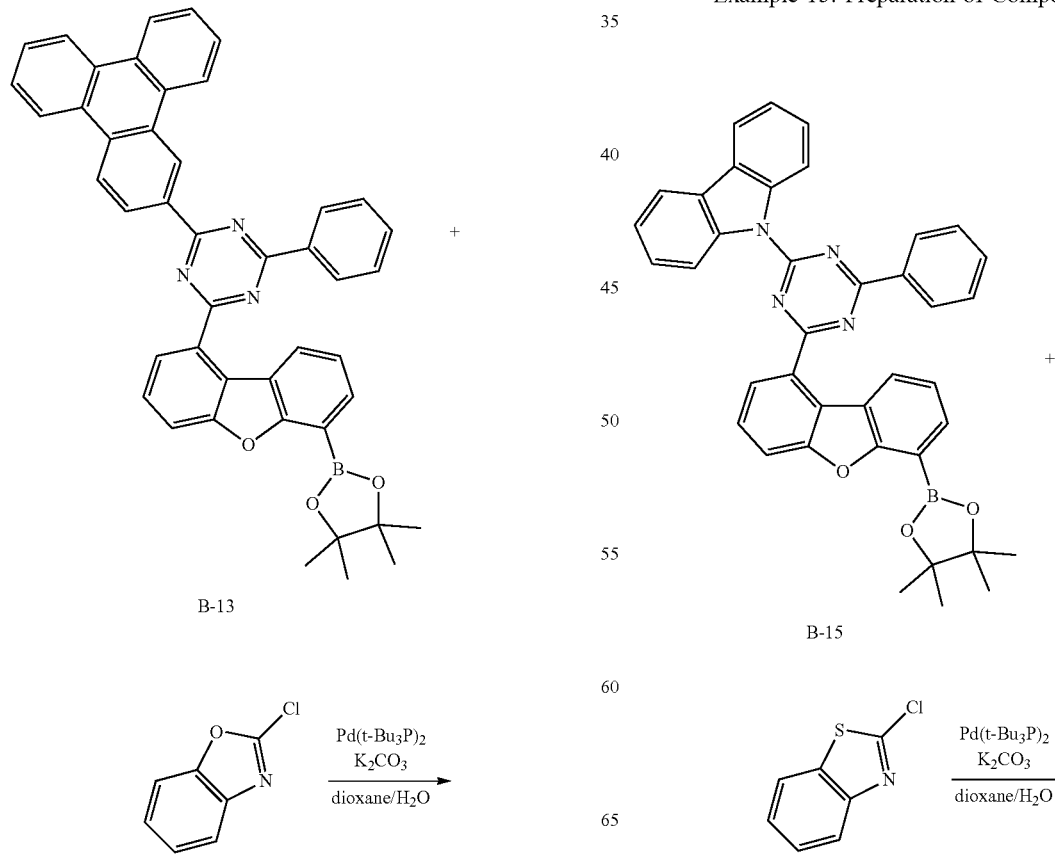

-continued

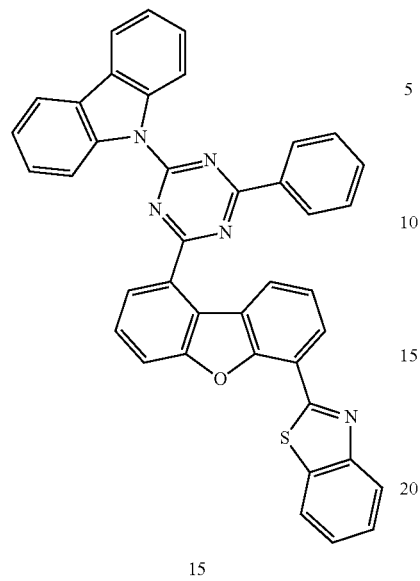

15

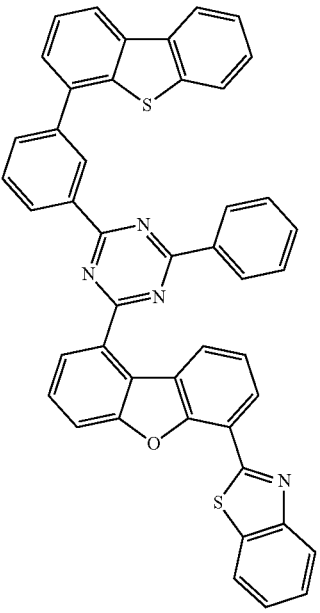

16

Compound 15 (6.5 g, yield 64%, MS: [M+H]⁺=622) was prepared in the same manner as in the preparation of Compound 1 of Example 1, except that Compound B-15 and 2-chloro-1-phenyl-1H-benzoimidazole were used instead of Compound A-6 and 2-chloro-oxazole.

Example 16: Preparation of Compound 16

Compound 16 (6.2 g, yield 61%, MS: [M+H]⁺=715) was prepared in the same manner as in the preparation of Compound 1 of Example 1, except that Compound B-17 and 2-chloro-thiazole were used instead of Compound A-6 and 2-chloro-oxazole.

Example 17: Preparation of Compound 17

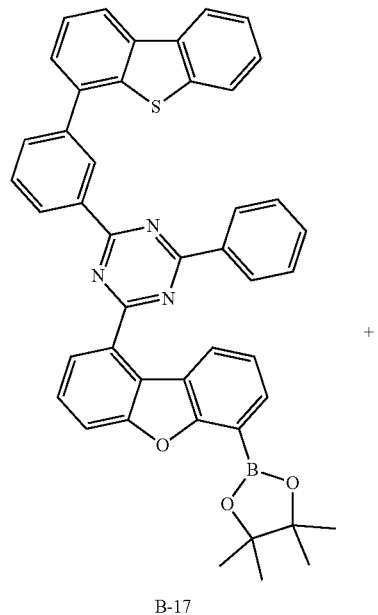

B-17

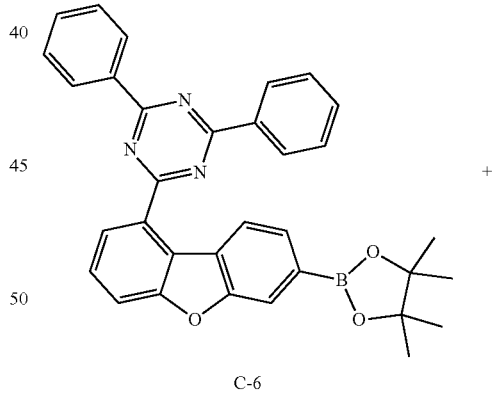

C-6

+

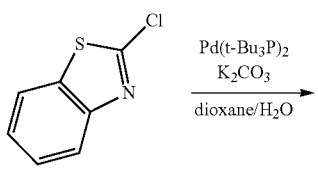

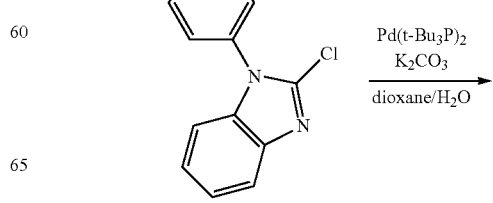

-continued

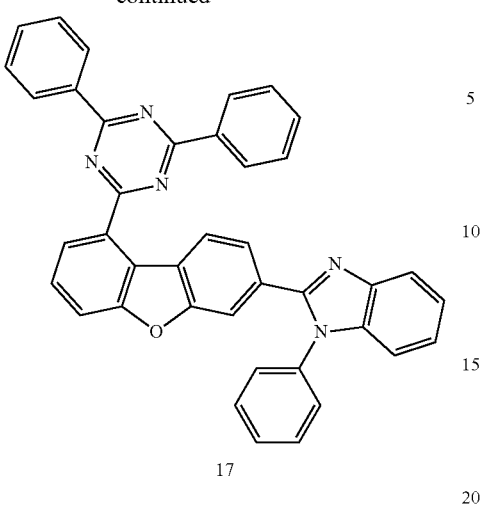

17

Compound 17 (7.2 g, yield 64%, MS: [M+H]⁺=592) was prepared in the same manner as in the preparation of Compound 1 of Example 1, except that Compound C-6 and 2-chloro-1-phenyl-1H-benzoimidazole were used instead of Compound A-6 and 2-chloro-oxazole.

Example 18: Preparation of Compound 18

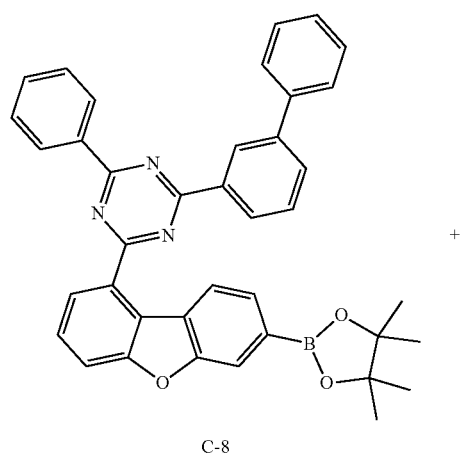

C-8

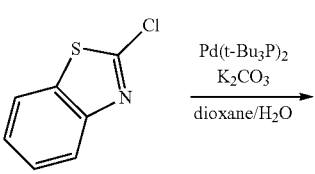

-continued

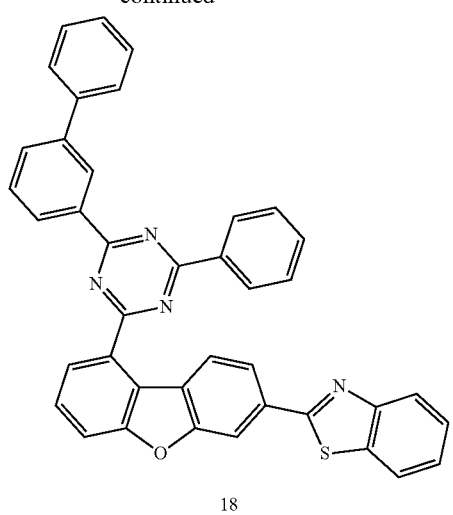

18

Compound 18 (6.8 g, yield 67%, MS: [M+H]⁺=609) was prepared in the same manner as in the preparation of Compound 1 of Example 1, except that Compound C-8 and 2-chloro-thiazole were used instead of Compound A-6 and 2-chloro-oxazole.

Example 19: Preparation of Compound 19

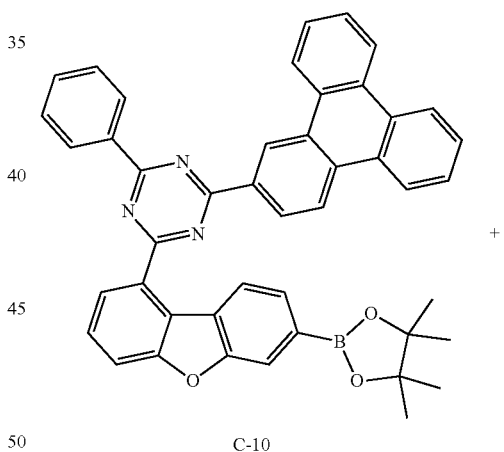

C-10

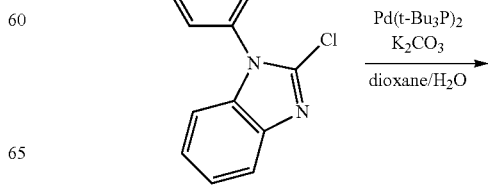

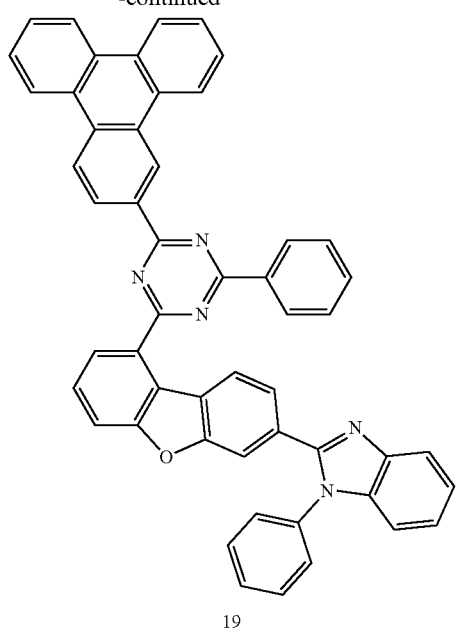

19

Compound 19 (7.6 g, yield 69%, MS: [M+H]⁺=742) was prepared in the same manner as in the preparation of Compound 1 of Example 1, except that Compound C-10 and 2-chloro-1-phenyl-1H-benzoimidazole were used instead of Compound A-6 and 2-chloro-oxazole.

Example 20: Preparation of Compound 20

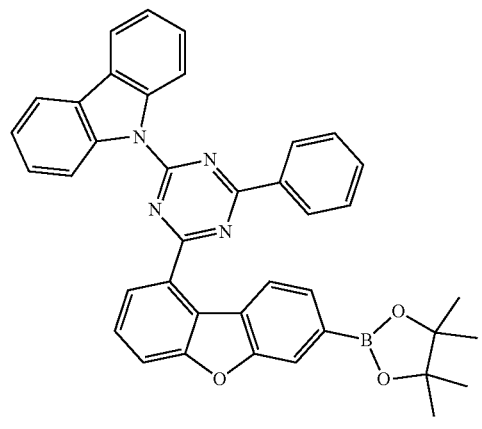

C-12

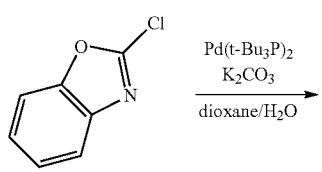

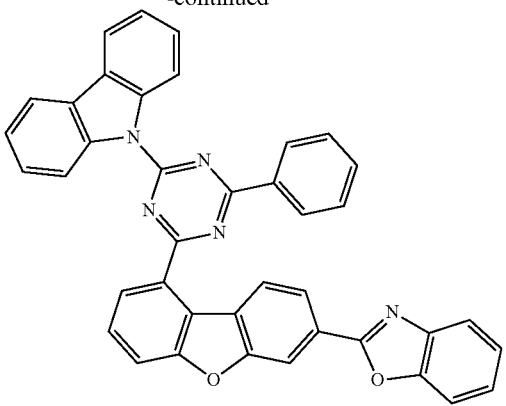

20

Compound 20 (6.6 g, yield 67%, MS: [M+H]⁺=606) was prepared in the same manner as in the preparation of Compound 1 of Example 1, except that Compound C-12 was used instead of Compound A-6.

Example 21: Preparation of Compound 21

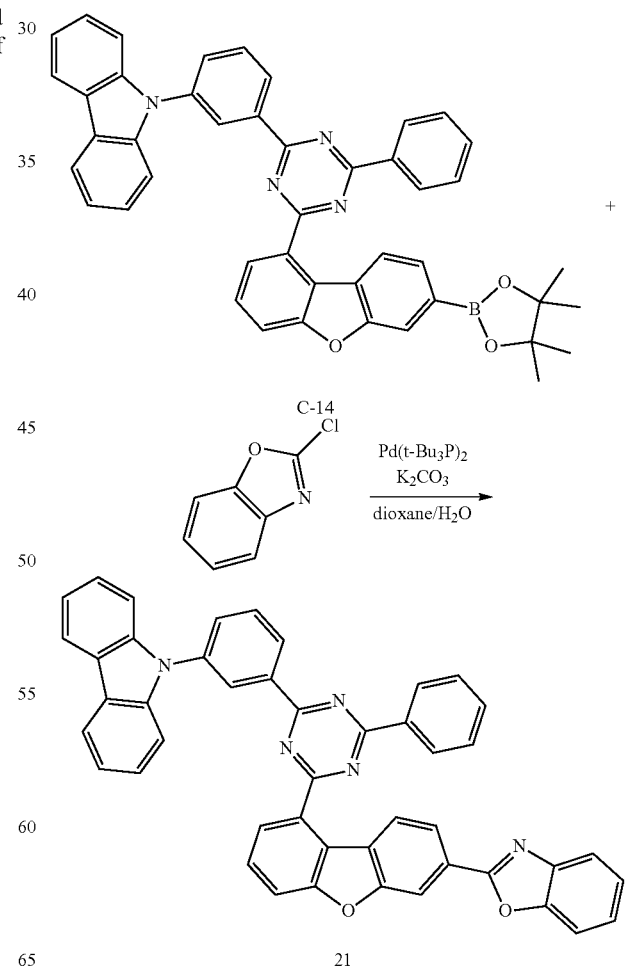

Compound 21 (6.5 g, yield 66%, MS: [M+H]⁺=682) was prepared in the same manner as in the preparation of Compound 1 of Example 1, except that Compound C-14 was used instead of Compound A-6.

Example 22: Preparation of Compound 22

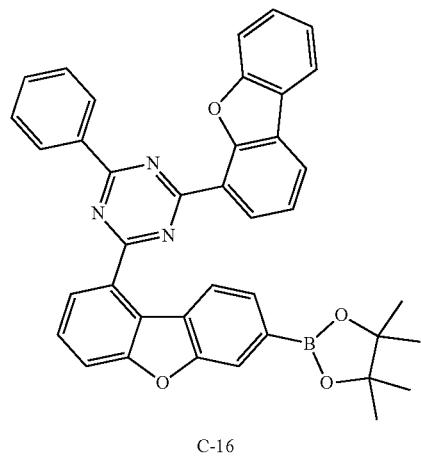

Example 23: Preparation of Compound 23

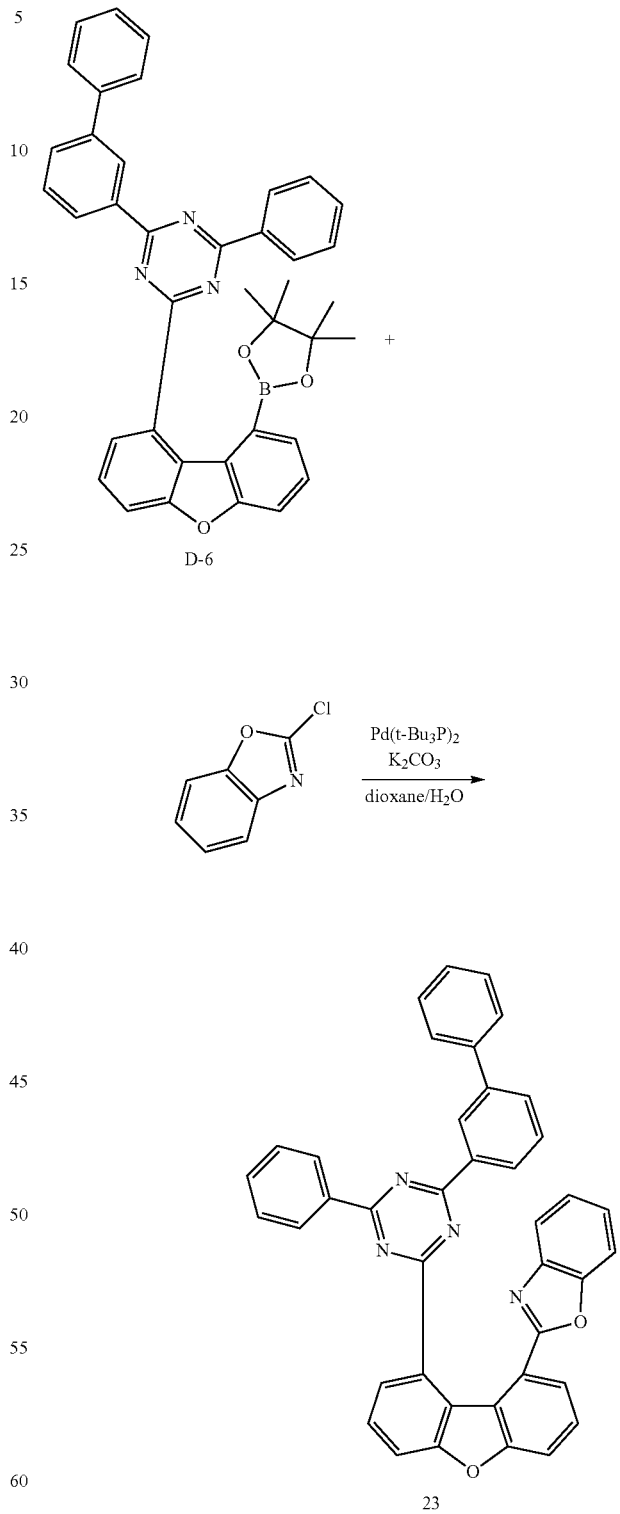

Compound 22 (6.9 g, yield 68%, MS: [M+H]⁺=623) was prepared in the same manner as in the preparation of Compound 1 of Example 1, except that Compound C-16 and 2-chloro-thiazole were used instead of Compound A-6 and 2-chloro-oxazole.

Compound 23 (6.0 g, yield 61%, MS: [M+H]⁺=593 was prepared in the same manner as in the preparation of Compound 1 of Example 1, except that Compound D-6 was used instead of Compound A-6.

Example 24: Preparation of Compound 24

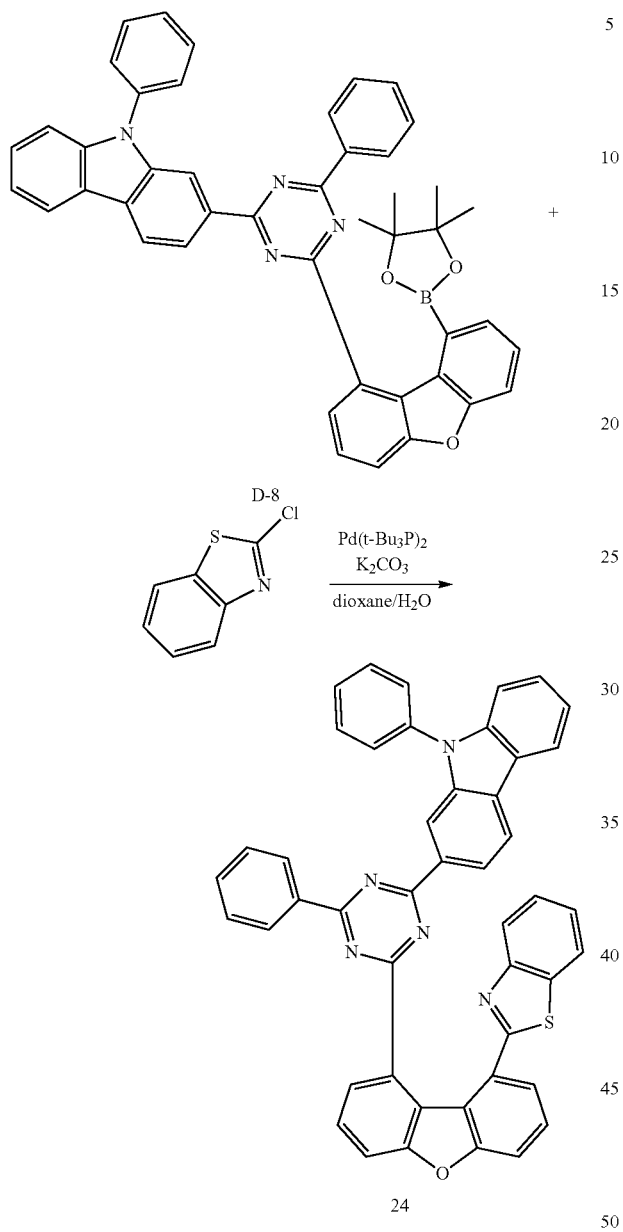

Compound 24 (6.3 g, yield 62%, MS: [M+H]$^+$=698) was prepared in the same manner as in the preparation of Compound 1 of Example 1, except that Compound D-8 and 2-chloro-thiazole were used instead of Compound A-6 and 2-chloro-oxazole.

EXPERIMENTAL EXAMPLES

Experimental Example 1

A glass substrate on which a thin film of ITO (indium tin oxide) was coated at a thickness of 1300 Å was put into distilled water containing a detergent dissolved therein and washed by ultrasonic waves. In this case, the detergent used was a product commercially available from Fisher Co., and the distilled water was one which had been filtered twice by using a filter that is commercially available from Millipore Co. The ITO was washed for 30 minutes, and ultrasonic washing was then repeated twice for 10 minutes by using distilled water. After the washing with distilled water was completed, the substrate was ultrasonically washed with a solvent of isopropyl alcohol, acetone, and methanol, and dried, after which it was transported to a plasma cleaner. Then, the substrate was cleaned with oxygen plasma for 5 minutes, and then transferred to a vacuum evaporator.

On the ITO transparent electrode thus prepared, a hexanitrile hexaazatriphenylene (HAT) compound below was thermally vacuum-deposited to a thickness of 50 Å to form a hole injection layer. 4,4'-bis-(1-naphthyl)-N-phenylamino] biphenyl (NPB; HT-1) as a hole transport material was thermally vacuum-deposited thereon to a thickness of 250 Å to form a hole transport layer, and a compound of Formula HT-2 below was vacuum-deposited on the HT-1 deposited film to a thickness of 50 Å to form an electron blocking layer. Then, a Compound 2 prepared as a host, a compound of Formula YGH-1 below, and a phosphorescent dopant of Formula YGD-1 below were co-deposited on the HT-2 deposited film at a weight ratio of 44:44:12 to form the light-emitting layer having a thickness of 400 Å. A material of Formula ET-1 below was vacuum-deposited on the light-emitting layer to a thickness of 250 Å, and additionally a material of Formula ET-2 below was co-deposited with 2 wt % Li to a thickness of 100 Å to form an electron transport layer and an electron injection layer. Aluminum was evaporated to a thickness of 1000 Å on the electron injection layer to form a cathode.

In the above process, the vapor deposition rate of the organic material was maintained at 0.4 to 0.7 Å/s, the vapor deposition rate of aluminum was maintained at 2 Å/s, and the degree of vacuum during vapor deposition was maintained at $1 \times 10^{-7}$ to $5 \times 10^{-8}$ torr to manufacture an organic light emitting device.

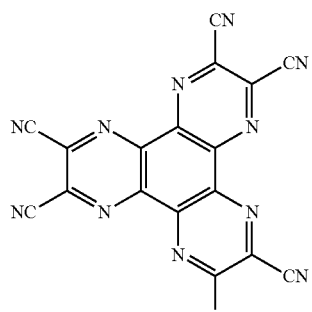

HAT

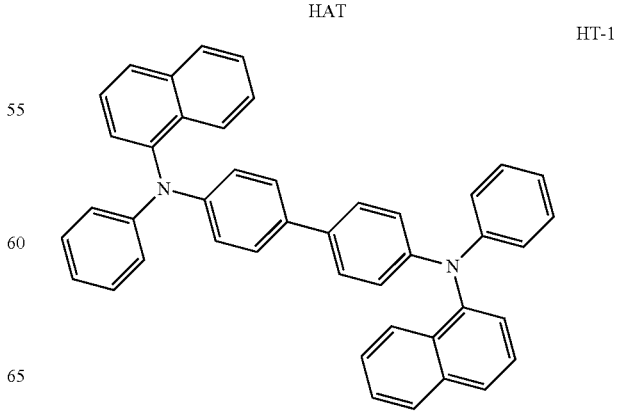

HT-1

HT-2

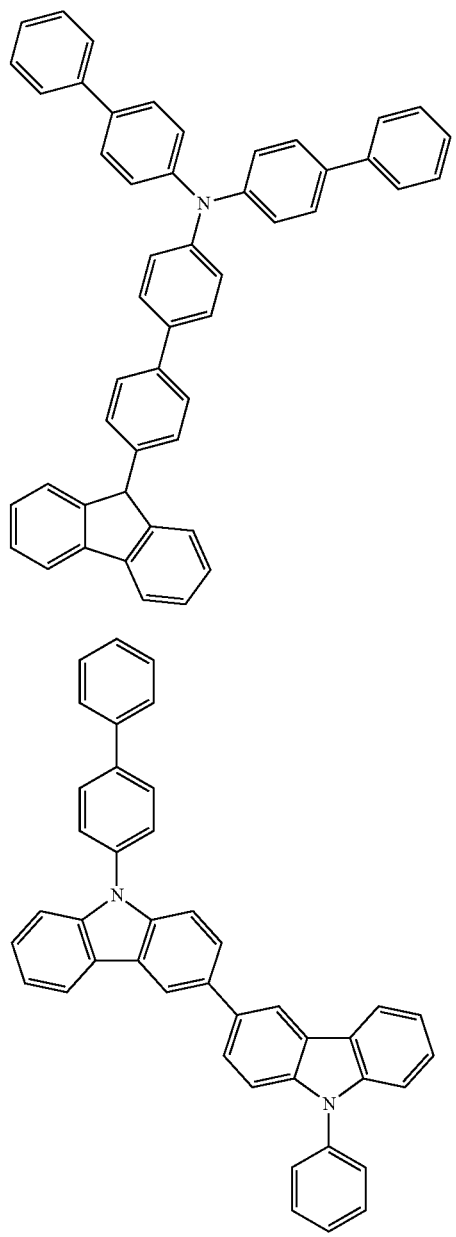

YGH-1

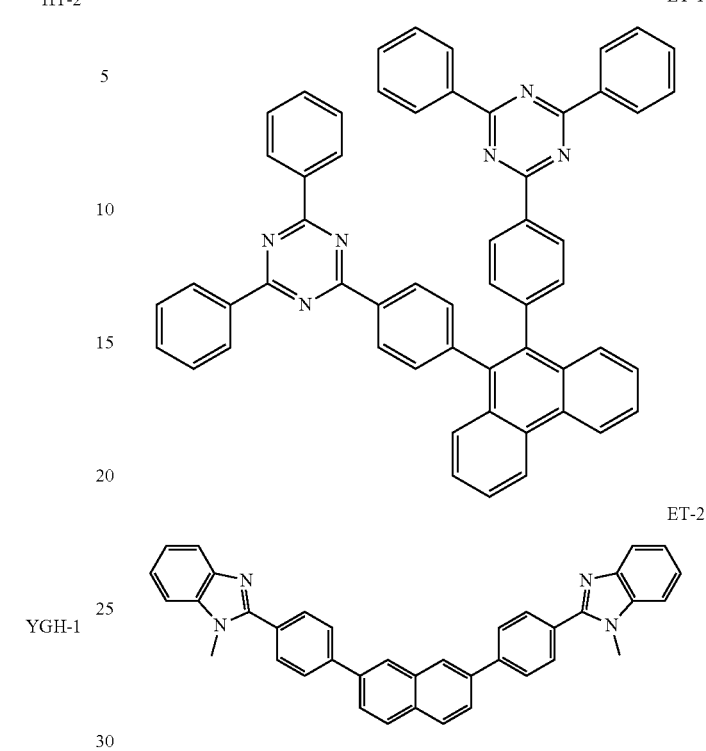

ET-1

ET-2

Experimental Examples 2 to 10

The organic light emitting device was manufactured in the same manner as in Experimental Example 1, except that the compounds shown in Table 1 below were used instead of Compound 2 as a phosphorescent host during the formulation of the light emitting layer in Experimental Example 1.

Comparative Examples 1 to 4

The organic light emitting devices of Comparative Examples 1 to 4 were respectively manufactured in the same manner as in Example 1, except that Compounds C1 to C4 shown in Table 2 below were used instead of Compound 2 as a host during the formulation of the light emitting layer.

YGD-1

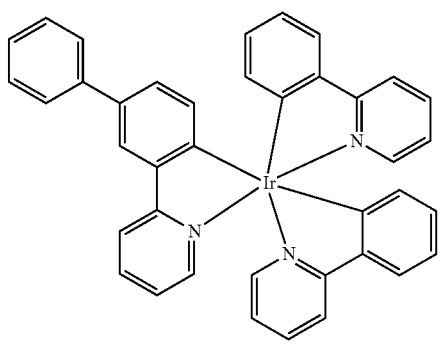

C1

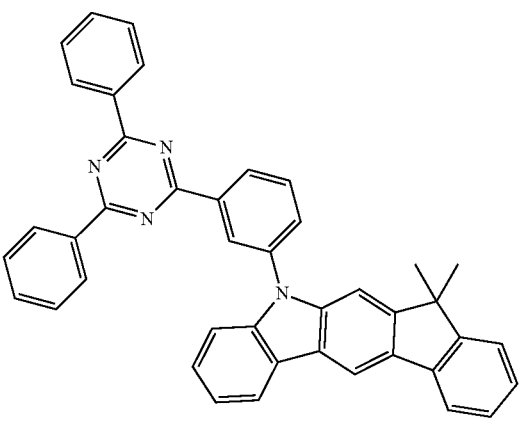

-continued

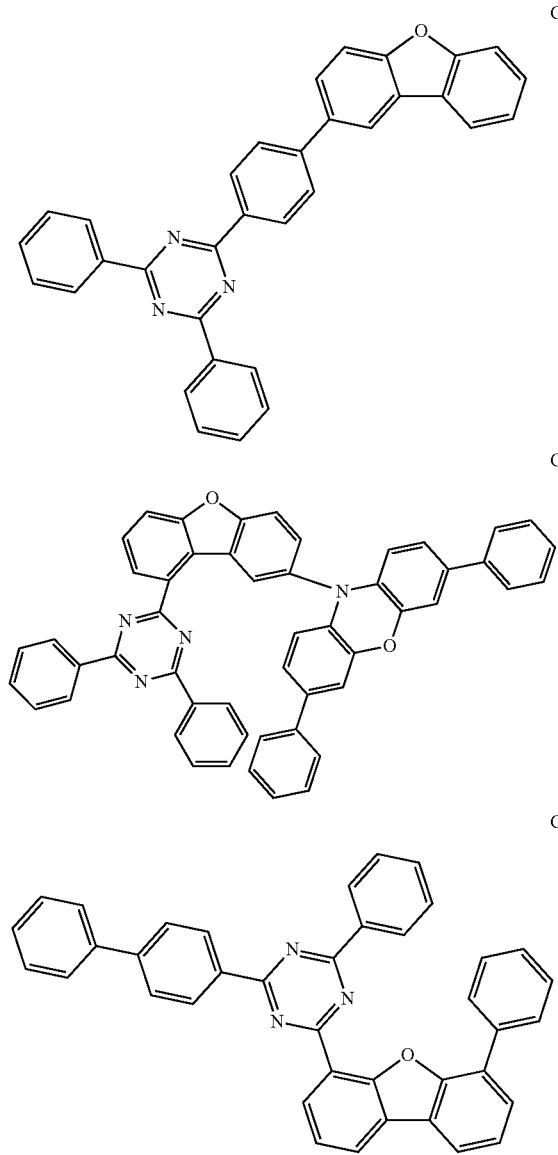

The voltage, efficiency, color coordinates, and lifetime were measured by applying a current to the organic light emitting devices manufactured in Experimental Examples 1 to 10 and Comparative Examples 1 to 4, and the results are shown in Table 1 below. T95 means the time required for the luminance to be reduced to 95% of the initial luminance.

TABLE 1

| Category | Compound | Voltage (V) (@10 mA/cm$^2$) | Efficiency (Cd/A) (@10 mA/cm$^2$) | Color coordinates (x, y) | Lifetime (h) (LT$_{95}$ at 50 mA/cm$^2$) |
|---|---|---|---|---|---|
| Experimental Example 1 | Compound 2 | 3.7 | 77 | 0.46, 0.53 | 160 |
| Experimental Example 2 | Compound 5 | 3.8 | 76 | 0.45, 0.52 | 140 |
| Experimental Example 3 | Compound 8 | 3.7 | 78 | 0.45, 0.53 | 135 |
| Experimental Example 4 | Compound 9 | 3.8 | 77 | 0.46, 0.54 | 110 |
| Experimental Example 5 | Compound 10 | 4.0 | 73 | 0.45, 0.53 | 120 |
| Experimental Example 6 | Compound 16 | 3.8 | 79 | 0.45, 0.54 | 150 |
| Experimental Example 7 | Compound 17 | 3.8 | 75 | 0.46, 0.53 | 130 |
| Experimental Example 8 | Compound 18 | 3.9 | 74 | 0.45, 0.52 | 145 |
| Experimental Example 9 | Compound 20 | 4.0 | 75 | 0.44, 0.53 | 120 |
| Experimental Example 10 | Compound 24 | 4.1 | 77 | 0.45, 0.53 | 130 |
| Comparative Experimental Example 1 | C1 | 3.6 | 68 | 0.45, 0.54 | 91 |
| Comparative Experimental Example 2 | C2 | 4.0 | 60 | 0.46, 0.53 | 61 |
| Comparative Experimental Example 3 | C3 | 4.4 | 50 | 0.45, 0.52 | 35 |
| Comparative Experimental Example 4 | C4 | 4.2 | 70 | 0.46, 0.54 | 81 |

As shown in Table 1, it is confirmed that the organic light emitting devices manufactured using the compound according to the present invention as a host of the light emitting layer exhibit superior performance in terms of driving voltage, current efficiency, and lifetime as compared with the organic light emitting device of the comparative examples.

In particular, it is confirmed that the organic light emitting devices according to the examples have a longer lifetime characteristic as the lifetime increases about 20-75% compared to the organic light-emitting devices according to Comparative Example 1 using Compound C1 which is a fluorescent host material commonly used in the art. In addition, when comparing with Comparative Example 2, which is a compound (C2) substituted only with a triazine substituent, the organic light emitting devices of the examples have high efficiency characteristics, and when the lifetime data are confirmed, it shows an increase in the lifetime from 80% to 262%. Further, when comparing Experimental Examples 1, 4, and 5 with Experimental Examples 2, 6, 8, and 10 and Comparative Experimental Examples 3 and 4, it can be confirmed that the difference in lifetime is demonstrated according to the substitution position and substituent type of dibenzofurane of the compounds of the examples. It has been found that the present invention exhibits improved lifetime with certain substituents and substitution sites.

Experimental Examples

Experimental Example 11

On the ITO transparent electrode prepared as in Experimental Example 1, the hexanitrile hexaazatriphenylene (HAT) compound below was thermally vacuum-deposited to a thickness of 500 Å to form a hole injection layer. A compound of Formula HT-1 below was thermally vacuum-deposited on the hole injection layer to a thickness of 800 Å, and sequentially a compound of Formula HT-3 below was vacuum-deposited to a thickness of 500 Å to form a hole transport layer. Then, Compound 2 prepared as a host, a compound of formula H2 below, and a phosphorescent dopant of formula GD below were co-deposited on the hole transport layer at a weight ratio of 47:47:6 to form a light emitting layer having a thickness of 350 Å. A material of Formula ET-3 below was vacuum-deposited on the light emitting layer to a thickness of 50 Å to form a hole blocking layer, and a material of Formula ET-4 below and LiQ (lithium quinolate) were vacuum-deposited on the hole blocking layer at a weight ratio of 1:1 to form an electron transport layer having a thickness of 250 Å. Lithium fluoride (LiF) was deposited on the electron transport layer to a thickness of 10 Å, and sequentially aluminum was deposited thereon to a thickness of 1000 Å to form a cathode.

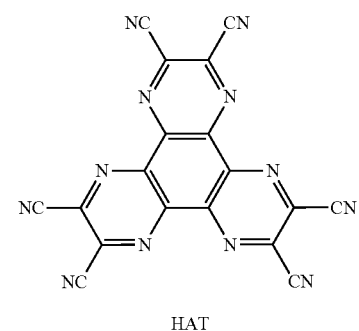

HAT

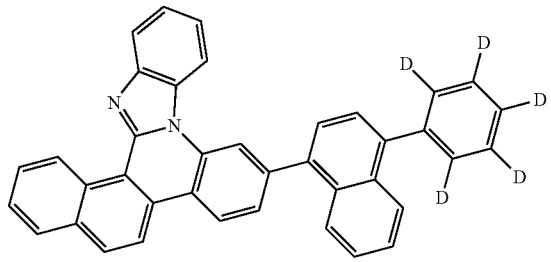

ET-3

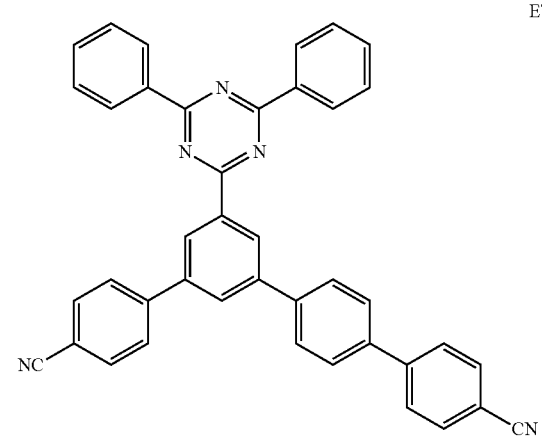

ET-4

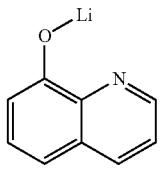

LiQ

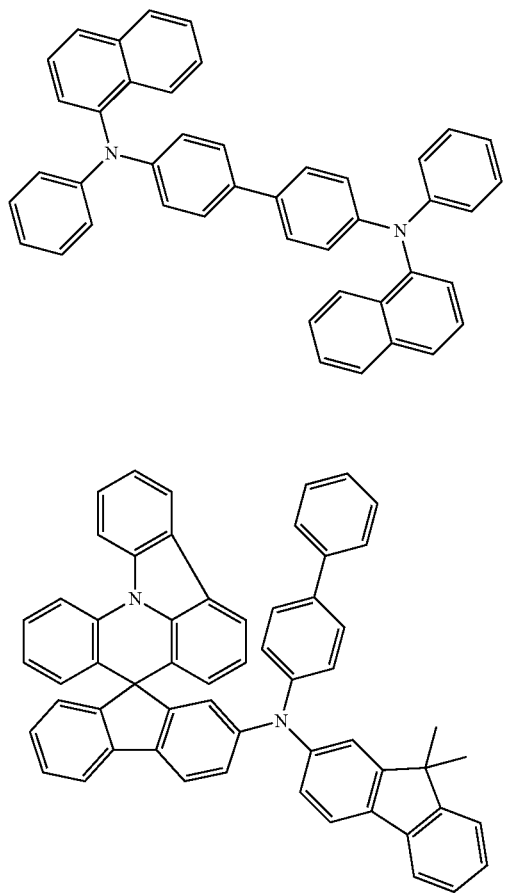

HT-1

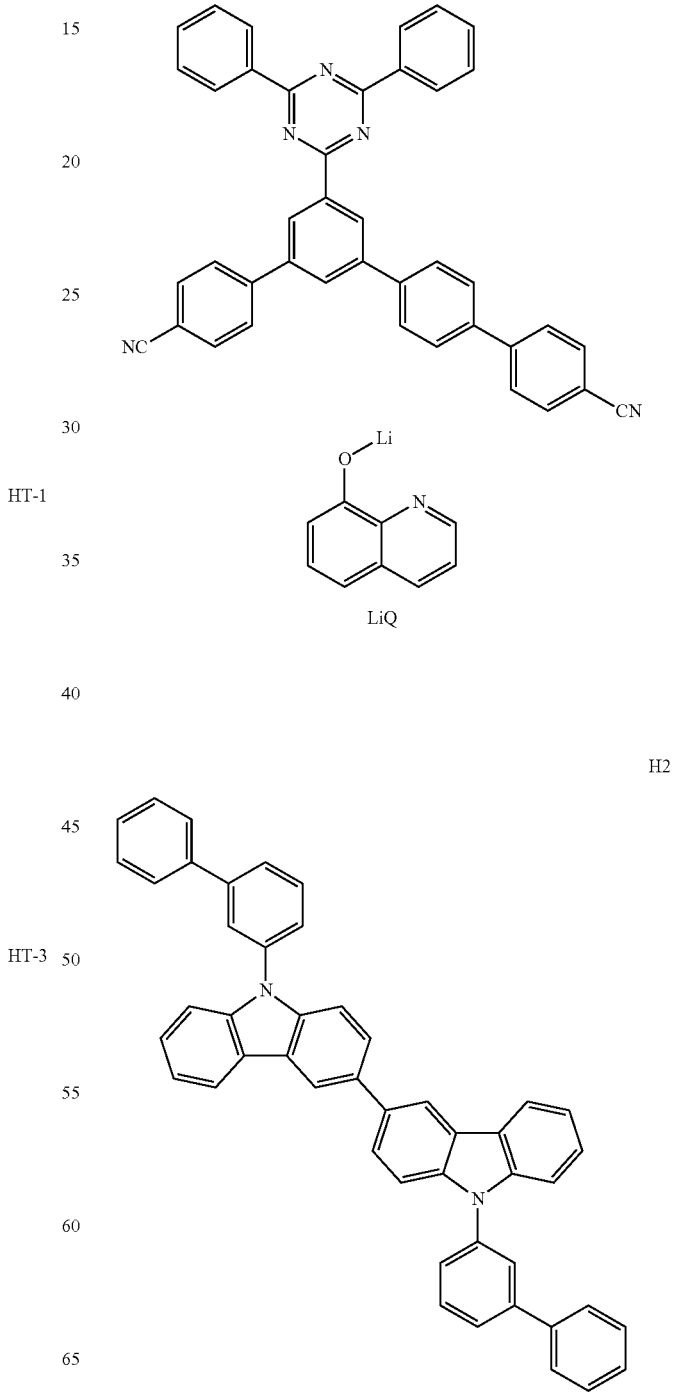

HT-3

H2

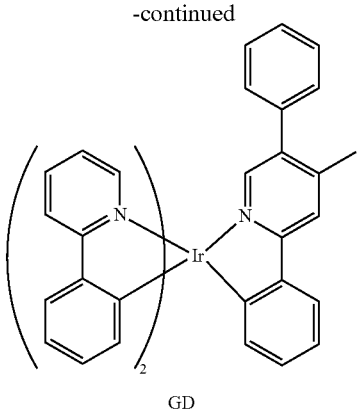

GD

In the above process, the vapor deposition rate of the organic material was maintained at 0.4 to 0.7 Å/s, the vapor deposition rate of lithium fluoride of the cathode was maintained at 0.3 Å/s, and the vapor deposition rate of aluminum was maintained at 2 Å/s. The degree of vacuum during vapor deposition was maintained at $1\times10^{-7}$~$5\times10^{-8}$ tor.

Experimental Examples 12 to 17

The organic light emitting devices of Experimental Examples 12 to 17 were respectively manufactured in the same manner as in Experimental Example 2, except that the compounds shown in Table 2 were used instead of Compound 2 as a host during the formulation of the light emitting layer. In this case, when a mixture of two kinds of compounds is used as the host, the parentheses mean the weight ratio between the host compounds.

Comparative Examples 5 to 8

The organic light emitting devices of Comparative Examples 5 to 8 were respectively manufactured in the same manner as in Experimental Example 11, except that the compounds shown in Table 2 were used instead of Compound 1 as a host during the formulation of the light emitting layer. The compounds shown in Table 2 are the same as the compounds used in Experimental Example 1 described above.

The voltage, efficiency, and lifetime were measured by applying a current to the organic light emitting devices manufactured in Experimental Examples 11 to 17 and Comparative Examples 5 to 8, and the results are shown in Table 2 below. T95 means the time required for the luminance to be reduced to 95% of the initial luminance.

TABLE 2

| Category | Compound | Voltage (V) (@10 mA/cm$^2$) | Efficiency (Cd/A) (@10 mA/cm$^2$) | Color coordinates (x, y) | Lifetime (h) (LT$_{95}$ at 50 mA/cm$^2$) |
|---|---|---|---|---|---|
| Experimental Example 11 | Compound 2 | 3.7 | 77 | 0.36, 0.62 | 110 |
| Experimental Example 12 | Compound 3 | 3.8 | 76 | 0.35, 0.61 | 95 |
| Experimental Example 13 | Compound 4 | 3.7 | 78 | 0.36, 0.60 | 80 |
| Experimental Example 14 | Compound 7 | 3.8 | 77 | 0.35, 0.62 | 100 |
| Experimental Example 15 | Compound 11 | 4.0 | 73 | 0.35, 0.63 | 90 |
| Experimental Example 16 | Compound 12 | 3.8 | 79 | 0.36, 0.62 | 85 |
| Experimental Example 17 | Compound 22 | 3.8 | 75 | 0.35, 0.61 | 90 |
| Comparative Experimental Example 5 | C1 | 4.2 | 55 | 0.35, 0.61 | 55 |
| Comparative Experimental Example 6 | C2 | 4.6 | 49 | 0.35, 0.62 | 35 |
| Comparative Experimental Example 7 | C3 | 4.7 | 50 | 0.35, 0.61 | 27 |
| Comparative Experimental Example 8 | C4 | 4.4 | 61 | 0.34, 0.63 | 30 |

As can be seen in Table 2, it is confirmed that the case of using the compounds of the present invention as a light emitting layer material exhibits superior characteristics in terms of lifetime, similar to Experimental Examples 1 to 10, as compared with the case of using the materials of the comparative examples.

In addition, when comparing Experimental Examples 11, 12, and 7 and Comparative Experimental Example 7, it can be confirmed that the characteristics appear differently in terms of the driving voltage and the lifetime characteristic according to the type of the substituent even though the substituted position in dibenzofuran is the same. In particular, it can be understood that the substituent of the compounds of the present invention is elementally (electrically) more stable than the substituent of C4 which is the compound of Comparative Experimental Example 7.

As described above, it can be confirmed that the compounds of the present invention exhibit superior characteristics in terms of driving voltage and lifetime according to the substituent position and substituent type, as compared with the compounds of the comparative examples.

DESCRIPTION OF ITEM NUMBERS

[Description of Item Numbers]

1: substrate  2: anode
3: light emitting layer  4: cathode
5: hole injection layer  6: hole transport layer
7: light emitting layer  8: electron transport layer

The invention claimed is:

1. A compound of the following Formula 1:

[Formula 1]

wherein in Formula 1 above:

$X_1$ is O or S;

$R_1$ is hydrogen or a substituted or unsubstituted $C_{1-60}$ alkyl;

$L_1$ and $L_2$ are each independently a direct bond or a substituted or unsubstituted $C_{6-60}$ arylene;

$Y_1$, $Y_2$, and $Y_3$ are each independently N or $CR_2$, provided that at least one of $Y_1$, $Y_2$, and $Y_3$ is N;

$R_2$ is hydrogen or a substituted or unsubstituted $C_{1-60}$ alkyl;

$Ar_1$ and $Ar_2$ are each independently a substituted or unsubstituted $C_{6-60}$ aryl or a substituted or unsubstituted $C_{5-60}$ heteroaryl containing at least one of N, O, and S, which can be combined with an adjacent $Y_1$, $Y_2$, or $Y_3$ to form a ring;

n and m are each independently 1 or 2;

each Het is independently a group represented by Formula 1-1:

[Formula 1-1]

wherein in Formula 1-1 above:

B is O or S;

each $R_3$ is independently hydrogen, a substituted or unsubstituted $C_{1-60}$ alkyl, or a substituted or unsubstituted $C_{6-60}$ aryl; and l is 1 or 2.

2. The compound of claim 1, wherein the compound group of Formula 1-1 is any one of the following Formulas 1-1-1 to 1-1-6:

[1-1-1]

[1-1-2]

[1-1-3]

[1-1-4]

[1-1-5]

wherein in Formulas 1-1-1 to 1-1-6 above:

B is O or S;

each $R_3$ is independently hydrogen, a substituted or unsubstituted $C_{1-60}$ alkyl, or a substituted or unsubstituted $C_{6-60}$ aryl; and l is 1 or 2.

3. The compound of claim 1, wherein Het is any one substituent selected from the group consisting of the following formulas:

4. The compound of claim 1, wherein the compound of Formula 1 is any one compound selected from compounds of the following Formulas 2 to 6:

[Formula 2]

-continued

[Formula 3]
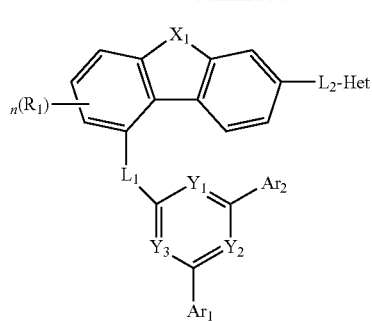

[Formula 4]
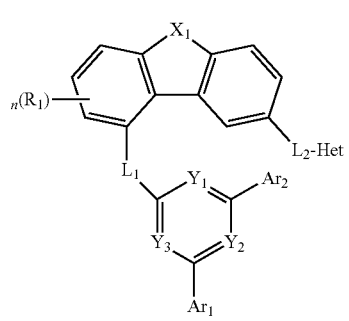

[Formula 5]
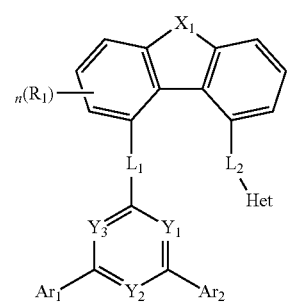

[Formula 6]
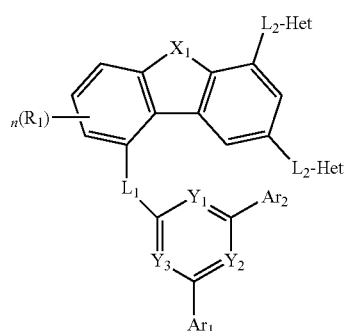

wherein in Formulas 2 to 6 above:

$X_1$ is O or S;

$R_1$ is hydrogen or a substituted or unsubstituted $C_{1-60}$ alkyl;

$L_1$ and $L_2$ are each independently a direct bond or a substituted or unsubstituted $C_{6-60}$ arylene;

$Y_1$, $Y_2$, and $Y_3$ are each independently N or $CR_2$, provided that at least one of $Y_1$, $Y_2$, and $Y_3$ is N;

$R_2$ is hydrogen or a substituted or unsubstituted $C_{1-60}$ alkyl;

$Ar_1$ and $Ar_2$ are each independently a substituted or unsubstituted $C_{6-60}$ aryl or a substituted or unsubstituted $C_{5-60}$ heteroaryl containing at least one of N, O, and S, which can be combined with an adjacent $Y_1$, $Y_2$, or $Y_3$ to form a ring;

n is 1 or 2;

each Het is independently a compound of the following Formula 1-1:

[Formula 1-1]
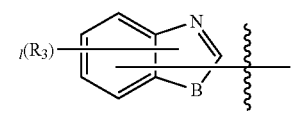

wherein Formula 1-1 above:

B is O or S;

each $R_3$ is independently hydrogen, a substituted or unsubstituted $C_{1-60}$ alkyl, or a substituted or unsubstituted $C_{6-60}$ aryl; and l is 1 or 2.

5. The compound of claim 1, wherein the compound of Formula 1 is any one compound selected from compounds of the following Formulas 7 to 9:

[Formula 7]
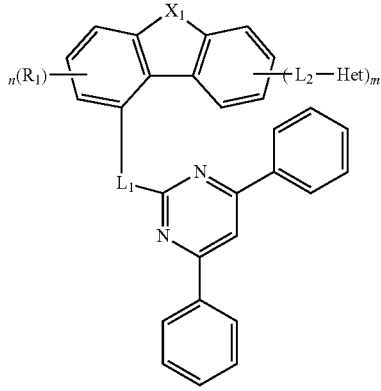

[Formula 8]
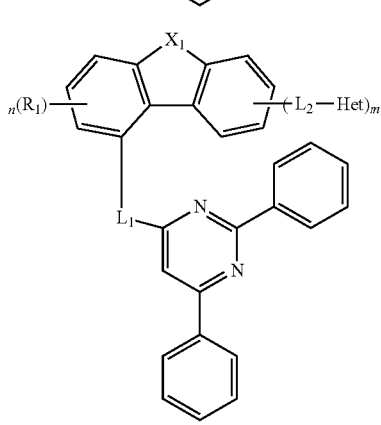

[Formula 9]

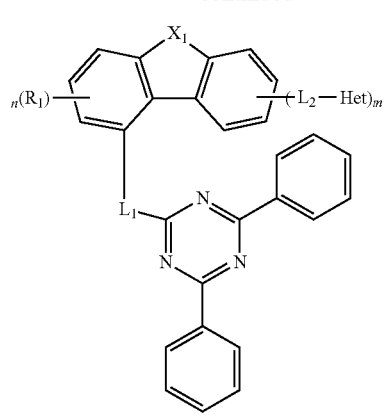

wherein in Formulas 7 to 9 above:

$X_1$ is O or S;

$R_1$ is hydrogen or a substituted or unsubstituted $C_{1-60}$ alkyl;

$L_1$ and $L_2$ are each independently a direct bond or a substituted or unsubstituted $C_{6-60}$ arylene;

n and m are each independently 1 or 2;

each Het is independently a compound of the following Formula 1-1;

[Formula 1-1]

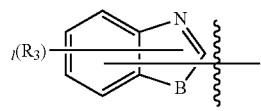

wherein in Formula 1-1 above:

B is O or S;

each $R_3$ is independently hydrogen, a substituted or unsubstituted $C_{1-60}$ alkyl, or a substituted or unsubstituted $C_{6-60}$ aryl; and l is 1 or 2.

6. The compound of claim 1, wherein $R_1$ is hydrogen or a substituted or unsubstituted $C_{1-10}$ alkyl.

7. The compound of claim 1, wherein $R_3$ is hydrogen or phenyl.

8. The compound of claim 1, wherein $L_1$ and $L_2$ are each independently a direct bond or

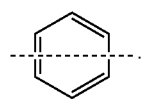

9. The compound of claim 1, wherein $Ar_1$ and $Ar_2$ are each independently a substituent selected from the group consisting of the following formulas:

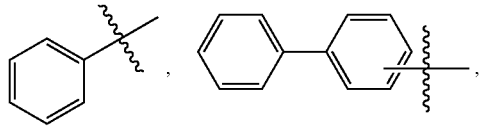

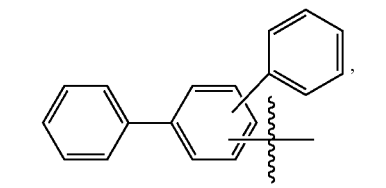

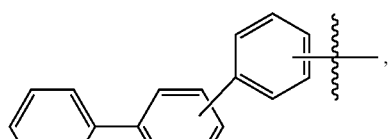

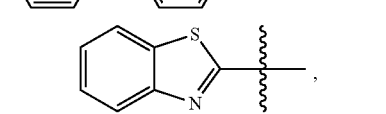

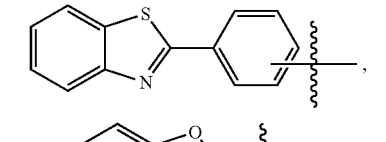

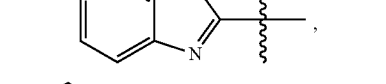

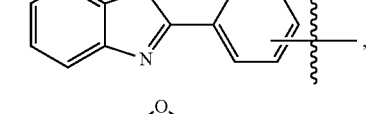

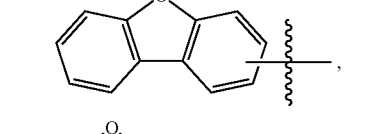

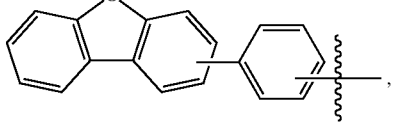

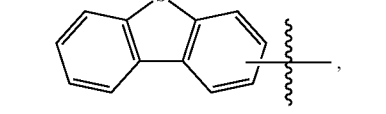

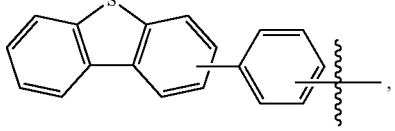

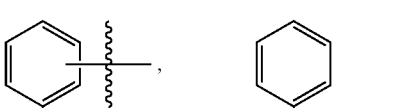

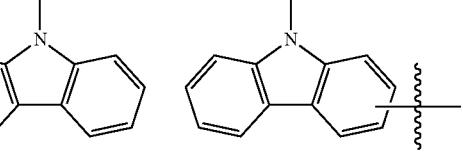

467
-continued
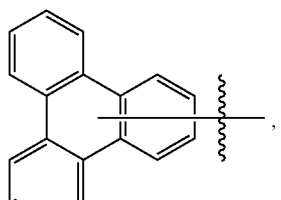
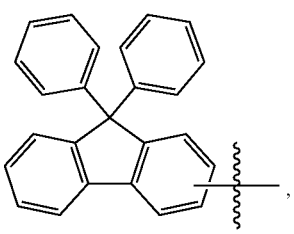
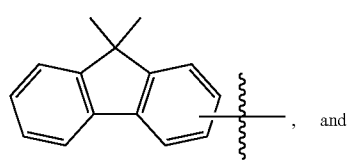
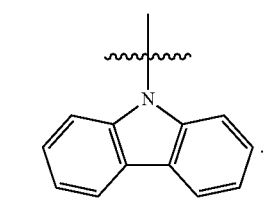
10. The compound of claim 1, wherein the compound of Formula 1 is any one compound selected from the group consisting of compounds of the following formulas:
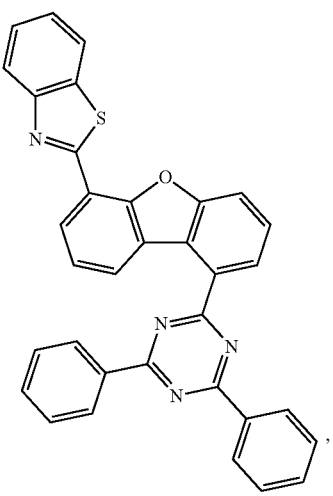
468
-continued
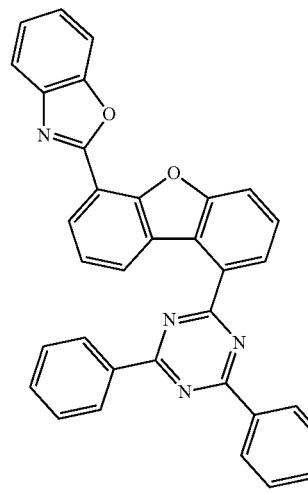
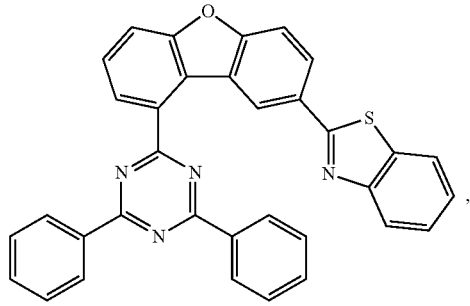
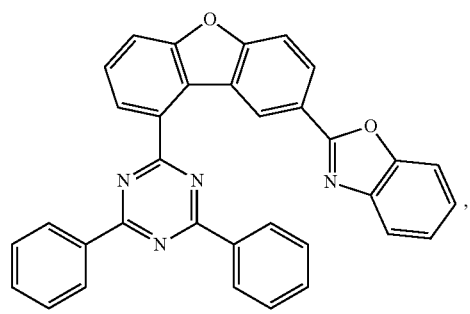
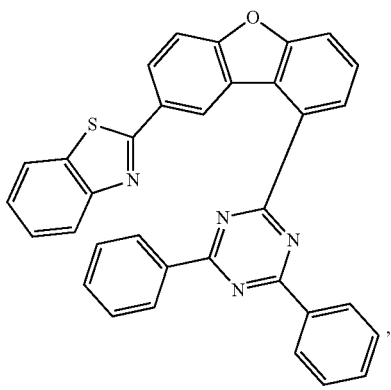

469
-continued
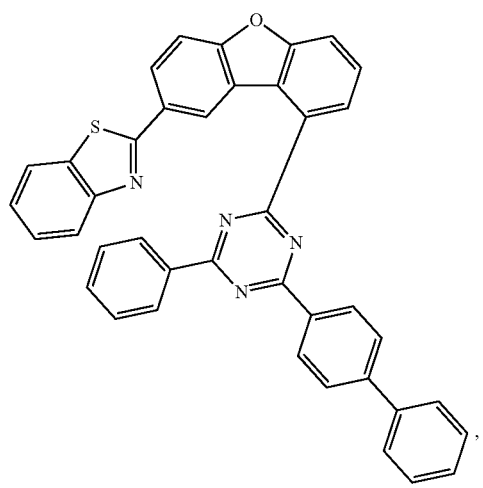
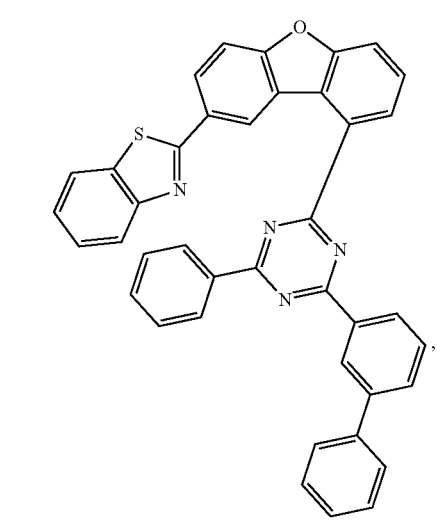
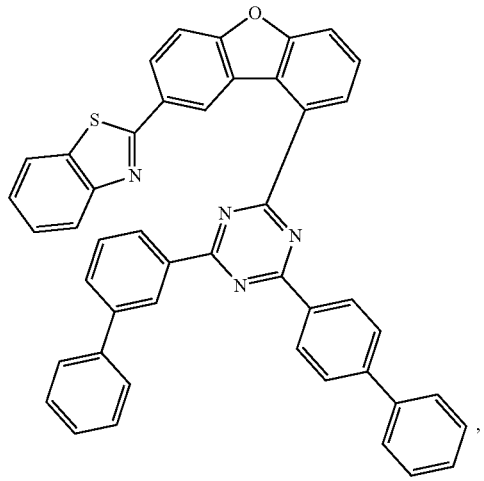
470
-continued
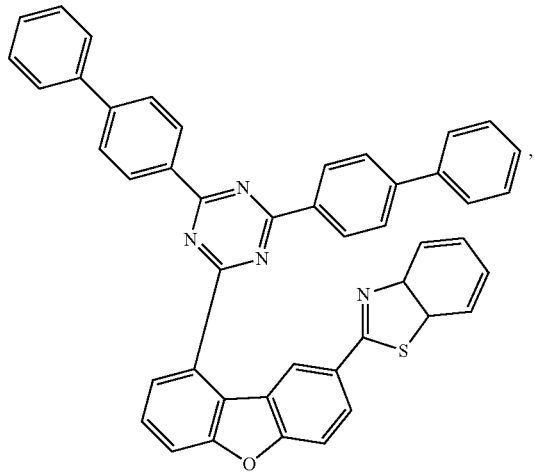
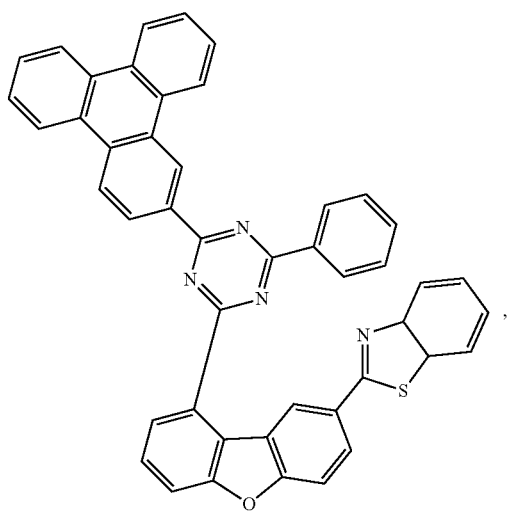
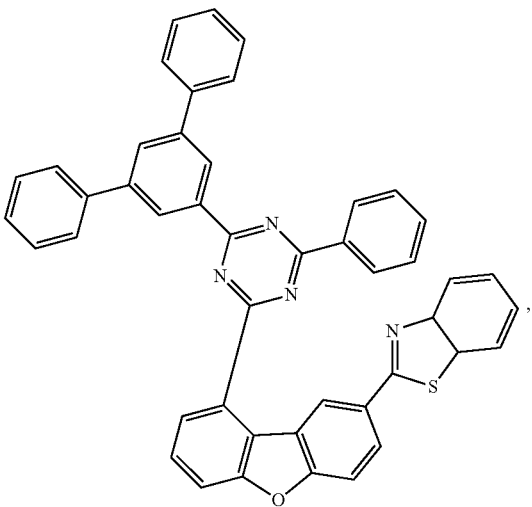

471
-continued
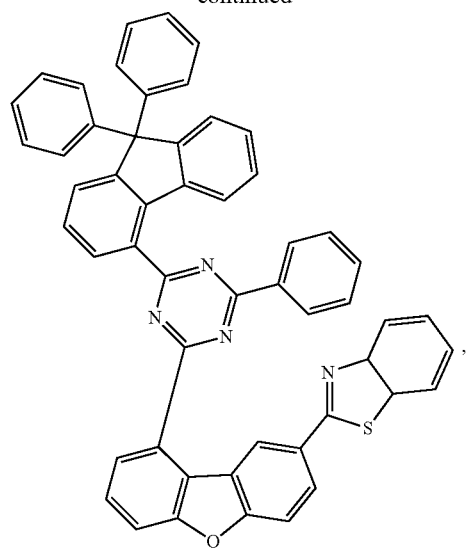
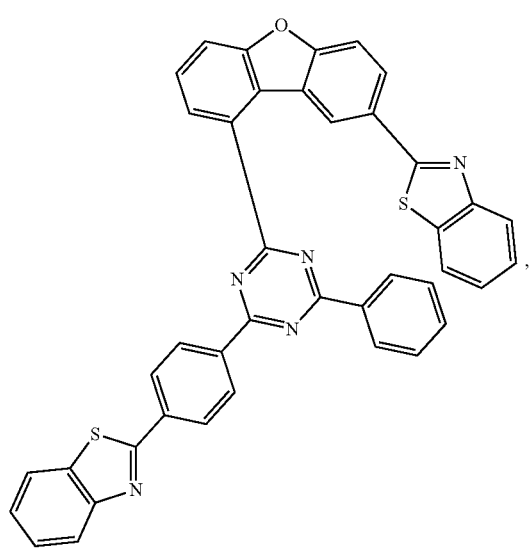
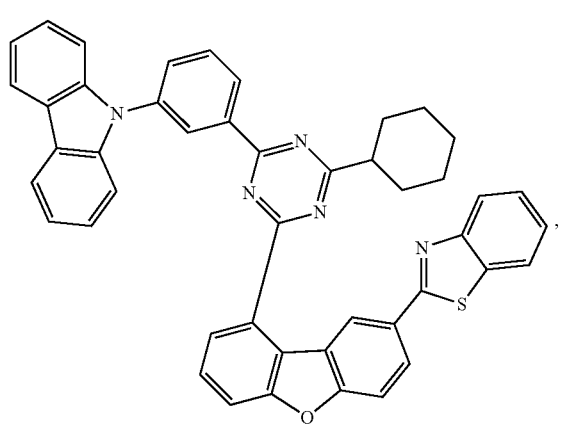
472
-continued
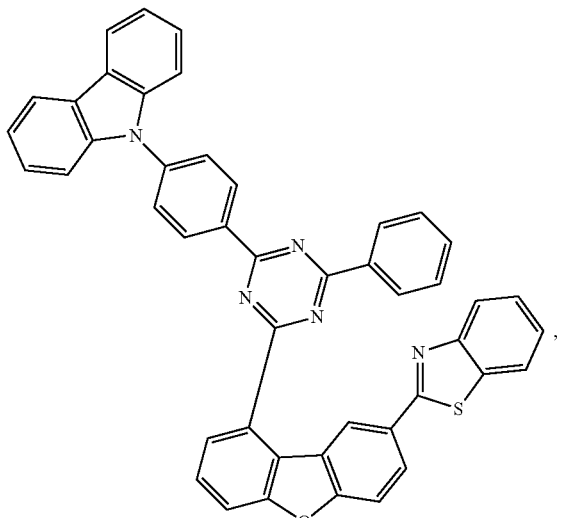
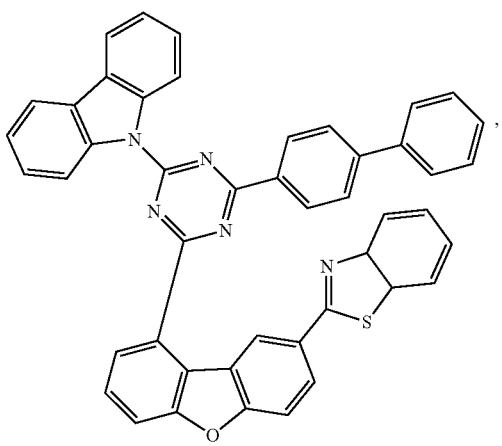
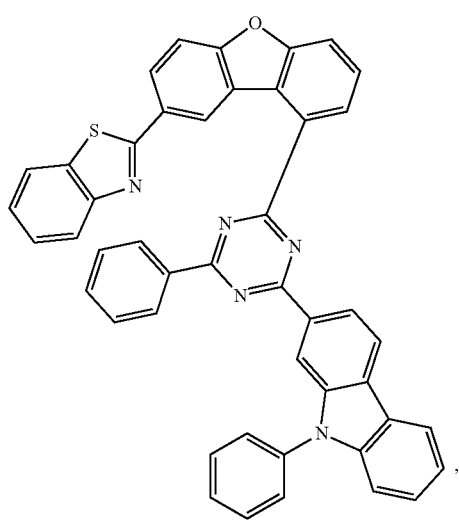

473
-continued
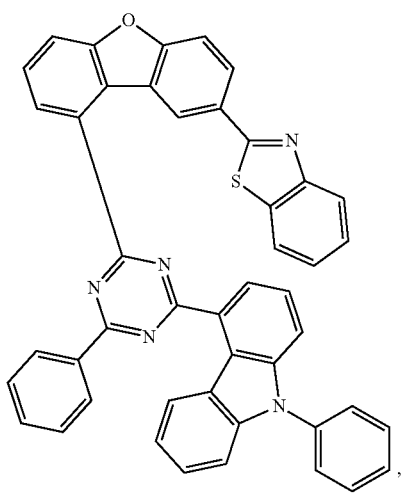
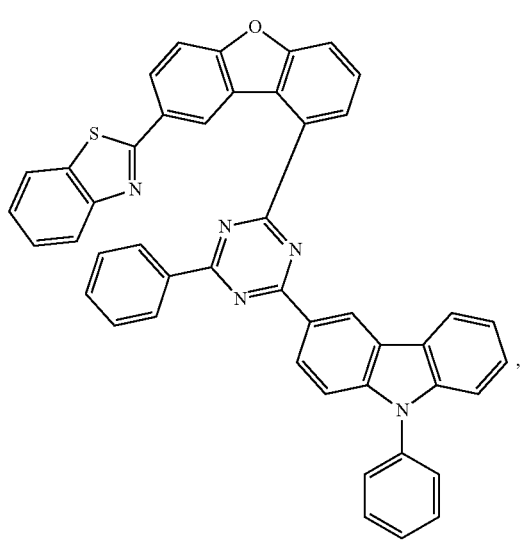
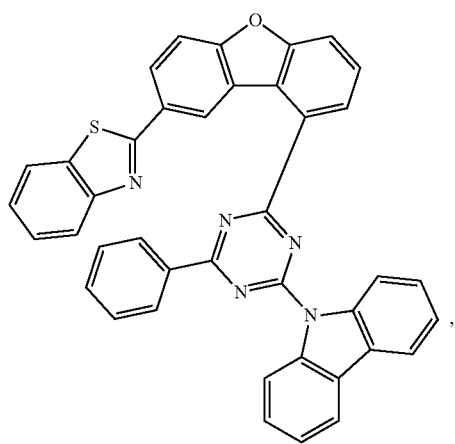
474
-continued
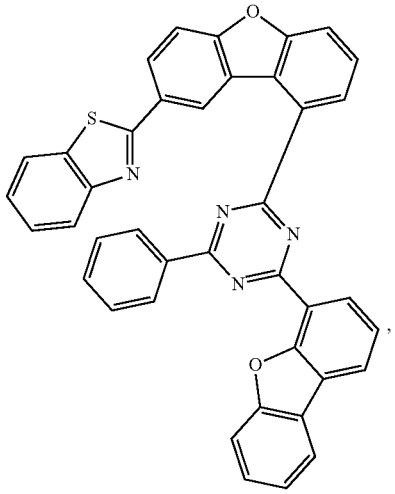
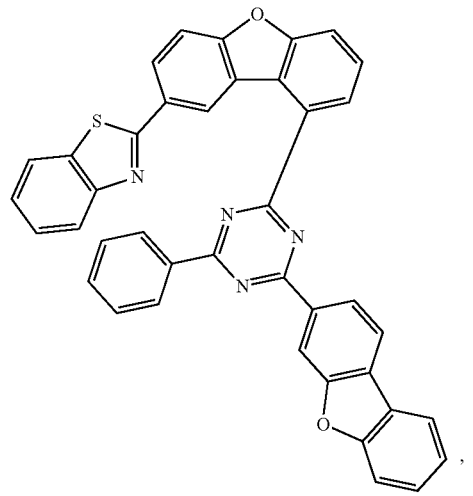
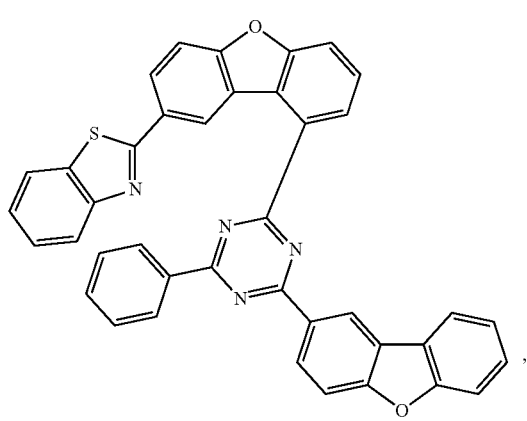

475
-continued
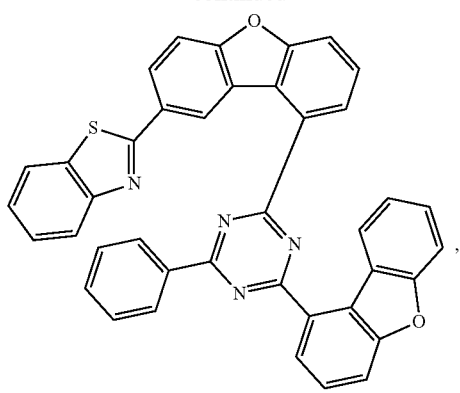
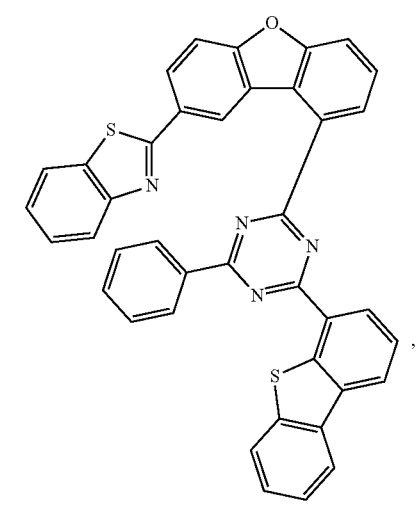
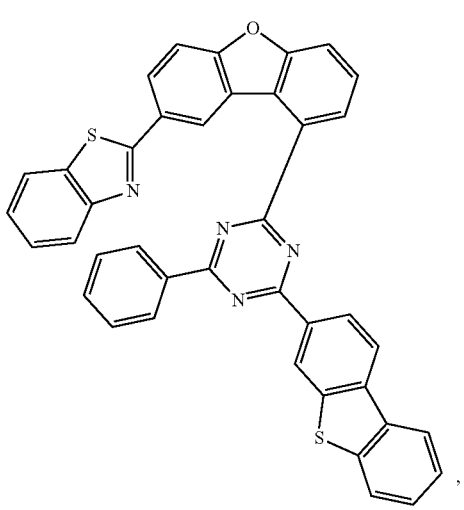
476
-continued
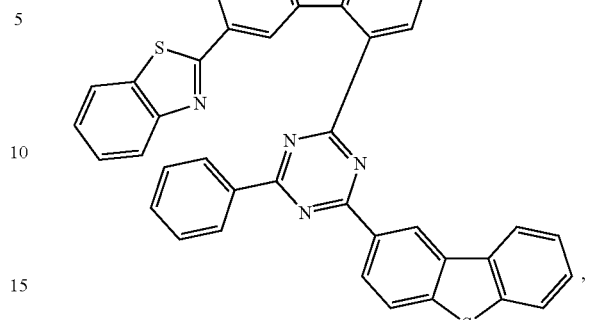
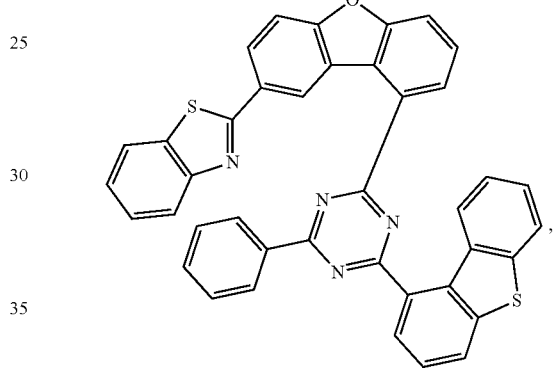
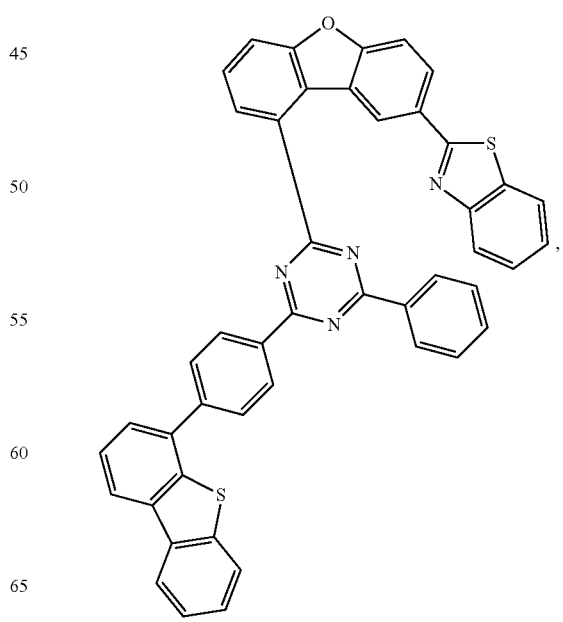

477
-continued
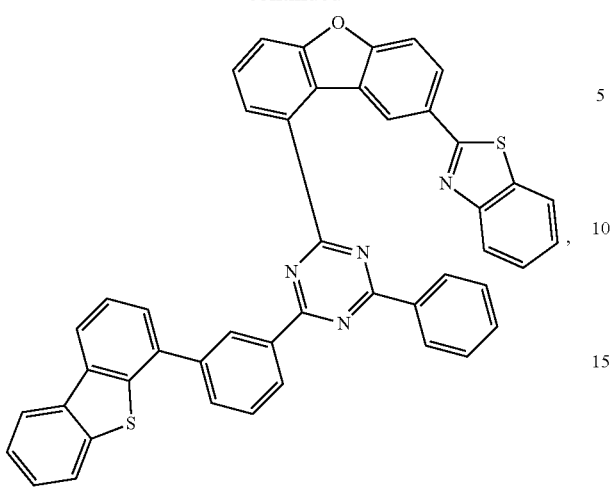
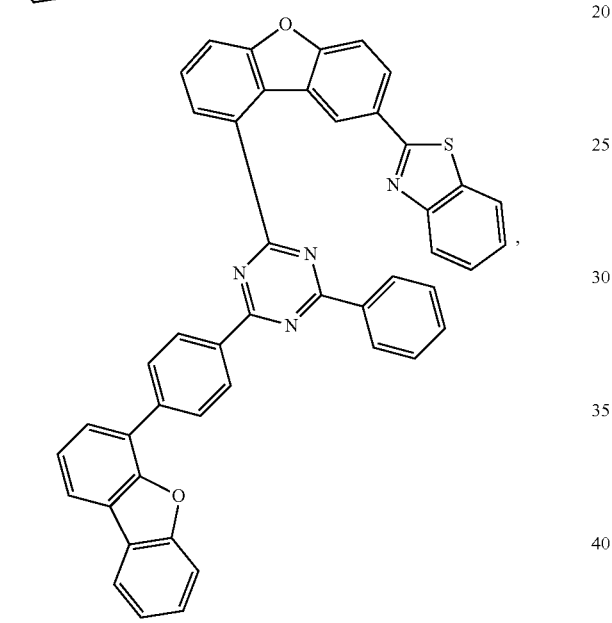
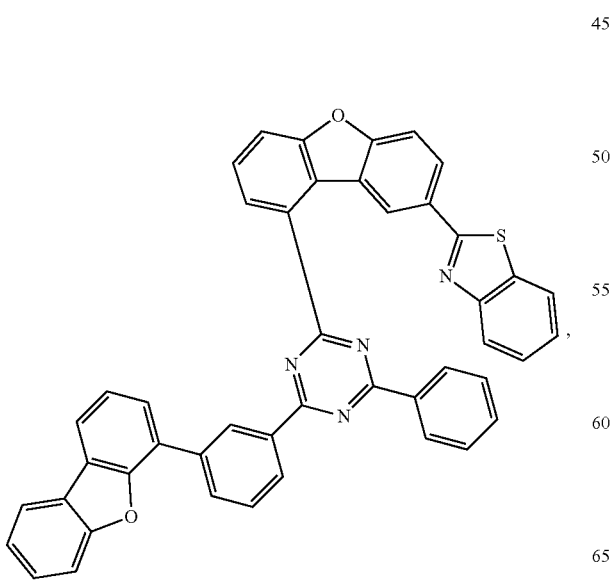
478
-continued
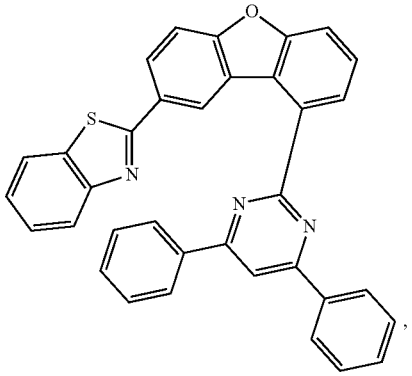
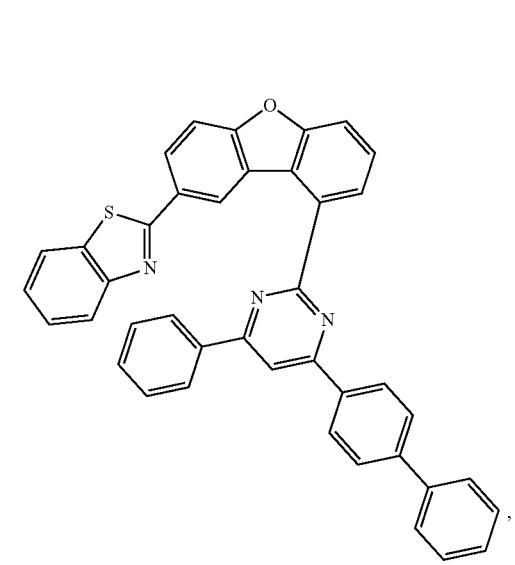
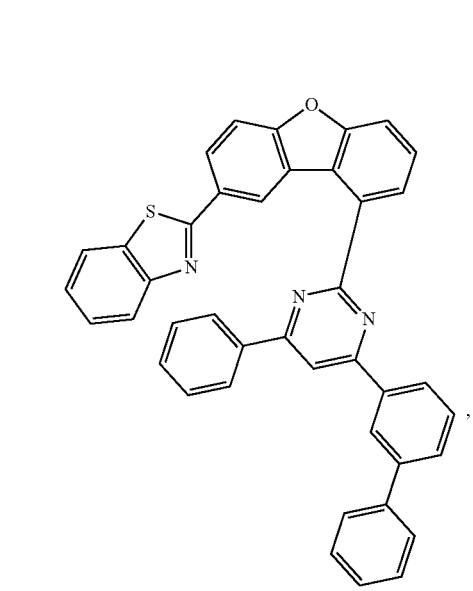

479
-continued
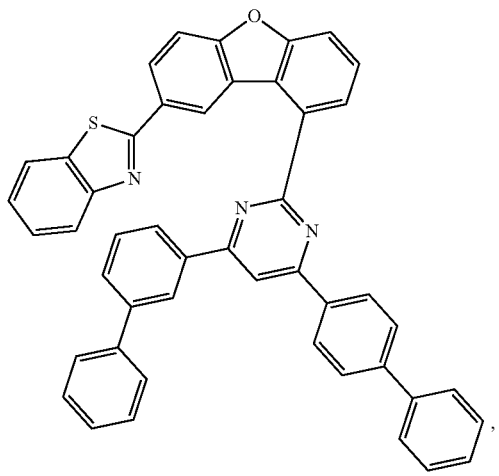
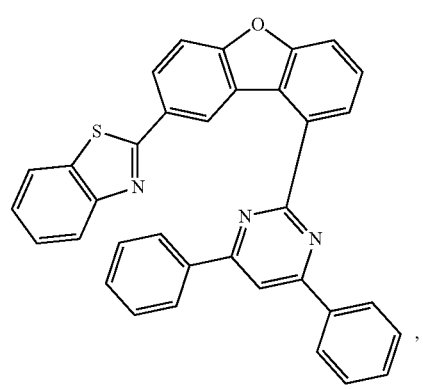
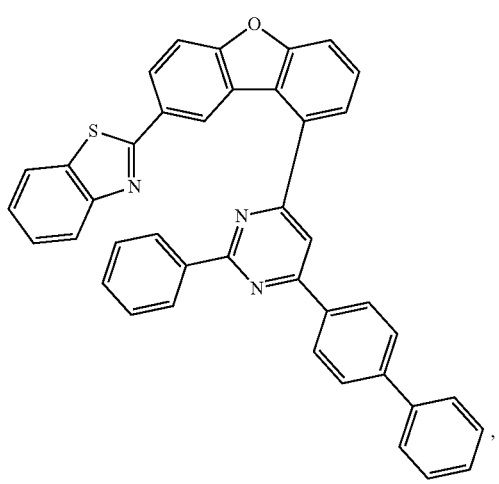
480
-continued
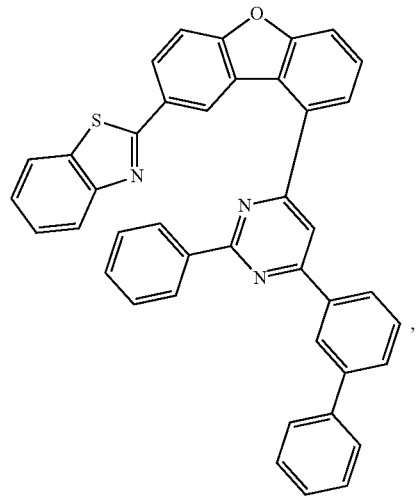
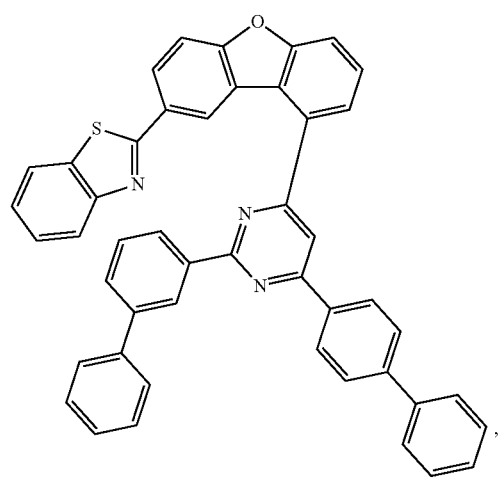
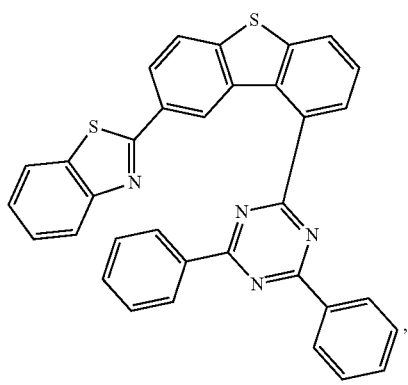

481
-continued
482
-continued
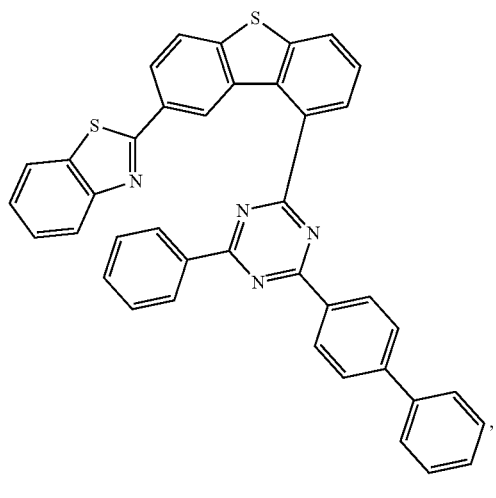
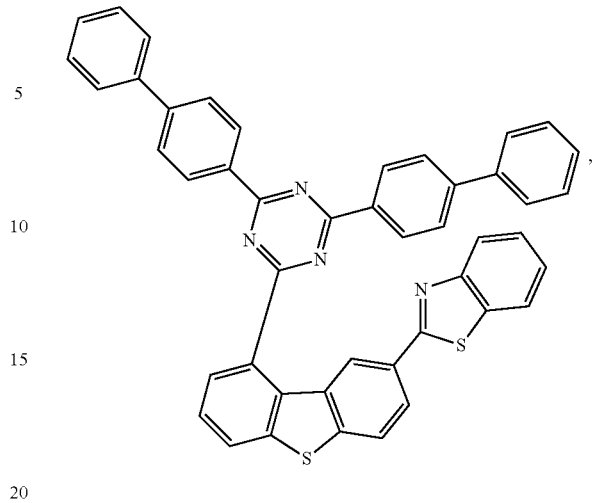
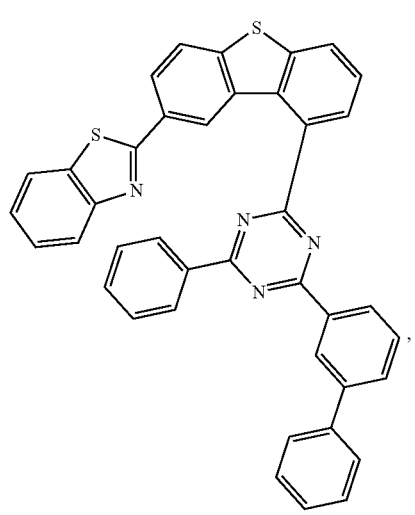
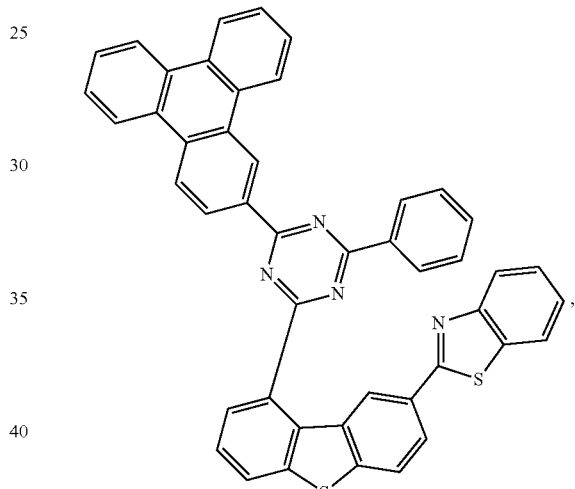
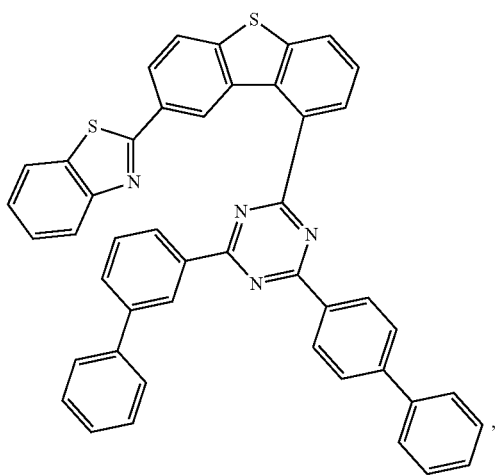
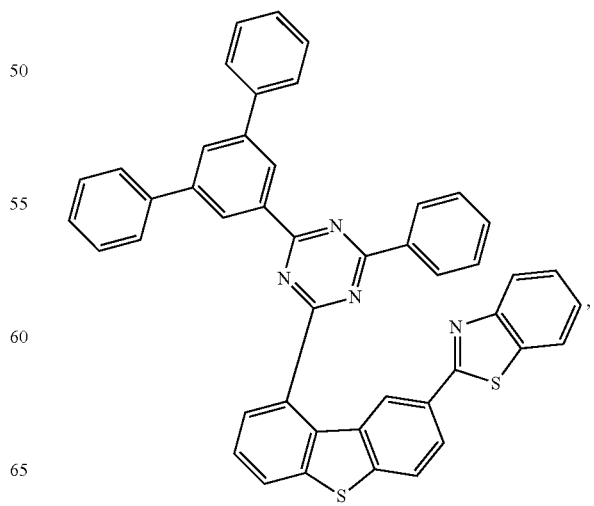

483
-continued
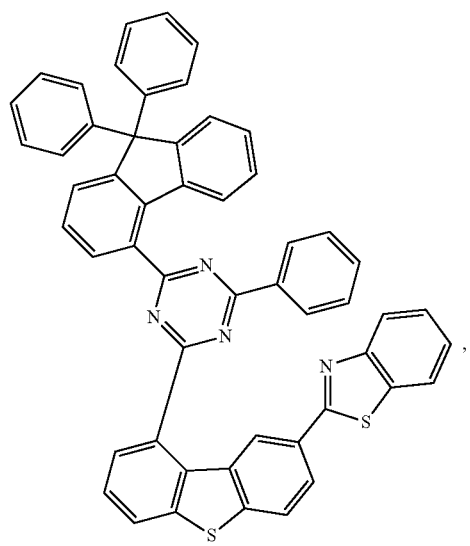
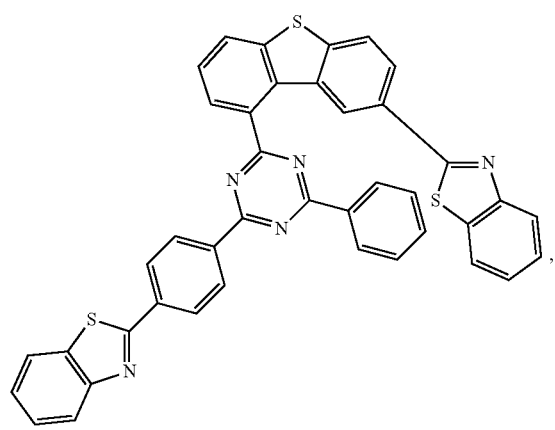
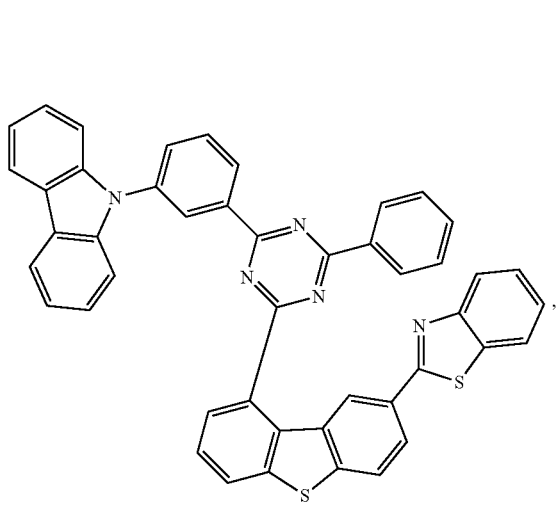
484
-continued
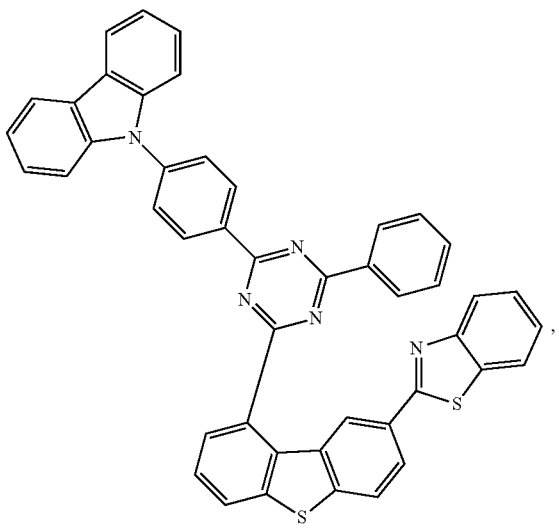
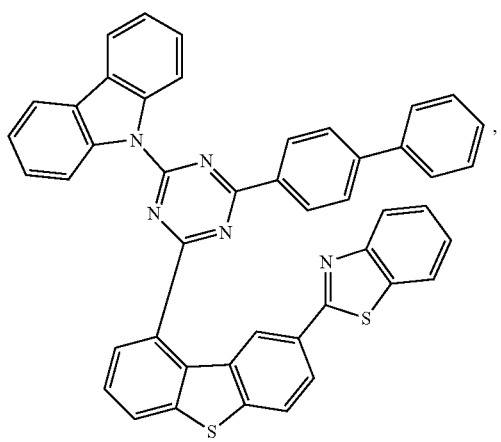
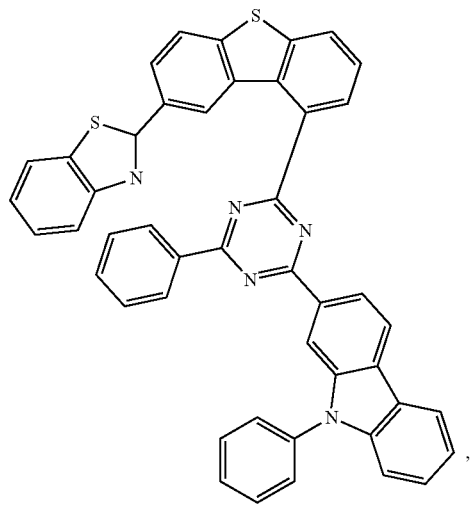

485
-continued
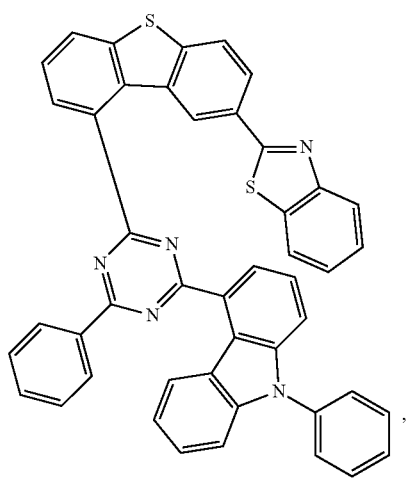
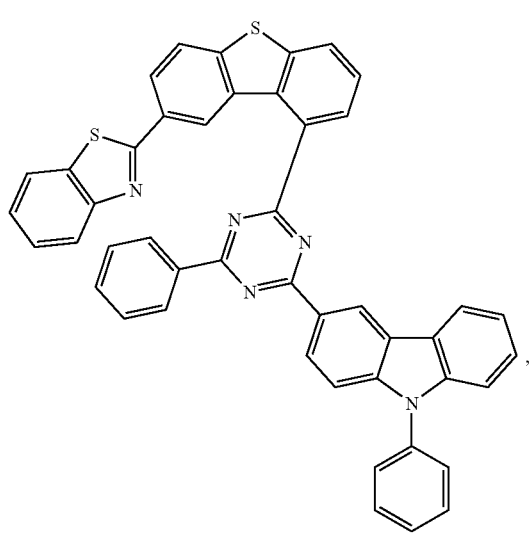
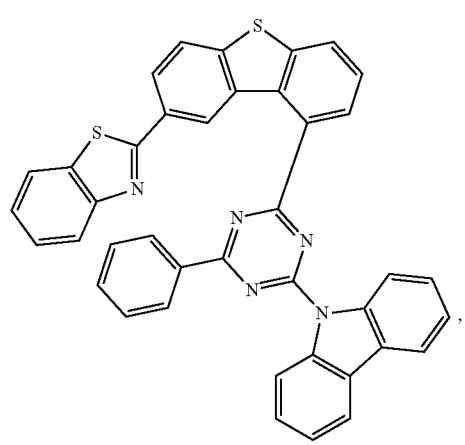
486
-continued
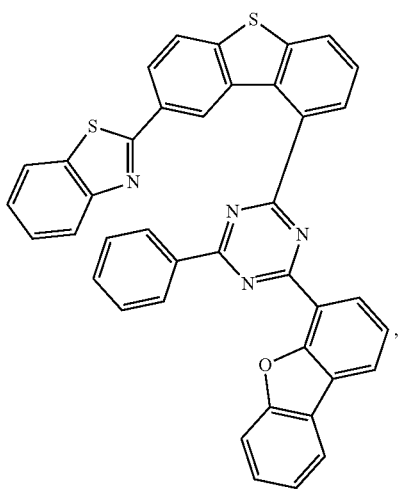
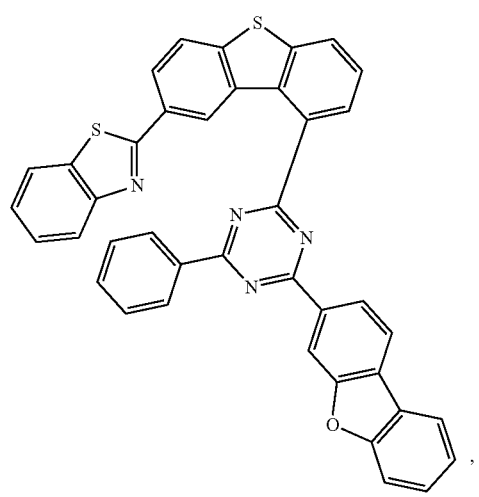
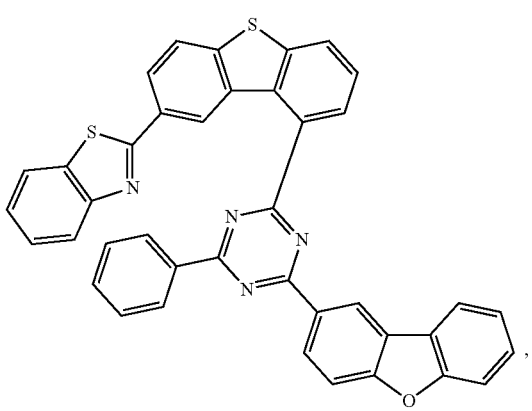

487
-continued
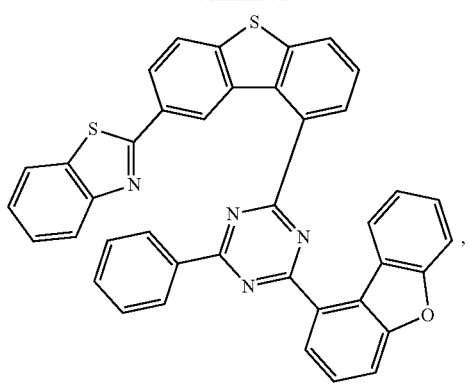
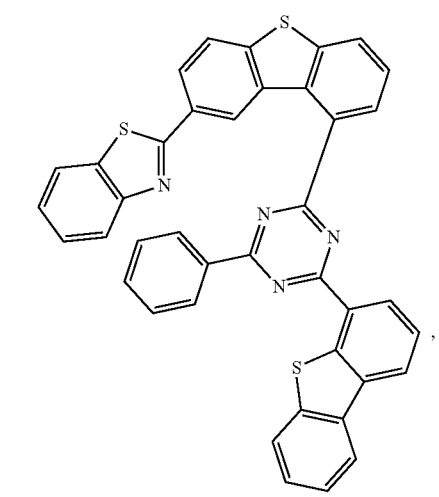
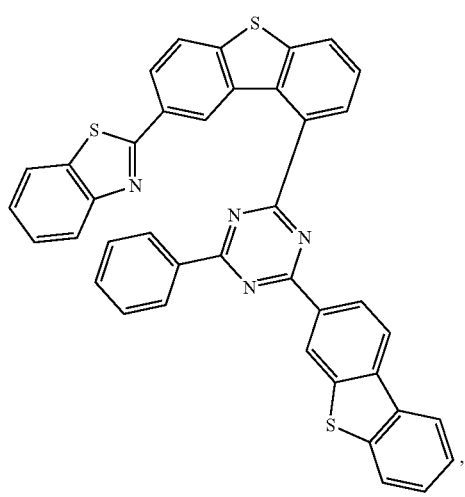
488
-continued
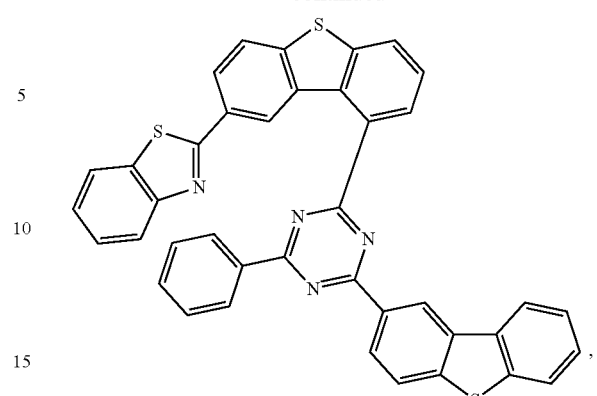
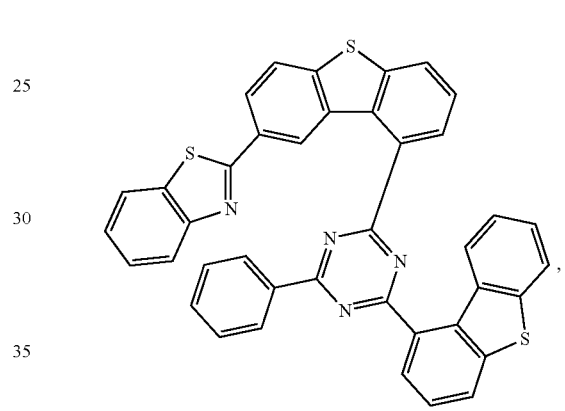
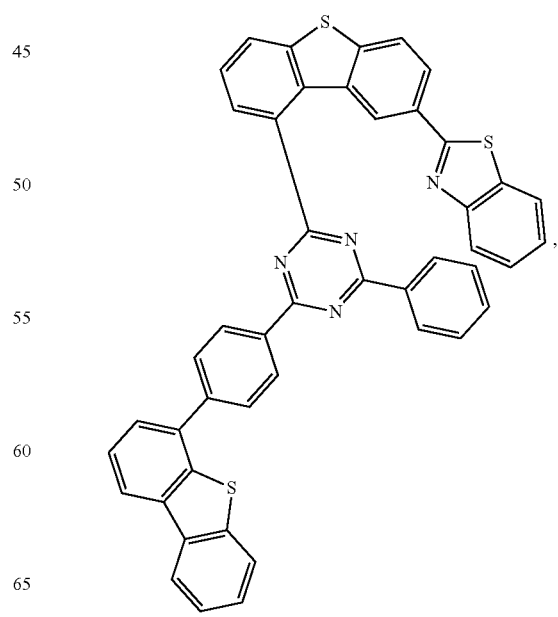

489
-continued
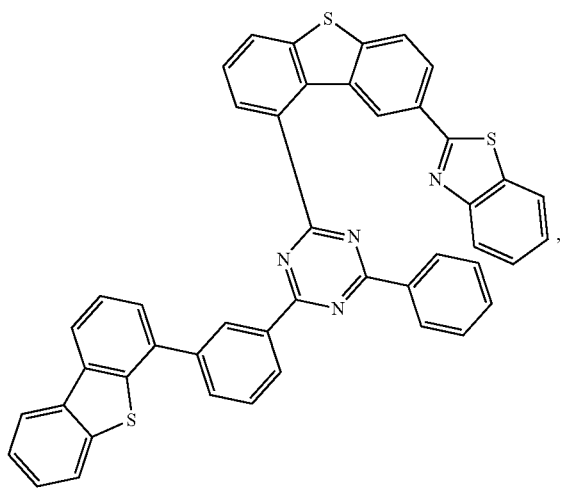,
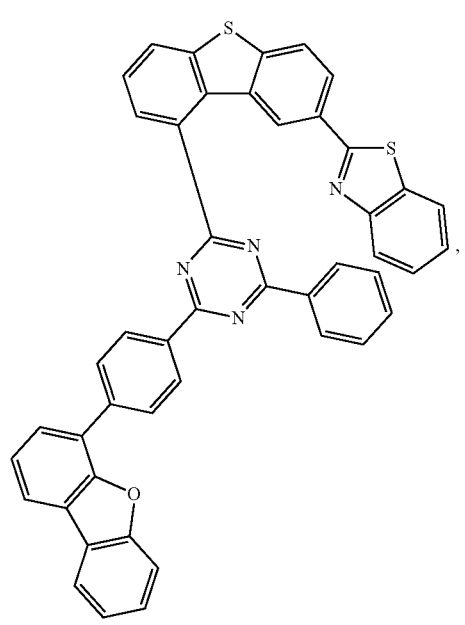,
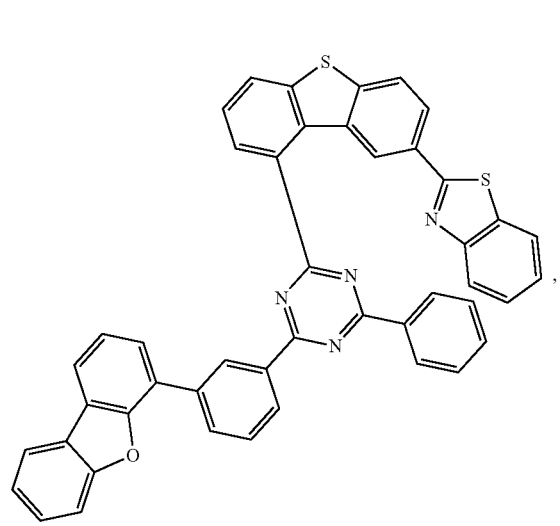,
490
-continued
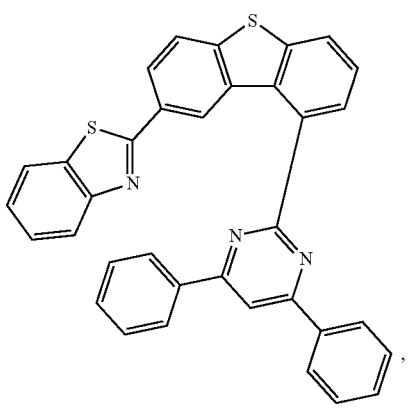,
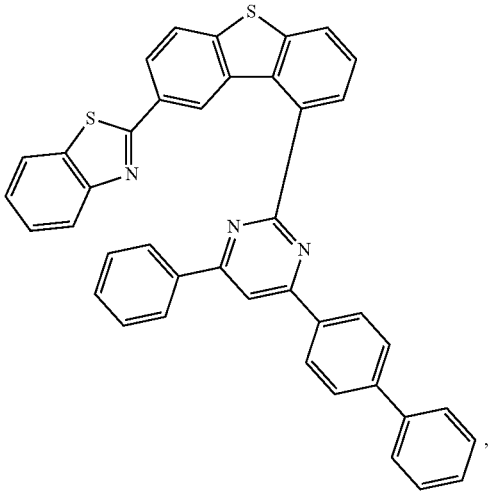,
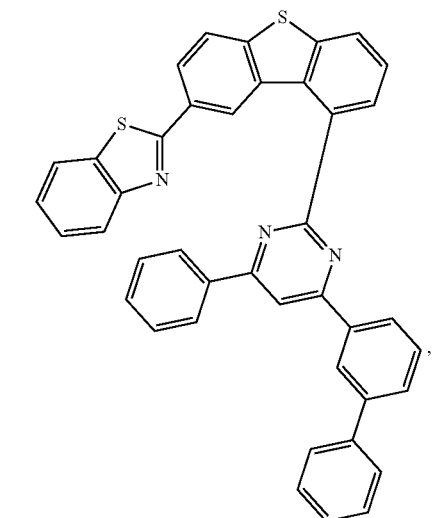, 491
-continued
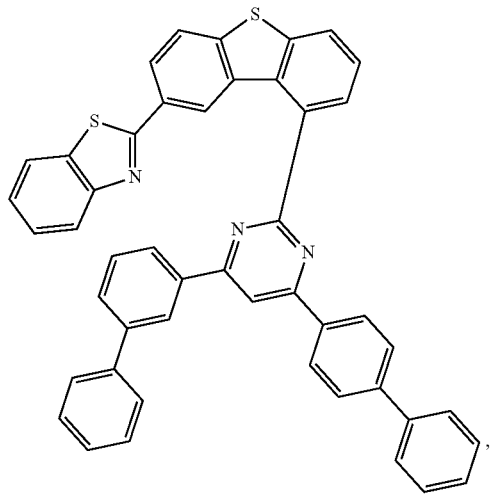
,
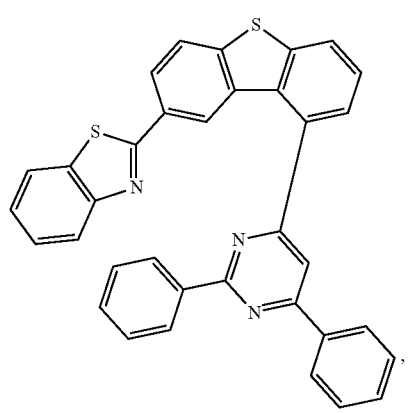
,
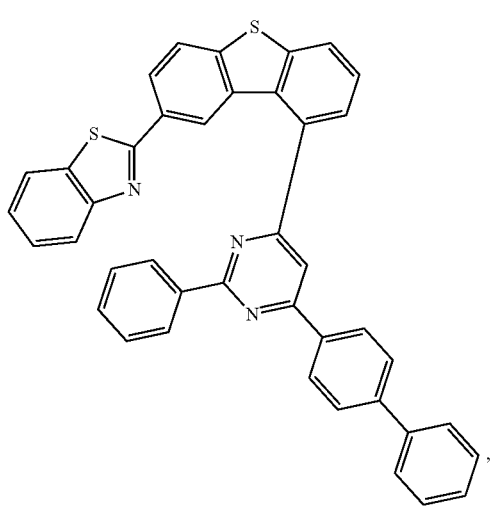
,
492
-continued
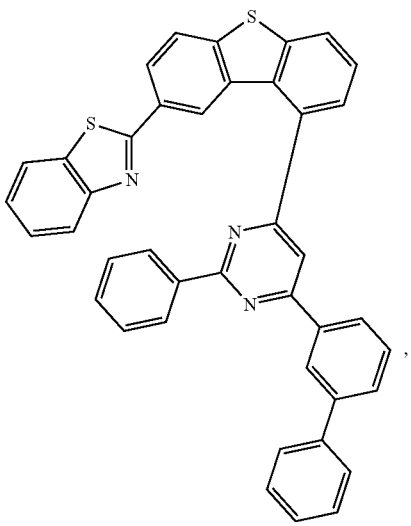
,
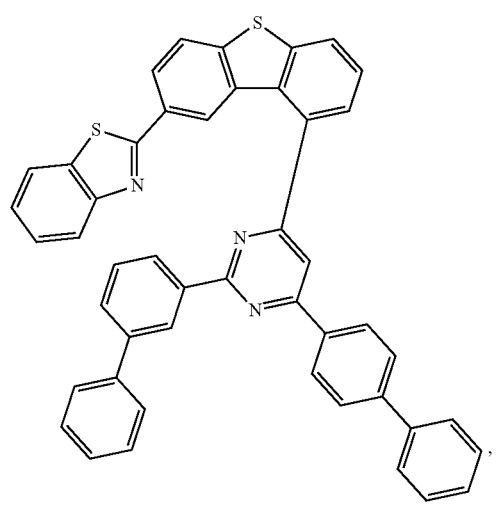
,
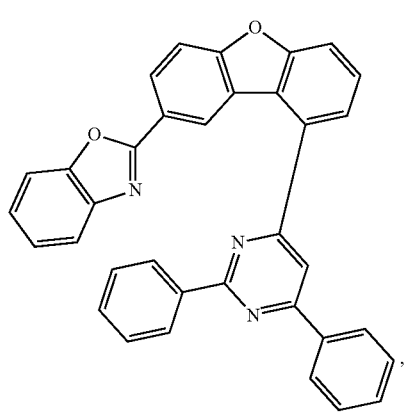
, 493
-continued
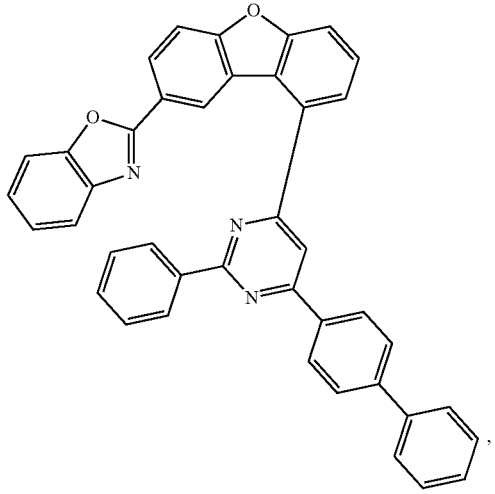
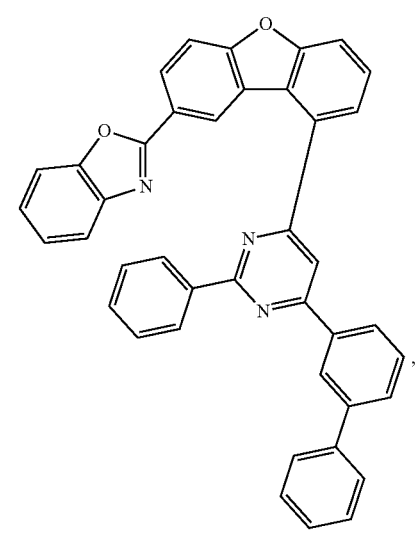
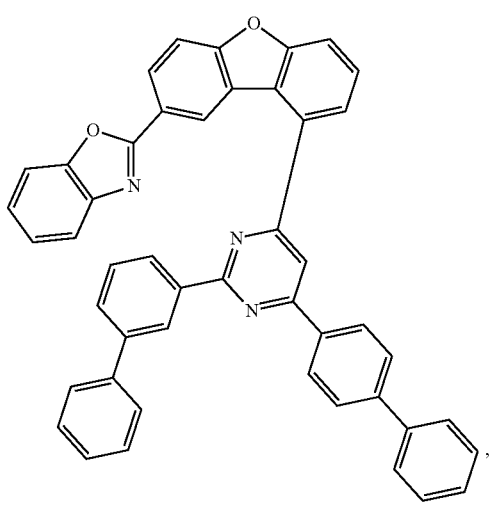
494
-continued
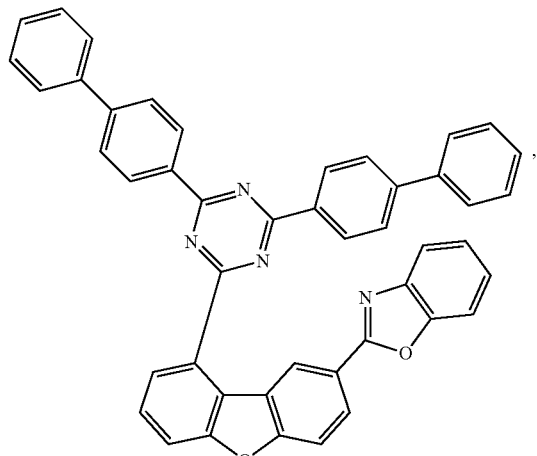
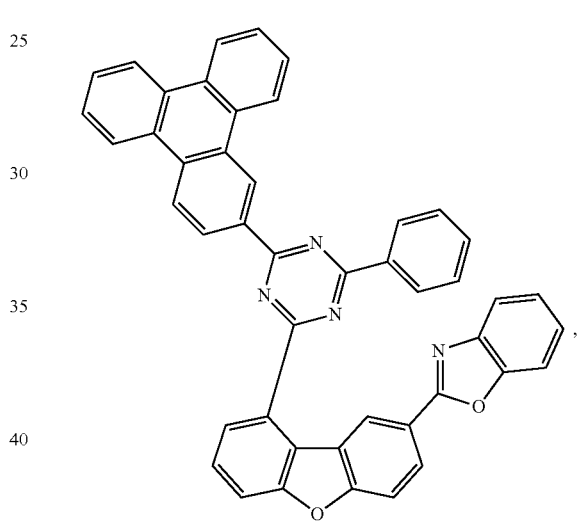
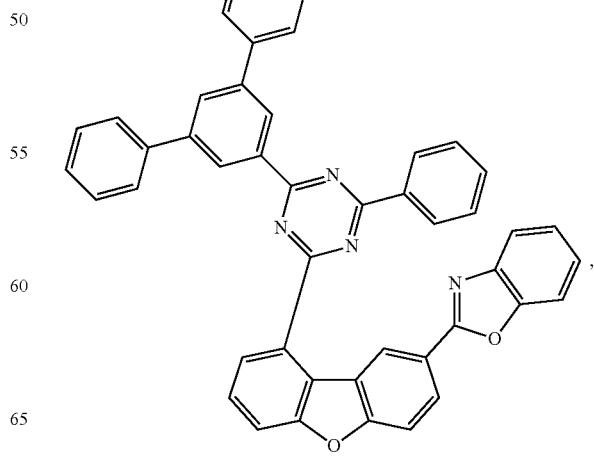

495
-continued
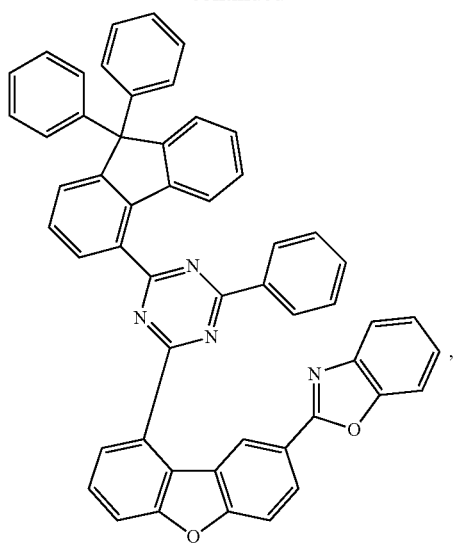
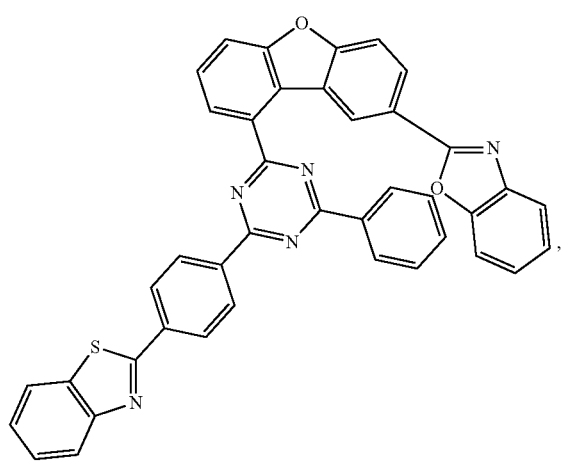
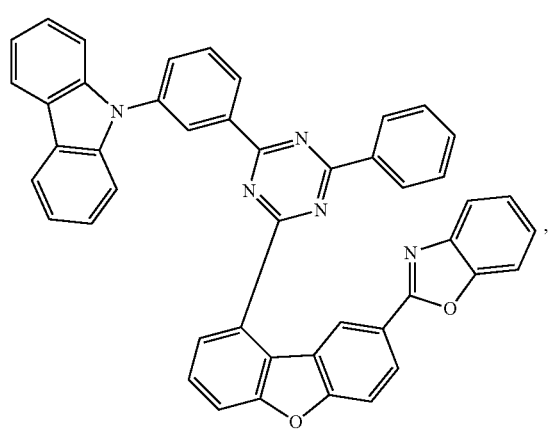
496
-continued
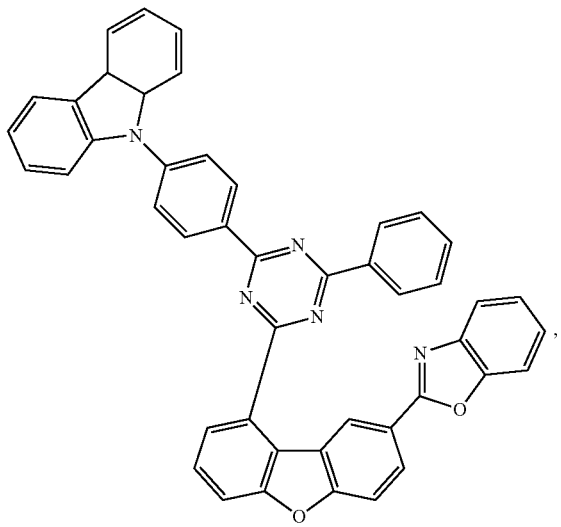
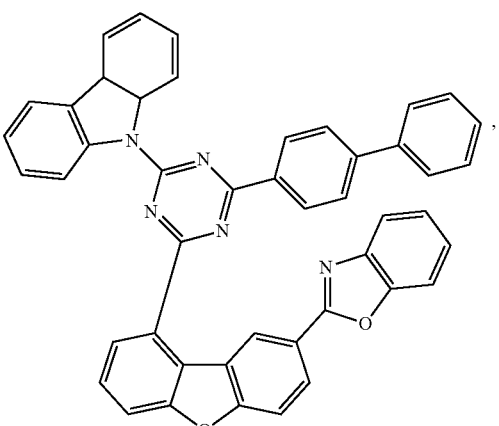
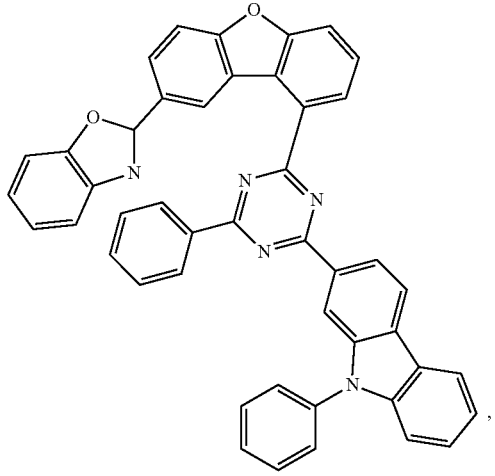

497
-continued
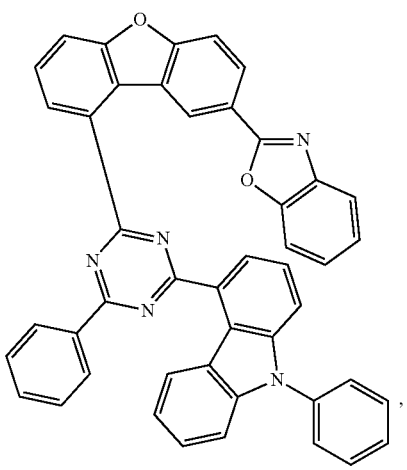
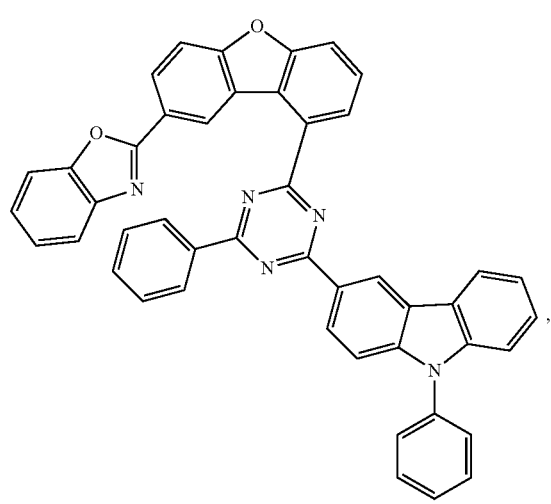
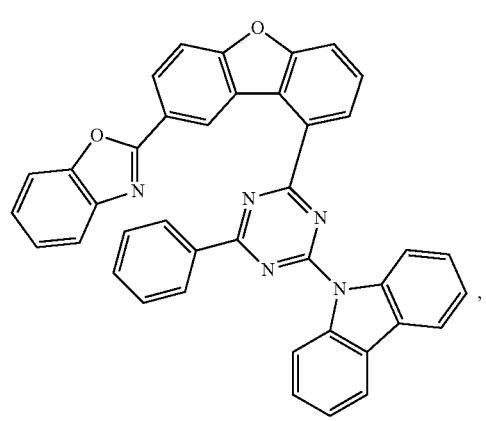
498
-continued
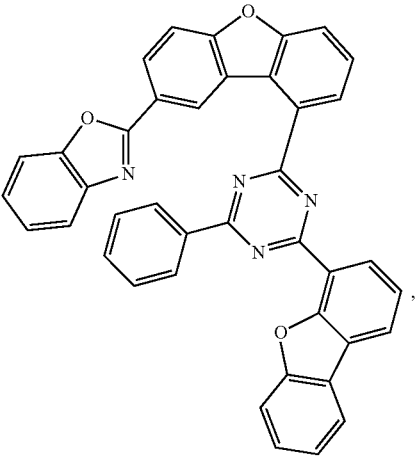
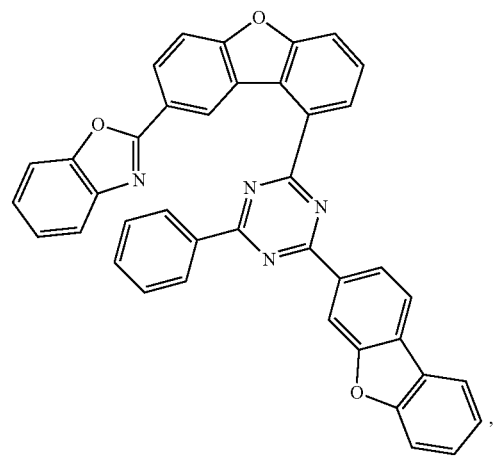
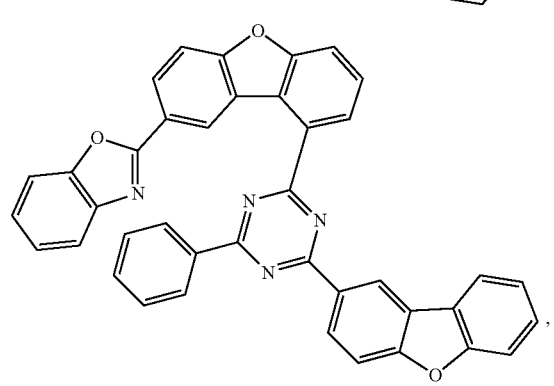
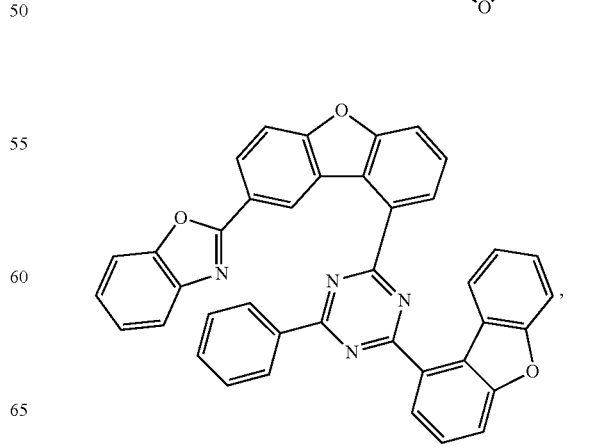

499
-continued
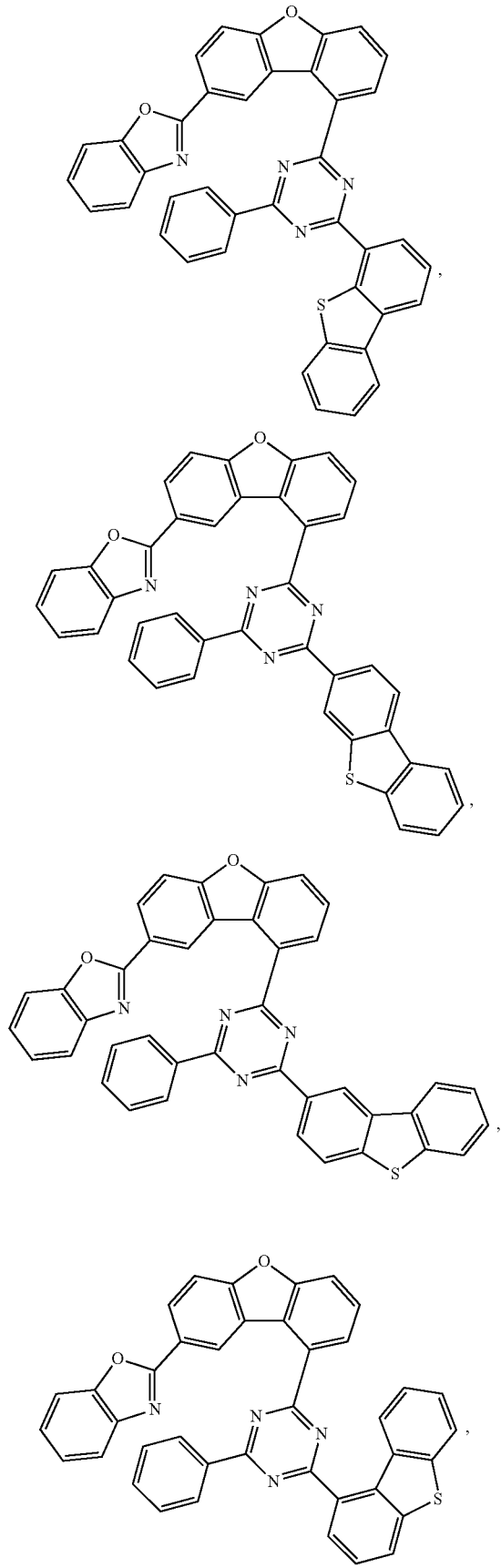
500
-continued
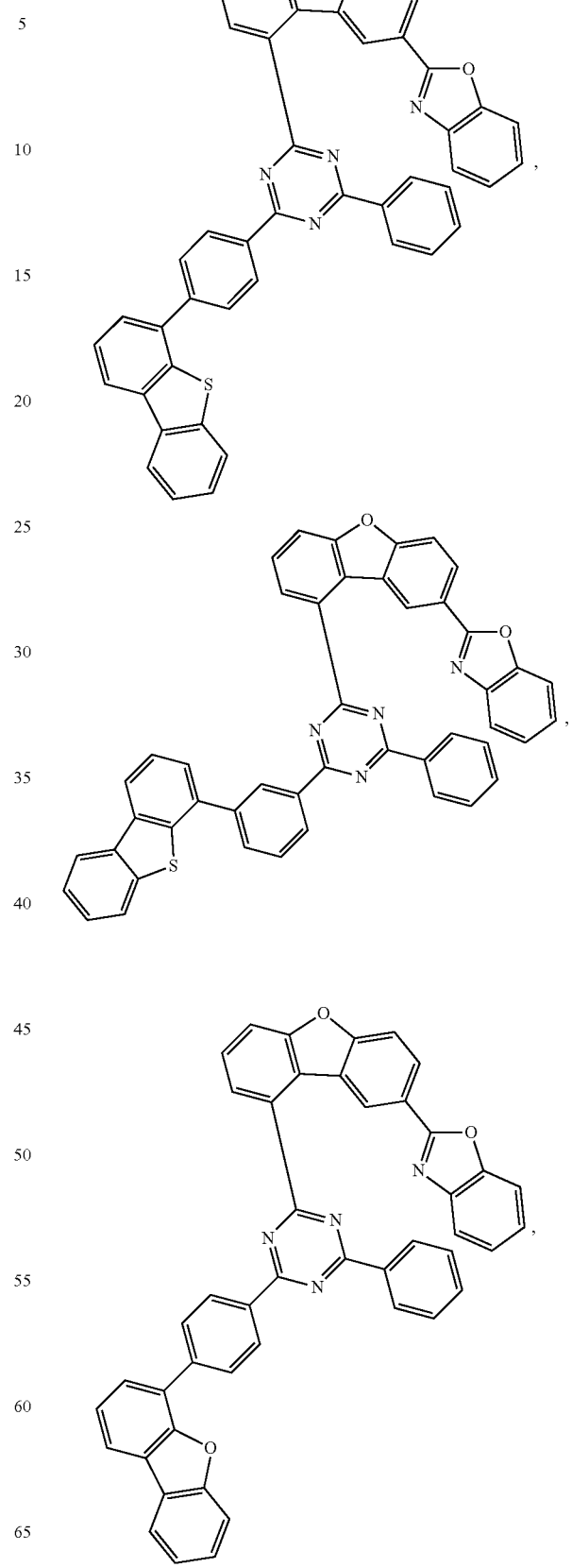

501
-continued
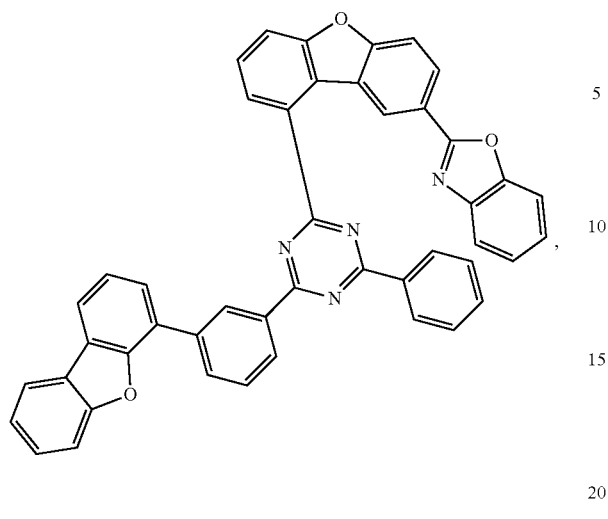
,
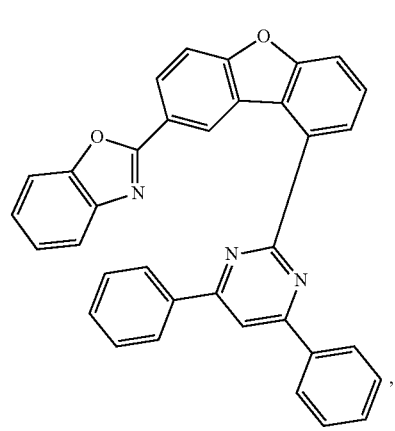
,
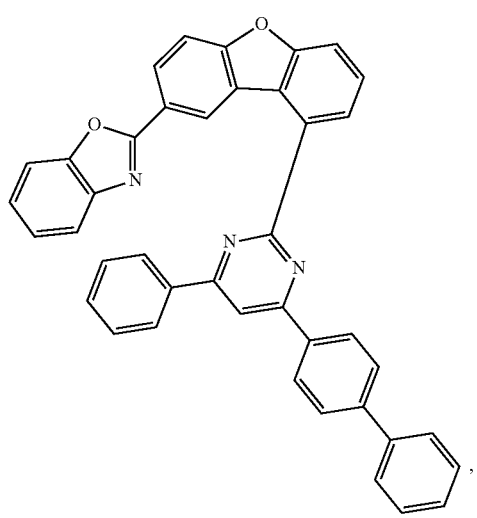
,
502
-continued
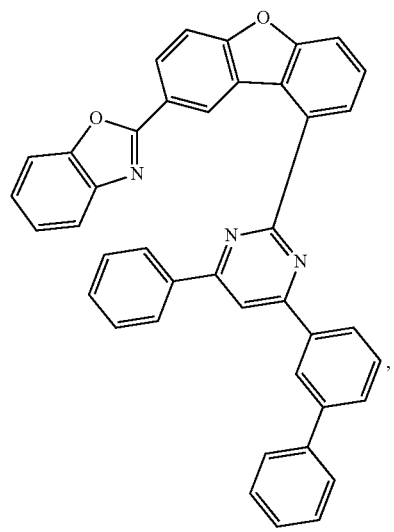
,
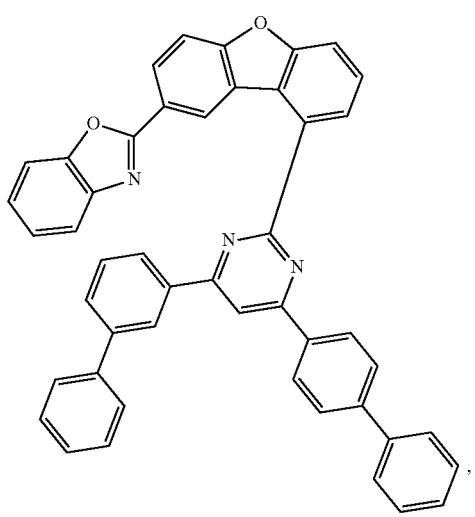
,
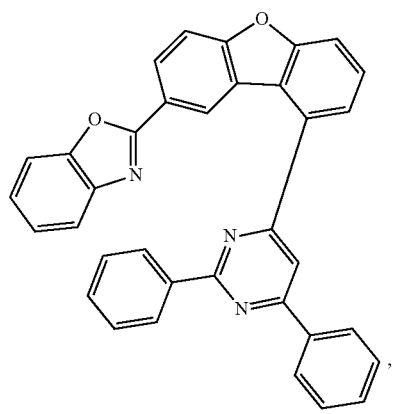
, 503
-continued
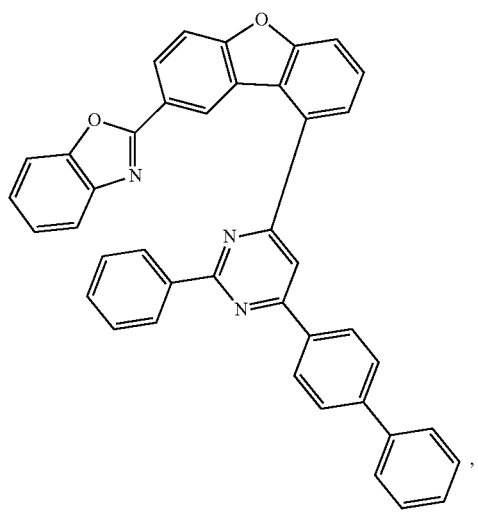
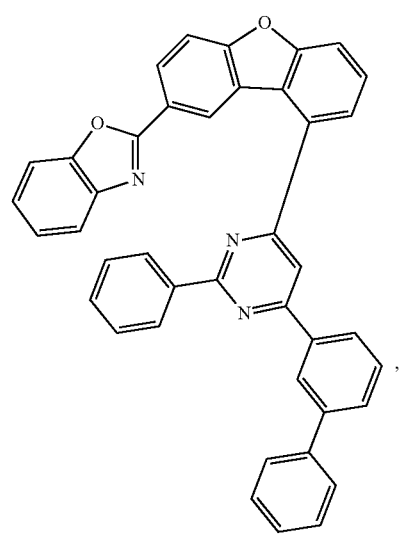
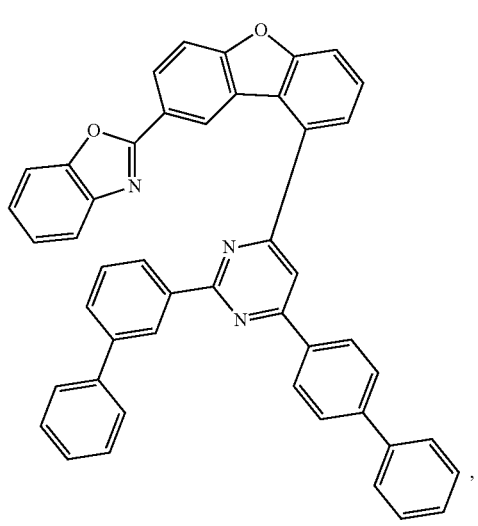
504
-continued
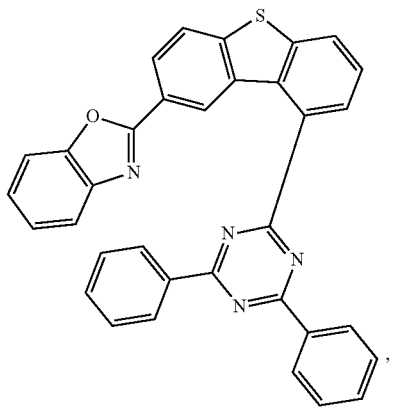
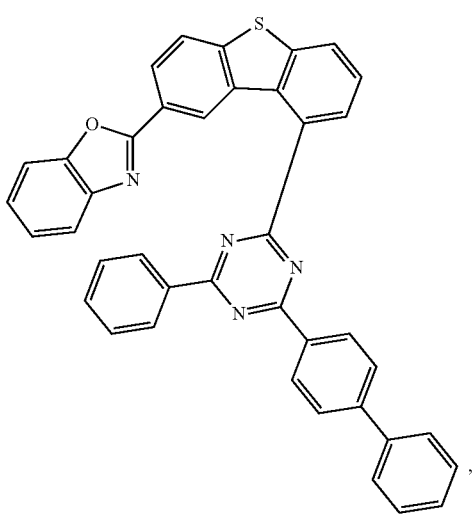
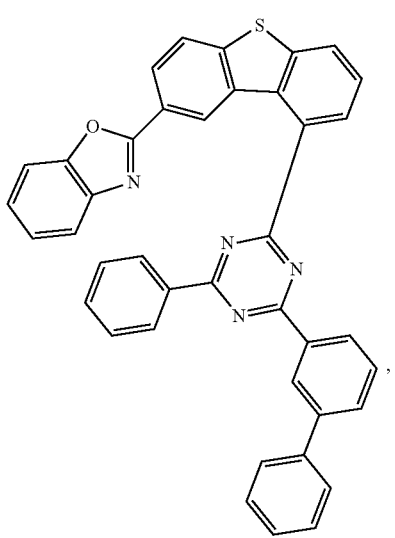

505
-continued
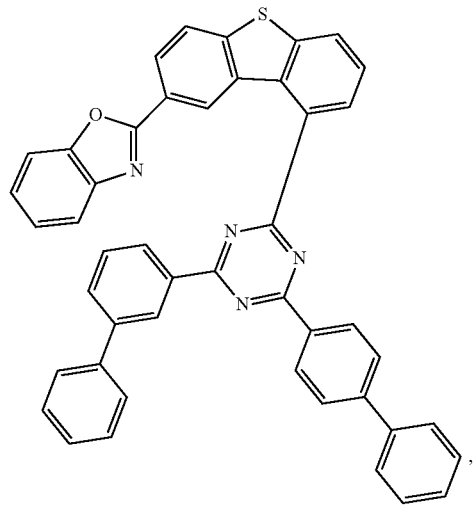
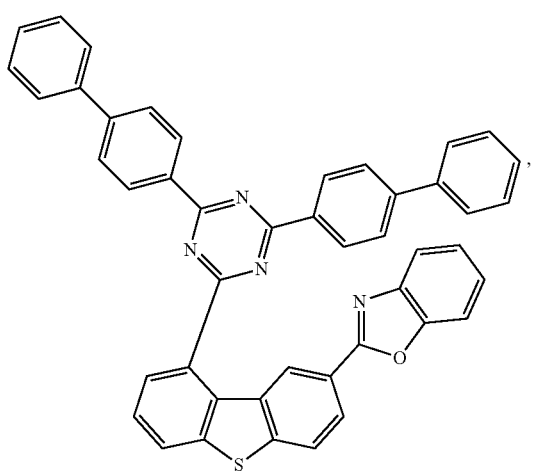
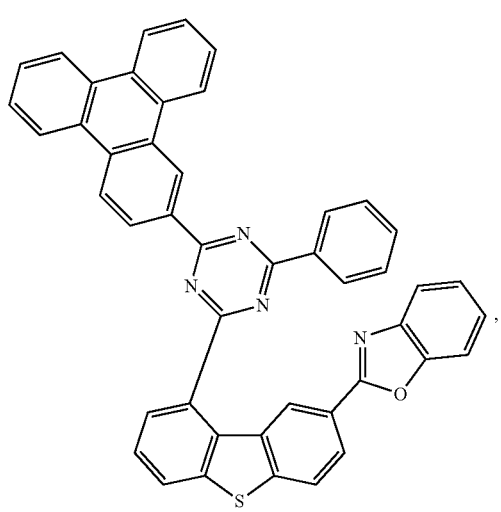
506
-continued
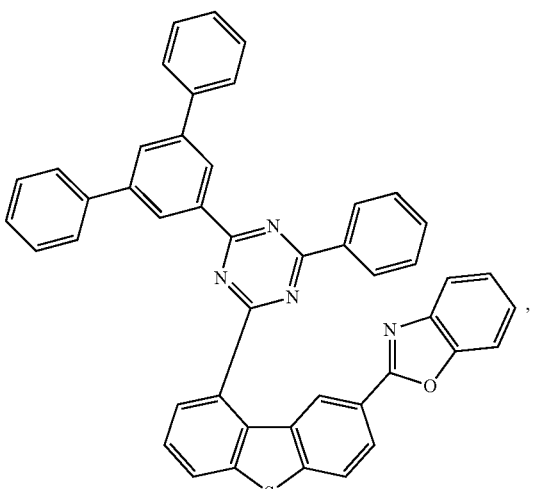
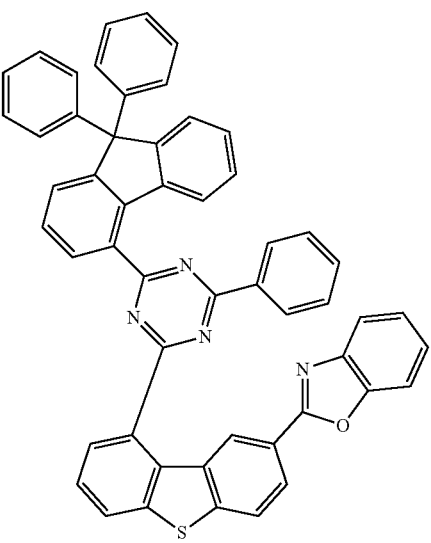
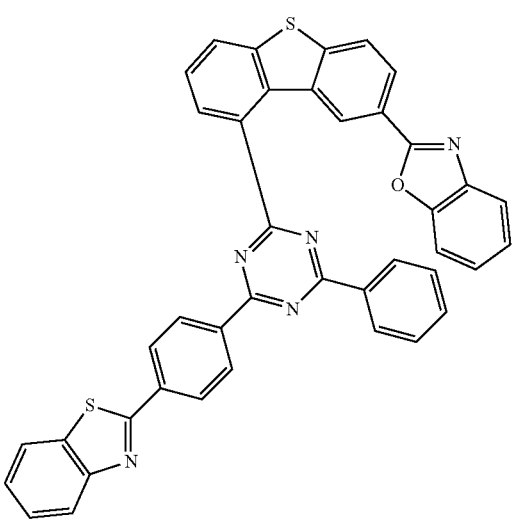

507
-continued
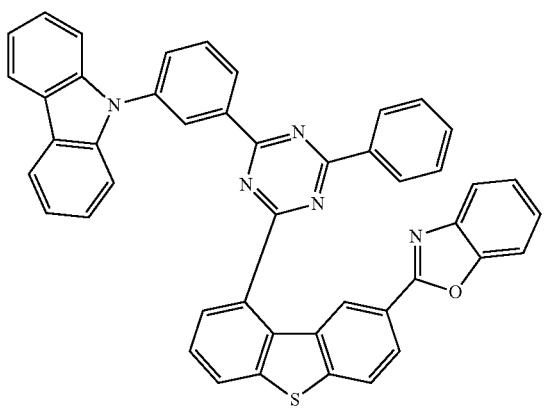
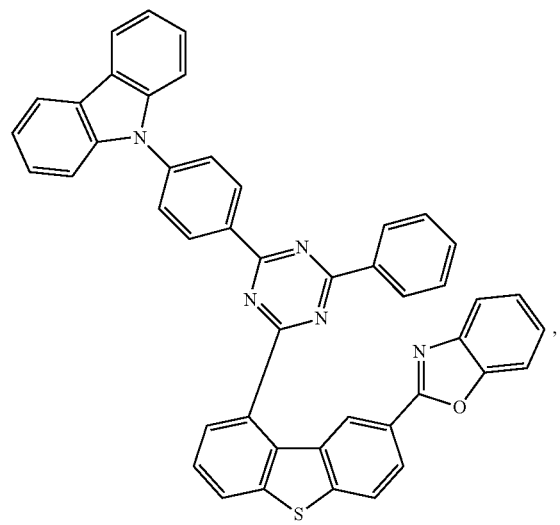
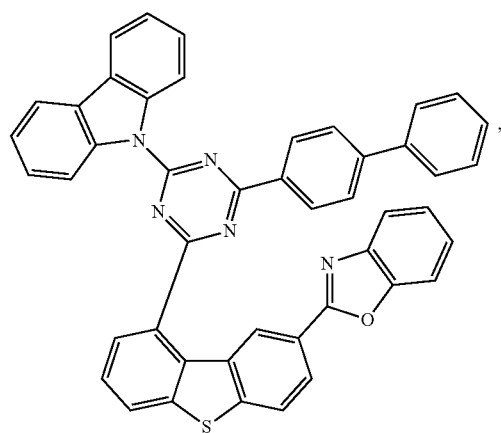
508
-continued
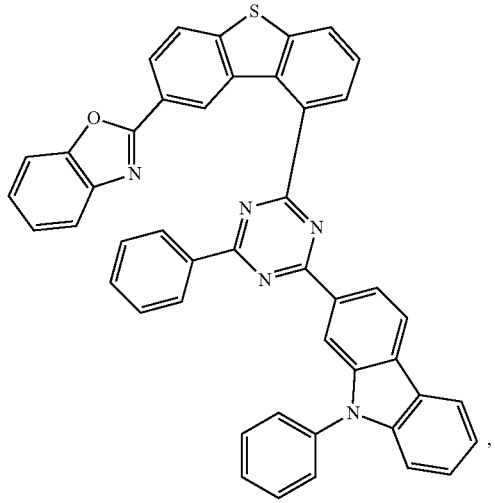
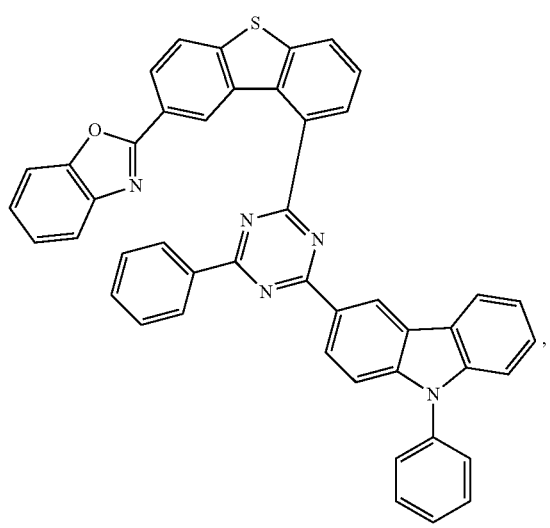

509
-continued
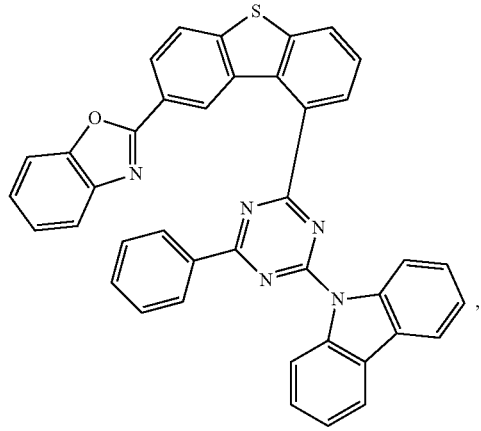
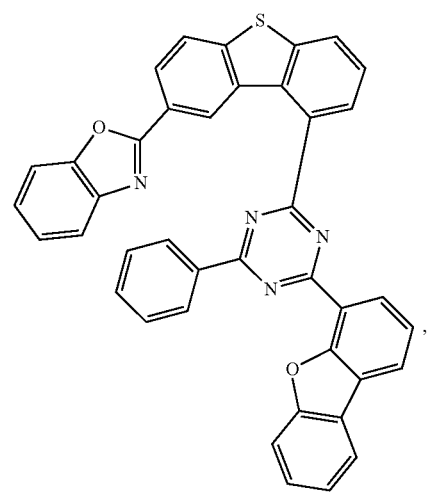
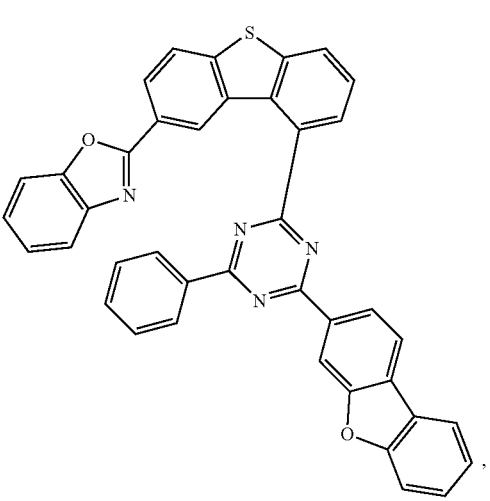
510
-continued
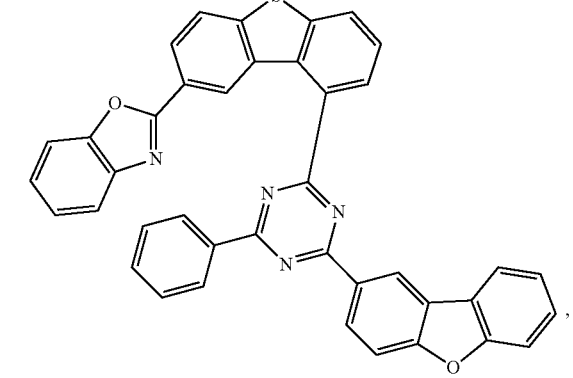
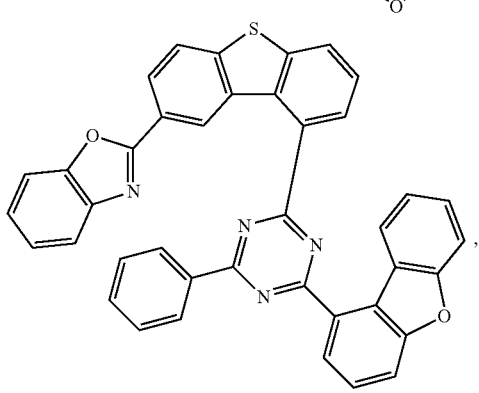
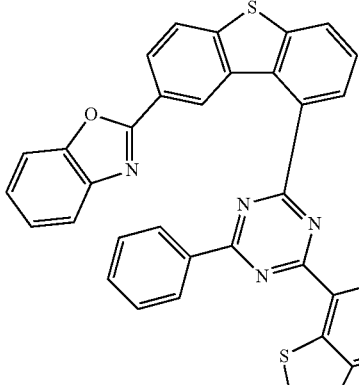
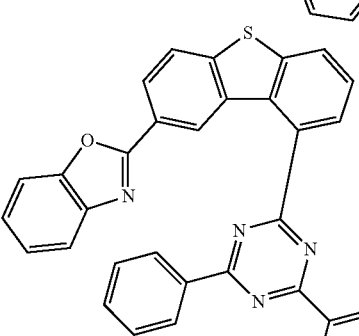

511
-continued
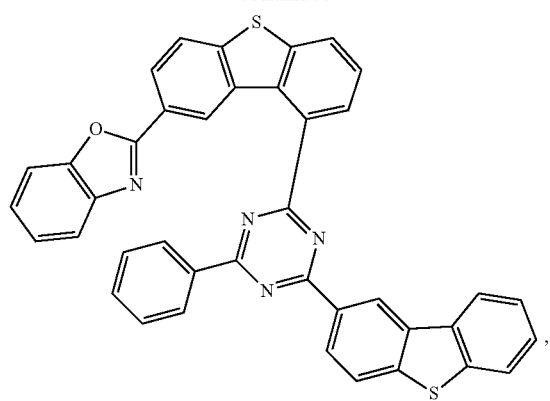
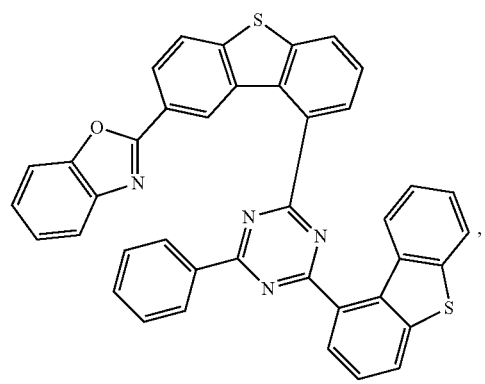
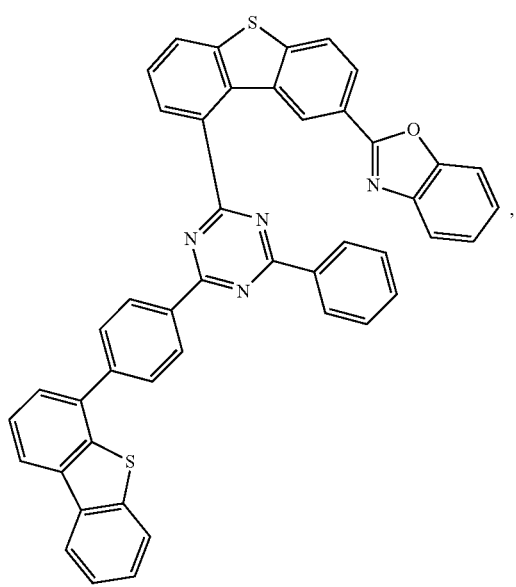
512
-continued
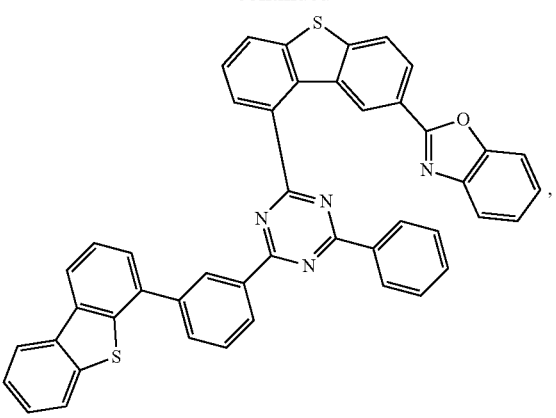
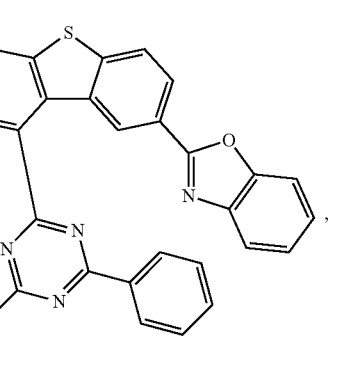
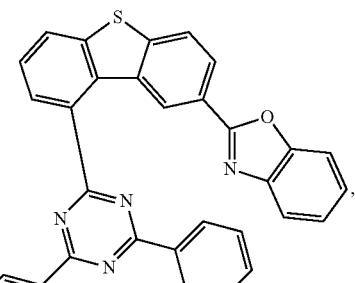

513
-continued
514
-continued
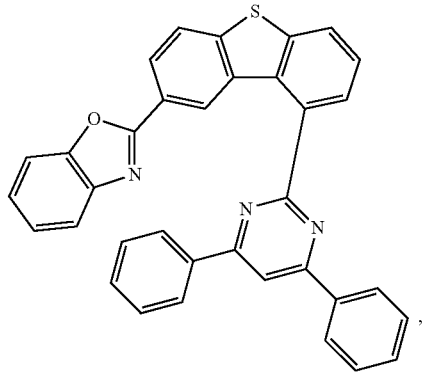
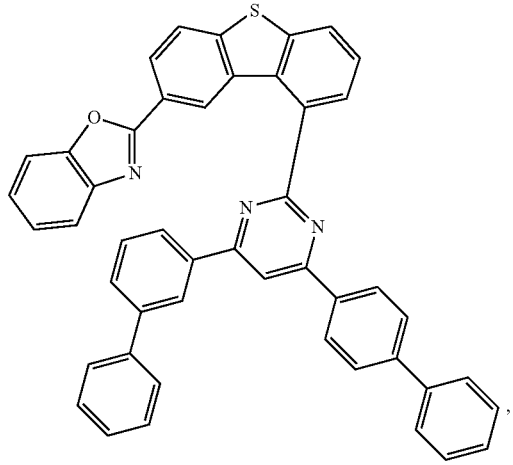
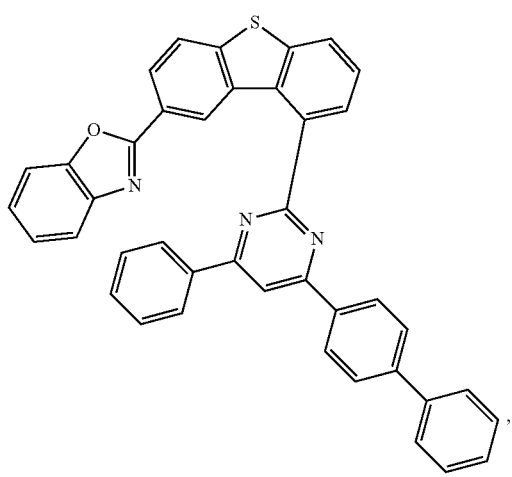
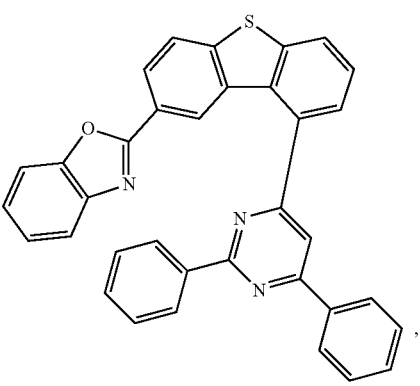
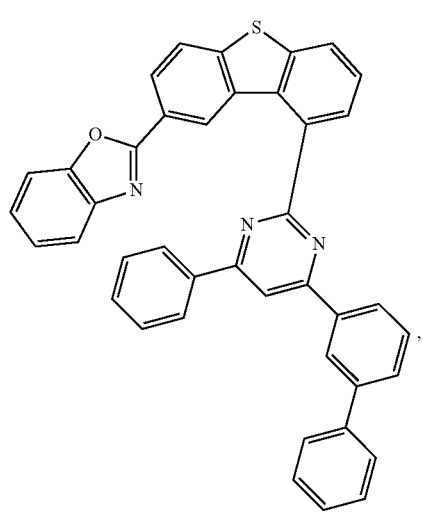
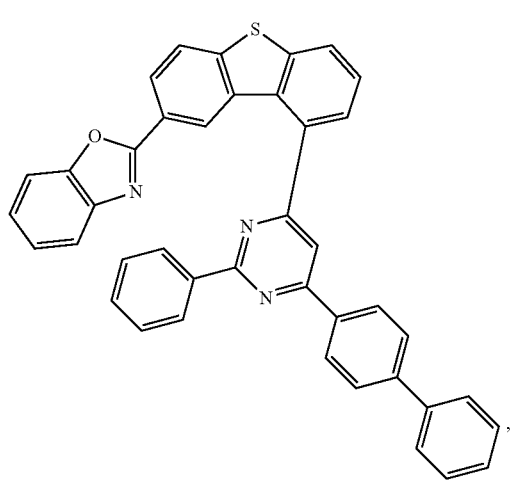

515
-continued
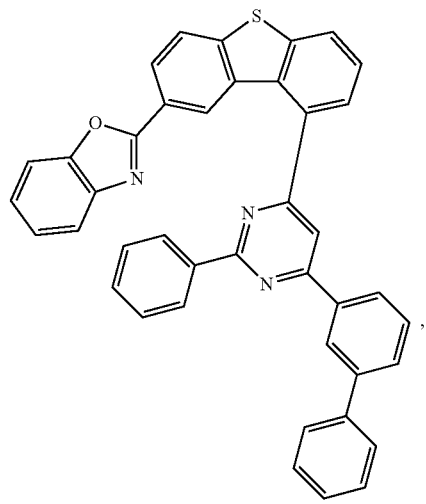
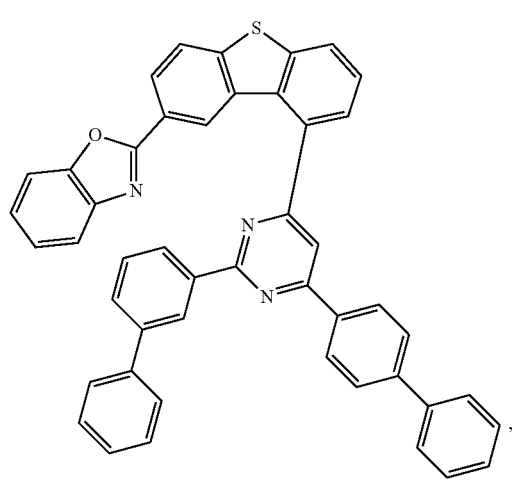
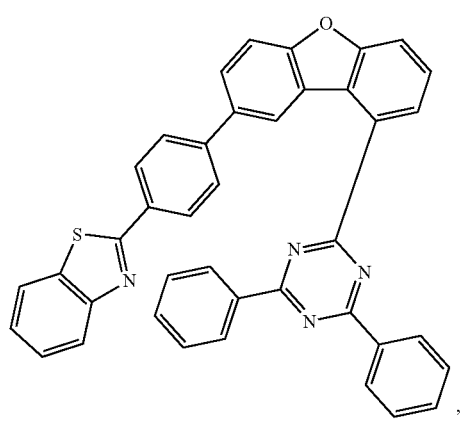
516
-continued
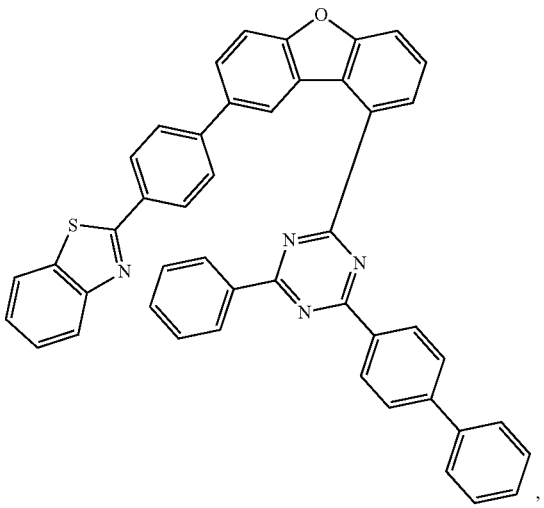
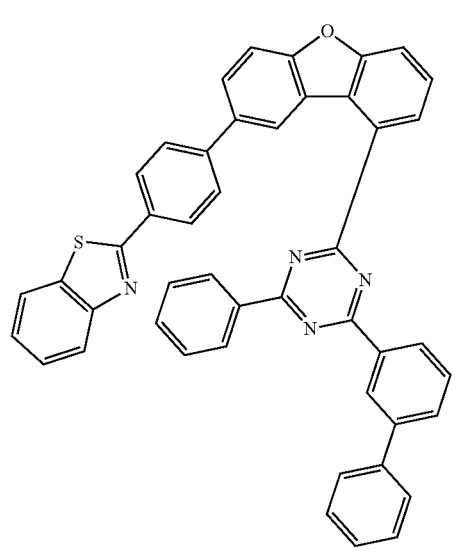
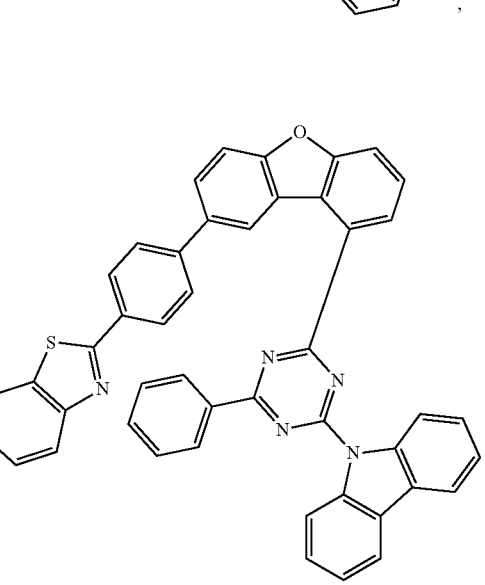

517
-continued
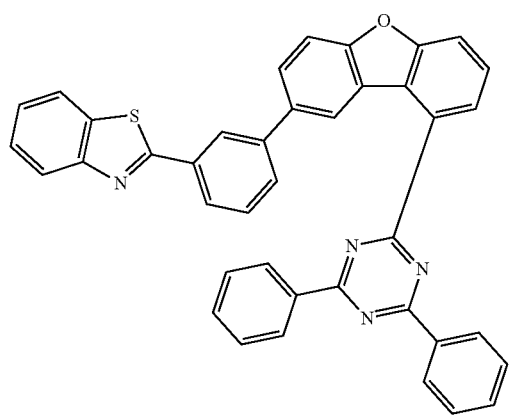
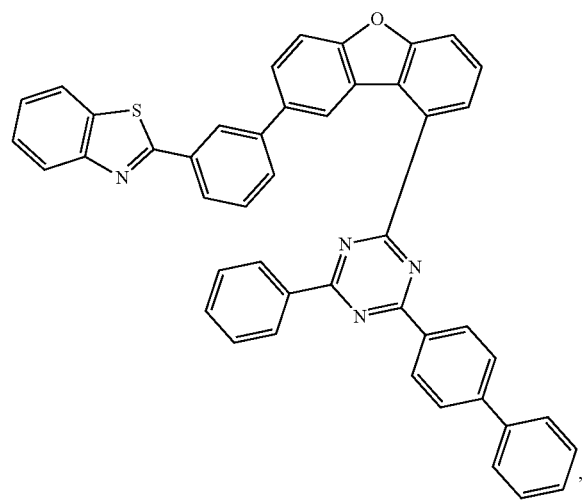
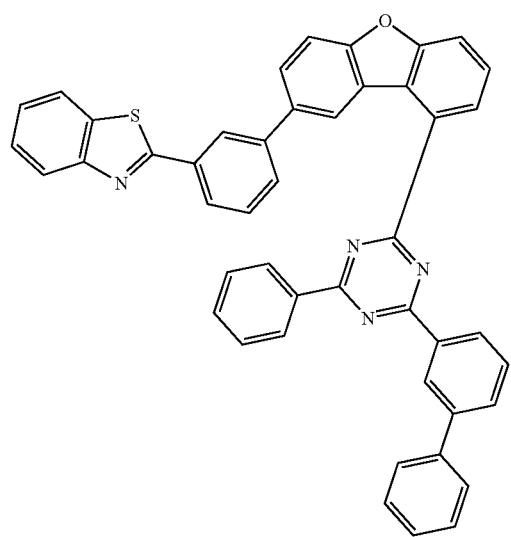
518
-continued
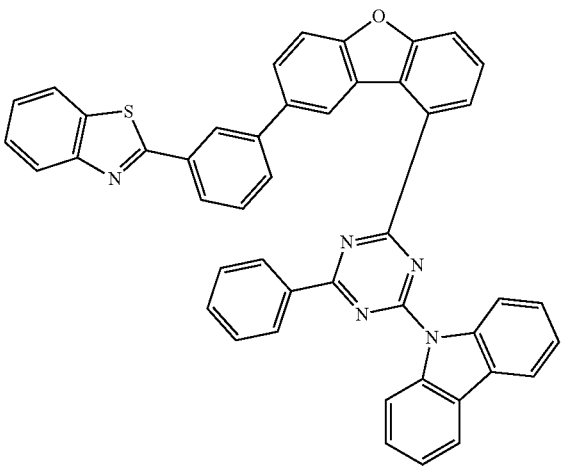
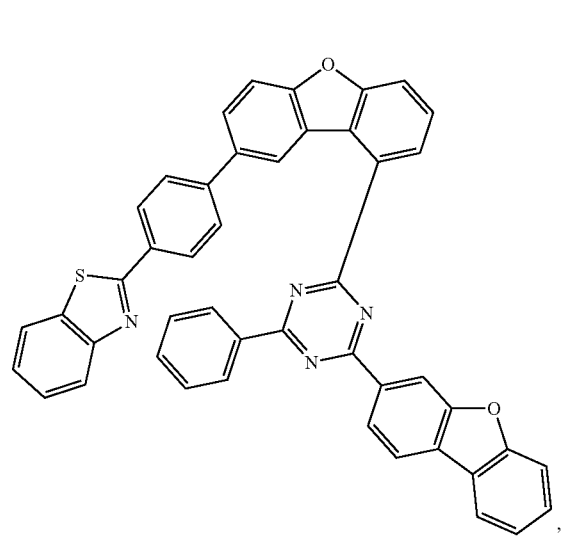

519
-continued
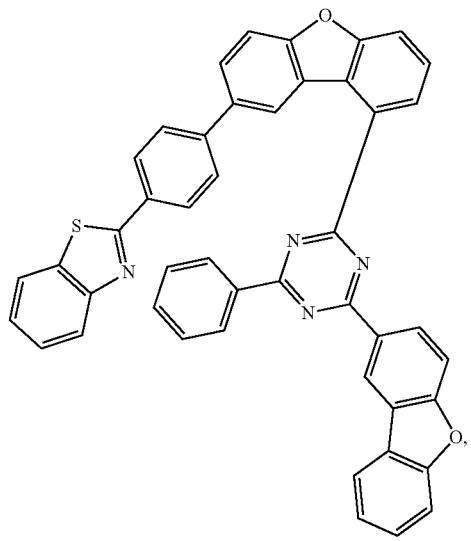
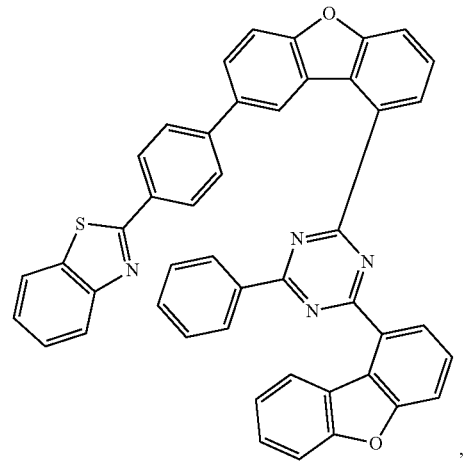
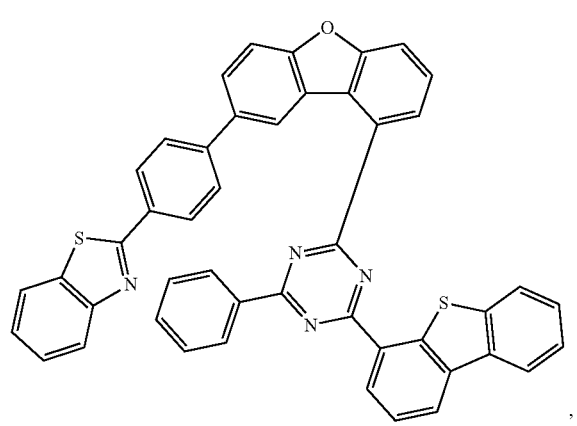
520
-continued
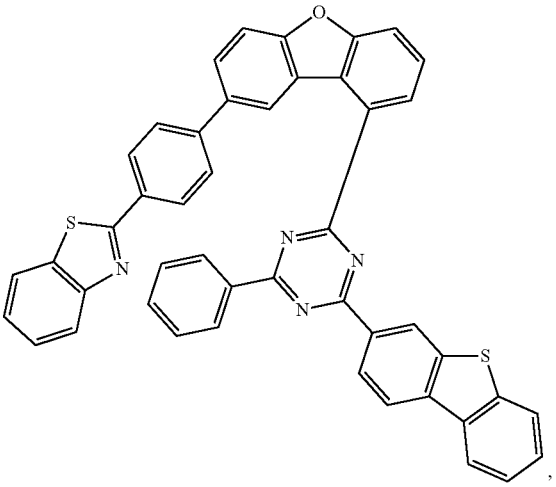
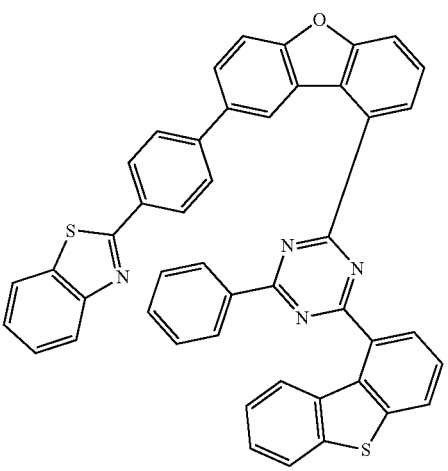

521
-continued
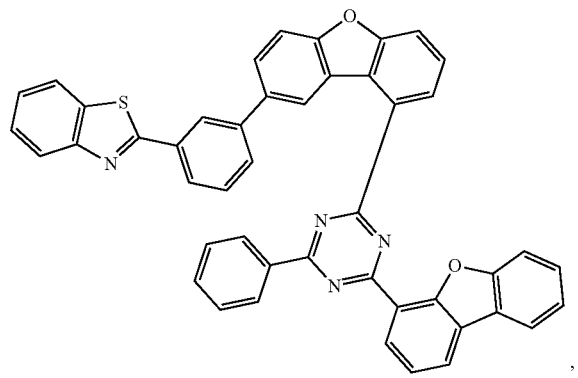
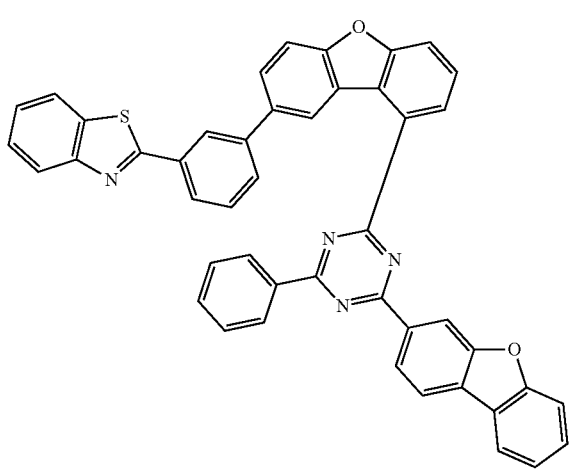
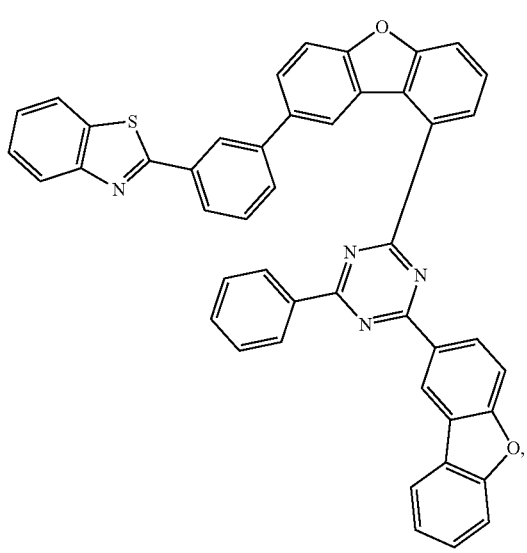
522
-continued
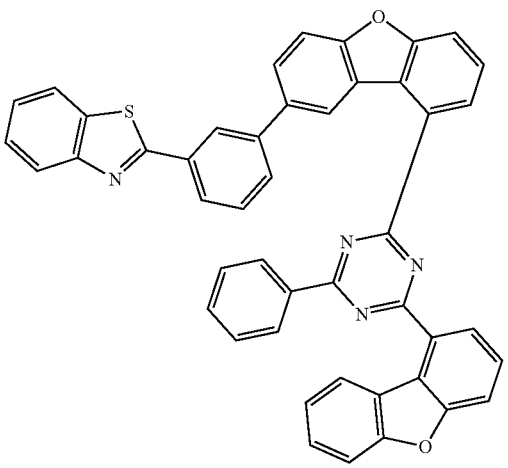
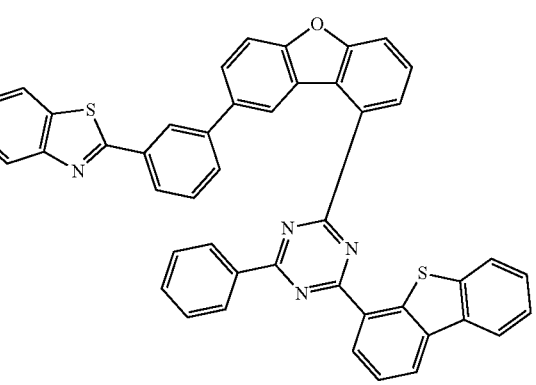
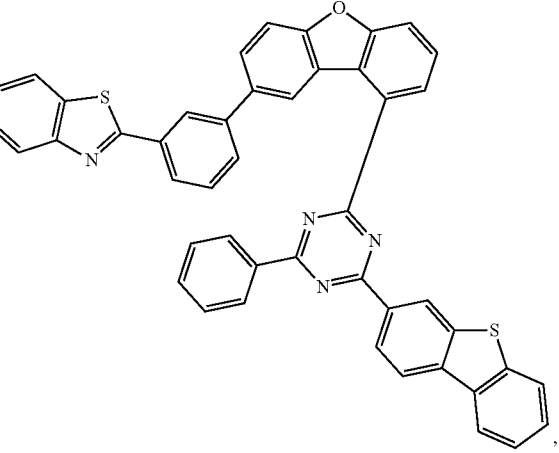

523
-continued
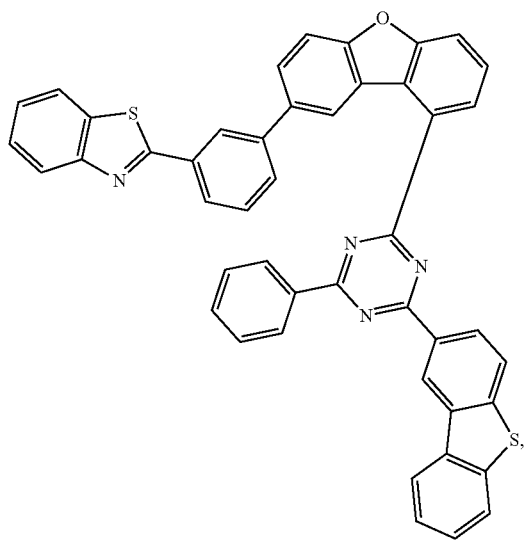
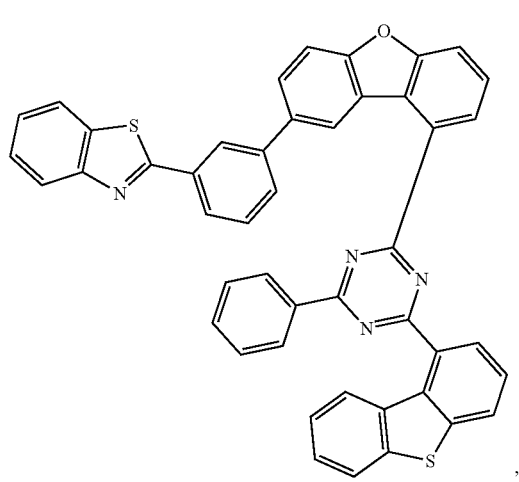
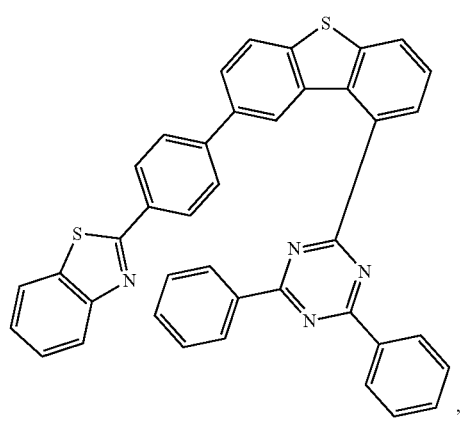
524
-continued
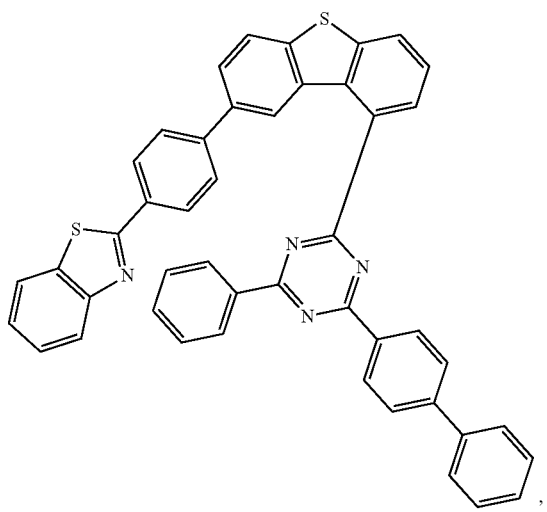
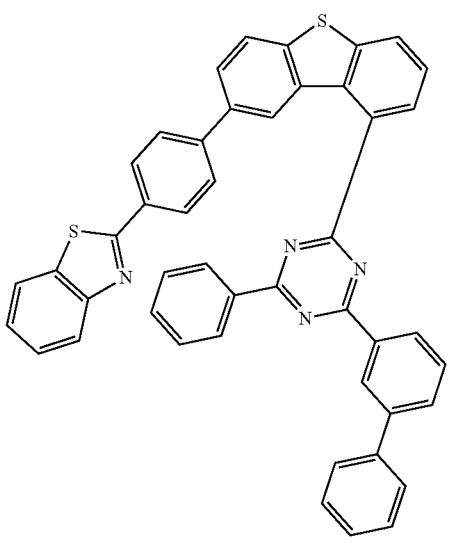
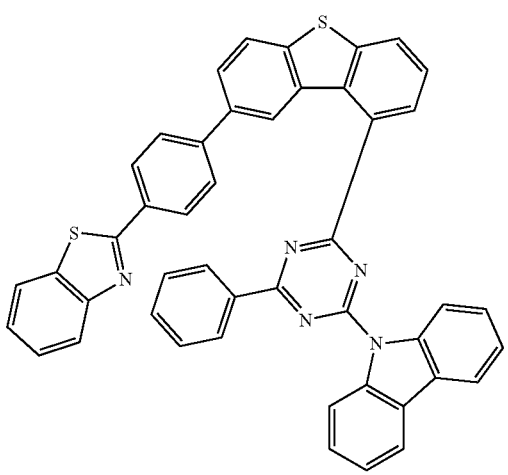

525
-continued
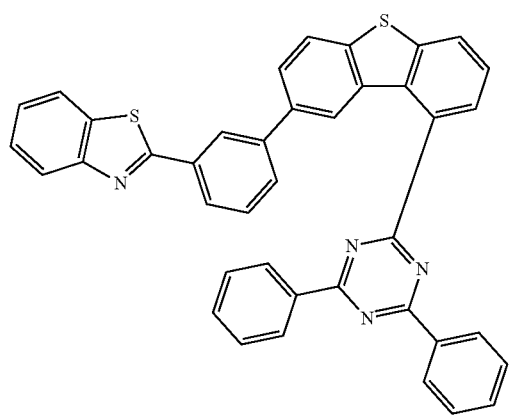
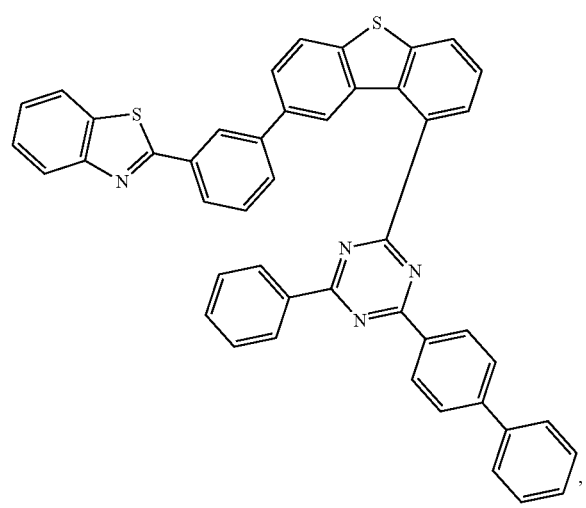
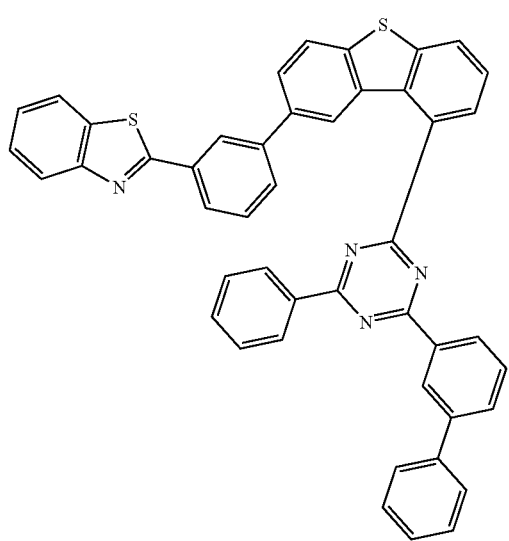
526
-continued
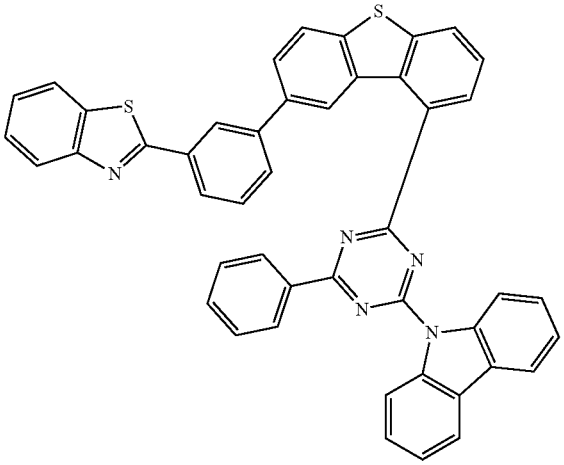
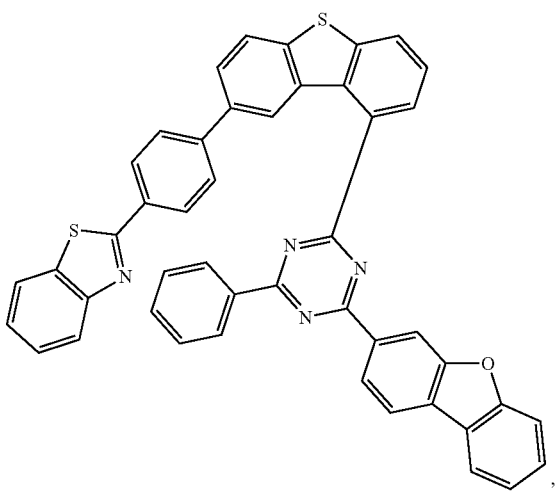

527
-continued
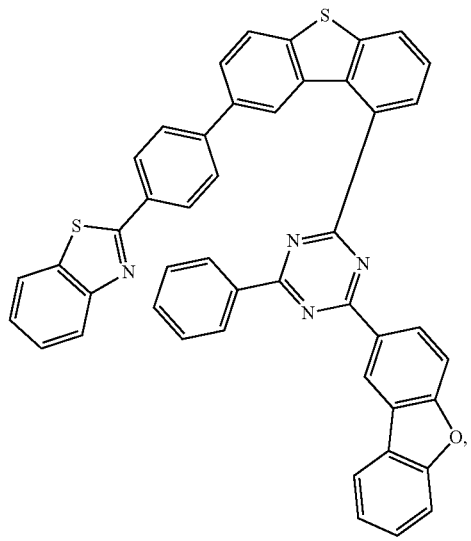
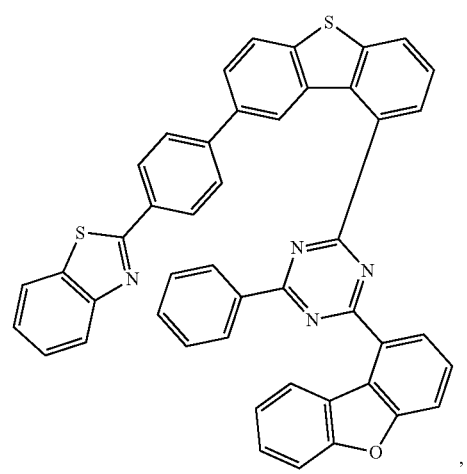
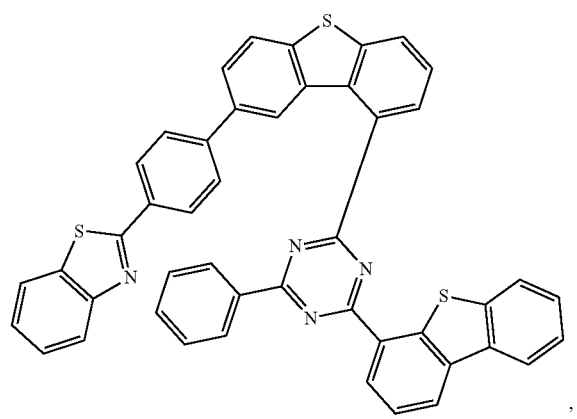
528
-continued
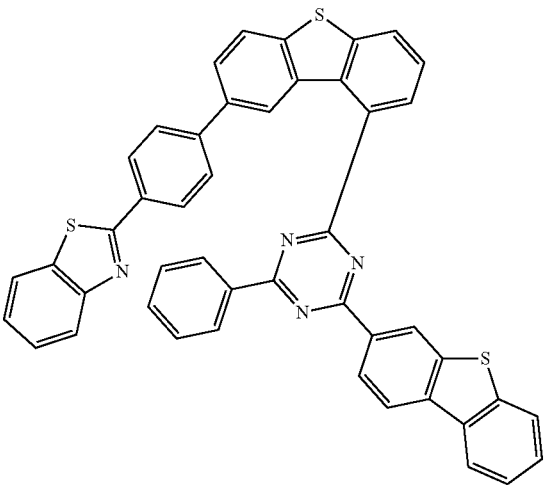
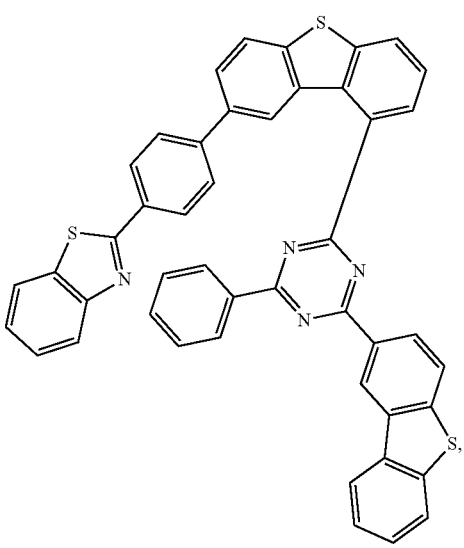
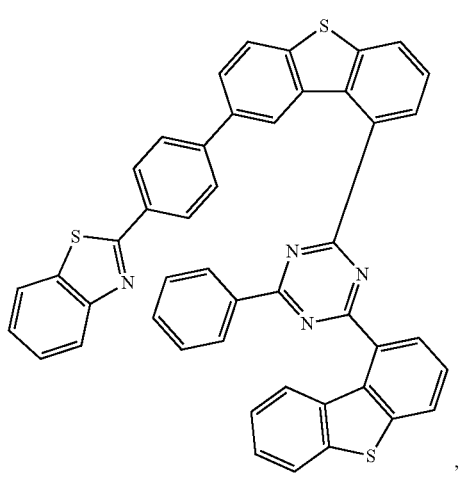

529
-continued
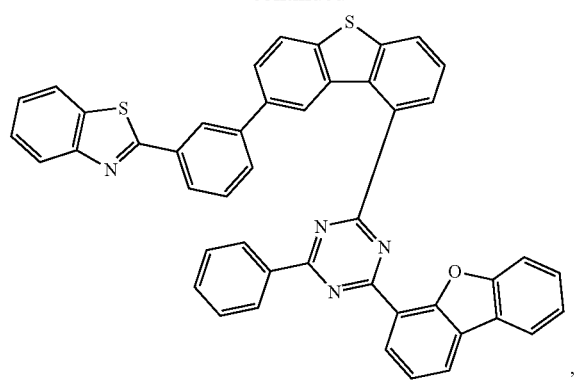
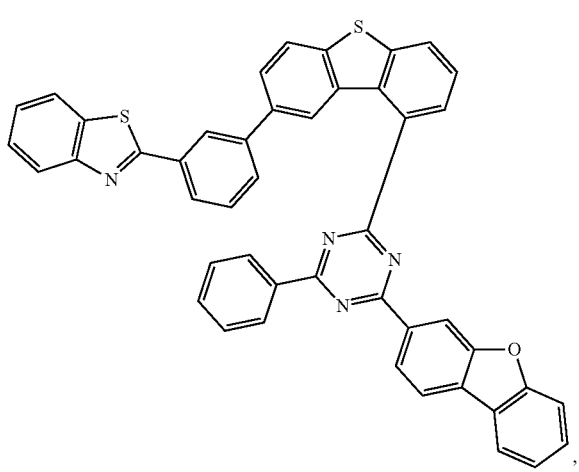
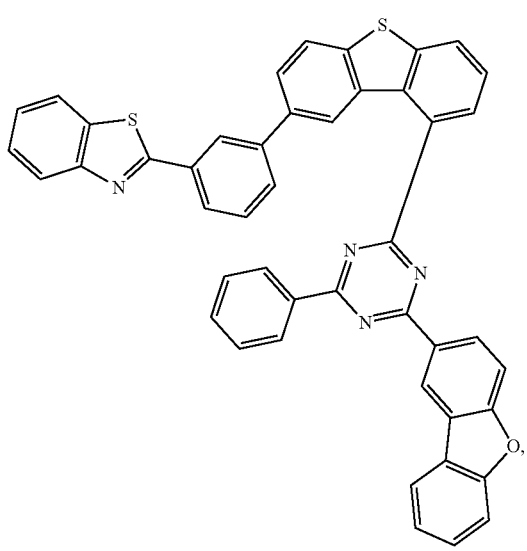
530
-continued
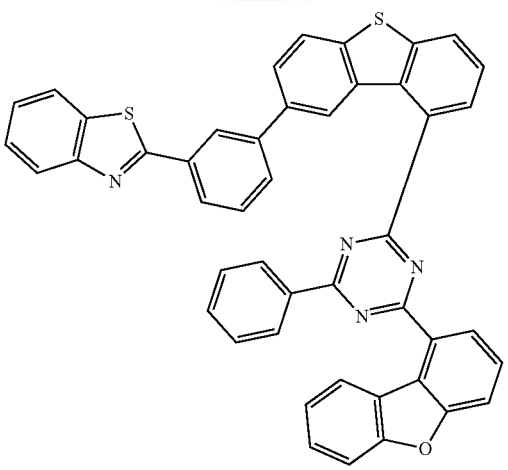
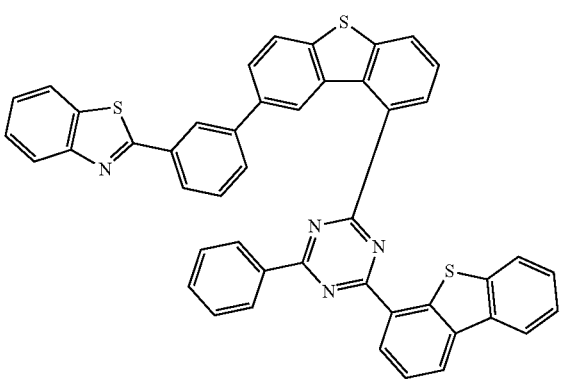
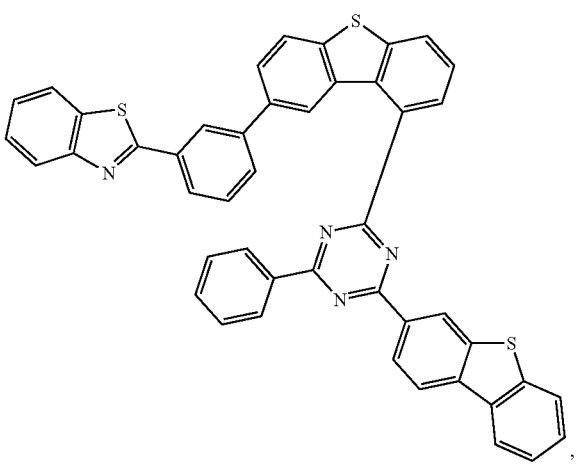

531
-continued
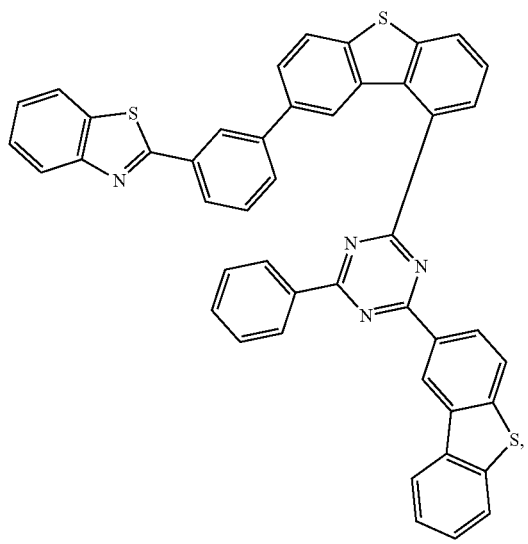
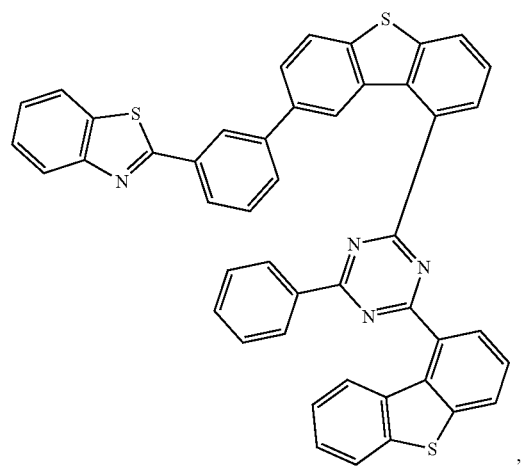
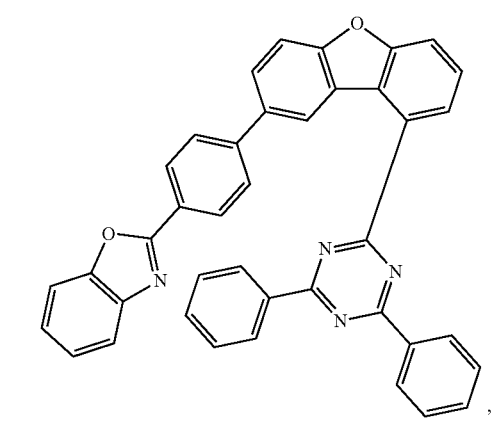
532
-continued
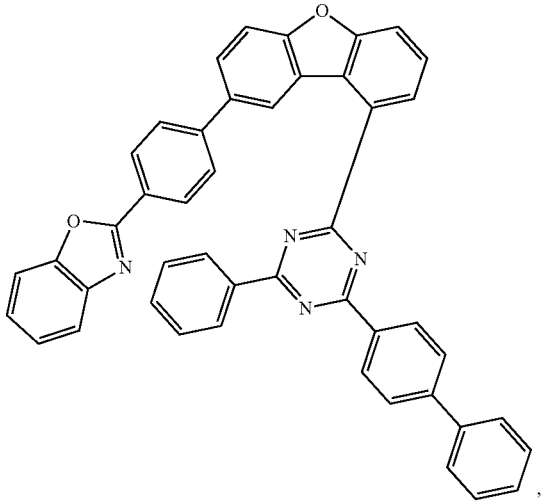
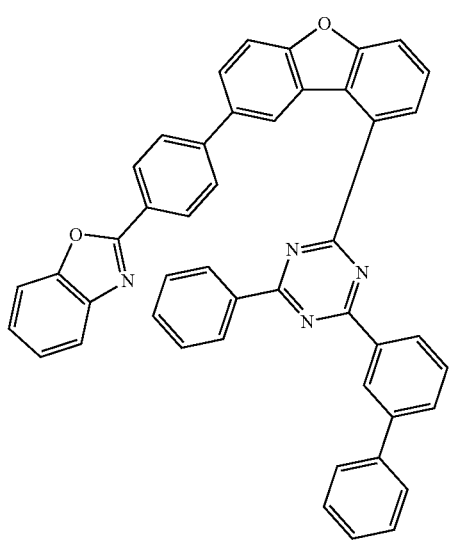
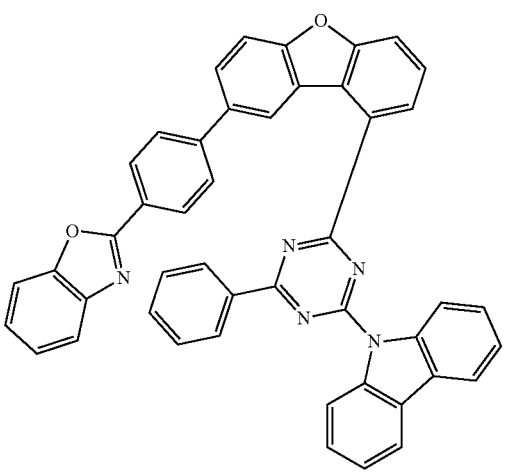

533
-continued
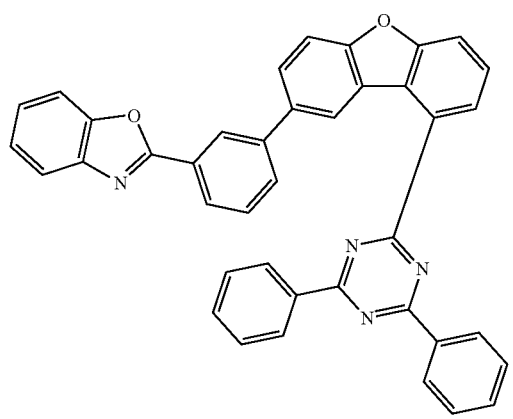
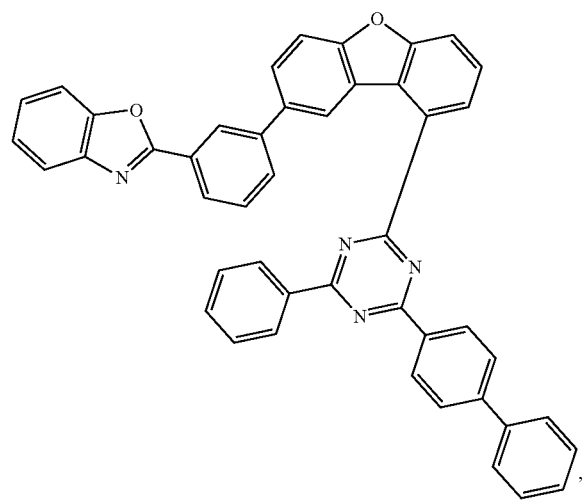
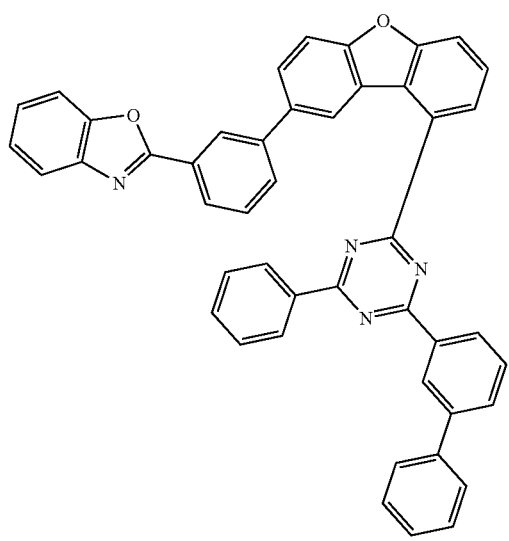
534
-continued
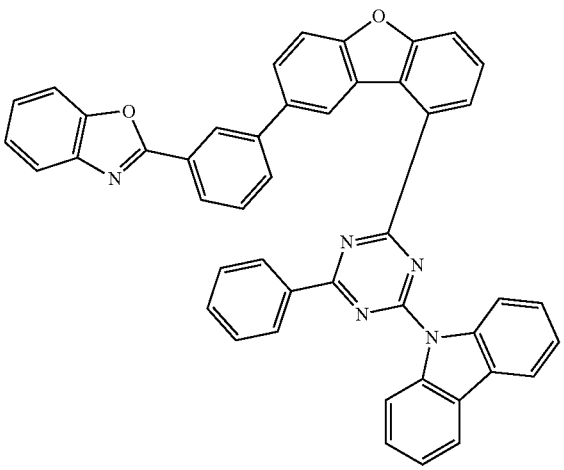
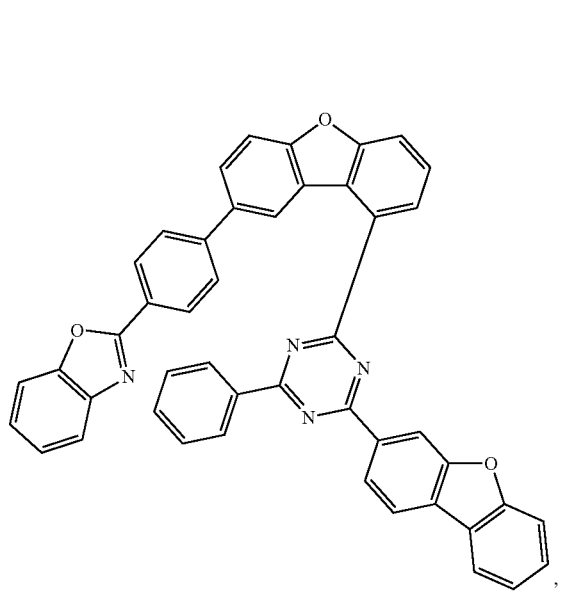

535
-continued
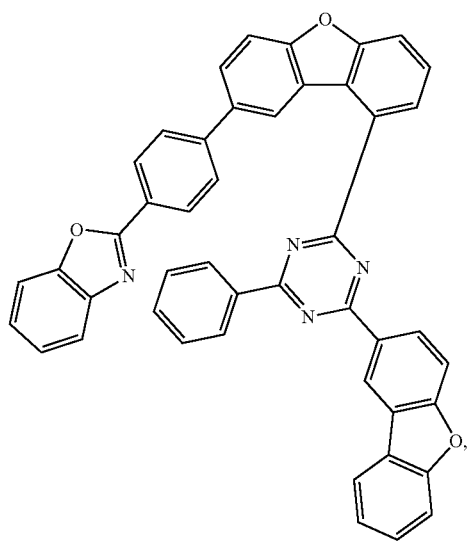
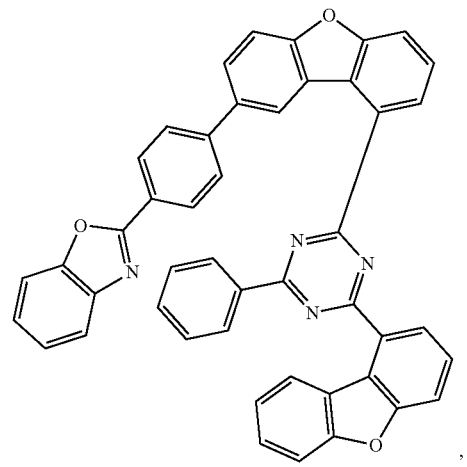
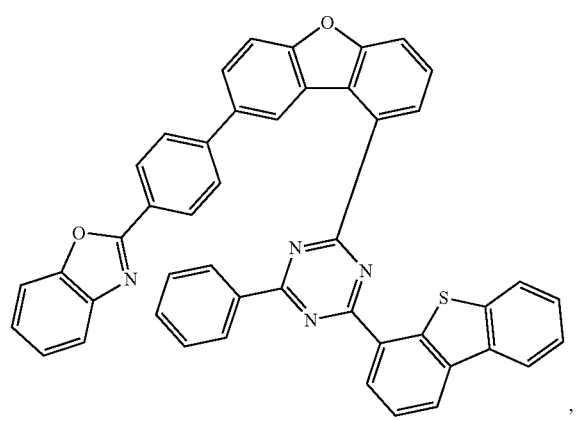
536
-continued
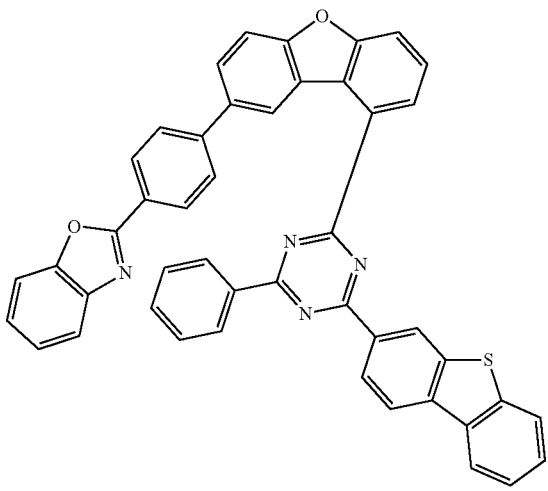
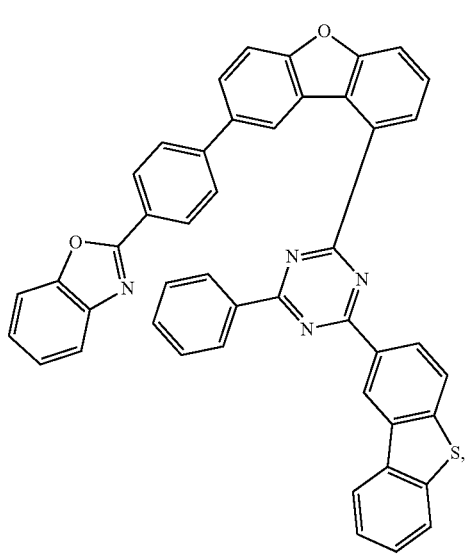
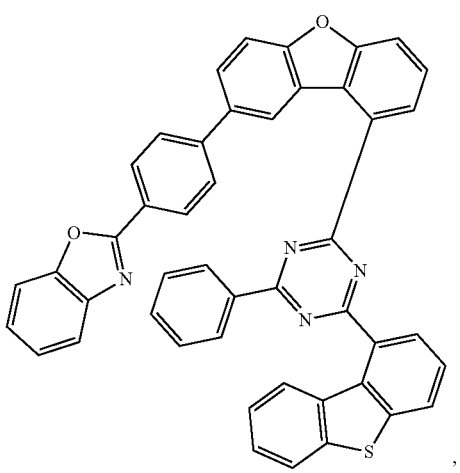

537
-continued
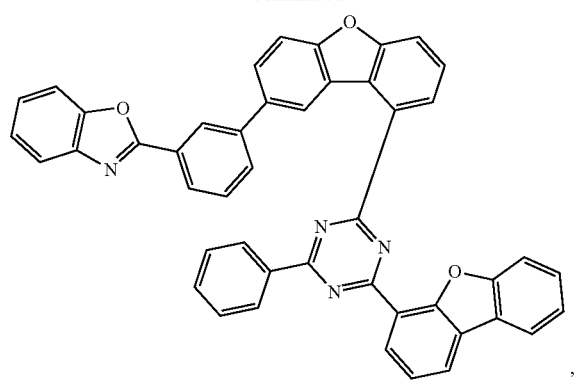
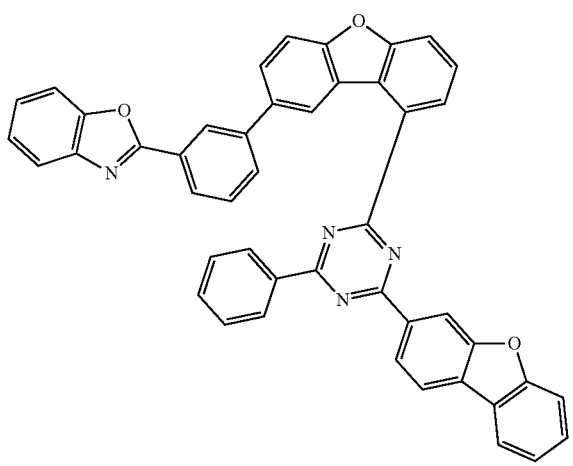
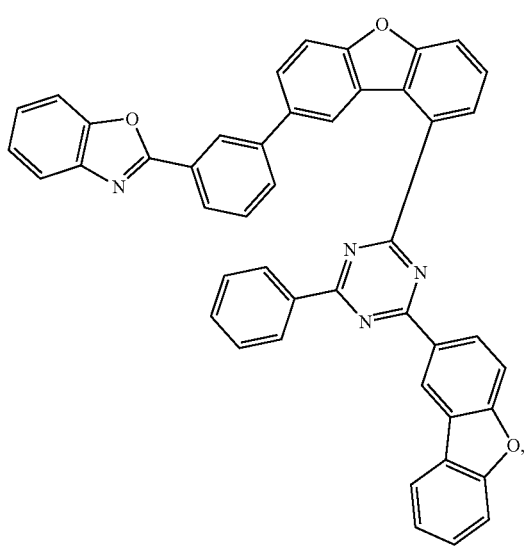
538
-continued
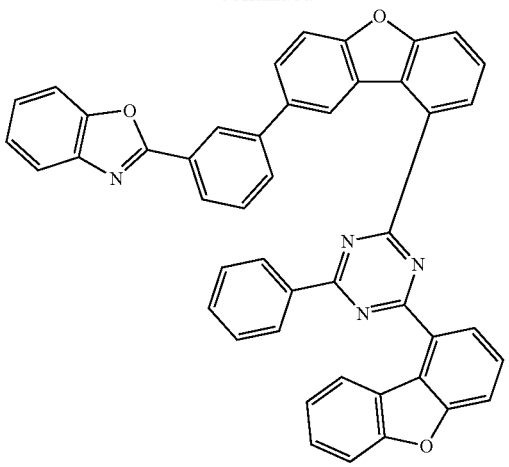
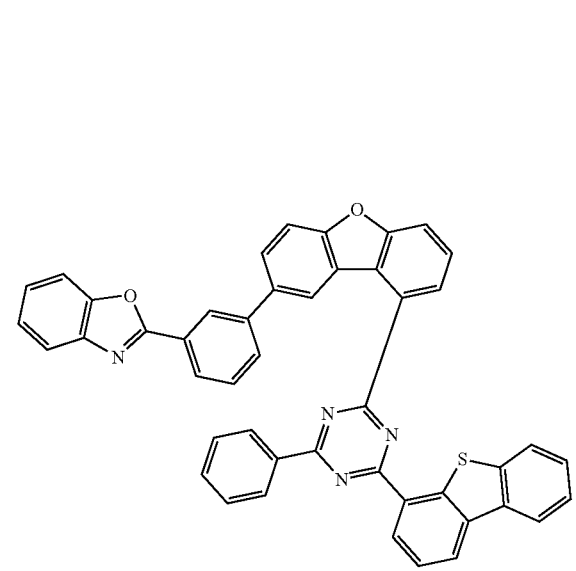
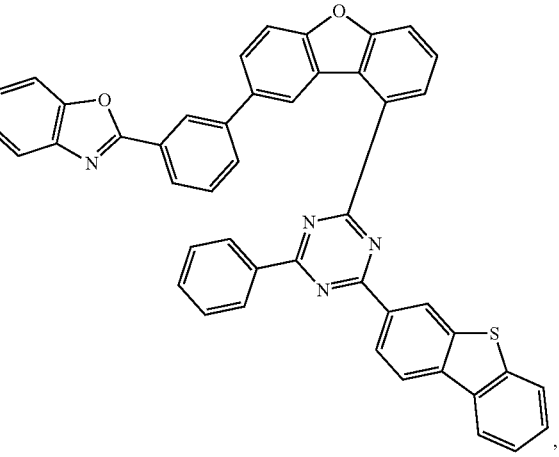

539
-continued
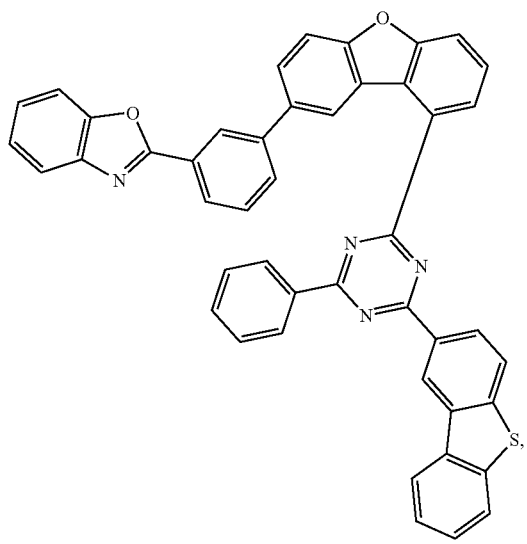
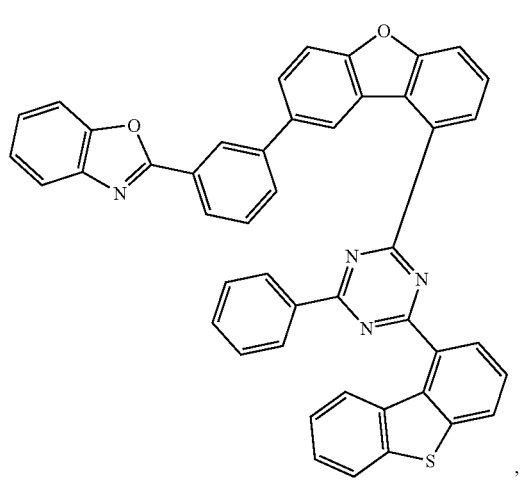
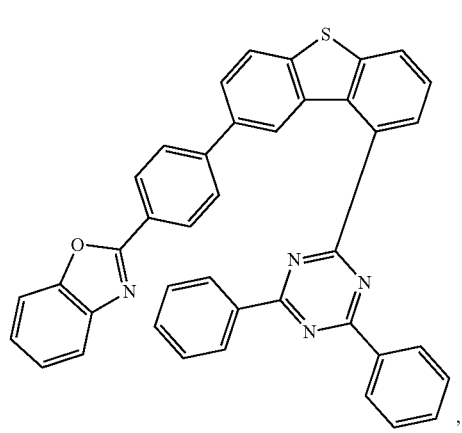
540
-continued
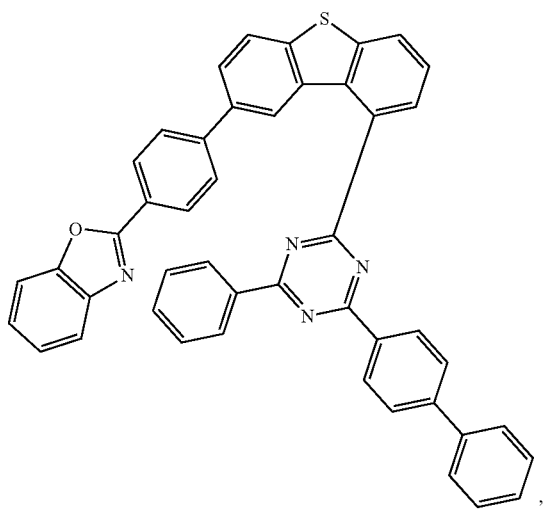
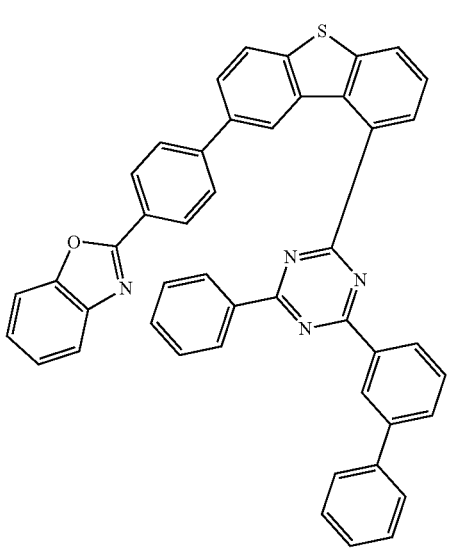
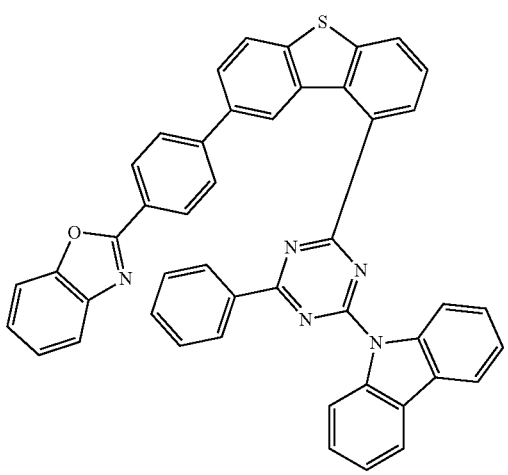

541
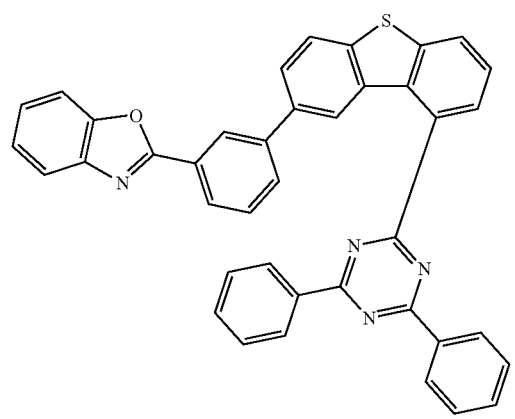
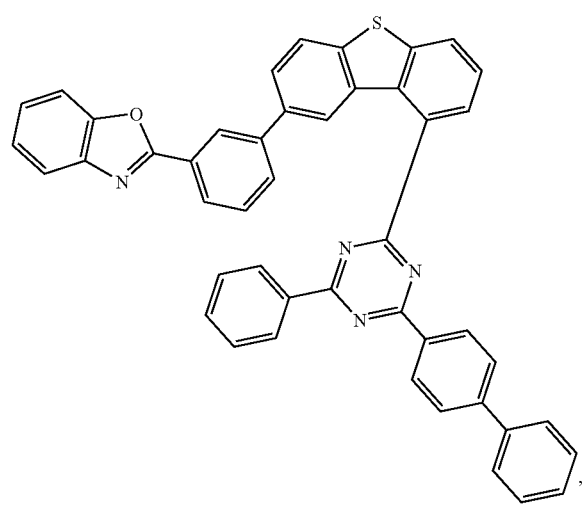
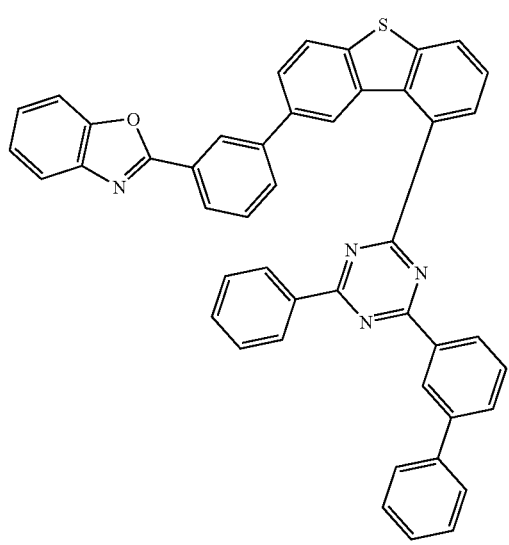
542
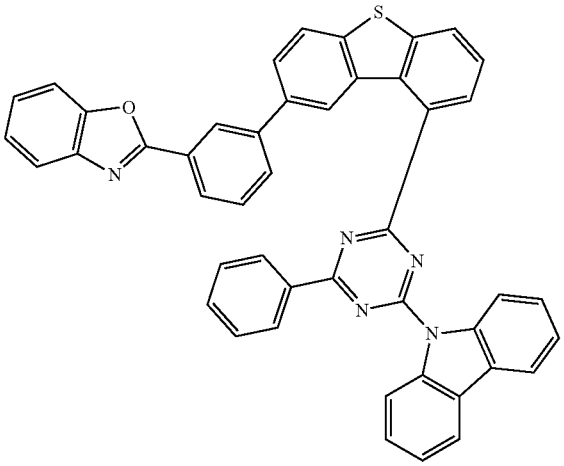
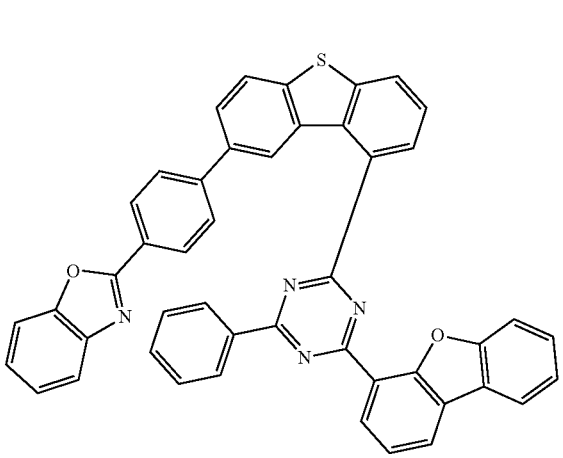
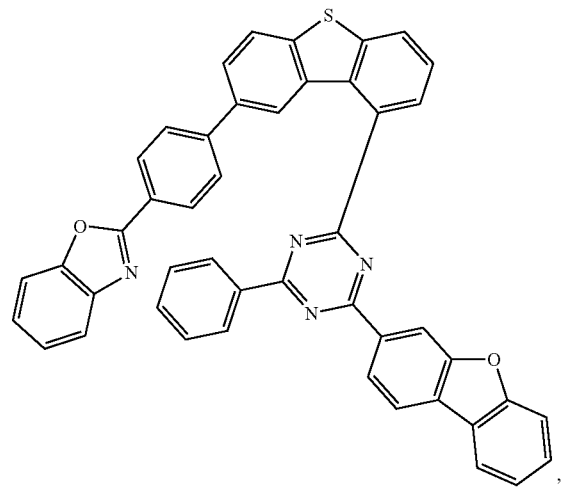

543
-continued
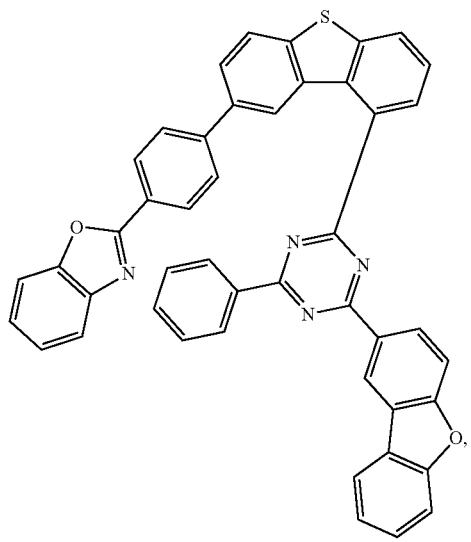
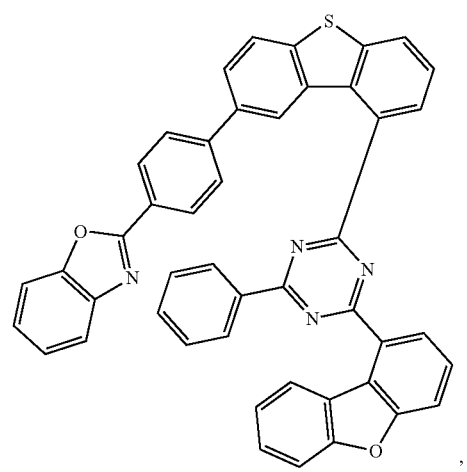
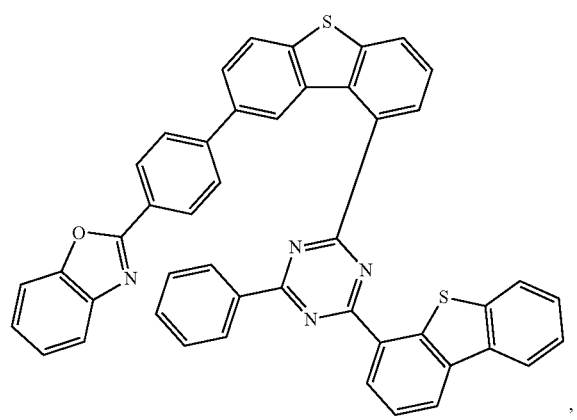
544
-continued
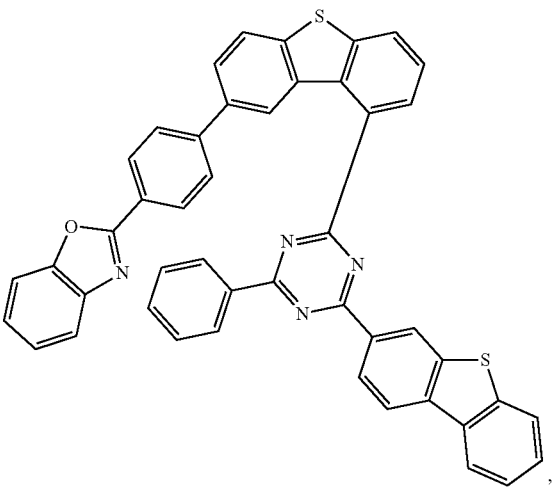
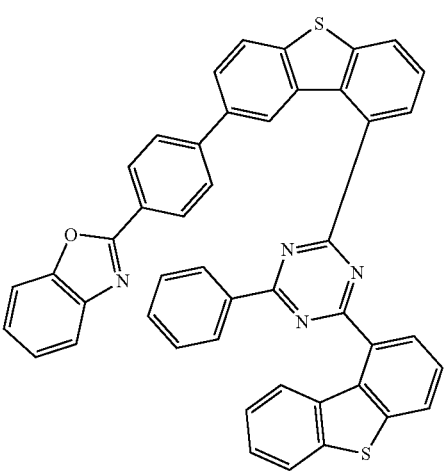

545
-continued
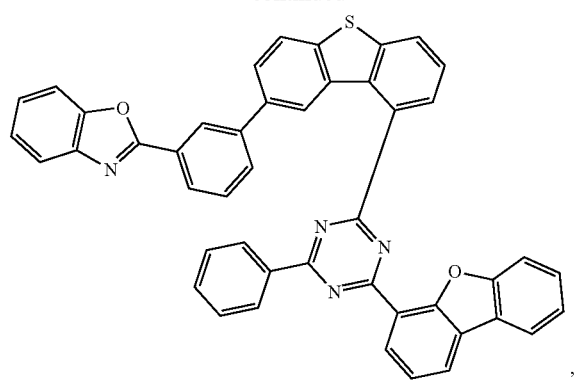
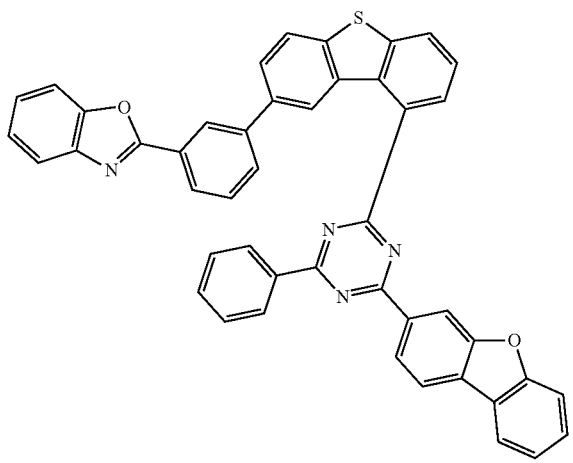
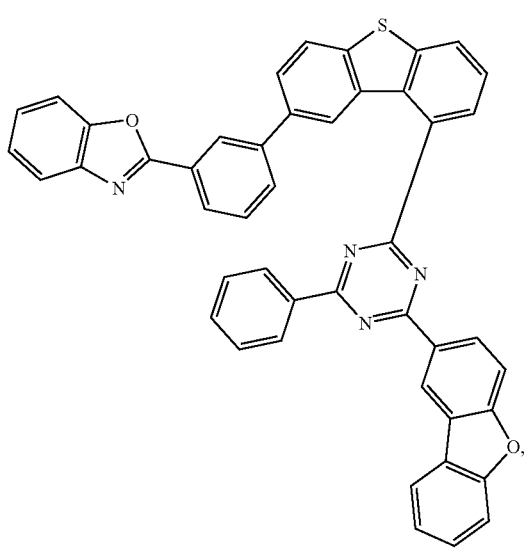
546
-continued
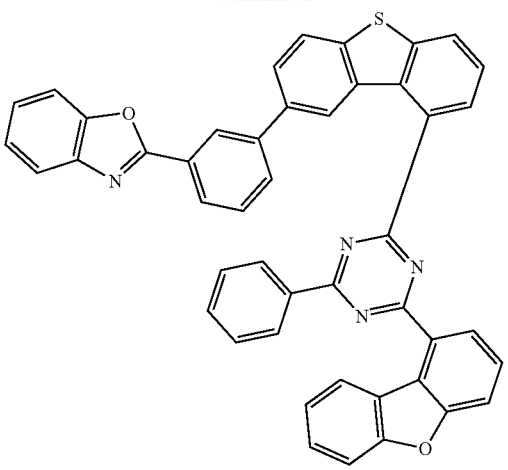
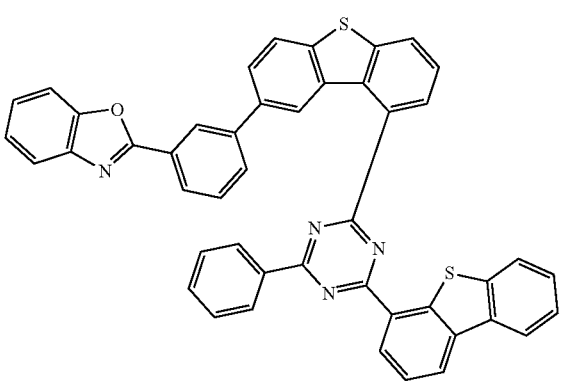
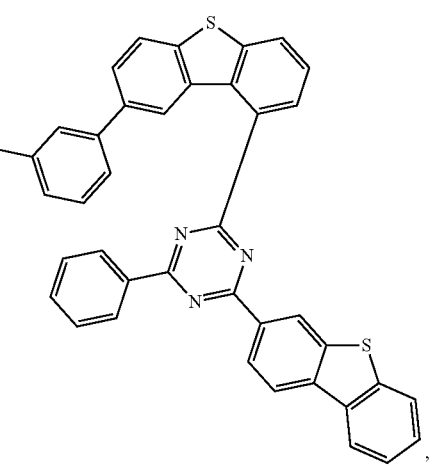

547
-continued
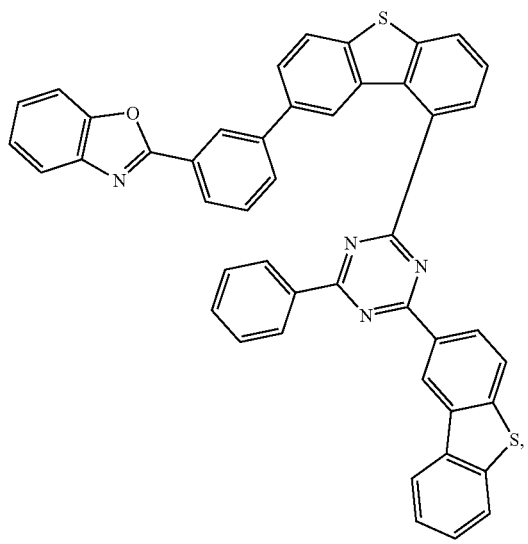
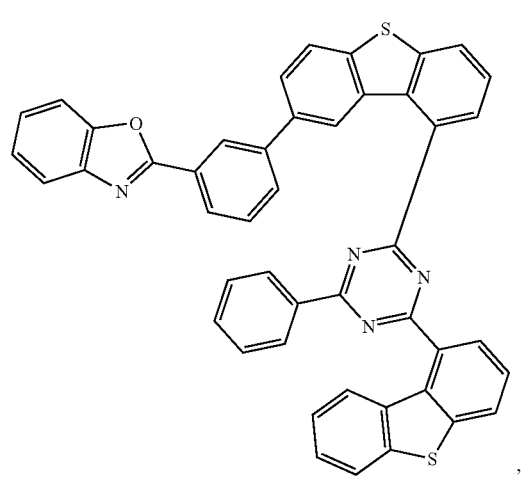
548
-continued
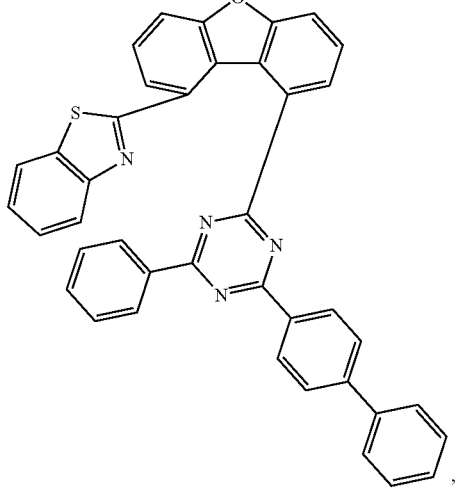
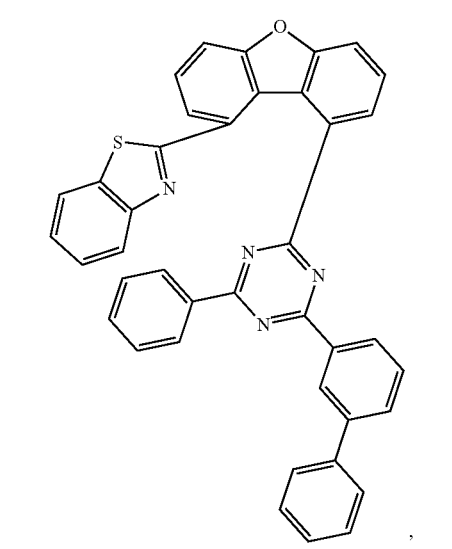
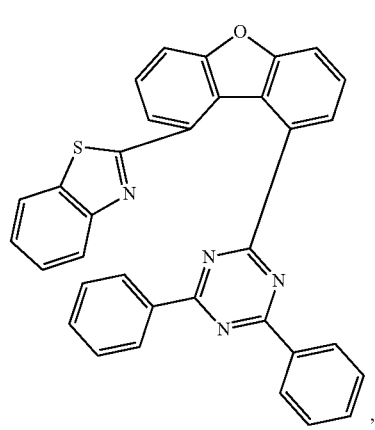
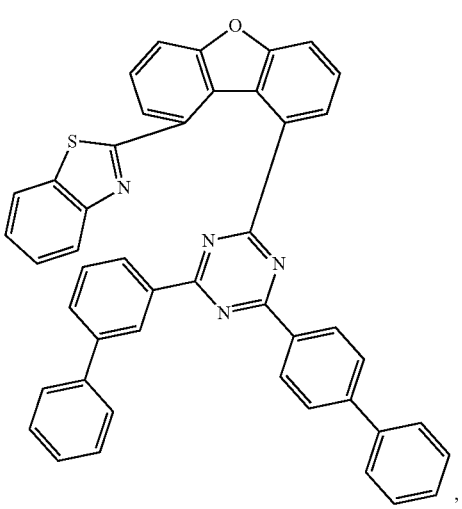

549
-continued
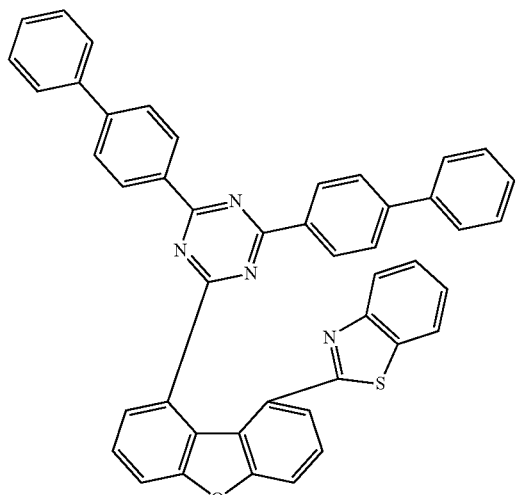
,
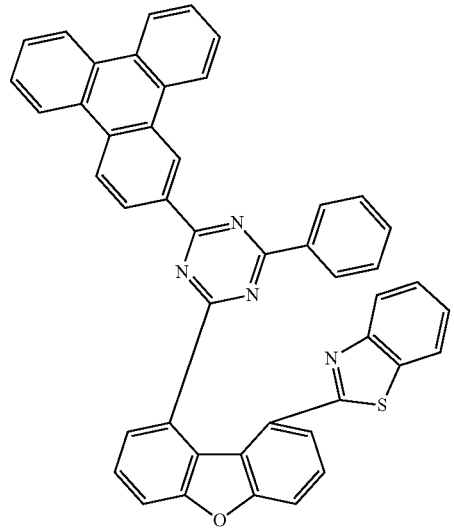
,
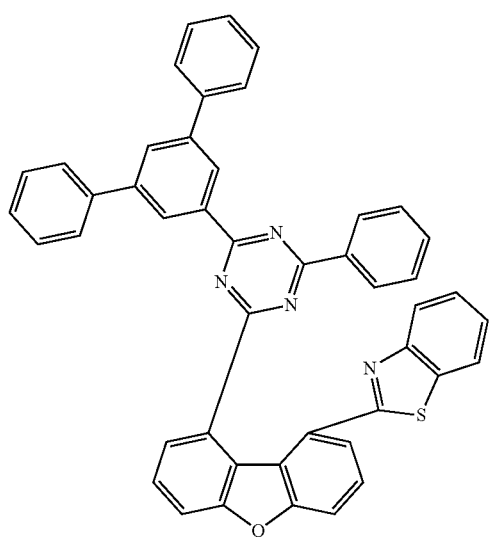
,
550
-continued
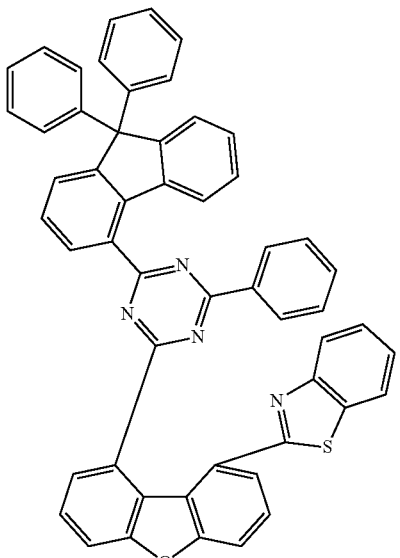
,
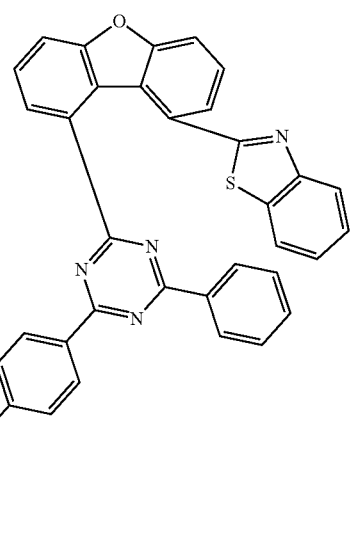
,
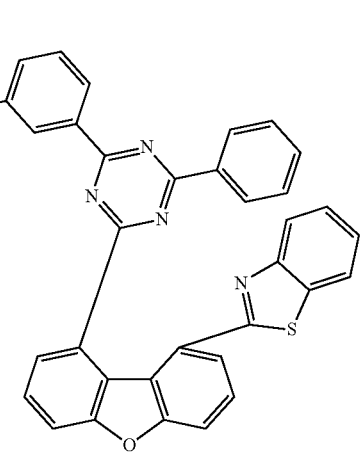
, 551
-continued
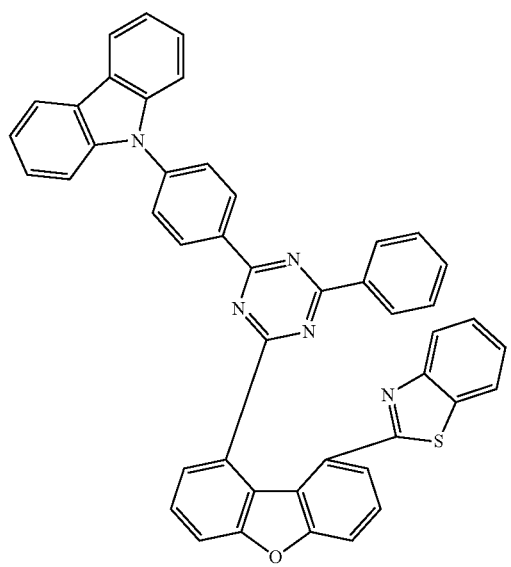
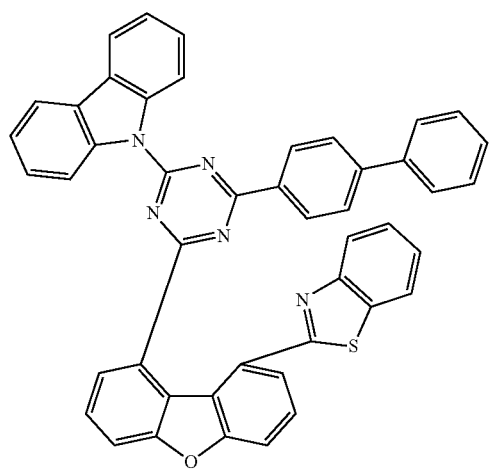
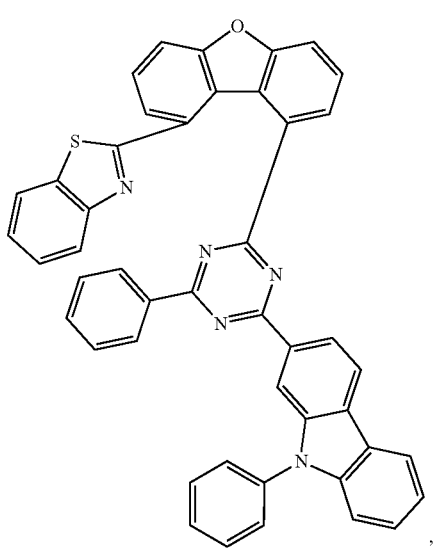
552
-continued
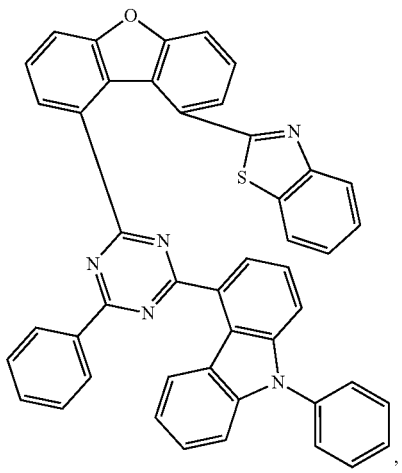
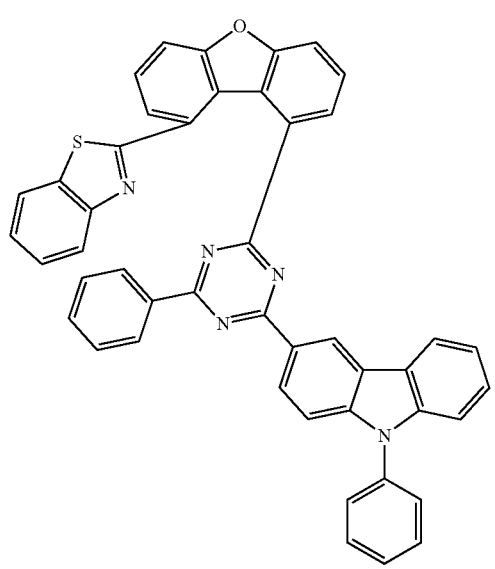
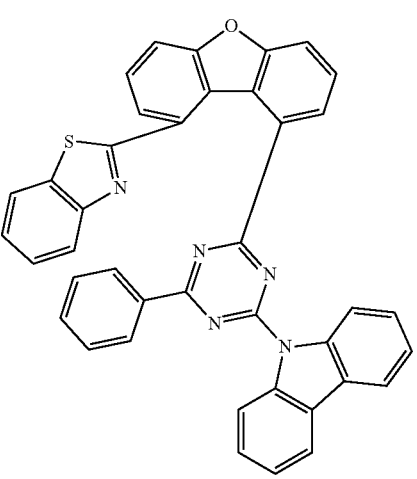

553
-continued
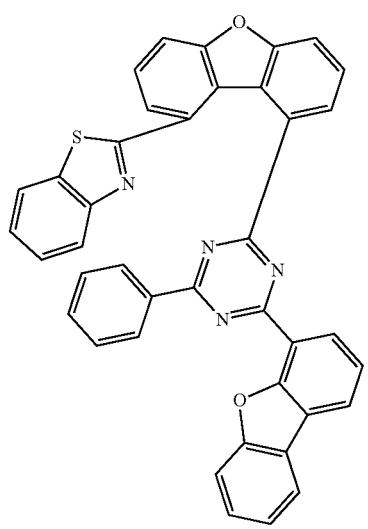
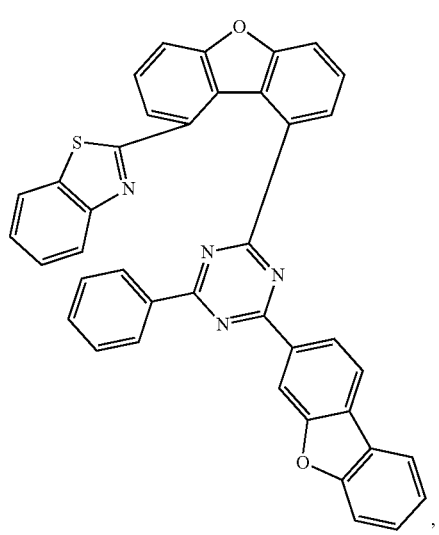
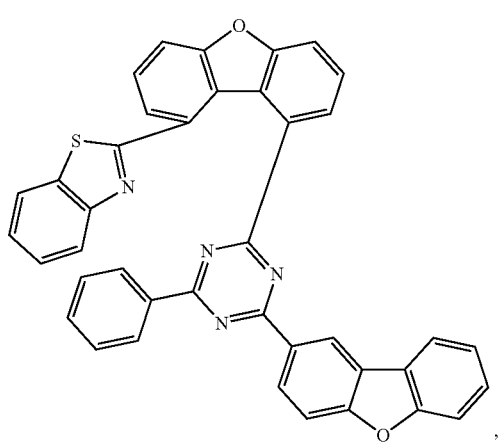
554
-continued
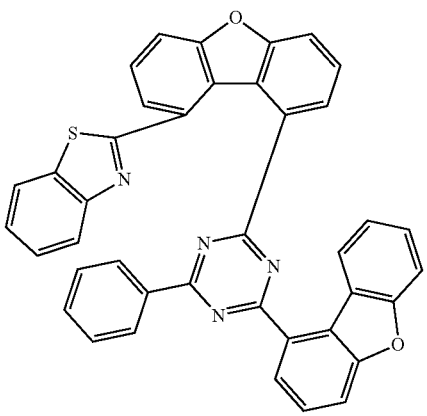
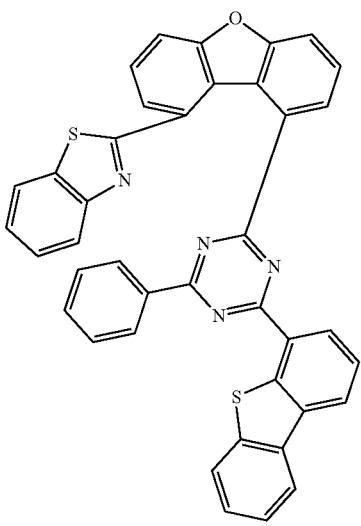
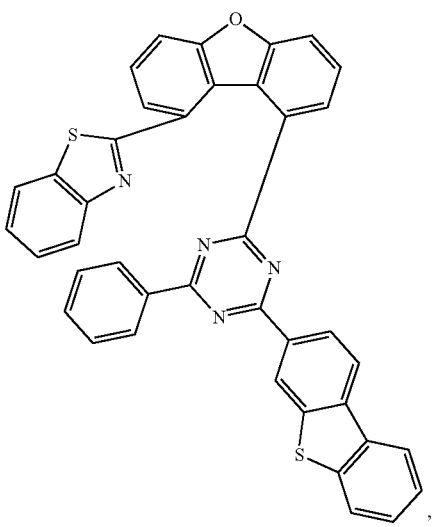

555
-continued
556
-continued
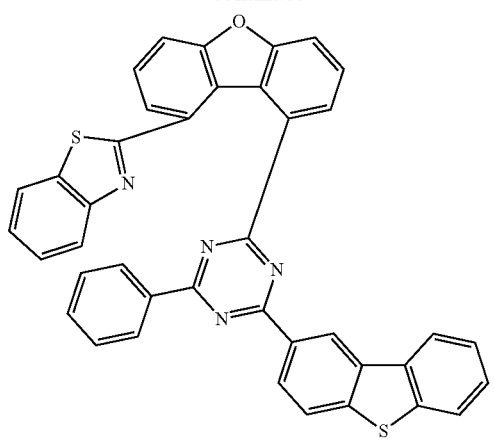
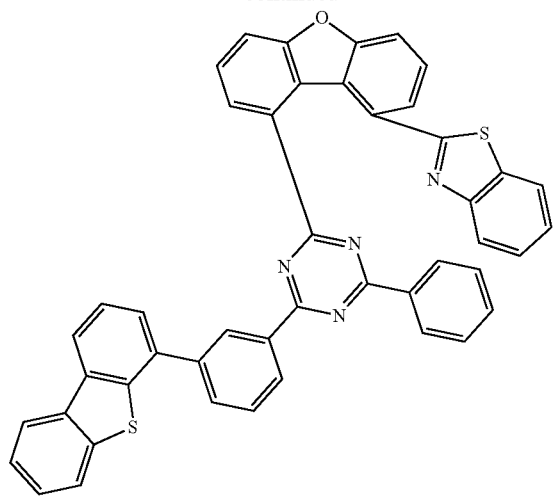
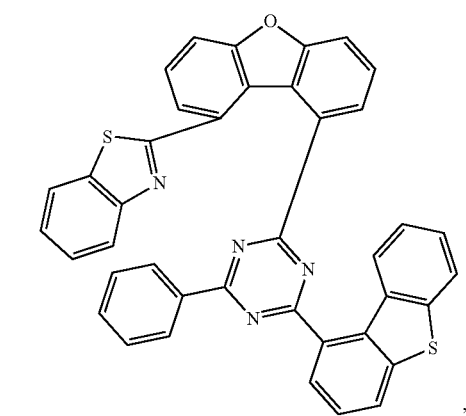
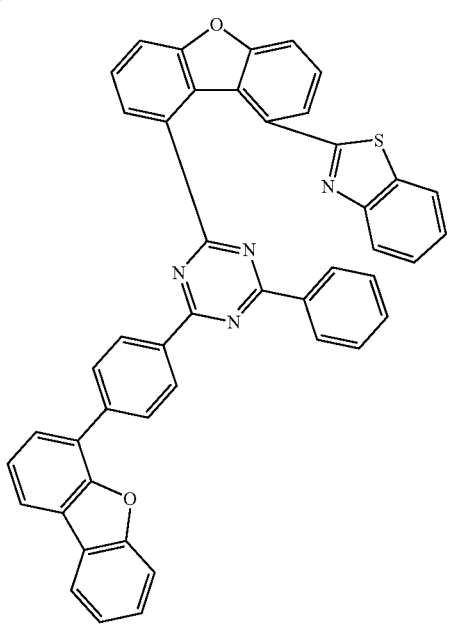
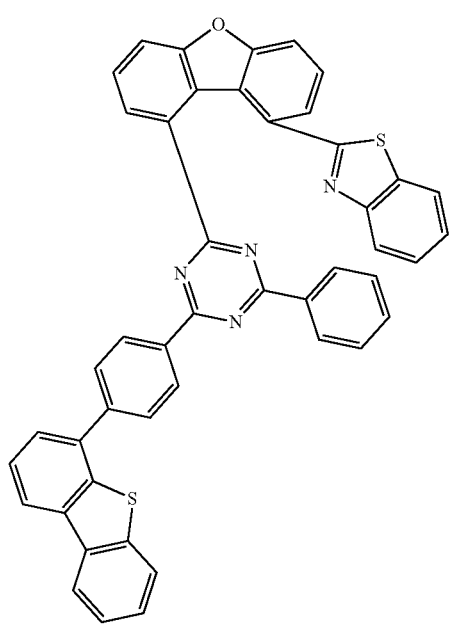
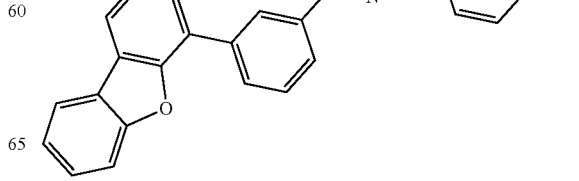

557
-continued
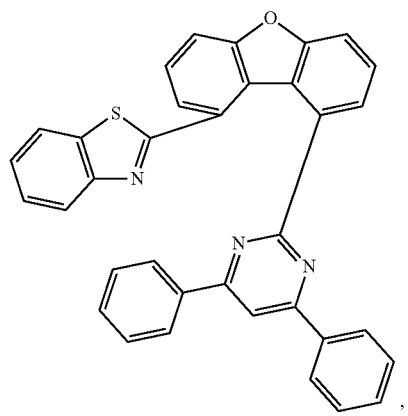
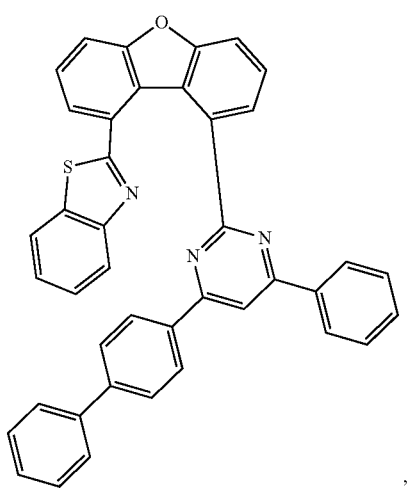
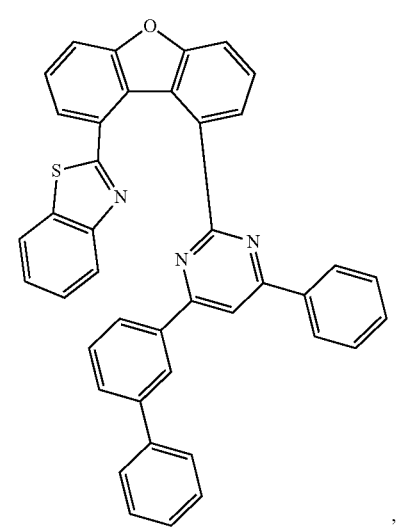
558
-continued
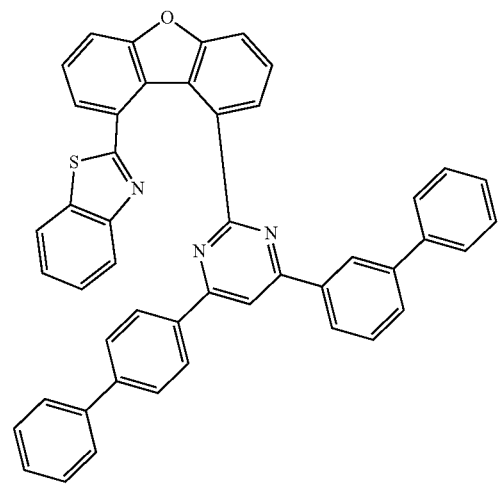
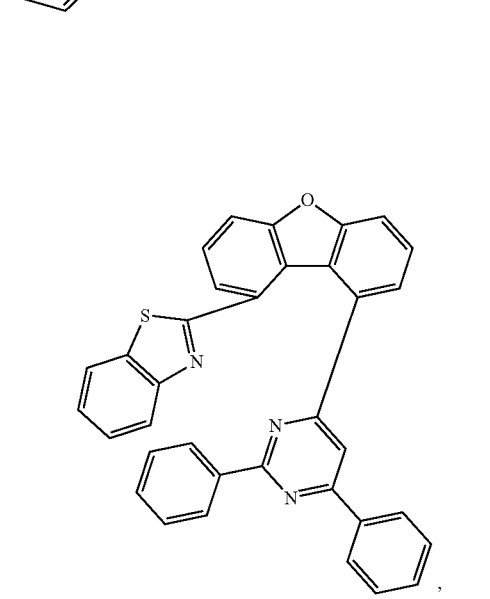
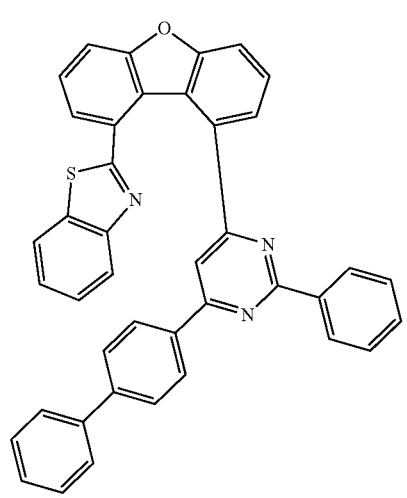

559
-continued
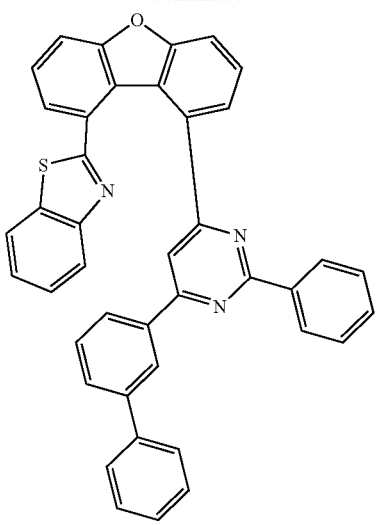
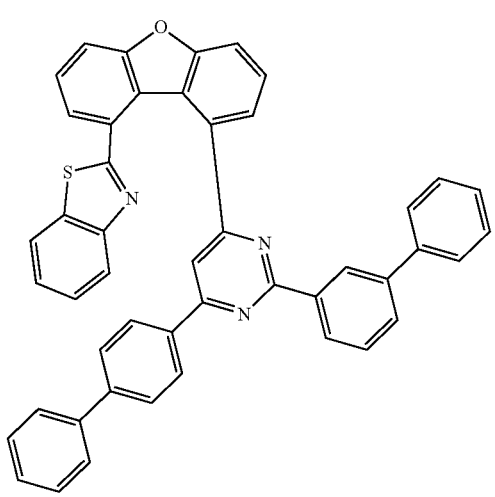
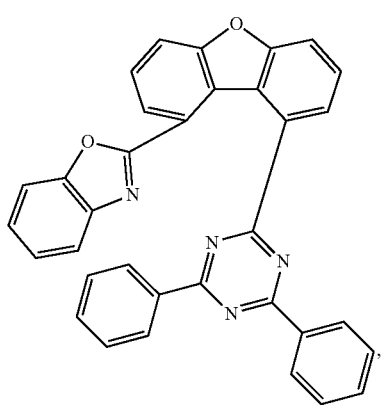
560
-continued
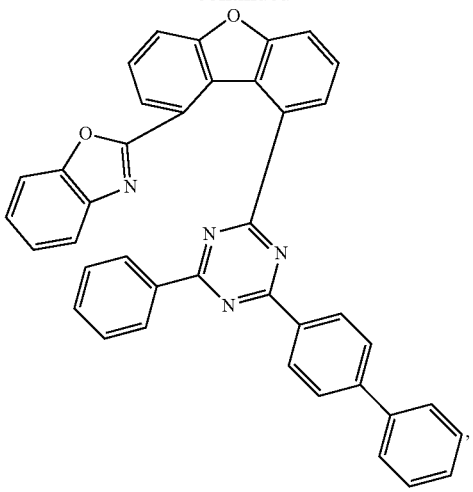
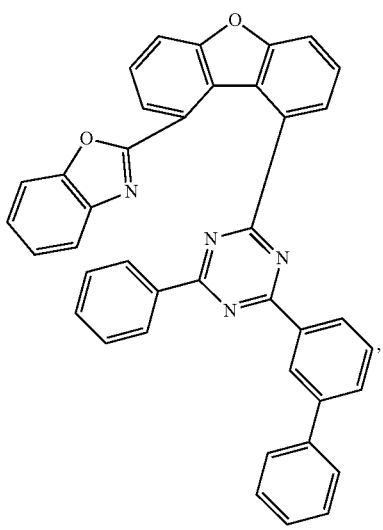
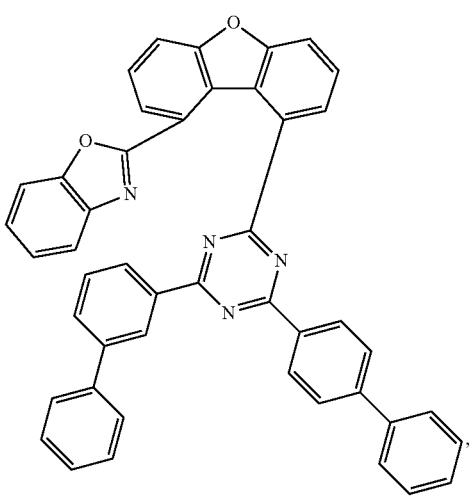

561
-continued
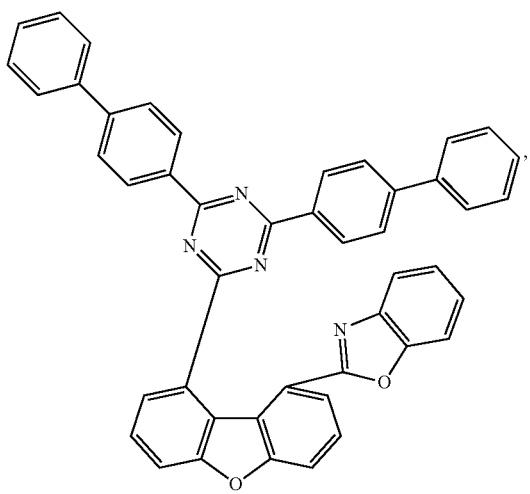
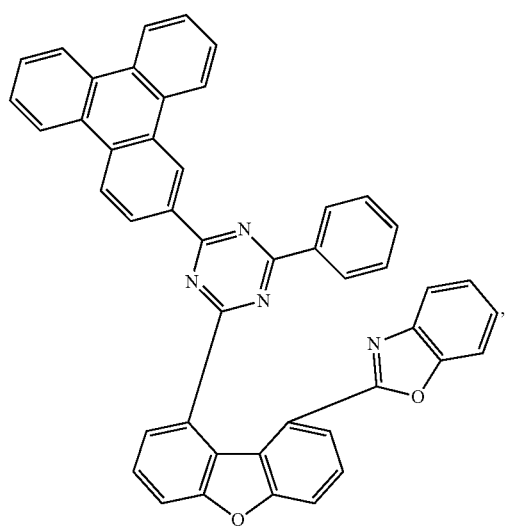
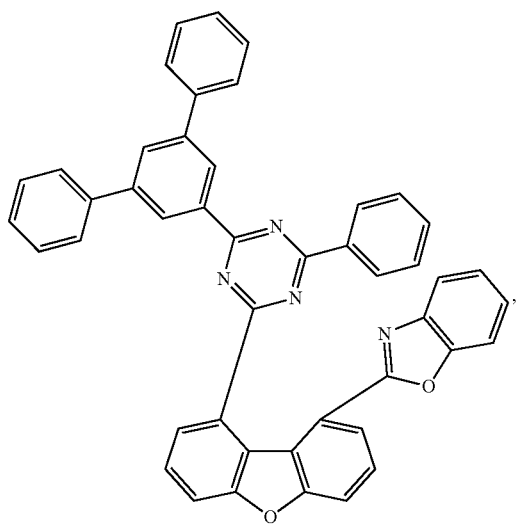
562
-continued
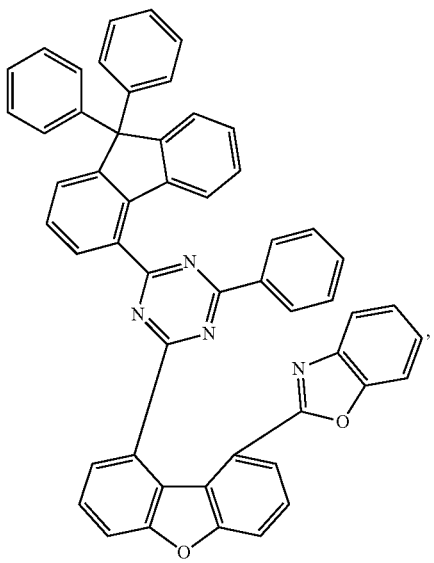
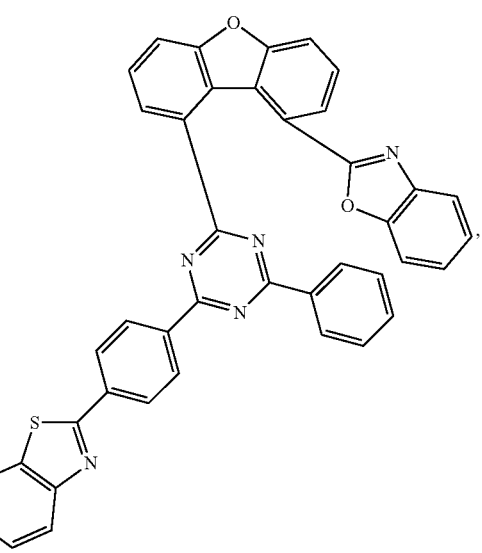
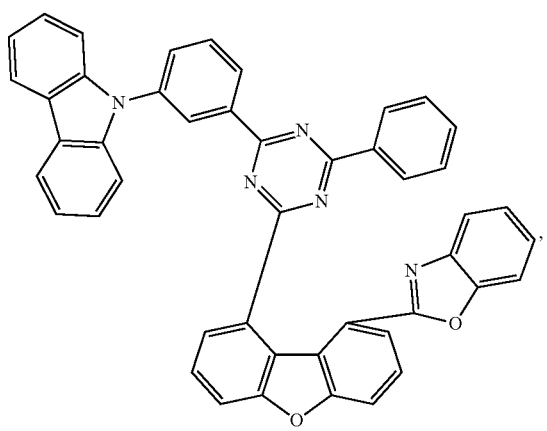

563
-continued
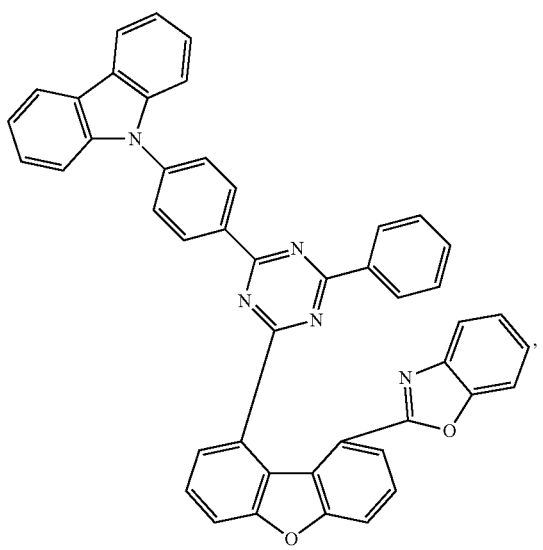
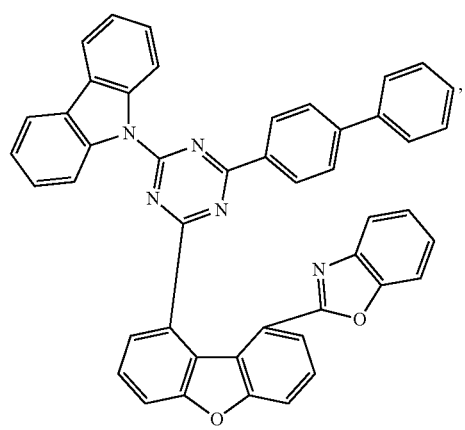
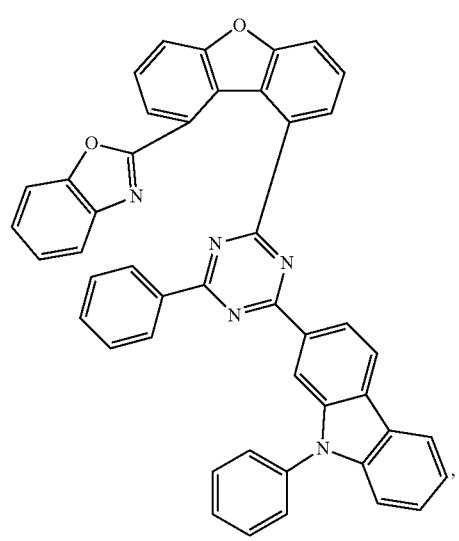
564
-continued
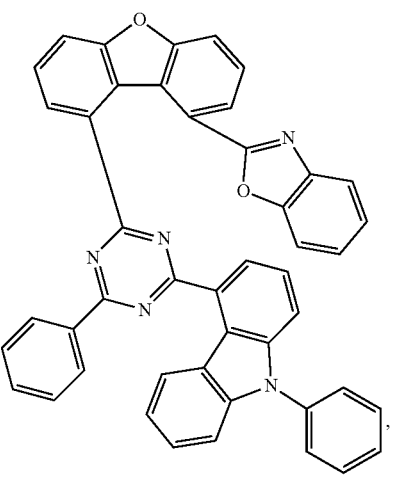
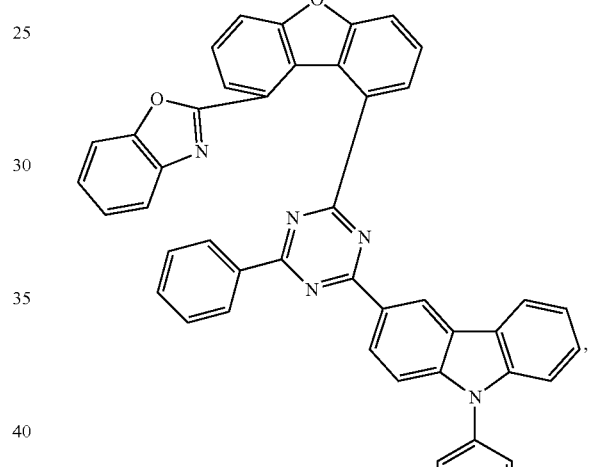
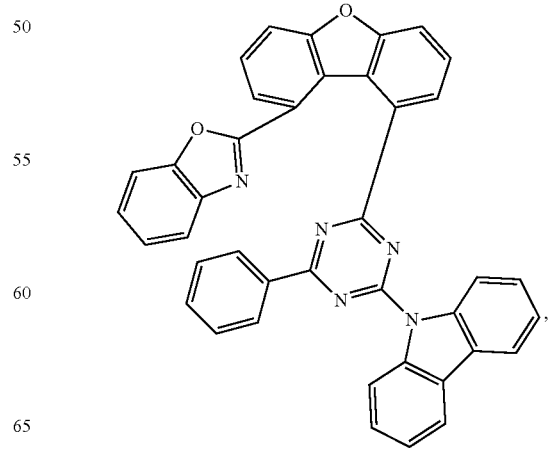

565
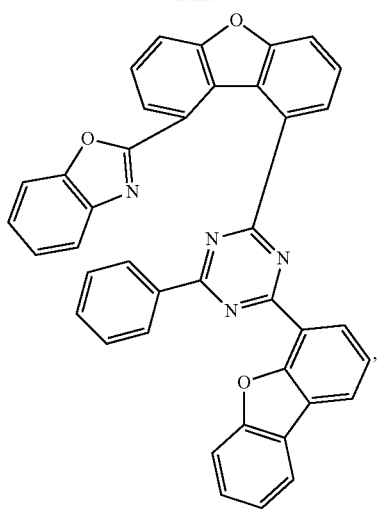
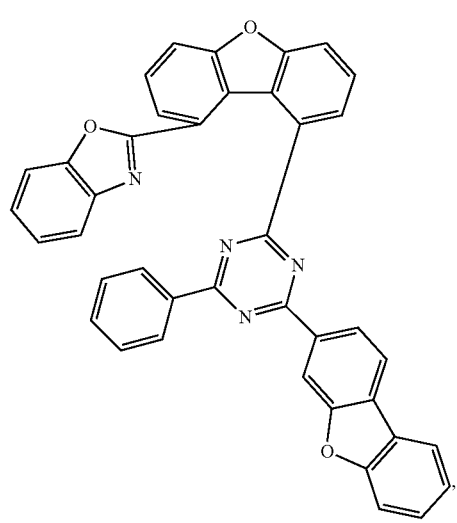
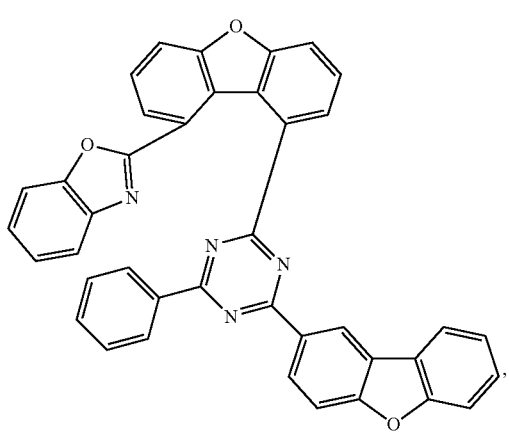
566
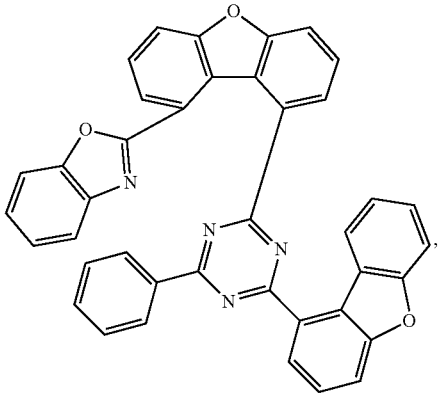
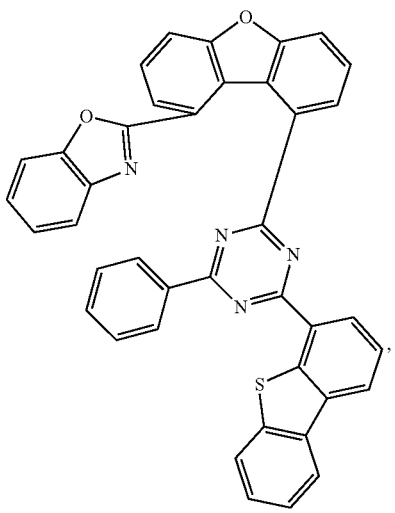
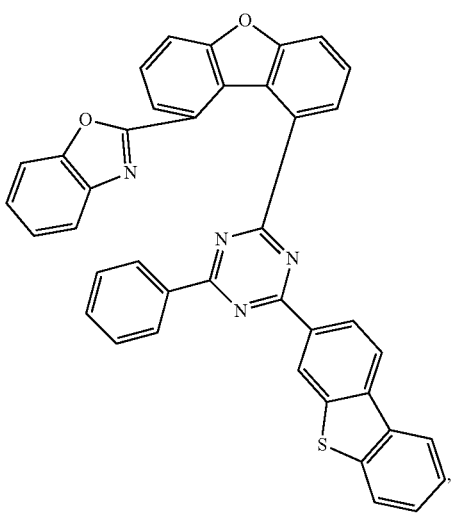

567
-continued
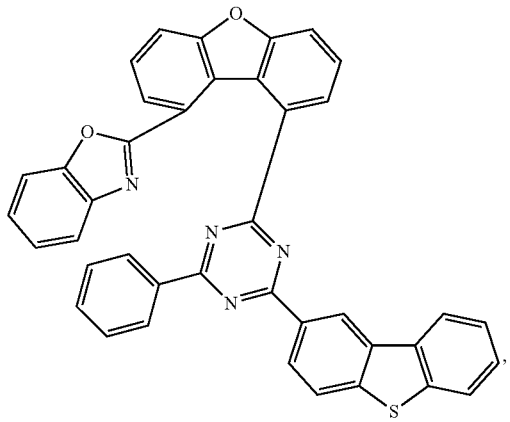
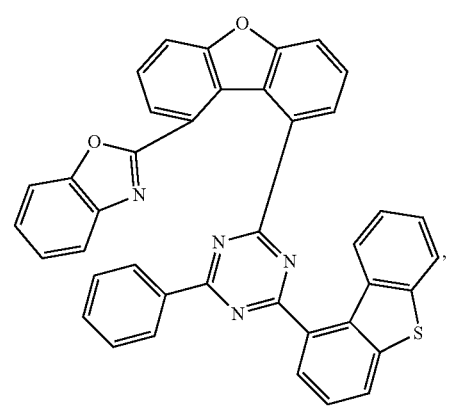
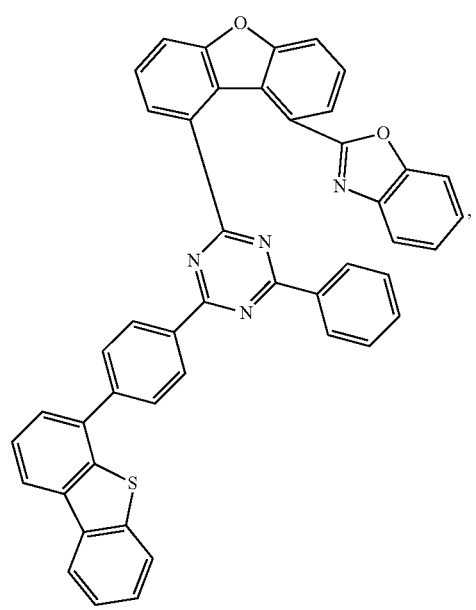
568
-continued
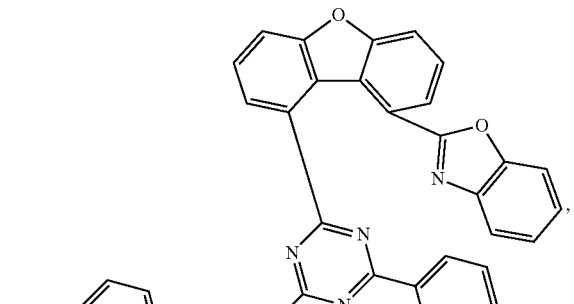
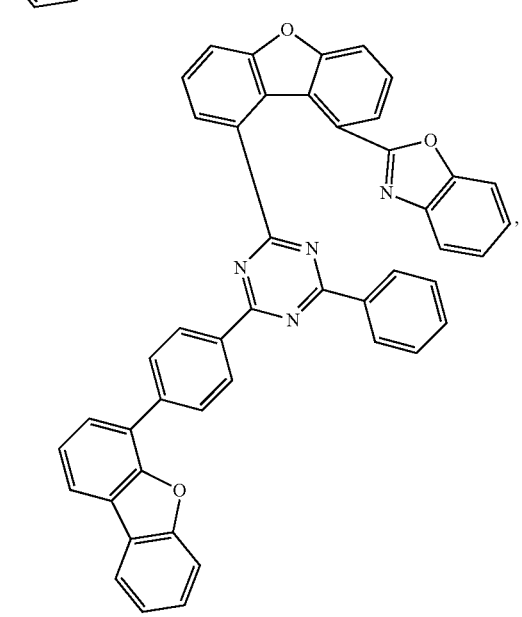
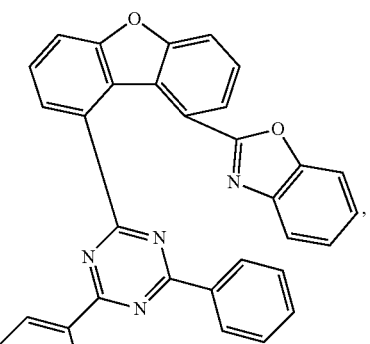

569
-continued
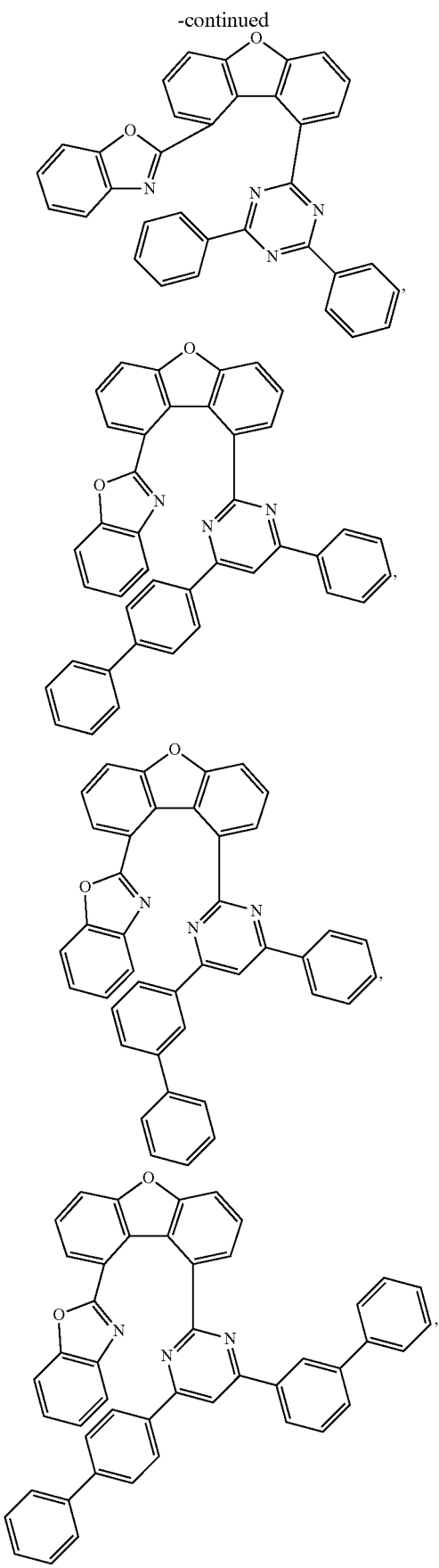
570
-continued
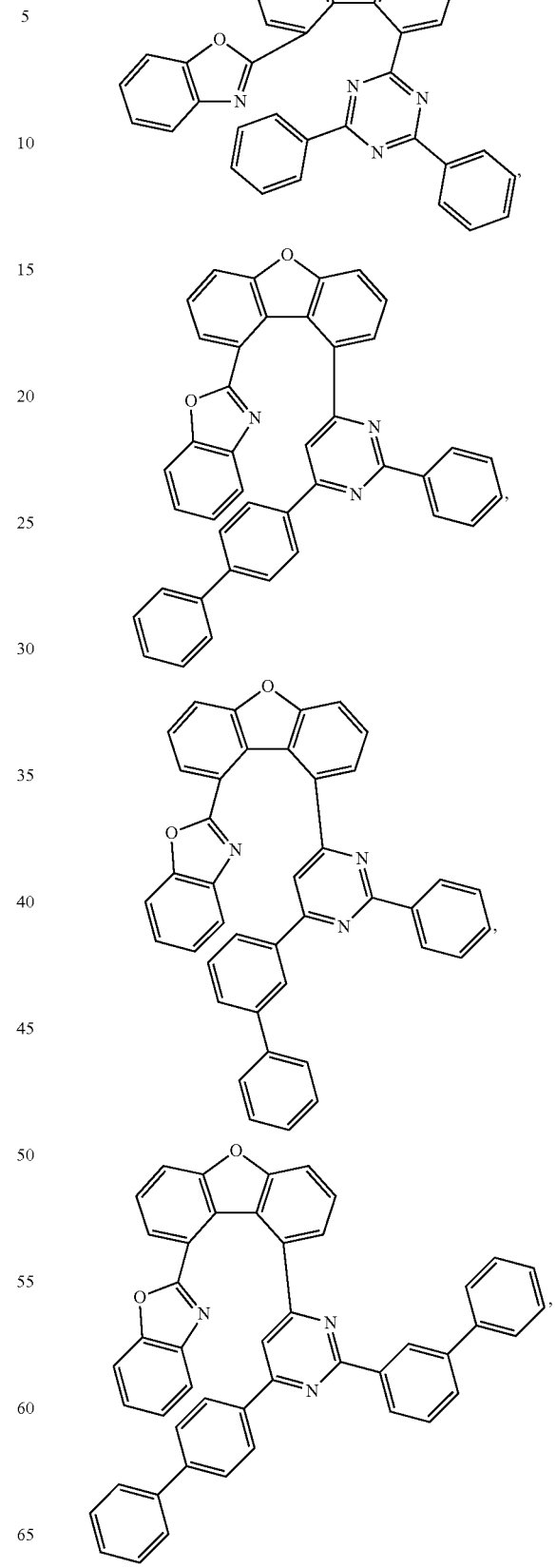

571
-continued
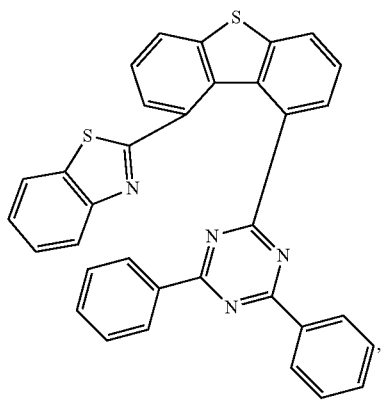
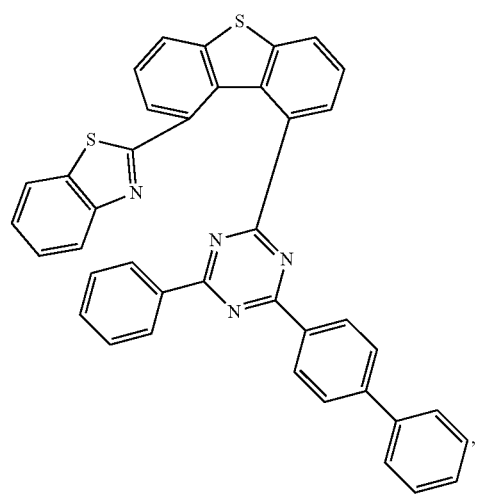
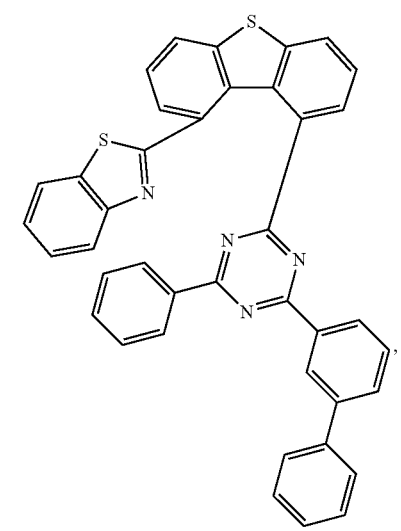
572
-continued
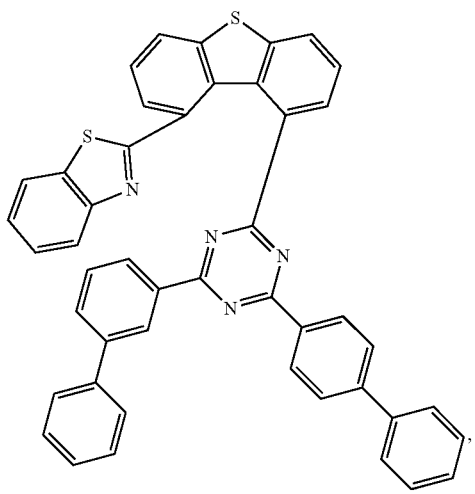
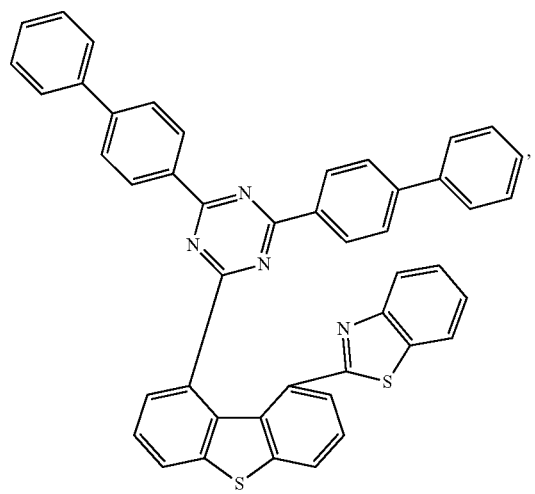
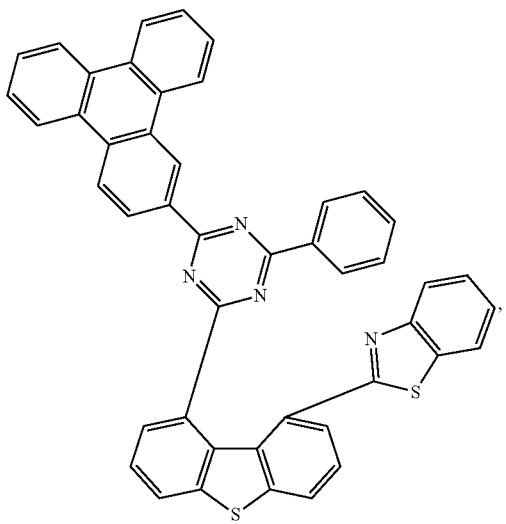

573
-continued
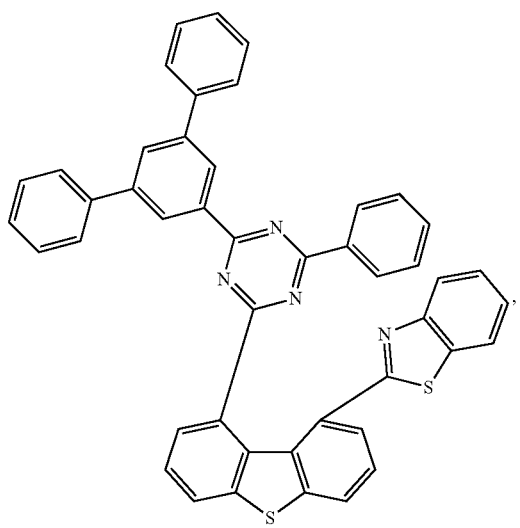
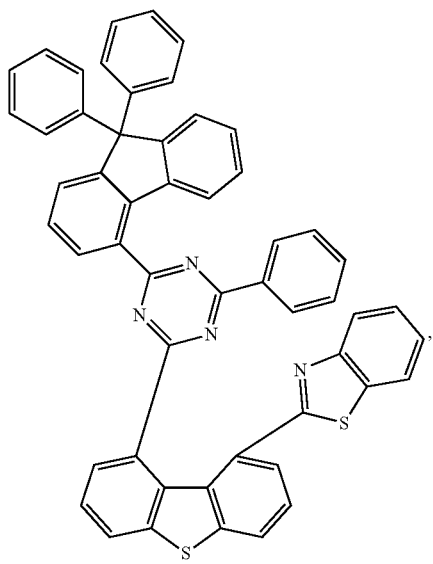
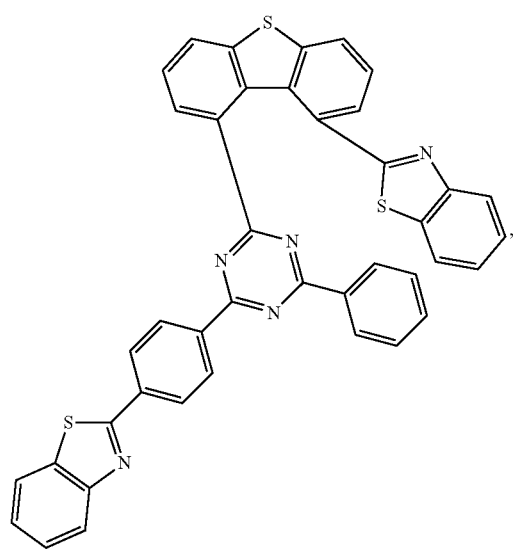
574
-continued
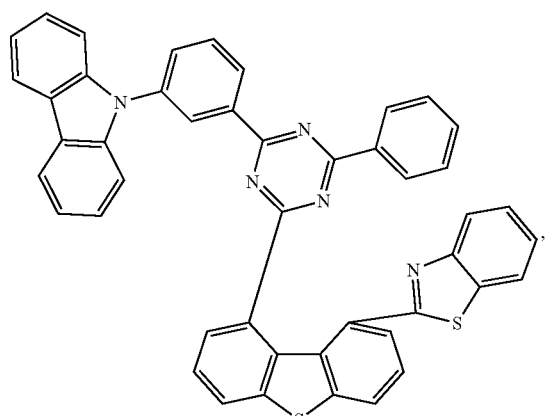
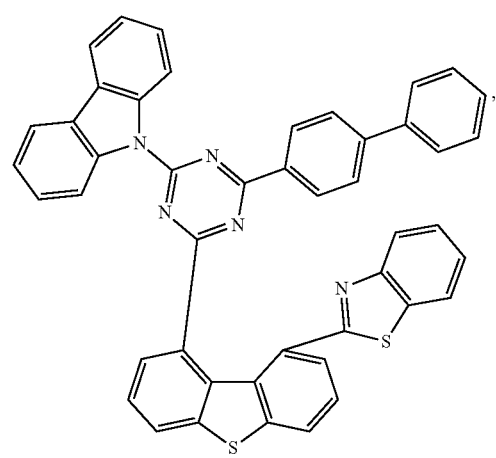

575
-continued
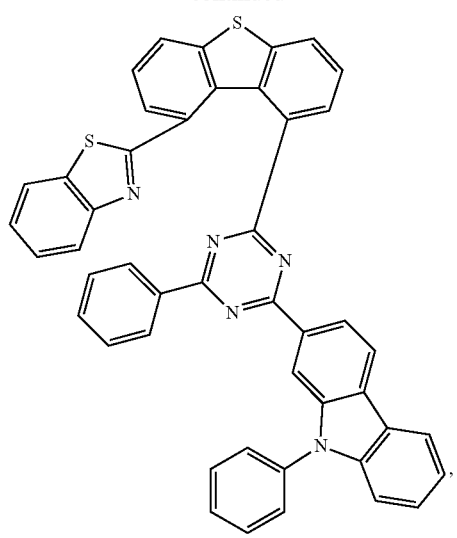
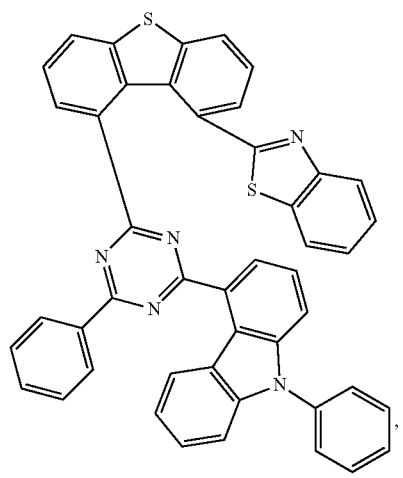
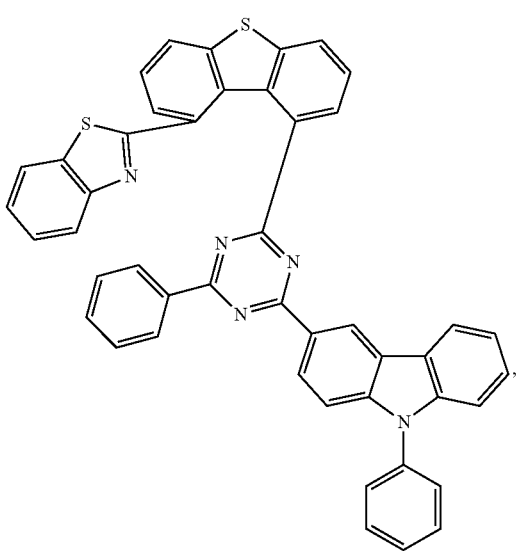
576
-continued
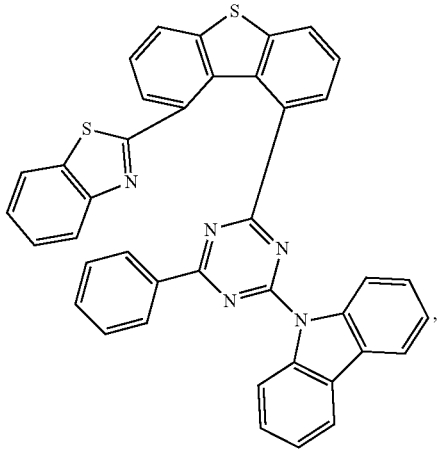
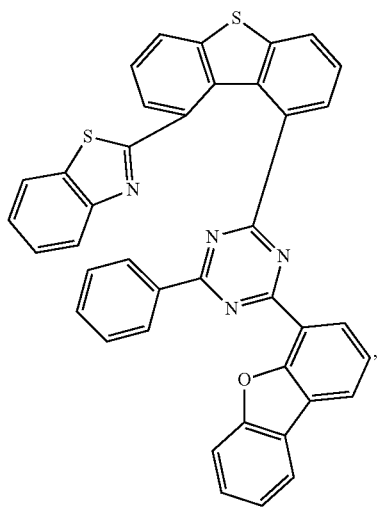
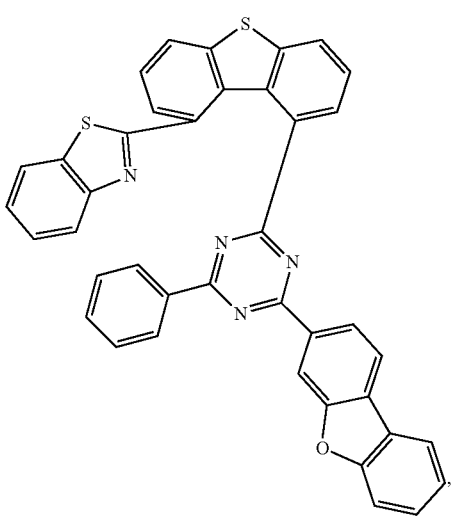

577
-continued
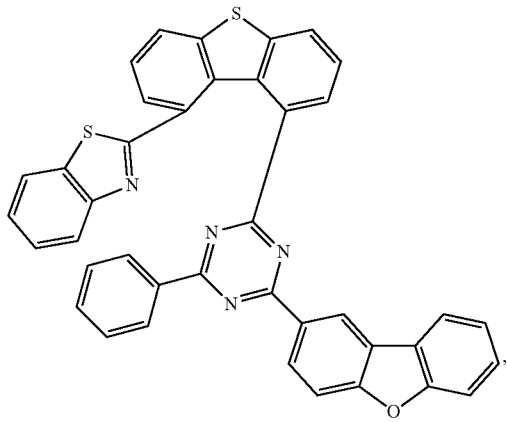
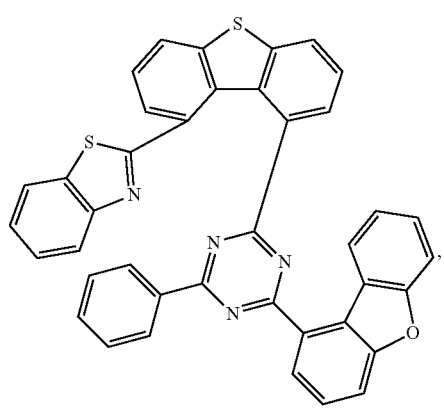
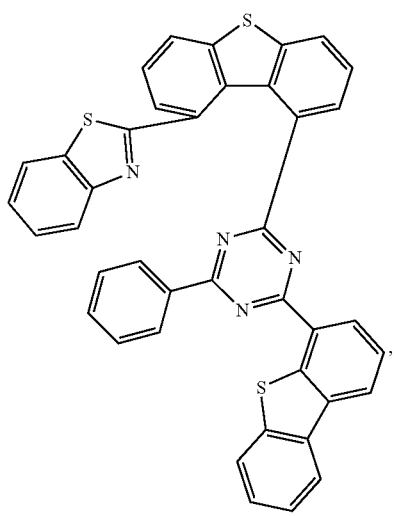
578
-continued
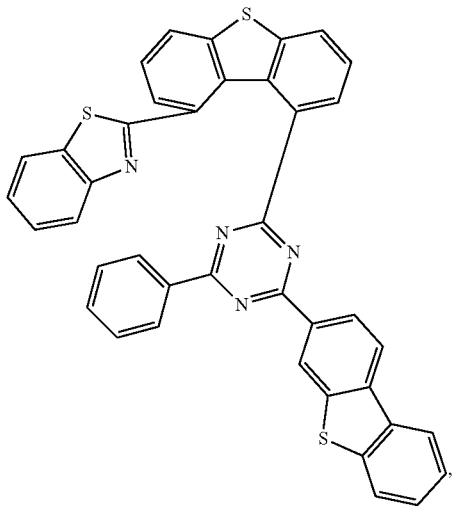
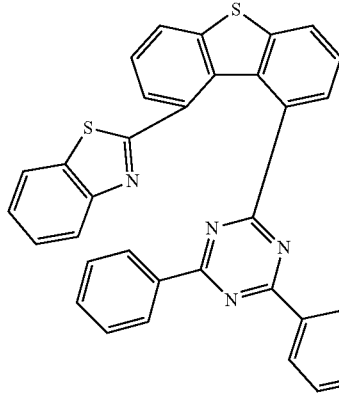
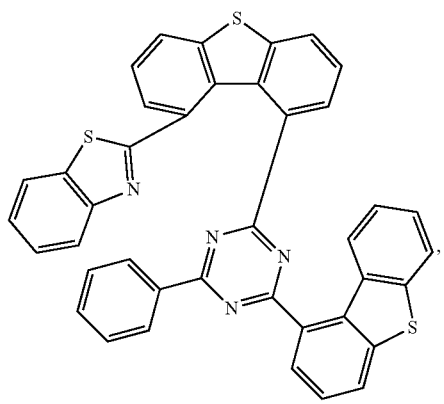

579
-continued
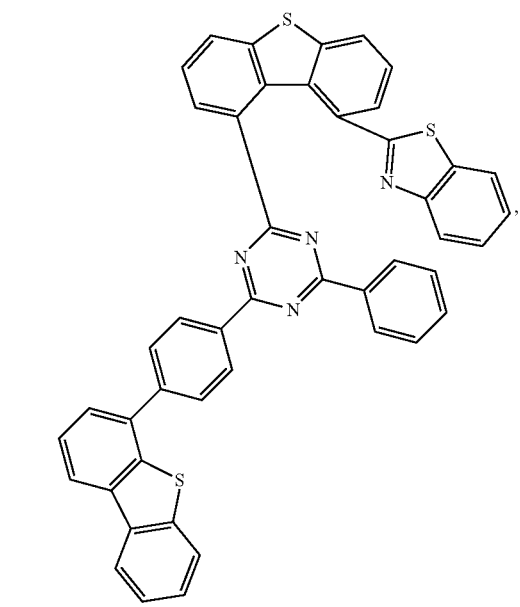
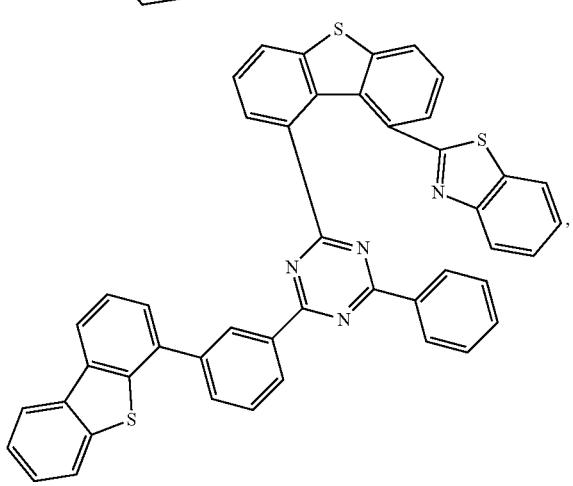
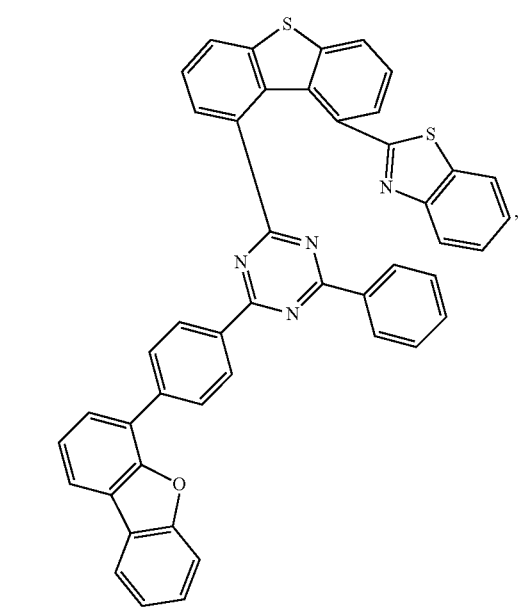
580
-continued
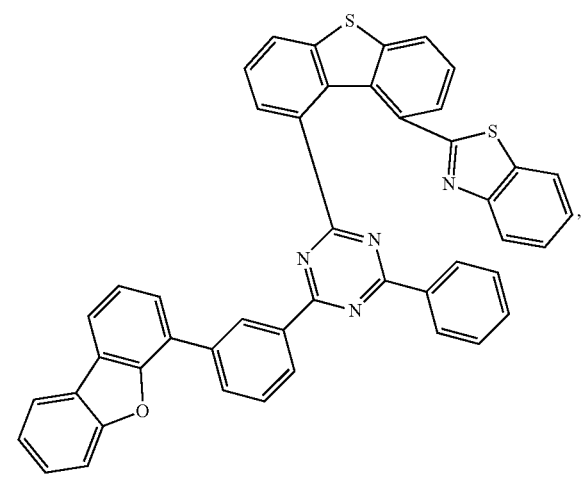
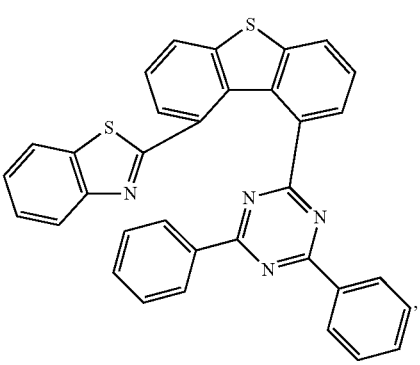
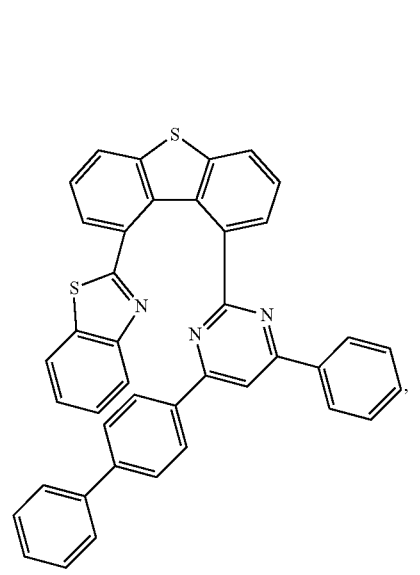

581
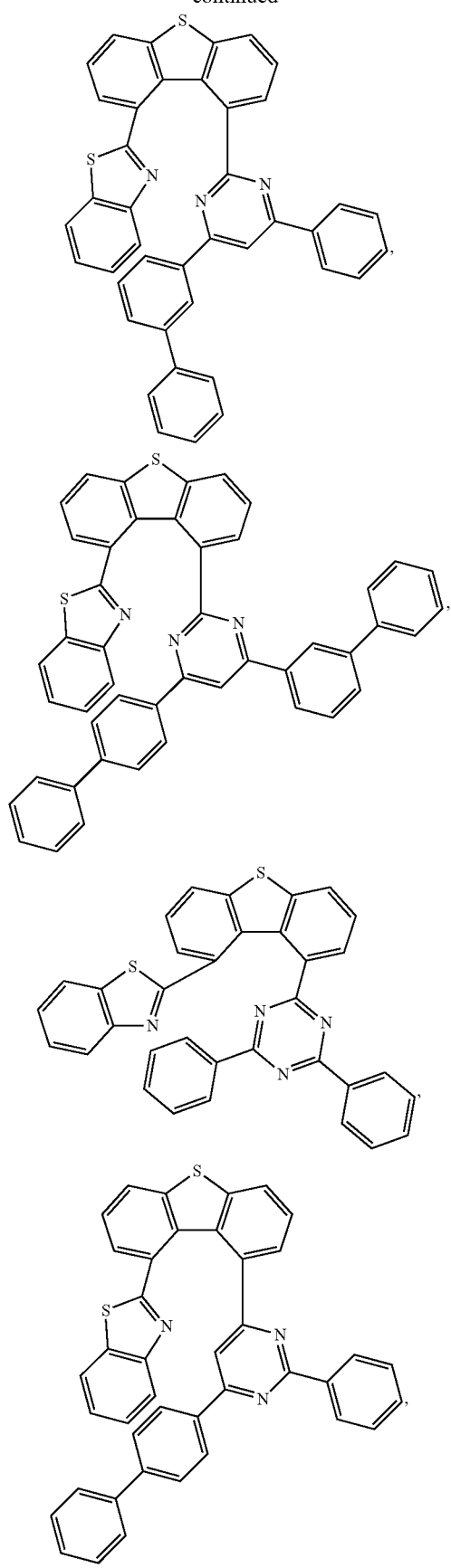
582
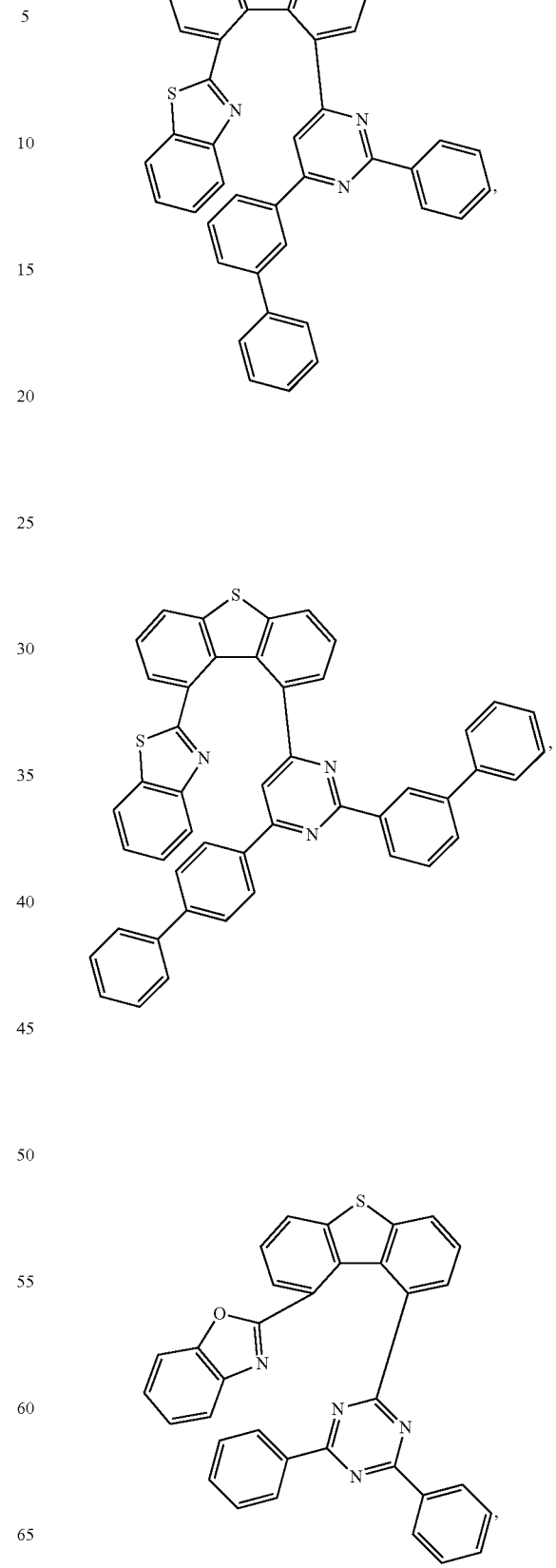

583
-continued
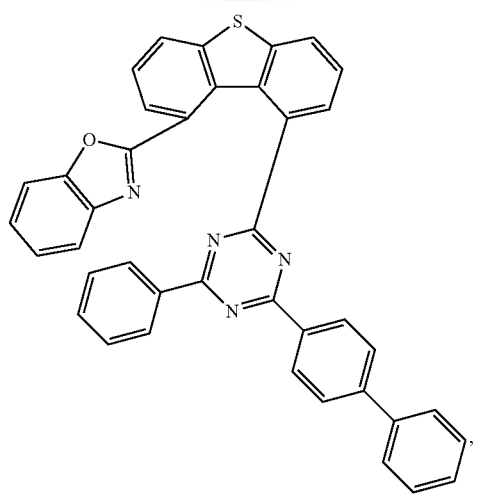
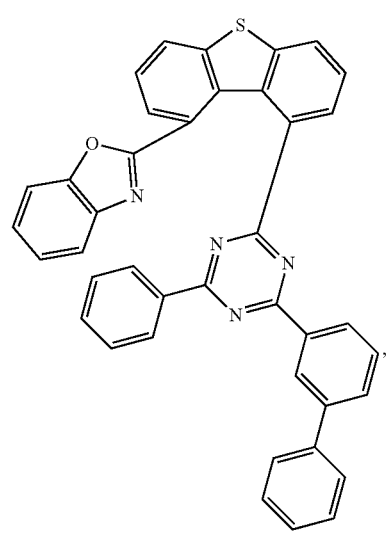
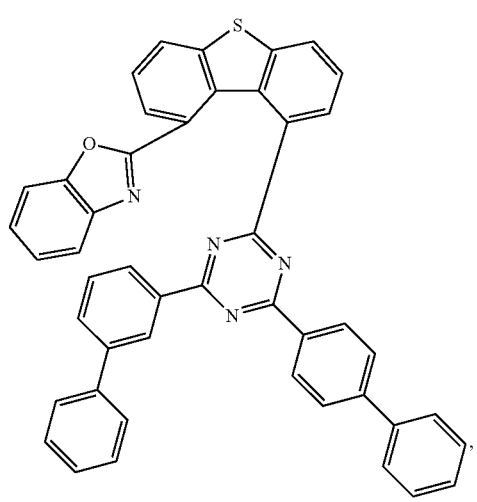
584
-continued
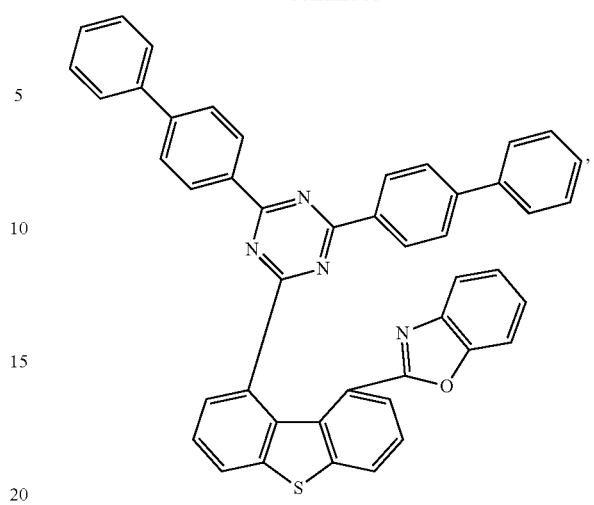
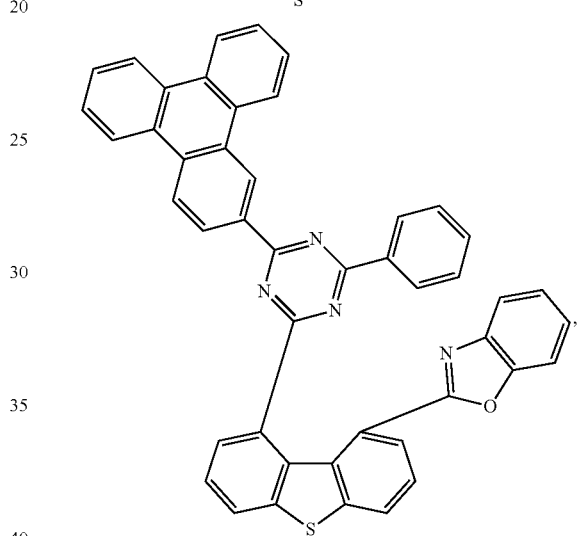
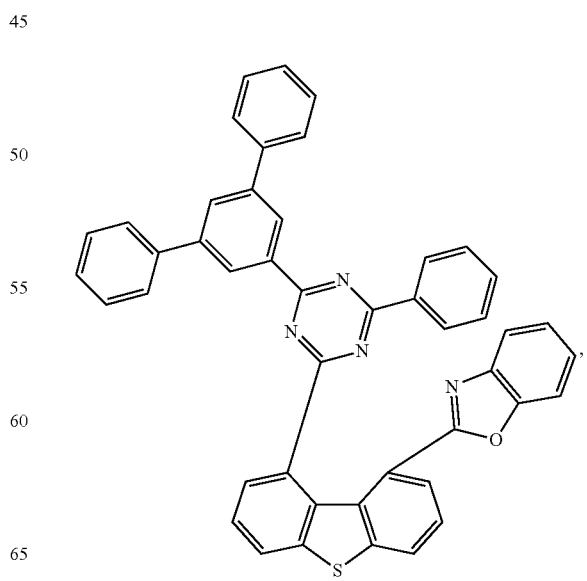

585
-continued
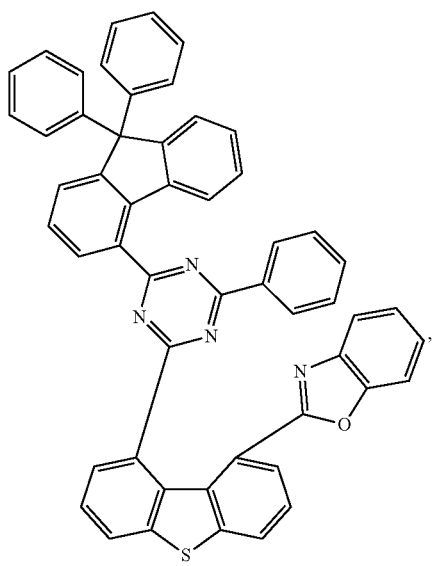
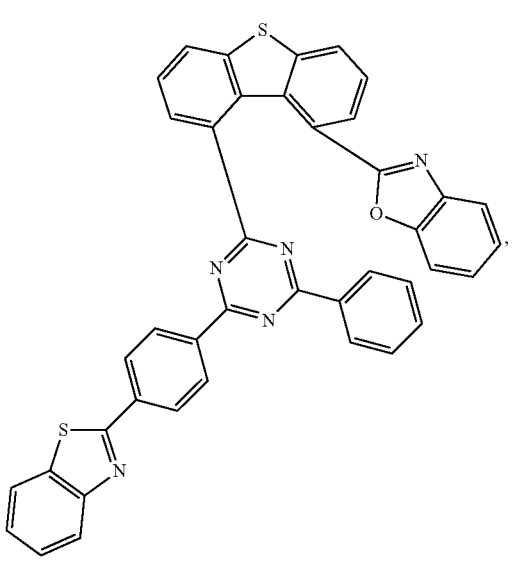
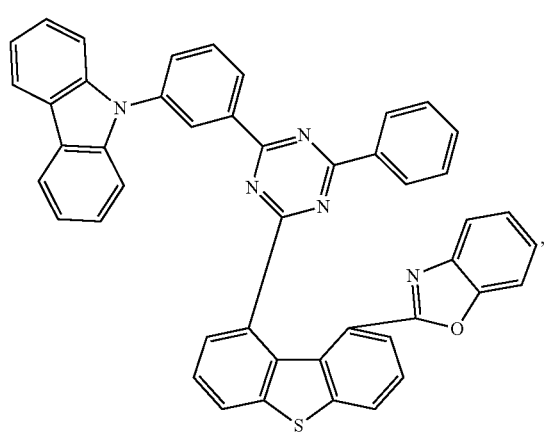
586
-continued
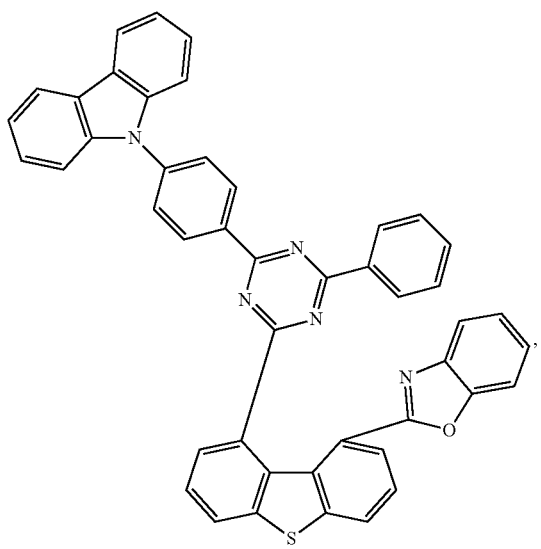
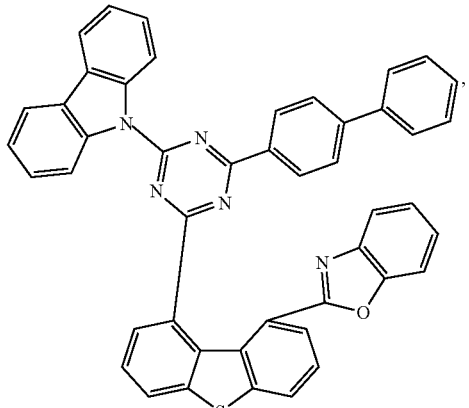
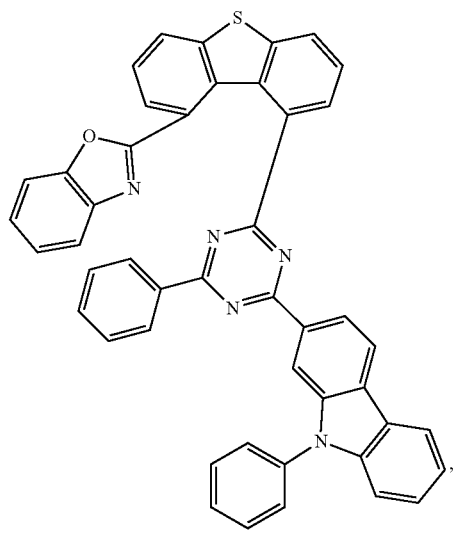

587
-continued
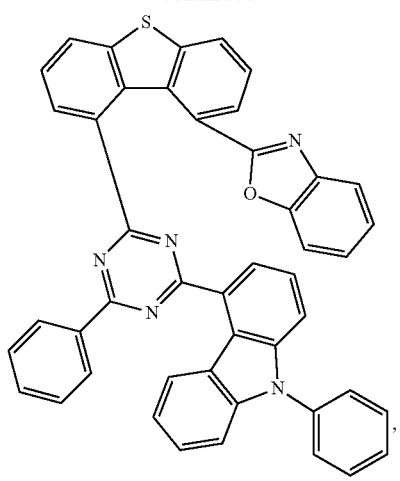
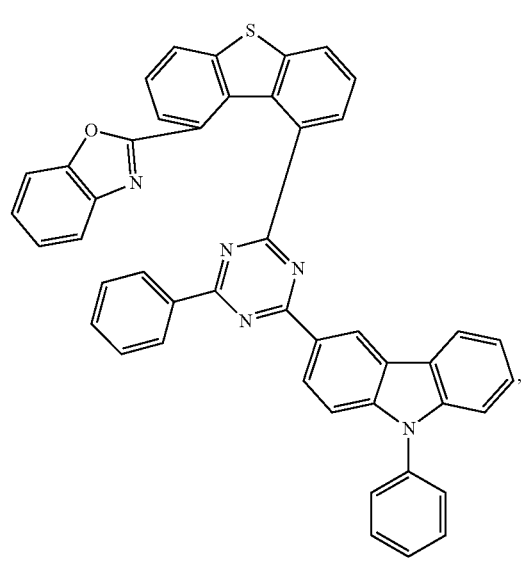
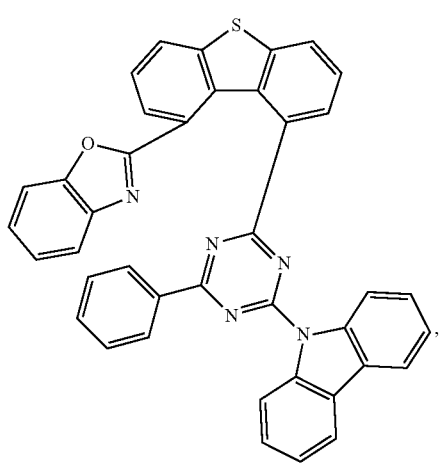
588
-continued
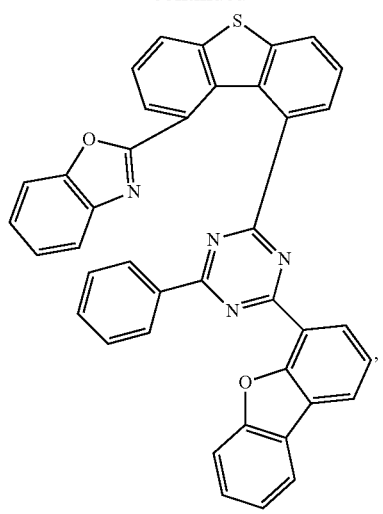
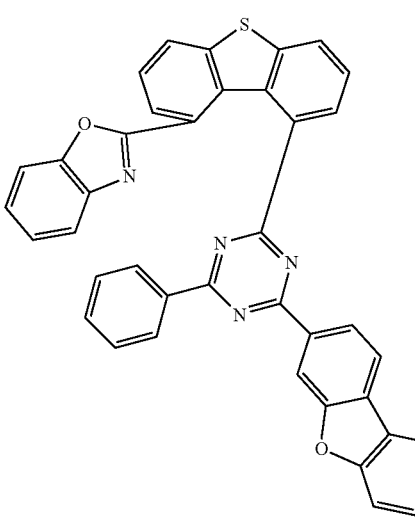
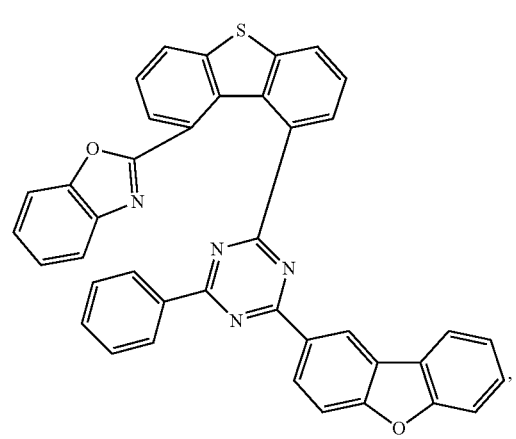

| 589 -continued | 590 -continued |
|---|---|
| 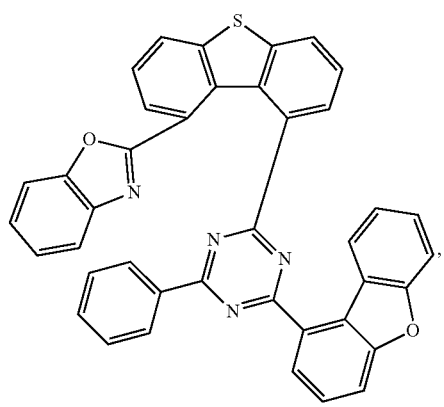 | 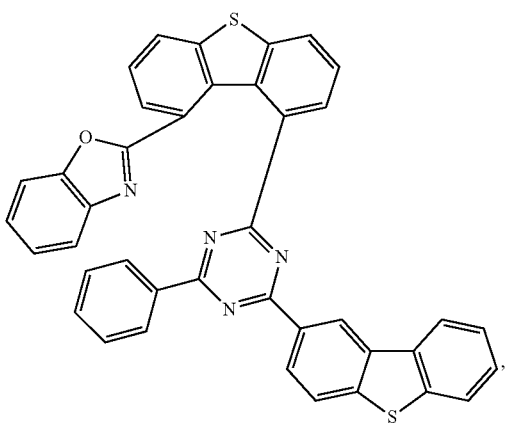 |
| 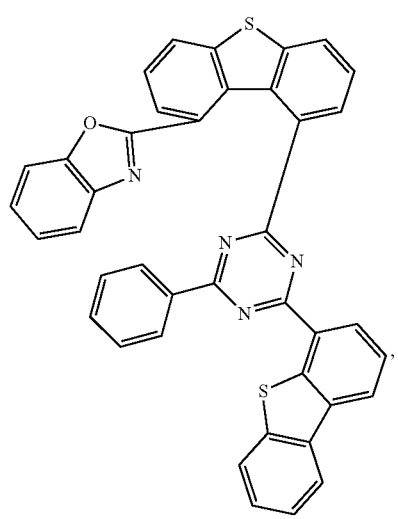 | 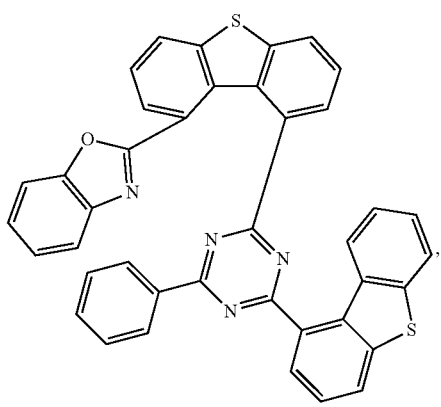 |
| 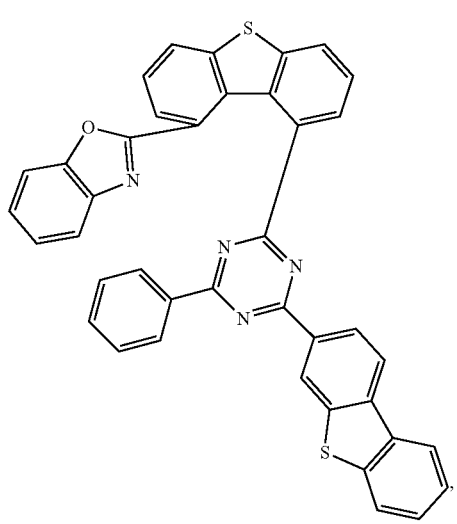 | 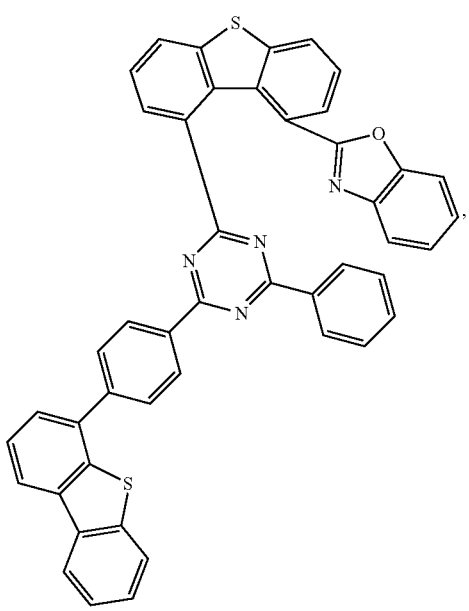 |

591
-continued
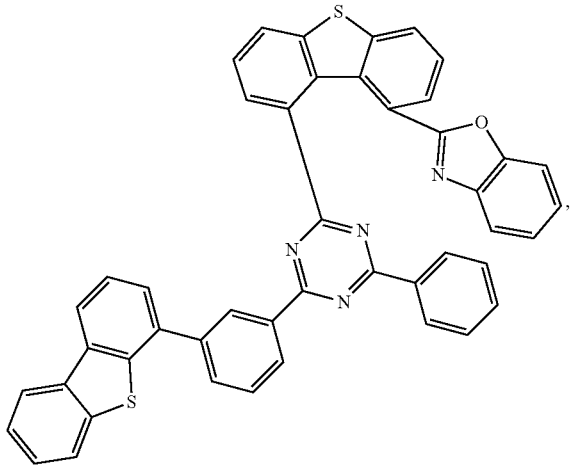
592
-continued
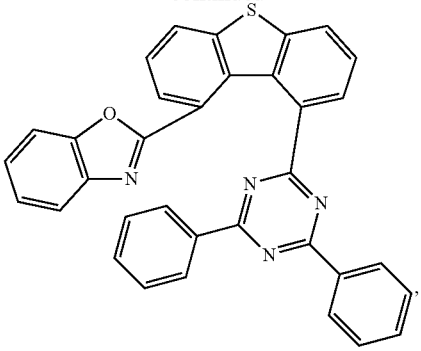
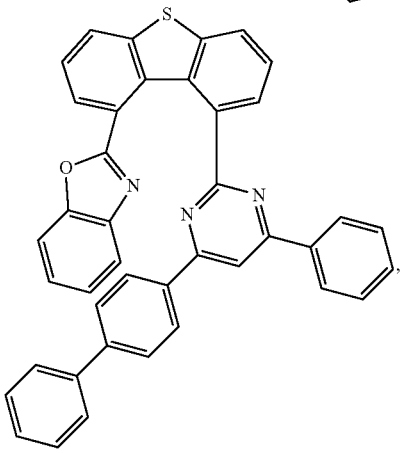
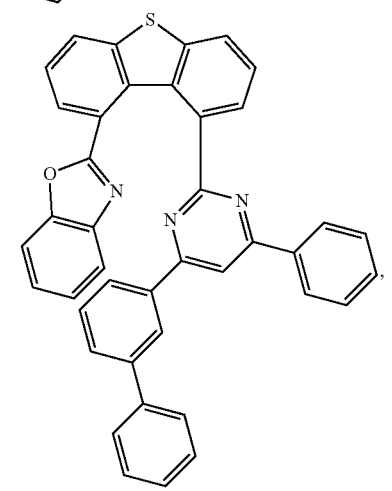
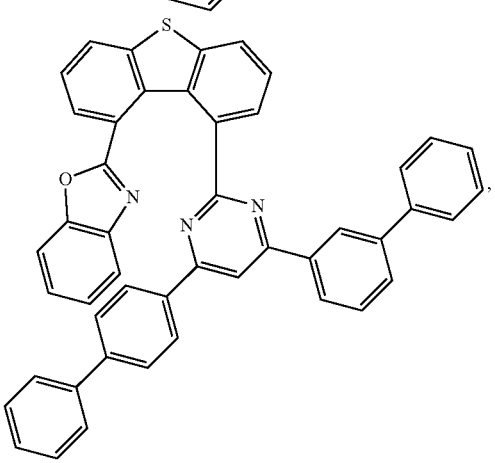

593
-continued
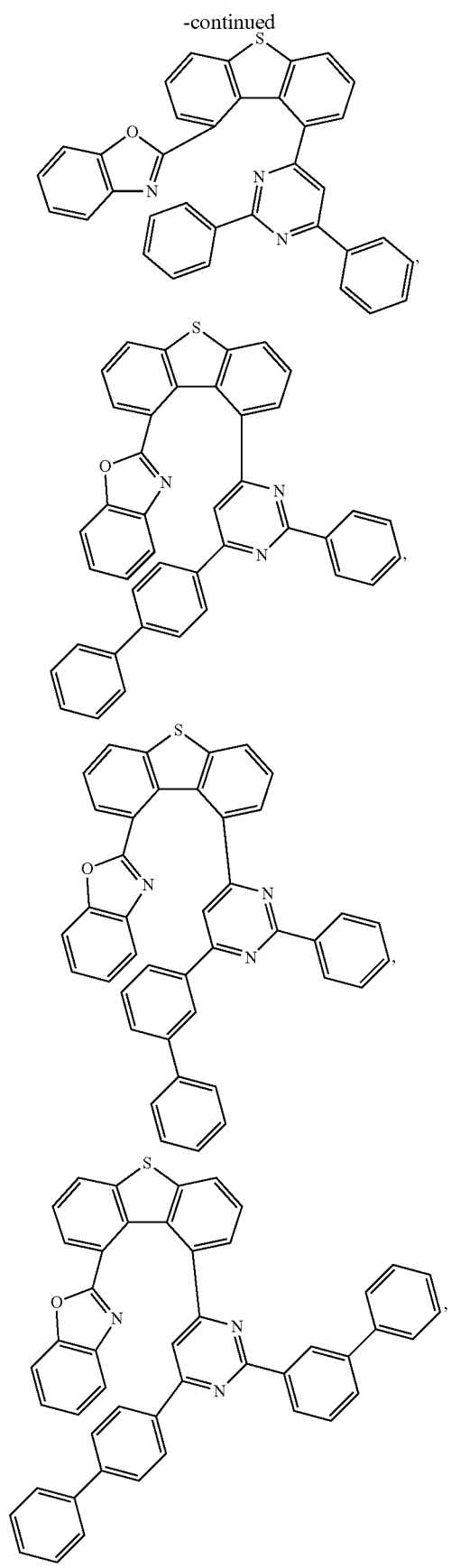
594
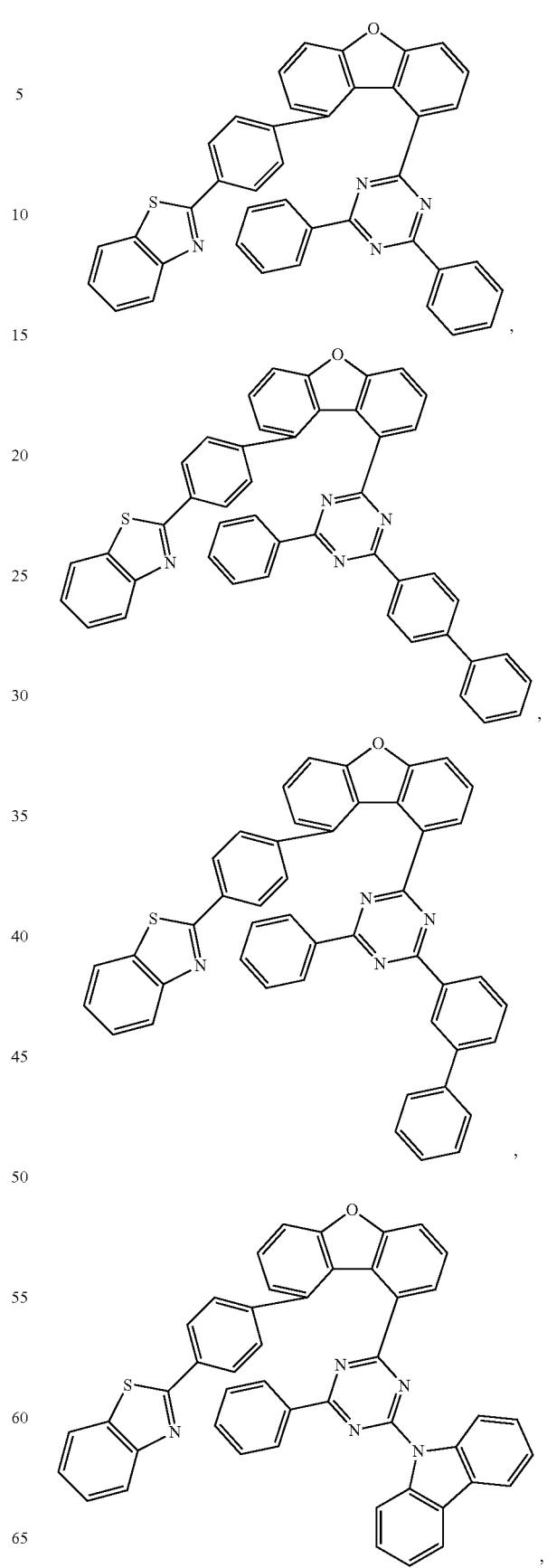

595
-continued
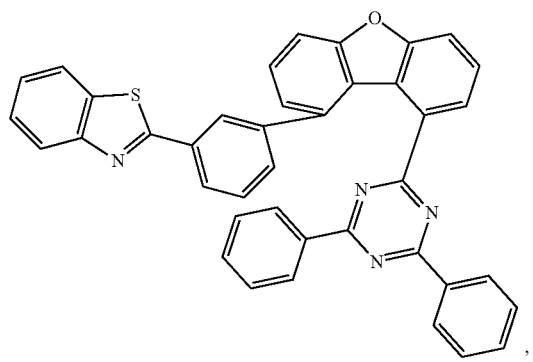
596
-continued
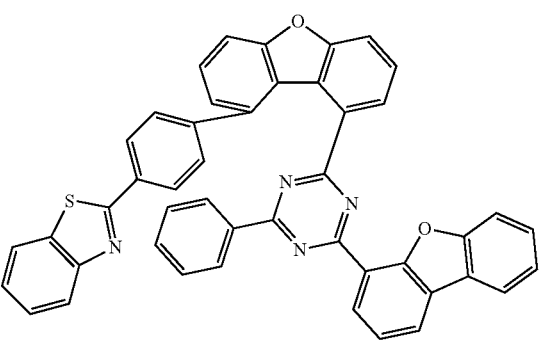
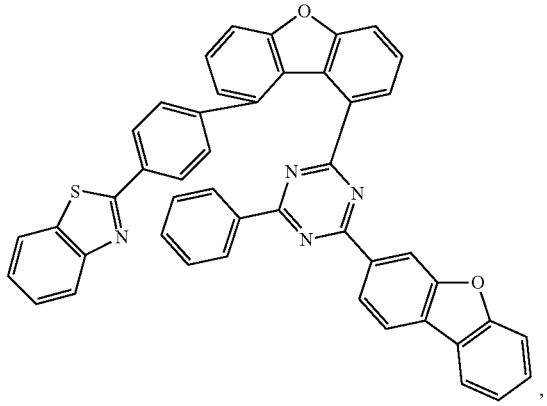
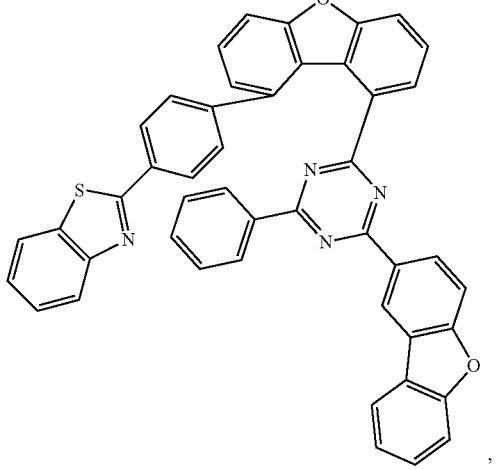
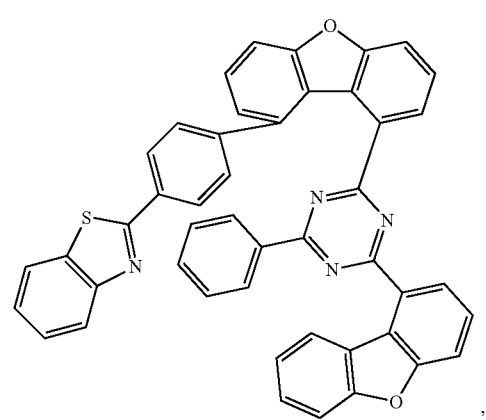

597
-continued
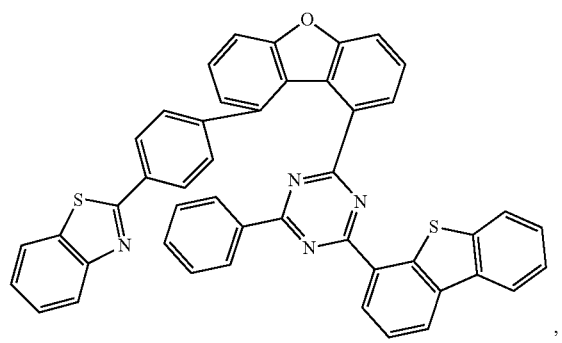
,
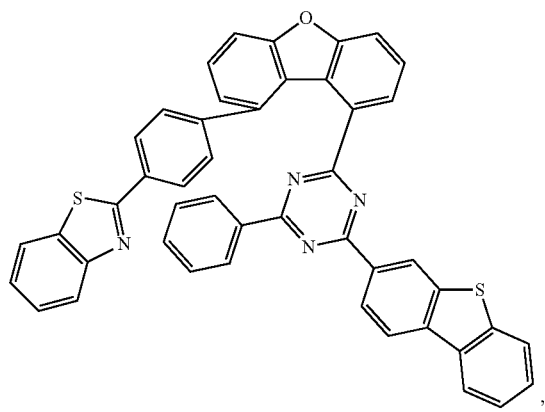
,
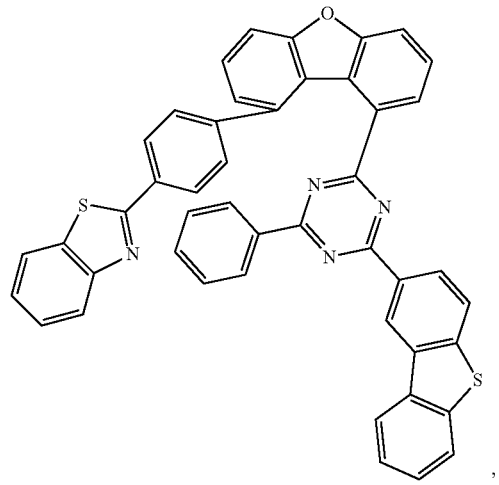
,
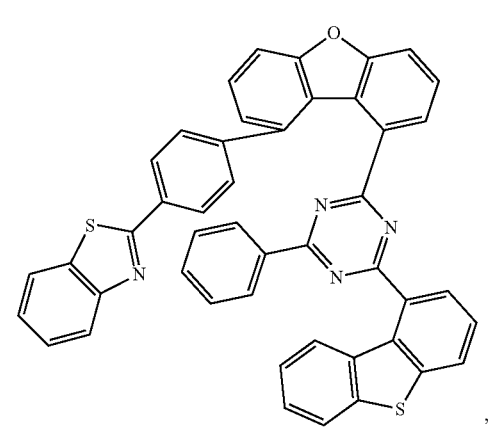
,
598
-continued
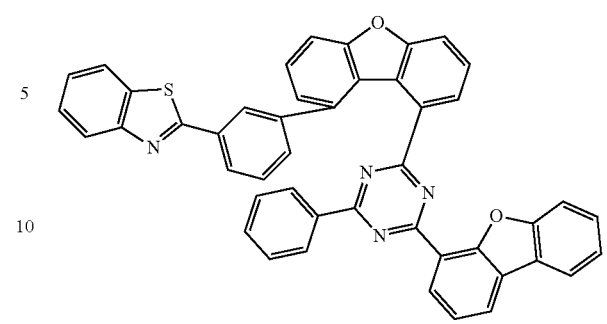
,
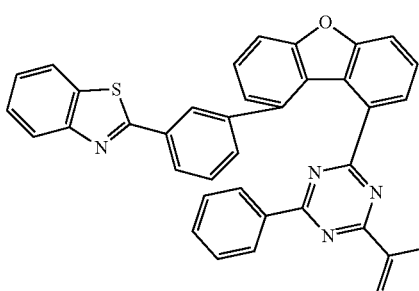
,
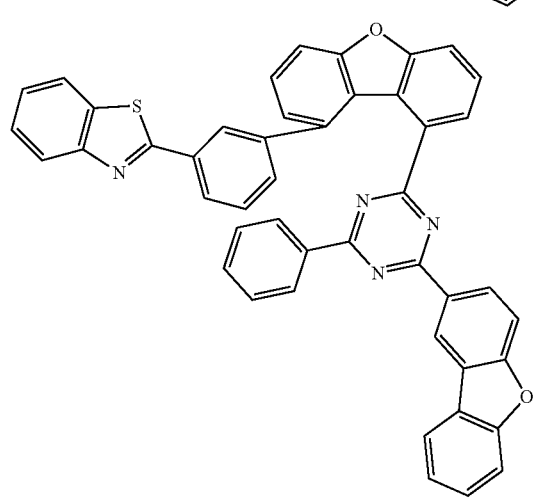
,
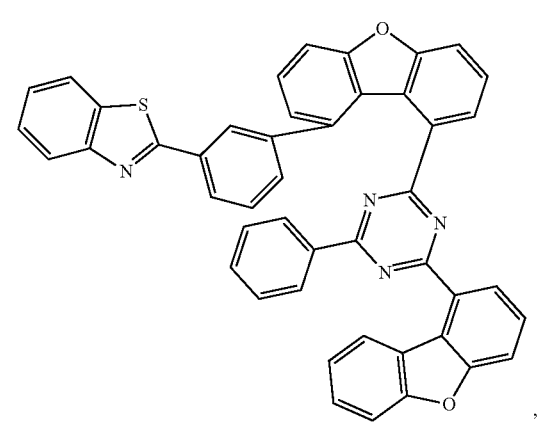
, 599
-continued
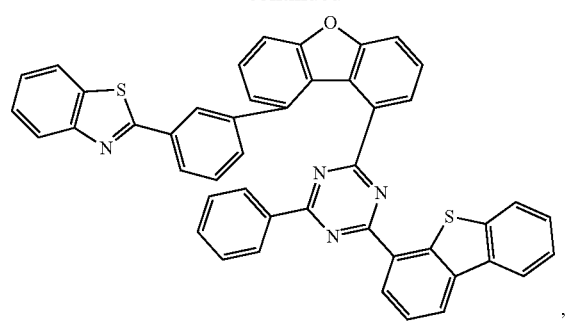
,
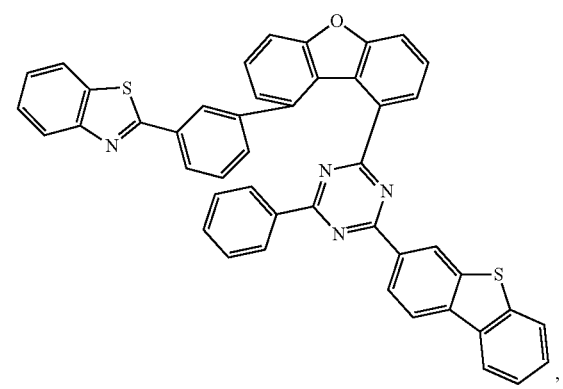
,
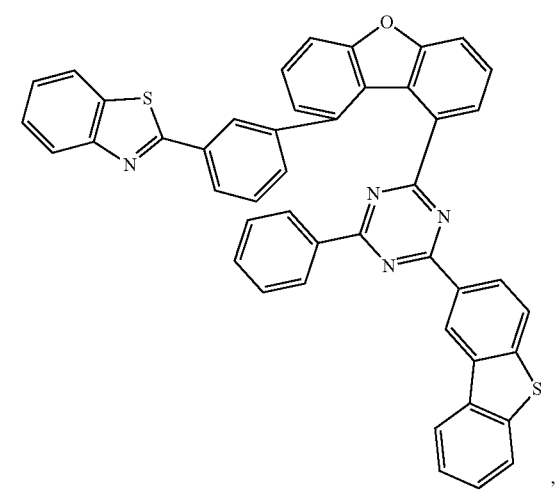
,
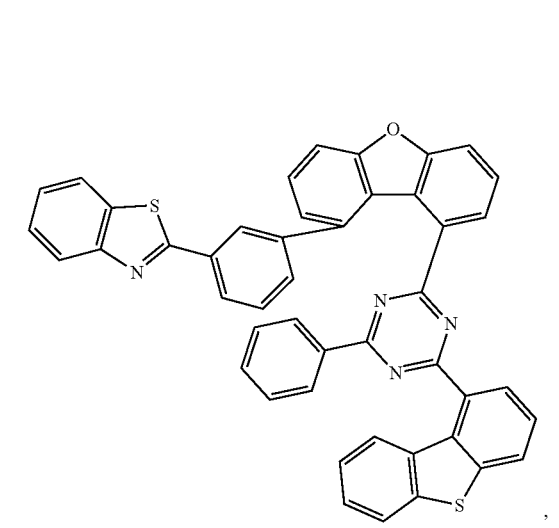
,
600
-continued
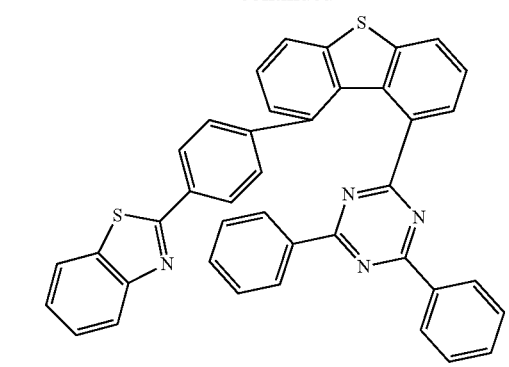
,
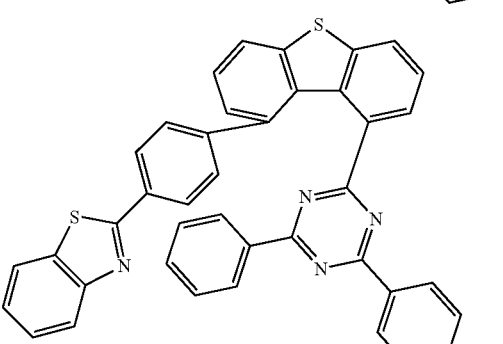
,
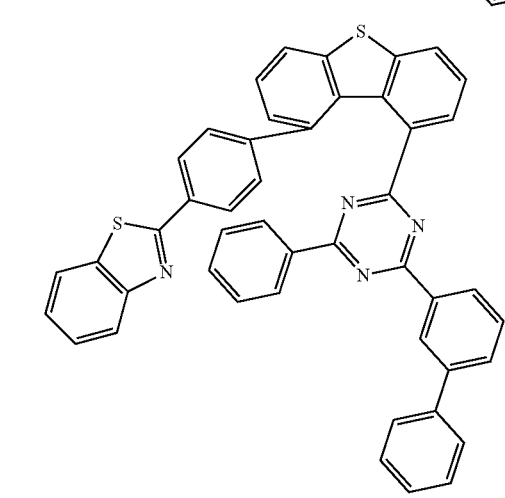
,
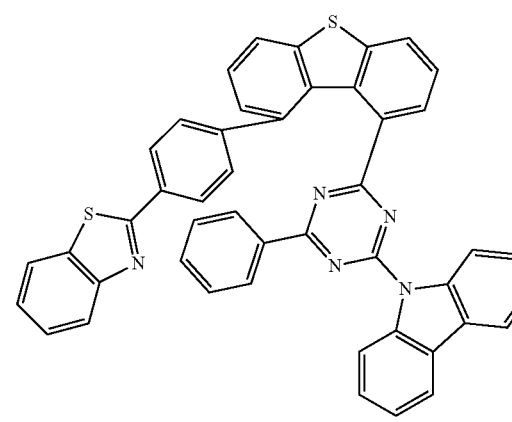
,

601
-continued
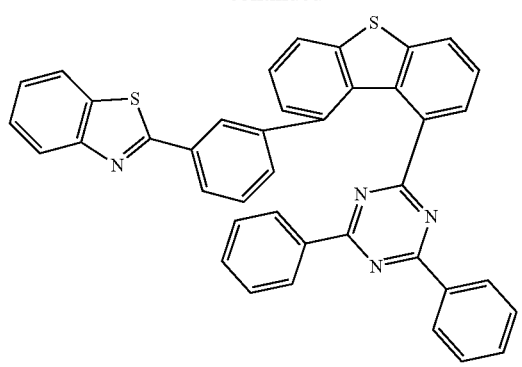
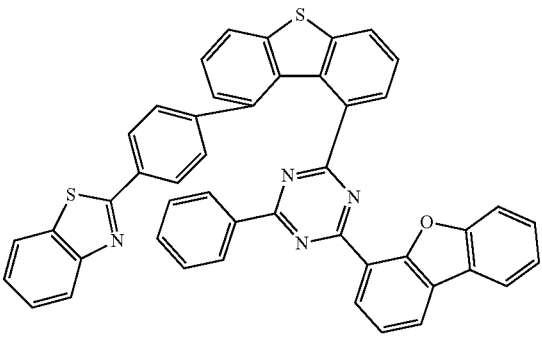
602
-continued
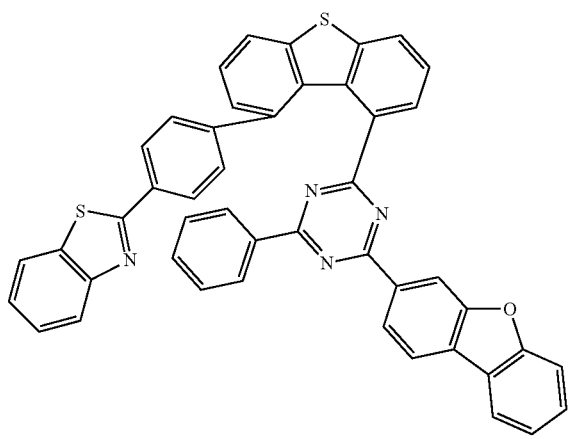
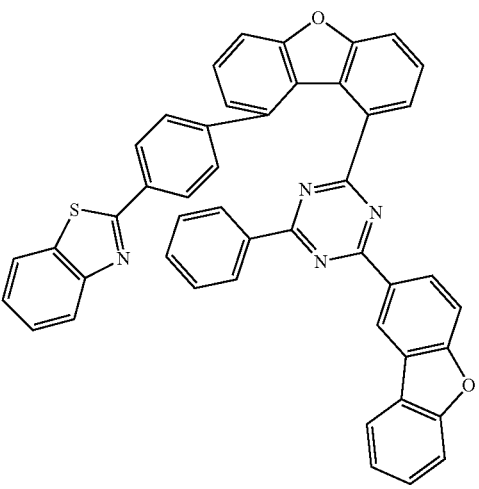
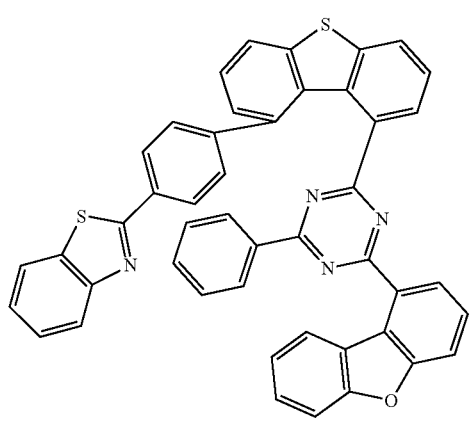

603
-continued
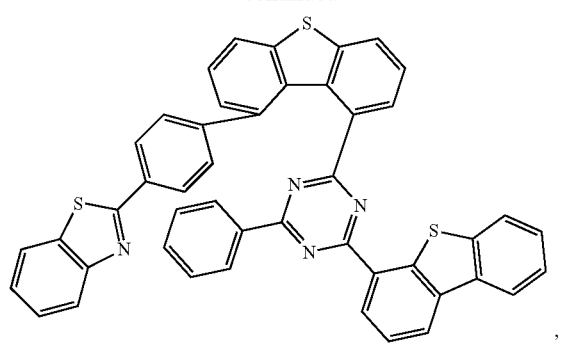
,
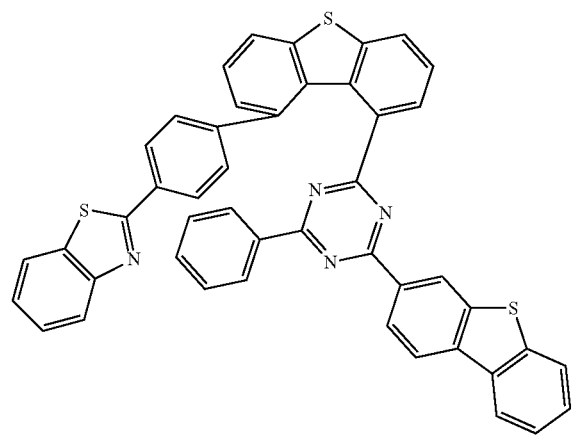
,
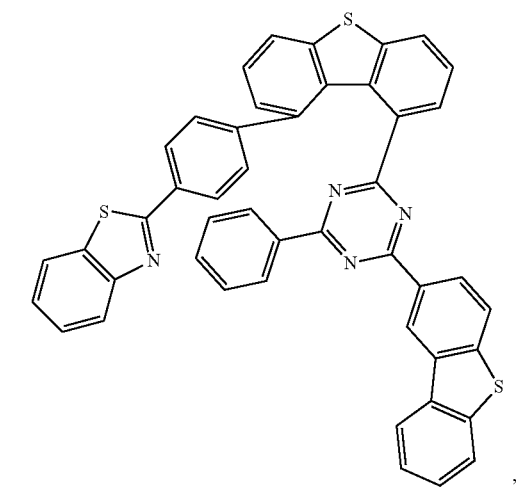
,
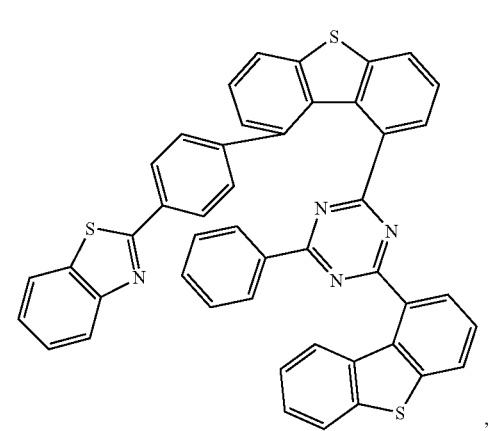
,
604
-continued
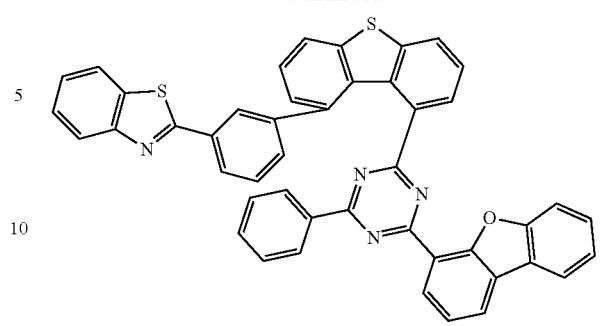
,
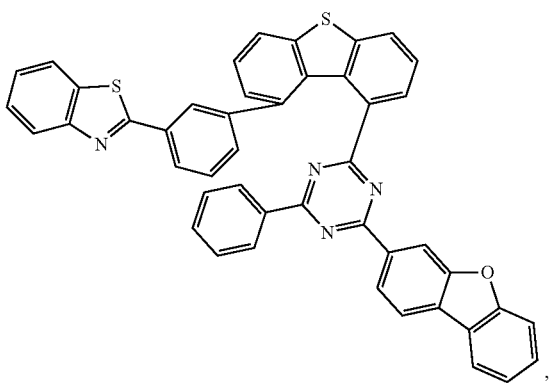
,
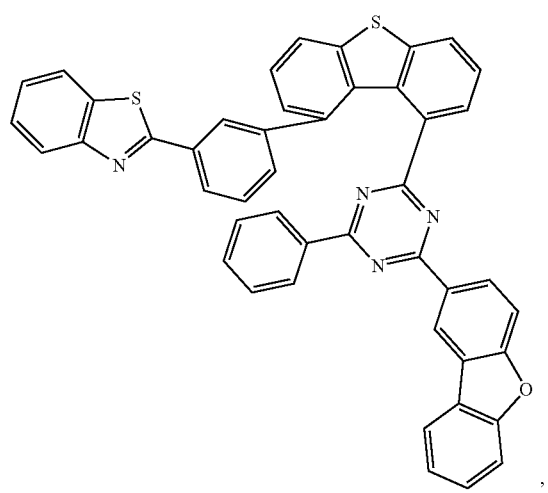
,
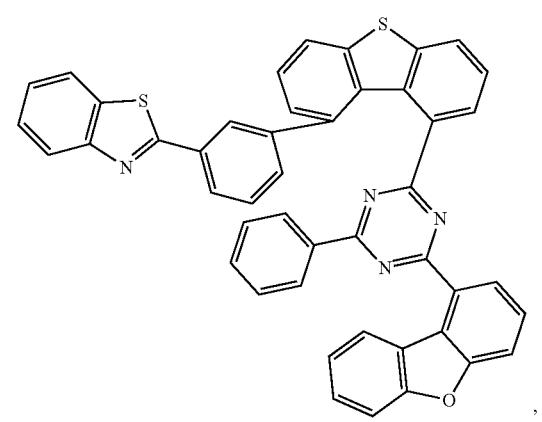
, 605
-continued
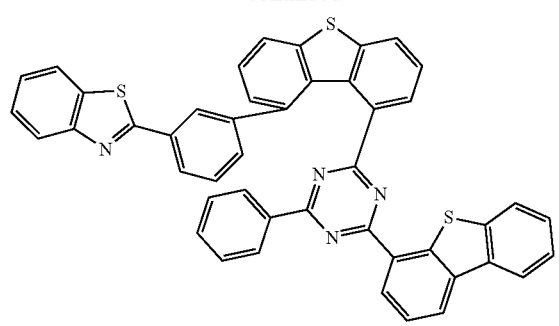
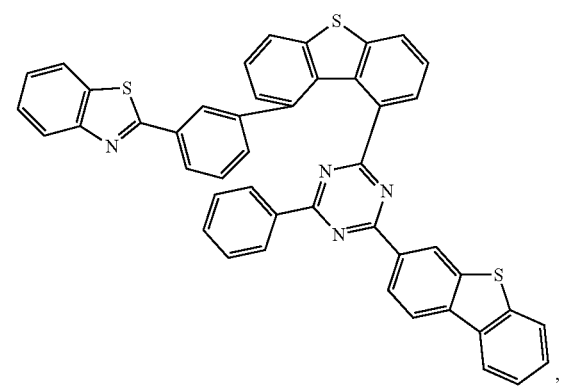
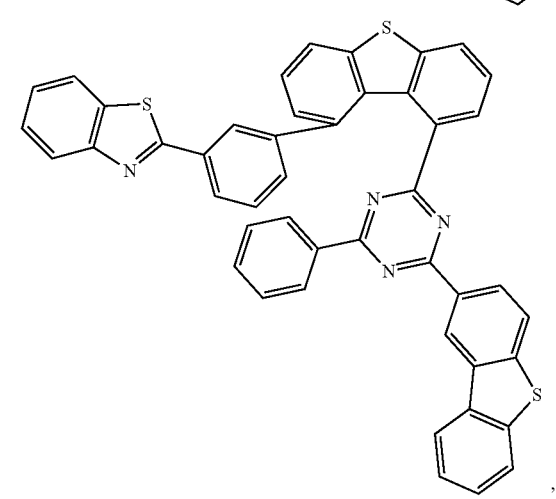
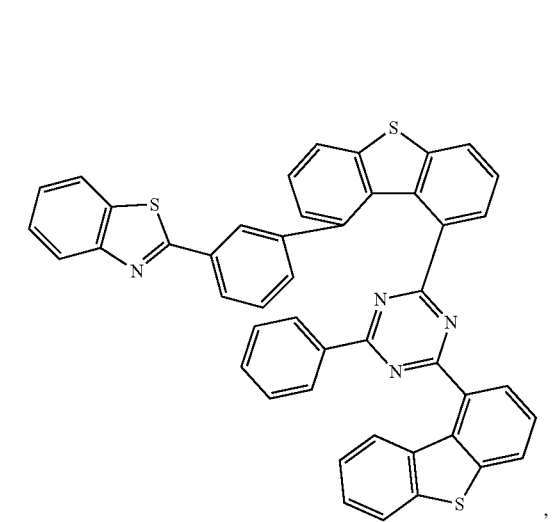
606
-continued
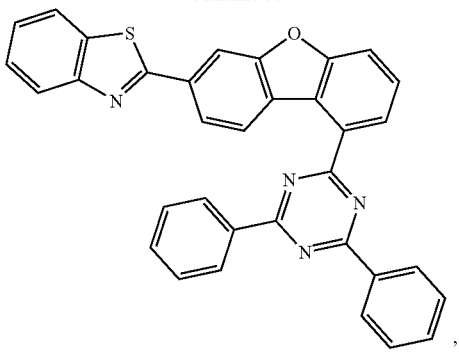
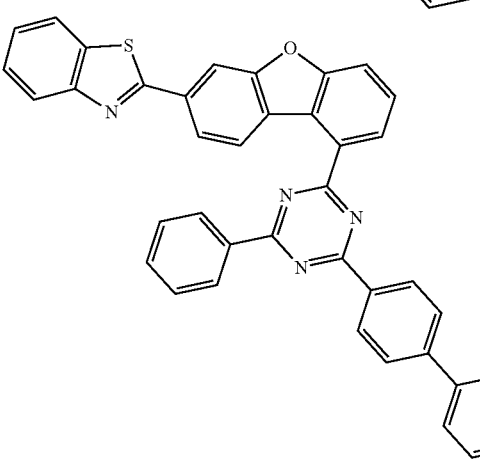
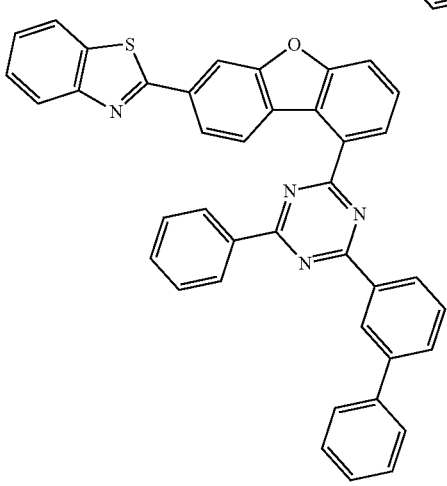
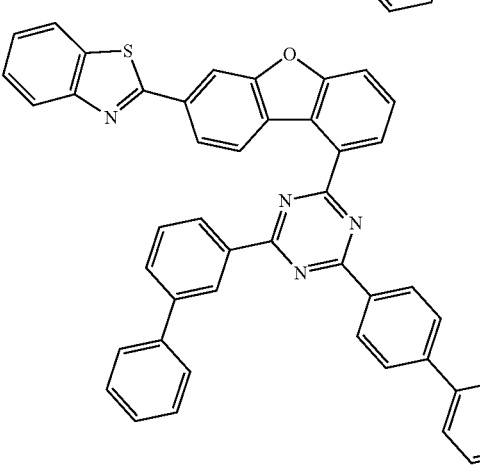

607
-continued
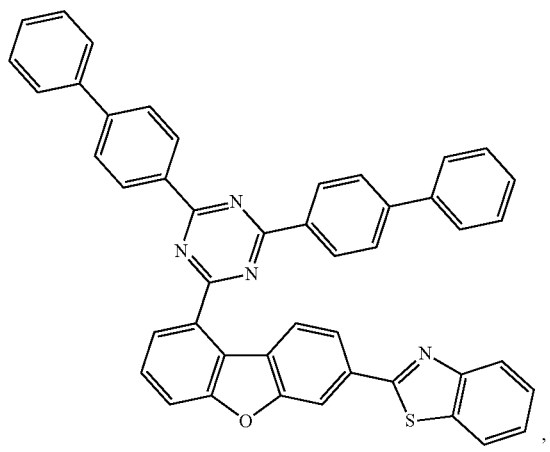
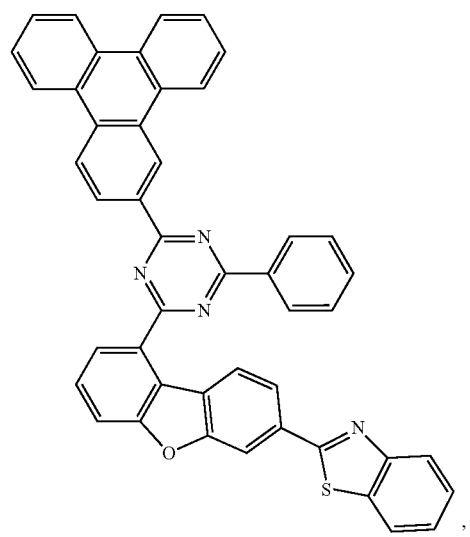
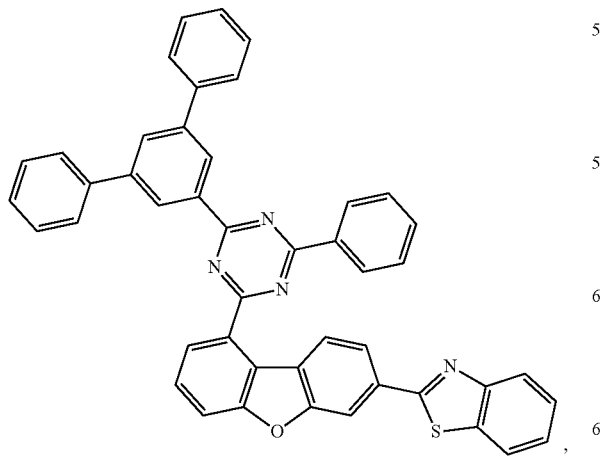
608
-continued
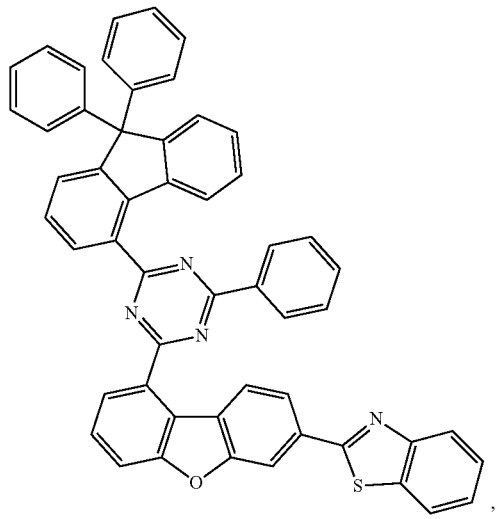
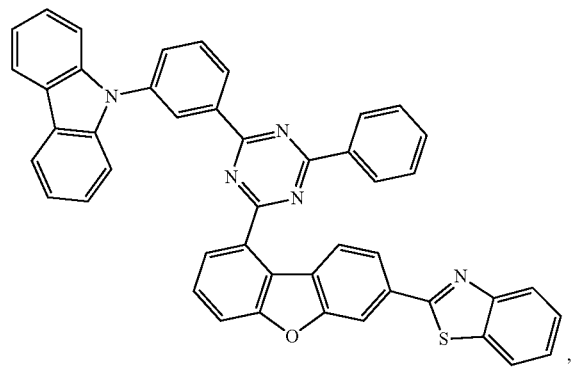

609
-continued
610
-continued
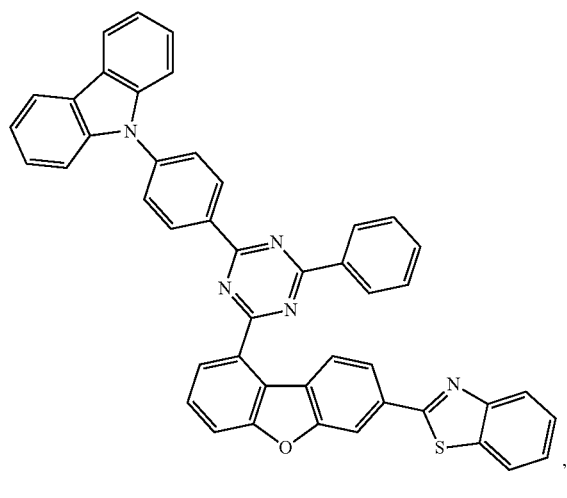
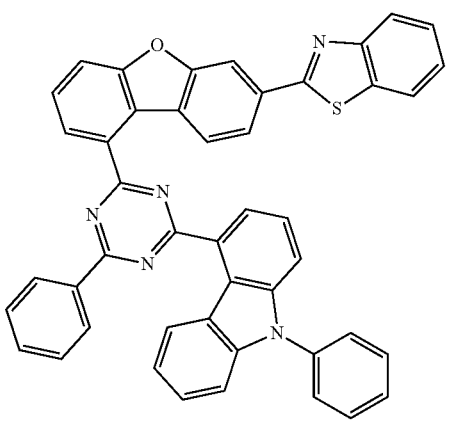
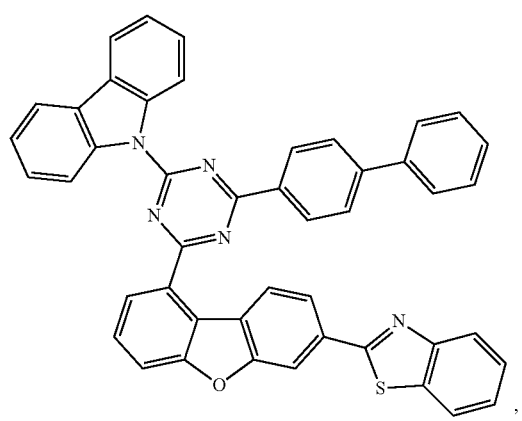
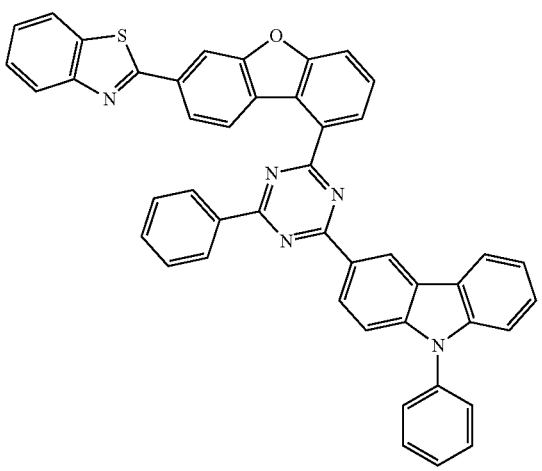
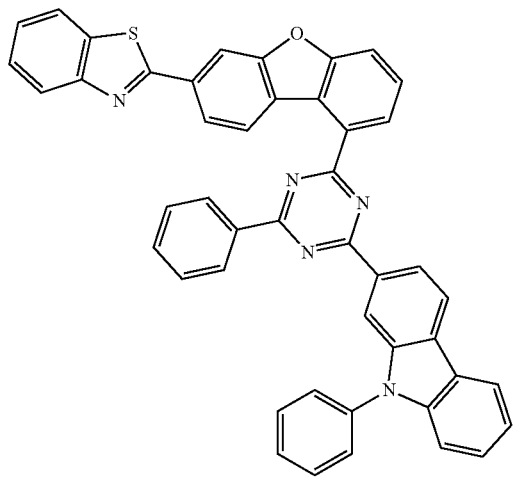
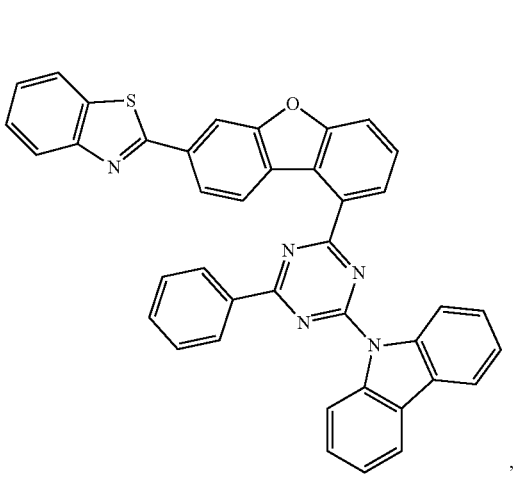

611
-continued
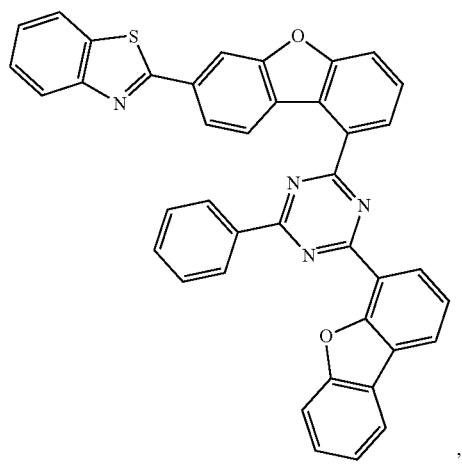
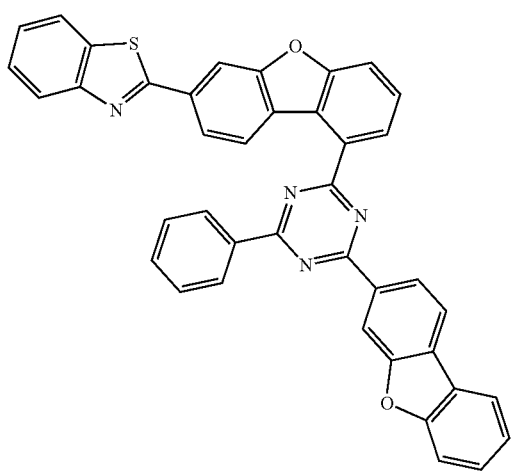
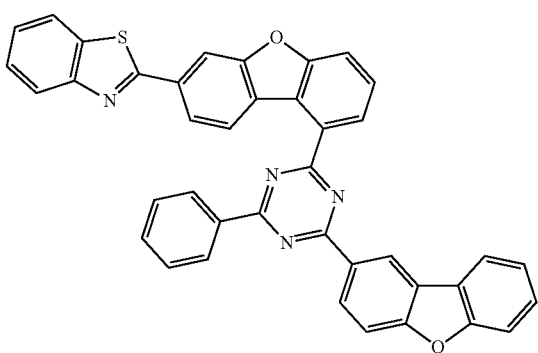
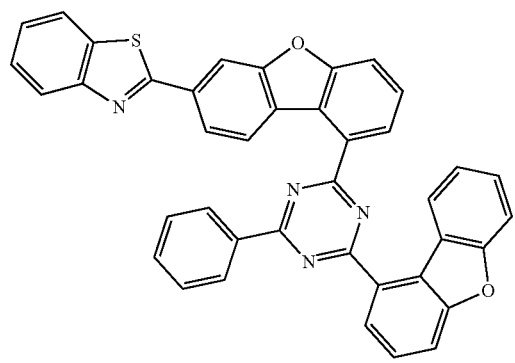
612
-continued
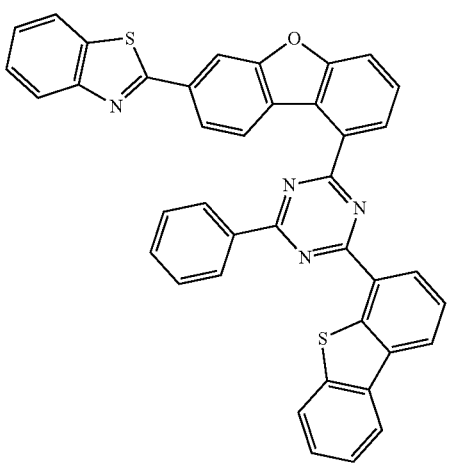
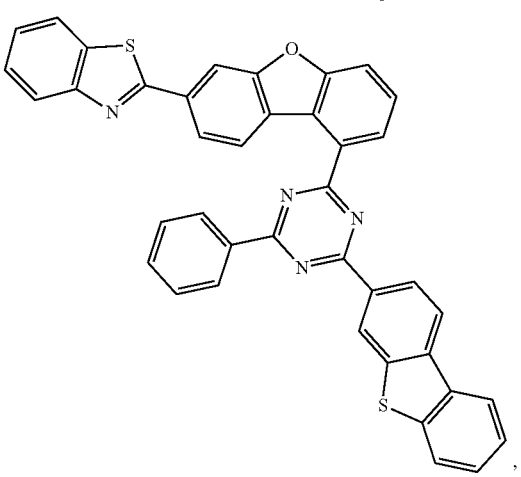
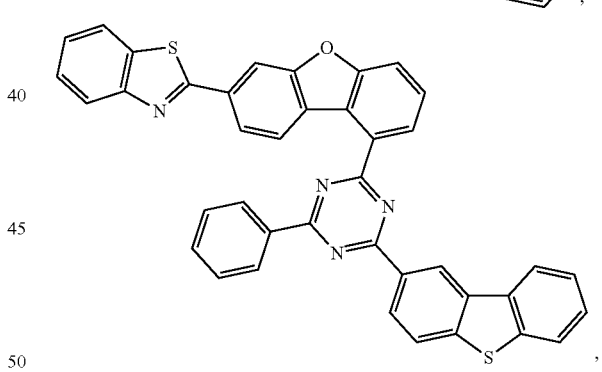
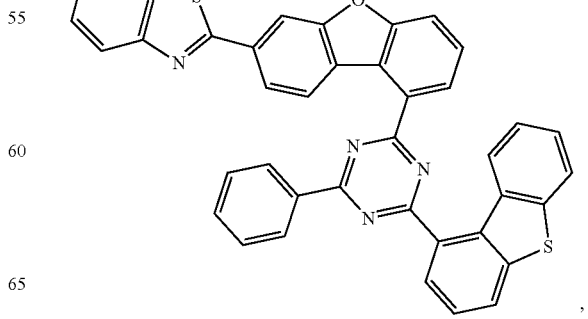

613
-continued
614
-continued
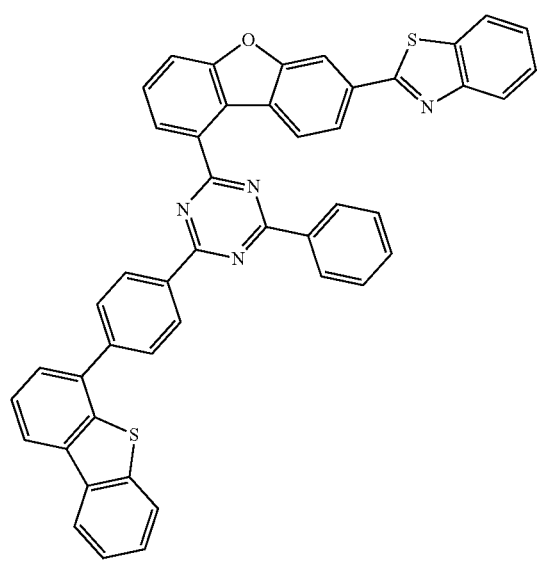
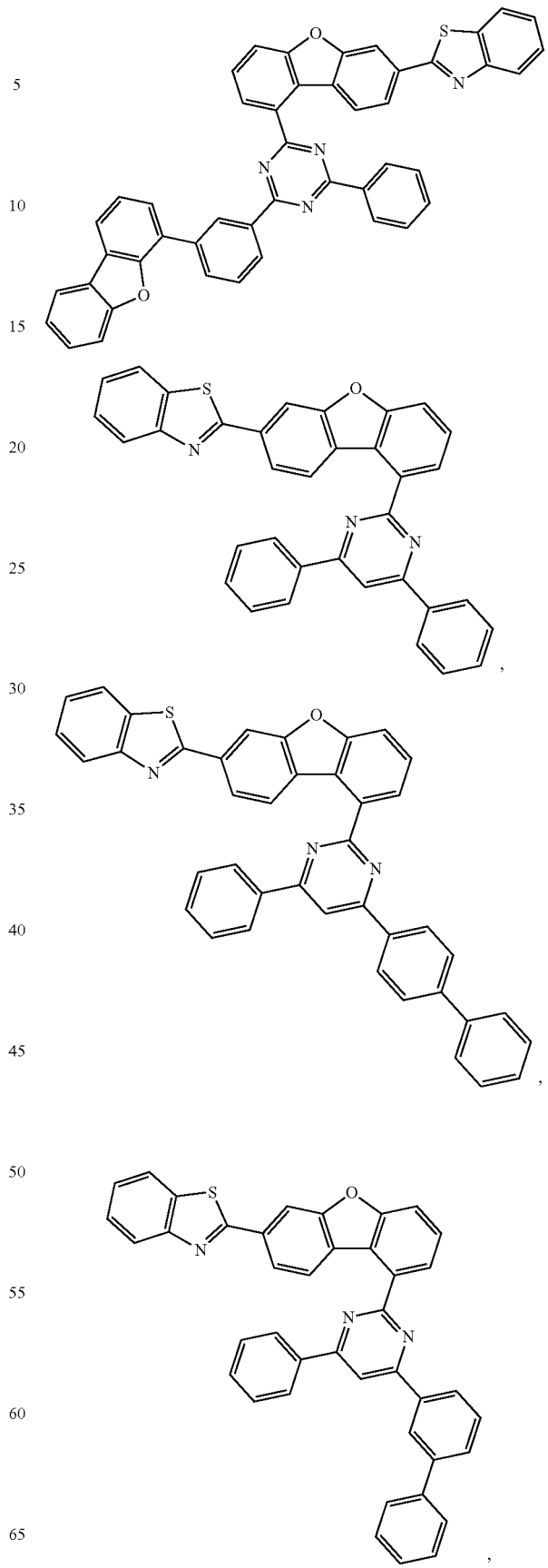

615
-continued
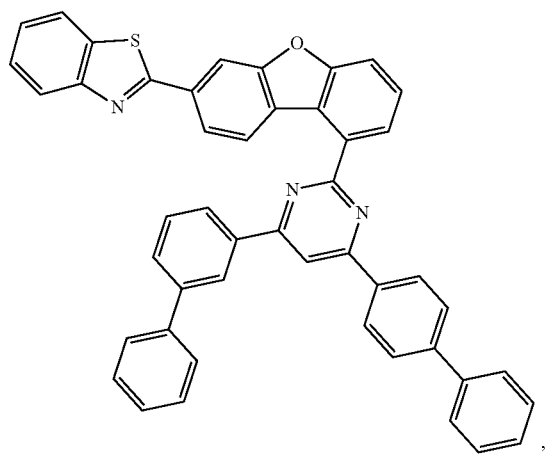
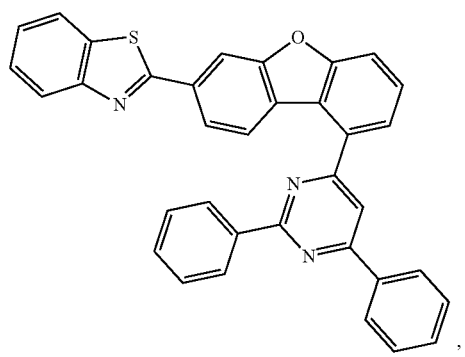
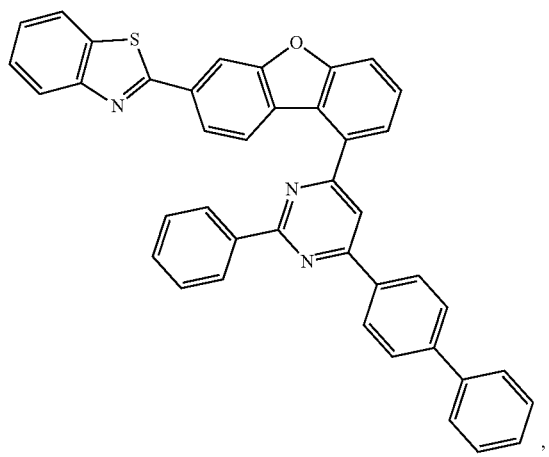
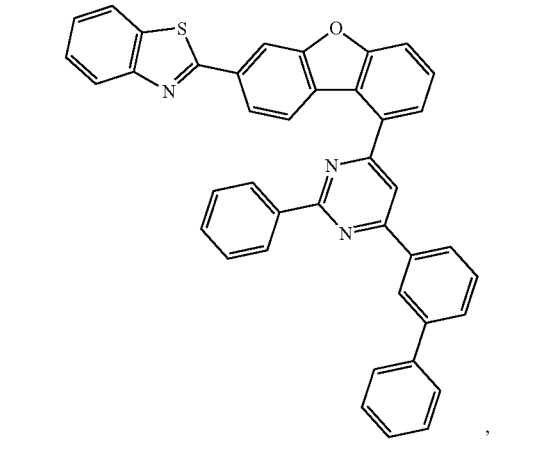
616
-continued
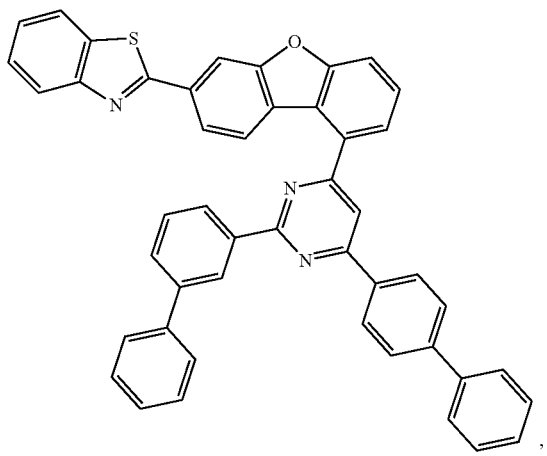
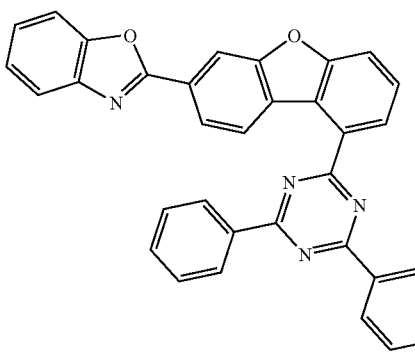
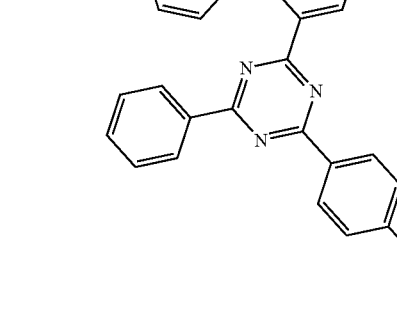
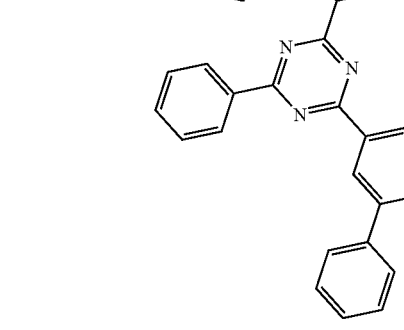

617
-continued
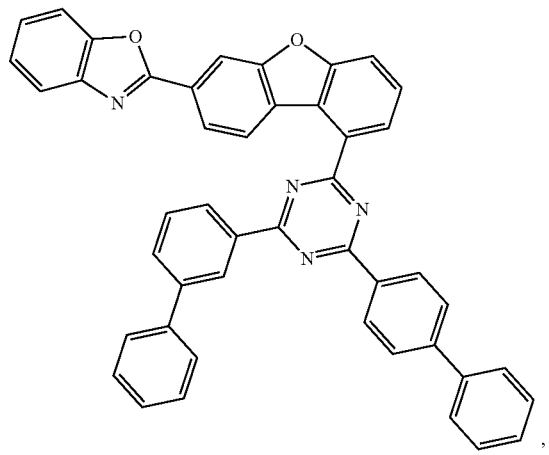
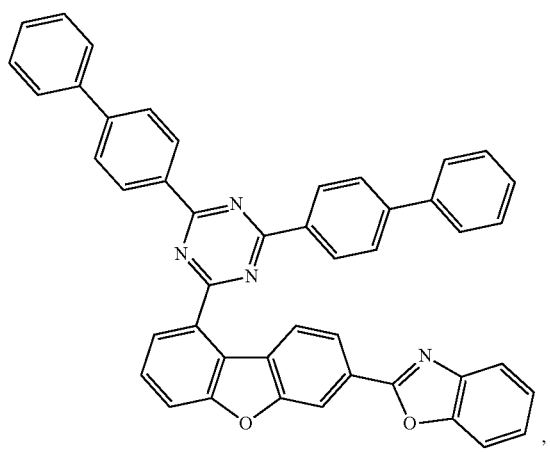
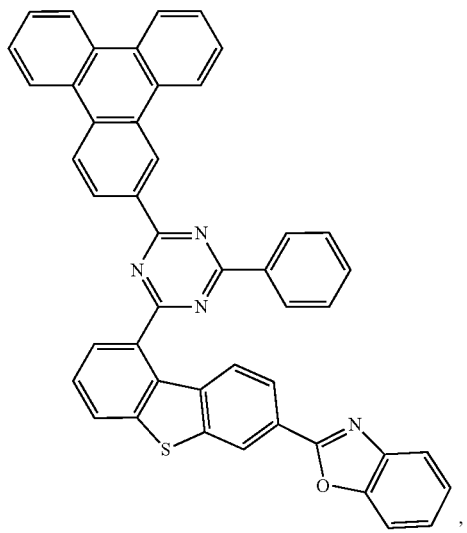
618
-continued
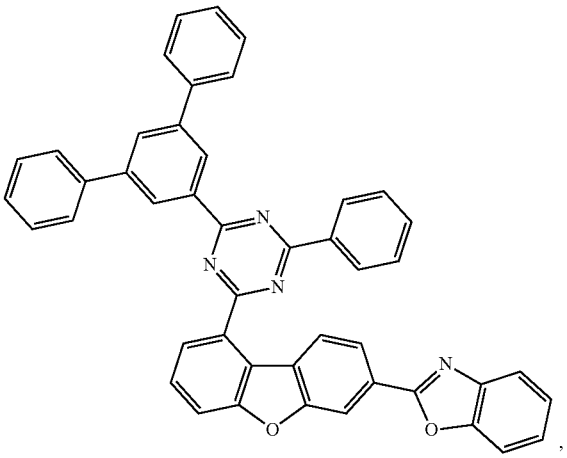
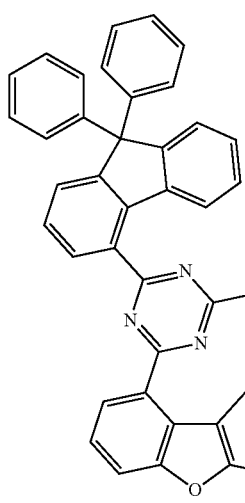
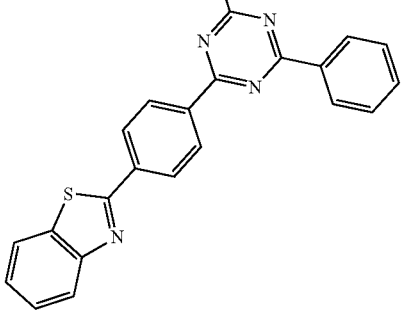

619
-continued
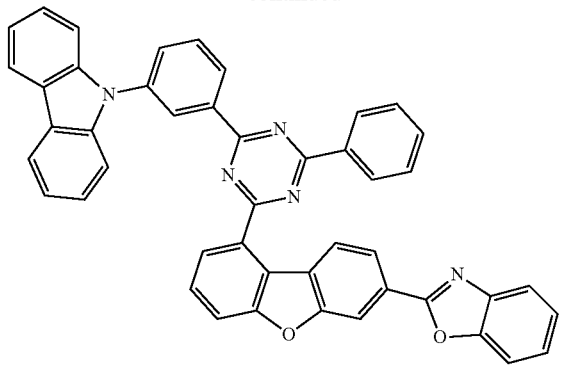
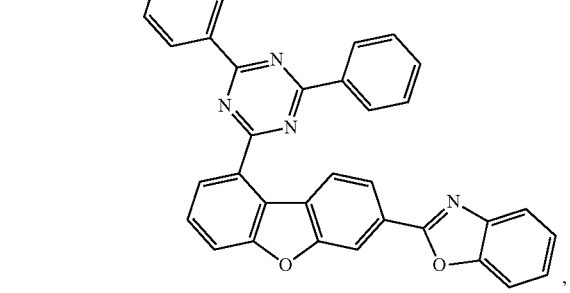
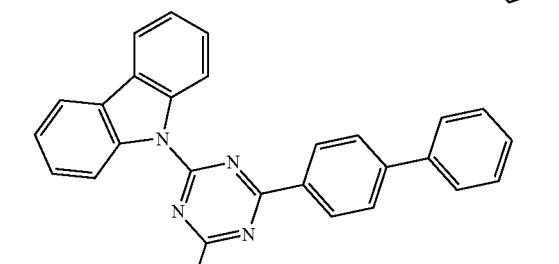
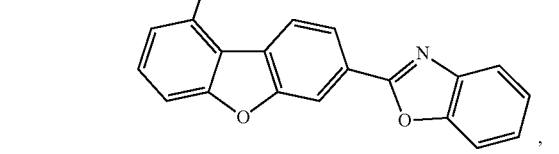
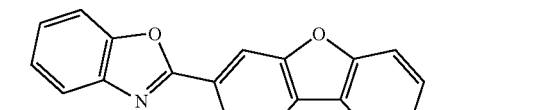
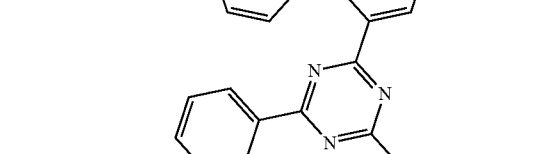
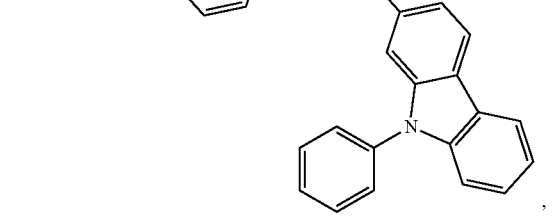
620
-continued
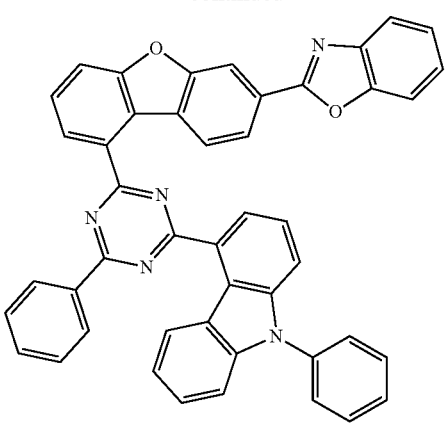
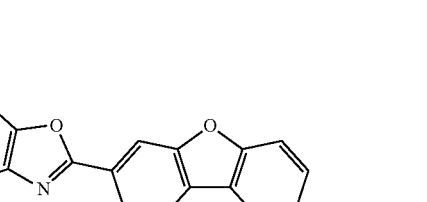
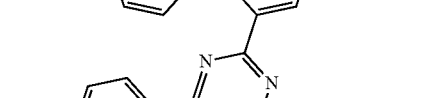
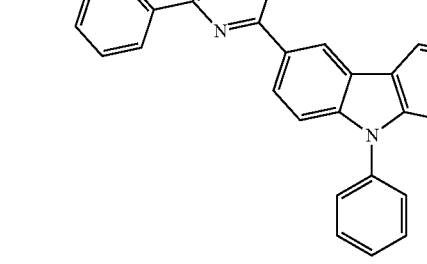
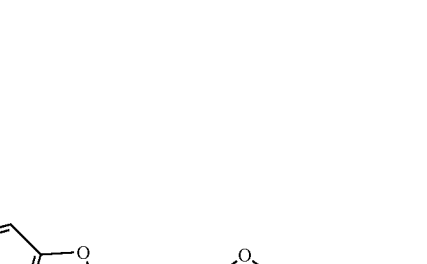
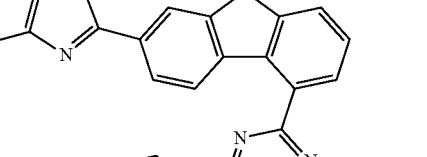
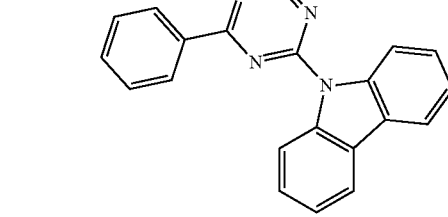

621
-continued
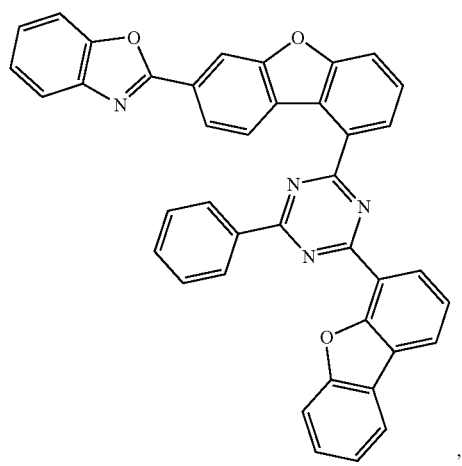
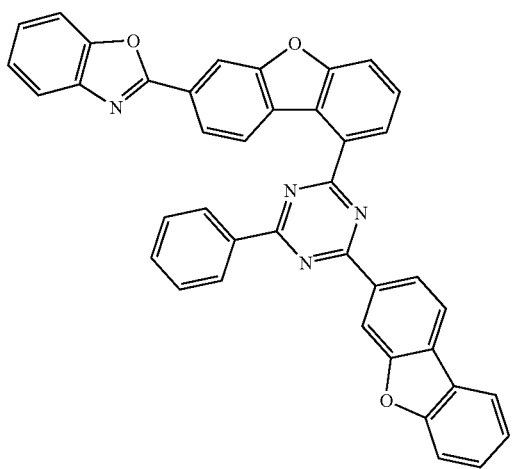
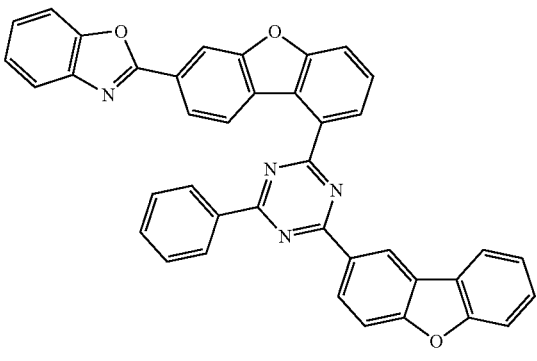
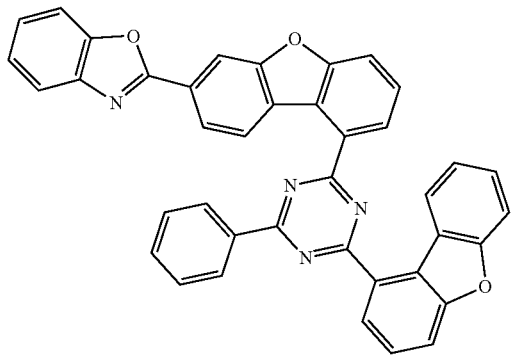
622
-continued
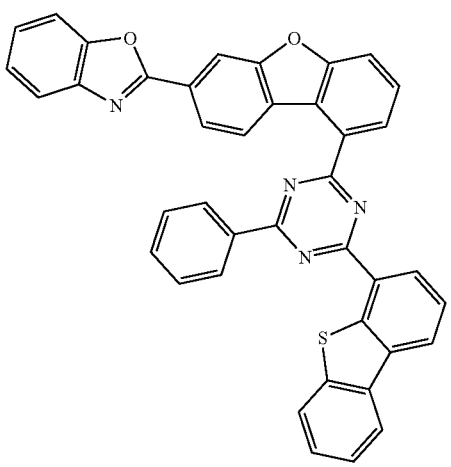
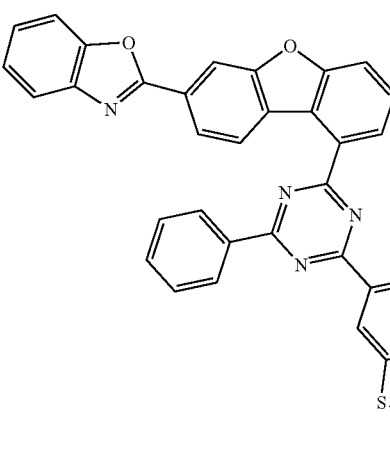
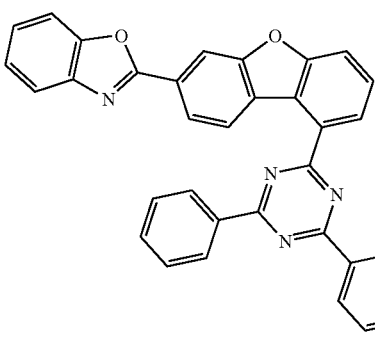
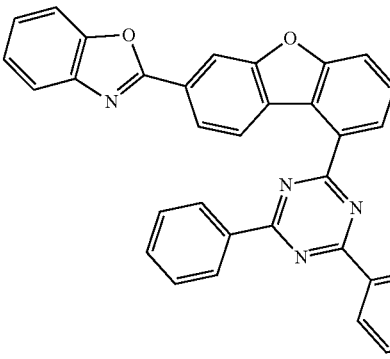

623
-continued
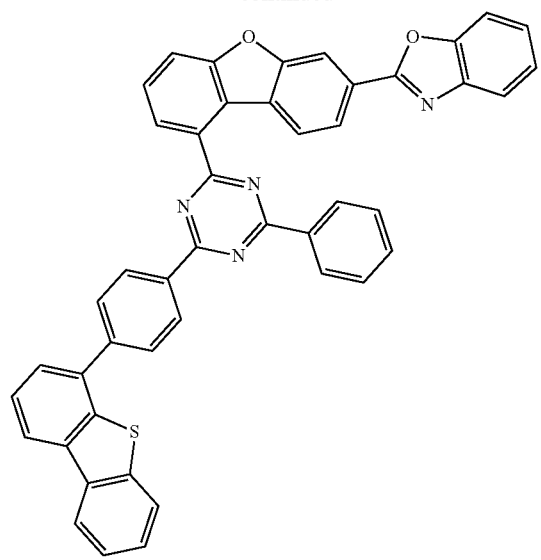
,
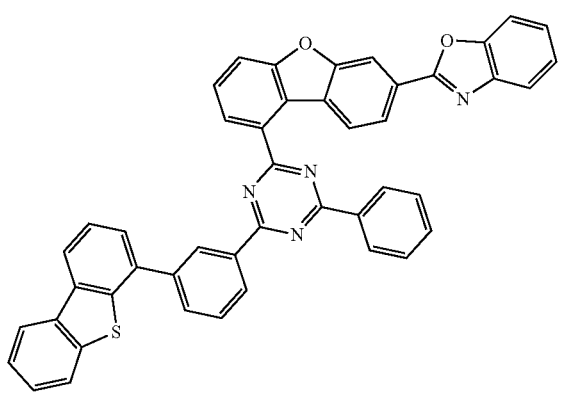
,
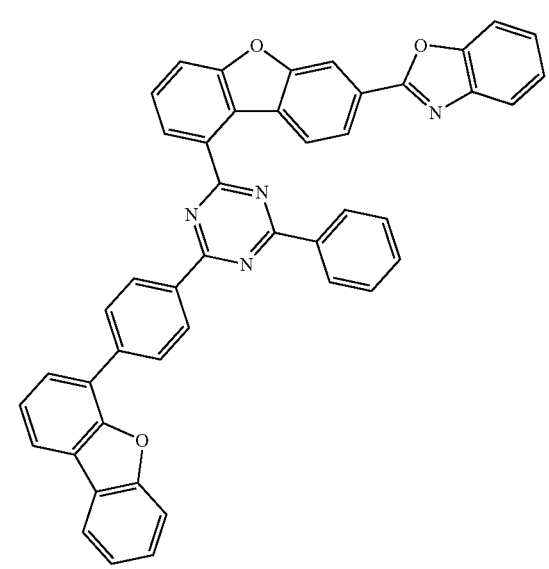
,
624
-continued
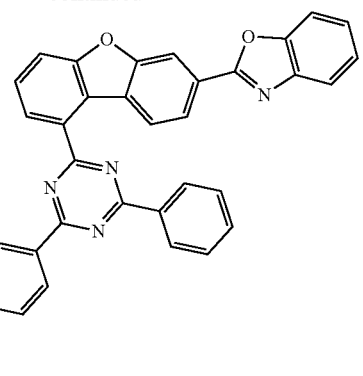
,
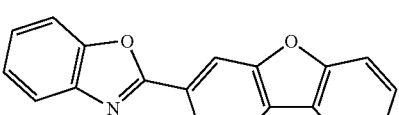
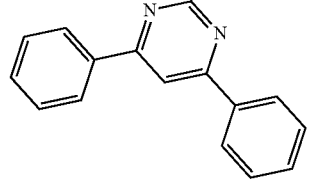
,
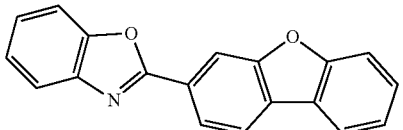
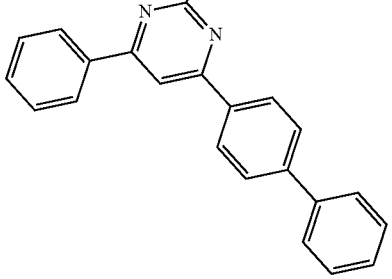
,
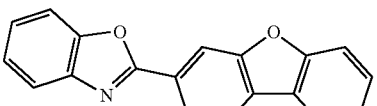
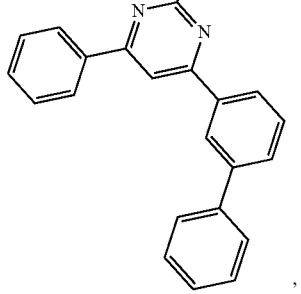
, 625
-continued
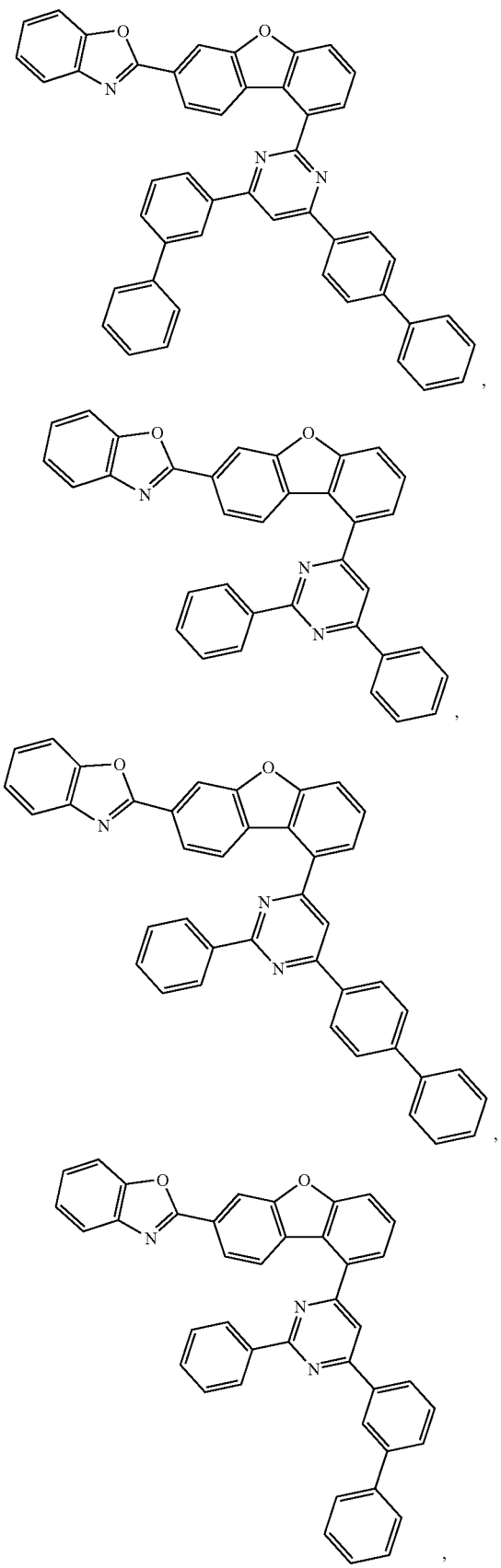
626
-continued
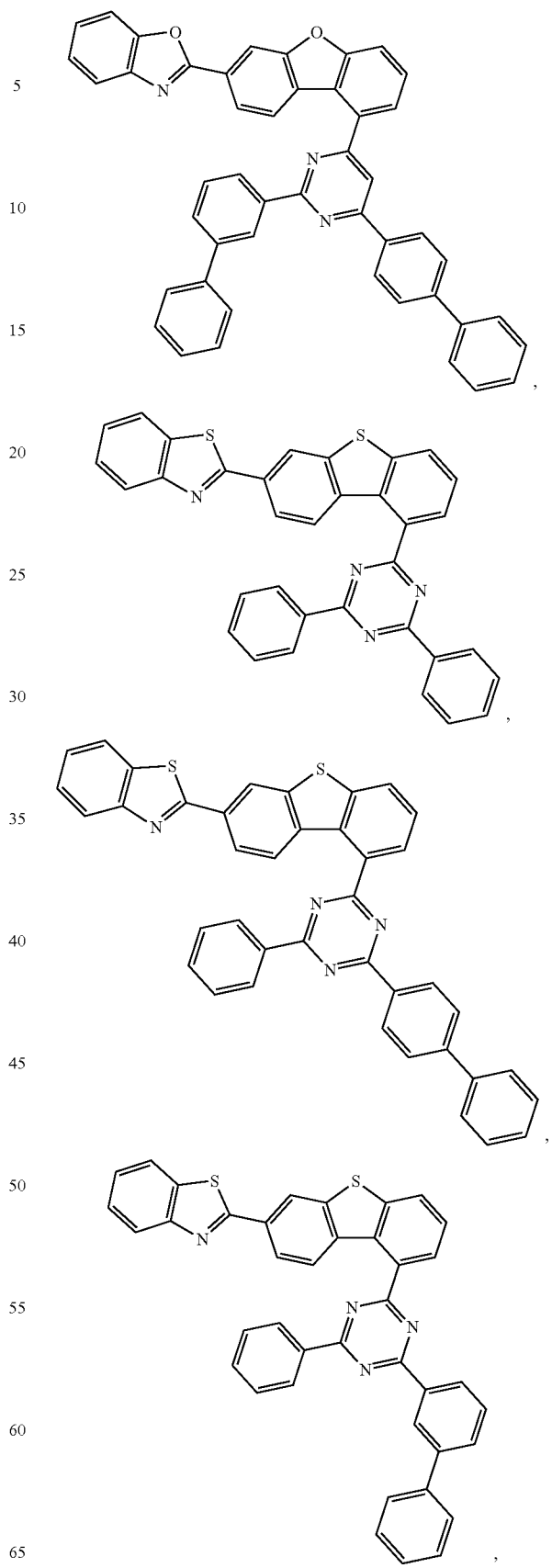

627
-continued
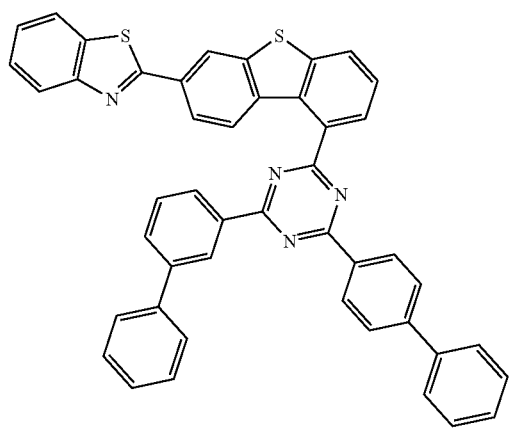
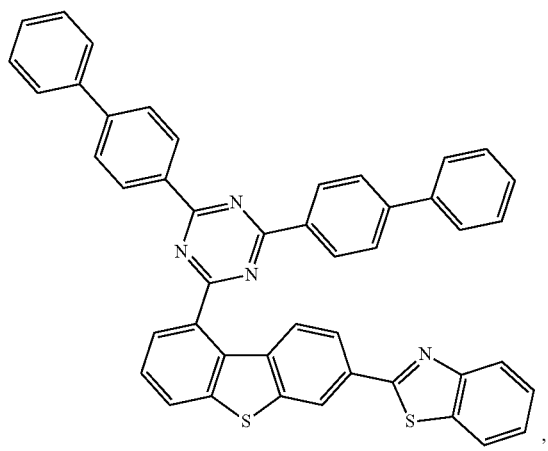
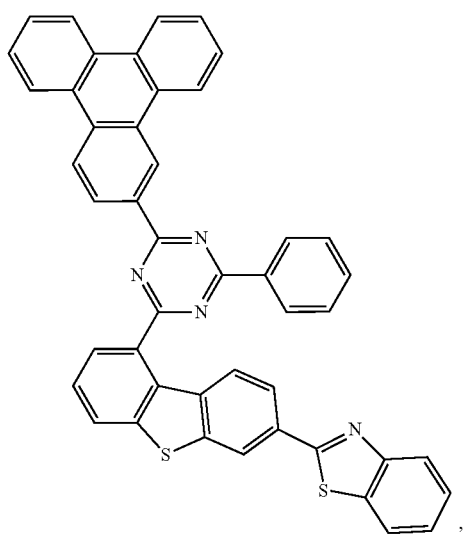
628
-continued
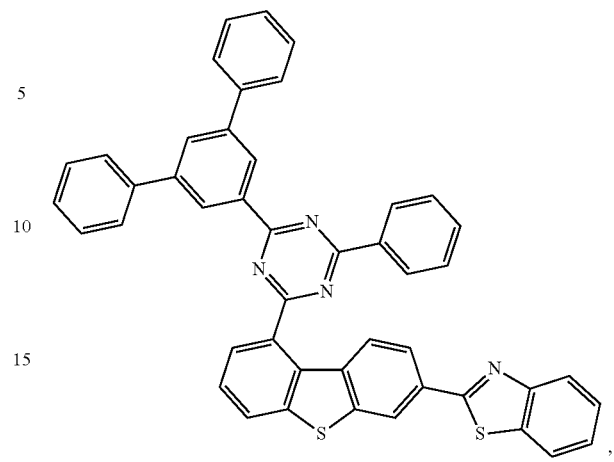
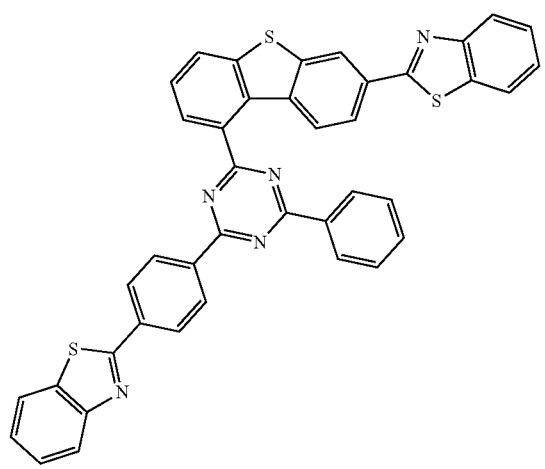

629
-continued
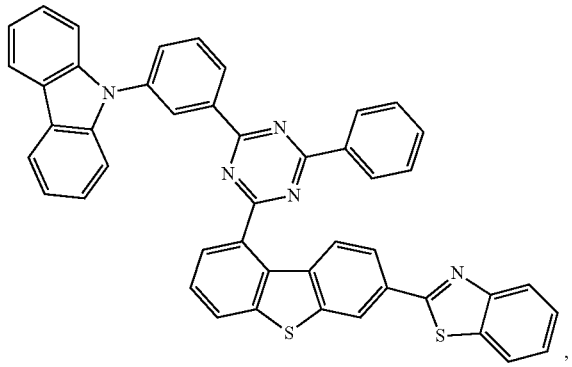
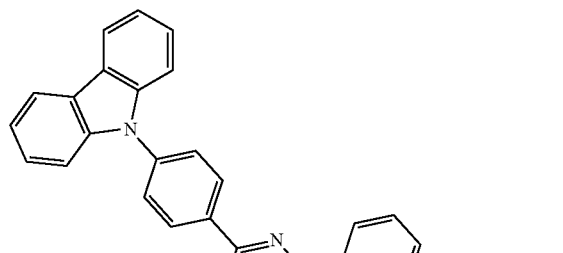
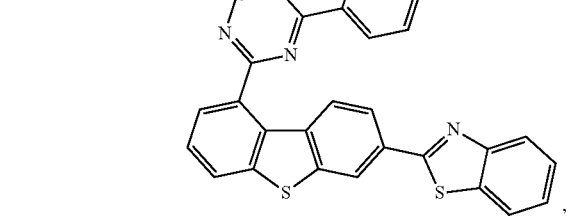
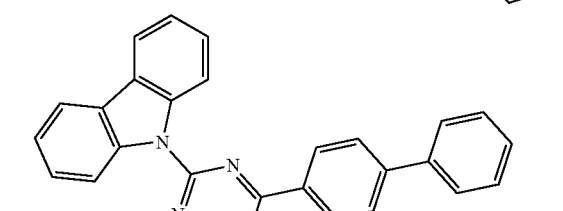
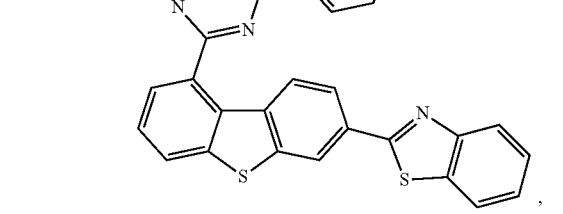
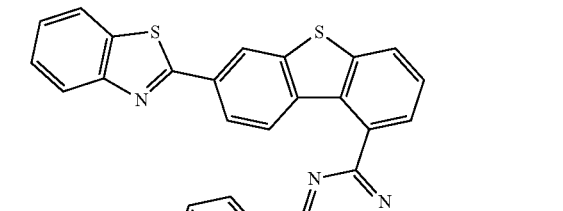
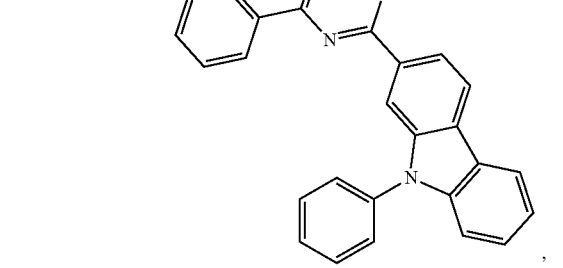
630
-continued
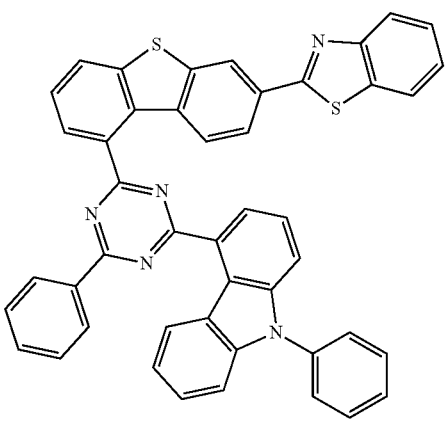
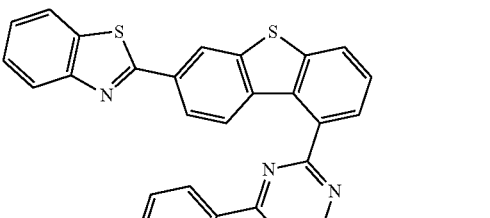
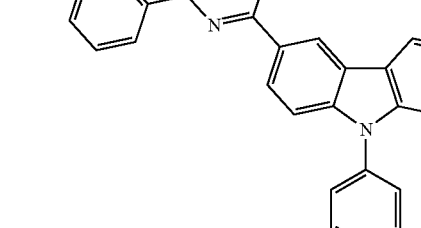
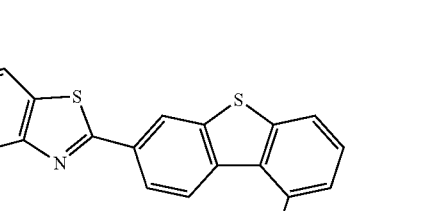
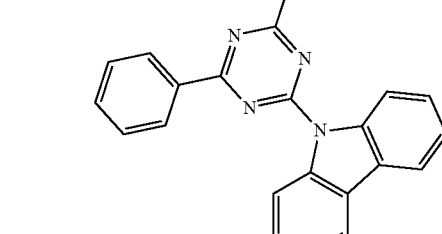

631
-continued
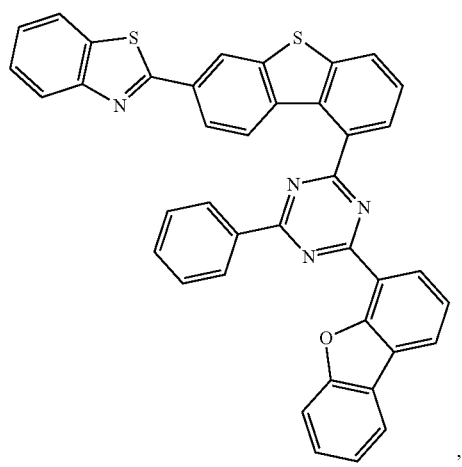
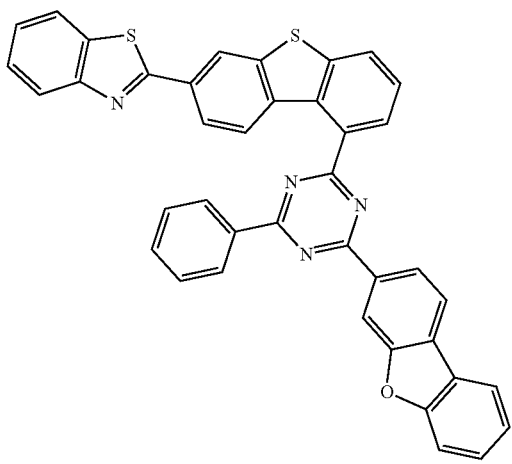
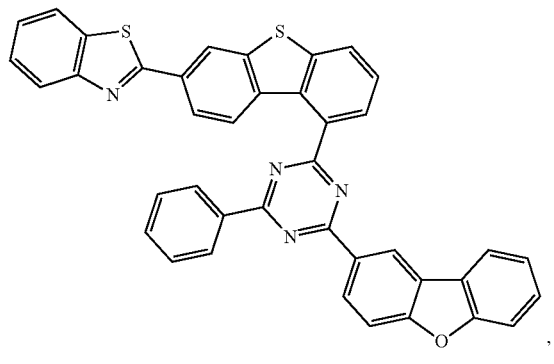
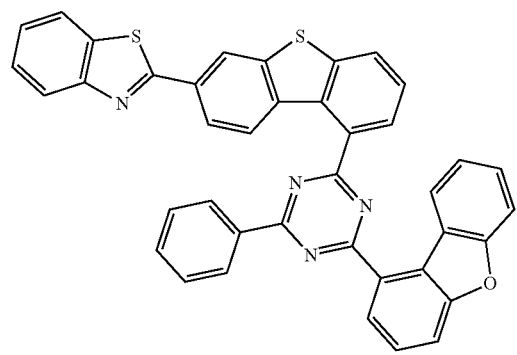
632
-continued
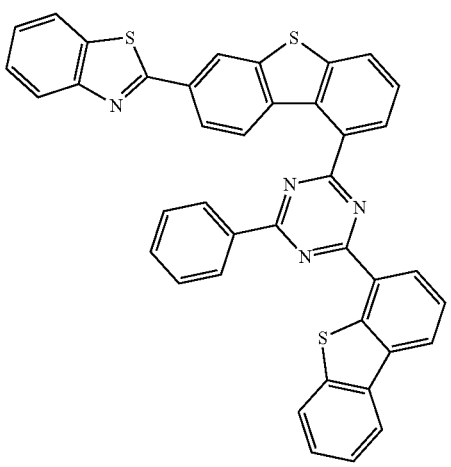
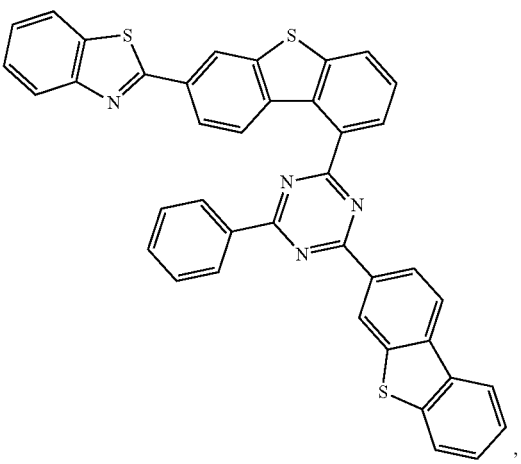
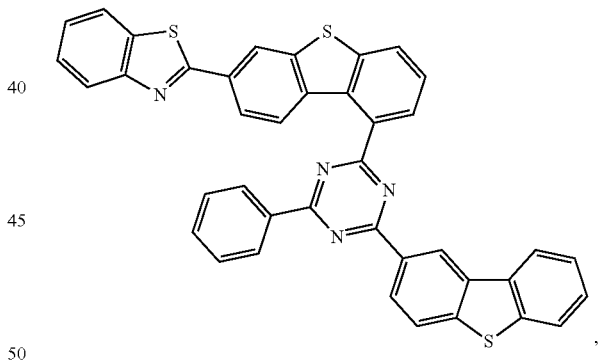
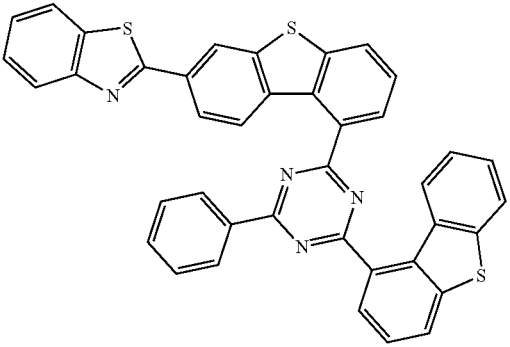

633
-continued
634
-continued
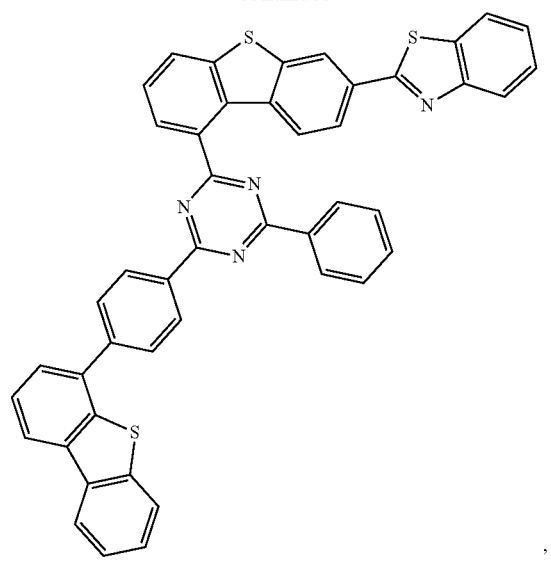
,
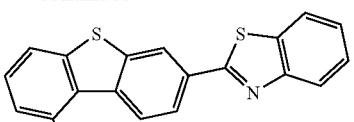
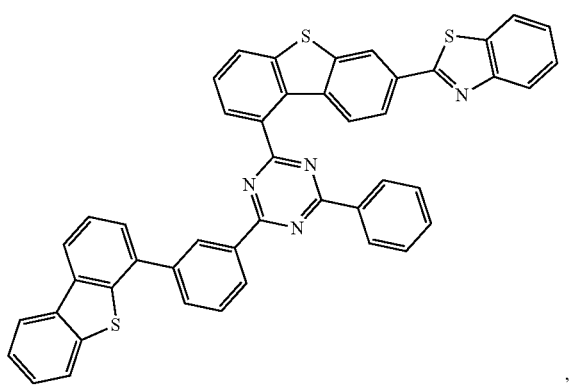
,
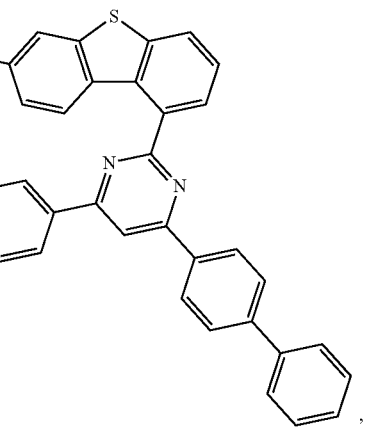
,
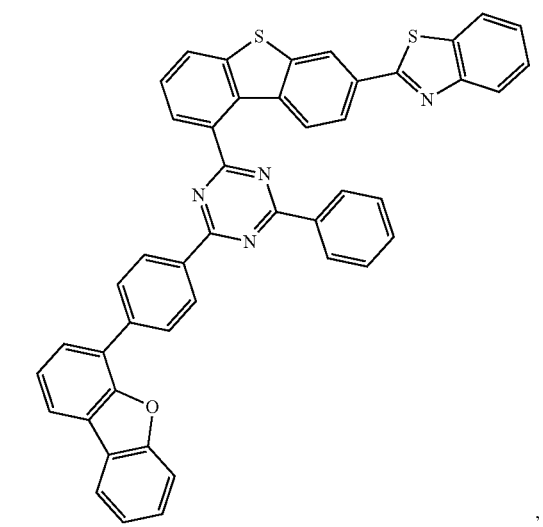
,
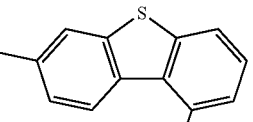
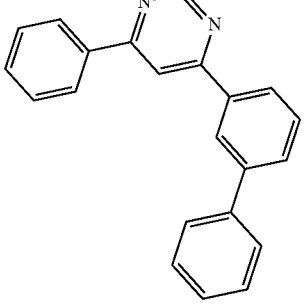
, 635
-continued
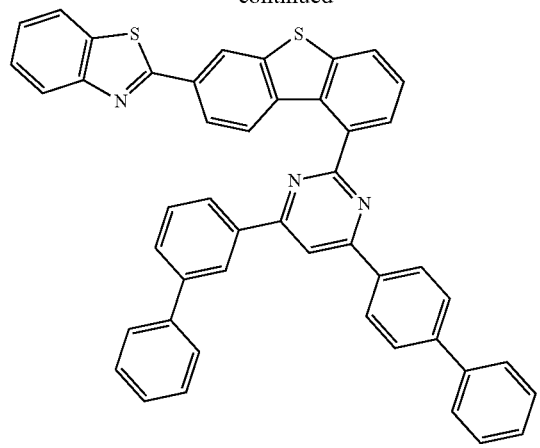
,
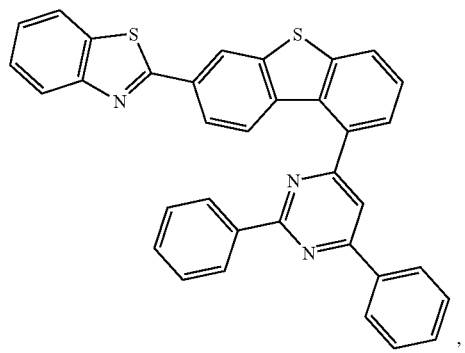
,
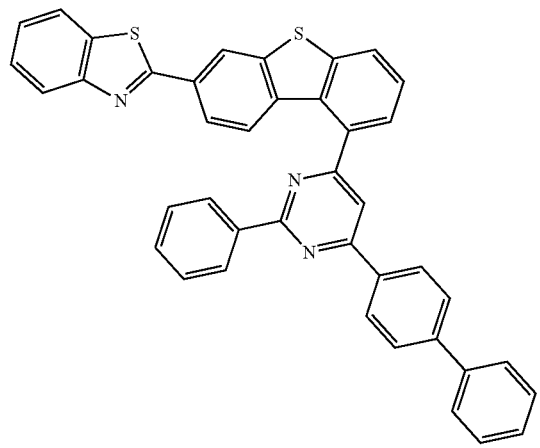
,
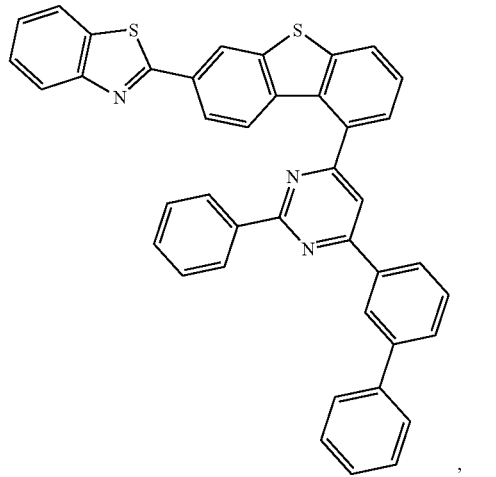
,
636
-continued
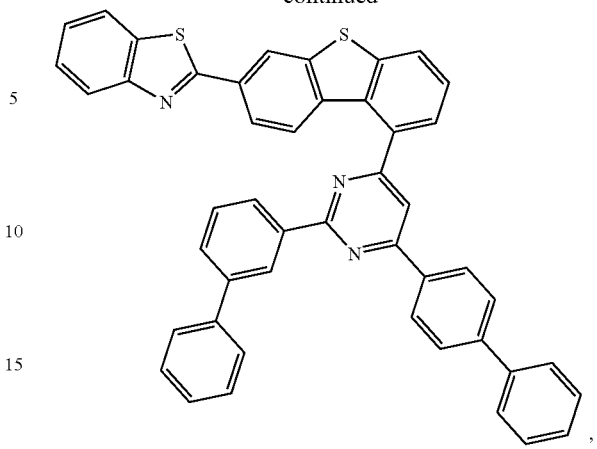
,
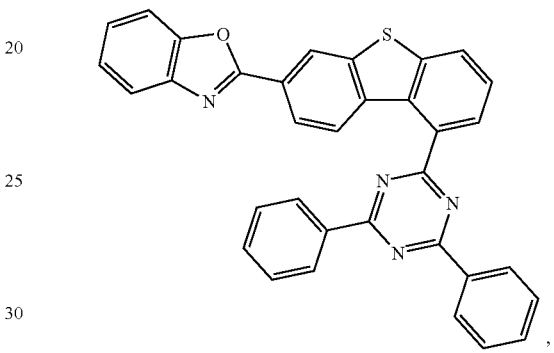
,
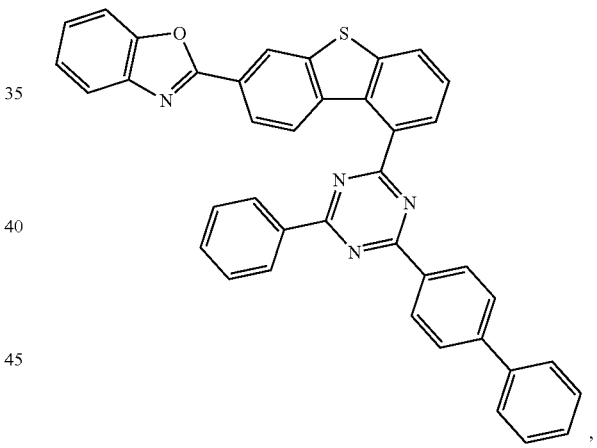
,
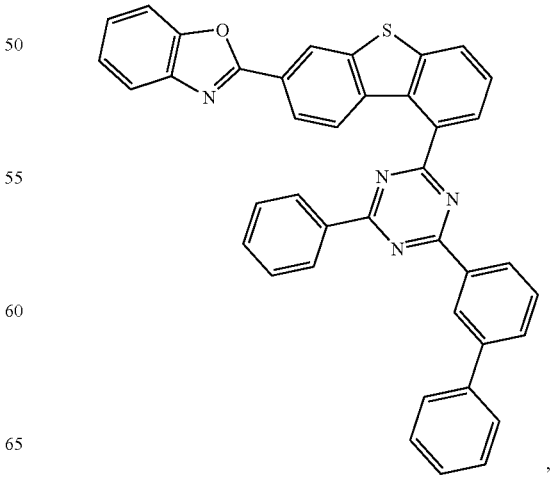
, 637
-continued
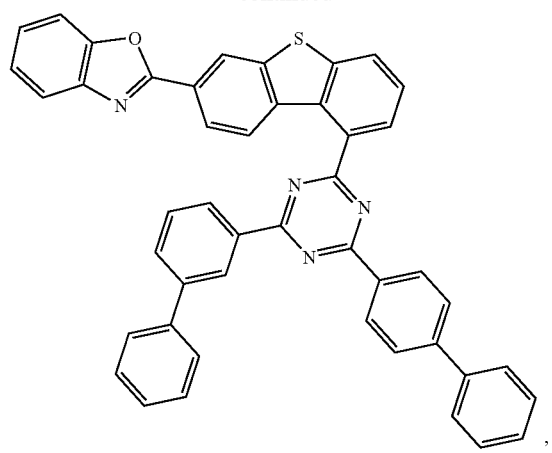
,
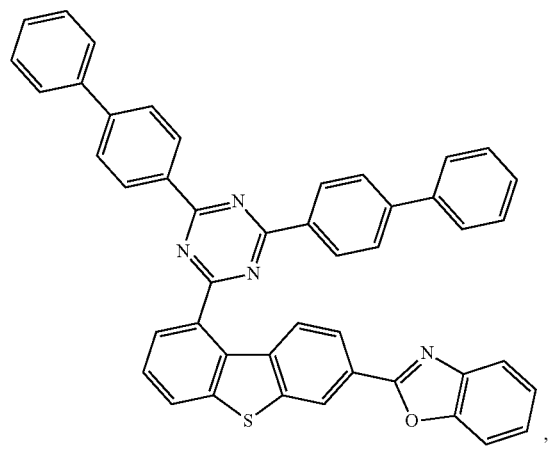
,
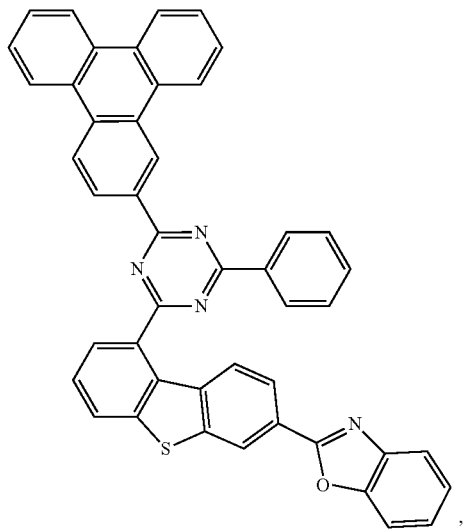
,
638
-continued
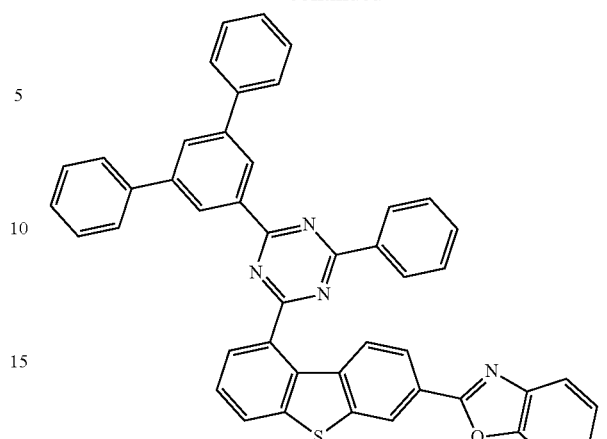
,
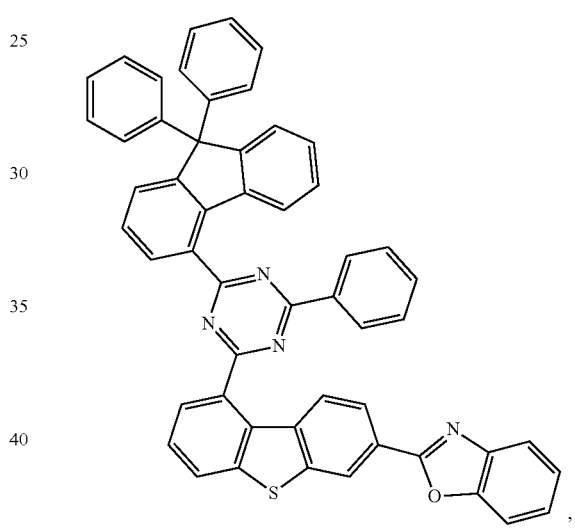
,
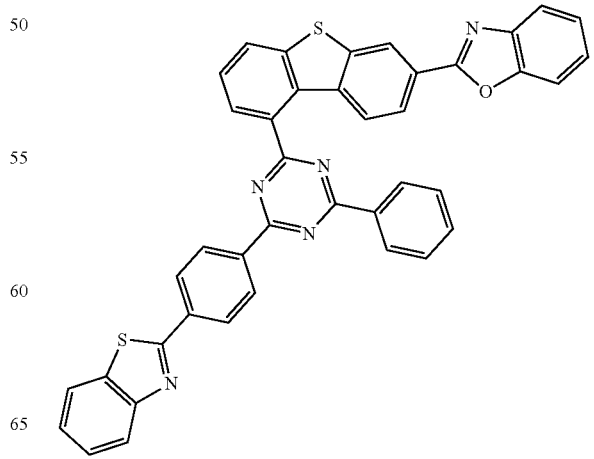
, 639
-continued
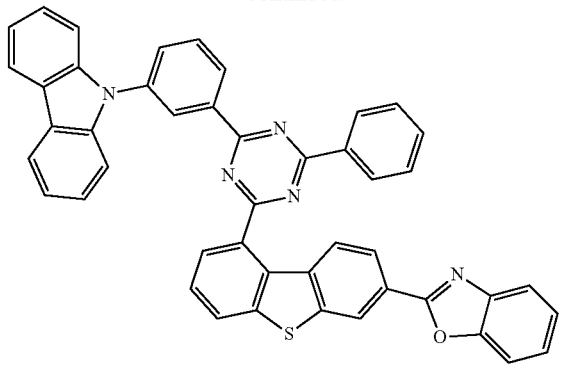
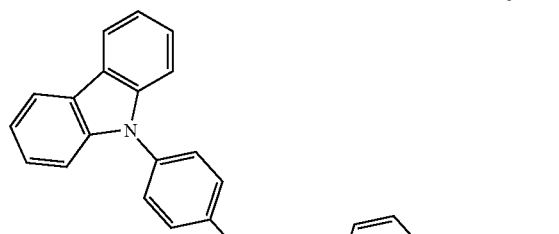
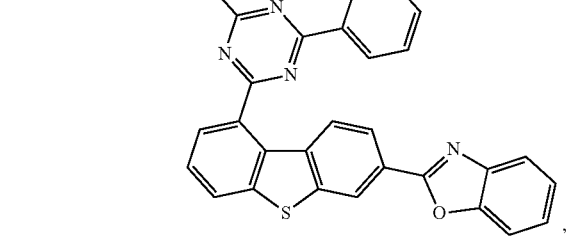
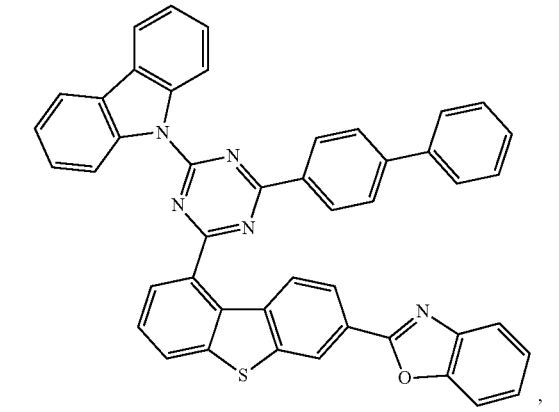
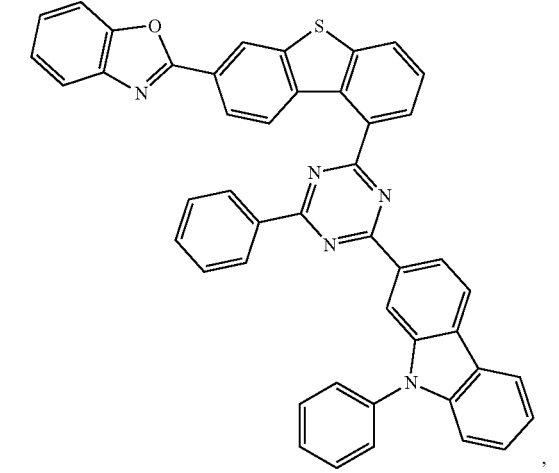
640
-continued
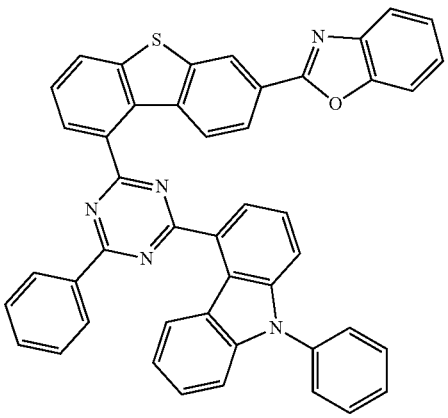

641
-continued
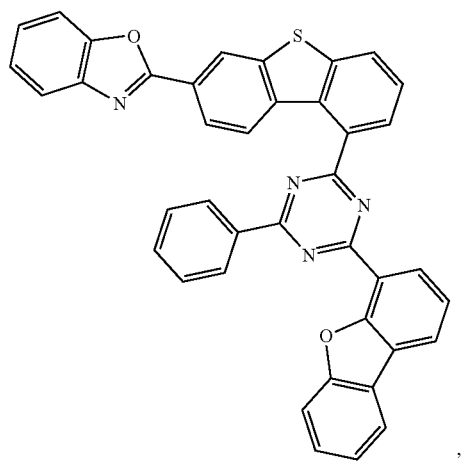
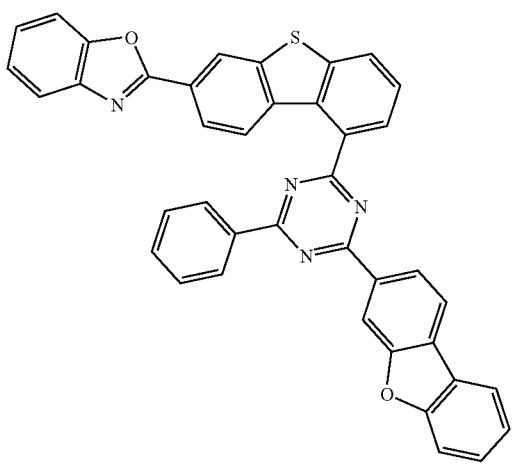
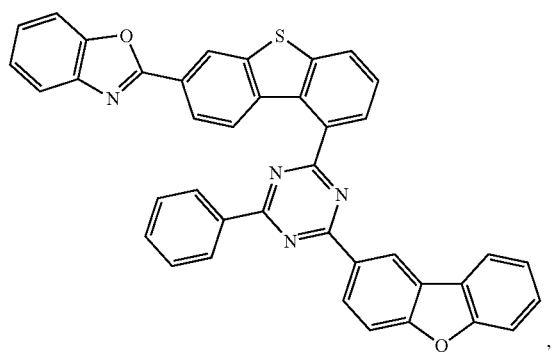
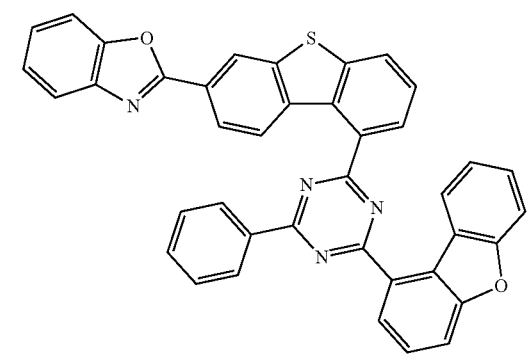
642
-continued
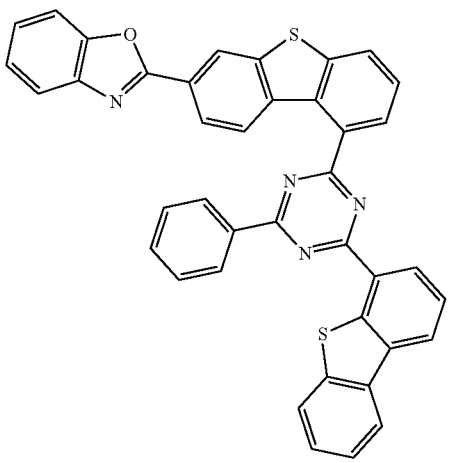
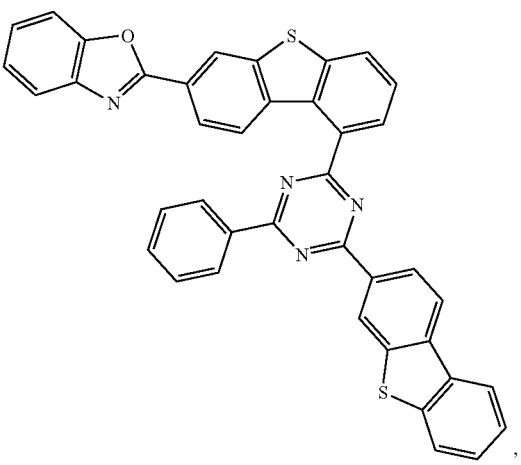
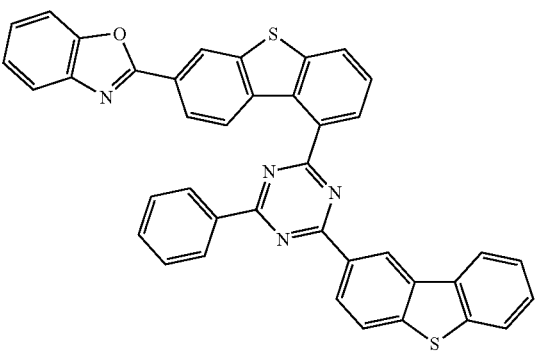
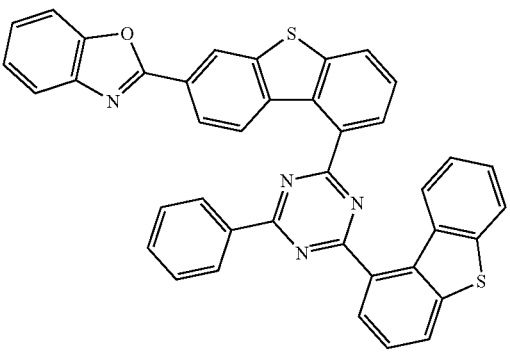

643
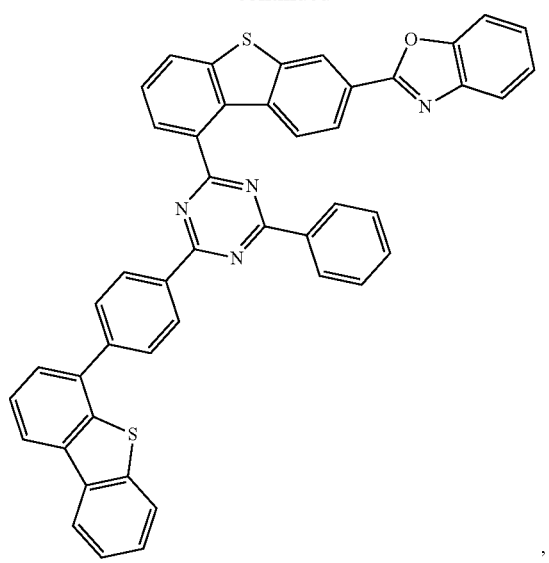
,
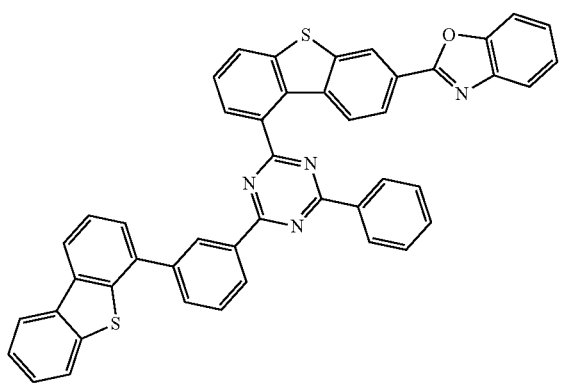
,
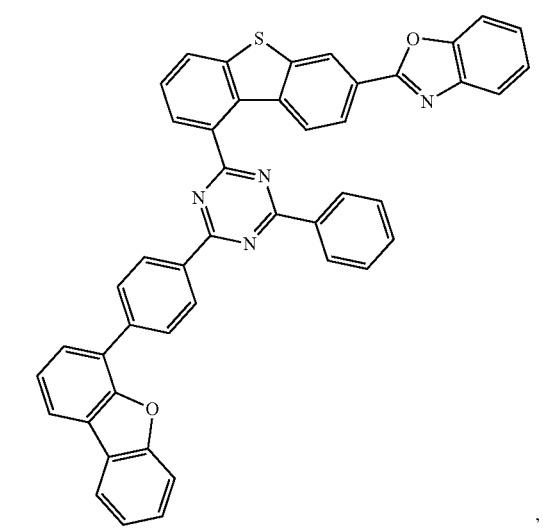
,
644
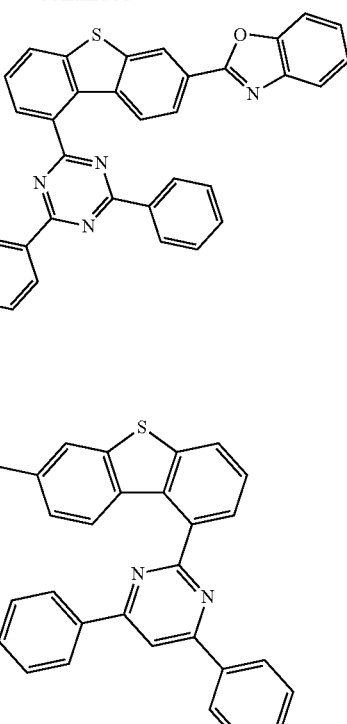
,
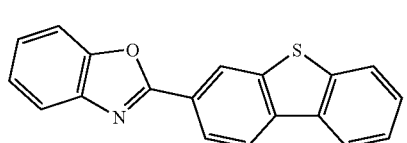
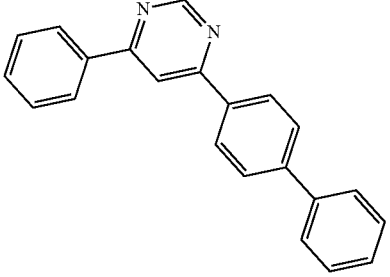
,
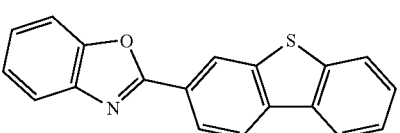
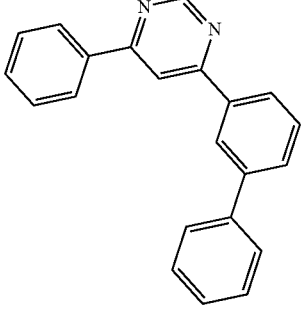
, 645
-continued
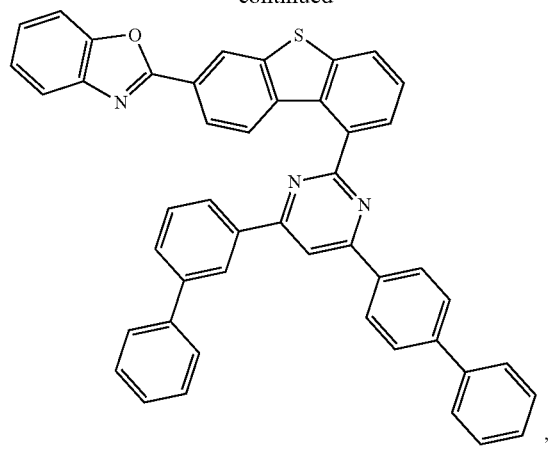
,
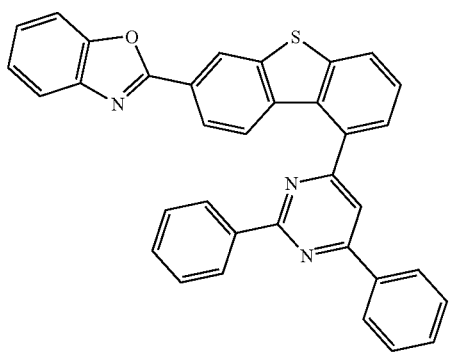
,
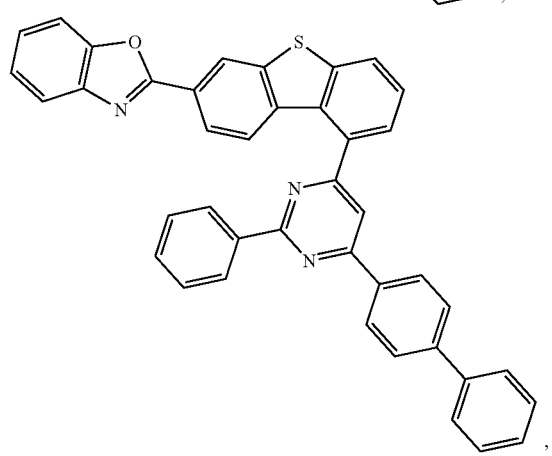
,
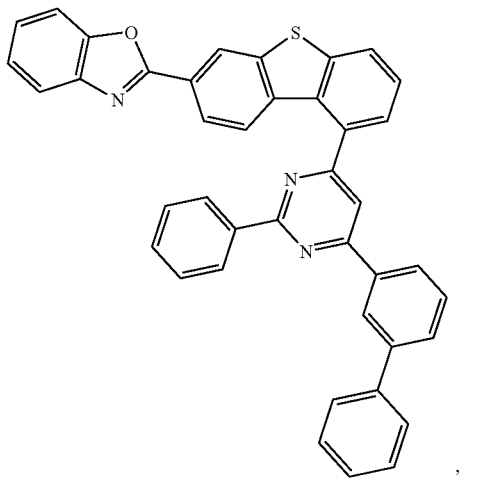
,
646
-continued
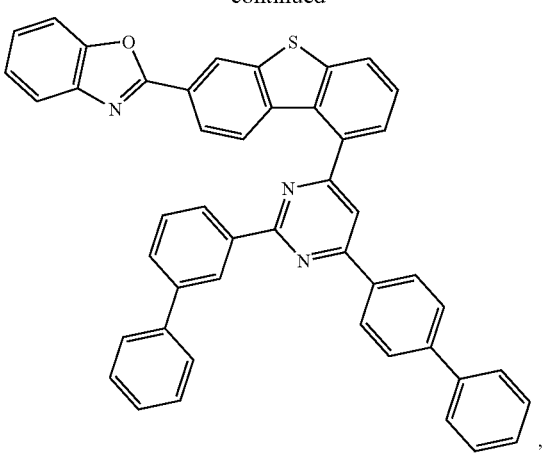
,
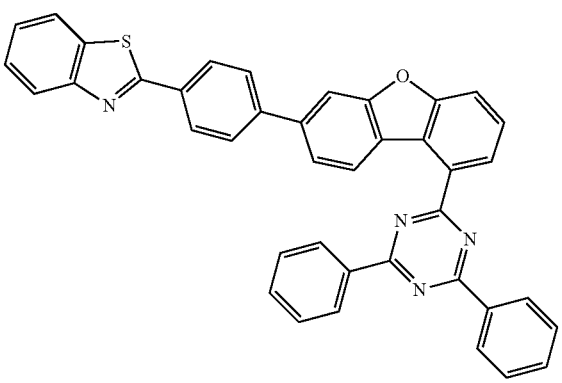
,
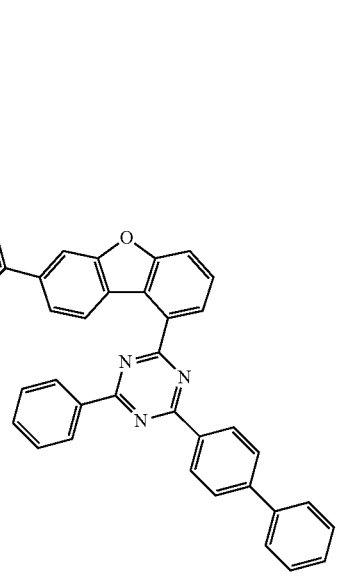
, 647
-continued
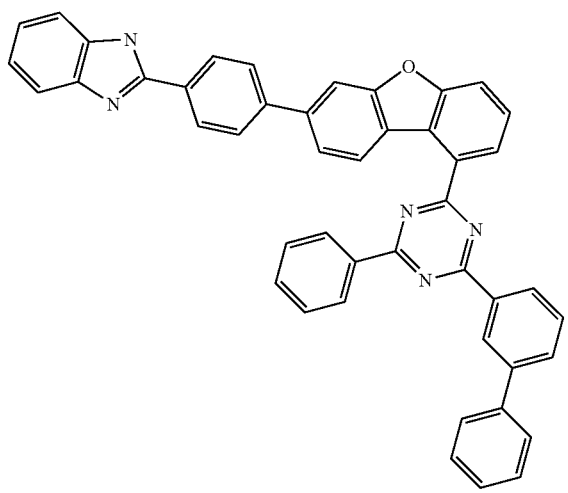
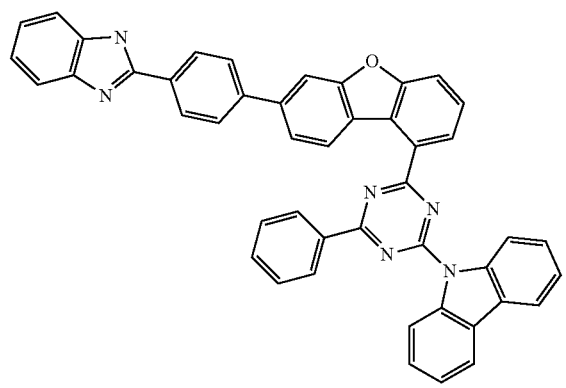
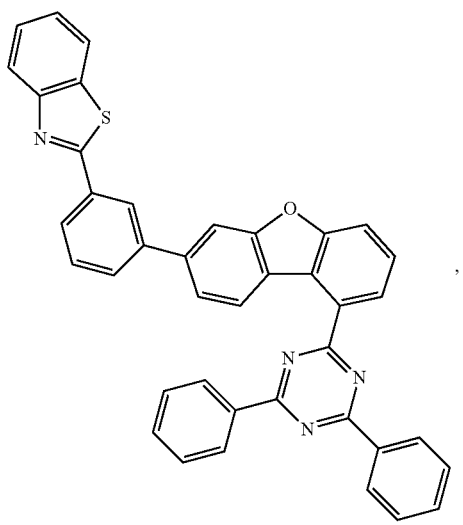
648
-continued
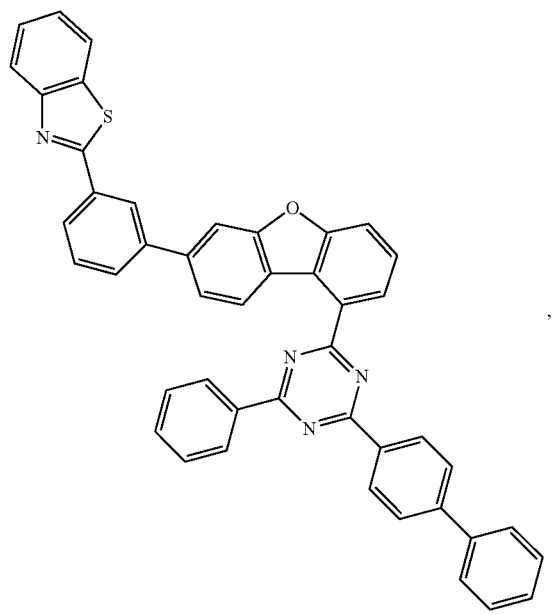
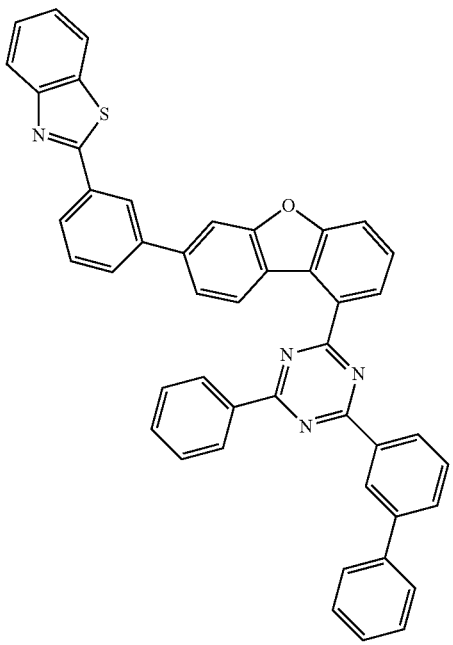

649 650
-continued -continued
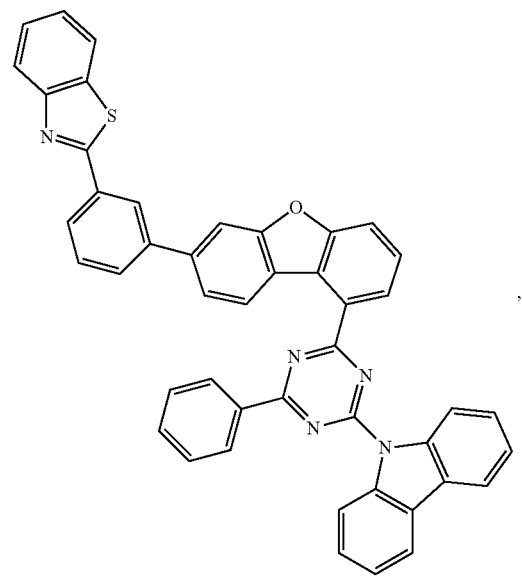
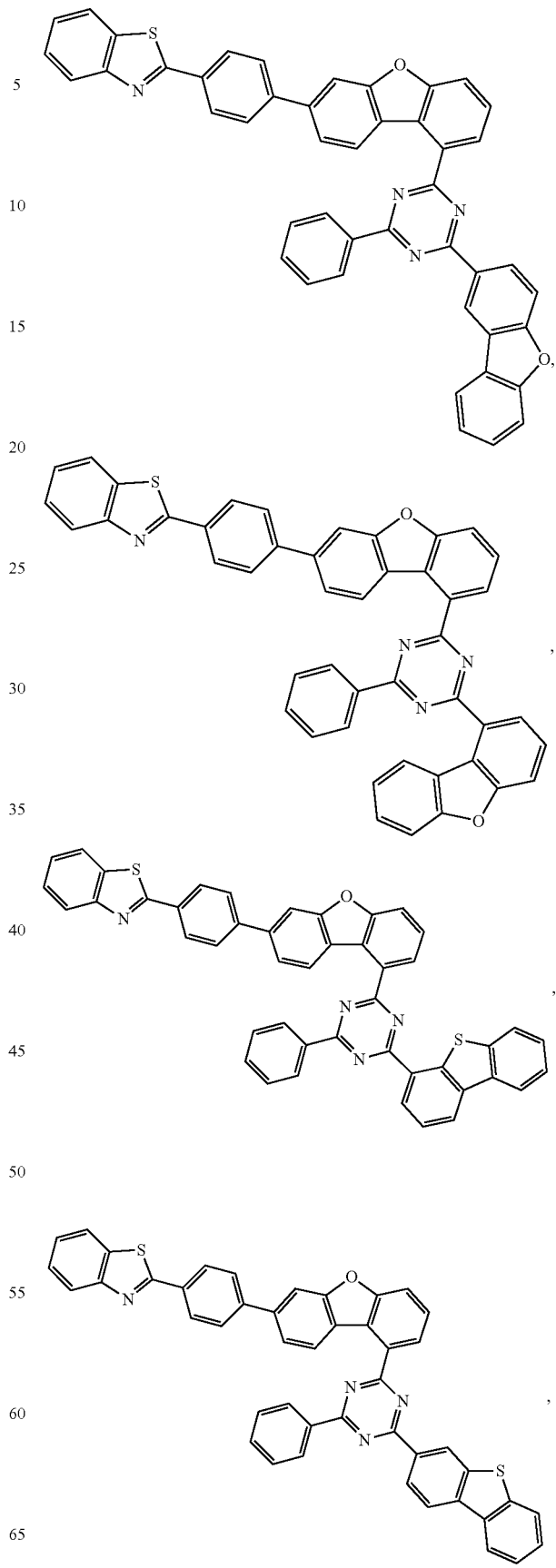

651
-continued
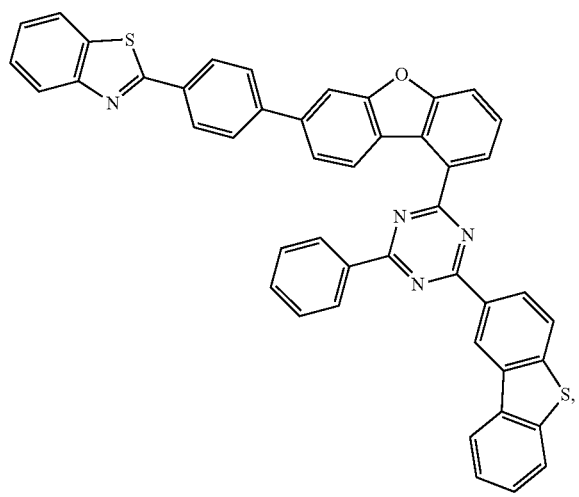
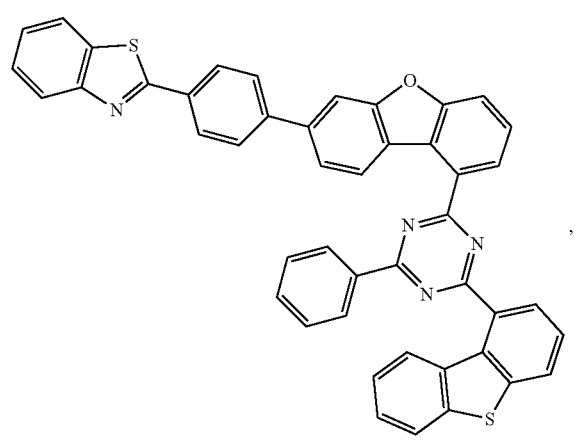
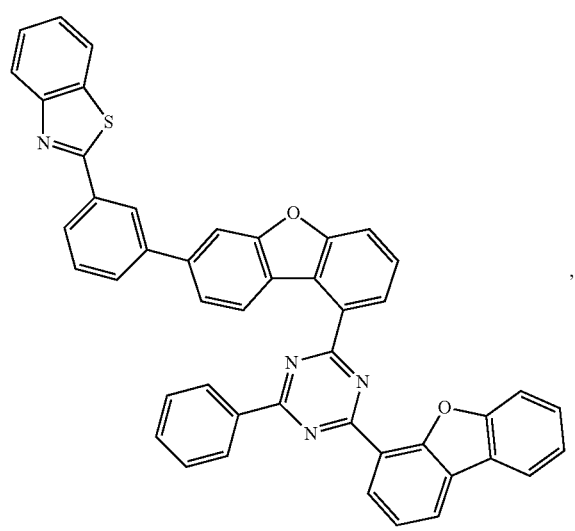
652
-continued
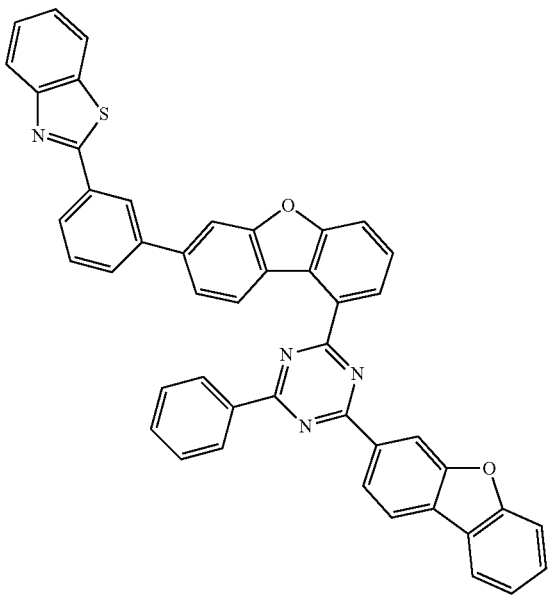

653
-continued
654
-continued
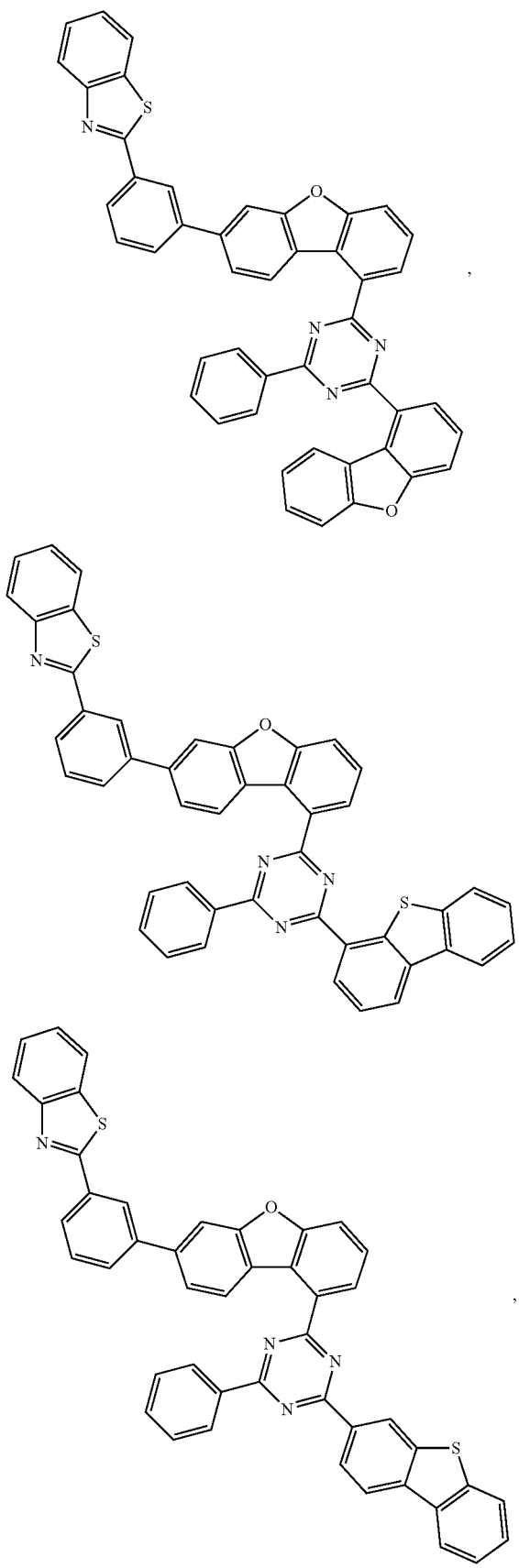
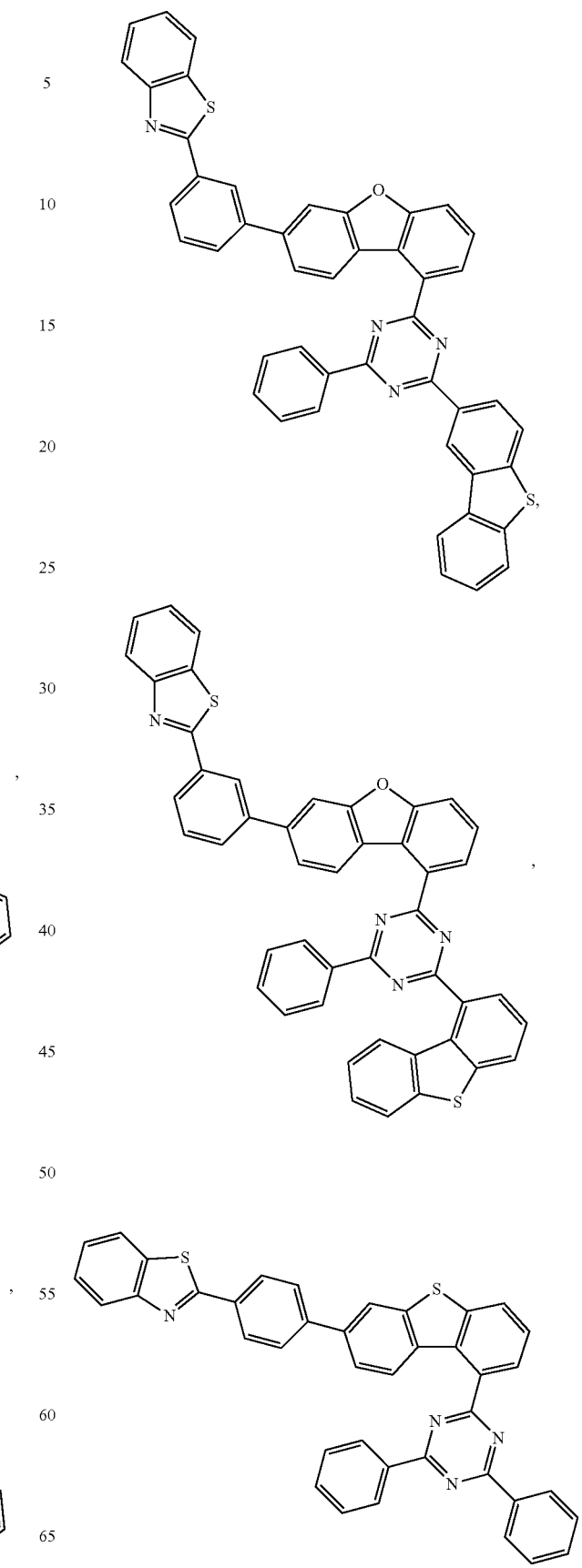

655
-continued
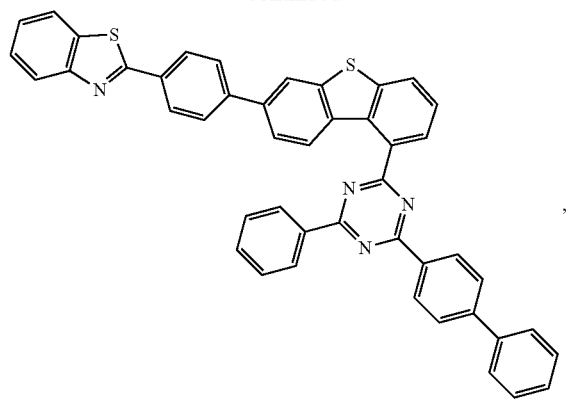
,
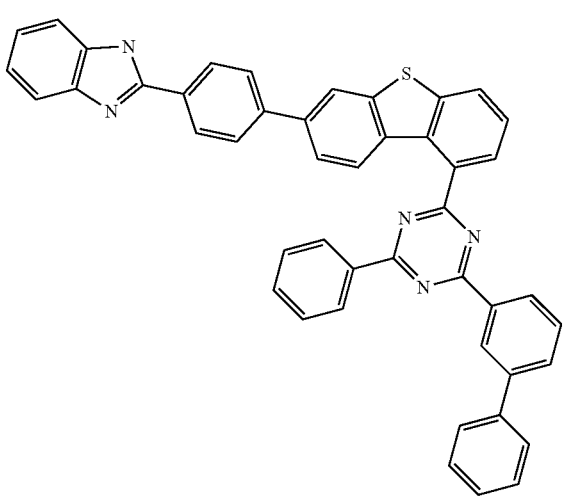
,
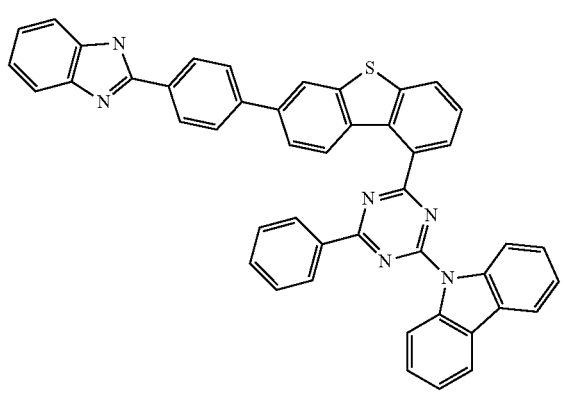
,
656
-continued
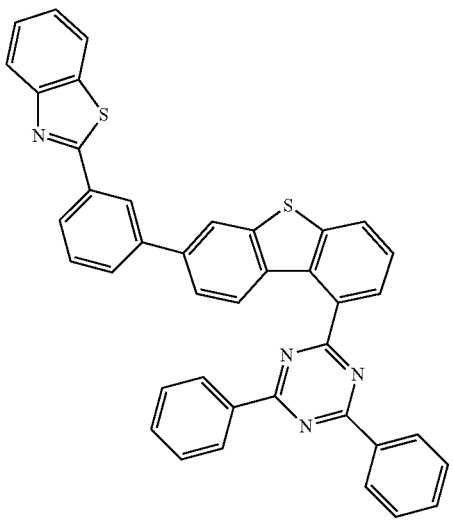
,
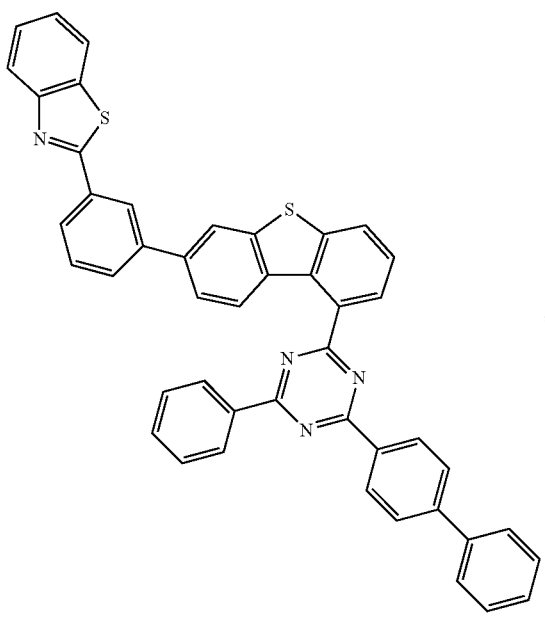
, 657
-continued
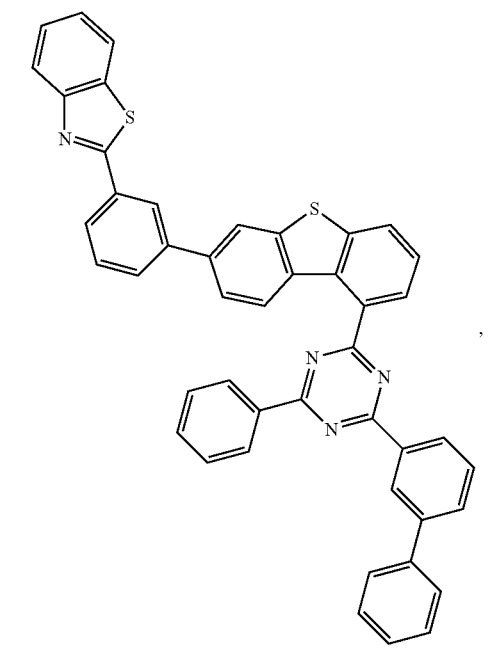
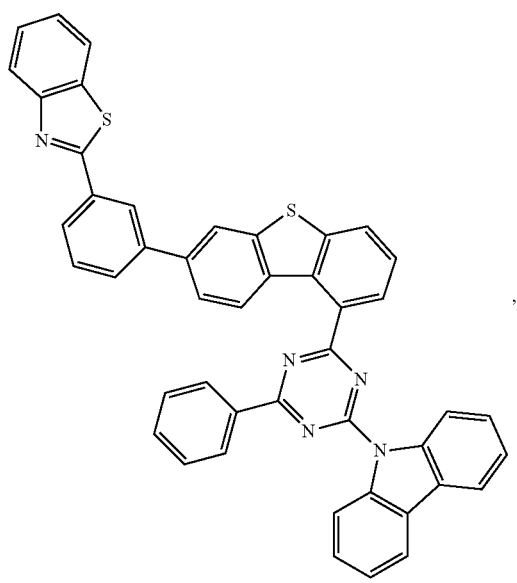
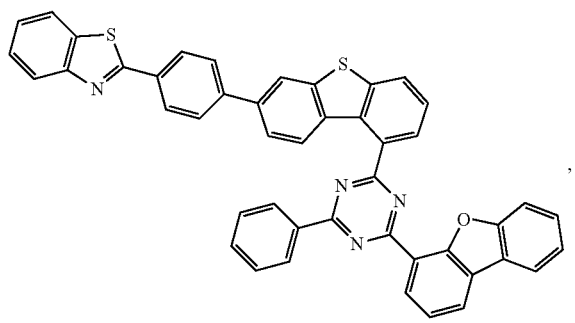
658
-continued
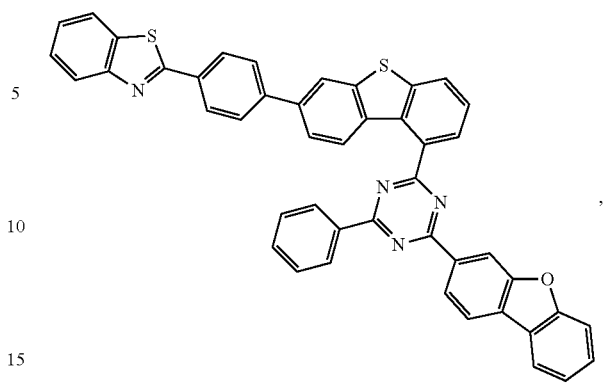
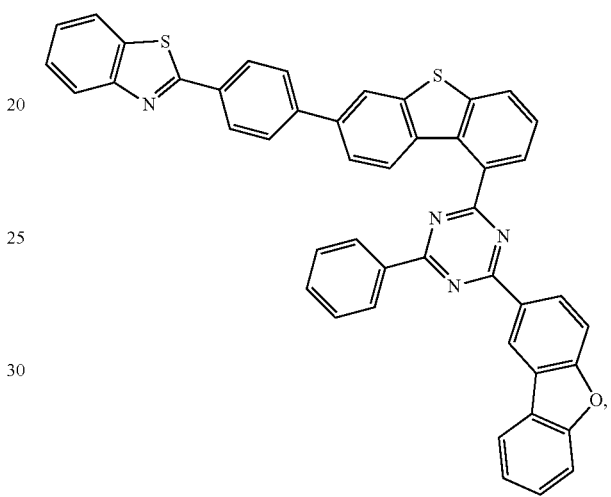
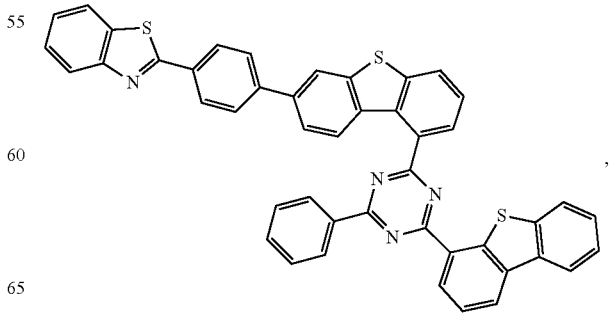

659
-continued
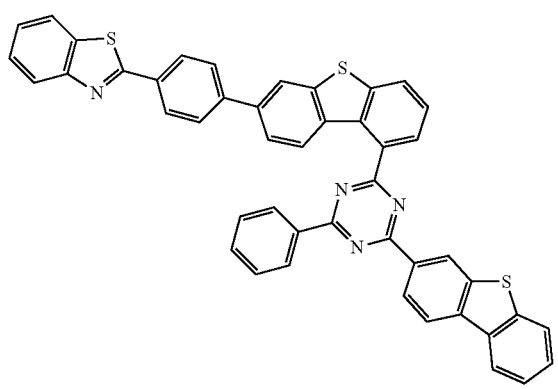
,
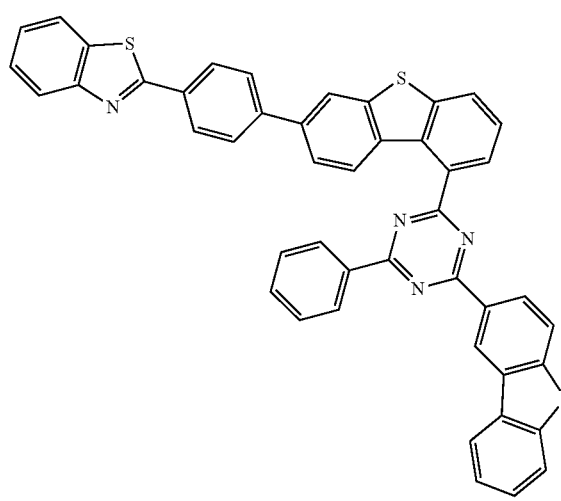
,
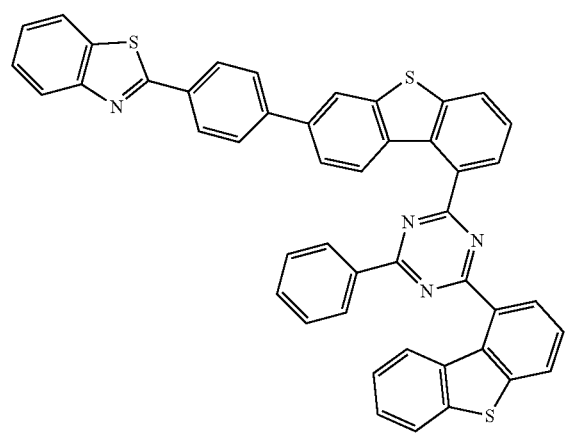
,
660
-continued
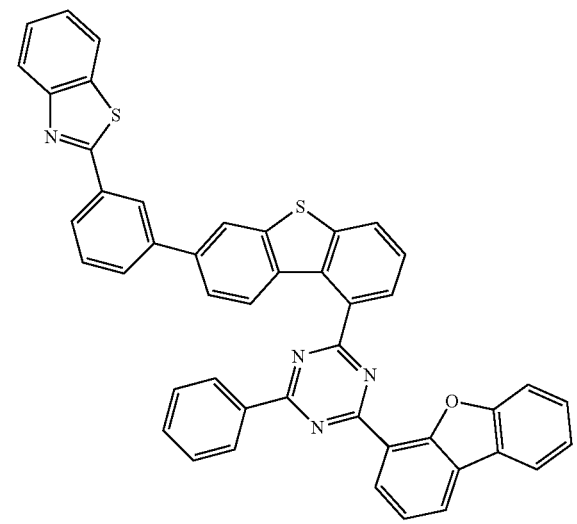
,

661
-continued
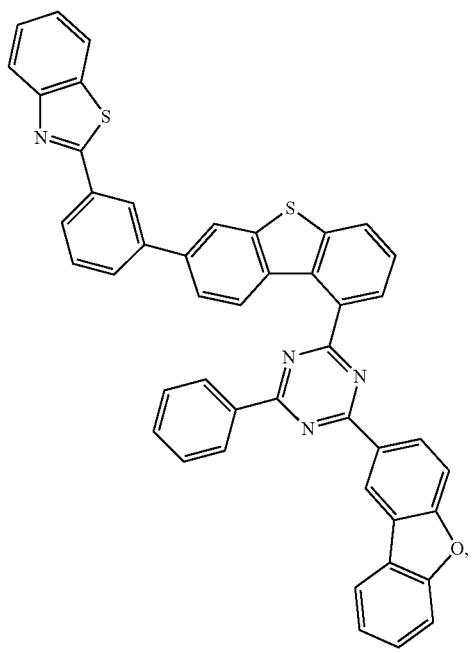
662
-continued
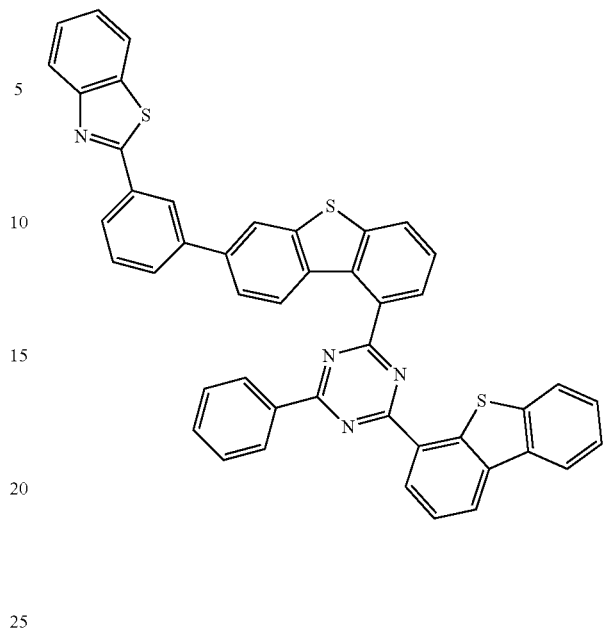
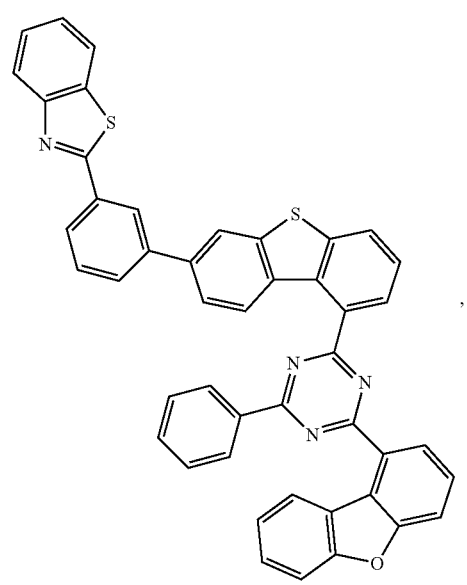
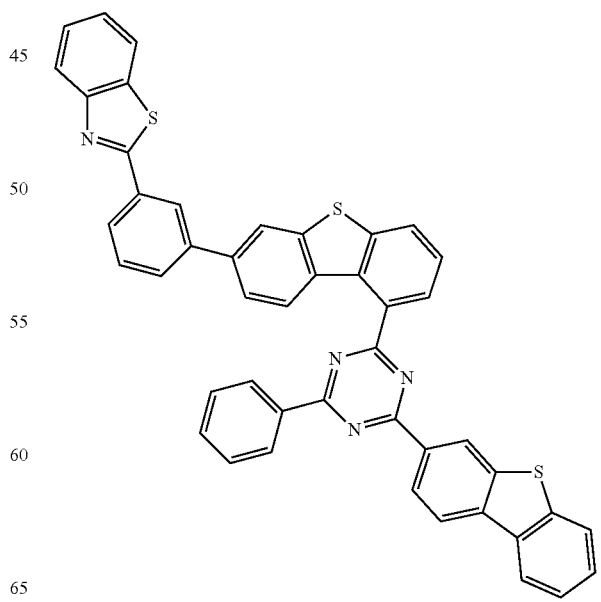

663
-continued
664
-continued
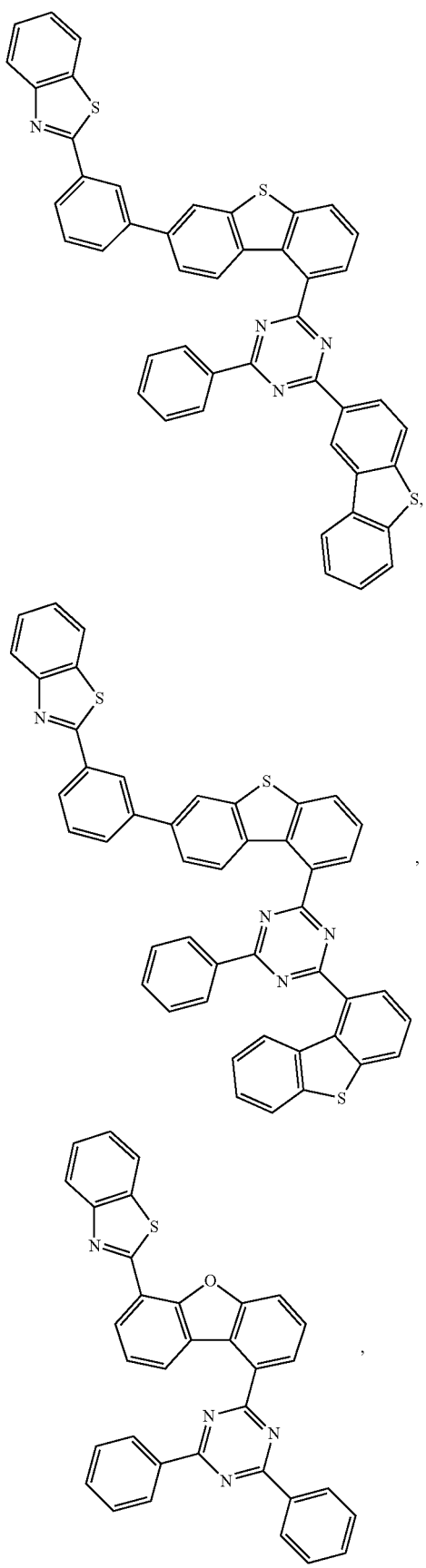

665
-continued
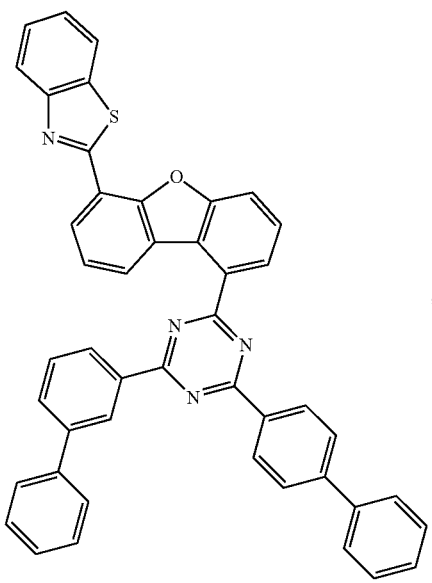
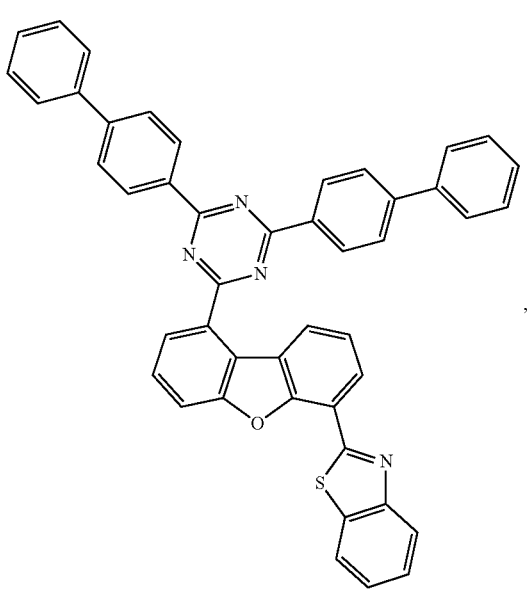
666
-continued
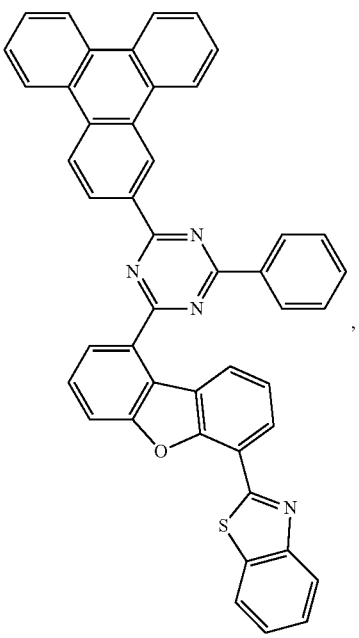
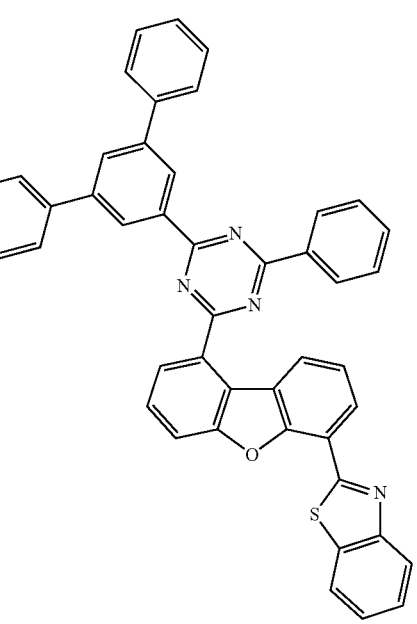

667
-continued
668
-continued
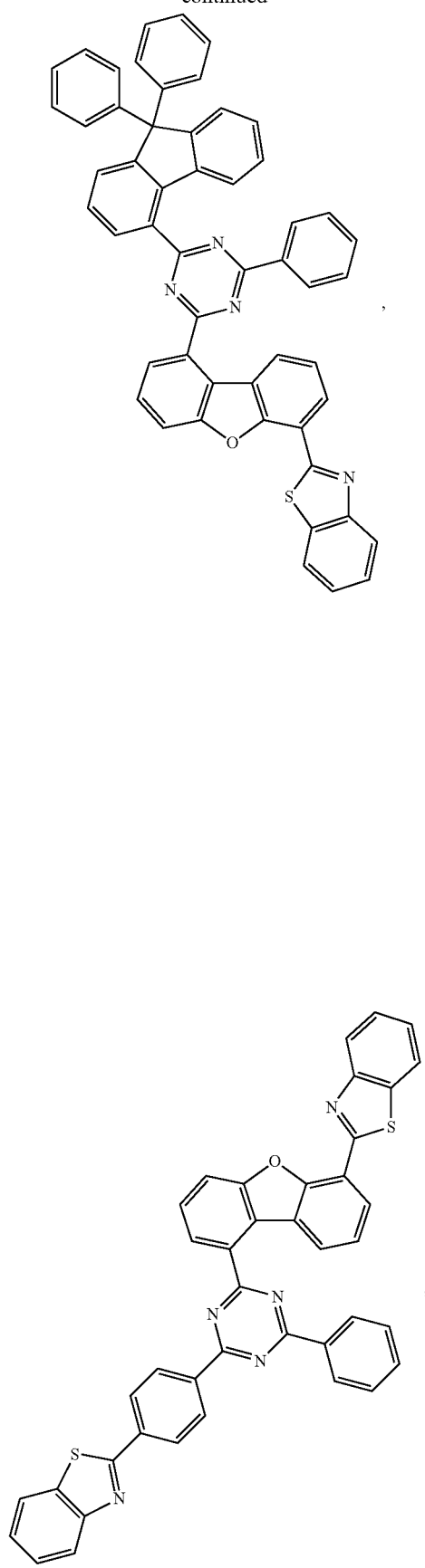
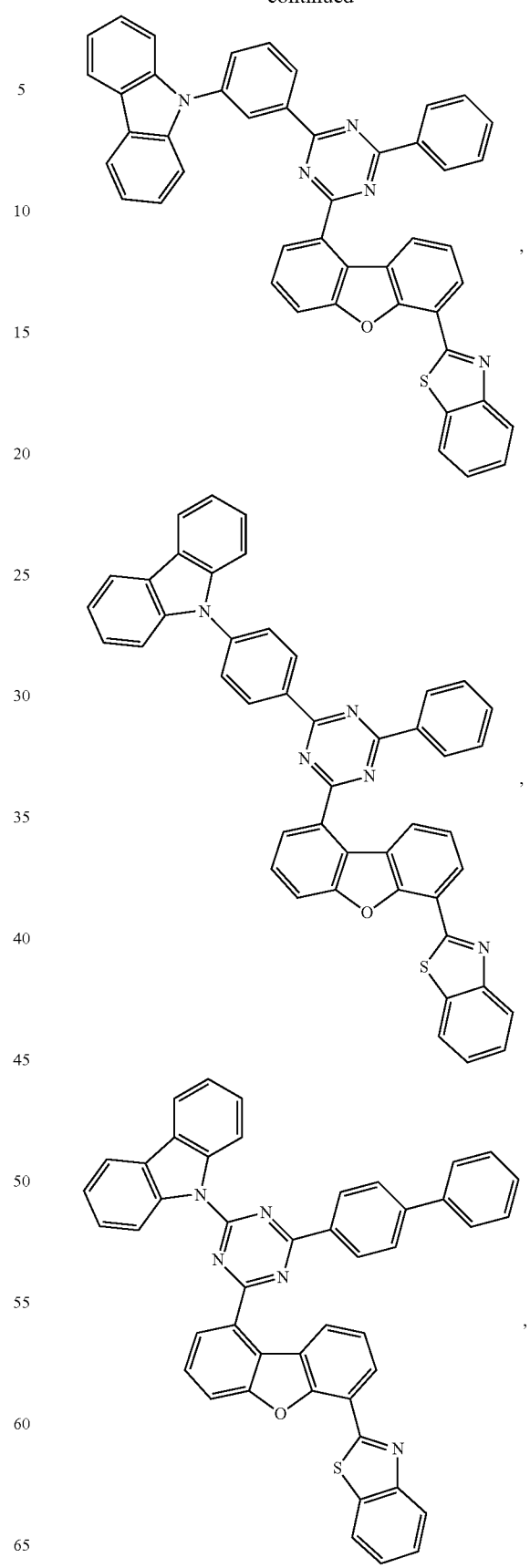

669
-continued
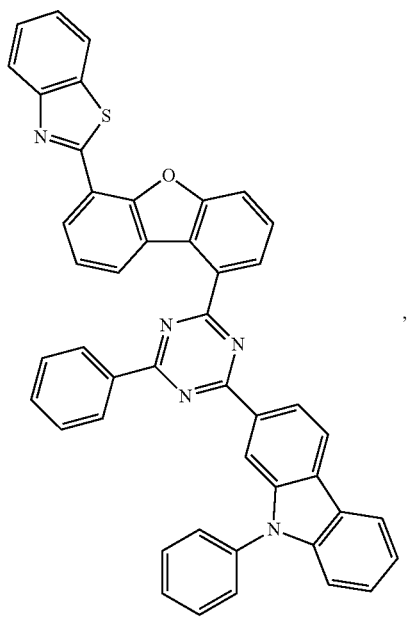
,
670
-continued
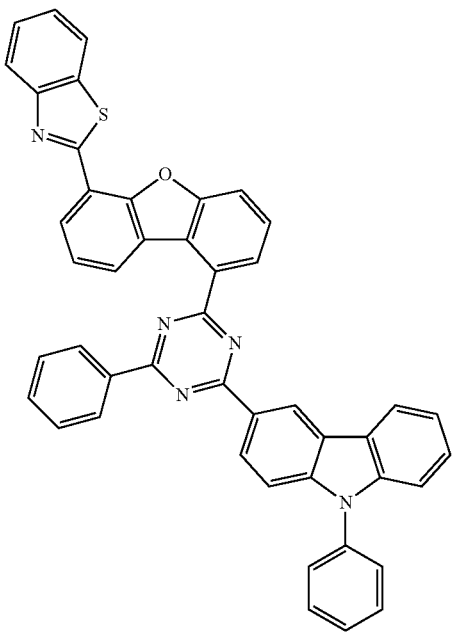
,
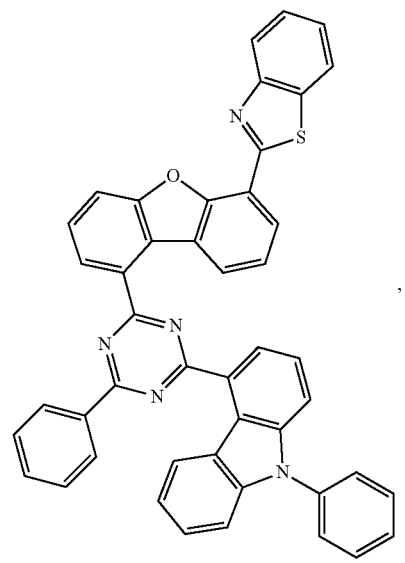
,
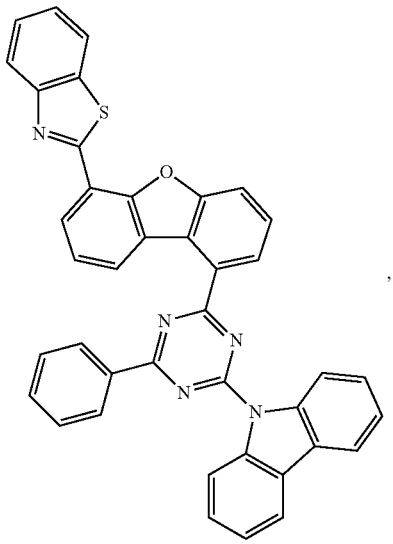
, 671
-continued
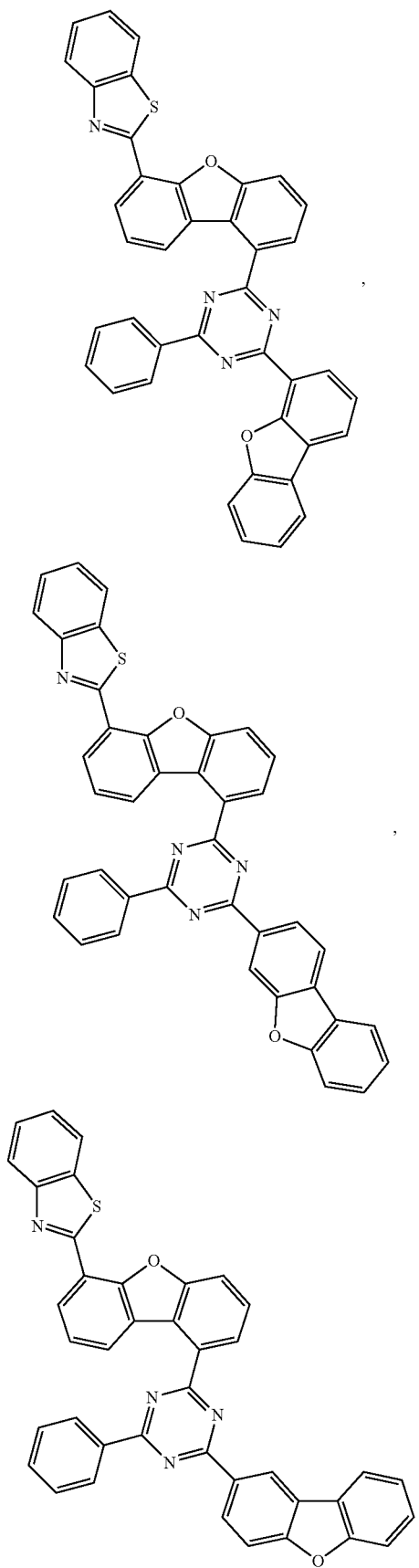
672
-continued
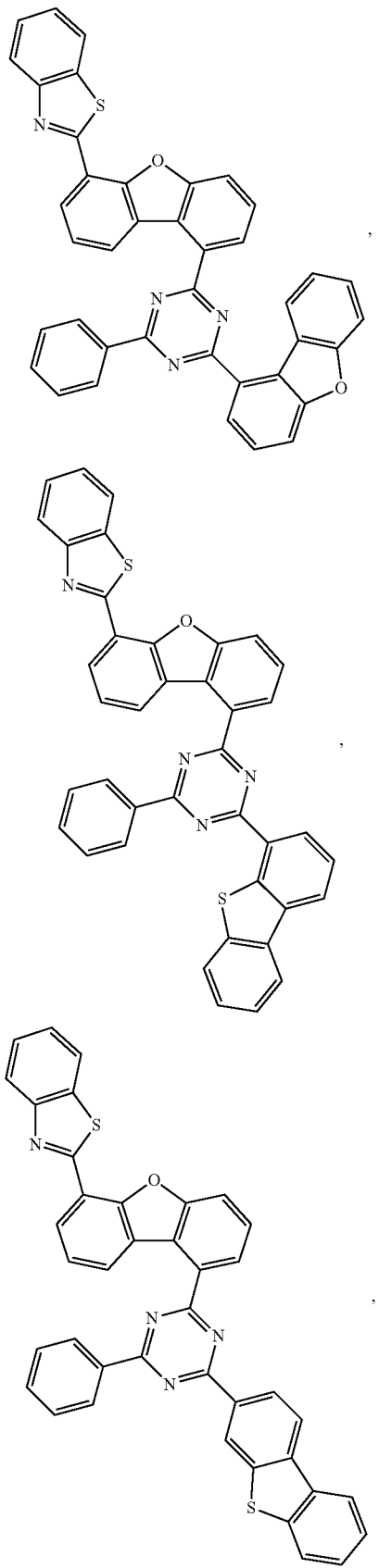

673
-continued
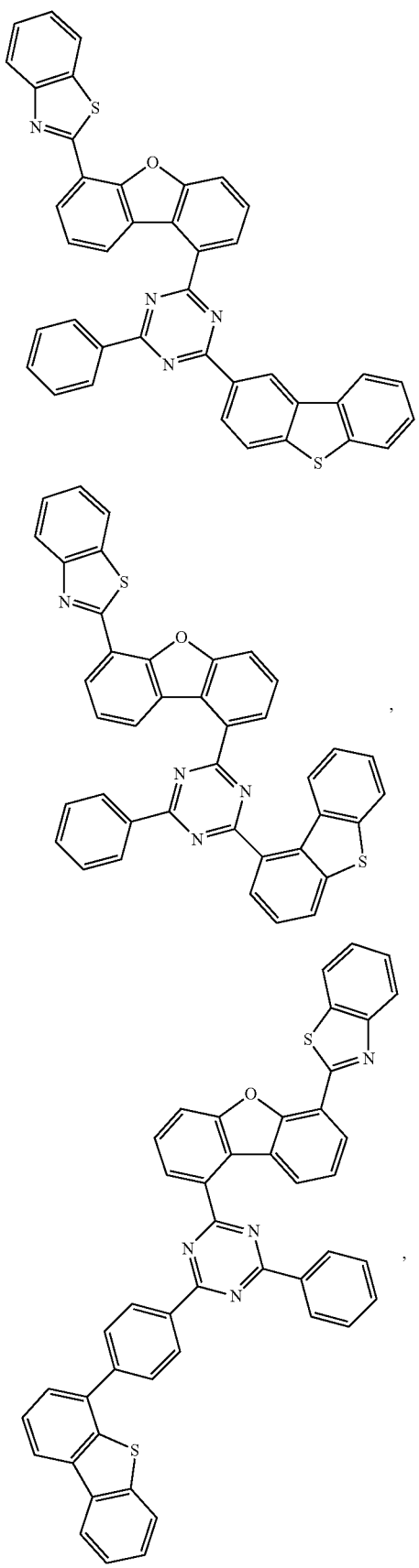
674
-continued
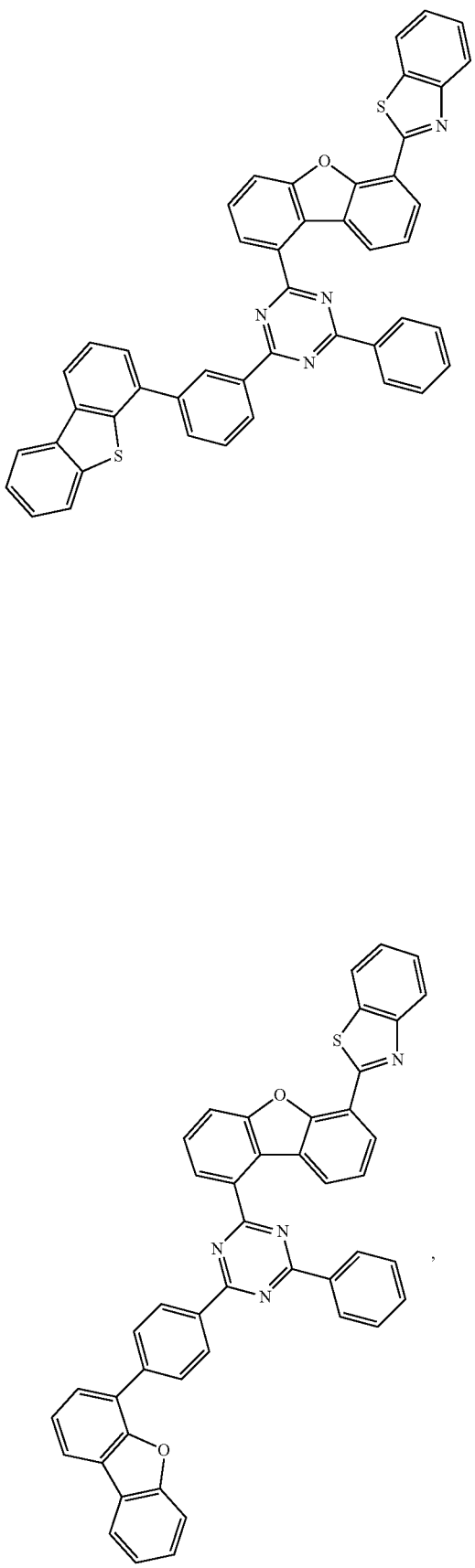

675
-continued
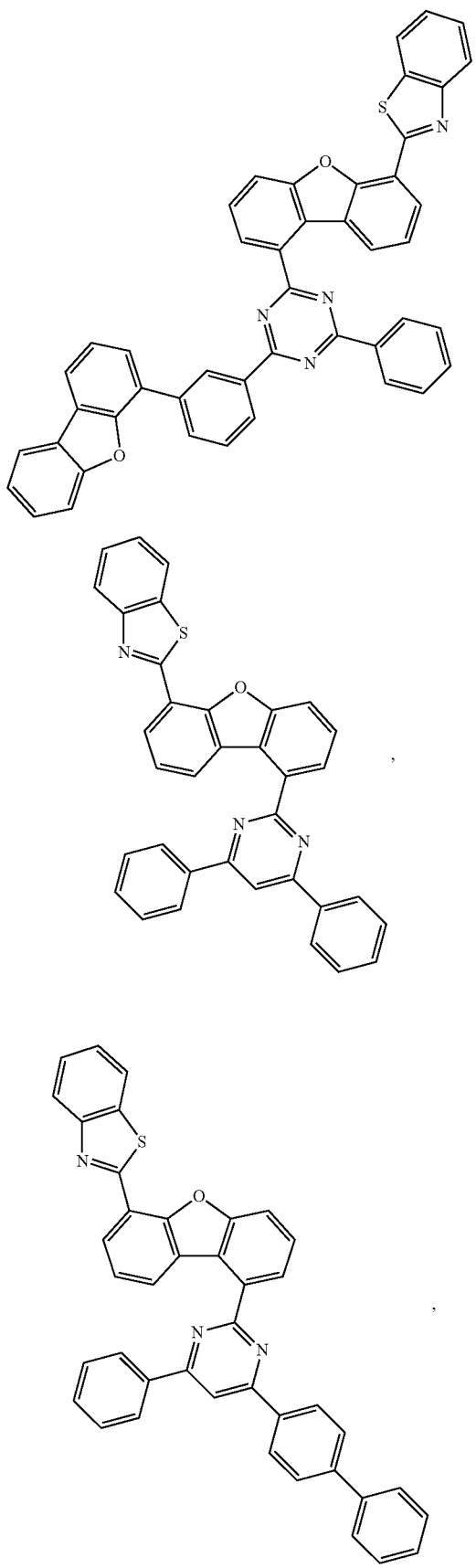
676
-continued
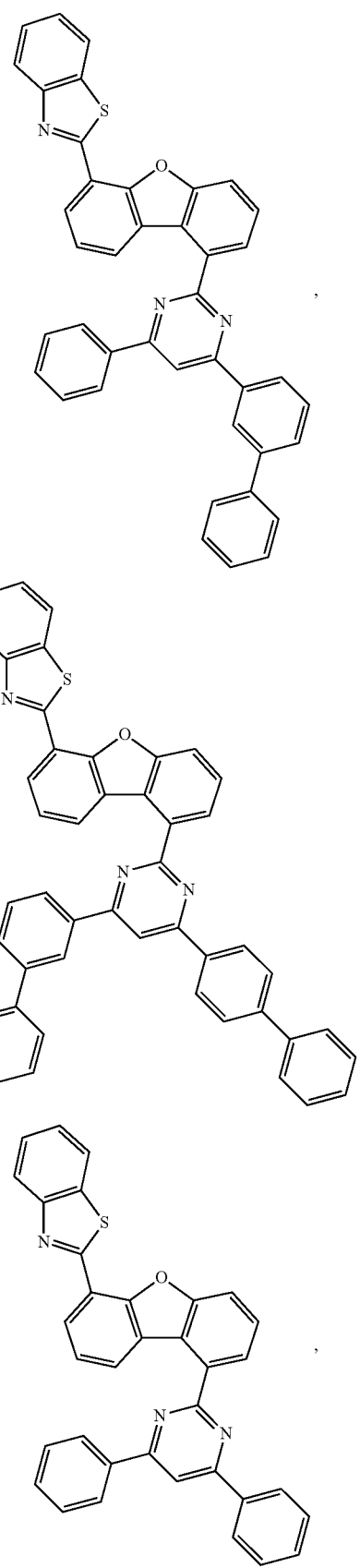

677
-continued
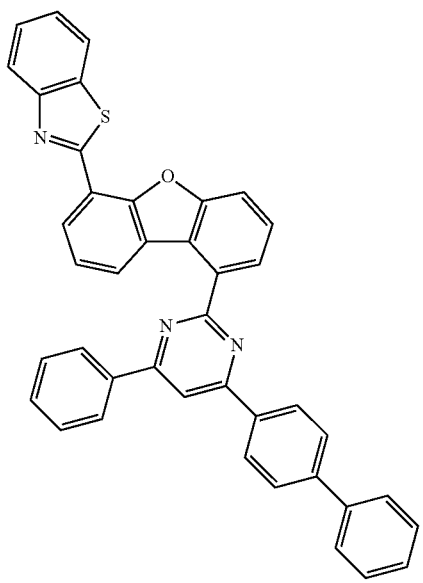
678
-continued
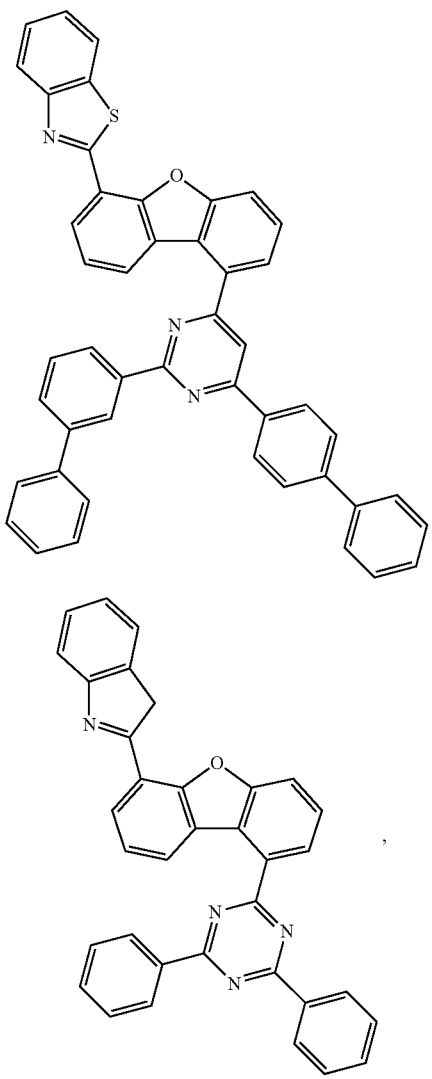
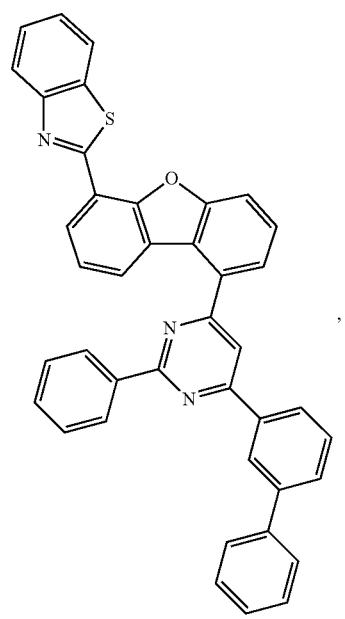
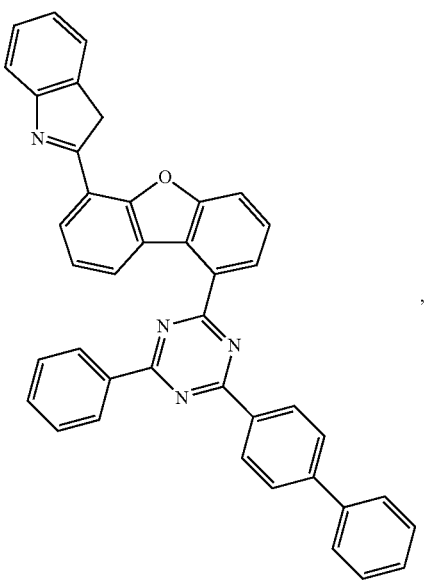

679
-continued
680
-continued
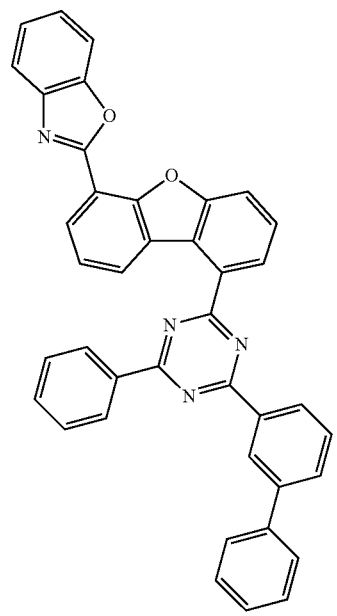
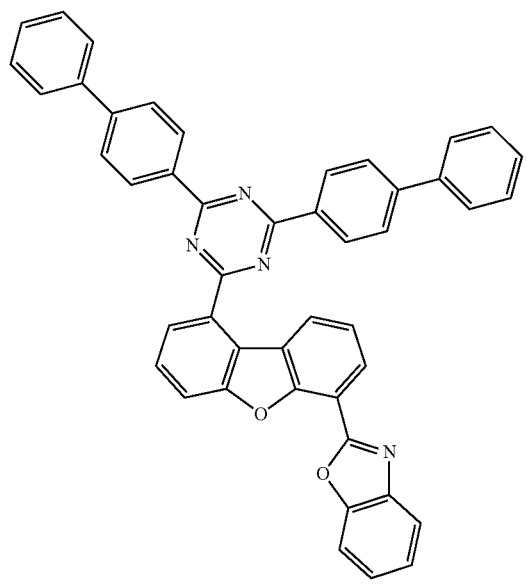
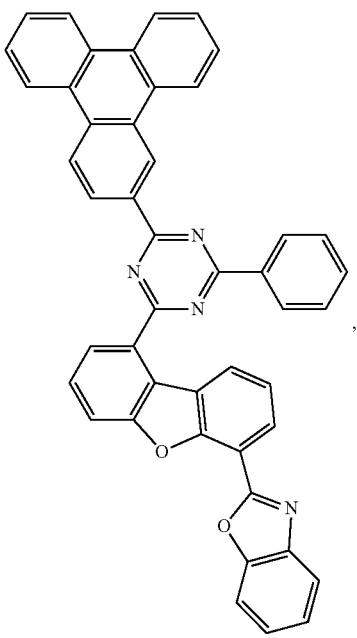

681
-continued
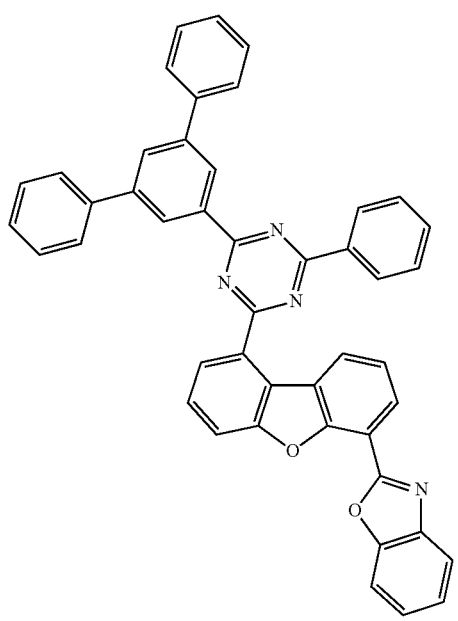
,
682
-continued
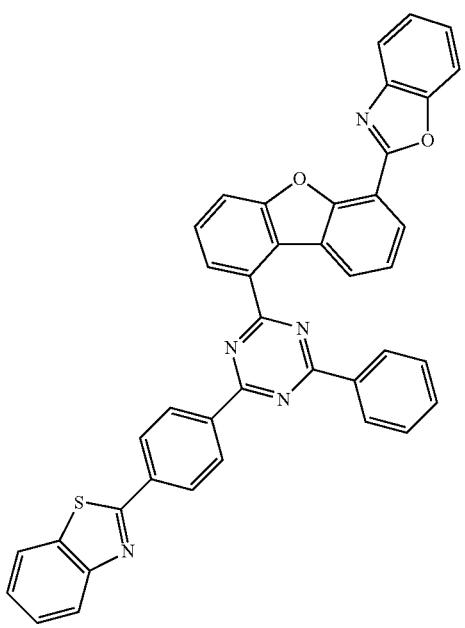
,
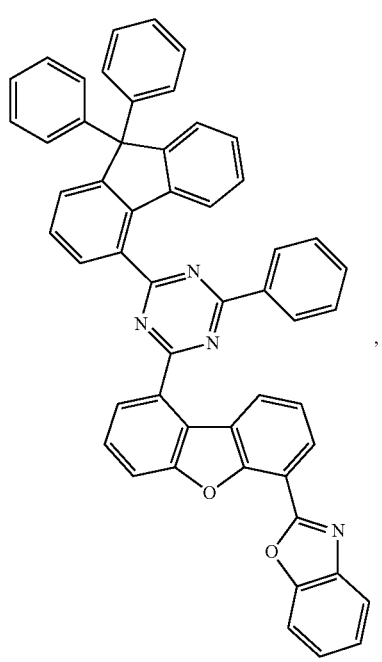
,
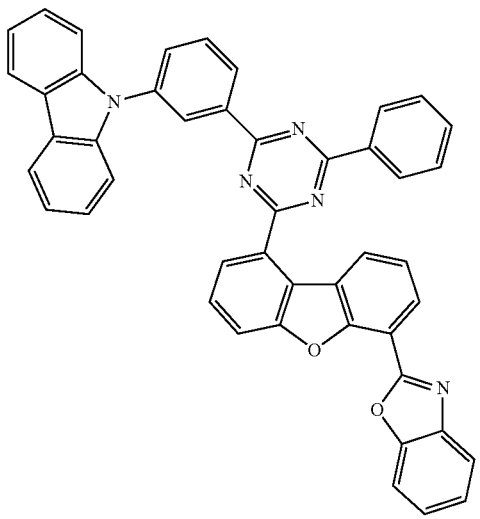
, 683
-continued
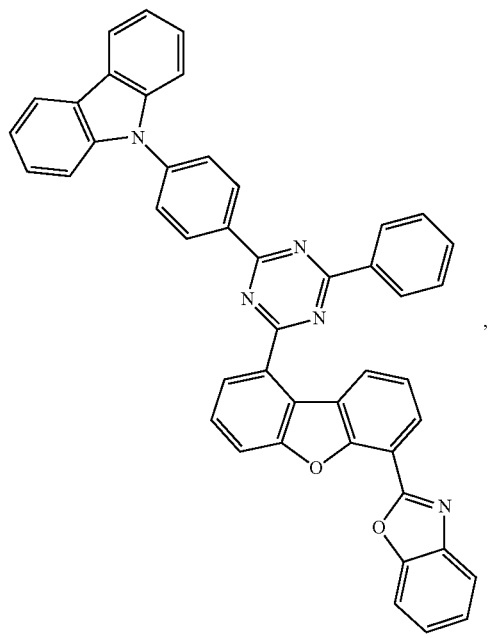
,
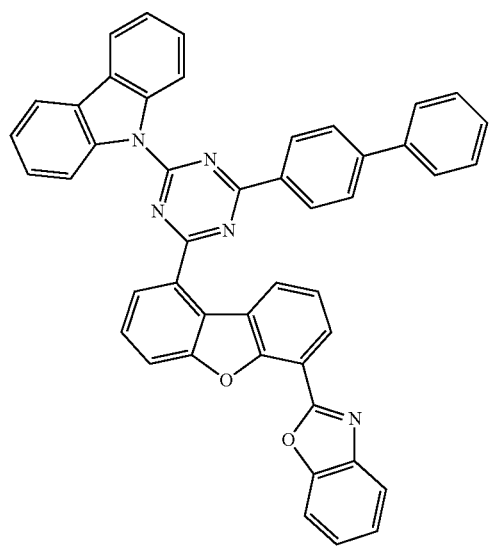
,
684
-continued
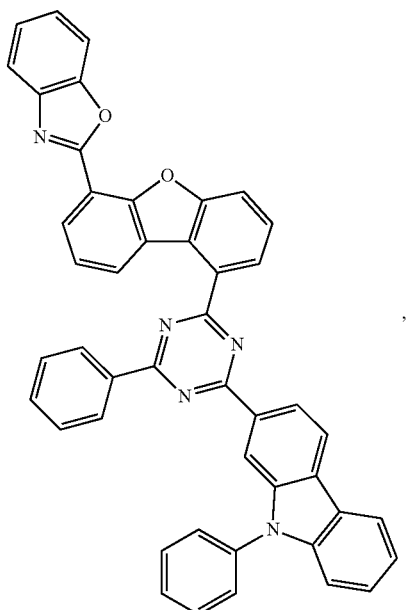
,
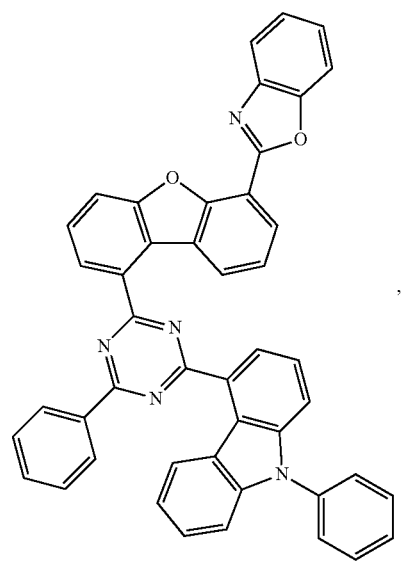
, 685
-continued
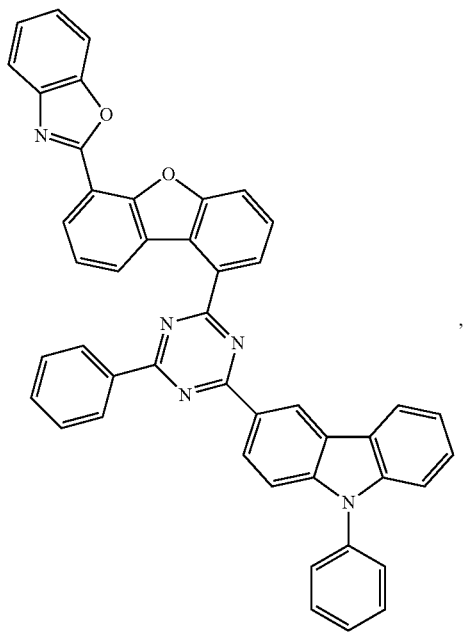
,
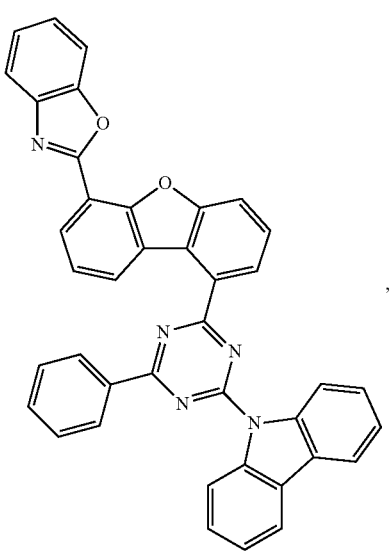
,
686
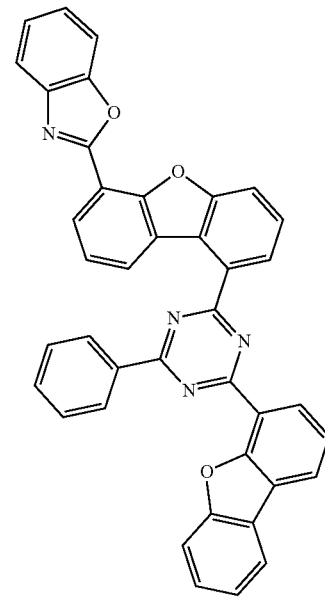
,
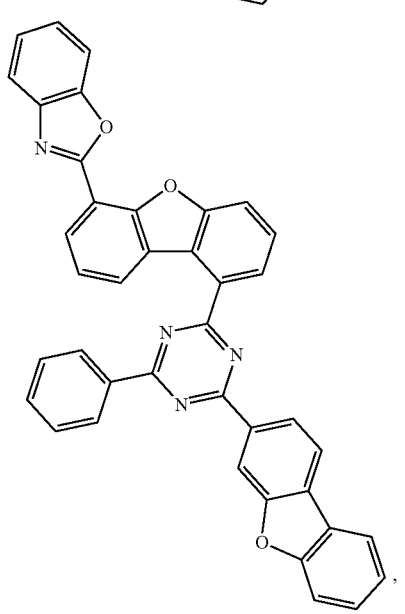
,
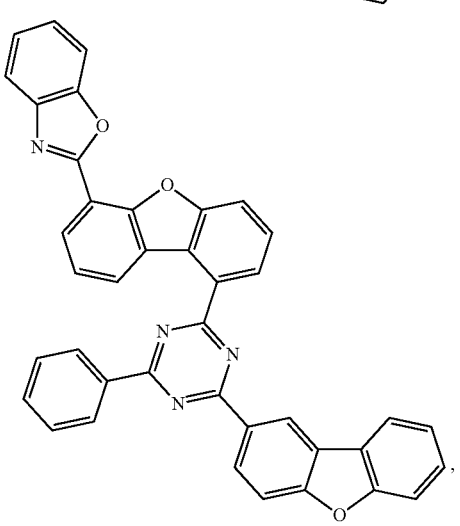
, 687
-continued
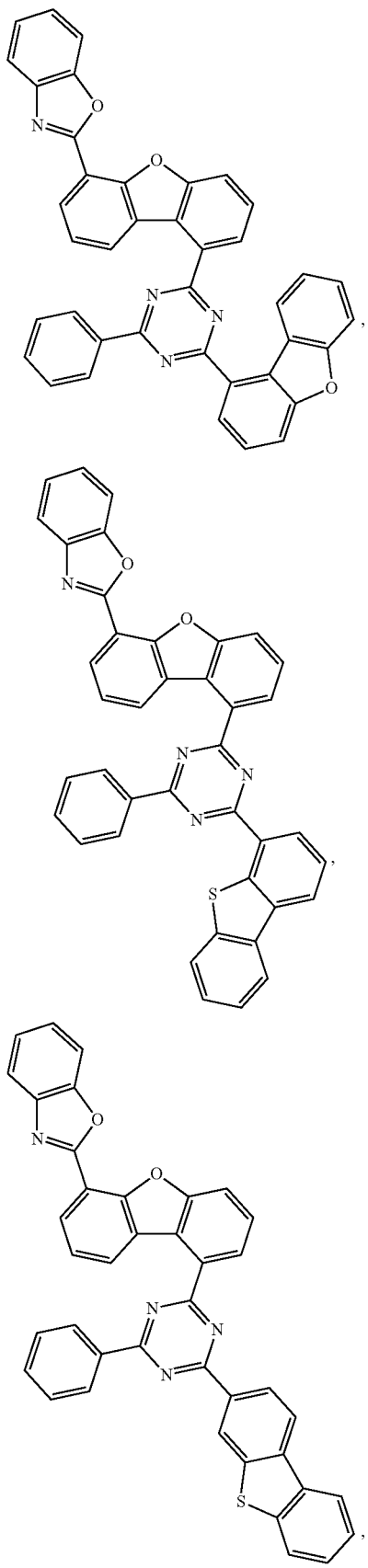
688
-continued
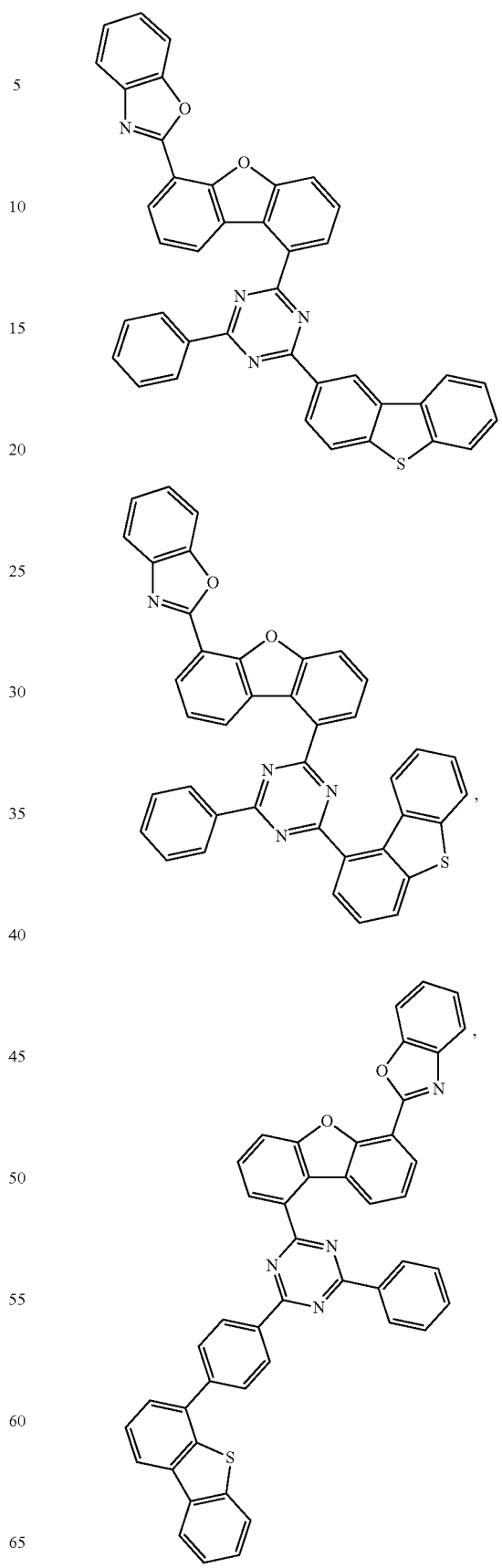

689
-continued
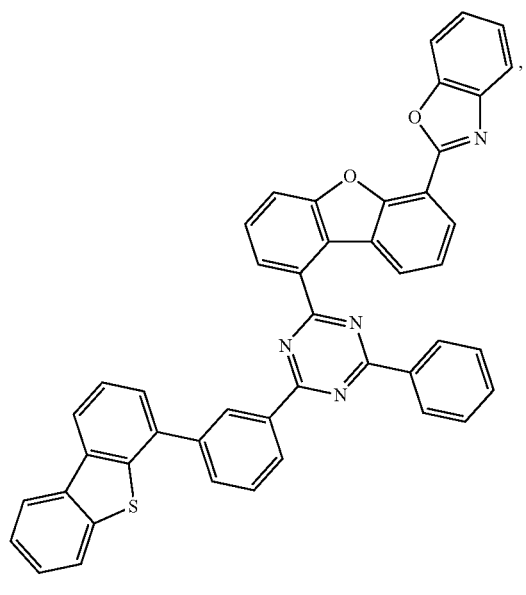
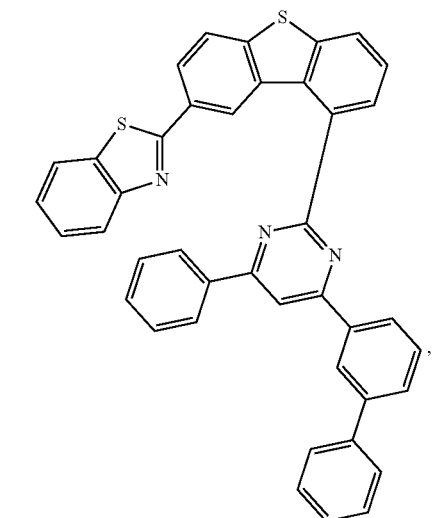
690
-continued
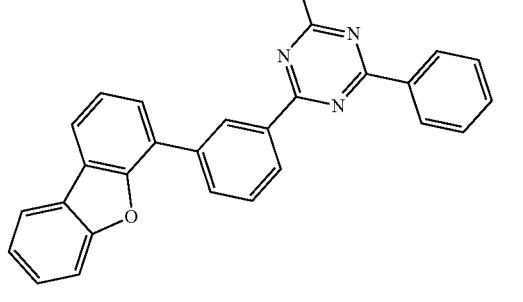
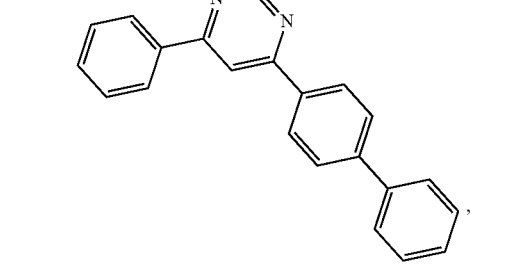

691
-continued
692
-continued
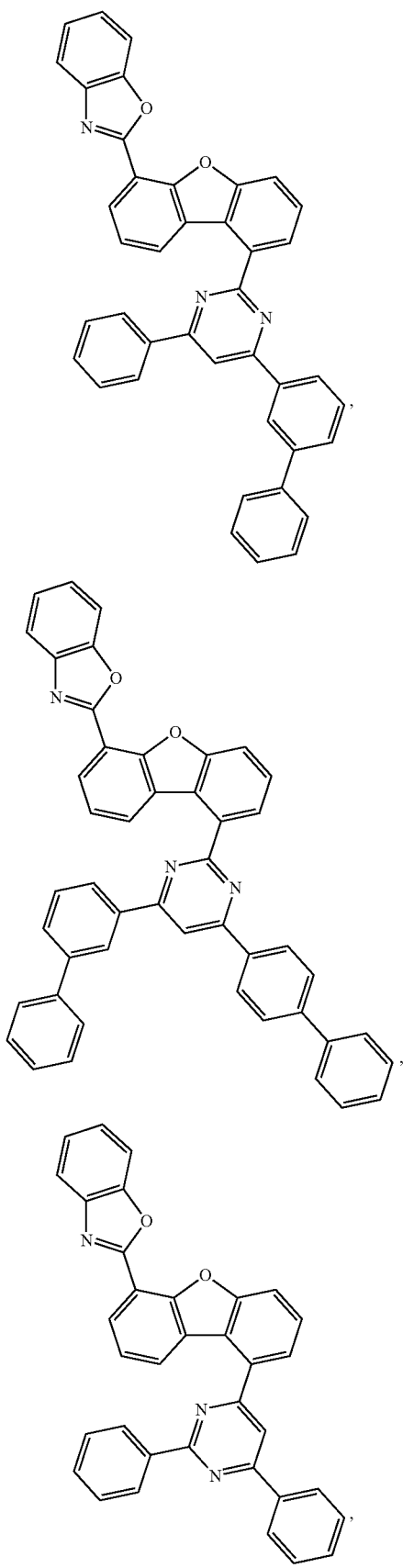

693
-continued
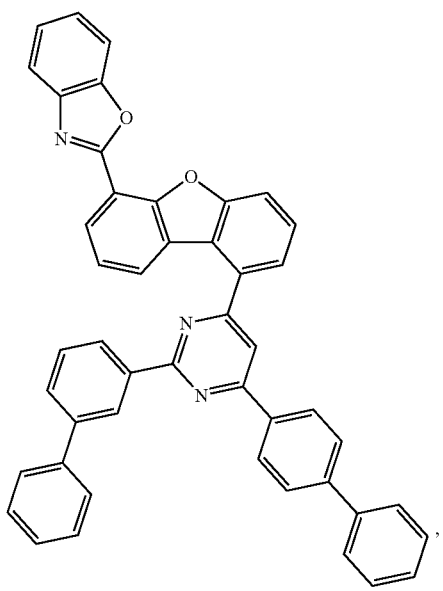
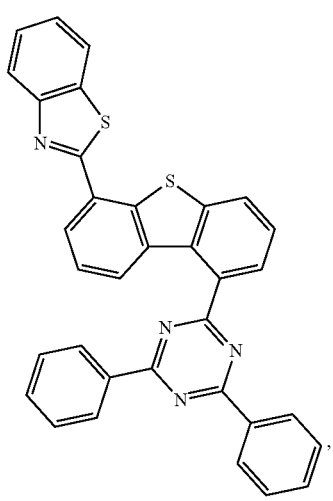
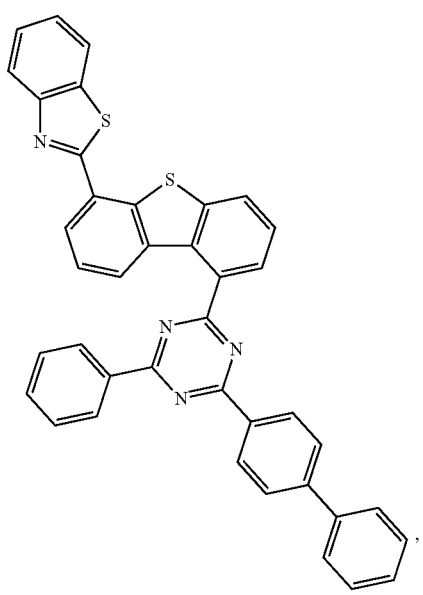
694
-continued
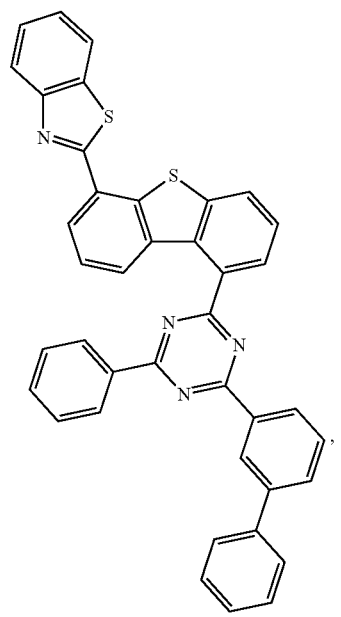
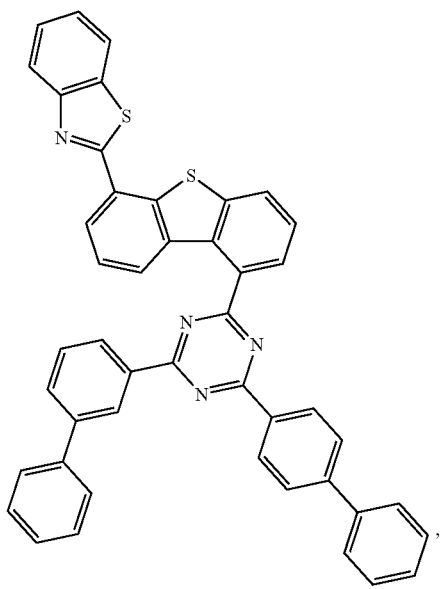

695
-continued
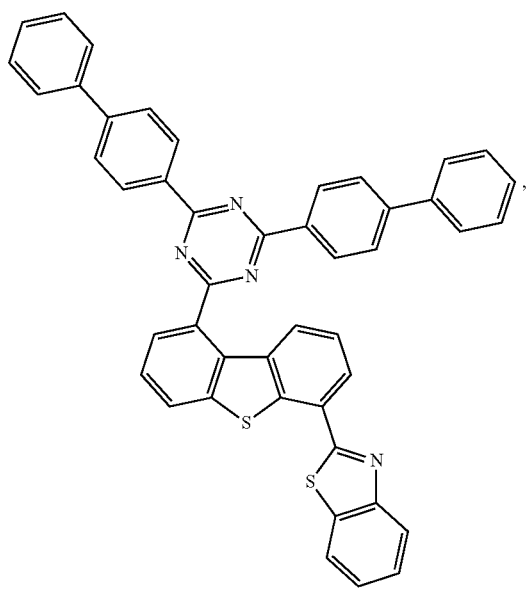
696
-continued
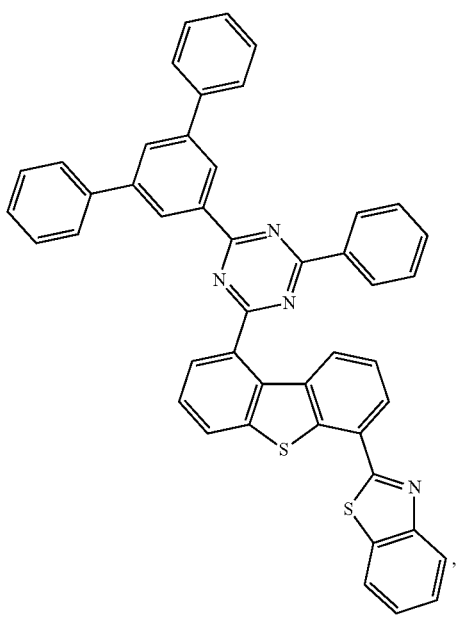
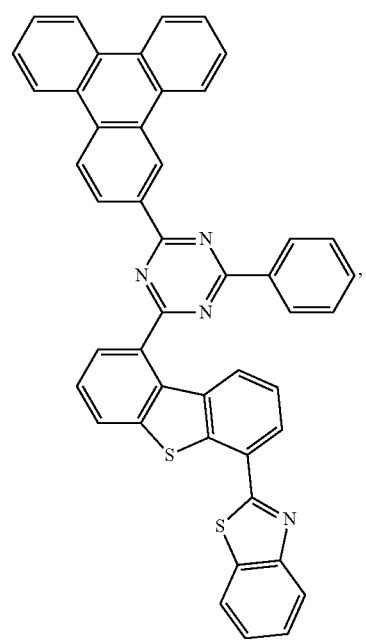
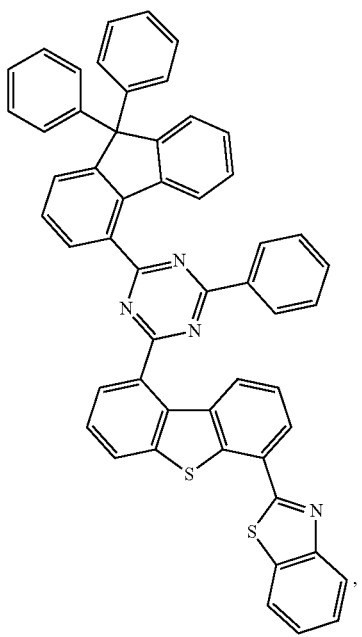

697
-continued
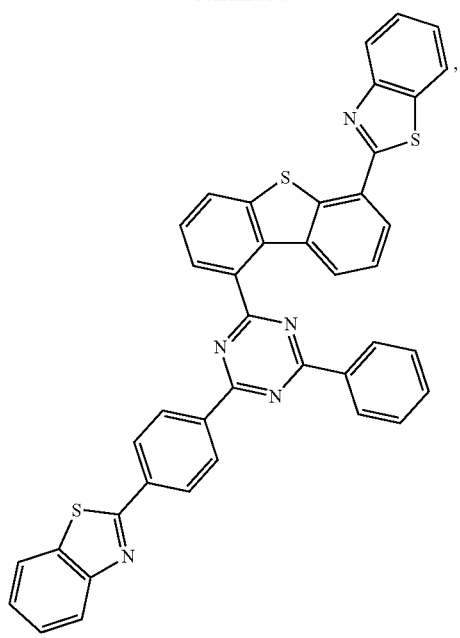
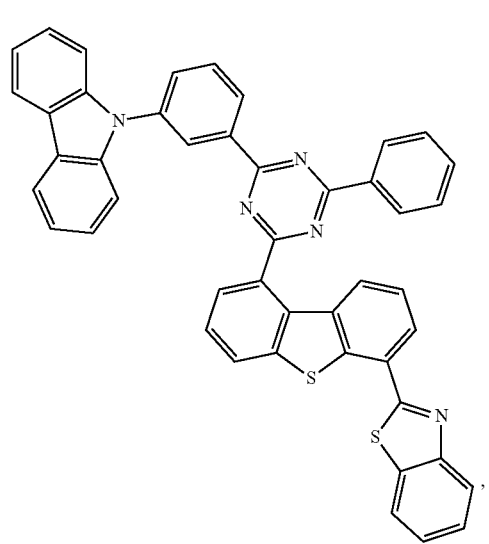
698
-continued
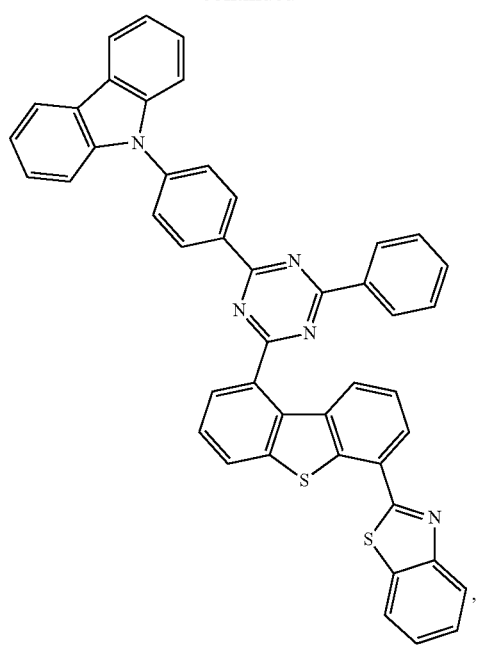
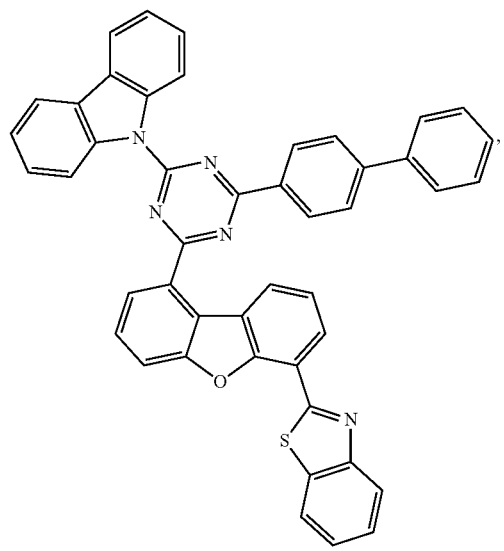

699
-continued
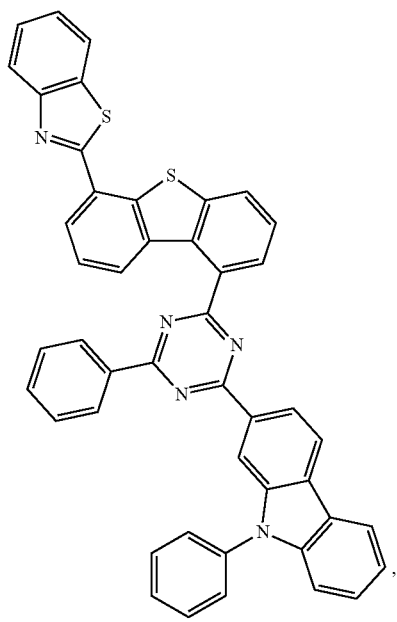
700
-continued
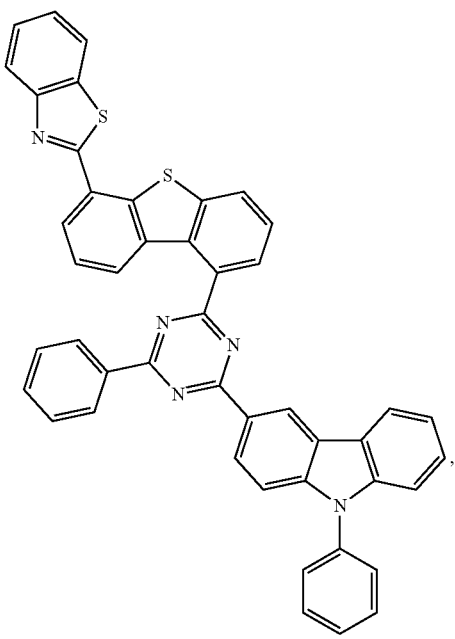
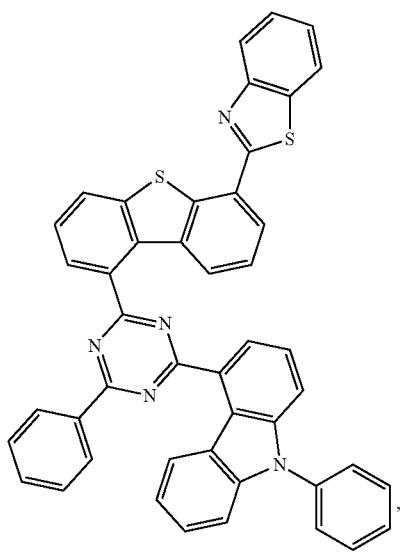
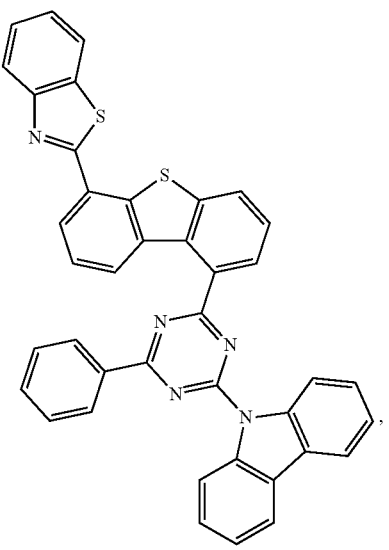

701
-continued
702
-continued
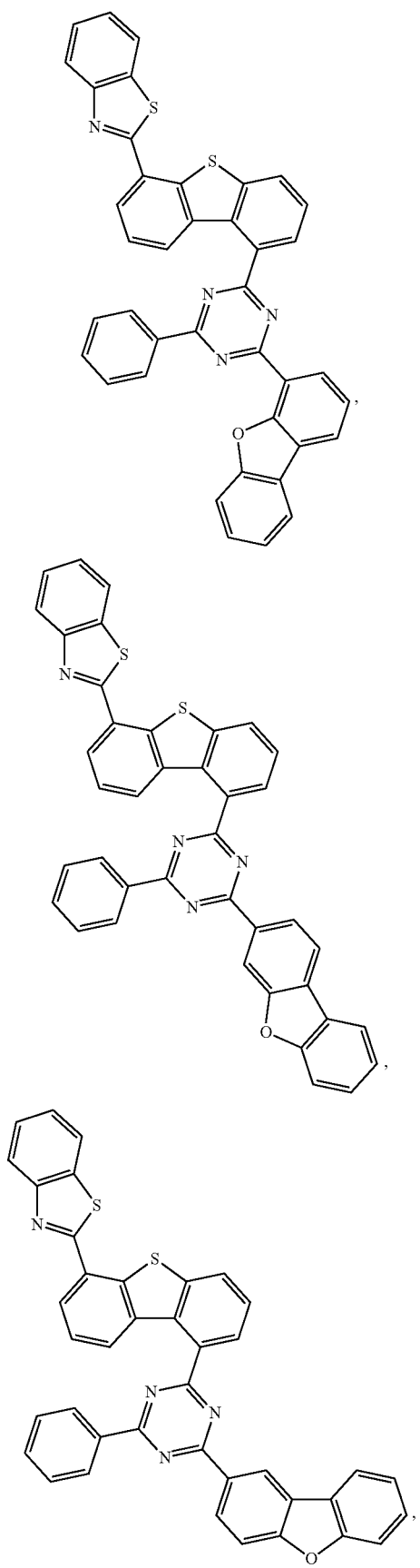
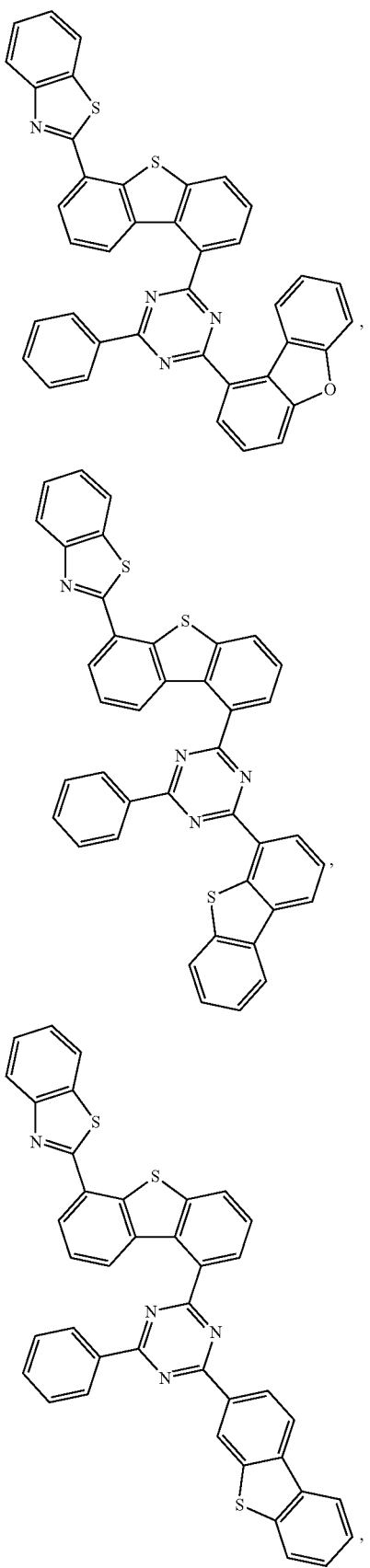

703
-continued
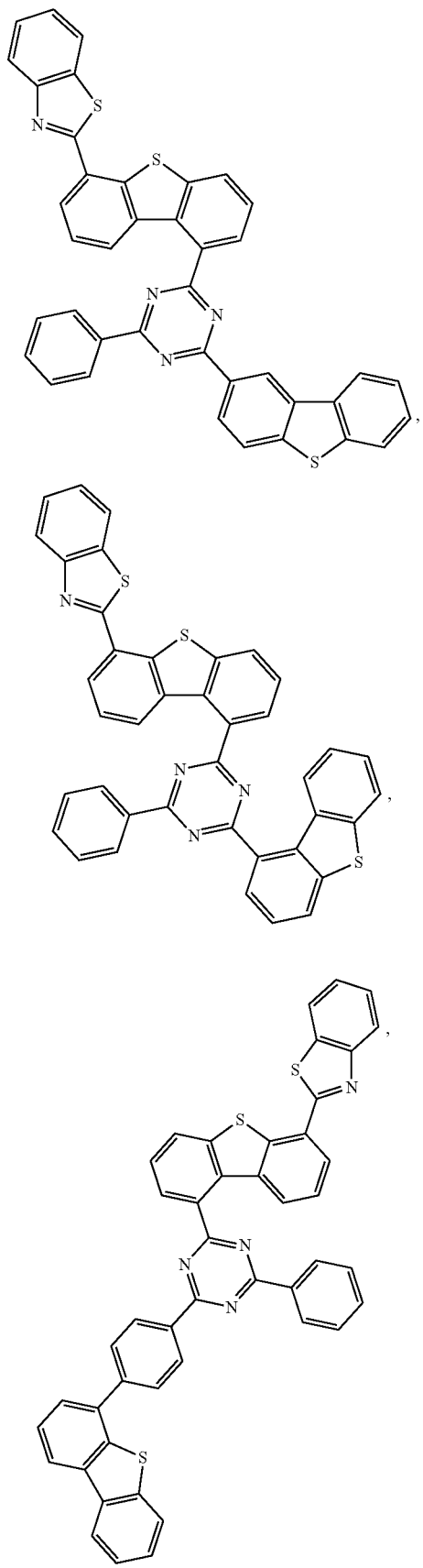
704
-continued
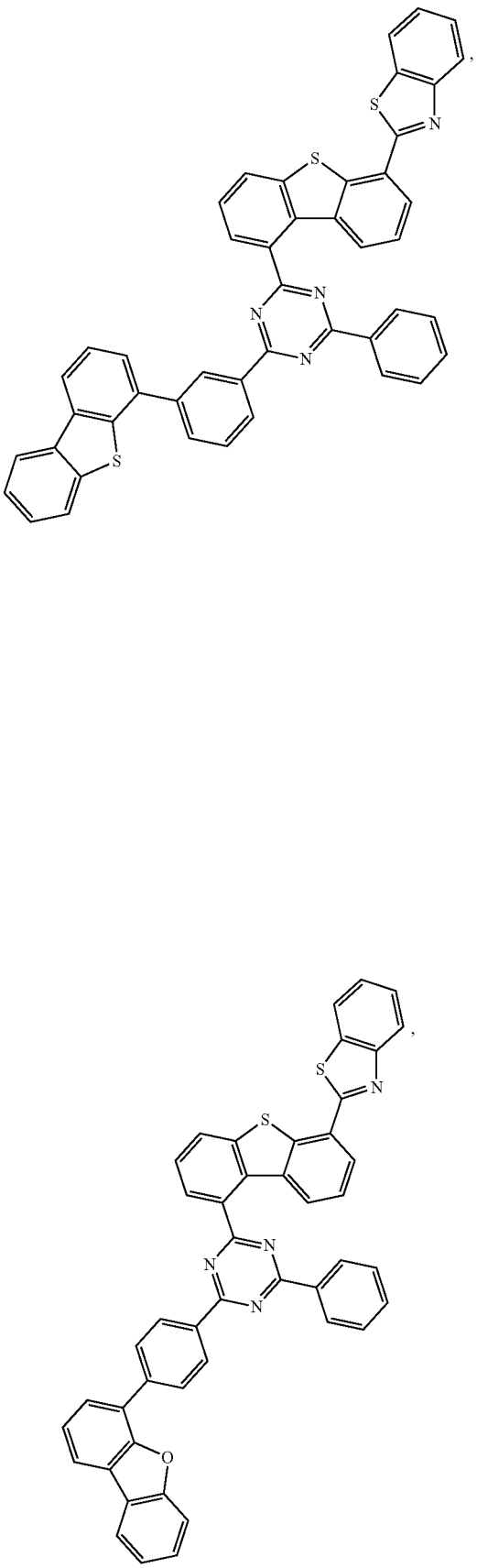

705
-continued
706
-continued
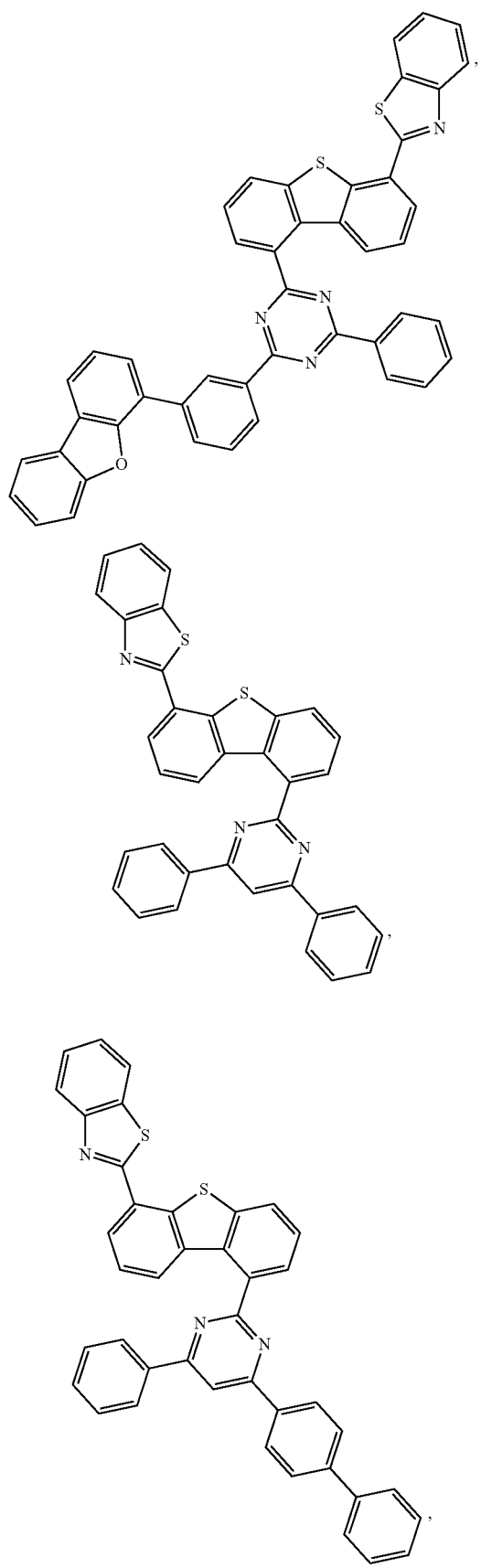
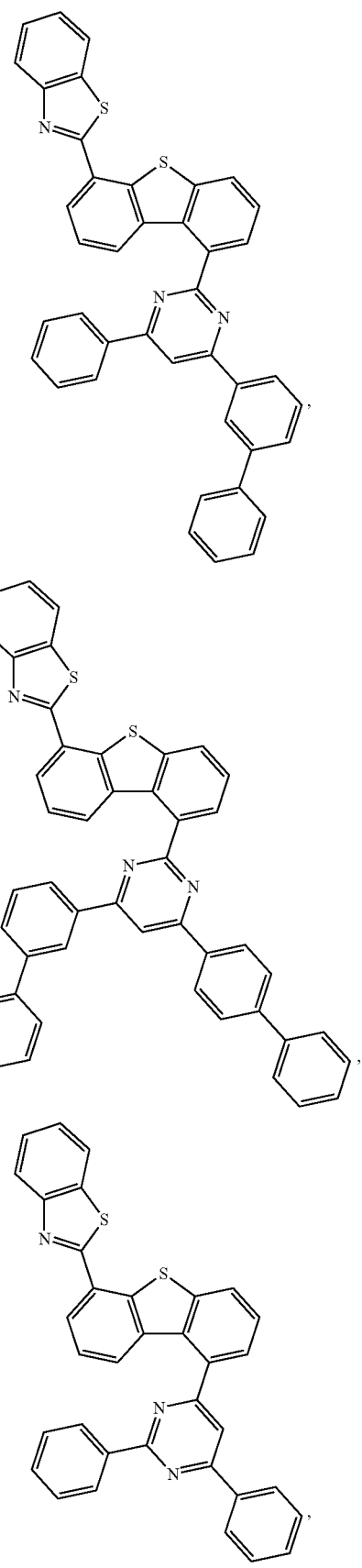

707
-continued
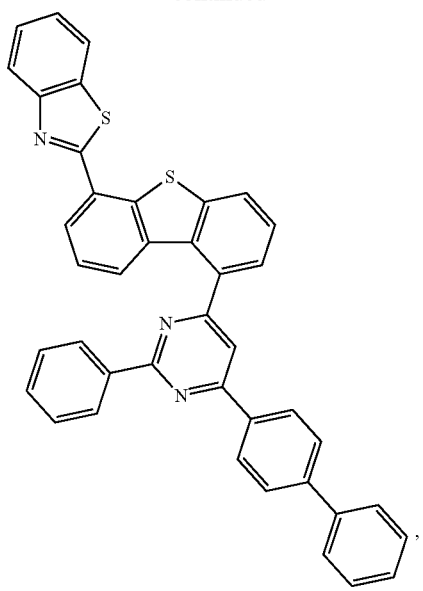
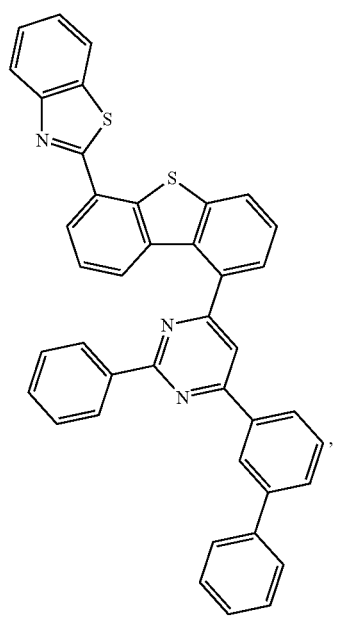
708
-continued
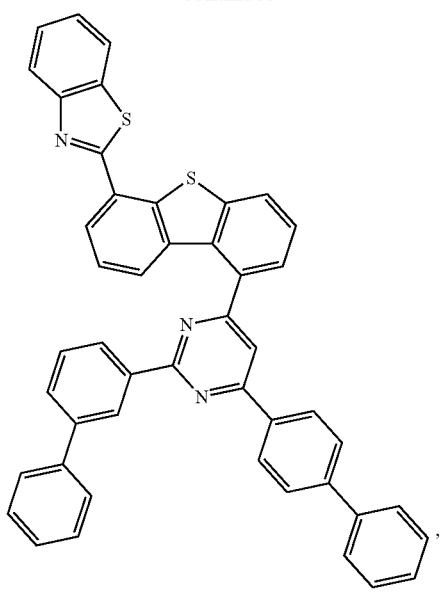
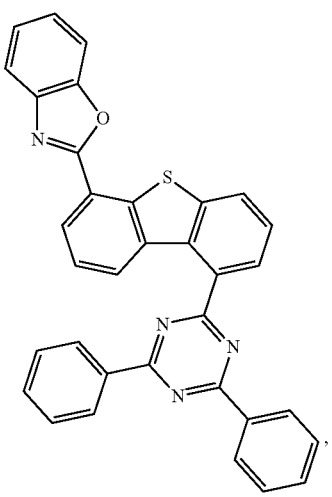
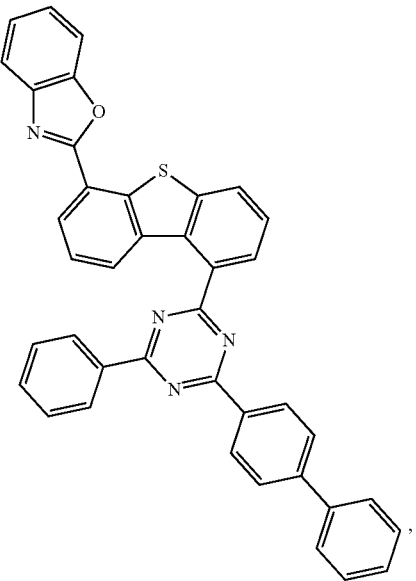

709
-continued
710
-continued
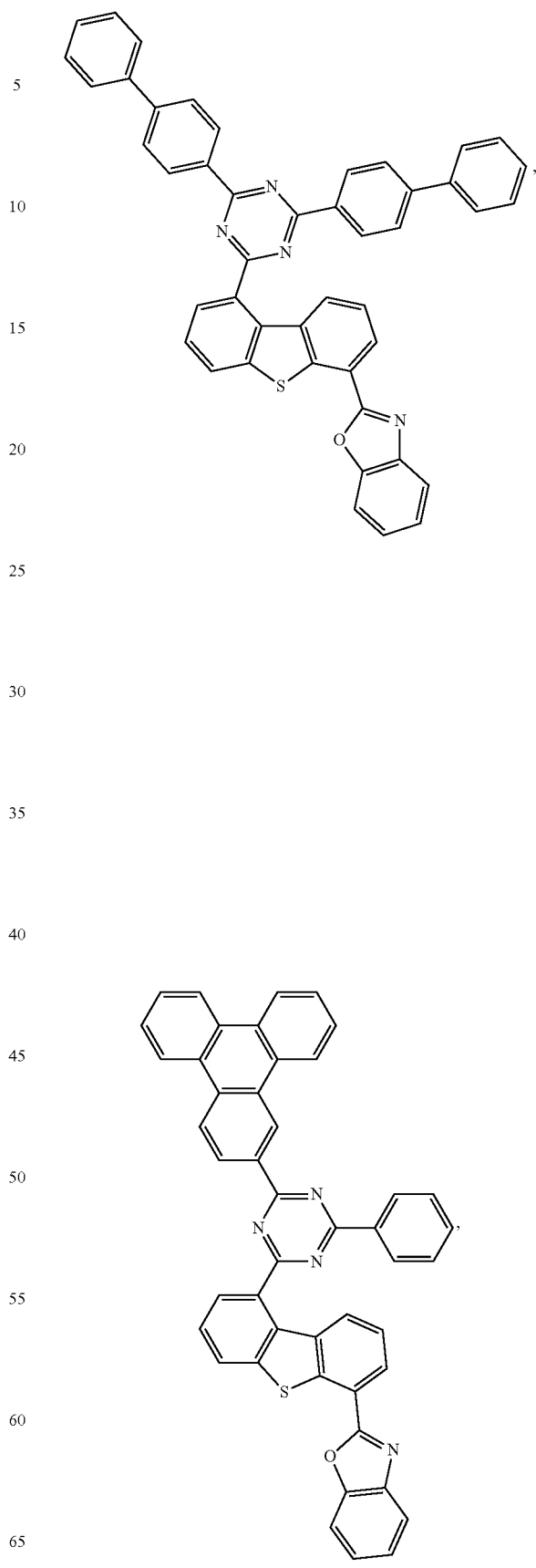

711
-continued
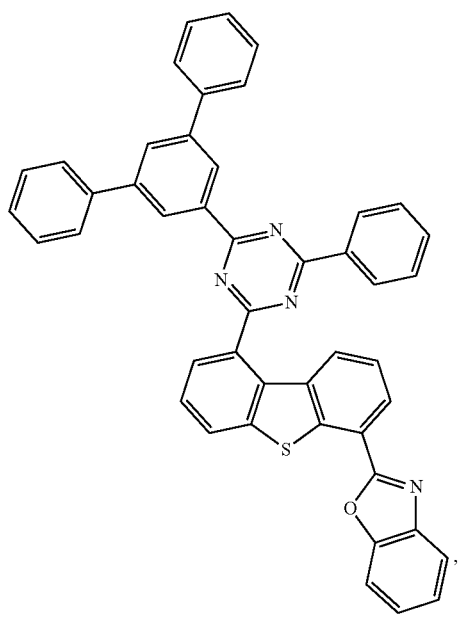
712
-continued
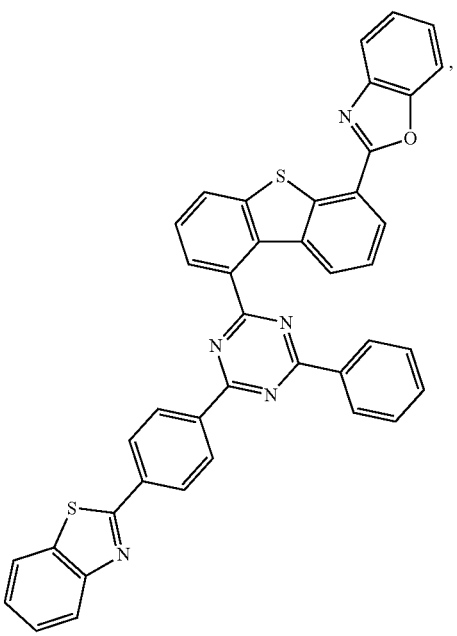
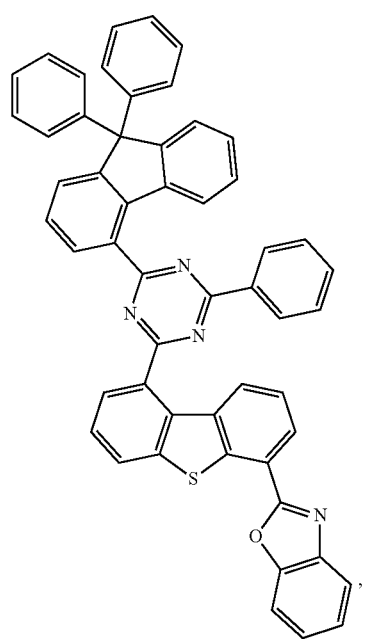
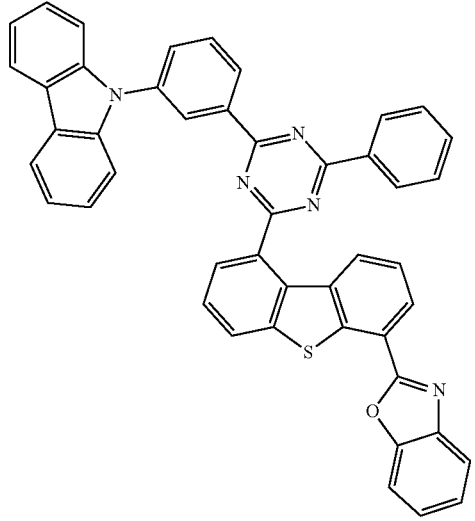

713
-continued
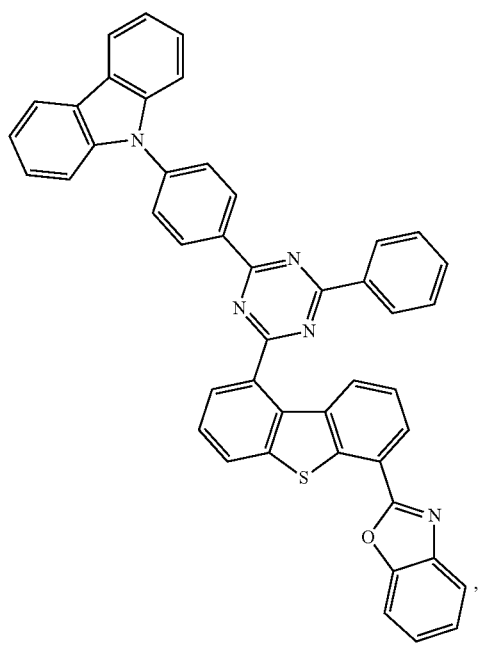
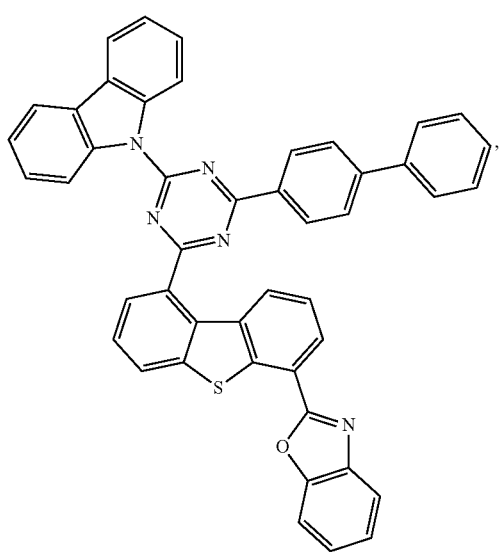
714
-continued
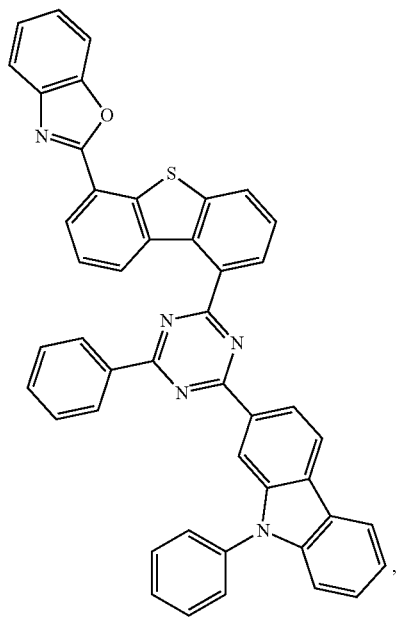
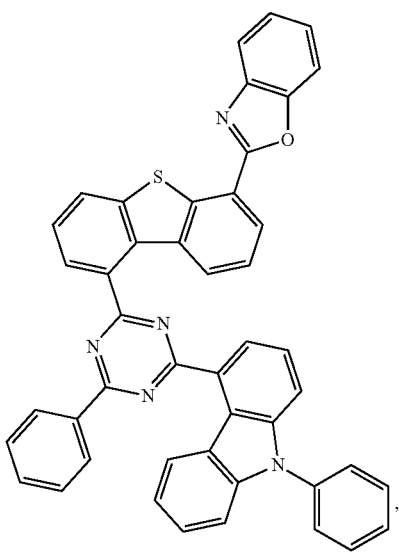

715
-continued
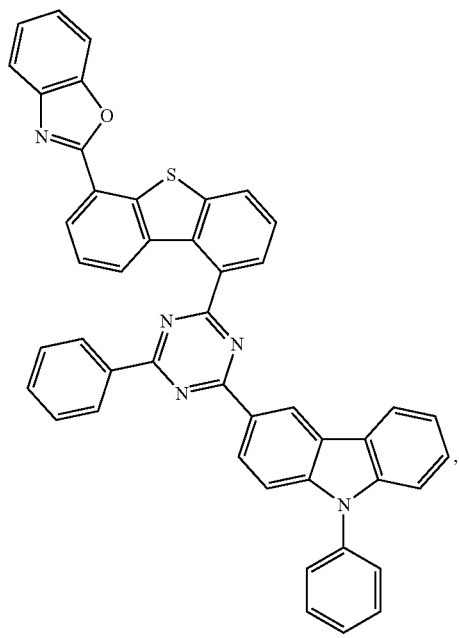
716
-continued
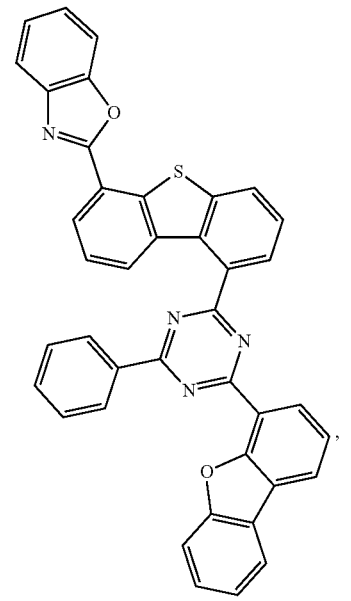
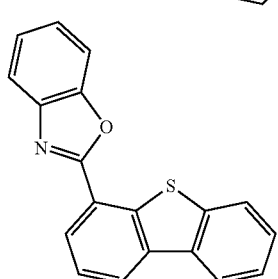
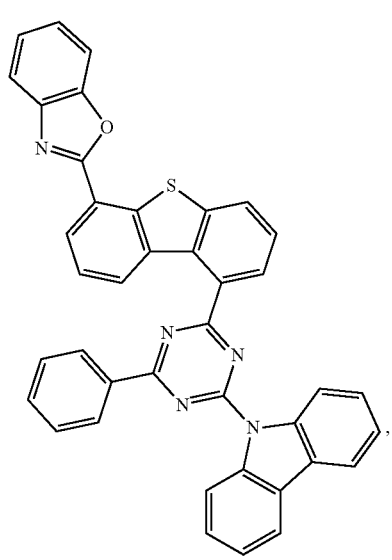
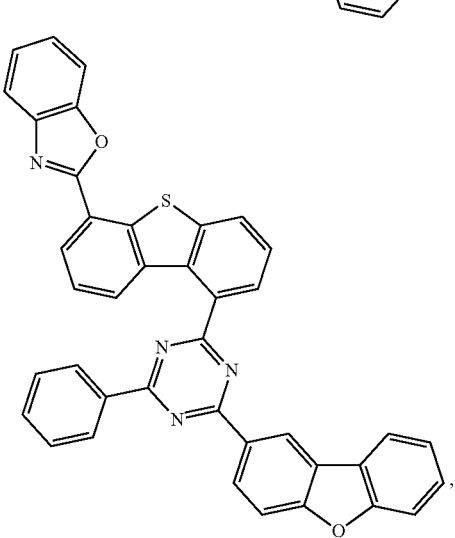

717
-continued
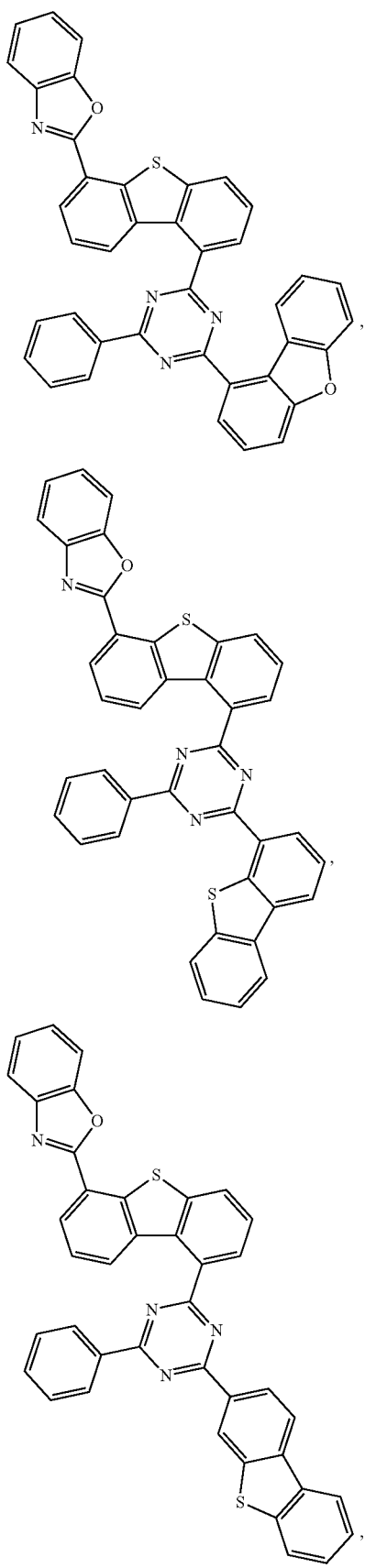
718
-continued
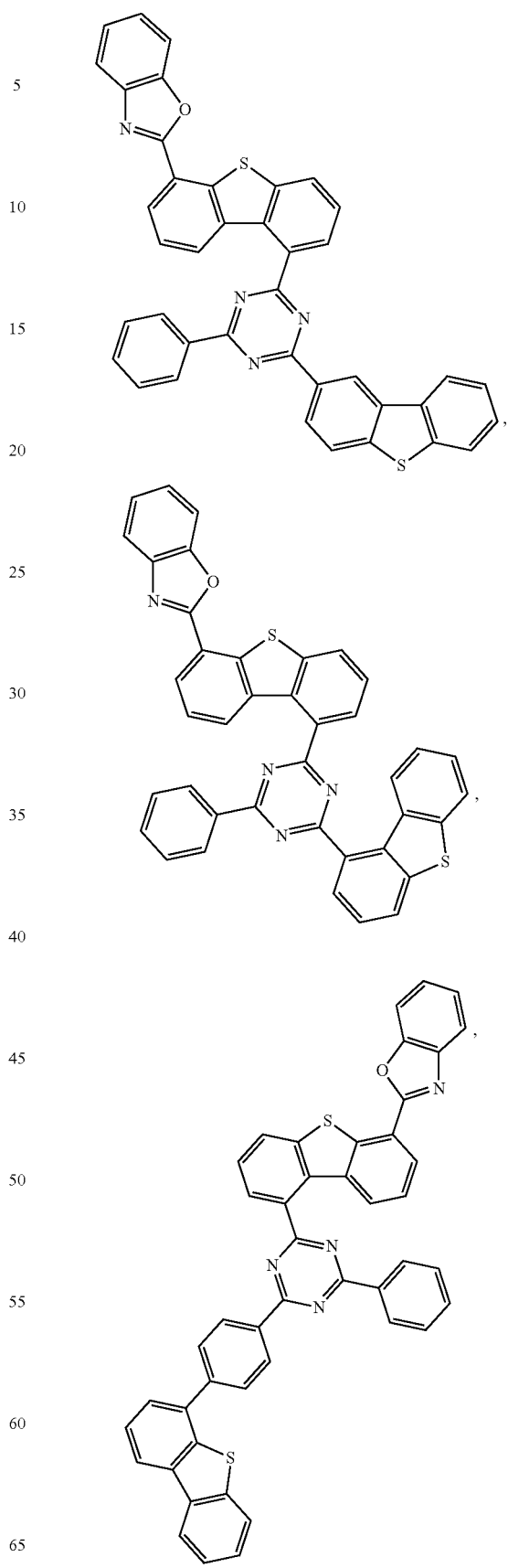

719
-continued
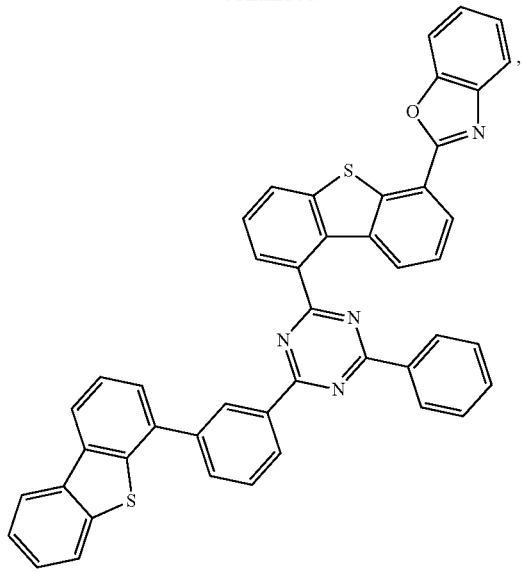
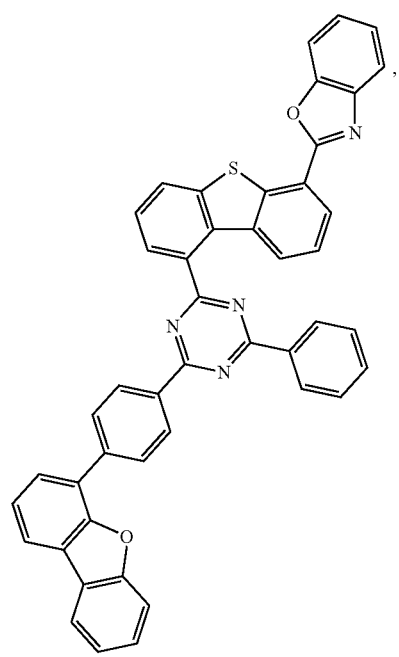
720
-continued
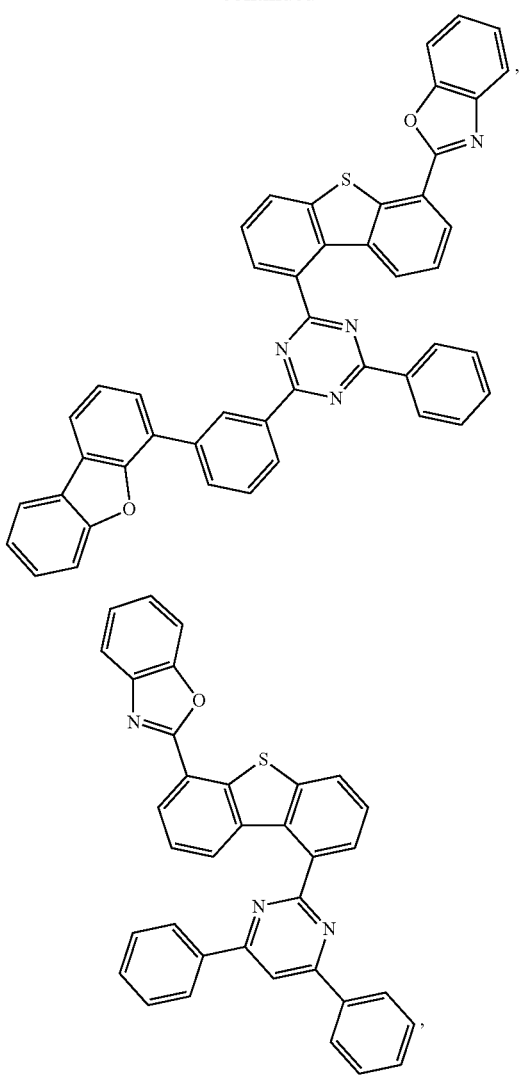

721
-continued
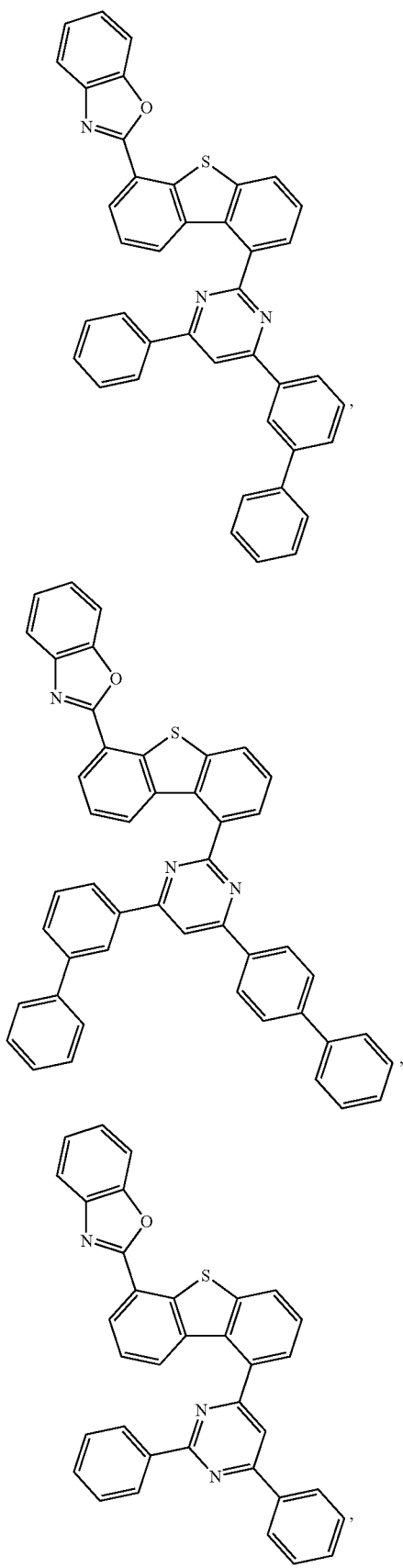
722
-continued

723
-continued
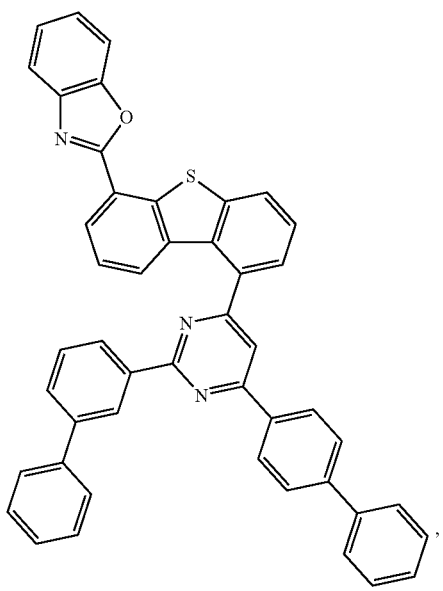
724
-continued
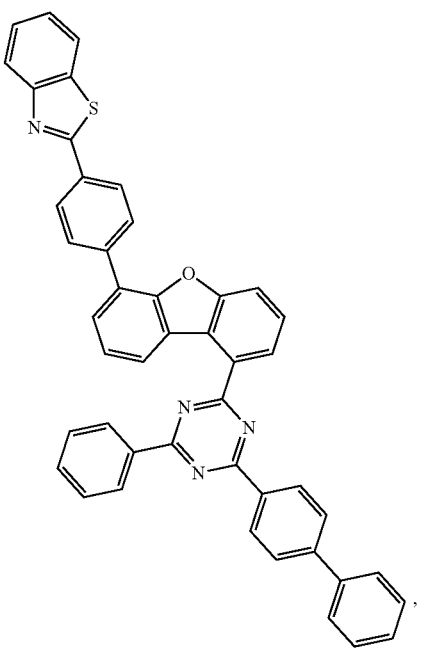
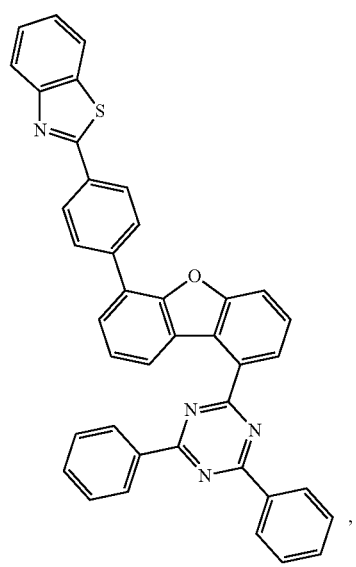
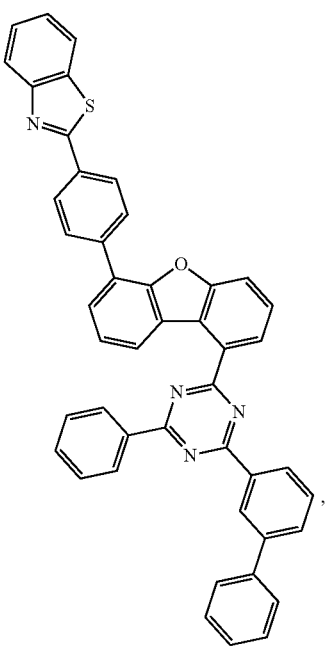

725
-continued
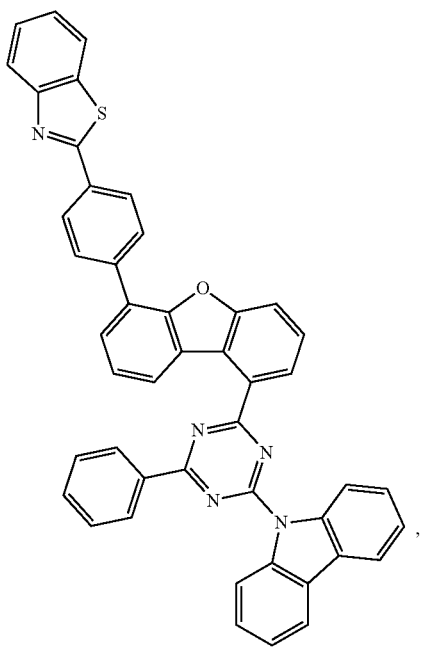
726
-continued
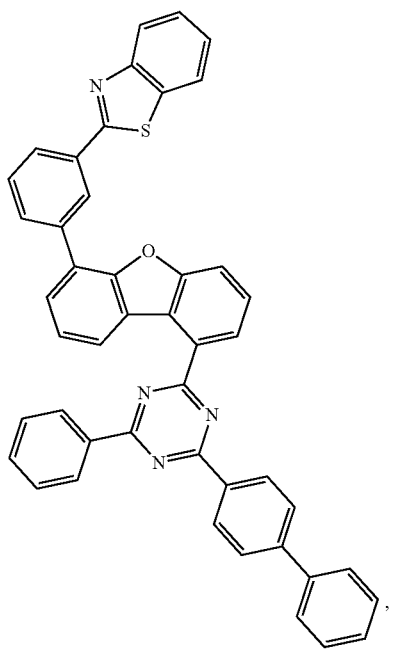
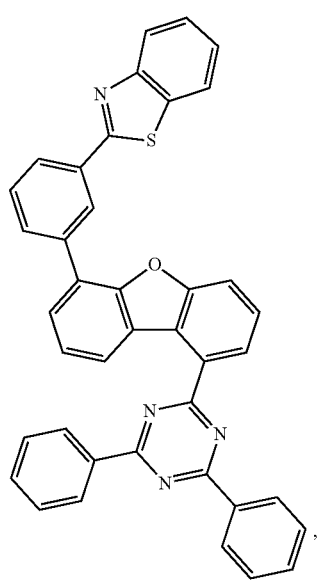
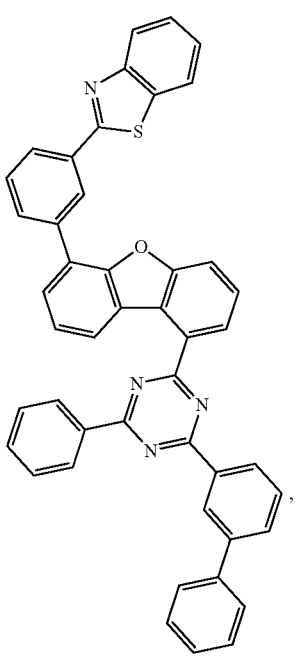

727
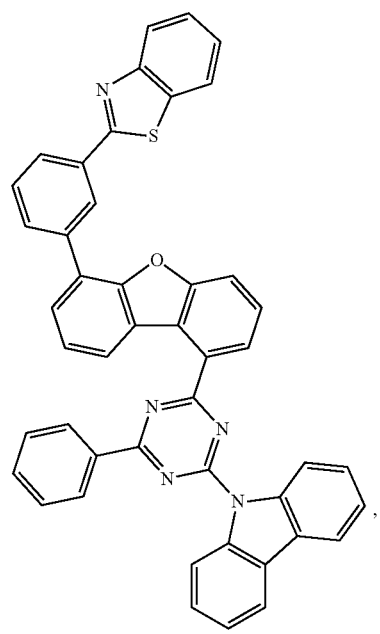
728
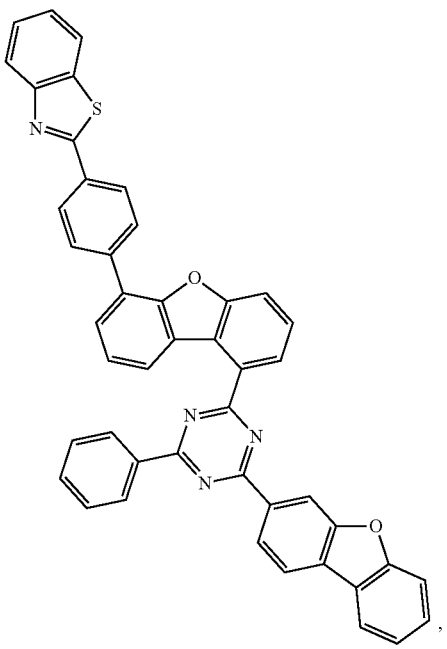
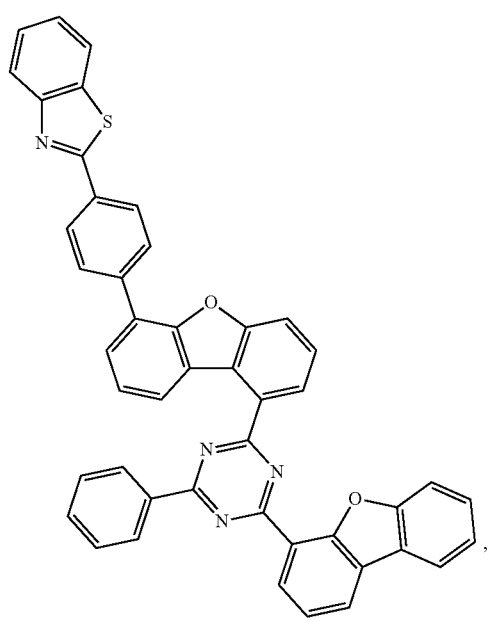
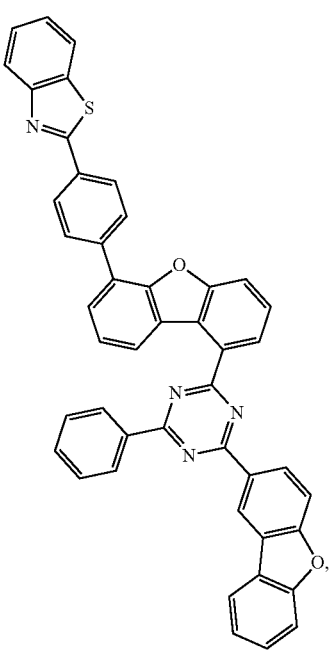

729
-continued
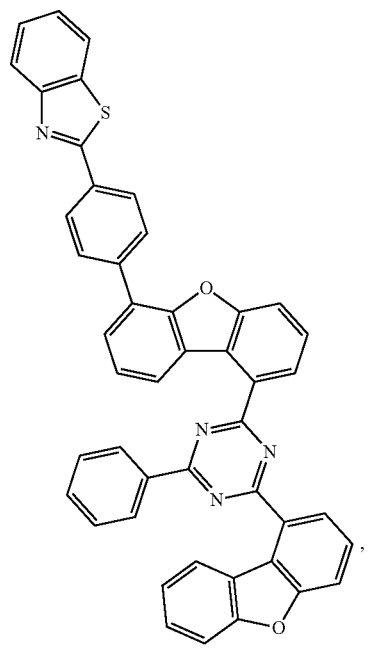
730
-continued
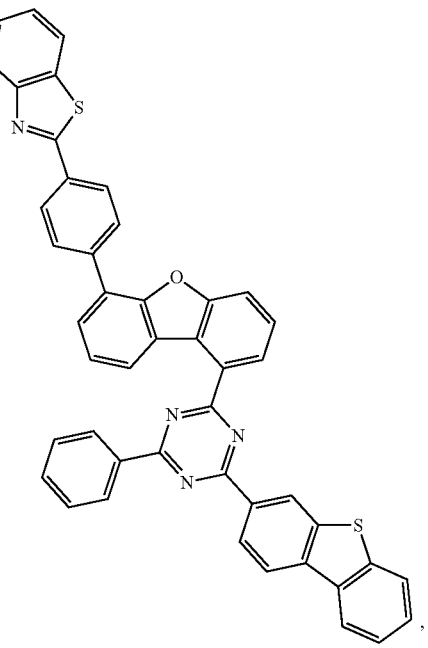
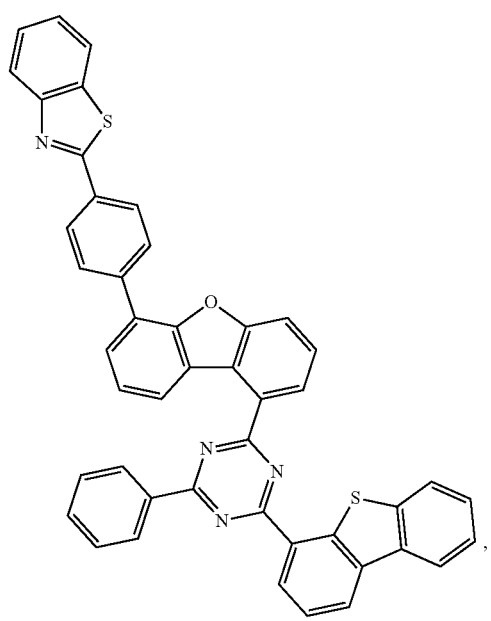
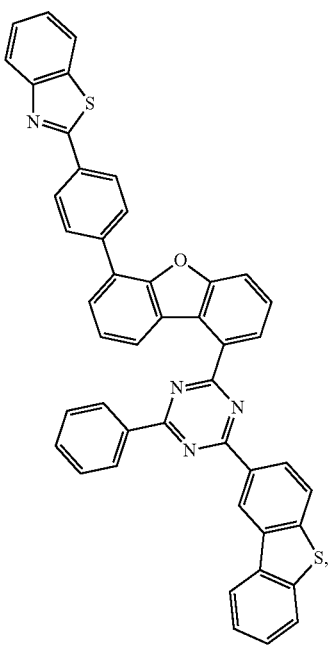

731
-continued
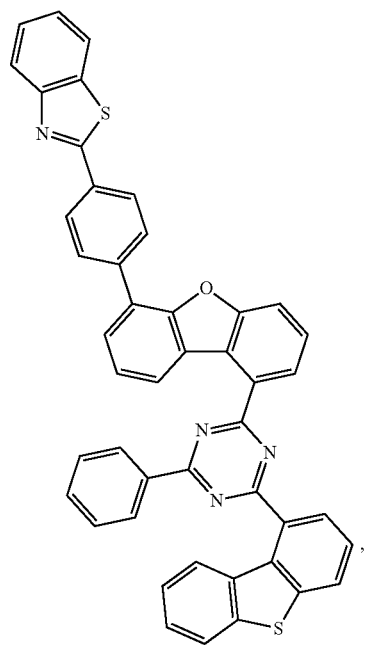
732
-continued
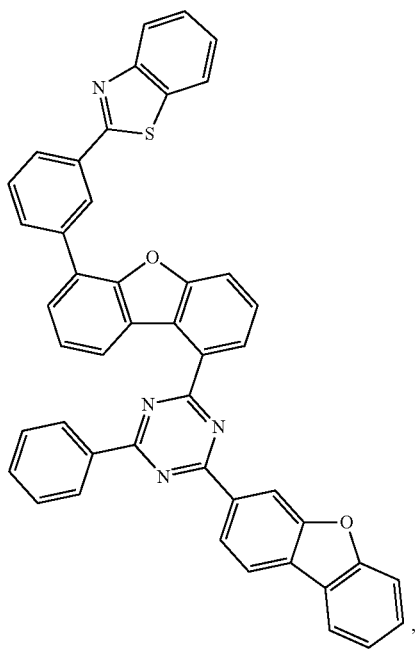
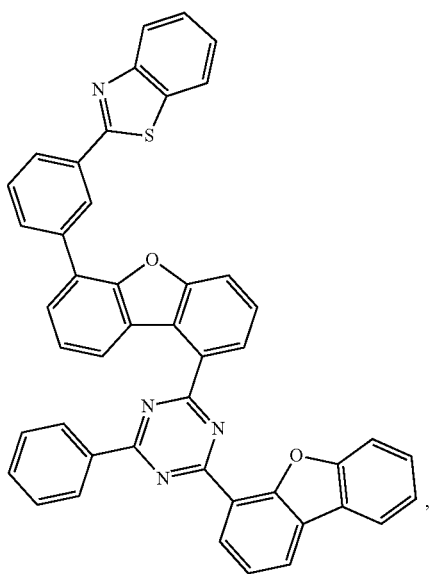
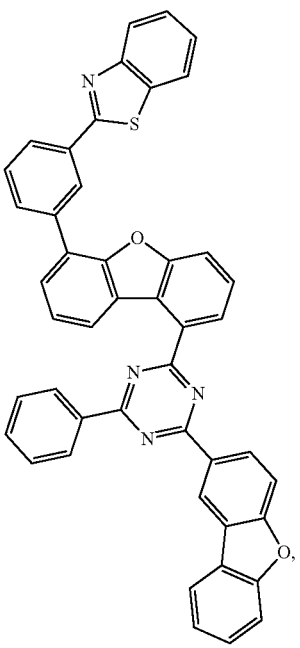

733
-continued
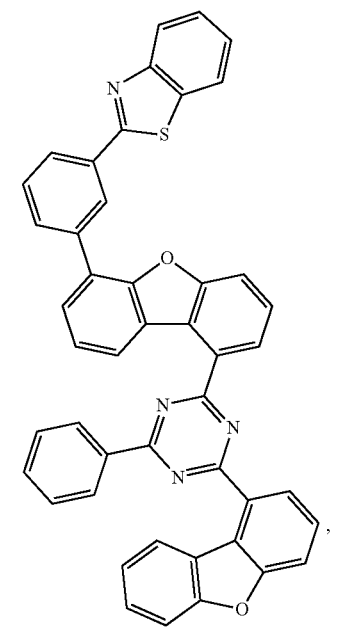
734
-continued
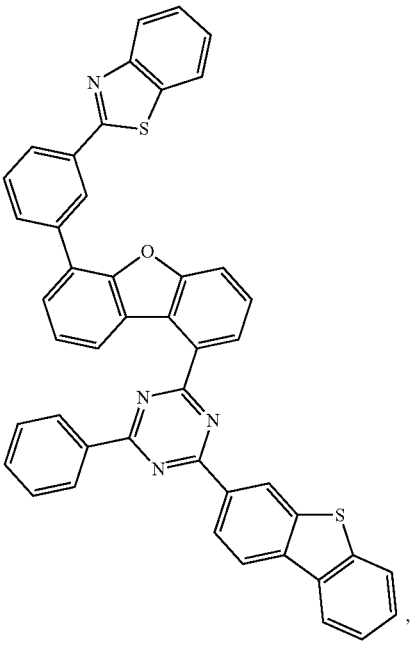
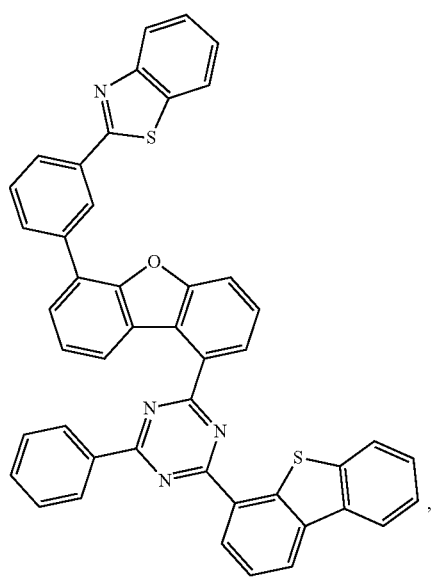
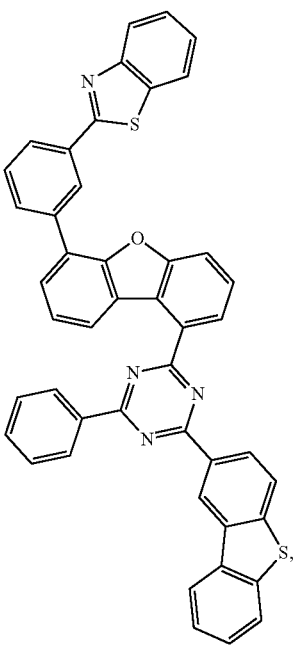

735
-continued
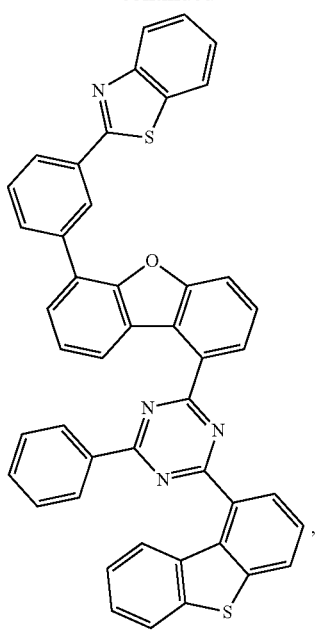
736
-continued
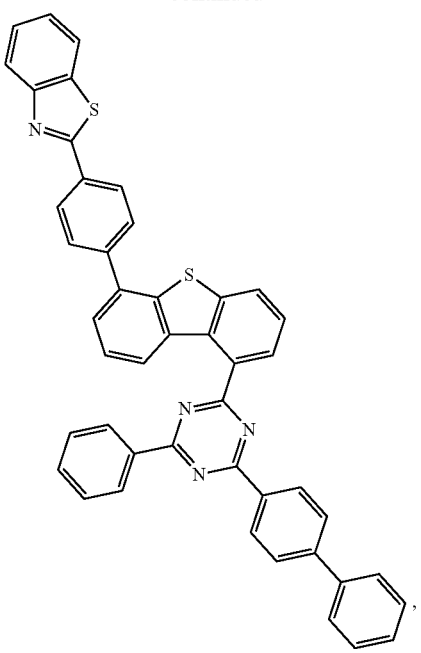
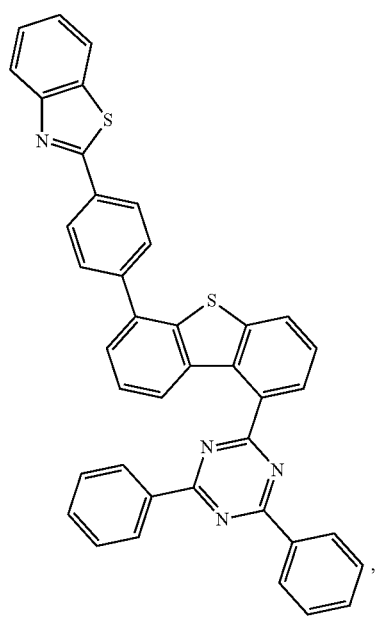
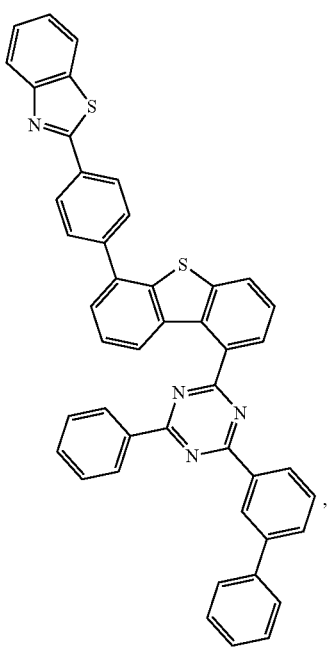

737
-continued
738
-continued
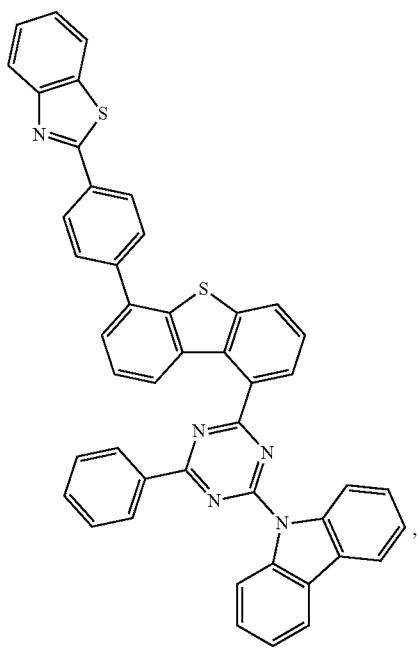
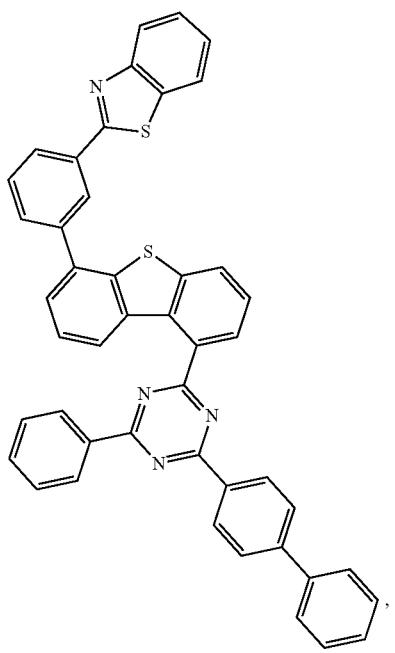

739
-continued
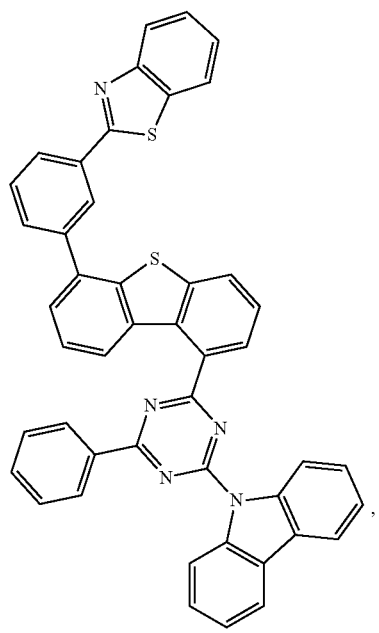
740
-continued
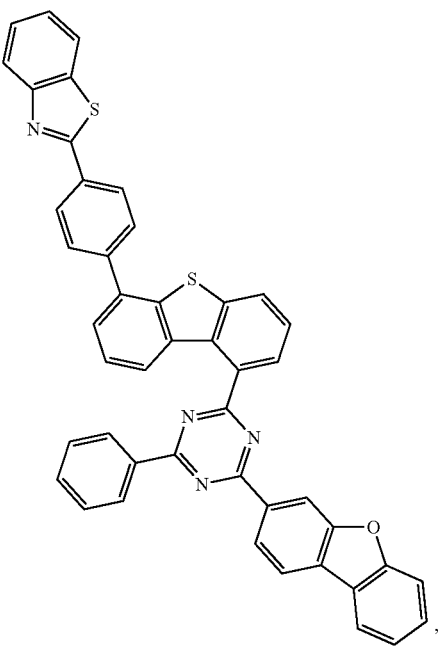
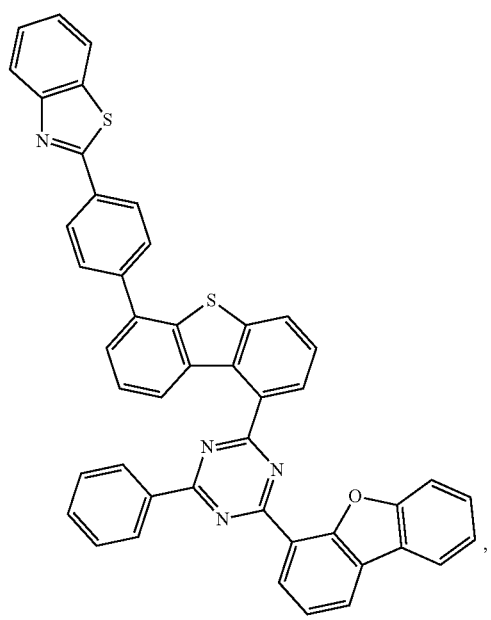
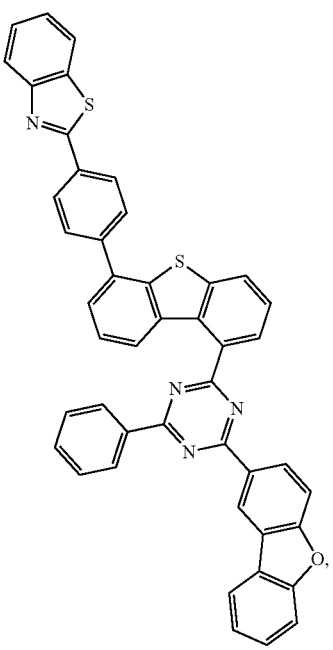

741
-continued
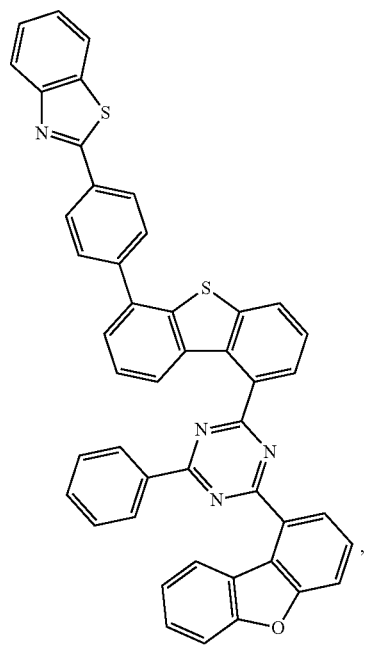
742
-continued
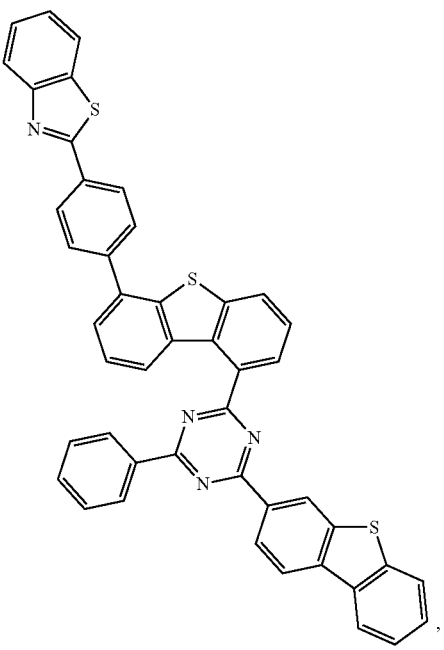
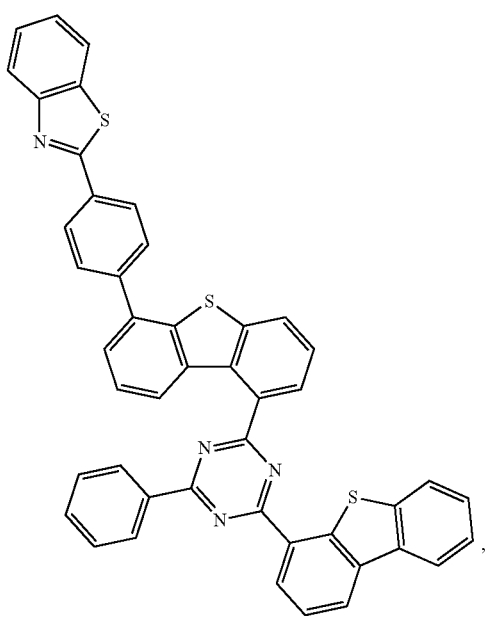
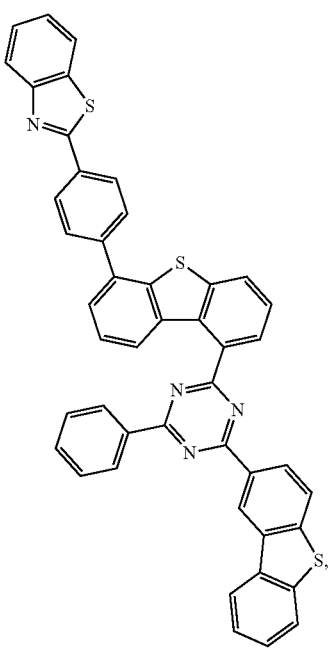

743
-continued
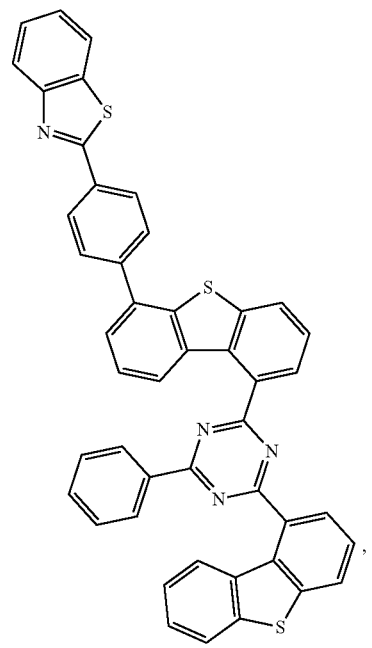
744
-continued
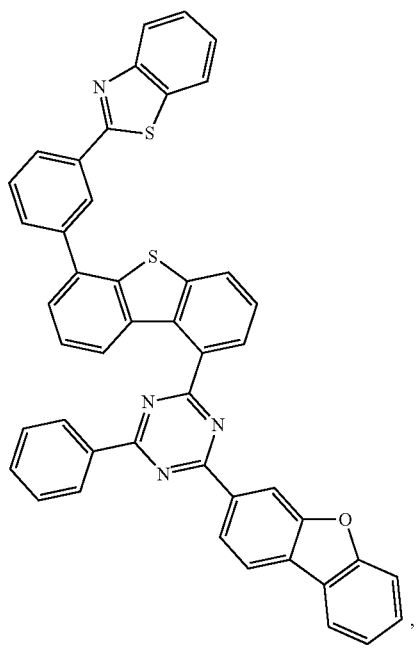
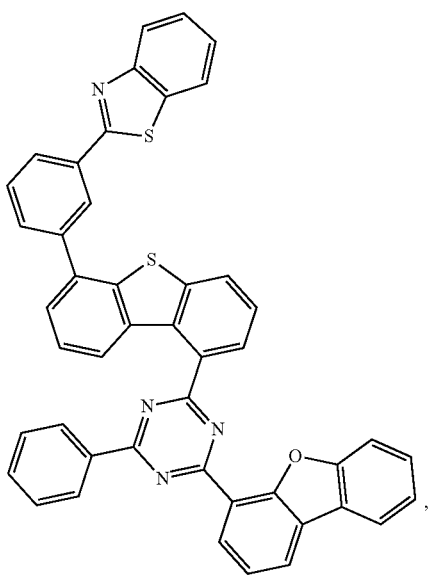
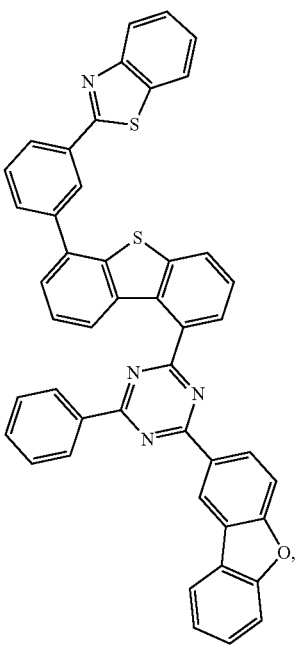

745
-continued
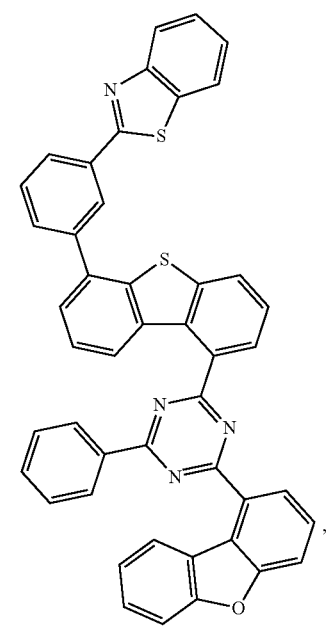
746
-continued
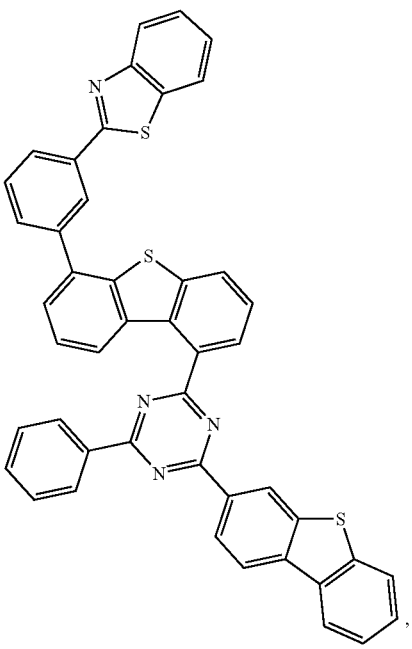
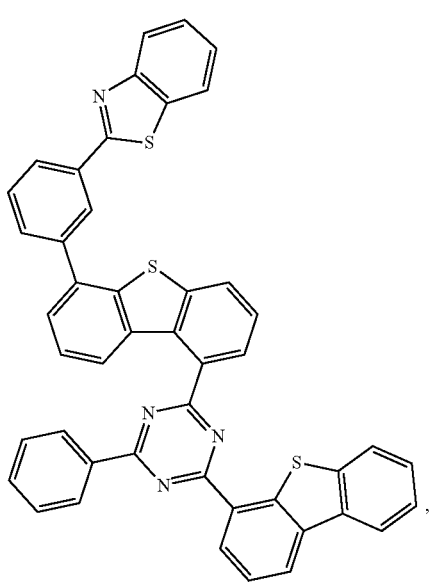
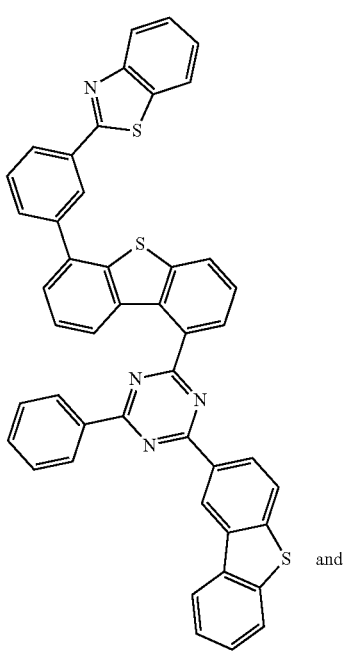 and -continued

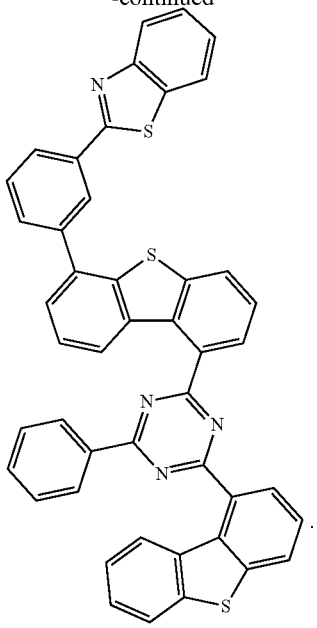

11. An organic light emitting device comprising:
a first electrode;
a second electrode provided at a side opposite to the first electrode; and
at least one organic material layer provided between the first electrode and the second electrode, wherein the at least one organic material layer comprises the compound of claim 1.

12. The organic light emitting device of claim 11, wherein the organic material layer comprising said compound is a light emitting layer.

13. The organic light emitting device of claim 12, wherein the compound is a host material in the light emitting layer.

14. The organic light emitting device of claim 13, wherein the light emitting layer further comprises a dopant material.

15. The organic light emitting device of claim 11, wherein the organic material layer is an electron injection layer, an electron transport layer, or a layer simultaneously performing electron injection and electron transport.

* * * * *